(12) United States Patent
Wilson et al.

(10) Patent No.: US 11,970,498 B2
(45) Date of Patent: *Apr. 30, 2024

(54) CDK2 INHIBITORS

(71) Applicant: BLUEPRINT MEDICINES CORPORATION, Cambridge, MA (US)

(72) Inventors: Douglas Wilson, Ayer, MA (US); Neil Bifulco, Jr., Sudbury, MA (US); Natasja Brooijmans, Boston, MA (US); Joseph L. Kim, Wayland, MA (US); Philip D. Ramsden, Cambridge, MA (US); Richard Vargas, Cambridge, MA (US); Steven Mark Wenglowsky, Cambridge, MA (US)

(73) Assignee: BLUEPRINT MEDICINES CORPORATION, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/166,178

(22) Filed: Feb. 8, 2023

(65) Prior Publication Data
US 2023/0322791 A1    Oct. 12, 2023

Related U.S. Application Data

(63) Continuation of application No. 17/850,453, filed on Jun. 27, 2022.

(60) Provisional application No. 63/215,901, filed on Jun. 28, 2021.

(51) Int. Cl.
| | | |
|---|---|---|
| *C07D 487/04* | (2006.01) | |
| *A61K 31/4985* | (2006.01) | |
| *A61K 31/519* | (2006.01) | |
| *A61K 45/06* | (2006.01) | |
| *A61P 35/00* | (2006.01) | |
| *C07D 519/00* | (2006.01) | |

(52) U.S. Cl.
CPC ......... *C07D 487/04* (2013.01); *C07D 519/00* (2013.01); *C07B 2200/05* (2013.01)

(58) Field of Classification Search
CPC .............. C07D 487/04; C07D 519/00; C07B 2200/05; A61K 31/4985; A61K 31/519; A61K 45/06; A61K 2300/00; A61P 35/00
See application file for complete search history.

(56) References Cited

U.S. PATENT DOCUMENTS

| | | |
|---|---|---|
| 8,058,290 B2 | 11/2011 | Bjergarde et al. |
| 8,334,291 B2 | 12/2012 | Schirok et al. |
| 2009/0197911 A1 | 8/2009 | Georg et al. |
| 2023/0002376 A1 | 1/2023 | Hummel et al. |
| 2023/0159535 A1* | 5/2023 | Wilson .............. A61P 35/00 514/249 |

FOREIGN PATENT DOCUMENTS

| | | |
|---|---|---|
| WO | WO-2002/018346 A1 | 3/2002 |
| WO | WO-2002/022601 A1 | 3/2002 |
| WO | WO-2002/022602 A2 | 3/2002 |
| WO | WO-2002/022604 A1 | 3/2002 |
| WO | WO-2002/022606 A1 | 3/2002 |
| WO | WO-2002/022607 A1 | 3/2002 |
| WO | WO-2002/050065 A2 | 6/2002 |
| WO | WO-2002/050066 A2 | 6/2002 |
| WO | WO-2002/059111 A2 | 8/2002 |
| WO | WO-2002/066461 A1 | 8/2002 |
| WO | WO-2002/068415 A1 | 9/2002 |
| WO | WO-2005/068452 A1 | 7/2005 |
| WO | WO-2007/017577 A1 | 2/2007 |
| WO | WO-2007/024680 A1 | 3/2007 |
| WO | WO-2010/078900 A2 | 7/2010 |
| WO | WO-2011/055911 A1 | 5/2011 |
| WO | WO-2012/077932 A2 | 6/2012 |
| WO | WO-2014/181137 A1 | 11/2014 |
| WO | WO-2014/181287 A1 | 11/2014 |
| WO | WO-2015/017502 A1 | 2/2015 |
| WO | WO-2016/057322 A1 | 4/2016 |
| WO | WO-2016/193939 A1 | 12/2016 |
| WO | WO-2018/106667 A1 | 6/2018 |
| WO | WO-2019/183364 A1 | 9/2019 |

(Continued)

OTHER PUBLICATIONS

CAS Registry No. 439214-73-0, STN entry date: Jul. 18, 2002; chemical name: 1H-Pyrazolo[3,4-b]pyrazin-6-amine, 3-methyl-5-phenyl-1-(phenylmethyl)-.

CAS Registry No. 439213-71-5, STN entry date: Jul. 18, 2002; chemical name: 1H-Pyrazolo[3,4-b]pyrazin-6-amine, 5-(4-chlorophenyl)-3-methyl-1-(phenylmethyl)-.

Etemadmoghadam et al., "Synthetic lethality between CCNE1 amplification and loss of BRCA1," PNAS, 2013, 110(48), pp. 19489-19494.

(Continued)

*Primary Examiner* — Sun Jae Yoo
(74) *Attorney, Agent, or Firm* — Goodwin Procter LLP

(57) ABSTRACT

The present disclosure provides a compound represented by structural Formula (I):

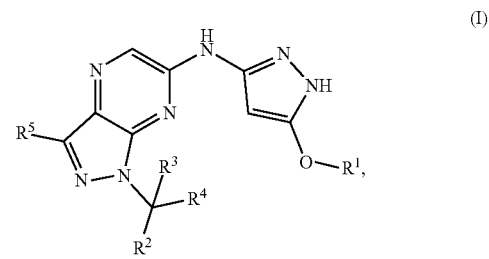

or a pharmaceutically acceptable salt thereof useful for treating a cancer.

26 Claims, No Drawings

(56) References Cited

FOREIGN PATENT DOCUMENTS

| WO | WO-2019/220147 A1 | 11/2019 |
|----|-------------------|---------|
| WO | WO-2020/108516 A1 | 6/2020 |
| WO | WO-2020/108613 A1 | 6/2020 |
| WO | WO-2020/157652 A2 | 8/2020 |
| WO | WO-2020/205560 A1 | 10/2020 |
| WO | WO-2020/264420 A1 | 12/2020 |
| WO | WO-2021/072232 A1 | 4/2021 |
| WO | WO-2022/061155 A1 | 3/2022 |
| WO | WO-2022/245776 A1 | 11/2022 |
| WO | WO-2022/266190 A1 | 12/2022 |
| WO | WO-2023/278326 A1 | 1/2023 |
| WO | WO-2023/092088 A1 | 5/2023 |
| WO | WO-2023/092107 A1 | 5/2023 |

OTHER PUBLICATIONS

Honda et al., "The structure of cyclin E1/CDK2: implications for CDK2 activation and CDK2-independent roles," EMBO J, 2005, 24(3), pp. 452-463.

Hu et al., "Specific CP110 Phosphorylation Sites Mediate Anaphase Catastrophe after CDK2 Inhibition: Evidence for Cooperation with USP33 Knockdown," Mol. Cancer Ther., 2015, 14(11), pp. 2576-2585.

International Search Report and Written Opinion dated Sep. 14, 2022, in Internationl Patent Application No. PCT/US2022/035122, filed Jun. 27, 2022, by Blueprint Medicines Corp.

International Search Report and Written Opinion dated Sep. 9, 2022, in Internationl Patent Application No. PCT/US2022/033576, filed Jun. 15, 2022, by Blueprint Medicines Corp.

Le Brazidec et al: "Synthesis, SAR and biological evaluation of 1,6-disubstituted-1-pyrazolo[3,4-]pyrimidinyes as dual inhibitors of Aurora kinases and CDK1," Bioorganic & Medicinal Chemistry Letters, 2019, 22(5), pp. 2070-2074.

Molenaar et al., "Inactivation of CDK2 is synthetically lethal to MYCN over-expressing cancer cells," PNAS USA, 106(31), pp. 12968-12973.

Noske et al., "Detection of CCNE1/URI (19q12) amplification by in situ hybridisation is common in high grade and type II endometrial cancer," Oncotarget, 2016, 8, pp. 14794-14805.

Ohtsubo et al., "Human cyclin E, a nuclear protein essential for the G1-to-S phase transition," Mol. Cell Biol., 1995, 15(5), pp. 2612-2624.

Ooi et al., "Gene amplification of CCNE1, CCND1, and CDK6 in gastric cancers detected by multiplex ligation-dependent probe amplification and fluorescence in situ hybridization," Human Pathology, 2017, 61, pp. 58-67.

Scaltriti et al., "Cyclin E amplification/overexpression is a mechanism of trastuzumab resistance in HER2+ breast cancer patients," PNAS, 2011, 108(9), pp. 3761-3766.

Schenone et al: "Biologically Driven Synthesis of Pyrazolo[3,4-d]pyrimidines as Protein Kinase Inhibitors: An Old Scaffold as a New Tool for Medicinal Chemistry and Chemical Biology Studies," Chemical Review, 2014.

Tadesse et al., "Targeting CDK2 in cancer: challenges and opportunites for therapy," Drug Discovery Today, 2020, 25(2), pp. 406-413.

Takada et al., "FBW7 Loss Promotes Chromosomal Instability and Tumorigenesis via Cyclin E1/CDK2-Mediated Phosphorylation of CENP-A," Cancer Res., 2017, 77(18), pp. 4881-4893.

Zhang et al: "CDK inhibitors in cancer therapy, an overview of recent development," American Journal of Cancer Research, 2021, pp. 1913-1935.

U.S. Appl. No. 17/850,453 US 2023/0159535, CDK2 Inhibitors, filed Jun. 27, 2022, Published.

Brown et al. "BLU-222, an investigational, potent, and selective CDK2 inhibitor, demonstrated robust antitumor activity in CCNE1-amplified ovarian cancer models," Poster No. 2306 presented at AACR Annual Meeting Apr. 8-13, 2022.

Brown et al. "CDK2 inhibition with BLU-222 in combination with ribociclib demonstrates robust antitumor activity in pre-clinical models of CDK4/6 inhibitor-naive and -resistant HR+/HER2-breast cancer," Poster P6-10-07, San Antonio Breast Cancer Symposium—Dec. 6-10, 2022.

Choi et al. "Development of a selective CDK2-E Inhibitor in CCNE-aberrant cancers," Poster 1279 presented at AACR Apr. 9-14, 2021.

NCT05252416, entitled "(VELA) Study of BLU-222 in Advanced Solid Tumors," ClinicalTrials.gov, Aug. 23, 2023 (11 pages).

Mascarenhas et al. (2008) "An efficient tool for identifying inhibitors based on 3D-QSAR and docking using feature-shape pharmacophore of biologically active conformation—A case study with CDK2/CyclinA," European Journal of Medicinal Chemistry, 43(12) 2008.

U.S. Appl. No. 18/570,274, Substituted Pyrimidinyl-Pyrazoles as CDK2 Inhibitors, filed Dec. 14, 2023, Pending.

Brown et al., "Abstract 2306: BLU-222, an investigational, potent, and selective CDK2 inhibitor, demonstrated robust antitumor activity in *CCNE1*-amplified ovarian cancer models," Cancer Res, 2022, 82 (12_Supplement): 2306 (3 pages).

Brown et al., "Abstract P6-10-07: CDK2 inhibition with BLU-222 in combination with ribociclib demonstrates robust antitumor activity in pre-clinical models of CDK4/6 inhibitor-naïve and -resistant HR+/HER2-breast cancer," Cancer Res, 2023, 83 (5_Supplement): P6-10-07 (3 pages).

Brown et al., "CDK2 regulates collapsed replication fork repair in CCNE1-amplified ovarian cancer cells via homologous recombination," NAR Cancer, 2023, 5(3), pp. 1-16.

Choi et al., "Abstract 1279: Development of a selective CDK2-E inhibitor in CCNE driven cancers," Cancer Res, 2021, 81 (13_Supplement): 1279 (4 pages).

Patel et al., "BLU-222, an oral, potent and selective CDK2 inhibitor, in patients with advanced solid tumors: phase 1 monotherapy dose escalation," Poster 293, ASCO Annual Meeting—Jun. 2-6, 2023 (1 page).

Patel et al., "BLU-222, an oral, potent, and selective CDK2 inhibitor, in patients with advanced solid tumors: Phase 1 monotherapy dose escalation," ASCO Annual Meeting, 2023, 41 (16_Suppl): 3095 (1 page).

Yap et al., "491TiP a first-in-human phase I/II study of BLU-222, a potent, selective CDK2 inhibitor in patients with CCNE1-amplified or CDK4/6 inhibitor-resistant advance solid tumors," ESMO, 2022, 33, Supplement 7, S765 (1 page).

Yap et al., "A first-in-human phase 1/2 study of BLU-222, a potent, selective CDK2 inhibitor in patients with *CCNE1*-amplified or CDK4/6 inhibitor-resistant advanced solid tumors," Poster 491TiP, ESMOCongress—Sep. 9-13, 2022 (1 page).

Yap et al., "VELA: A first-in-human phase 1/2 study of BLU-222, a potent, selective cyclin-dependent kinase (CDK) 2 inhibitor in patients with cyclin E1 gene (CCNE1)-amplified or CDK4/6 inhibitor (CDK4/6i)-resistant advanced solid tumors (1275)," Gynecologic Oncology, 2023, 176: S173 (1 page).

\* cited by examiner

CDK2 INHIBITORS

CROSS REFERENCE TO RELATED APPLICATIONS

This application is a continuation application of U.S. patent application Ser. No. 17/850,453, filed on Jun. 27, 2022, which claims the benefit of and priority to U.S. Provisional Patent Application No. 63/215,901, filed on Jun. 28, 2021, the disclosure of each of which is hereby incorporated by reference in its entirety for all purposes.

BACKGROUND

Cyclin-Dependent Kinase (CDK) are serine/threonine protein kinases that have a central role in cell cycle progression. CDK levels remain relatively constant throughout the cell cycle, and it is the selective activation of specific CDKs allows for the proper ordering of the steps in cell cycle progression. Activation of CDKs requires heterodimerization with regulatory subunits known as cyclins. Cell cycle deregulation is a common feature of human cancer.

Cyclin-dependent kinase 2 (Cdk2) participates in a range of biological activities. CDK2 is a key cell cycle regulator, active from the late $G_1$-phase and throughout the S-phase. CDK2 is involved in DNA damage response (DDR) through the homologous recombination (HR) pathway. CDK2 also regulates aspects of apoptotic pathways. Cyclin E1 (CCNE1), cyclin E2 (CCNE2), cyclin A1 (CCNA1), and cyclin A2 (CCNA2), along with p21Cip1/Waf1, p27Kip1 and p57Kip2 (the cyclin dependent kinase inhibitors of the cyclin-CDK2 complex) are the main regulators of CDK2 activity. In cancer, dysregulation of the binding of CDK2 by cyclin E1, E2, A1, or A2 or the activity of the cyclin-dependent kinase inhibitor proteins may occur. (See S. Tadesse et al., Drug Discovery Today, Volume 25, Number 2 Feb. 2020)

The dysregulation of CDK2 can occur through several mechanisms. Amplification and/or overexpression of CCNE1 has been identified occurring in ovarian and breast cancer (See Scaltriti, M. et al., Proc. Natl Acad. Sci. USA 108, 3761-3766 (2011) and Etemadmoghadam, D. et al. Proc. Natl Acad. Sci. USA 110, 19489-19494 (2013). Poor outcomes in gastric, endometrial, and other cancers have been associated with overexpression and/or amplification of CCNE1 (See Ooi et al. Hum Pathol. (2017) 61:58-67, and Noske et al, Oncotarget (2017) 8: 14794-14805).

While these findings indicate CDK2 is a potential target for cancers with deregulated CDK2 activity, no agents selectively targeting CDK2 have been approved to date. Therefore, there is a need to develop new CDK2 inhibitors.

SUMMARY

The applicant has discovered novel compounds which are effective inhibitors of CDK2 (see Synthetic Examples 1-227). In particular, it has been demonstrated that the compounds of the present disclosure effectively inhibit CDK2. Compounds of the disclosure (also referred to herein as the "disclosed compounds") or pharmaceutically acceptable salts thereof effectively inhibit CDK2. (see Biological Example 1) and can be used treat various cancers. Importantly, the disclosed compounds are selective CDK2 inhibitors, i.e., the disclosed compounds have no or low activity against CDK-family kinases, most notably CDK1. Advantages associated with such selectivity may include facilitating efficacious dosing and reducing CDK1-mediated on-target toxicities. Some of the disclosed compounds also have the advantage of having high microsomal stability. Compounds of the disclosure also may have favorable toxicity profiles related to other non-kinase targets.

In one aspect, the present disclosure provides a compound represented by the following structural Formula (I):

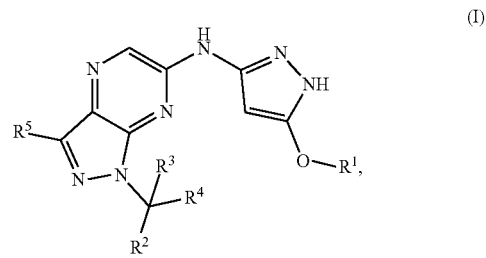

or a pharmaceutically acceptable salt thereof, the definition of each variable is provided below.

In another aspect, the present disclosure provides a compound represented by the following structural Formula (Ia):

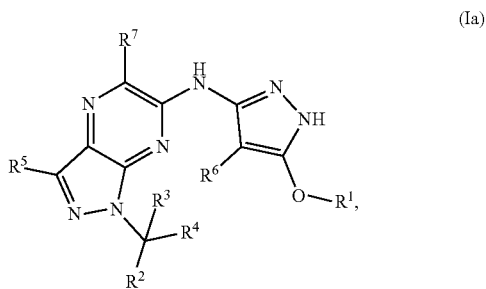

or a pharmaceutically acceptable salt thereof, the definition of each variable is provided below.

In another aspect, the present disclosure provides a pharmaceutical composition comprising a pharmaceutically acceptable carrier or diluent and one or more of the compounds disclosed herein, or a pharmaceutically acceptable salt thereof (a "pharmaceutical composition of the disclosure").

The present disclosure provides a method of treating a subject with cancer, comprising administering to the subject an effective amount of a compound of the disclosure (e.g., a compound of Formula (I) or Formula (Ia)) or a pharmaceutically acceptable salt thereof or a pharmaceutical composition of the disclosure. In one embodiment, the cancer is uterine cancer (including uterine carcinosarcoma (UCS), uterine corpus endometrial carcinoma (UCEC)), endometrial cancer, breast cancer (including breast invasive carcinoma (BRCA), TNBC (triple negative breast cancer), HR+ breast cancer (hormone receptor positive breast cancer), ER+ breast cancer (estrogen receptor positive breast cancer), HR+HER2− breast cancer (hormone receptor positive, human epidermal growth factor 2 negative breast cancer), ER+HER2− breast cancer (estrogen receptor positive, human epidermal growth factor 2 negative breast cancer), HER2− breast cancer (human epidermal growth factor 2 negative breast cancer), HER2-low breast cancer (human epidermal growth factor 2 low breast cancer), and HER2+ breast cancer (human epidermal growth factor 2 positive breast cancer), ovarian cancer (e.g. ovarian serous cystadenocarcinoma (OV)), stomach cancer (including stomach adenocarcinoma (STAD)), gastric cancer (including gastrointestinal stromal tumor), colorectal cancer, pancreatic cancer (including pancreatic adenocarcinoma (PAAD), kidney cancer, head and neck cancer, liver cancer, prostate cancer, skin cancer, leukemia (including AML (acute myeloid leukemia)), lymphoma (including B-cell lymphoma), myelodysplastic syndromes (MDS), myeloproliferative neoplasms (MPN), sarcoma (SARC), esophageal cancer (including esophageal carcinoma (ESCA)), bladder cancer (including bladder urothelial carcinoma), lung cancer (including lung squamous carcinoma and non-small cell lung cancer, e.g., EGFRm (epidermal growth factor receptor mutant)+non-small cell lung cancer), cholangiocarcinoma, adrenocortical carcinoma (ACC), or mesothelioma. In some embodiments, the cancer is breast cancer. In one embodiment, the subject has CCNE1 amplified advanced/relapsed tumors. In one embodiment, the subject has CCNE1 amplified platinum-resistant or platinum-refectory ovarian cancer. In one embodiment, the subject has endometrial cancer (with prior platinum therapy, e.g., wherein the patient has been previously treated with a platinum therapy) that has progressed following 2 or more lines of therapies (including the platinum therapy). In one embodiment, the subject has CCNE1 amplified endometrial cancer that has failed 2 or more lines of therapies (which may include a prior platinum therapy). In one embodiment, the subject has gastric cancer (with prior platinum therapy e.g., wherein the patient has been previously treated with a platinum therapy) that has progressed following 2 or more lines of therapies (including the platinum therapy). In one embodiment, the subject has ER+HER– breast cancer that has progressed despite treatment with one or more CDK4/6 inhibitors.

In one embodiment, the cancer as described herein to be treated (e.g., the cancer as described in paragraphs [0010], [0020], [0120]-[0129], [0131], and [0133]-[0148], e.g., breast cancer) has CCNE1 amplification and/or overexpression.

In one embodiment, the cancer as described herein to be treated (e.g., the cancer as described in paragraphs [0010], [0020], [0120]-[0129], [0131], and [0133]-[0148], e.g., breast cancer) does not have a CCNE1 amplification and/or overexpression.

The treatment method disclosed herein further comprises administering to the subject an effective amount of palbociclib (e.g., Ibrance®), ribociclib, abemaciclib, tamoxifen, letrozole, olaparib (e.g., Lynparza®), niraparib, carboplatin, cisplatin, paclitaxel, gemcitabine, megestrol acetate, medroxyprogesterone acetate, capecitabine (e.g., Xeloda®), regorafenib (e.g., Stivarga®), afatinib (e.g., Gilotrif®), osimertinib (e.g., Tagrisso®), gefitinib (e.g., Iressa®), erlotinib (e.g., Tarceva®), ramucirumab (e.g., Cyramza®), an EGFR inhibitor, pralsetinib, ABT-263 (navitoclax), MK-1775 (adavosertib), BAY-1895344, berzosertib, ceralasertib, SRA-737, LY2603618 (rabusertib), or trastuzumab (e.g., Herceptin®), or combinations thereof. The EGFR inhibitor may be selected from afatinib, osimertinib, lapatinib, erlotinib, dacomitinib, poziotinib, neratinib, gefitinib JBJ-04-125-02, alflutinib (AST 2818), aumolertinib (formerly almonertinib) (HS10296), BBT-176, BI-4020, BPI-361175, BPI-D0316, CH7233163, gilitertinib, icotinib, JND-3229, lazertinib, nazartinib (EGF 816), avitinib, PCC-0208027, rezivertinib (BPI-7711), TQB3804, zorifertinib (AZ-3759), or DZD9008; an EGFR antibody such as cetuximab, panitumumab, necitumumab, HLX07, JMT101; or a bispecific EGFR and MET antibody (e.g., amivantamab ((JNJ-61186372, JNJ-372)).

The present disclosure also provides a method of inhibiting CDK2 in a subject in need thereof, comprising administering to the subject an effective amount of a compound of the disclosure (e.g., a compound of Formula (I) or Formula (Ia)) or a pharmaceutically acceptable salt thereof or a pharmaceutical composition of the disclosure.

The present disclosure also provides the use of an effective amount of a compound of the disclosure (e.g., a compound of Formula (I) or Formula (Ia)), or a pharmaceutically acceptable salt thereof, or a pharmaceutical composition of the disclosure, for the preparation of a medicament for the treatment of cancers.

In another aspect, provided herein is a compound of Formula (I) or Formula (Ia), or a pharmaceutically acceptable salt thereof, or a pharmaceutical composition of the disclosure for use in treating cancers.

In one aspect, the present disclosure provides a method of treating a subject having, or at risk of developing, a disease or disorder associated with CDK2, comprising administering to the subject a therapeutically effective amount of a compound disclosed herein, or a pharmaceutically acceptable salt thereof, or a pharmaceutical composition disclosed herein, wherein the subject has an amplification of the CCNE1 gene and/or have an expression level of CCNE1 higher than a control expression level of CCNE1. In some embodiments, the disease or disorder associated with CDK2 is cancer.

The present disclosure also provides a method of treating a subject having, or at risk of developing, a disease or disorder associated with CDK2, comprising administering to the subject a therapeutically effective amount of a compound disclosed herein, or a pharmaceutically acceptable salt thereof, or a pharmaceutical composition disclosed herein, wherein the subject has an amplification of the CCNE1 gene and/or have an expression level of CCNE1 similar to a control expression level of CCNE1. In some embodiments, the disease or disorder associated with CDK2 is cancer.

Also provided herein is a method of treating a patient having an amplified expression level of CCNE1 and suffering from, or at risk of developing, a solid tumor cancer, comprising administering to the patient a therapeutically effective amount of a compound disclosed herein, or a pharmaceutically acceptable salt thereof, or a pharmaceutical composition disclosed herein.

The contemplated solid tumor cancer may be at least one of: uterine cancer (including uterine carcinosarcoma, uterine corpus endometrial carcinoma (UCEC)), endometrial cancer, breast cancer (including breast invasive carcinoma, TNBC (triple negative breast cancer), ER (estrogen receptor)+HER2 (human epidermal growth factor 2)—breast cancer, HR (hormone receptor)+HER2 (human epidermal growth factor 2)—breast cancer, HER2– breast cancer and HER2+ breast cancer), ovarian cancer (e.g. ovarian serous cystadenocarcinoma), stomach cancer (including stomach adenocarcinoma), gastric cancer (including gastrointestinal stromal tumor), colorectal cancer, pancreatic cancer, kidney cancer, head and neck cancer, liver cancer, prostate cancer, skin cancer, lymphoma (including B-cell lymphoma), sarcoma, esophageal cancer (including esophageal carcinoma and esophageal adenocarcinoma), bladder cancer (including bladder urothelial carcinoma (BLCA)), lung cancer (including lung squamous carcinoma and non-small cell lung cancer, e.g., EGFRm (epidermal growth factor receptor mutant)+non-small cell lung cancer), cholangiocarcinoma, adrenocortical carcinoma, or mesothelioma.

DETAILED DESCRIPTION

Definitions

The term "halo" as used herein means halogen and includes chloro, fluoro, bromo and iodo.

The term "alkyl" used alone or as part of a larger moiety, such as "alkoxy" or "haloalkyl" and the like, means saturated aliphatic straight-chain or branched monovalent hydrocarbon radical. Unless otherwise specified, an alkyl group typically has 1-4 carbon atoms, i.e. ($C_1$-$C_4$)alkyl. As used herein, a "($C_1$-$C_4$)alkyl" group means a radical having from 1 to 4 carbon atoms in a linear or branched arrangement. Examples include methyl, ethyl, n-propyl, iso-propyl, and the like.

The term "alkoxy" means an alkyl radical attached through an oxygen linking atom, represented by —O-alkyl. For example, "($C_1$-$C_4$)alkoxy" includes methoxy, ethoxy, propoxy, and butoxy.

The term "cycloalkyl" refers to a monocyclic saturated hydrocarbon ring system. Unless otherwise specified, cycloalkyl has from 3-10 carbon atoms. In some embodiments, cycloalkyl has from 3-6 carbon atoms. For example, a $C_3$-$C_{10}$ cycloalkyl includes cyclopropyl, cyclobutyl, cyclopentyl and cyclohexyl. Unless otherwise described, a "cycloalkyl" has from three to ten carbon atoms.

The term "heterocyclyl" or "heterocyclic" refers to a radical of a 4- to 12-membered non-aromatic ring system having ring carbon atoms and 1 to 4 ring heteroatoms, wherein each heteroatom is independently selected from nitrogen, quaternary nitrogen, oxidized nitrogen (e.g., NO), oxygen, and sulfur, including sulfoxide and sulfone ("4-12 membered heterocyclyl). In some embodiments, heterocyclyl is a 3- to 6-membered non-aromatic ring system having ring carbon atoms and 1 to 4 ring heteroatoms, wherein each heteroatom is independently selected from nitrogen, quaternary nitrogen, oxidized nitrogen (e.g., NO), oxygen, and sulfur, including sulfoxide and sulfone. In some embodiment, hetrocyclyl has 1 to 2 ring heteroatoms, wherein each heteroatom is independently selected from nitrogen, quaternary nitrogen, oxidized nitrogen (e.g., NO), oxygen, and sulfur, including sulfoxide and sulfone. In heterocyclyl groups that contain one or more nitrogen atoms, the point of attachment can be a carbon or nitrogen atom, as valency permits. Exemplary heterocyclyl groups include azetidinyl, oxetanyl, thietanyl, tetrahydrofuranyl, pyrrolidinyl, piperidinyl, tetrahydropyranyl, piperazinyl, morpholinyl, azepanyl, oxepanyl, thiepanyl, tetrahydropyridinyl, and the like.

The term "heteroaryl" refers to a radical of a 4-12 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl). A heteroaryl group may be described as, e.g., a 6-10-membered heteroaryl, wherein the term "membered" refers to the non-hydrogen ring atoms within the moiety It will be apparent to one skilled in the art that certain compounds disclosed herein may exist in tautomeric forms, all such tautomeric forms of the compounds being within the scope of the disclosure. The term "tautomers" refer to compounds that are interchangeable forms of a particular compound structure, and that vary in the displacement of hydrogen atoms and electrons. Thus, two structures may be in equilibrium through the movement of π electrons and an atom (usually H).

Compounds of the Present Disclosure

Disclosed herein are embodiments of compounds having a general structure of Formula (I) or Formula (Ia). The present invention provides a compound of the present invention or a pharmaceutically acceptable salt thereof for use in the treatment of cancer. These compounds are selective inhibitors of CDK2.

In a first embodiment, the present disclosure provides a compound represented by the following structural Formula (I):

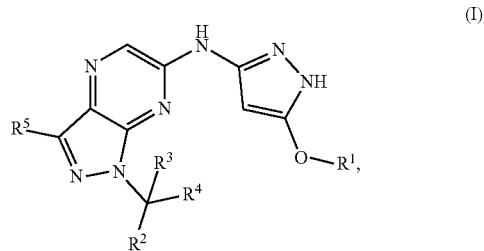

or a pharmaceutically acceptable salt thereof, wherein
$R^1$ is $C_1$-$C_4$alkyl optionally substituted with 1 to 4 halo;
$R^2$ is $C_1$-$C_4$alkyl or Ring A, wherein the $C_1$-$C_4$alkyl is optionally substituted with 1 to 4 groups each independently selected from halo, CN, and OH and/or 1 group of 5 to 6 membered heteroaryl having 1 to 3 ring heteroatoms each independently selected from the group consisting of O, S and $NR^d$; and
$R^3$ is selected from the group consisting of H, $C_1$-$C_4$alkyl, $C_3$-$C_{10}$cycloalkyl, and 4 to 12-membered heterocyclyl, wherein the $C_1$-$C_4$alkyl and $C_3$-$C_{10}$cycloalkyl are each optionally substituted with 1 to 4 $R^c$, wherein the 4 to 12-membered heterocyclyl has 1 to 4 ring heteroatoms each independently selected from the group consisting of O, S and $NR^d$ and then is optionally substituted on a ring carbon with 1 to 4 $R^c$; or
$R^2$ and $R^3$ are taken together with the carbon atom to which they are attached to form Ring B, wherein Ring B is $C_3$-$C_{10}$cycloalkyl or 4 to 12-membered heterocyclyl, wherein the $C_3$-$C_{10}$cycloalkyl is optionally substituted with 1 to 4 $R^b$, wherein the 4 to 12-membered heterocyclyl has 1 to 4 ring heteroatoms each independently selected from the group consisting of $NR^d$, O, and S and then is optionally substituted on a ring carbon by 1 to 4 $R^b$;
Ring A is selected from the group consisting of $C_3$-$C_{10}$cycloalkyl, phenyl, naphthyl, 4 to 12-membered heterocyclyl, and 4 to 12-membered heteroaryl, wherein the $C_3$-$C_{10}$cycloalkyl, phenyl, and naphthyl are each optionally substituted with 1 to 4 $R^a$, wherein the 4 to 12-membered heterocyclyl and 4 to 12-membered heteroaryl have 1 to 4 ring heteroatoms each independently selected from the group consisting of O, S and $NR^d$ and then are optionally substituted on a ring carbon with 1 to 4 $R^a$;

Each $R^a$ is independently selected from the group consisting of halo, OH, CN, $C_1$-$C_4$alkyl, and $C_1$-$C_4$alkoxy, or two $R^a$, attached to the same atom, form a =O, wherein the $C_1$-$C_4$alkyl and $C_1$-$C_4$alkoxy are each optionally substituted with 1 to 4 groups each independently selected from the group consisting of halo, OH and CN;

Each $R^b$ is independently selected from the group consisting of halo, OH, CN, $C_1$-$C_4$alkyl, and $C_1$-$C_4$alkoxy, or two $R^b$, attached to the same atom, form a =O, wherein the $C_1$-$C_4$alkyl and $C_1$-$C_4$alkoxy are each optionally substituted with 1 to 4 groups each independently selected from the group consisting of halo, OH and CN;

Each $R^c$ is independently selected from the group consisting of halo, OH, CN, $C_1$-$C_4$alkyl, and $C_1$-$C_4$alkoxy, or two $R^c$, attached to the same atom, form a =O, wherein the $C_1$-$C_4$alkyl and $C_1$-$C_4$alkoxy are each optionally substituted with 1 to 4 groups each independently selected from the group consisting of halo, OH, and CN; or Each $R^d$ is independently H or $C_1$-$C_6$alkyl;

$R^4$ is H or $C_1$-$C_4$alkyl optionally substituted with 1 to 4 groups each independently selected from halo and OH; and $R^5$ is selected from the group consisting of H, halo, CN, and $C_1$-$C_4$alkyl, wherein the $C_1$-$C_4$alkyl is optionally substituted with 1 to 4 groups each independently selected from halo and OH.

In another embodiment, the present disclosure provides a compound represented by the following structural formula (Ia):

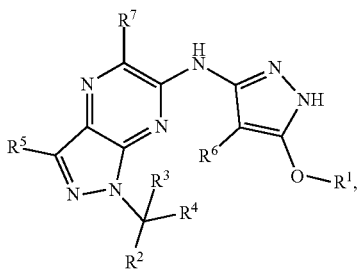

(Ia)

or a pharmaceutically acceptable salt thereof, wherein $R^1$ is $C_1$-$C_4$alkyl optionally substituted with 1 to 4 groups each independently selected from halo and D;

$R^2$ is $C_1$-$C_4$alkyl or Ring A, wherein the $C_1$-$C_4$alkyl is optionally substituted with 1 to 4 groups each independently selected from halo, D, CN, and OH and/or 1 group of 5 to 6 membered heteroaryl having 1 to 3 ring heteroatoms each independently selected from the group consisting of O, S and $NR^d$; and $R^3$ is selected from the group consisting of H, D, $C_1$-$C_4$alkyl, $C_3$-$C_{10}$cycloalkyl, and 4 to 12-membered heterocyclyl, wherein the $C_1$-$C_4$alkyl and $C_3$-$C_{10}$cycloalkyl are each optionally substituted with 1 to 4 $R^c$, wherein the 4 to 12-membered heterocyclyl has 1 to 4 ring heteroatoms each independently selected from the group consisting of O, S, and $NR^d$ and then is optionally substituted on a ring carbon with 1 to 4 $R^c$; or $R^2$ and $R^3$ are taken together with the carbon atom to which they are attached to form Ring B, wherein Ring B is $C_3$-$C_{10}$cycloalkyl or 4 to 12-membered heterocyclyl, wherein the $C_3$-$C_{10}$cycloalkyl is optionally substituted with 1 to 4 $R^b$, wherein the 4 to 12-membered heterocyclyl has 1 to 4 ring heteroatoms each independently selected from the group consisting of $NR^d$, O, and S and then is optionally substituted on a ring carbon by 1 to 4 $R^b$;

Ring A is selected from the group consisting of $C_3$-$C_{10}$cycloalkyl, phenyl, naphthyl, 4 to 12-membered heterocyclyl, and 4 to 12-membered heteroaryl, wherein the $C_3$-$C_{10}$cycloalkyl, phenyl, and naphthyl are each optionally substituted with 1 to 4 $R^a$, wherein the 4 to 12-membered heterocyclyl and 4 to 12-membered heteroaryl have 1 to 4 ring heteroatoms each independently selected from the group consisting of O, S, and $NR^d$ and then are optionally substituted on a ring carbon with 1 to 4 $R^a$;

Each $R^a$ is independently selected from the group consisting of D, halo, OH, CN, $C_1$-$C_4$alkyl, and $C_1$-$C_4$alkoxy, or two $R^a$, attached to the same atom, form a =O, wherein the $C_1$-$C_4$alkyl and $C_1$-$C_4$alkoxy are each optionally substituted with 1 to 4 groups each independently selected from the group consisting of halo, OH and CN;

Each $R^b$ is independently selected from the group consisting of D, halo, OH, CN, $C_1$-$C_4$alkyl, and $C_1$-$C_4$alkoxy, or two $R^b$, attached to the same atom, form a =O, wherein the $C_1$-$C_4$alkyl and $C_1$-$C_4$alkoxy are each optionally substituted with 1 to 4 groups each independently selected from the group consisting of halo, OH and CN;

Each $R^c$ is independently selected from the group consisting of D, halo, OH, CN, $C_1$-$C_4$alkyl, and $C_1$-$C_4$alkoxy, or two $R^c$, attached to the same atom, form a =O, wherein the $C_1$-$C_4$alkyl and $C_1$-$C_4$alkoxy are each optionally substituted with 1 to 4 groups each independently selected from the group consisting of halo, OH, and CN; or Each $R^d$ is independently selected from the group consisting of H, D, and $C_1$-$C_6$alkyl;

$R^4$ is selected from the group consisting of H, D, and $C_1$-$C_4$alkyl optionally substituted with 1 to 4 groups each independently selected from halo, D and OH;

$R^5$ is selected from the group consisting of H, D, halo, CN, and $C_1$-$C_4$alkyl, wherein the $C_1$-$C_4$alkyl is optionally substituted with 1 to 4 groups each independently selected from halo and OH;

$R^6$ is H or D; and $R^7$ is H or D.

In some embodiments, each $R^a$ is independently selected from the group consisting of halo, OH, CN, $C_1$-$C_4$alkyl, and $C_1$-$C_4$alkoxy, or two $R^a$, attached to the same atom, form a =O, wherein the $C_1$-$C_4$alkyl and $C_1$-$C_4$alkoxy are each optionally substituted with 1 to 4 groups each independently selected from the group consisting of halo, OH and CN; each $R^b$ is independently selected from the group consisting of halo, OH, CN, $C_1$-$C_4$alkyl, and $C_1$-$C_4$alkoxy, or two $R^b$, attached to the same atom, form a =O, wherein the $C_1$-$C_4$alkyl and $C_1$-$C_4$alkoxy are each optionally substituted with 1 to 4 groups each independently selected from the group consisting of halo, OH and CN; each $R^c$ is independently selected from the group consisting of halo, OH, CN, C$_1$-C$_4$alkyl, and C$_1$-C$_4$alkoxy, or two R$^c$, attached to the same atom, form a =O, wherein the C$_1$-C$_4$alkyl and C$_1$-C$_4$alkoxy are each optionally substituted with 1 to 4 groups each independently selected from the group consisting of halo, OH, and CN; or each R$^d$ is independently H or C$_1$-C$_6$alkyl.

In some embodiments, R$^2$ is C$_1$-C$_4$alkyl or Ring A, wherein the C$_1$-C$_4$alkyl is optionally substituted with 1 to 4 groups each independently selected from halo, CN, and OH and/or 1 group of 5 to 6 membered heteroaryl having 1 to 3 ring heteroatoms each independently selected from the group consisting of O, S and NR$^d$; or R$^1$ is selected from the group consisting of H, D, and C$_1$-C$_4$alkyl optionally substituted with 1 to 4 groups each independently selected from halo and OH.

In some embodiments, R$^1$ is methyl or ethyl, each optionally substituted with 1 to 4 halo.

In some embodiments, R$^1$ is methyl or ethyl, each optionally substituted with 1 to 4 halo or D.

In some embodiments, R$^1$ is selected from the group consisting of methyl, ethyl, CF$_3$, CH$_2$F, and CHF$_2$.

In some embodiments, R$^1$ is selected from the group consisting of methyl, ethyl, CD$_3$, CD$_2$H, CDH$_2$, CF$_3$, CH$_2$F, and CHF$_2$.

In some embodiments, R$^1$ is CHF$_2$.

In some embodiments, R$^1$ is CD$_3$.

In some embodiments, R$^2$ is selected from the group consisting of Ring A, methyl, ethyl, CH(OH)CH$_3$, CH$_2$F, CHF$_2$, CH$_2$OH, CH(CH$_3$)CH$_2$OH, CH$_2$, CH$_2$OH, In some embodiments, Ring A is selected from the group consisting of:

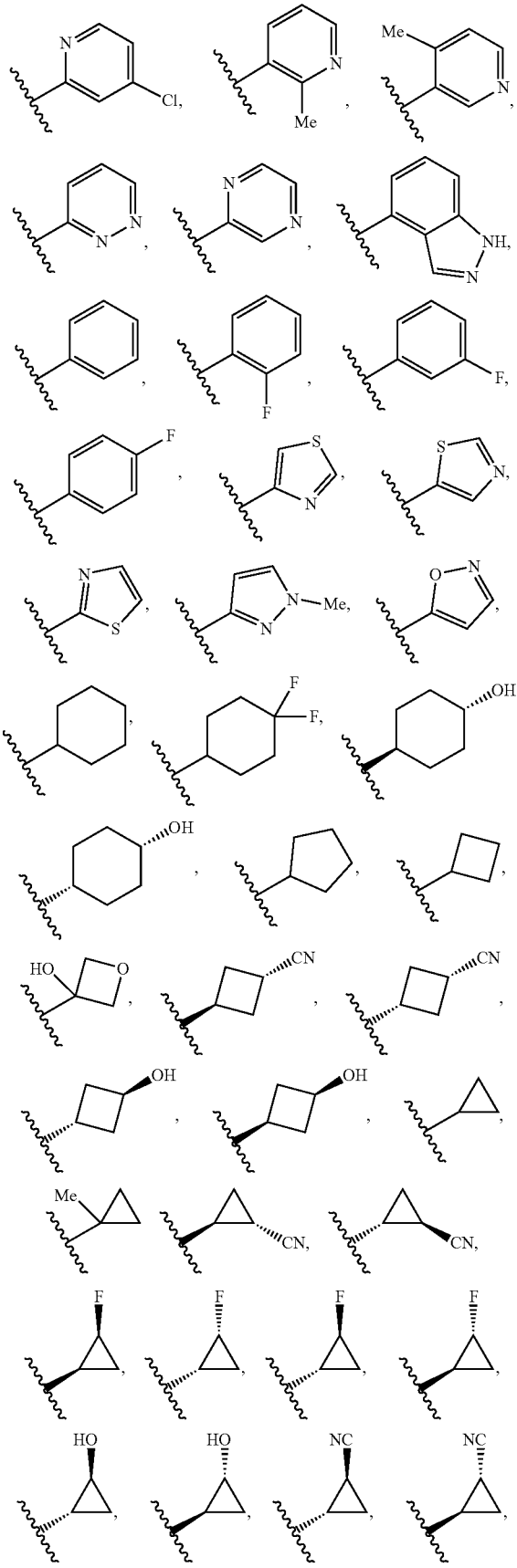

-continued

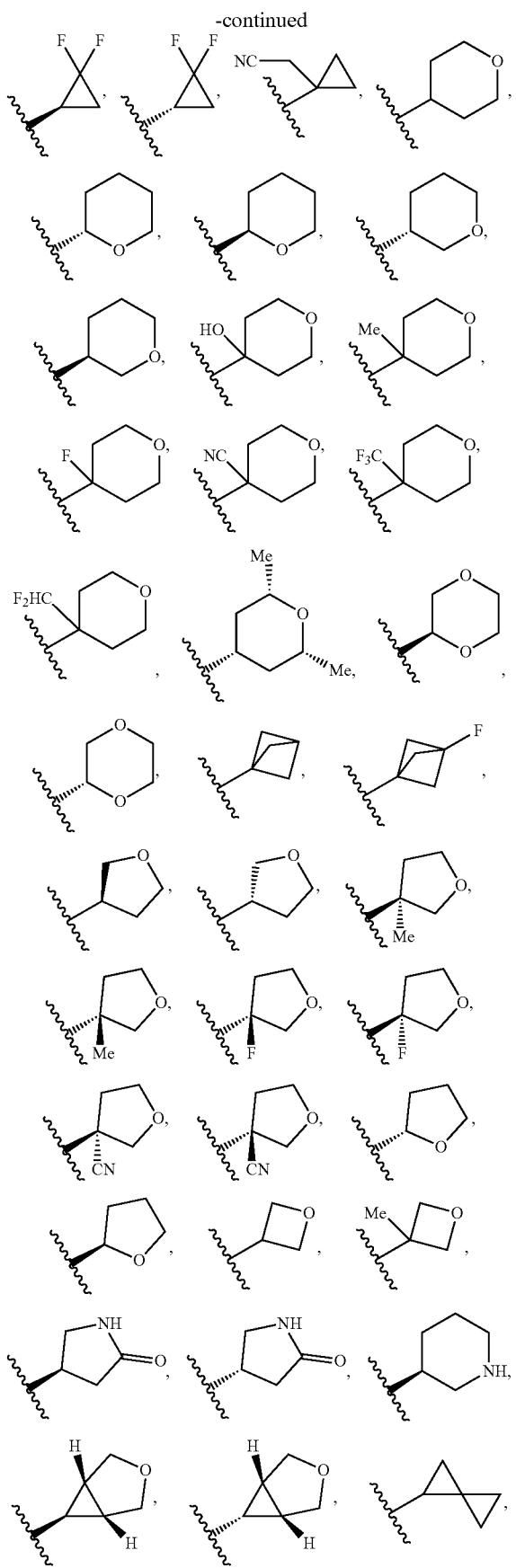

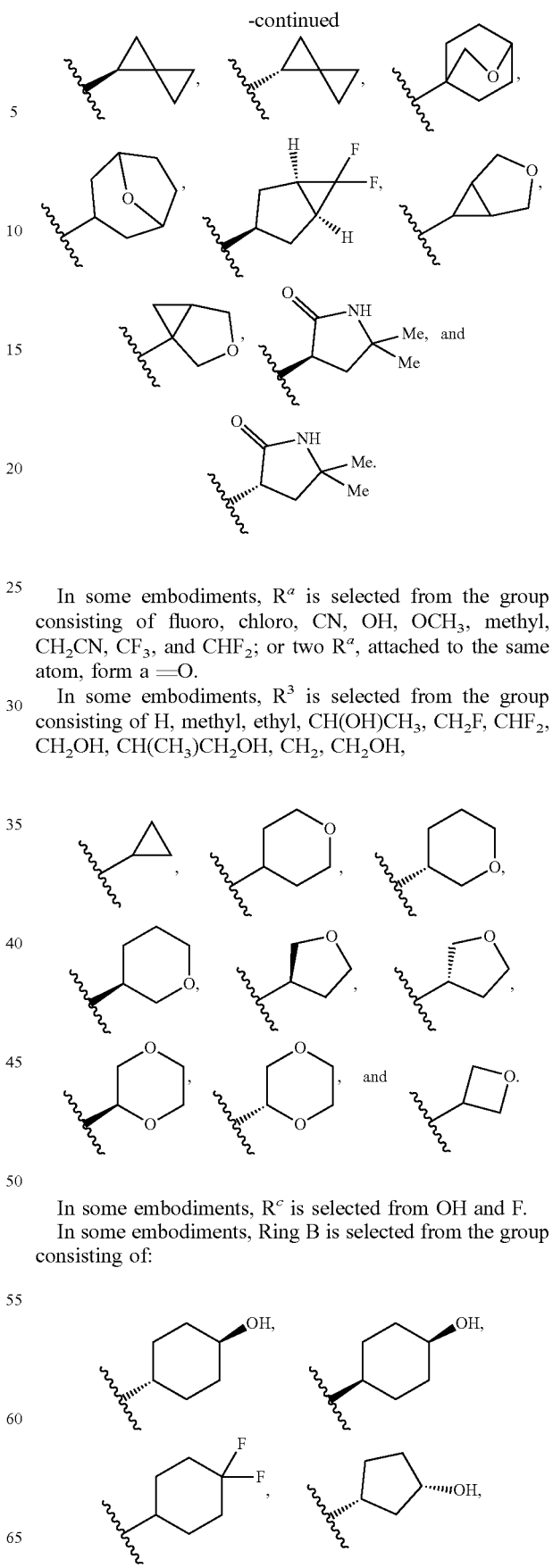

In some embodiments, $R^a$ is selected from the group consisting of fluoro, chloro, CN, OH, $OCH_3$, methyl, $CH_2CN$, $CF_3$, and $CHF_2$; or two $R^a$, attached to the same atom, form a =O.

In some embodiments, $R^3$ is selected from the group consisting of H, methyl, ethyl, $CH(OH)CH_3$, $CH_2F$, $CHF_2$, $CH_2OH$, $CH(CH_3)CH_2OH$, $CH_2$, $CH_2OH$, In some embodiments, $R^c$ is selected from OH and F.
In some embodiments, Ring B is selected from the group consisting of:

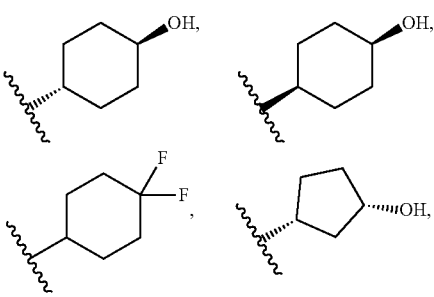

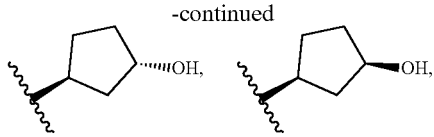

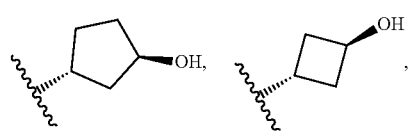

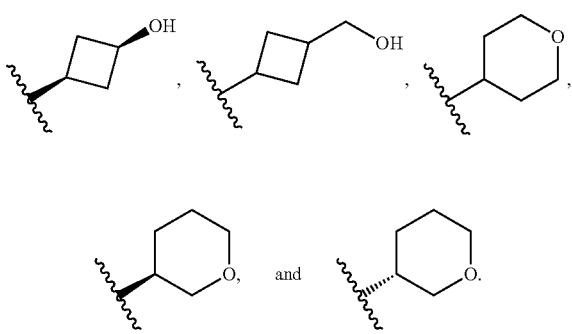

In some embodiments, $R^b$ is selected from the group consisting of OH, F, and $CH_2OH$.

In some embodiments, $R^4$ is selected from the group consisting of H, methyl, and ethyl, $CH(OH)CH_3$, $CH_2F$, $CHF_2$, $CH_2OH$, $CH(CH_3)CH_2OH$, $CH_2$, $CH_2OH$.

In some embodiments, $R^4$ is $C_1$-$C_4$alkyl substituted with OH or F.

In some embodiments, $R^d$ is H or methyl.

In some embodiments, $R^5$ is selected from the group consisting of H, F, Cl, CN, methyl, and $CH(OH)CH_3$.

In some embodiments, the present disclosure provides a compound represented by the following structural formula (IIa):

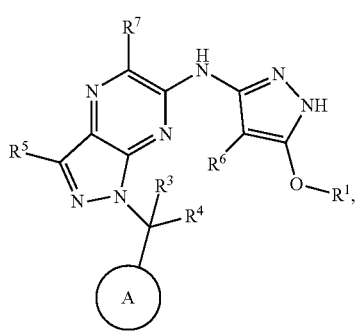

(IIa)

or a pharmaceutically acceptable salt thereof.

In some embodiments, the present disclosure provides a compound represented by the following structural formula (II):

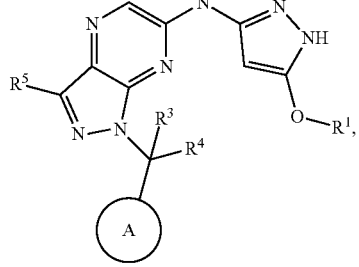

(II)

or a pharmaceutically acceptable salt thereof.

In some embodiments, Ring A is $C_3$-$C_8$cycloalkyl, optionally substituted with 1 to 3 groups each independently selected from the group consisting of halo, OH, =O, CN, $C_1$-$C_4$alkyl, and $C_1$-$C_4$alkoxy, wherein the $C_1$-$C_4$alkyl and $C_1$-$C_4$alkoxy are each optionally substituted with 1 to 3 groups each independently selected from the group consisting of halo, OH, and CN.

In some embodiments, Ring A is $C_3$-$C_8$cycloalkyl, optionally substituted with 1 to 3 groups each independently selected from the group consisting of D, halo, OH, =O, CN, $C_1$-$C_4$alkyl, and $C_1$-$C_4$alkoxy, wherein the $C_1$-$C_4$alkyl and $C_1$-$C_4$alkoxy are each optionally substituted with 1 to 3 groups each independently selected from the group consisting of halo, OH, and CN.

In some embodiments, Ring A is phenyl, optionally substituted with 1 to 3 groups each independently selected from the group consisting of halo, OH, =O, CN, $C_1$-$C_4$alkyl, and $C_1$-$C_4$alkoxy, wherein the $C_1$-$C_4$alkyl and $C_1$-$C_4$alkoxy are each optionally substituted with 1 to 3 groups each independently selected from the group consisting of halo, OH, and CN.

In some embodiments, Ring A is phenyl, optionally substituted with 1 to 3 groups each independently selected from the group consisting of D, halo, OH, =O, CN, $C_1$-$C_4$alkyl, and $C_1$-$C_4$alkoxy, wherein the $C_1$-$C_4$alkyl and $C_1$-$C_4$alkoxy are each optionally substituted with 1 to 3 groups each independently selected from the group consisting of halo, OH, and CN.

In some embodiments, Ring A is 4 to 10-membered heterocyclyl, optionally substituted on a ring carbon with 1 to 3 groups each independently selected from the group consisting of halo, OH, =O, CN, $C_1$-$C_4$alkyl, and $C_1$-$C_4$alkoxy, wherein the $C_1$-$C_4$alkyl and $C_1$-$C_4$alkoxy are each optionally substituted with 1 to 3 groups each independently selected from the group consisting of halo, OH, and CN.

In some embodiments, Ring A is 4 to 10-membered heterocyclyl, optionally substituted on a ring carbon with 1 to 3 groups each independently selected from the group consisting of D, halo, OH, =O, CN, $C_1$-$C_4$alkyl, and $C_1$-$C_4$alkoxy, wherein the $C_1$-$C_4$alkyl and $C_1$-$C_4$alkoxy are each optionally substituted with 1 to 3 groups each independently selected from the group consisting of halo, OH, and CN.

In some embodiments, Ring A is

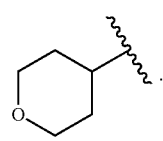 [SMILES: *C1CCOCC1]

In some embodiments, Ring A is 4 to 10-membered heteroaryl, optionally substituted on a ring carbon with 1 to 3 groups each independently selected from the group consisting of halo, OH, =O, CN, $C_1$-$C_4$alkyl, and $C_1$-$C_4$alkoxy, wherein the $C_1$-$C_4$alkyl and $C_1$-$C_4$alkoxy are each optionally substituted with 1 to 3 groups each independently selected from the group consisting of halo, OH, and CN.

In some embodiments, Ring A is 4 to 10-membered heteroaryl, optionally substituted on a ring carbon with 1 to 3 groups each independently selected from the group consisting of D, halo, OH, =O, CN, $C_1$-$C_4$alkyl, and $C_1$-$C_4$alkoxy, wherein the $C_1$-$C_4$alkyl and $C_1$-$C_4$alkoxy are each optionally substituted with 1 to 3 groups each independently selected from the group consisting of halo, OH, and CN.

In some embodiments, the present disclosure provides a compound represented by the following structural formula (IIIa):

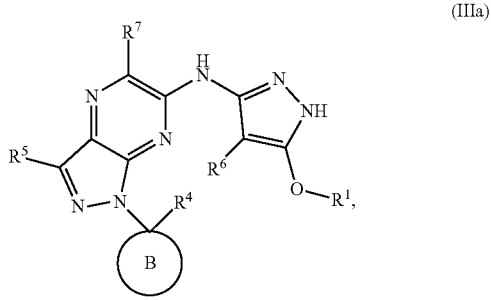

(IIIa)

or a pharmaceutically acceptable salt thereof.

In some embodiments, the present disclosure provides a compound represented by the following structural formula (III):

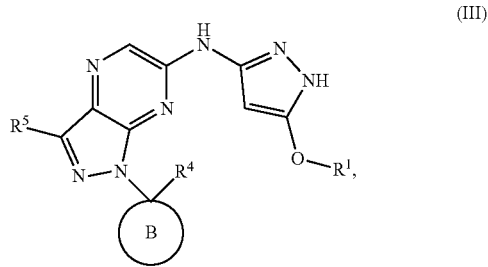

(III)

or a pharmaceutically acceptable salt thereof.

In some embodiments, Ring B is $C_3$-$C_8$cycloalkyl, optionally substituted with 1 to 3 groups each independently selected from the group consisting of halo, OH, =O, CN, $C_1$-$C_4$alkyl, and $C_1$-$C_4$alkoxy, wherein the $C_1$-$C_4$alkyl and $C_1$-$C_4$alkoxy are each optionally substituted with 1 to 3 groups each independently selected from the group consisting of halo, OH, and CN.

In some embodiments, Ring B is $C_3$-$C_8$cycloalkyl, optionally substituted with 1 to 3 groups each independently selected from the group consisting of D, halo, OH, =O, CN, $C_1$-$C_4$alkyl, and $C_1$-$C_4$alkoxy, wherein the $C_1$-$C_4$alkyl and $C_1$-$C_4$alkoxy are each optionally substituted with 1 to 3 groups each independently selected from the group consisting of halo, OH, and CN.

In some embodiments, Ring B is 4 to 10-membered heterocyclyl, optionally substituted on a ring carbon with 1 to 3 groups each independently selected from the group consisting of halo, OH, =O, CN, $C_1$-$C_4$alkyl, and $C_1$-$C_4$alkoxy, wherein the $C_1$-$C_4$alkyl and $C_1$-$C_4$alkoxy are each optionally substituted with 1 to 3 groups each independently selected from the group consisting of halo, OH, and CN.

In some embodiments, Ring B is 4 to 10-membered heterocyclyl, optionally substituted on a ring carbon with 1 to 3 groups each independently selected from the group consisting of D, halo, OH, =O, CN, $C_1$-$C_4$alkyl, and $C_1$-$C_4$alkoxy, wherein the $C_1$-$C_4$alkyl and $C_1$-$C_4$alkoxy are each optionally substituted with 1 to 3 groups each independently selected from the group consisting of halo, OH, and CN.

In some embodiments, $R^2$ is selected from the group consisting of methyl, ethyl, n-propyl, isopropyl, n-butyl, sec-butyl, isobutyl, and tert-butyl, each of which is optionally substituted with 1 to 4 groups each independently selected from the group consisting of halo, OH, CN, and 5 to 6-membered heteroaryl.

In some embodiments, $R^2$ is selected from the group consisting of methyl, ethyl, n-propyl, isopropyl, n-butyl, sec-butyl, isobutyl, and tert-butyl, each of which is optionally substituted with 1 to 4 groups each independently selected from the group consisting of D, halo, OH, CN, and 5 to 6-membered heteroaryl.

In some embodiments, $R^3$ is selected from the group consisting of H, $C_1$-$C_4$alkyl, $C_3$-$C_8$cycloalkyl, and 4 to 10-membered heterocyclyl, wherein the $C_1$-$C_4$alkyl, $C_3$-$C_8$cycloalkyl, and 4 to 10-membered heterocyclyl are each optionally substituted (on a ring carbon if $R^3$ is 4 to 10-membered heterocyclyl) with 1 to 3 groups each independently selected from halo and OH.

In some embodiments, $R^3$ is selected from the group consisting of H, D, $C_1$-$C_4$alkyl, $C_3$-$C_8$cycloalkyl, and 4 to 10-membered heterocyclyl, wherein the $C_1$-$C_4$alkyl, $C_3$-$C_8$cycloalkyl, and 4 to 10-membered heterocyclyl are each optionally substituted (on a ring carbon if $R^3$ is 4 to 10-membered heterocyclyl) with 1 to 3 groups each independently selected from the group consisting of D, halo, and OH.

In some embodiments, $R^3$ is selected from the group consisting of H, methyl, ethyl, cyclopropyl, and oxetanyl, each of which is optionally substituted (on a ring carbon if $R^3$ is oxetanyl) with 1 to 3 groups each independently selected from halo and OH.

In some embodiments, $R^3$ is selected from the group consisting of H, D, methyl, ethyl, cyclopropyl, and oxetanyl, each of which is optionally substituted (on a ring carbon if $R^3$ is oxetanyl) with 1 to 3 groups each independently selected from the group consisting of D, halo, and OH.

In some embodiments, $R^3$ is H.
In some embodiments, $R^3$ is D.
In some embodiments, $R^4$ is H or $CH_3$.
In some embodiments, $R^4$ is selected from the group consisting of H, D, and $CH_3$.
In some embodiments, $R^4$ is H.
In some embodiments, $R^4$ is D.
In some embodiments, $R^5$ is selected from the group consisting of H, halo, CN, methyl, and ethyl, wherein the methyl and ethyl are optionally substituted with OH.
In some embodiments, $R^5$ is selected from the group consisting of H, D, halo, CN, methyl, and ethyl, wherein the methyl and ethyl are optionally substituted with OH.

In some embodiments, $R^5$ is H.
In some embodiments, $R^5$ is D.
In some embodiments, the compound is of Formula IVa-1 or IVb-1:

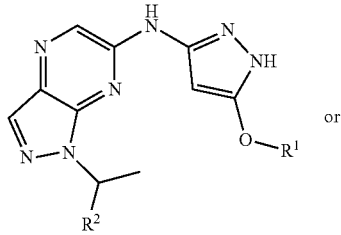

(IVa-1)

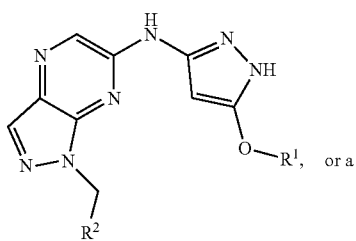

(IVb-1), or a pharmaceutically acceptable salt thereof.

In some embodiments, the compound is of Formula IVa or IVb:

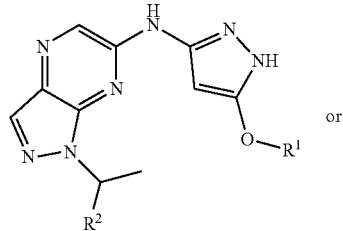

(IVa)

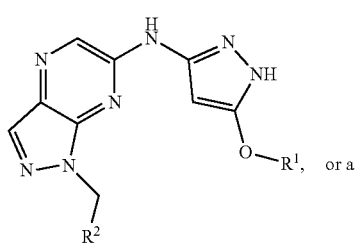

(IVb), or a pharmaceutically acceptable salt thereof.

In some embodiments, the compound is selected from a compound of Formula Va-1, Vb-1, Vc-1, and Vd-1:

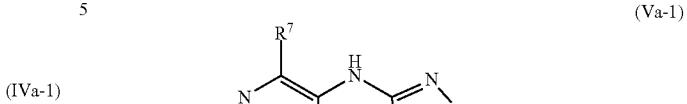

(Va-1)

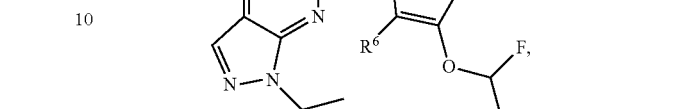

(Vb-1)

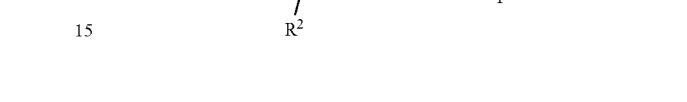

(Vc-1), and

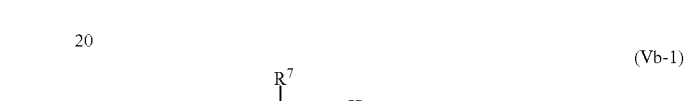

(Vd-1), or a pharmaceutically acceptable salt thereof.

In some embodiments, $R^6$ is H. In some embodiments, $R^6$ is D.

In some embodiments, $R^7$ is H. In some embodiments, $R^7$ is D.

In some embodiments, the compound is selected from a compound of Formula Va, Vb, Vc, and Vd:
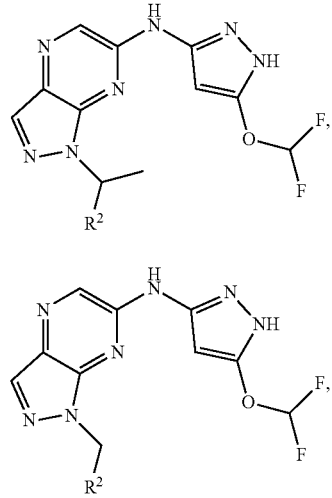
(Va)
(Vb)
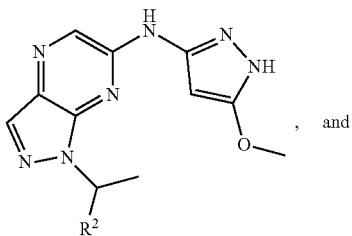
(Vc)
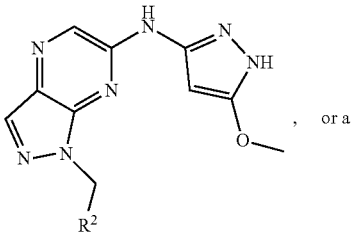
(Vd)
, and
, or a
pharmaceutically acceptable salt thereof.
In one embodiment, the compound is a compound or a pharmaceutically acceptable salt thereof selected from the following table:
| Example Number | Structure |
|---|---|
| 1 | 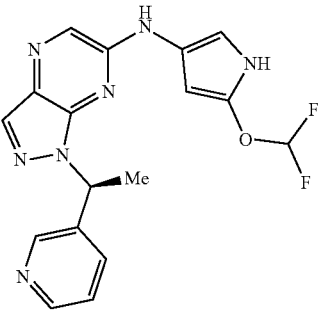 [SMILES: C[C@@H](c1cccnc1)n1ncc2ncc(Nc3c[nH]c(OC(F)F)c3)nc21] |
| 2 | 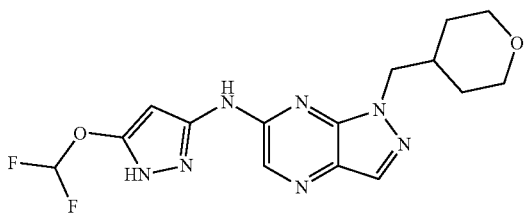 [SMILES: FC(F)Oc1cc(Nc2cnc3cnn(CC4CCOCC4)c3n2)n[nH]1] |
| 3 | 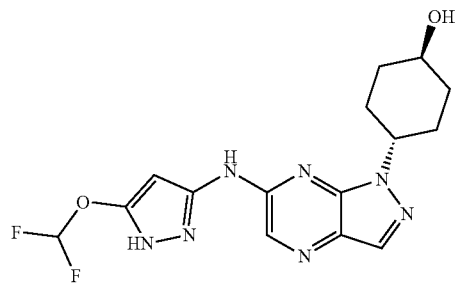 [SMILES: O[C@H]1CC[C@H](n2ncc3ncc(Nc4cc(OC(F)F)[nH]n4)nc32)CC1] |

-continued
| Example Number | Structure |
|---|---|
| 4 | 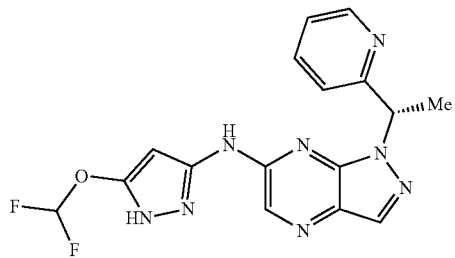 |
| 5 | 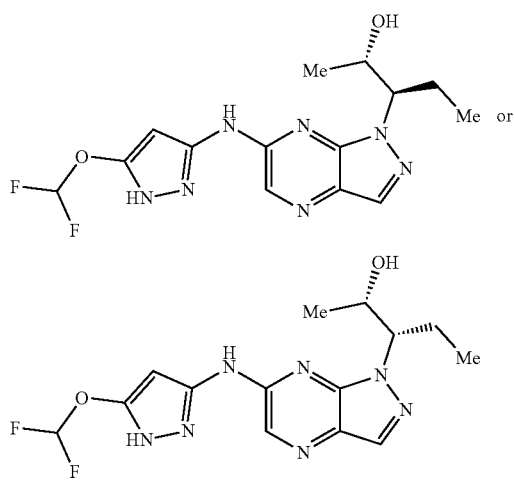 [SMILES: CC[C@H]([C@H](C)O)n1ncc2ncc(Nc3cc(OC(F)F)[nH]n3)nc21 ; CC[C@@H]([C@H](C)O)n1ncc2ncc(Nc3cc(OC(F)F)[nH]n3)nc21] |
| 6 | 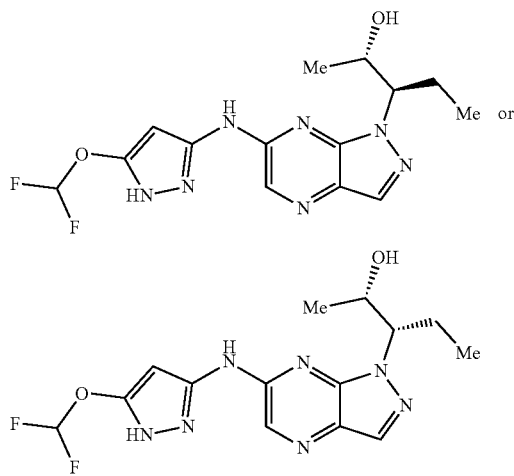 |
| 7 | 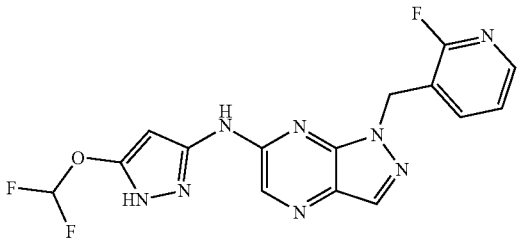 |

-continued
| Example Number | Structure |
|---|---|
| 8 | 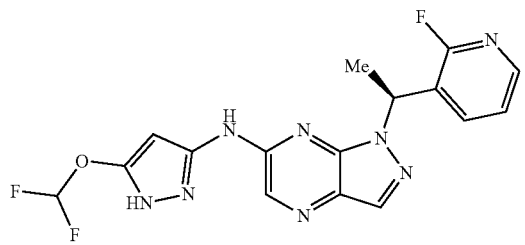 [SMILES: C[C@@H](c1cccnc1F)n1ncc2ncc(Nc3cc(OC(F)F)[nH]n3)nc21] |
| 9 | 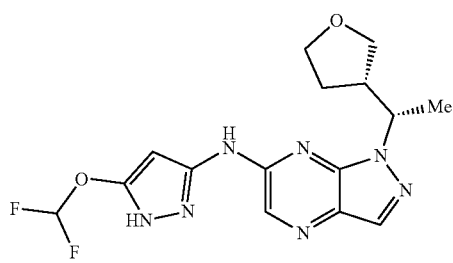
or
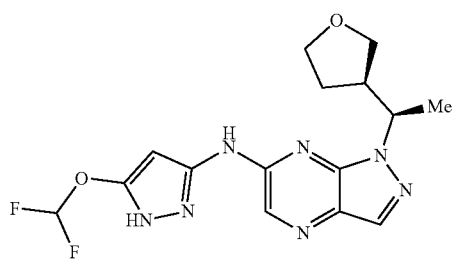
or
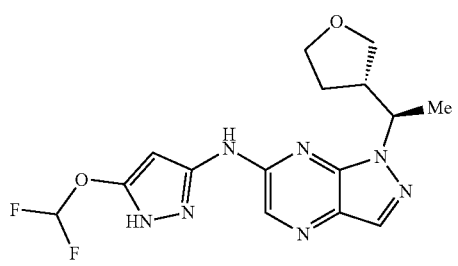
or
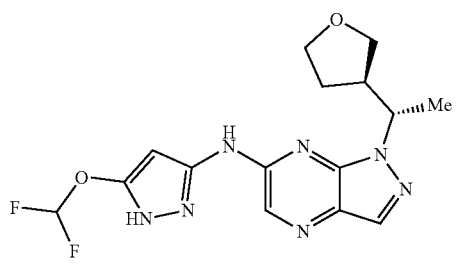 |

-continued
| Example Number | Structure |
|---|---|
| 10 | 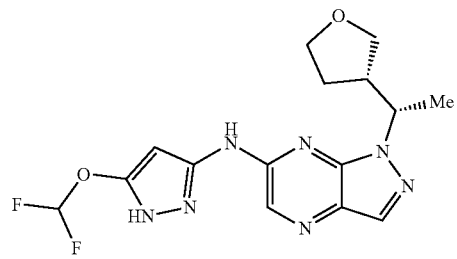
or
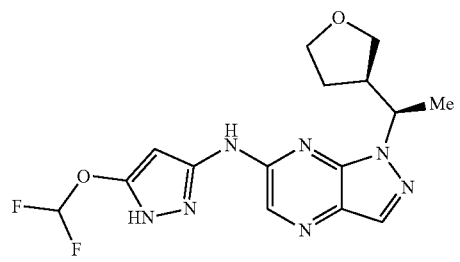
or
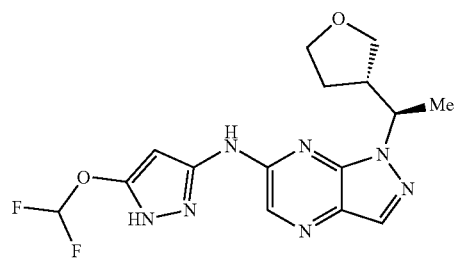
or
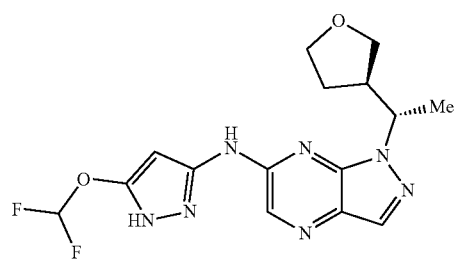 |

-continued
| Example Number | Structure |
|---|---|
| 11 | 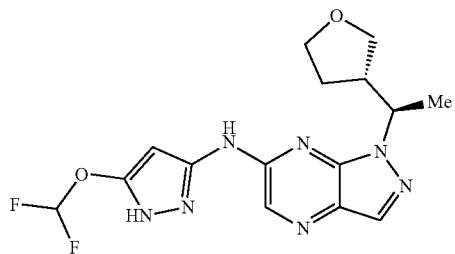
or
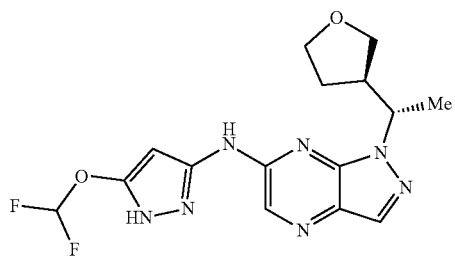
or |
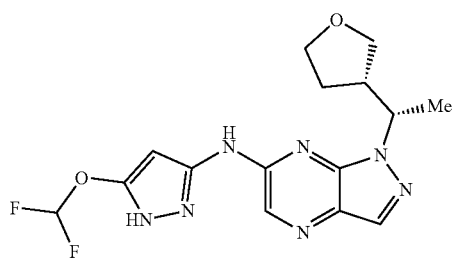
or
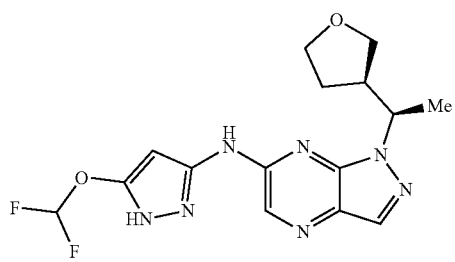

| Example Number | Structure |
|---|---|
| 12 | 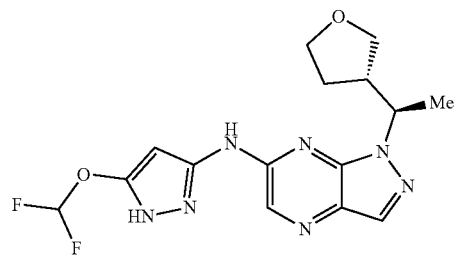
or
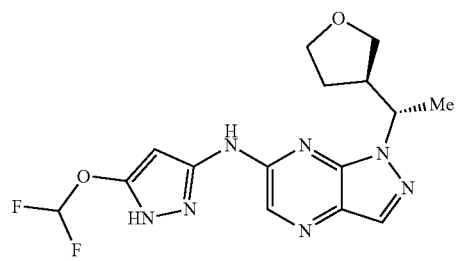
or
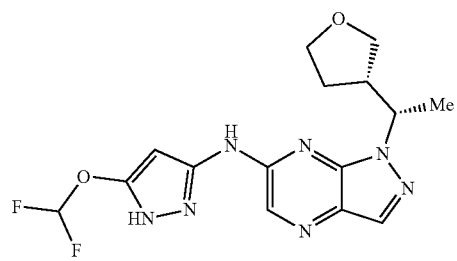
or
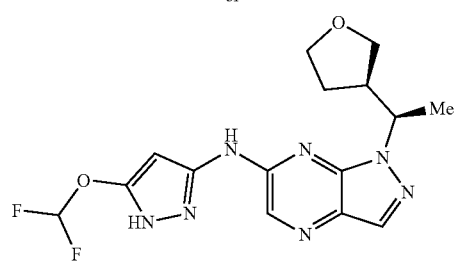 |

| Example Number | Structure |
|---|---|
| 13 | 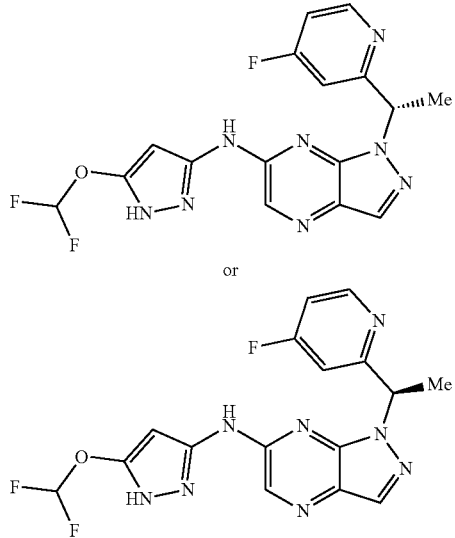 [SMILES: C[C@@H](c1cc(F)ccn1)n1ncc2ncc(Nc3cc(OC(F)F)[nH]n3)nc21 ; C[C@H](c1cc(F)ccn1)n1ncc2ncc(Nc3cc(OC(F)F)[nH]n3)nc21] |
| 14 | 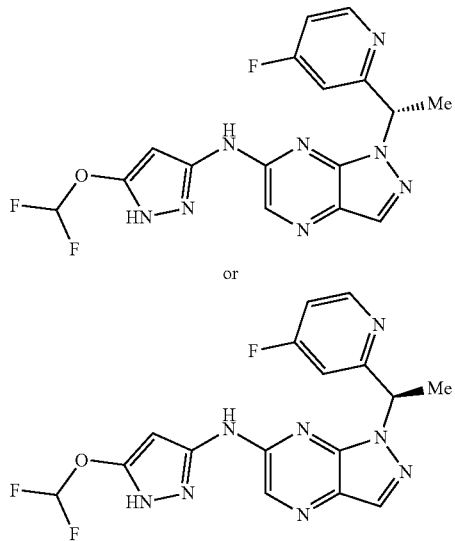 [SMILES: C[C@@H](c1cc(F)ccn1)n1ncc2ncc(Nc3cc(OC(F)F)[nH]n3)nc21 ; C[C@H](c1cc(F)ccn1)n1ncc2ncc(Nc3cc(OC(F)F)[nH]n3)nc21] |

-continued
| Example Number | Structure |
|---|---|
| 15 | 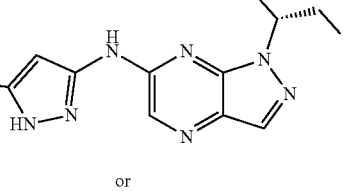 or 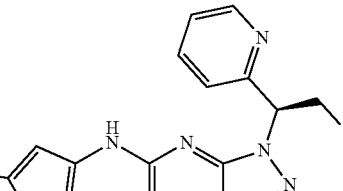 |
| 16 | 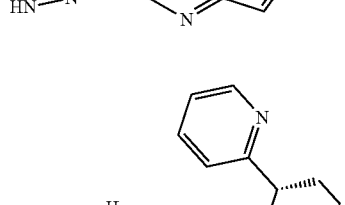 or 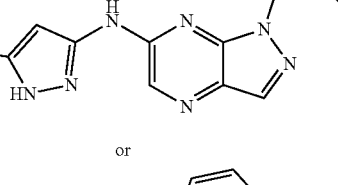 |
| 17 | 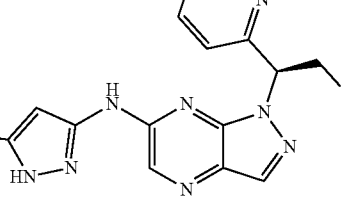 |

-continued
| Example Number | Structure |
|---|---|
| 18 | 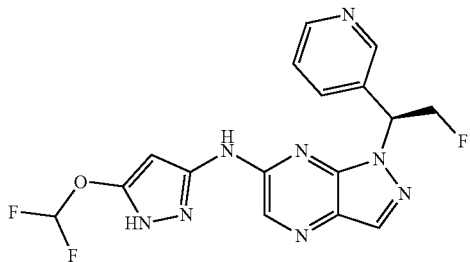<br>or<br>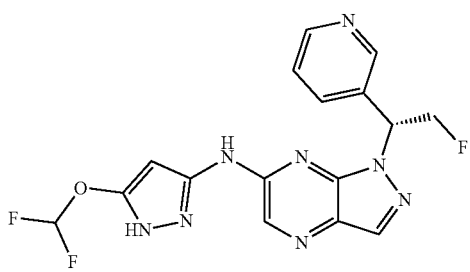 |
| 19 | 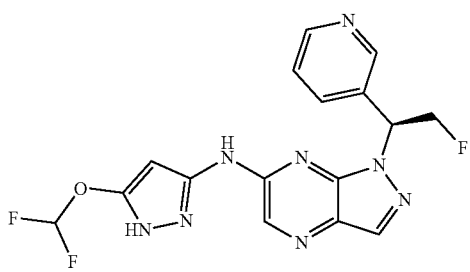<br>or<br>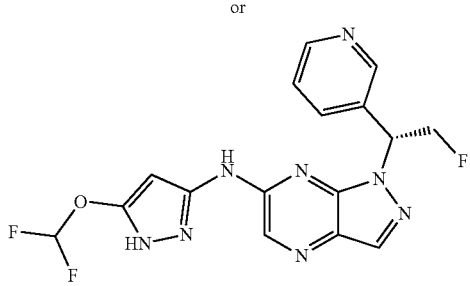 |
| 20 | 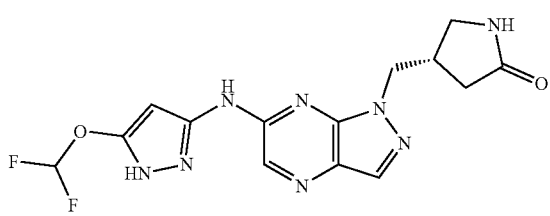<br>or<br>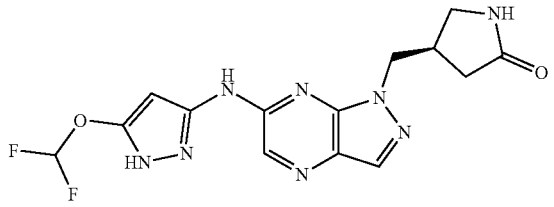 |

| Example Number | Structure |
|---|---|
| 21 | 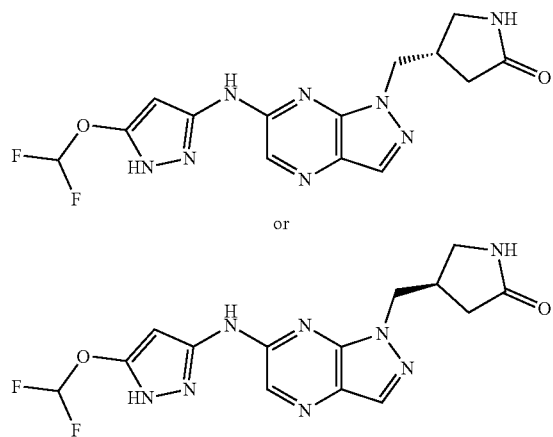 [SMILES: O=C1C[C@H](Cn2ncc3ncc(Nc4cc(OC(F)F)[nH]n4)nc32)CN1 ; O=C1C[C@@H](Cn2ncc3ncc(Nc4cc(OC(F)F)[nH]n4)nc32)CN1] |
| 22 | 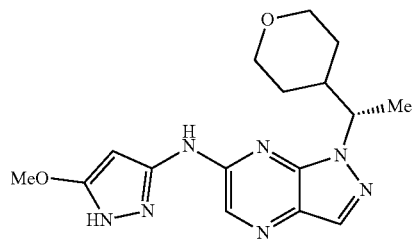 [SMILES: COc1cc(Nc2cnc3cnn([C@@H](C)C4CCOCC4)c3n2)n[nH]1] |
| 23 | 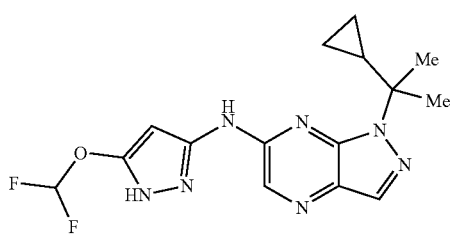 [SMILES: CC(C)(C1CC1)n1ncc2ncc(Nc3cc(OC(F)F)[nH]n3)nc21] |
| 24 | 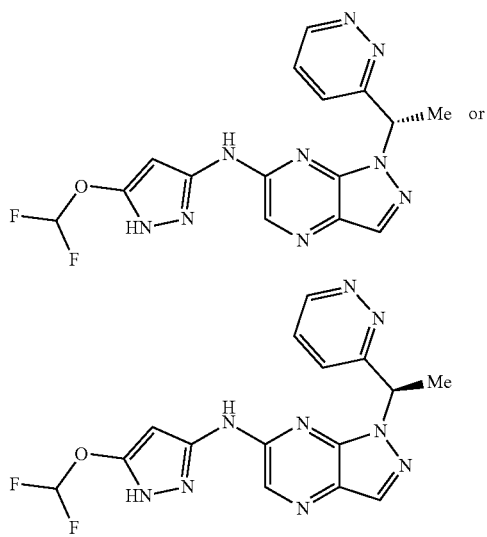 |

| Example Number | Structure |
|---|---|
| 25 | 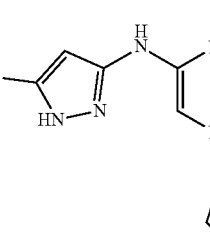 |
| 26 | 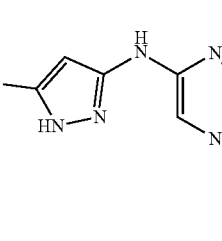 |
| 27 | 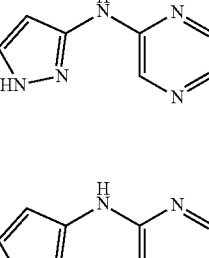 |
| 28 | 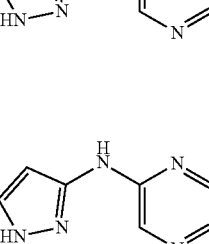 |

| Example Number | Structure |
|---|---|
|  | 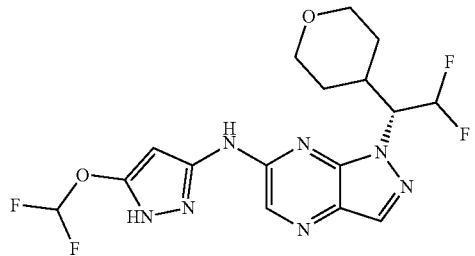 |
| 29 | 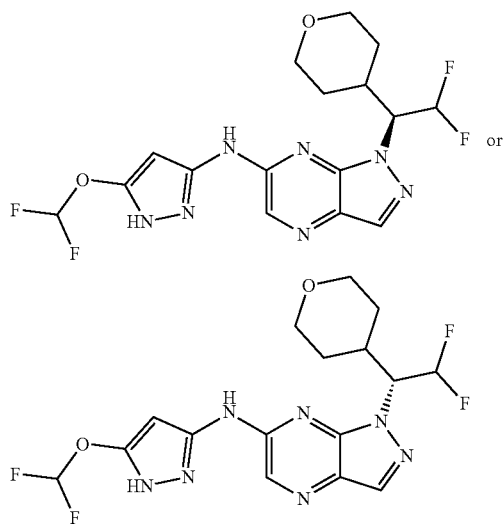 or |
| 30 | 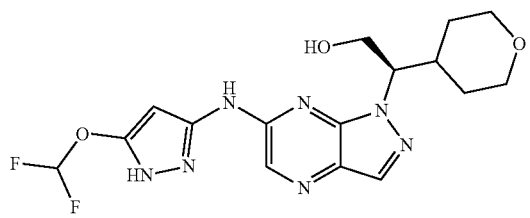 [SMILES: OC[C@@H](C1CCOCC1)n1ncc2ncc(Nc3cc(OC(F)F)[nH]n3)nc21] |
| 31 | 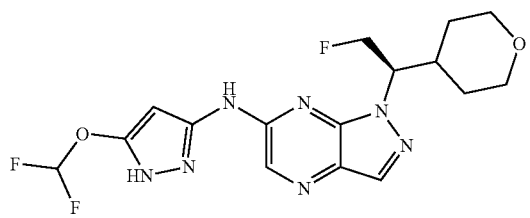 [SMILES: FC[C@@H](C1CCOCC1)n1ncc2ncc(Nc3cc(OC(F)F)[nH]n3)nc21] |
| 32 | 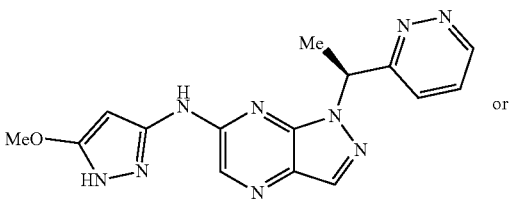 or |

| Example Number | Structure |
|---|---|
| | 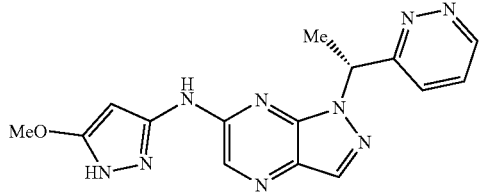 |
| 33 | 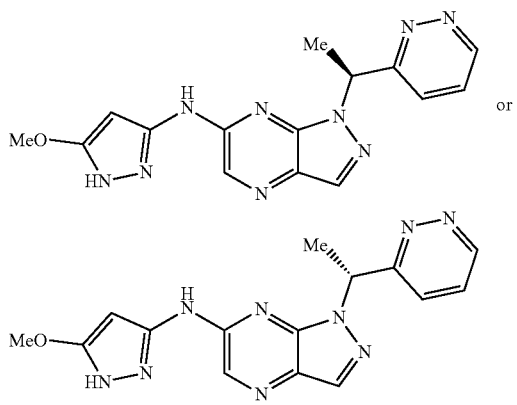 or |
| 34 | 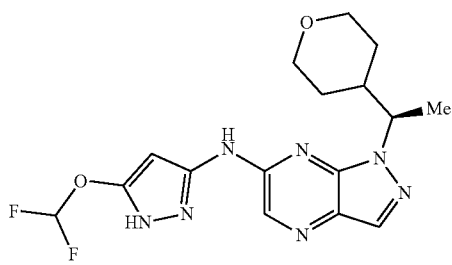 |
| 35 | 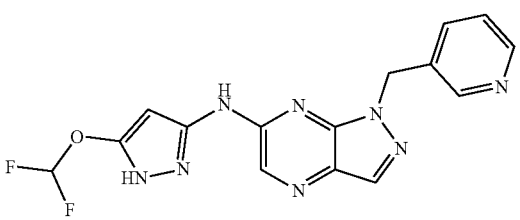 |
| 36 | 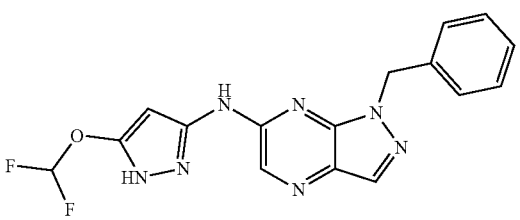 |
| 37 | 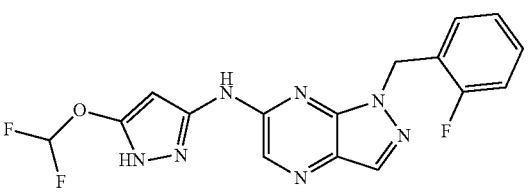 [SMILES: Fc1ccccc1Cn1ncc2ncc(Nc3cc(OC(F)F)[nH]n3)nc21] |

-continued

| Example Number | Structure |
|---|---|
| 38 | 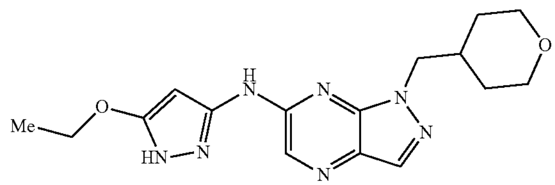 [SMILES: CCOc1cc(Nc2cnc3cnn(CC4CCOCC4)c3n2)n[nH]1] |
| 39 | 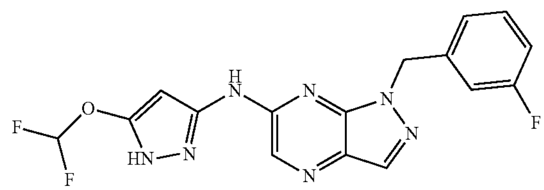 [SMILES: Fc1cccc(Cn2ncc3ncc(Nc4cc(OC(F)F)[nH]n4)nc32)c1] |
| 40 | 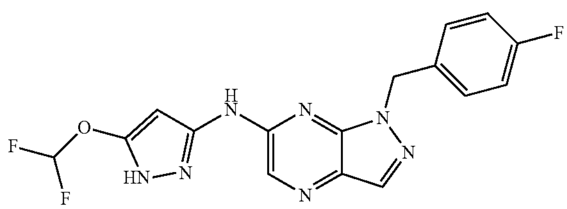 [SMILES: Fc1ccc(Cn2ncc3ncc(Nc4cc(OC(F)F)[nH]n4)nc32)cc1] |
| 41 | 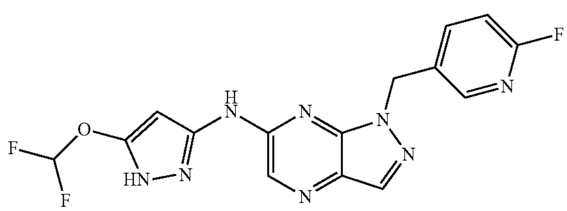 [SMILES: Fc1ccc(Cn2ncc3ncc(Nc4cc(OC(F)F)[nH]n4)nc32)cn1] |
| 42 | 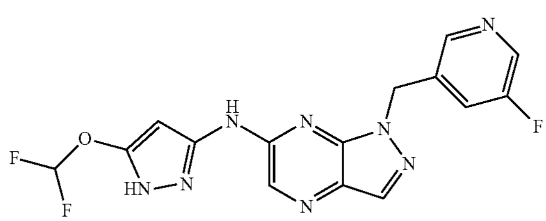 [SMILES: Fc1cncc(Cn2ncc3ncc(Nc4cc(OC(F)F)[nH]n4)nc32)c1] |
| 43 | 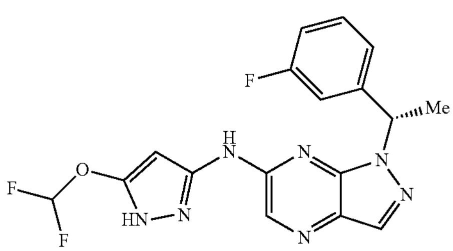 [SMILES: C[C@@H](c1cccc(F)c1)n1ncc2ncc(Nc3cc(OC(F)F)[nH]n3)nc21] |
| 44 | 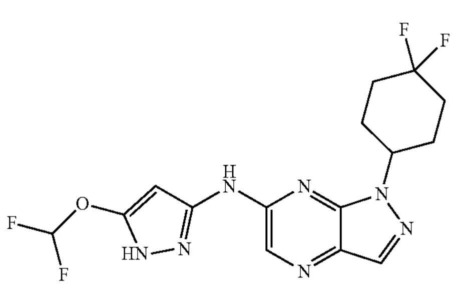 [SMILES: FC(F)Oc1cc(Nc2cnc3cnn(C4CCC(F)(F)CC4)c3n2)n[nH]1] |

-continued
| Example Number | Structure |
|---|---|
| 45 | 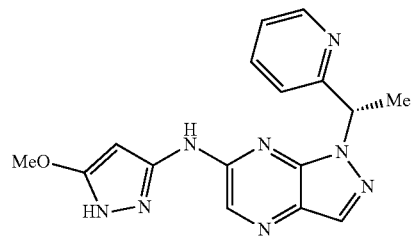 [SMILES: COc1cc(Nc2cnc3cnn([C@@H](C)c4ccccn4)c3n2)n[nH]1] |
| 46 | 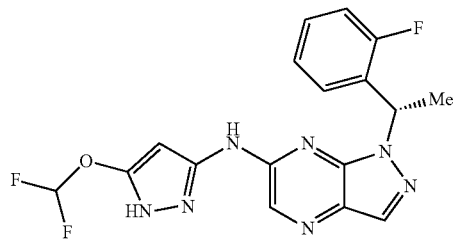 [SMILES: C[C@@H](c1ccccc1F)n1ncc2ncc(Nc3cc(OC(F)F)[nH]n3)nc21] |
| 47 | 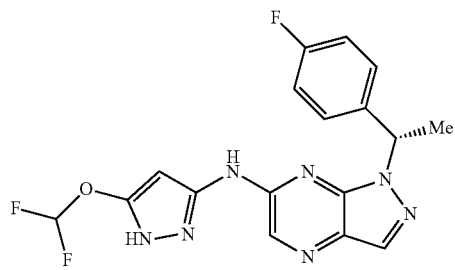 [SMILES: C[C@@H](c1ccc(F)cc1)n1ncc2ncc(Nc3cc(OC(F)F)[nH]n3)nc21] |
| 48 | 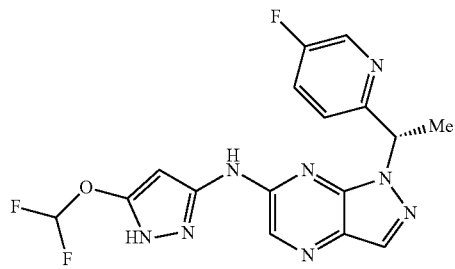 |
| 49 | 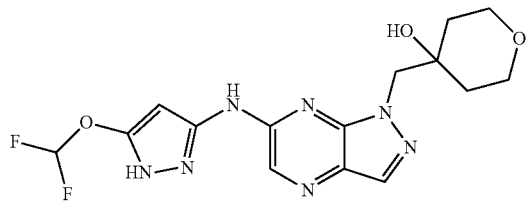 [SMILES: OC1(Cn2ncc3ncc(Nc4cc(OC(F)F)[nH]n4)nc32)CCOCC1] |
| 50 | 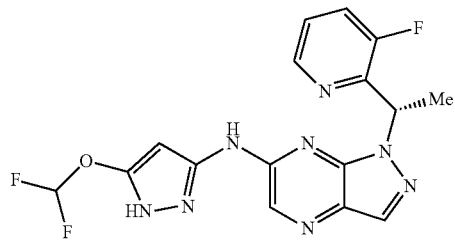 [SMILES: C[C@@H](c1ncccc1F)n1ncc2ncc(Nc3cc(OC(F)F)[nH]n3)nc21] |

-continued
| Example Number | Structure |
|---|---|
| 51 | 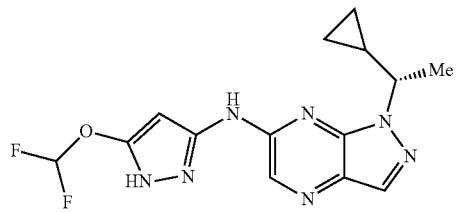 [SMILES: C[C@@H](C1CC1)n1ncc2ncc(Nc3cc(OC(F)F)[nH]n3)nc21] |
| 52 | 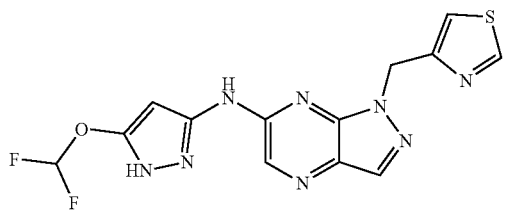 [SMILES: FC(F)Oc1cc(Nc2cnc3cnn(Cc4cscn4)c3n2)n[nH]1] |
| 53 | 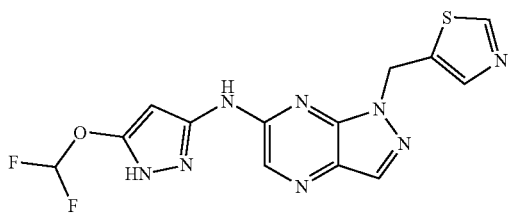 [SMILES: FC(F)Oc1cc(Nc2cnc3cnn(Cc4cncs4)c3n2)n[nH]1] |
| 54 | 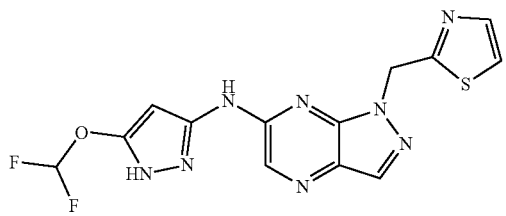 [SMILES: FC(F)Oc1cc(Nc2cnc3cnn(Cc4nccs4)c3n2)n[nH]1] |
| 55 | 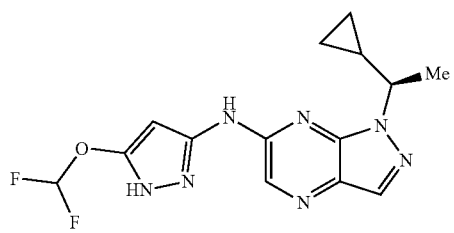 [SMILES: C[C@H](C1CC1)n1ncc2ncc(Nc3cc(OC(F)F)[nH]n3)nc21] |
| 56 | 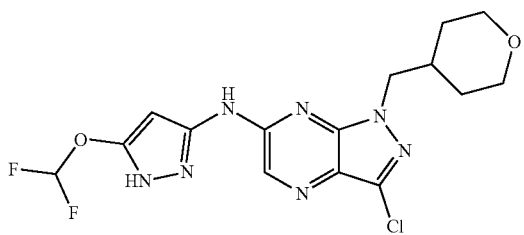 [SMILES: FC(F)Oc1cc(Nc2cnc3c(Cl)nn(CC4CCOCC4)c3n2)n[nH]1] |

-continued
| Example Number | Structure |
|---|---|
| 57 | 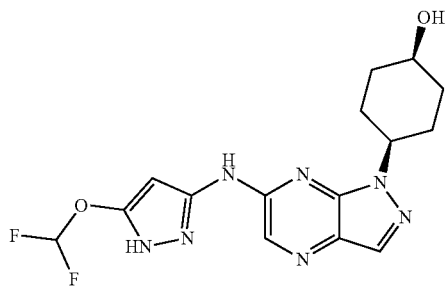 [SMILES: O[C@H]1CC[C@@H](n2ncc3ncc(Nc4cc(OC(F)F)[nH]n4)nc32)CC1] |
| 58 | 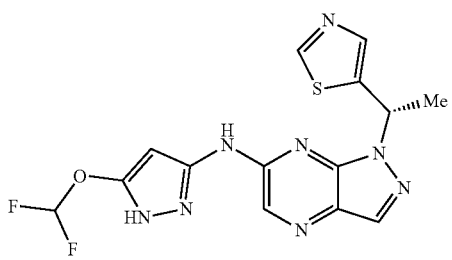 [SMILES: C[C@@H](c1cncs1)n1ncc2ncc(Nc3cc(OC(F)F)[nH]n3)nc21] |
| 59 | 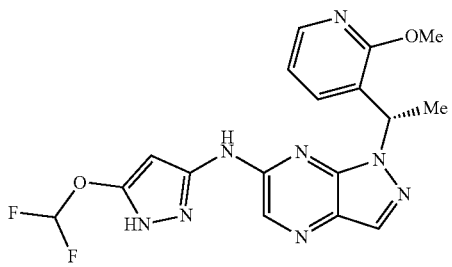 [SMILES: COc1ncccc1[C@H](C)n1ncc2ncc(Nc3cc(OC(F)F)[nH]n3)nc21] |
| 60 | 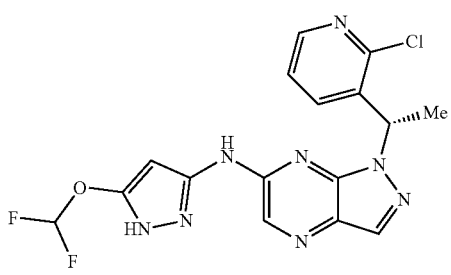 [SMILES: C[C@@H](c1cccnc1Cl)n1ncc2ncc(Nc3cc(OC(F)F)[nH]n3)nc21] |
| 61 | 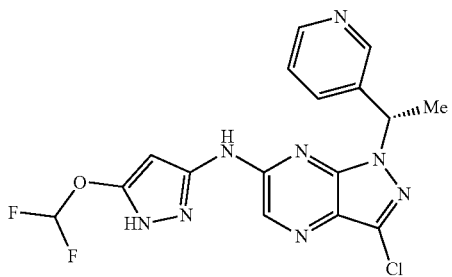 [SMILES: C[C@@H](c1cccnc1)n1nc(Cl)c2ncc(Nc3cc(OC(F)F)[nH]n3)nc21] |

| Example Number | Structure |
|---|---|
| 62 | 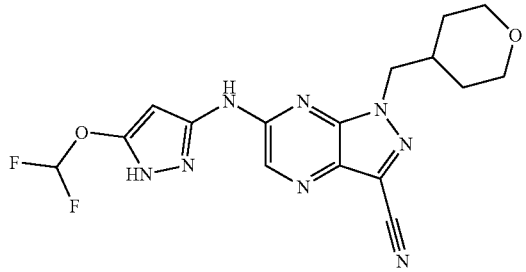 [SMILES: N#Cc1nn(CC2CCOCC2)c2nc(Nc3cc(OC(F)F)[nH]n3)cnc12] |
| 63 | 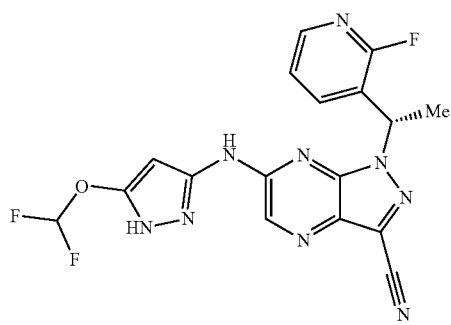 [SMILES: C[C@@H](c1cccnc1F)n1nc(C#N)c2ncc(Nc3cc(OC(F)F)[nH]n3)nc21] |
| 64 | 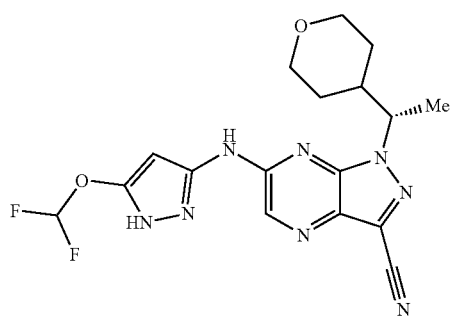 [SMILES: C[C@@H](C1CCOCC1)n1nc(C#N)c2ncc(Nc3cc(OC(F)F)[nH]n3)nc21] |
| 65 | 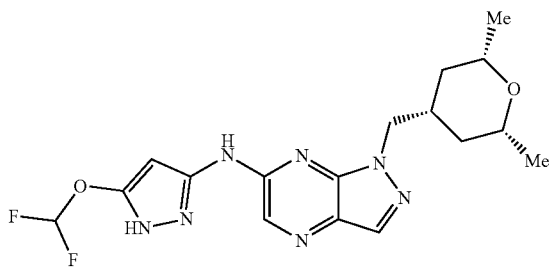 [SMILES: C[C@@H]1C[C@H](Cn2ncc3ncc(Nc4cc(OC(F)F)[nH]n4)nc32)C[C@H](C)O1] |
| 66 | 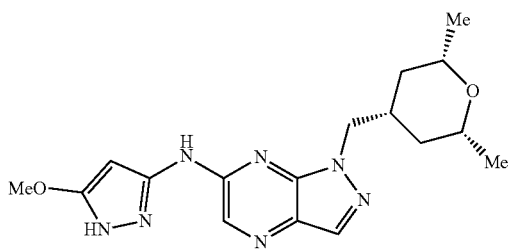 [SMILES: COc1cc(Nc2cnc3cnn(C[C@H]4C[C@@H](C)O[C@@H](C)C4)c3n2)n[nH]1] |

-continued
| Example Number | Structure |
|---|---|
| 67 | 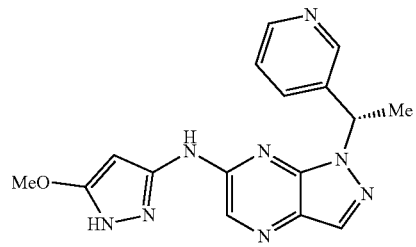 [SMILES: COc1cc(Nc2cnc3cnn([C@@H](C)c4cccnc4)c3n2)n[nH]1] |
| 68 | 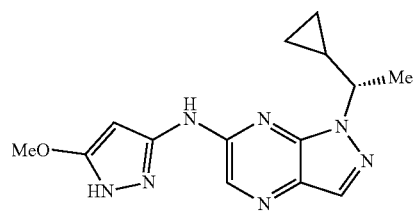 [SMILES: COc1cc(Nc2cnc3cnn([C@@H](C)C4CC4)c3n2)n[nH]1] |
| 69 | 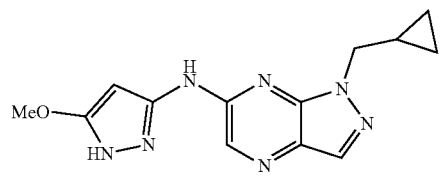 [SMILES: COc1cc(Nc2cnc3cnn(CC4CC4)c3n2)n[nH]1] |
| 70 | 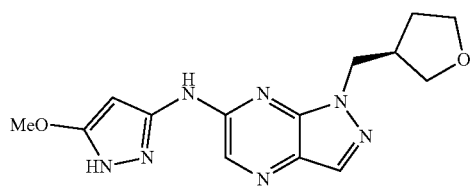 |
| 71 | 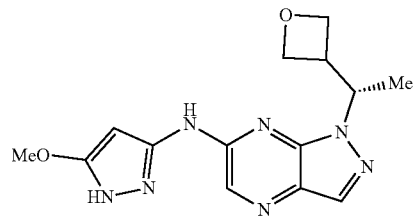 |
| 72 | 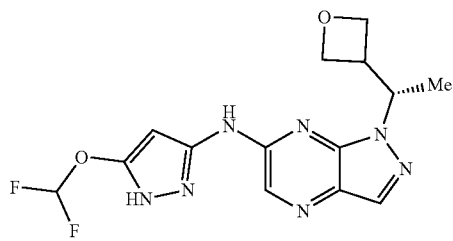 [SMILES: C[C@@H](C1COC1)n1ncc2ncc(Nc3cc(OC(F)F)[nH]n3)nc21] |
| 73 | 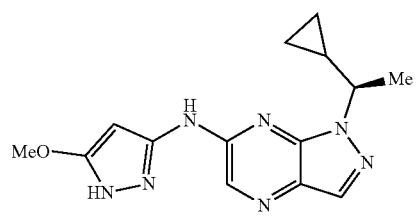 [SMILES: COc1cc(Nc2cnc3cnn([C@H](C)C4CC4)c3n2)n[nH]1] |

-continued
| Example Number | Structure |
|---|---|
| 74 | 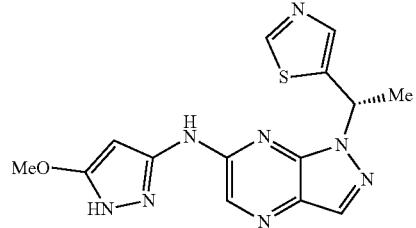 [SMILES: COc1cc(Nc2cnc3cnn([C@@H](C)c4cncs4)c3n2)n[nH]1] |
| 75 | 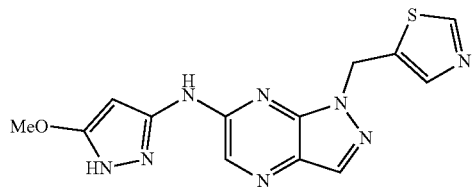 [SMILES: COc1cc(Nc2cnc3cnn(Cc4cncs4)c3n2)n[nH]1] |
| 76 | 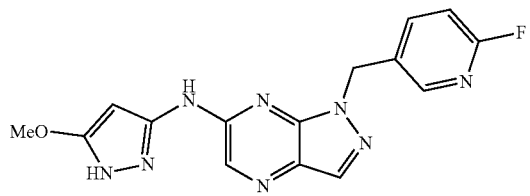 |
| 77 | 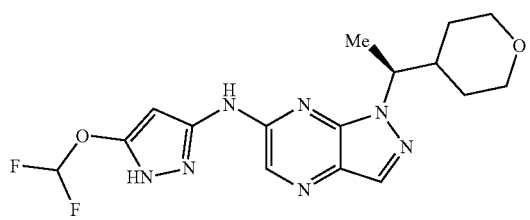 [SMILES: C[C@@H](C1CCOCC1)n1ncc2ncc(Nc3cc(OC(F)F)[nH]n3)nc21] |
| 78 | 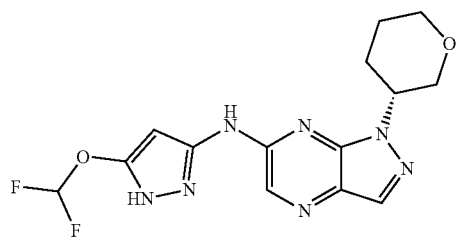 [SMILES: FC(F)Oc1cc(Nc2cnc3cnn([C@@H]4CCCOC4)c3n2)n[nH]1] |
| 79 | 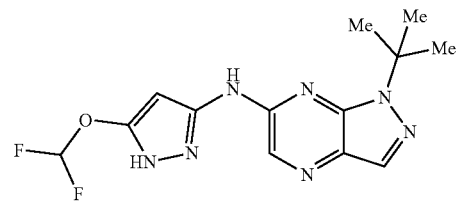 [SMILES: CC(C)(C)n1ncc2ncc(Nc3cc(OC(F)F)[nH]n3)nc21] |
| 80 | 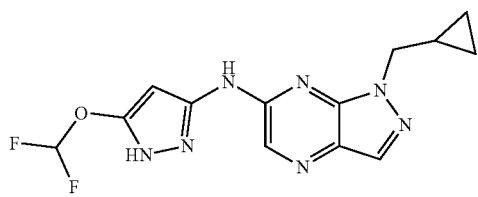 [SMILES: FC(F)Oc1cc(Nc2cnc3cnn(CC4CC4)c3n2)n[nH]1] |

-continued
| Example Number | Structure |
|---|---|
| 81 | 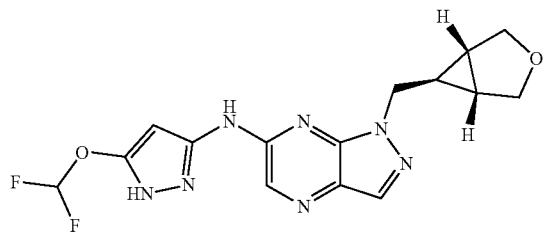 [SMILES: FC(F)Oc1cc(Nc2cnc3cnn(C[C@H]4[C@@H]5COC[C@@H]54)c3n2)n[nH]1] |
| 82 | 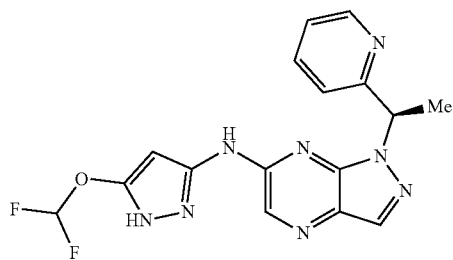 [SMILES: C[C@H](c1ccccn1)n1ncc2ncc(Nc3cc(OC(F)F)[nH]n3)nc21] |
| 83 | 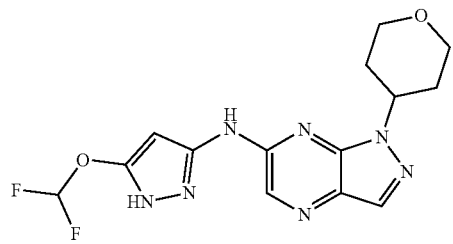 [SMILES: FC(F)Oc1cc(Nc2cnc3cnn(C4CCOCC4)c3n2)n[nH]1] |
| 84 | 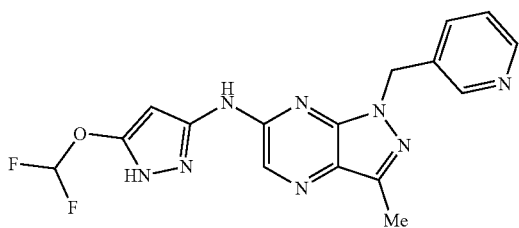 |
| 85 | 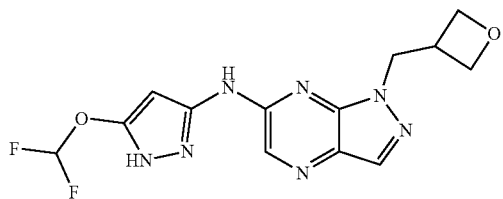 [SMILES: FC(F)Oc1cc(Nc2cnc3cnn(CC4COC4)c3n2)n[nH]1] |
| 86 | 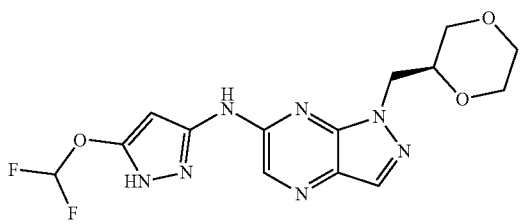 [SMILES: FC(F)Oc1cc(Nc2cnc3cnn(C[C@H]4COCCO4)c3n2)n[nH]1] |

-continued
| Example Number | Structure |
|---|---|
| 87 | 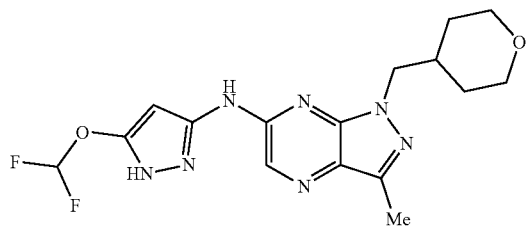 |
| 88 | 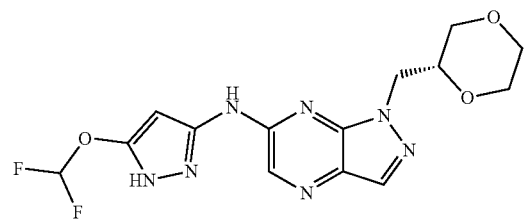 [SMILES: FC(F)Oc1cc(Nc2cnc3cnn(C[C@@H]4COCCO4)c3n2)n[nH]1] |
| 89 | 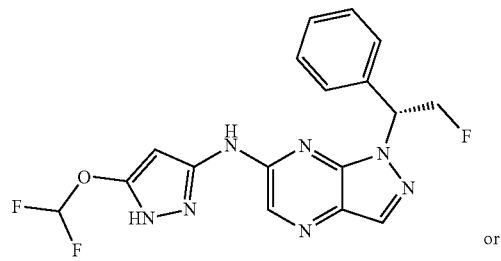 or 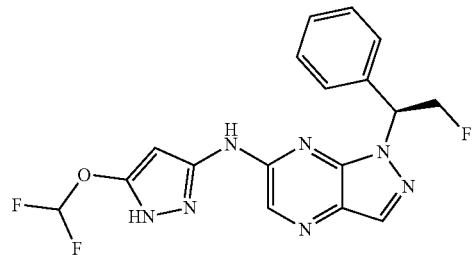 |
| 90 | 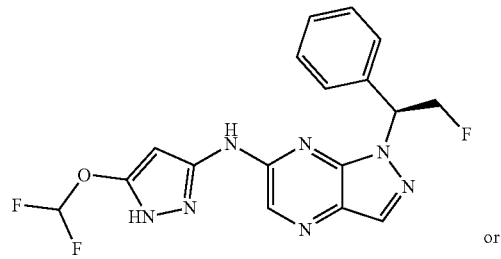 or 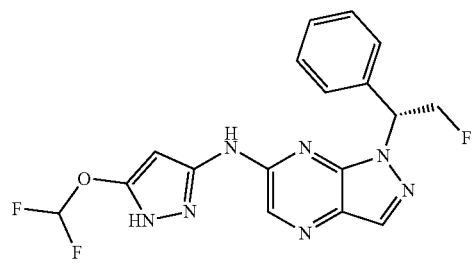 |

| Example Number | Structure |
|---|---|
| 91 | 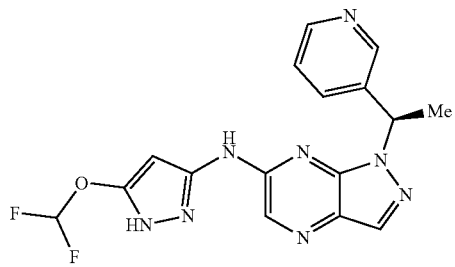 [SMILES: C[C@H](c1cccnc1)n1ncc2ncc(Nc3cc(OC(F)F)[nH]n3)nc21] |
| 92 | 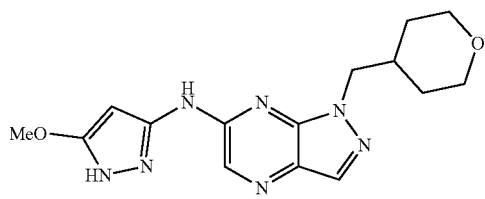 [SMILES: COc1cc(Nc2cnc3cnn(CC4CCOCC4)c3n2)n[nH]1] |
| 93 | 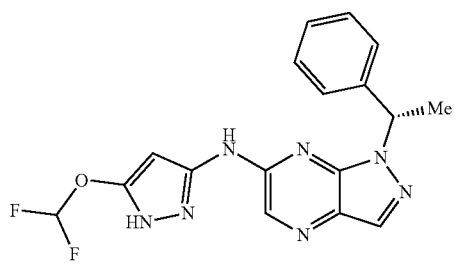 [SMILES: C[C@@H](c1ccccc1)n1ncc2ncc(Nc3cc(OC(F)F)[nH]n3)nc21] |
| 94 | 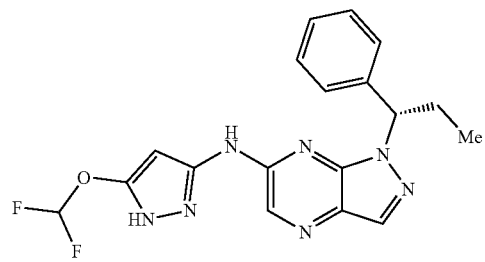 [SMILES: CC[C@@H](c1ccccc1)n1ncc2ncc(Nc3cc(OC(F)F)[nH]n3)nc21] |
| 95 | 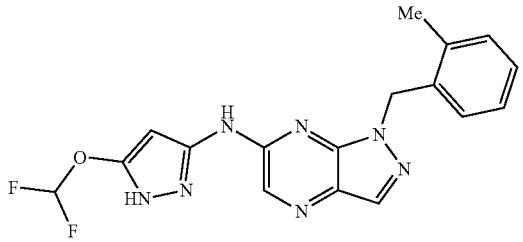 |
| 96 | 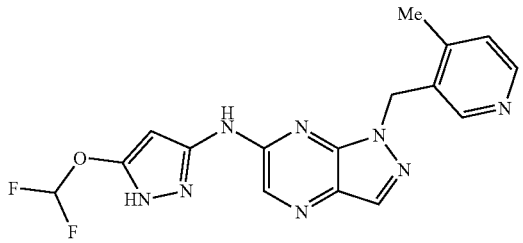 [SMILES: Cc1ccncc1Cn1ncc2ncc(Nc3cc(OC(F)F)[nH]n3)nc21] |

| Example Number | Structure |
|---|---|
| 97 | 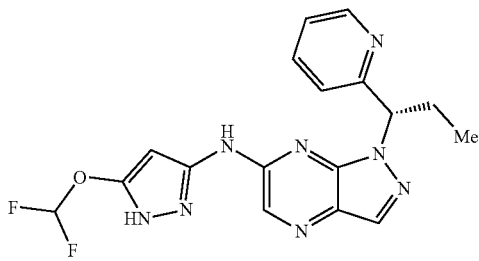 [SMILES: CC[C@@H](c1ccccn1)n1ncc2ncc(Nc3cc(OC(F)F)[nH]n3)nc21] |
| 98 | 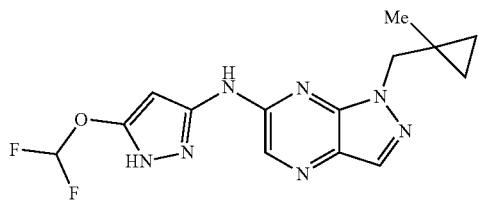 [SMILES: CC1(Cn2ncc3ncc(Nc4cc(OC(F)F)[nH]n4)nc32)CC1] |
| 99 | 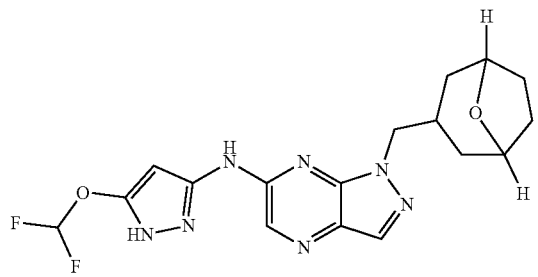 [SMILES: FC(F)Oc1cc(Nc2cnc3cnn(CC4CC5CCC(C4)O5)c3n2)n[nH]1] |
| 100 | 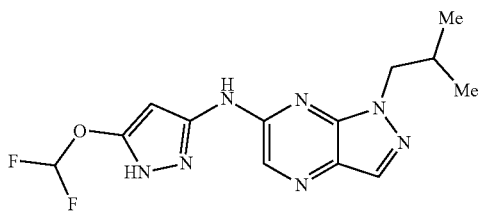 [SMILES: CC(C)Cn1ncc2ncc(Nc3cc(OC(F)F)[nH]n3)nc21] |
| 101 | 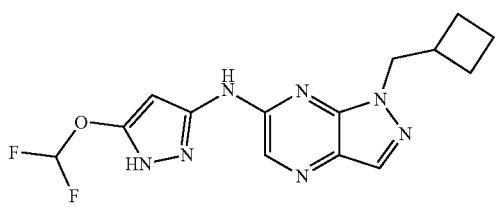 [SMILES: FC(F)Oc1cc(Nc2cnc3cnn(CC4CCC4)c3n2)n[nH]1] |
| 102 | 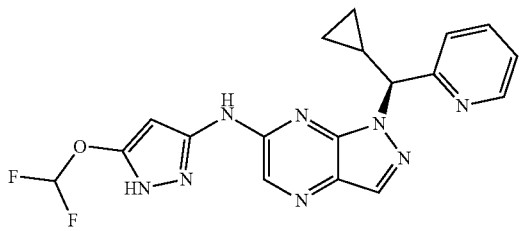 [SMILES: FC(F)Oc1cc(Nc2cnc3cnn([C@H](c4ccccn4)C4CC4)c3n2)n[nH]1] |

| Example Number | Structure |
|---|---|
| 103 | 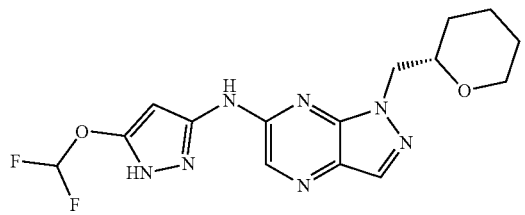 [SMILES: FC(F)Oc1cc(Nc2cnc3cnn(C[C@@H]4CCCCO4)c3n2)n[nH]1] |
| 104 | 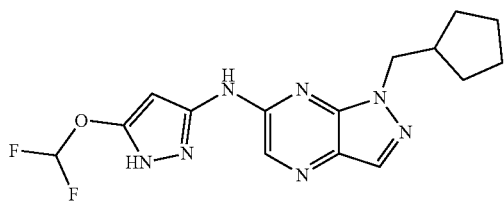 [SMILES: FC(F)Oc1cc(Nc2cnc3cnn(CC4CCCC4)c3n2)n[nH]1] |
| 105 | 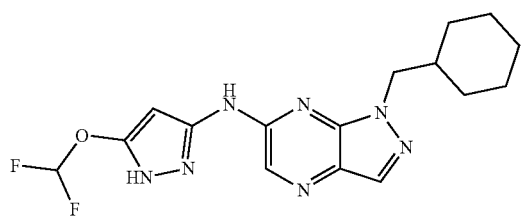 [SMILES: FC(F)Oc1cc(Nc2cnc3cnn(CC4CCCCC4)c3n2)n[nH]1] |
| 106 | 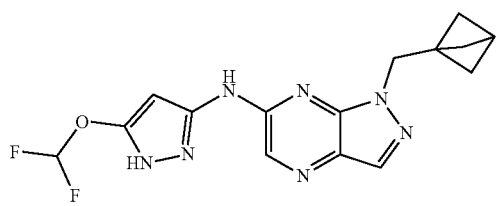 [SMILES: FC(F)Oc1cc(Nc2cnc3cnn(CC45CC(C4)C5)c3n2)n[nH]1] |
| 107 | 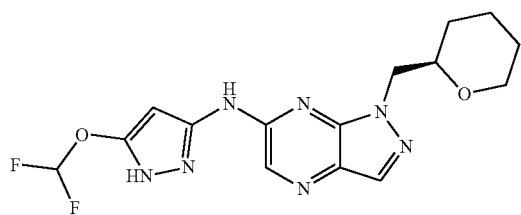 [SMILES: FC(F)Oc1cc(Nc2cnc3cnn(C[C@H]4CCCCO4)c3n2)n[nH]1] |
| 108 | 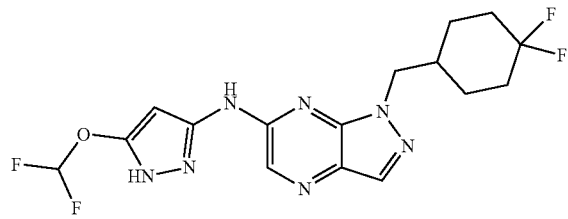 [SMILES: FC(F)Oc1cc(Nc2cnc3cnn(CC4CCC(F)(F)CC4)c3n2)n[nH]1] |
| 109 | 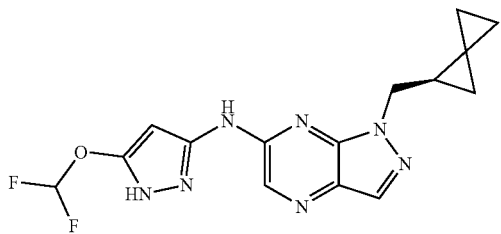 [SMILES: FC(F)Oc1cc(Nc2cnc3cnn(C[C@@H]4CC45CC5)c3n2)n[nH]1] |
and

| Example Number | Structure |
|---|---|
|  | 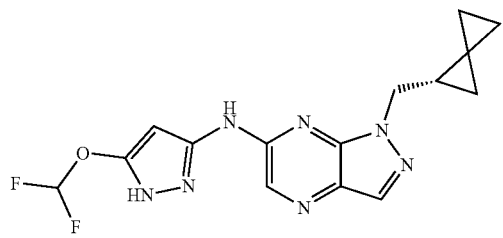 [SMILES: FC(F)Oc1cc(Nc2cnc3cnn(C[C@H]4CC45CC5)c3n2)n[nH]1] |
| 110 | 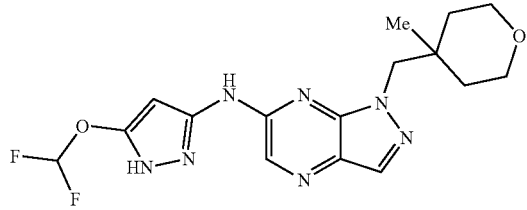 [SMILES: CC1(Cn2ncc3ncc(Nc4cc(OC(F)F)[nH]n4)nc32)CCOCC1] |
| 111 | 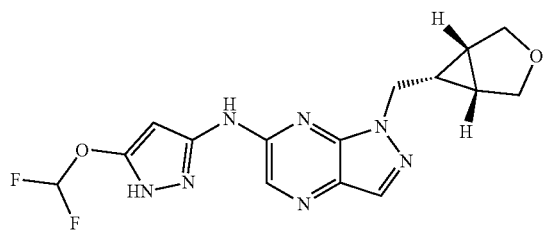 [SMILES: FC(F)Oc1cc(Nc2cnc3cnn(C[C@@H]4[C@@H]5COC[C@@H]54)c3n2)n[nH]1] |
| 112 | 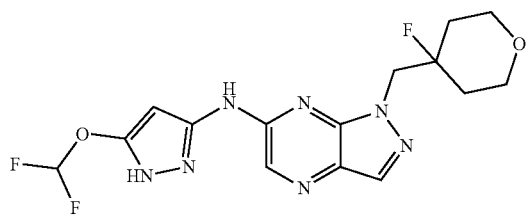 |
| 113 | 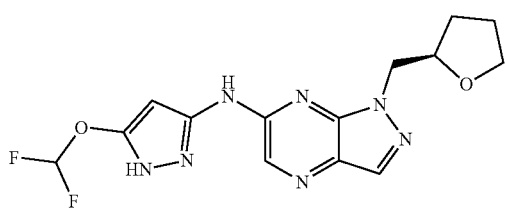 [SMILES: FC(F)Oc1cc(Nc2cnc3cnn(C[C@H]4CCCO4)c3n2)n[nH]1] |

| Example Number | Structure |
|---|---|
| 114 | 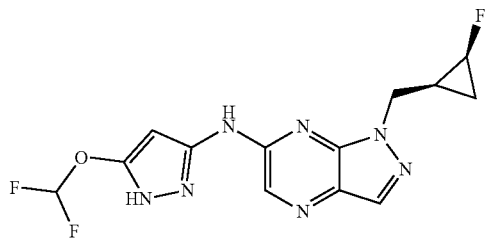 and 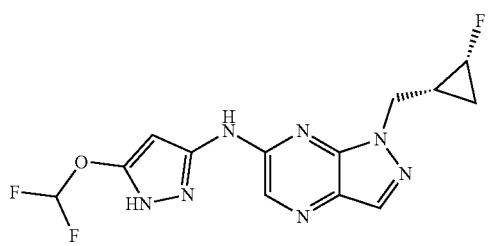 |
| 115 | 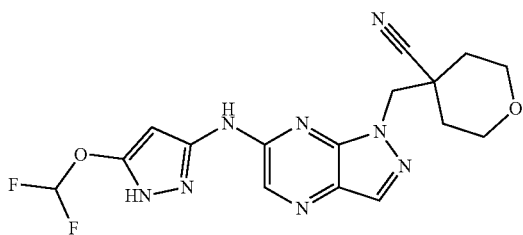 [SMILES: N#CC1(Cn2ncc3ncc(Nc4cc(OC(F)F)[nH]n4)nc32)CCOCC1] |
| 116 | 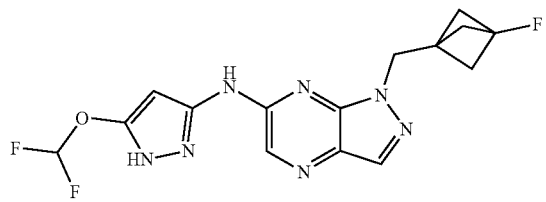 [SMILES: FC(F)Oc1cc(Nc2cnc3cnn(CC45CC(F)(C4)C5)c3n2)n[nH]1] |
| 117 | 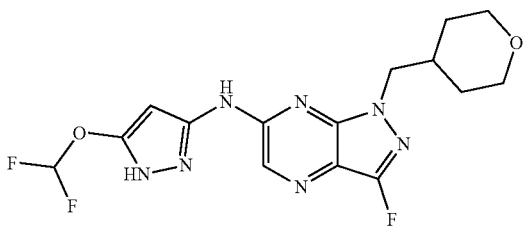 [SMILES: Fc1nn(CC2CCOCC2)c2nc(Nc3cc(OC(F)F)[nH]n3)cnc12] |
| 118 | 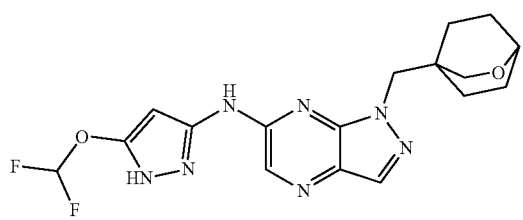 [SMILES: FC(F)Oc1cc(Nc2cnc3cnn(CC45CCC(CC4)OC5)c3n2)n[nH]1] |

-continued
| Example Number | Structure |
|---|---|
| 119 | 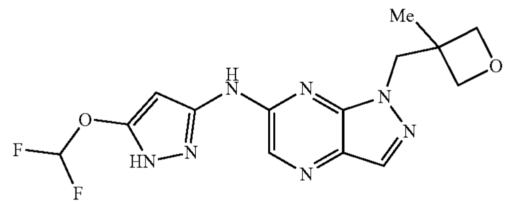 [SMILES: CC1(Cn2ncc3ncc(Nc4cc(OC(F)F)[nH]n4)nc32)COC1] |
| 120 | 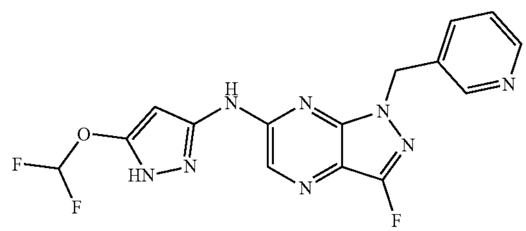 [SMILES: Fc1nn(Cc2cccnc2)c2nc(Nc3cc(OC(F)F)[nH]n3)cnc12] |
| 121 | 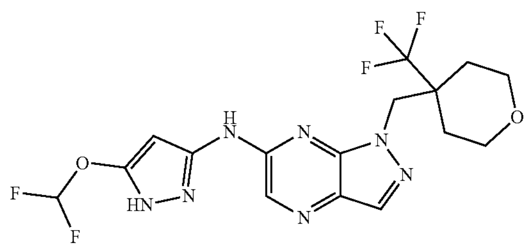 [SMILES: FC(F)Oc1cc(Nc2cnc3cnn(CC4(C(F)(F)F)CCOCC4)c3n2)n[nH]1] |
| 122 | 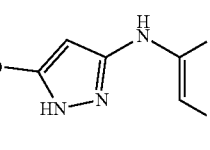 |
| 123 | 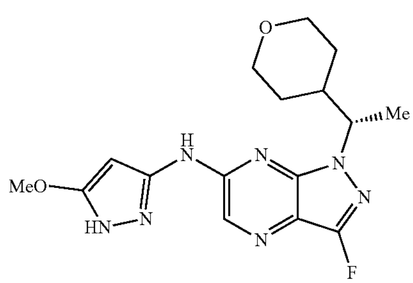 [SMILES: COc1cc(Nc2cnc3c(F)nn([C@@H](C)C4CCOCC4)c3n2)n[nH]1] |
| 124 | 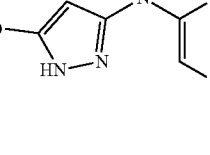 |

| Example Number | Structure |
|---|---|
| 125 | 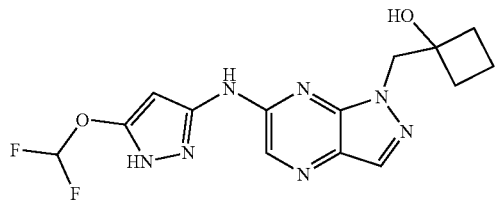 [SMILES: OC1(Cn2ncc3ncc(Nc4cc(OC(F)F)[nH]n4)nc32)CCC1] |
| 126 | 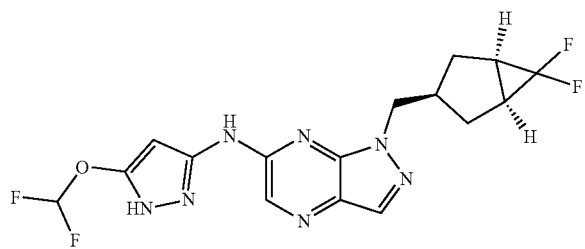 [SMILES: FC(F)Oc1cc(Nc2cnc3cnn(C[C@H]4C[C@@H]5[C@H](C4)C5(F)F)c3n2)n[nH]1] |
| 127 | 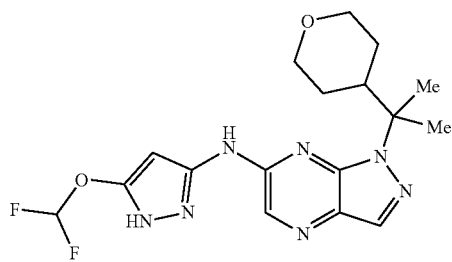 [SMILES: CC(C)(C1CCOCC1)n1ncc2ncc(Nc3cc(OC(F)F)[nH]n3)nc21] |
| 128 | 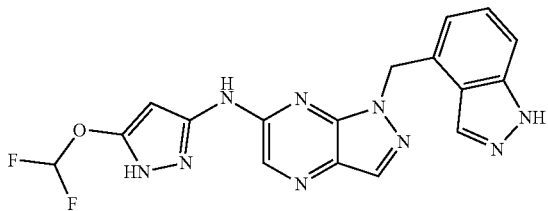 [SMILES: FC(F)Oc1cc(Nc2cnc3cnn(Cc4cccc5[nH]ncc45)c3n2)n[nH]1] |
| 129 | 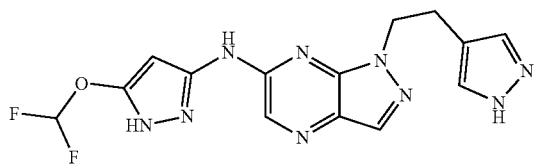 [SMILES: FC(F)Oc1cc(Nc2cnc3cnn(CCc4cn[nH]c4)c3n2)n[nH]1] |
| 130 | 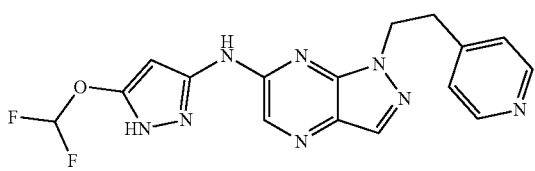 [SMILES: FC(F)Oc1cc(Nc2cnc3cnn(CCc4ccncc4)c3n2)n[nH]1] |
| 131 | 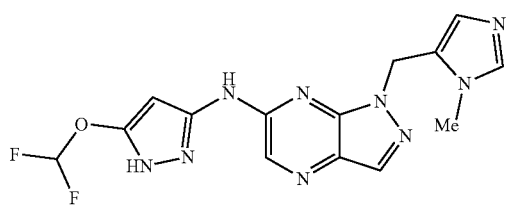 [SMILES: Cn1cncc1Cn1ncc2ncc(Nc3cc(OC(F)F)[nH]n3)nc21] |

| Example Number | Structure |
|---|---|
| 132 | 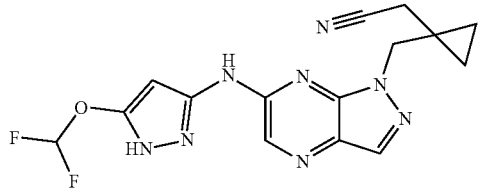 [SMILES: N#CCC1(Cn2ncc3ncc(Nc4cc(OC(F)F)[nH]n4)nc32)CC1] |
| 133 | 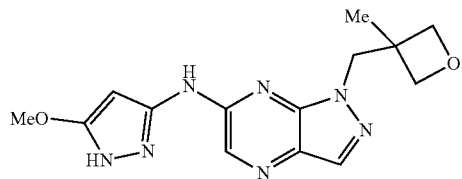 [SMILES: COc1cc(Nc2cnc3cnn(CC4(C)COC4)c3n2)n[nH]1] |
| 134 | 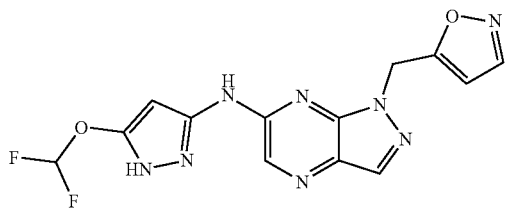 [SMILES: FC(F)Oc1cc(Nc2cnc3cnn(Cc4ccno4)c3n2)n[nH]1] |
| 135 | 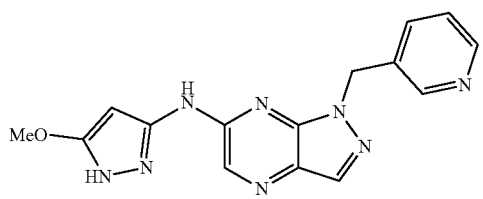 [SMILES: COc1cc(Nc2cnc3cnn(Cc4cccnc4)c3n2)n[nH]1] |
| 136 | 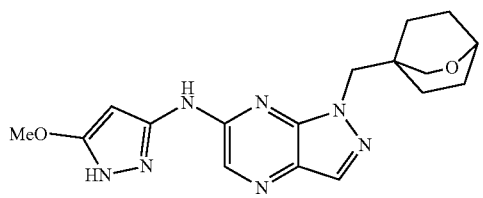 [SMILES: COc1cc(Nc2cnc3cnn(CC45CCC(CC4)OC5)c3n2)n[nH]1] |
| 137 | 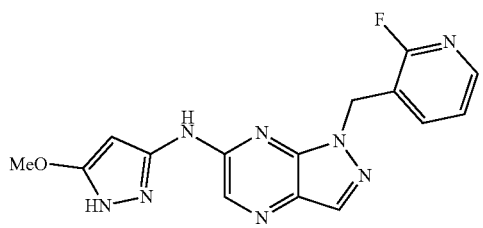 [SMILES: COc1cc(Nc2cnc3cnn(Cc4cccnc4F)c3n2)n[nH]1] |
| 138 | 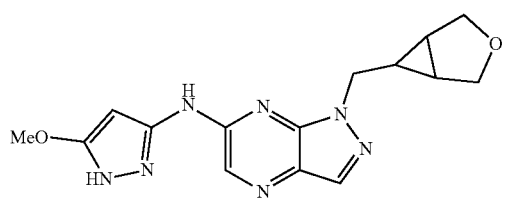 [SMILES: COc1cc(Nc2cnc3cnn(CC4C5COCC54)c3n2)n[nH]1] |

-continued
| Example Number | Structure |
|---|---|
| 139 | 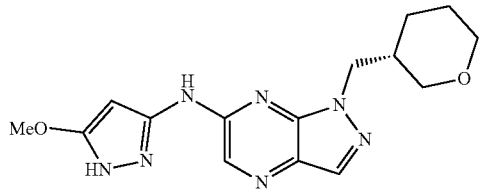 [SMILES: COc1cc(Nc2cnc3cnn(C[C@@H]4CCCOC4)c3n2)n[nH]1] |
| 140 | 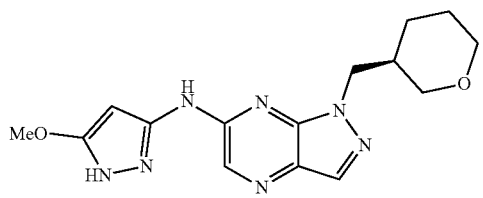 [SMILES: COc1cc(Nc2cnc3cnn(C[C@H]4CCCOC4)c3n2)n[nH]1] |
| 141 | 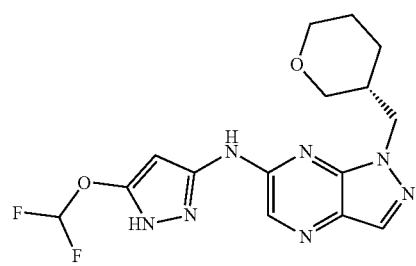 [SMILES: FC(F)Oc1cc(Nc2cnc3cnn(C[C@H]4CCCOC4)c3n2)n[nH]1] or 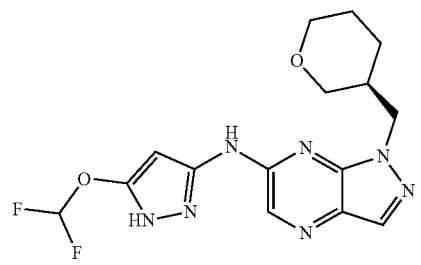 [SMILES: FC(F)Oc1cc(Nc2cnc3cnn(C[C@@H]4CCCOC4)c3n2)n[nH]1] |
| 142 | 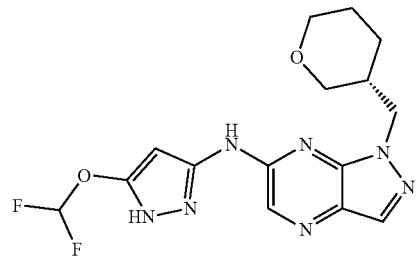 [SMILES: FC(F)Oc1cc(Nc2cnc3cnn(C[C@H]4CCCOC4)c3n2)n[nH]1] or 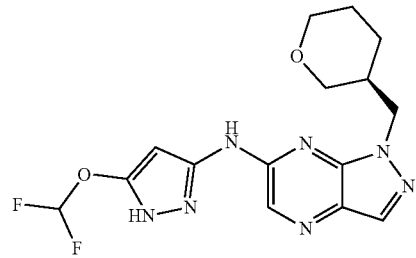 [SMILES: FC(F)Oc1cc(Nc2cnc3cnn(C[C@@H]4CCCOC4)c3n2)n[nH]1] |

-continued
| Example Number | Structure |
|---|---|
| 143 | 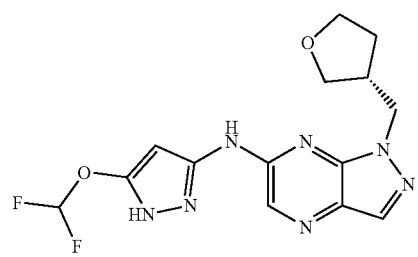 [SMILES: FC(F)Oc1cc(Nc2cnc3cnn(C[C@H]4CCOC4)c3n2)n[nH]1]<br>or<br>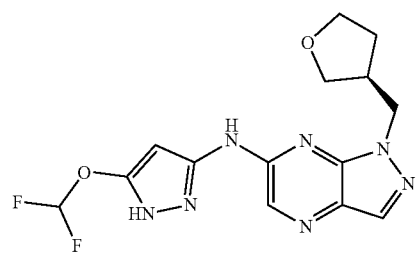 [SMILES: FC(F)Oc1cc(Nc2cnc3cnn(C[C@@H]4CCOC4)c3n2)n[nH]1] |
| 144 | 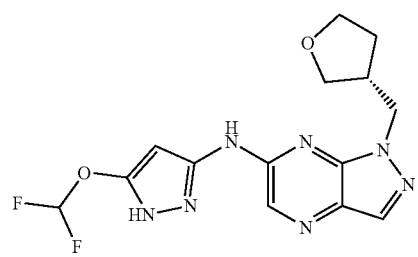 [SMILES: FC(F)Oc1cc(Nc2cnc3cnn(C[C@H]4CCOC4)c3n2)n[nH]1]<br>or<br>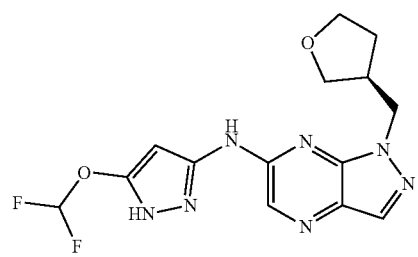 [SMILES: FC(F)Oc1cc(Nc2cnc3cnn(C[C@@H]4CCOC4)c3n2)n[nH]1] |
| 145 | 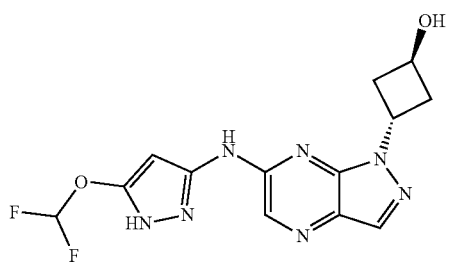 [SMILES: O[C@H]1C[C@H](n2ncc3ncc(Nc4cc(OC(F)F)[nH]n4)nc32)C1]<br>or |

| Example Number | Structure |
|---|---|
| | 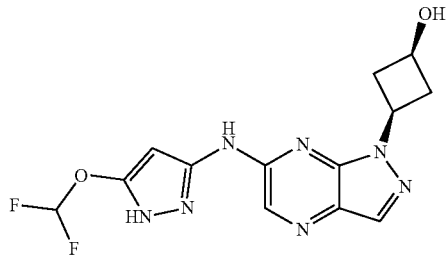 [SMILES: O[C@H]1C[C@@H](n2ncc3ncc(Nc4cc(OC(F)F)[nH]n4)nc32)C1] |
| 146 | 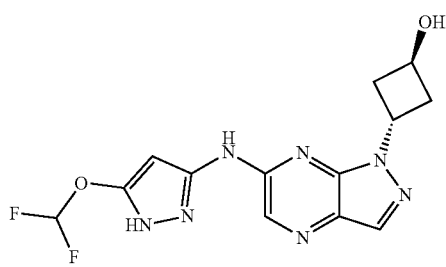 [SMILES: O[C@H]1C[C@H](n2ncc3ncc(Nc4cc(OC(F)F)[nH]n4)nc32)C1] |
| | or |
| | 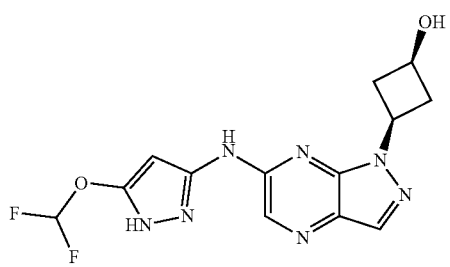 [SMILES: O[C@H]1C[C@@H](n2ncc3ncc(Nc4cc(OC(F)F)[nH]n4)nc32)C1] |
| 147 | 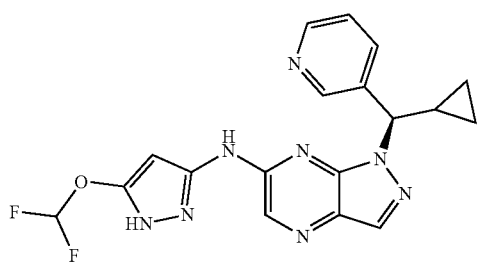 [SMILES: FC(F)Oc1cc(Nc2cnc3cnn([C@@H](c4cccnc4)C4CC4)c3n2)n[nH]1] |
| | or |
| | 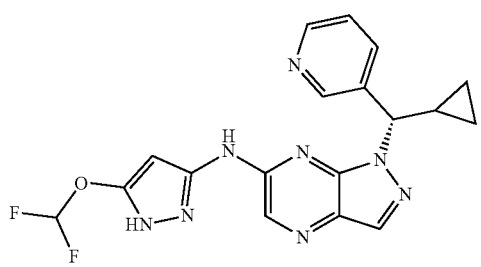 [SMILES: FC(F)Oc1cc(Nc2cnc3cnn([C@H](c4cccnc4)C4CC4)c3n2)n[nH]1] |

| Example Number | Structure |
|---|---|
| 148 | 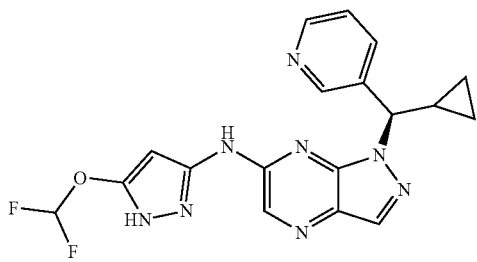 [SMILES: FC(F)Oc1cc(Nc2cnc3cnn([C@@H](c4cccnc4)C4CC4)c3n2)n[nH]1]<br>or<br>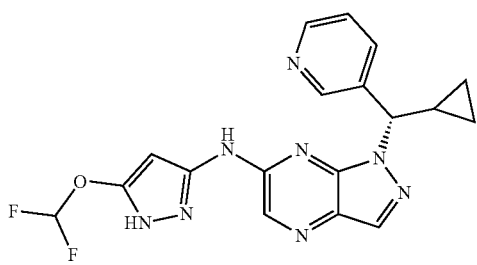 [SMILES: FC(F)Oc1cc(Nc2cnc3cnn([C@H](c4cccnc4)C4CC4)c3n2)n[nH]1] |
| 149 | 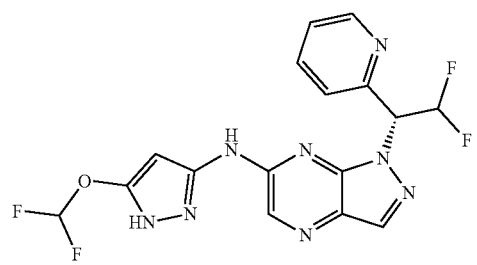 [SMILES: FC(F)Oc1cc(Nc2cnc3cnn([C@H](c4ccccn4)C(F)F)c3n2)n[nH]1]<br>or<br>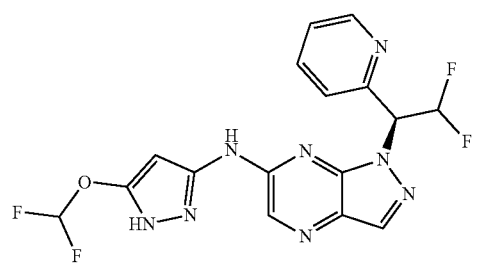 [SMILES: FC(F)Oc1cc(Nc2cnc3cnn([C@@H](c4ccccn4)C(F)F)c3n2)n[nH]1] |
| 150 | 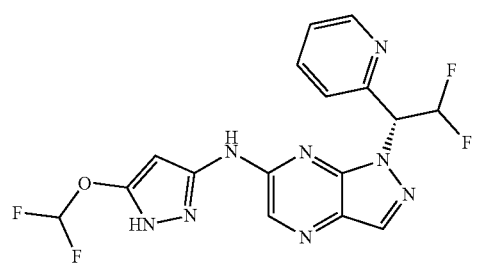 [SMILES: FC(F)Oc1cc(Nc2cnc3cnn([C@H](c4ccccn4)C(F)F)c3n2)n[nH]1]<br>or |

| Example Number | Structure |
|---|---|
|  | 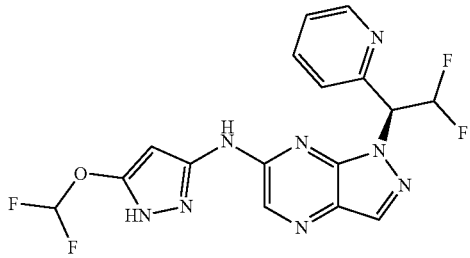 [SMILES: FC(F)Oc1cc(Nc2cnc3cnn([C@@H](c4ccccn4)C(F)F)c3n2)n[nH]1] |
| 151 | 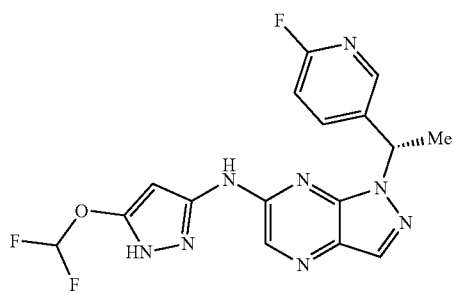 |
|  | or |
|  | 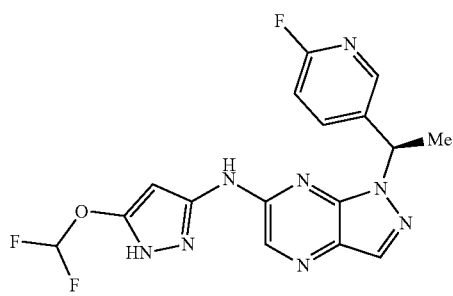 [SMILES: C[C@H](c1ccc(F)nc1)n1ncc2ncc(Nc3cc(OC(F)F)[nH]n3)nc21] |
| 152 | 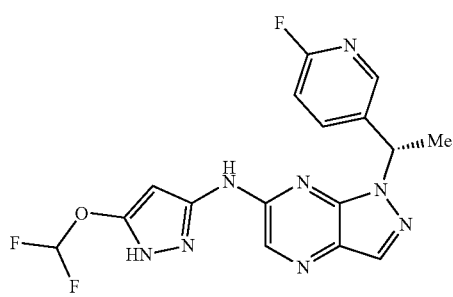 [SMILES: C[C@@H](c1ccc(F)nc1)n1ncc2ncc(Nc3cc(OC(F)F)[nH]n3)nc21] |
|  | or |
|  | 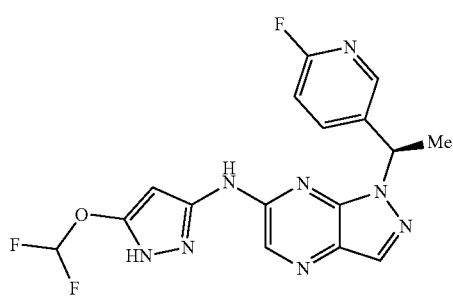 [SMILES: C[C@H](c1ccc(F)nc1)n1ncc2ncc(Nc3cc(OC(F)F)[nH]n3)nc21] |

| Example Number | Structure |
|---|---|
| 153 | 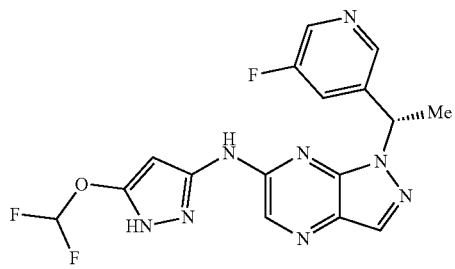 [SMILES: C[C@@H](c1cncc(F)c1)n1ncc2ncc(Nc3cc(OC(F)F)[nH]n3)nc21]<br>or<br>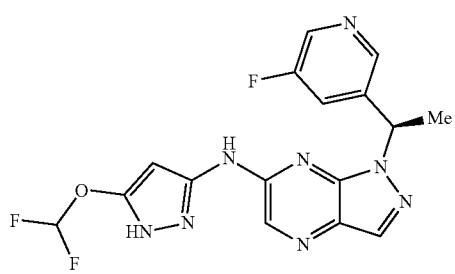 [SMILES: C[C@H](c1cncc(F)c1)n1ncc2ncc(Nc3cc(OC(F)F)[nH]n3)nc21] |
| 154 | 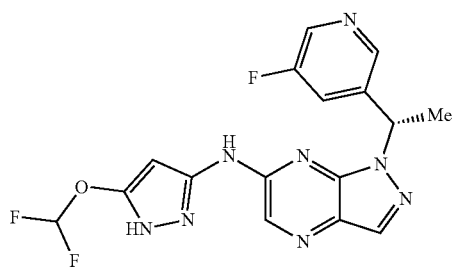 [SMILES: C[C@@H](c1cncc(F)c1)n1ncc2ncc(Nc3cc(OC(F)F)[nH]n3)nc21]<br>or<br>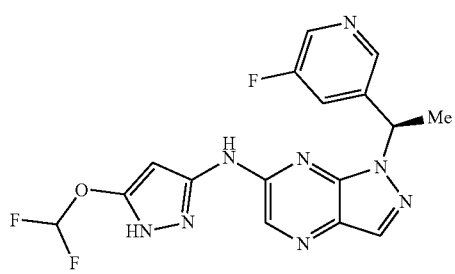 [SMILES: C[C@H](c1cncc(F)c1)n1ncc2ncc(Nc3cc(OC(F)F)[nH]n3)nc21] |
| 155 | 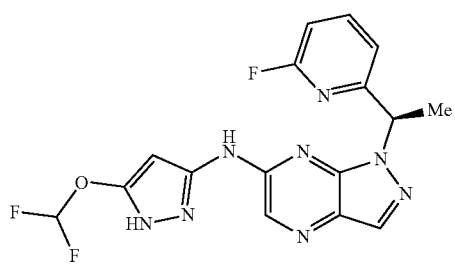 [SMILES: C[C@H](c1cccc(F)n1)n1ncc2ncc(Nc3cc(OC(F)F)[nH]n3)nc21]<br>or |

-continued
| Example Number | Structure |
|---|---|
| | 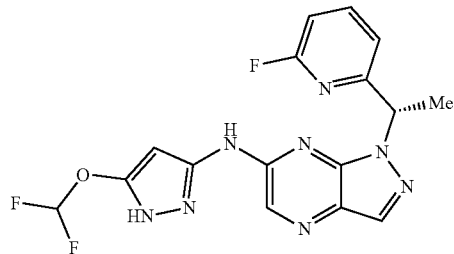 [SMILES: C[C@@H](c1cccc(F)n1)n1ncc2ncc(Nc3cc(OC(F)F)[nH]n3)nc21] |
| 156 | 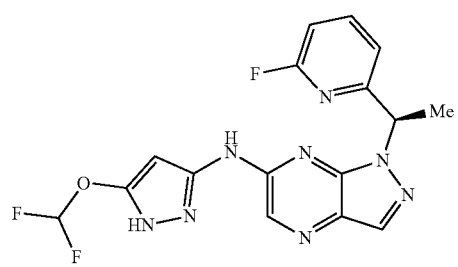 [SMILES: C[C@H](c1cccc(F)n1)n1ncc2ncc(Nc3cc(OC(F)F)[nH]n3)nc21] |
| | or |
| | 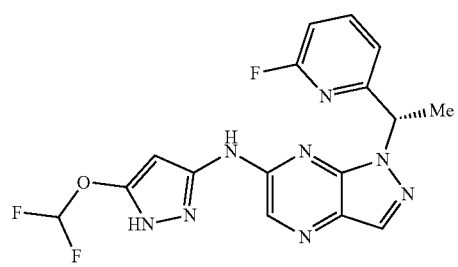 [SMILES: C[C@@H](c1cccc(F)n1)n1ncc2ncc(Nc3cc(OC(F)F)[nH]n3)nc21] |
| 157 | 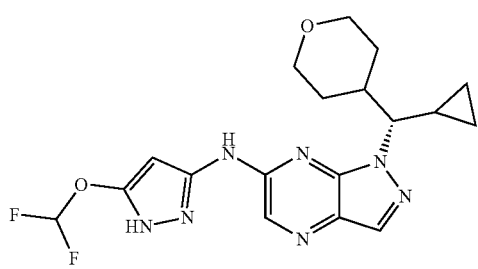 [SMILES: FC(F)Oc1cc(Nc2cnc3cnn([C@H](C4CCOCC4)C4CC4)c3n2)n[nH]1] |
| | or |
| | 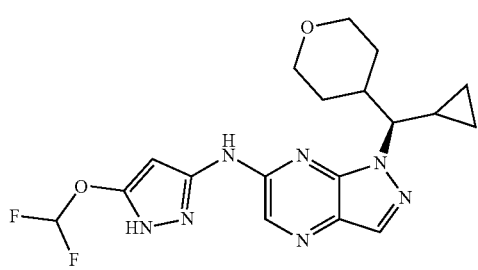 [SMILES: FC(F)Oc1cc(Nc2cnc3cnn([C@@H](C4CCOCC4)C4CC4)c3n2)n[nH]1] |

| Example Number | Structure |
|---|---|
| 158 | 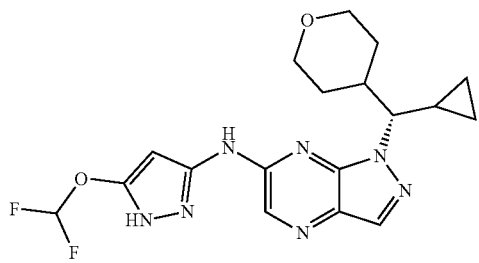 [SMILES: FC(F)Oc1cc(Nc2cnc3cnn([C@H](C4CCOCC4)C4CC4)c3n2)n[nH]1]<br>or<br>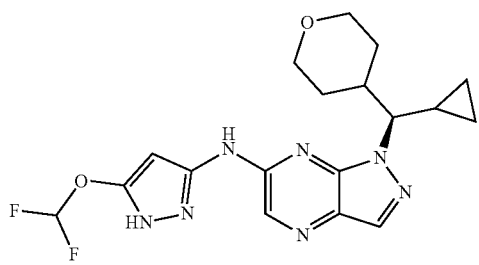 [SMILES: FC(F)Oc1cc(Nc2cnc3cnn([C@@H](C4CCOCC4)C4CC4)c3n2)n[nH]1] |
| 159 | 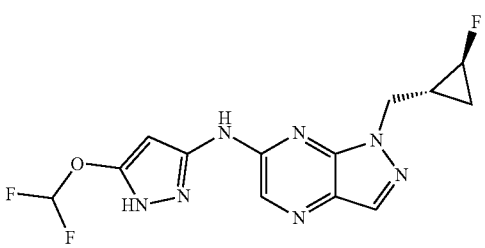 [SMILES: FC(F)Oc1cc(Nc2cnc3cnn(C[C@H]4C[C@@H]4F)c3n2)n[nH]1]<br>or<br>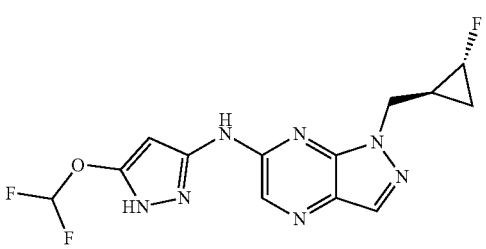 [SMILES: FC(F)Oc1cc(Nc2cnc3cnn(C[C@@H]4C[C@H]4F)c3n2)n[nH]1] |
| 160 | 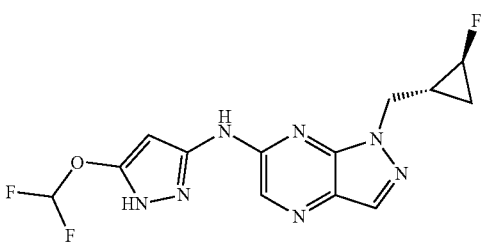 [SMILES: FC(F)Oc1cc(Nc2cnc3cnn(C[C@H]4C[C@@H]4F)c3n2)n[nH]1]<br>or |

| Example Number | Structure |
|---|---|
| | (structure) |
| 161 | (structure) or (structure) |
| 162 | (structure) or (structure) |

| Example Number | Structure |
|---|---|
| 163 | 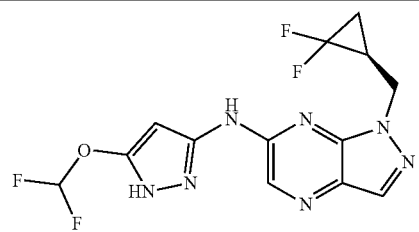<br>or<br>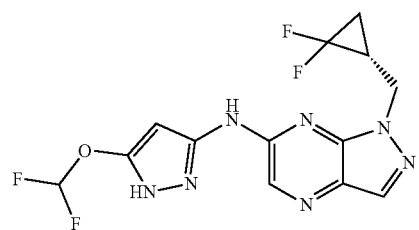 [SMILES: FC(F)Oc1cc(Nc2cnc3cnn(C[C@H]4CC4(F)F)c3n2)n[nH]1] |
| 164 | 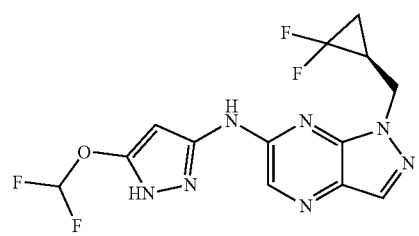 [SMILES: FC(F)Oc1cc(Nc2cnc3cnn(C[C@@H]4CC4(F)F)c3n2)n[nH]1]<br>or<br>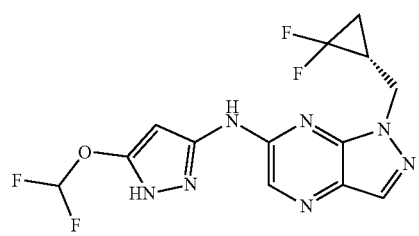 [SMILES: FC(F)Oc1cc(Nc2cnc3cnn(C[C@H]4CC4(F)F)c3n2)n[nH]1] |
| 165 | 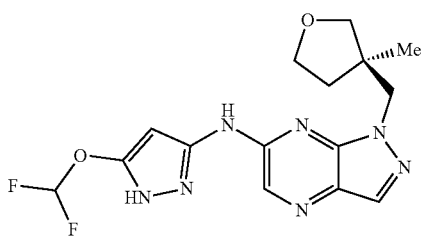 [SMILES: C[C@]1(Cn2ncc3ncc(Nc4cc(OC(F)F)[nH]n4)nc32)CCOC1]<br>or<br>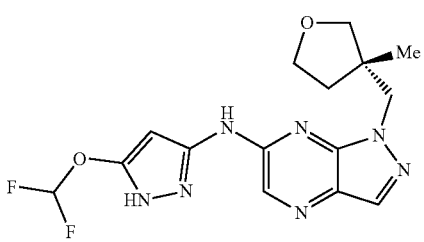 [SMILES: C[C@@]1(Cn2ncc3ncc(Nc4cc(OC(F)F)[nH]n4)nc32)CCOC1] |

-continued
| Example Number | Structure |
|---|---|
| 166 | 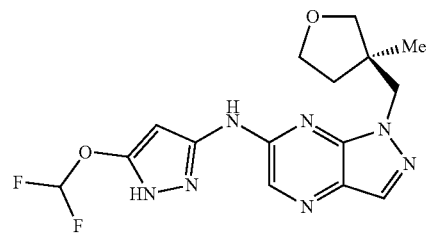 [SMILES: C[C@]1(Cn2ncc3ncc(Nc4cc(OC(F)F)[nH]n4)nc32)CCOC1]or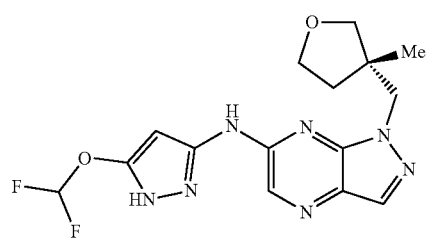 [SMILES: C[C@@]1(Cn2ncc3ncc(Nc4cc(OC(F)F)[nH]n4)nc32)CCOC1] |
| 167 | 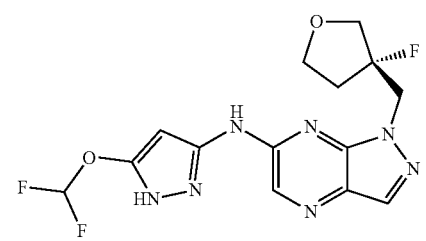 [SMILES: FC(F)Oc1cc(Nc2cnc3cnn(C[C@@]4(F)CCOC4)c3n2)n[nH]1]or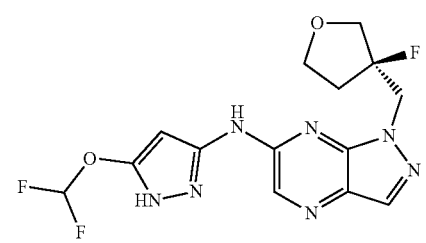 [SMILES: FC(F)Oc1cc(Nc2cnc3cnn(C[C@]4(F)CCOC4)c3n2)n[nH]1] |
| 168 | 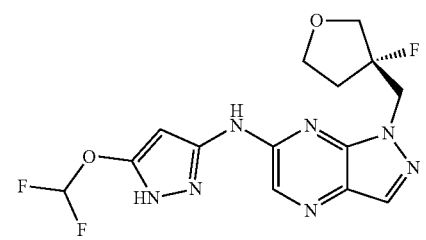 [SMILES: FC(F)Oc1cc(Nc2cnc3cnn(C[C@@]4(F)CCOC4)c3n2)n[nH]1]or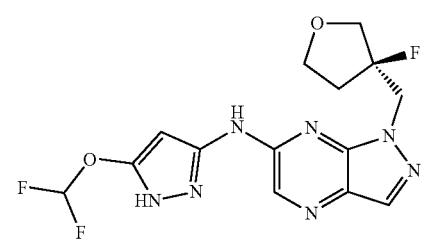 [SMILES: FC(F)Oc1cc(Nc2cnc3cnn(C[C@]4(F)CCOC4)c3n2)n[nH]1] |

| Example Number | Structure |
|---|---|
| 169 | 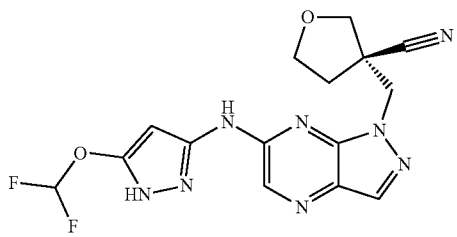 [SMILES: N#C[C@@]1(Cn2ncc3ncc(Nc4cc(OC(F)F)[nH]n4)nc32)CCOC1]<br>or<br>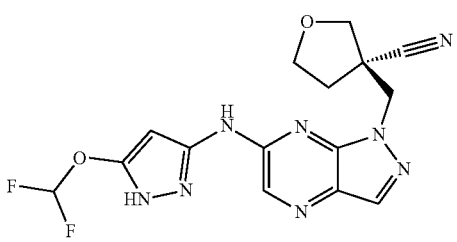 [SMILES: N#C[C@]1(Cn2ncc3ncc(Nc4cc(OC(F)F)[nH]n4)nc32)CCOC1] |
| 170 | 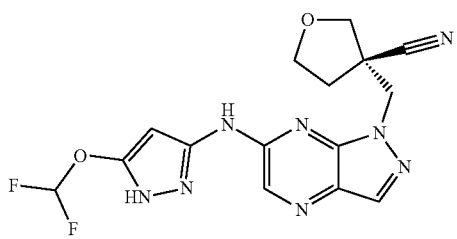 [SMILES: N#C[C@@]1(Cn2ncc3ncc(Nc4cc(OC(F)F)[nH]n4)nc32)CCOC1]<br>or<br>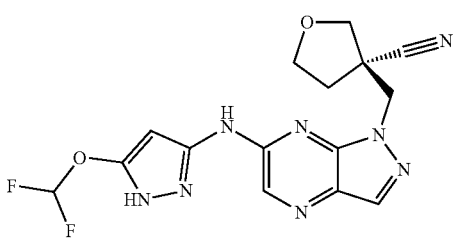 [SMILES: N#C[C@]1(Cn2ncc3ncc(Nc4cc(OC(F)F)[nH]n4)nc32)CCOC1] |
| 171 | 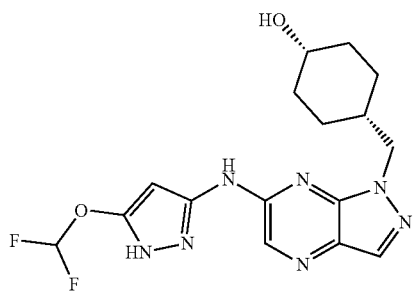 [SMILES: O[C@H]1CC[C@@H](Cn2ncc3ncc(Nc4cc(OC(F)F)[nH]n4)nc32)CC1]<br>or |

| Example Number | Structure |
|---|---|
| | 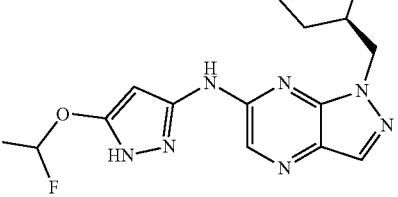 |
| 172 | 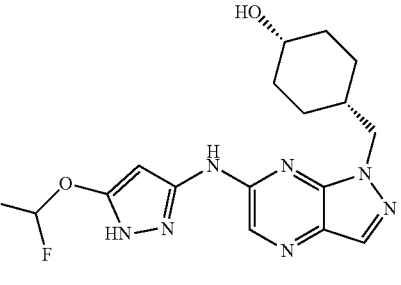
or
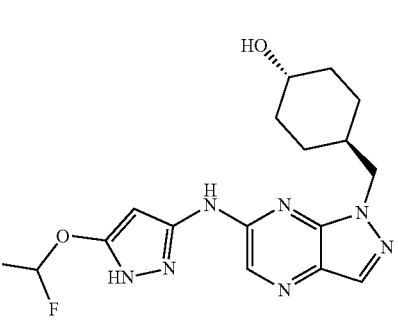 |
| 173 | 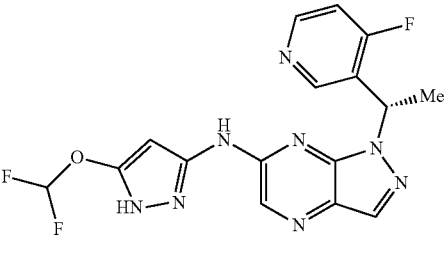 [SMILES: C[C@@H](c1cnccc1F)n1ncc2ncc(Nc3cc(OC(F)F)[nH]n3)nc21]
or
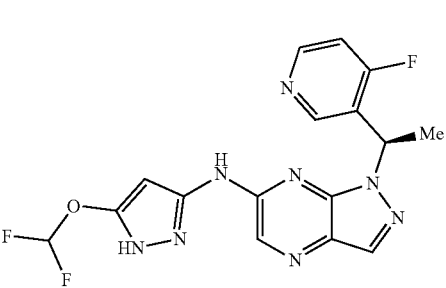 [SMILES: C[C@H](c1cnccc1F)n1ncc2ncc(Nc3cc(OC(F)F)[nH]n3)nc21] |

US 11,970,498 B2
-continued
| Example Number | Structure |
|---|---|
| 174 | 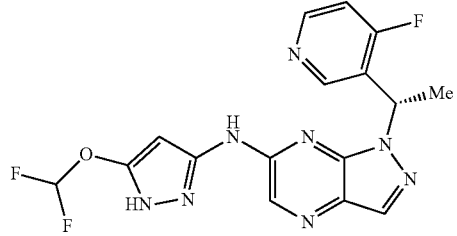 [SMILES: C[C@@H](c1cnccc1F)n1ncc2ncc(Nc3cc(OC(F)F)[nH]n3)nc21]
or
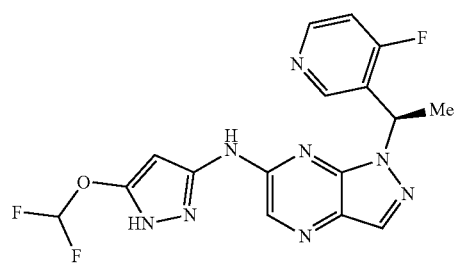 [SMILES: C[C@H](c1cnccc1F)n1ncc2ncc(Nc3cc(OC(F)F)[nH]n3)nc21] |
| 175 | 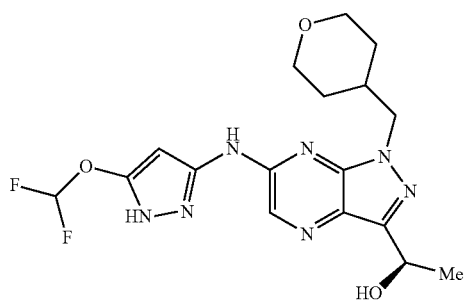 [SMILES: C[C@@H](O)c1nn(CC2CCOCC2)c2nc(Nc3cc(OC(F)F)[nH]n3)cnc12]
or
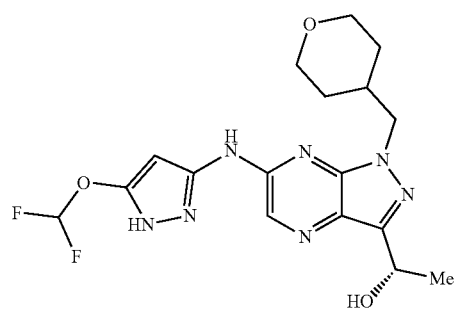 [SMILES: C[C@H](O)c1nn(CC2CCOCC2)c2nc(Nc3cc(OC(F)F)[nH]n3)cnc12] |
| 176 | 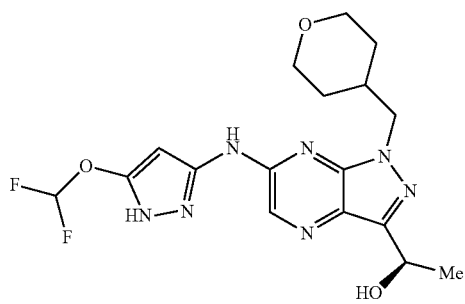 [SMILES: C[C@@H](O)c1nn(CC2CCOCC2)c2nc(Nc3cc(OC(F)F)[nH]n3)cnc12]
or |

| Example Number | Structure |
|---|---|
| | 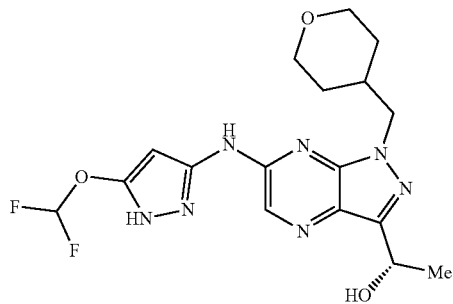 [SMILES: C[C@H](O)c1nn(CC2CCOCC2)c2nc(Nc3cc(OC(F)F)[nH]n3)cnc12] |
| 177 | 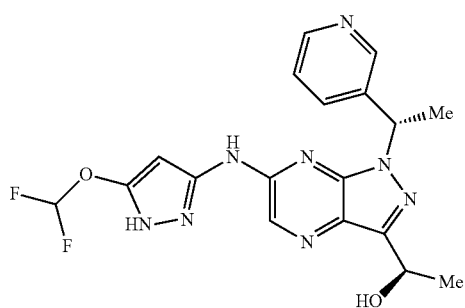 [SMILES: C[C@@H](O)c1nn([C@@H](C)c2cccnc2)c2nc(Nc3cc(OC(F)F)[nH]n3)cnc12]
or
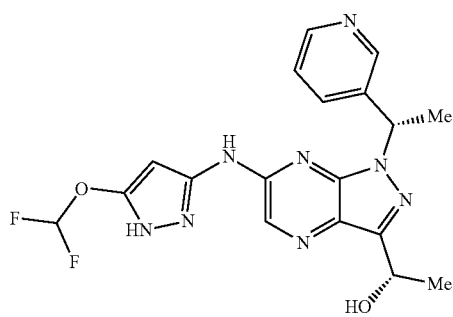 [SMILES: C[C@H](O)c1nn([C@@H](C)c2cccnc2)c2nc(Nc3cc(OC(F)F)[nH]n3)cnc12] |
| 178 | 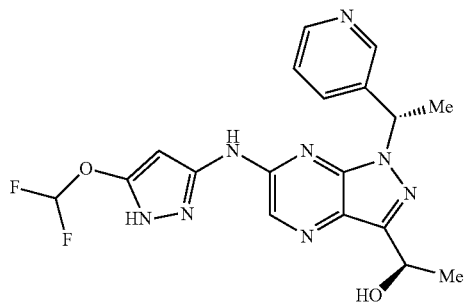 [SMILES: C[C@@H](O)c1nn([C@@H](C)c2cccnc2)c2nc(Nc3cc(OC(F)F)[nH]n3)cnc12]
or |

| Example Number | Structure |
|---|---|
| | 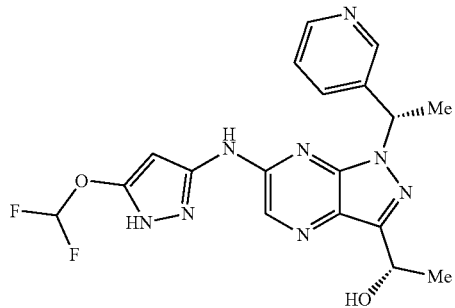 [SMILES: C[C@H](O)c1nn([C@@H](C)c2cccnc2)c2nc(Nc3cc(OC(F)F)[nH]n3)cnc12] |
| 179 | 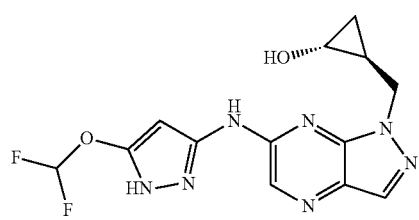 [SMILES: O[C@@H]1C[C@H]1Cn1ncc2ncc(Nc3cc(OC(F)F)[nH]n3)nc21]<br>or<br>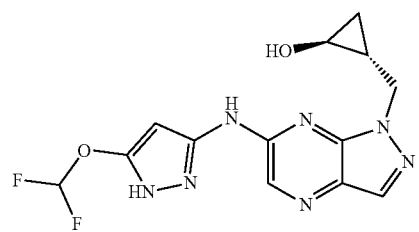 [SMILES: O[C@H]1C[C@@H]1Cn1ncc2ncc(Nc3cc(OC(F)F)[nH]n3)nc21] |
| 180 | 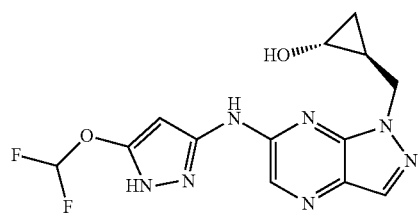 [SMILES: O[C@@H]1C[C@H]1Cn1ncc2ncc(Nc3cc(OC(F)F)[nH]n3)nc21]<br>or<br>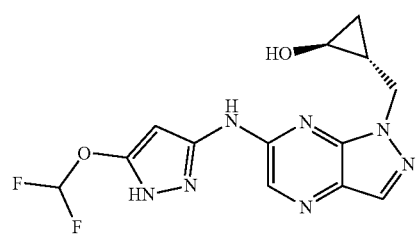 [SMILES: O[C@H]1C[C@@H]1Cn1ncc2ncc(Nc3cc(OC(F)F)[nH]n3)nc21] |

| Example Number | Structure |
|---|---|
| 181 | 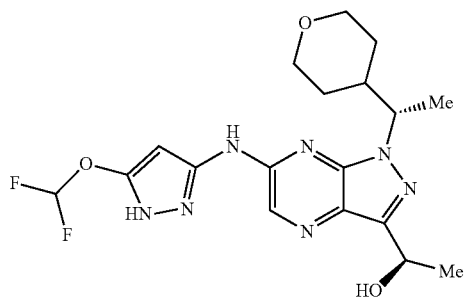 [SMILES: C[C@@H](O)c1nn([C@@H](C)C2CCOCC2)c2nc(Nc3cc(OC(F)F)[nH]n3)cnc12]<br>or<br>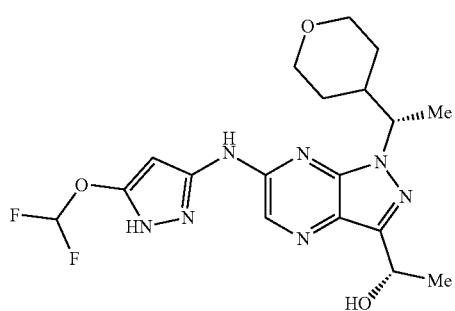 [SMILES: C[C@H](O)c1nn([C@@H](C)C2CCOCC2)c2nc(Nc3cc(OC(F)F)[nH]n3)cnc12] |
| 182 | 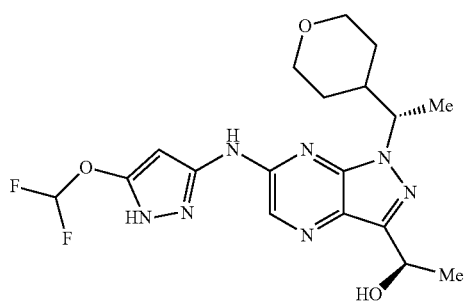 [SMILES: C[C@@H](O)c1nn([C@@H](C)C2CCOCC2)c2nc(Nc3cc(OC(F)F)[nH]n3)cnc12]<br>or<br>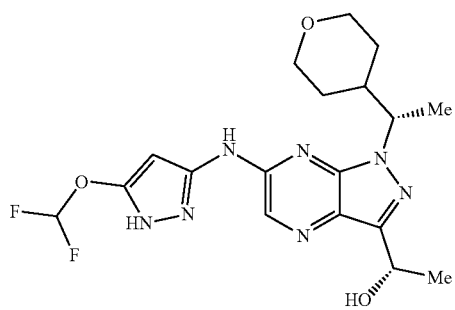 [SMILES: C[C@H](O)c1nn([C@@H](C)C2CCOCC2)c2nc(Nc3cc(OC(F)F)[nH]n3)cnc12] |
| 183 | 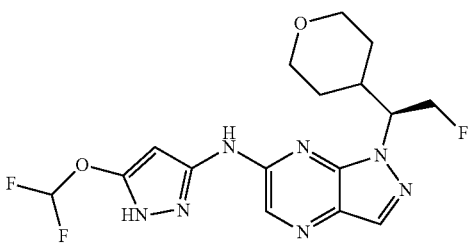 [SMILES: FC[C@H](C1CCOCC1)n1ncc2ncc(Nc3cc(OC(F)F)[nH]n3)nc21] |

| Example Number | Structure |
|---|---|
| 184 | 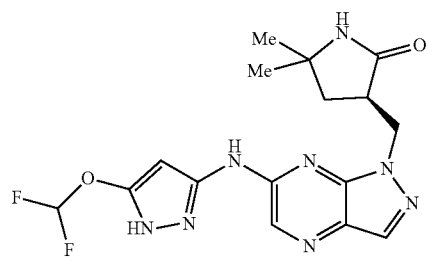 [SMILES: CC1(C)C[C@H](Cn2ncc3ncc(Nc4cc(OC(F)F)[nH]n4)nc32)C(=O)N1]<br>or<br>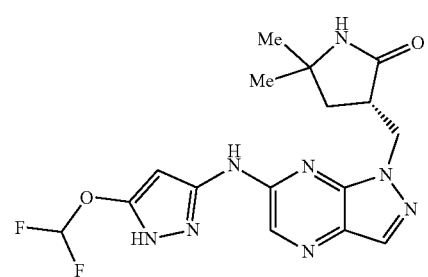 [SMILES: CC1(C)C[C@@H](Cn2ncc3ncc(Nc4cc(OC(F)F)[nH]n4)nc32)C(=O)N1] |
| 185 | 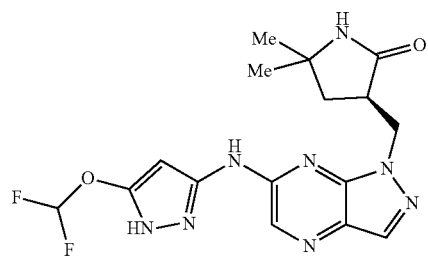 [SMILES: CC1(C)C[C@H](Cn2ncc3ncc(Nc4cc(OC(F)F)[nH]n4)nc32)C(=O)N1]<br>or<br>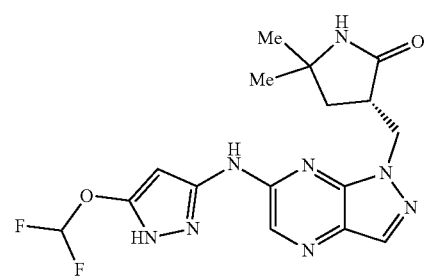 [SMILES: CC1(C)C[C@@H](Cn2ncc3ncc(Nc4cc(OC(F)F)[nH]n4)nc32)C(=O)N1] |
| 186 | 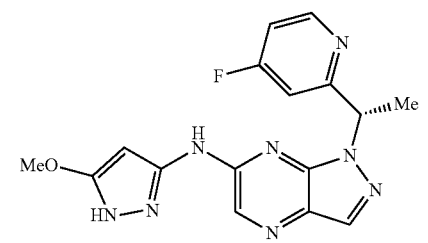 [SMILES: COc1cc(Nc2cnc3cnn([C@@H](C)c4cc(F)ccn4)c3n2)n[nH]1]<br>or |

-continued
| Example Number | Structure |
|---|---|
| | 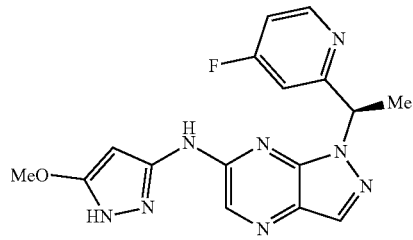 [SMILES: COc1cc(Nc2cnc3cnn([C@H](C)c4cc(F)ccn4)c3n2)n[nH]1] |
| 187 | 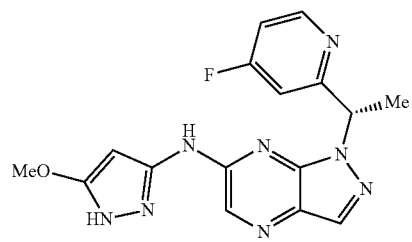 [SMILES: COc1cc(Nc2cnc3cnn([C@@H](C)c4cc(F)ccn4)c3n2)n[nH]1] |
| | or |
| | 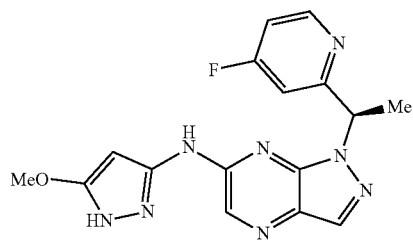 [SMILES: COc1cc(Nc2cnc3cnn([C@H](C)c4cc(F)ccn4)c3n2)n[nH]1] |
| 188 | 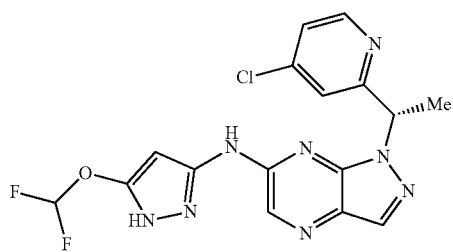 [SMILES: C[C@@H](c1cc(Cl)ccn1)n1ncc2ncc(Nc3cc(OC(F)F)[nH]n3)nc21] |
| | or |
| | 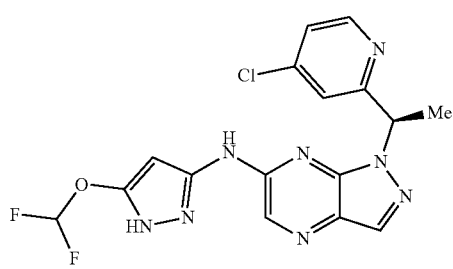 [SMILES: C[C@H](c1cc(Cl)ccn1)n1ncc2ncc(Nc3cc(OC(F)F)[nH]n3)nc21] |

| Example Number | Structure |
|---|---|
| 189 | 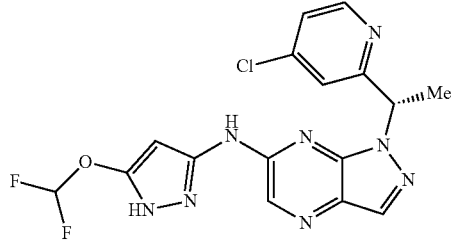 [SMILES: C[C@@H](c1cc(Cl)ccn1)n1ncc2ncc(Nc3cc(OC(F)F)[nH]n3)nc21]
or
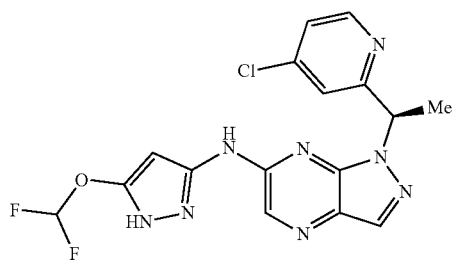 [SMILES: C[C@H](c1cc(Cl)ccn1)n1ncc2ncc(Nc3cc(OC(F)F)[nH]n3)nc21] |
| 190 | 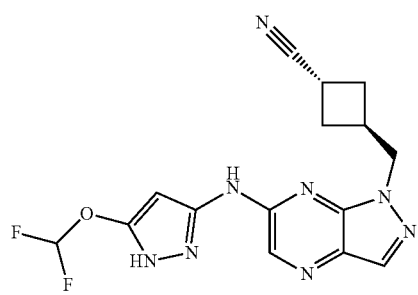 [SMILES: N#C[C@H]1C[C@H](Cn2ncc3ncc(Nc4cc(OC(F)F)[nH]n4)nc32)C1]
or
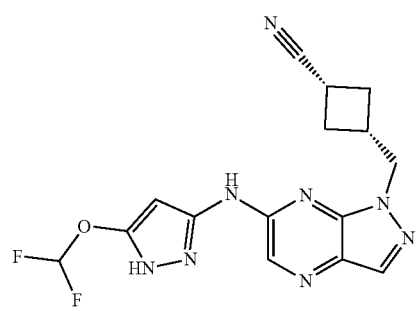 [SMILES: N#C[C@H]1C[C@@H](Cn2ncc3ncc(Nc4cc(OC(F)F)[nH]n4)nc32)C1] |
| 191 | 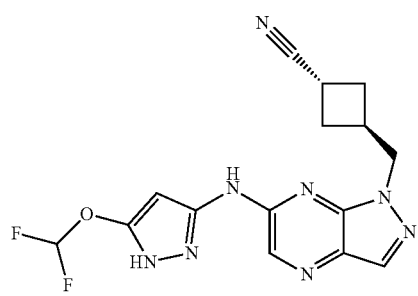 [SMILES: N#C[C@H]1C[C@H](Cn2ncc3ncc(Nc4cc(OC(F)F)[nH]n4)nc32)C1]
or |

| Example Number | Structure |
|---|---|
| | 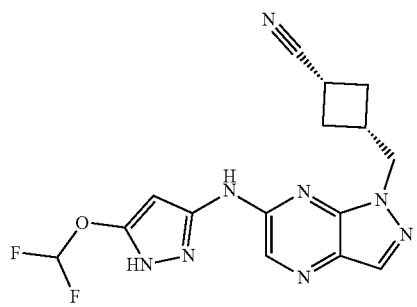 [SMILES: N#C[C@H]1C[C@@H](Cn2ncc3ncc(Nc4cc(OC(F)F)[nH]n4)nc32)C1] |
| 192 | 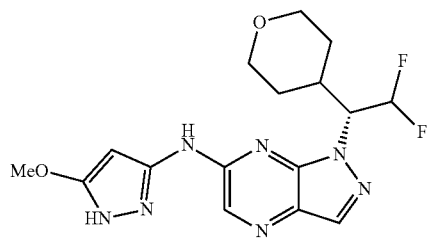 [SMILES: COc1cc(Nc2cnc3cnn([C@@H](C(F)F)C4CCOCC4)c3n2)n[nH]1] |
| | or |
| | 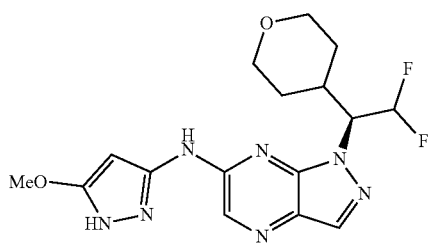 [SMILES: COc1cc(Nc2cnc3cnn([C@H](C(F)F)C4CCOCC4)c3n2)n[nH]1] |
| 193 | 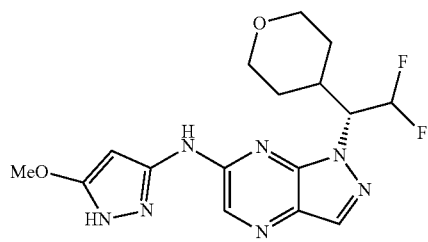 [SMILES: COc1cc(Nc2cnc3cnn([C@@H](C(F)F)C4CCOCC4)c3n2)n[nH]1] |
| | or |
| | 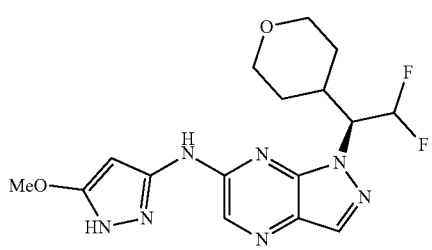 [SMILES: COc1cc(Nc2cnc3cnn([C@H](C(F)F)C4CCOCC4)c3n2)n[nH]1] |

| Example Number | Structure |
|---|---|
| 194 | 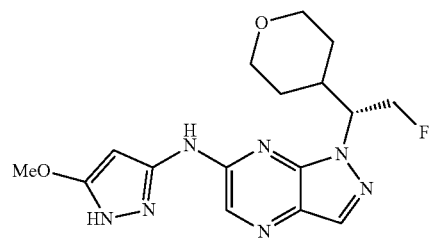 [SMILES: COc1cc(Nc2cnc3cnn([C@@H](CF)C4CCOCC4)c3n2)n[nH]1]<br>or<br>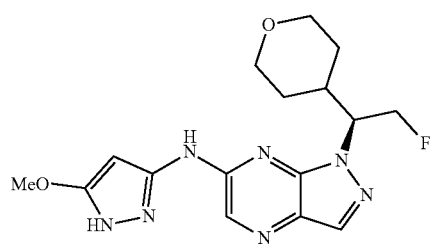 [SMILES: COc1cc(Nc2cnc3cnn([C@H](CF)C4CCOCC4)c3n2)n[nH]1] |
| 195 | 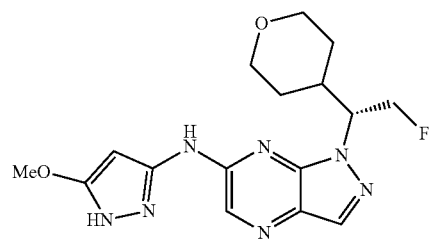 [SMILES: COc1cc(Nc2cnc3cnn([C@@H](CF)C4CCOCC4)c3n2)n[nH]1]<br>or<br>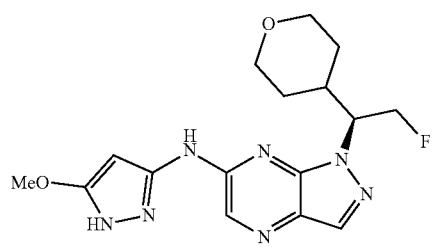 [SMILES: COc1cc(Nc2cnc3cnn([C@H](CF)C4CCOCC4)c3n2)n[nH]1] |
| 196 | 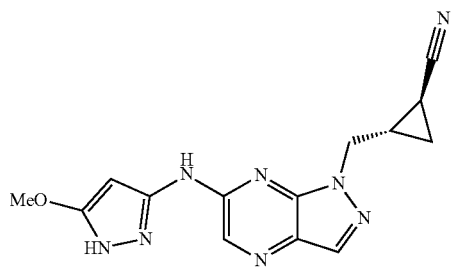 [SMILES: COc1cc(Nc2cnc3cnn(C[C@H]4C[C@@H]4C#N)c3n2)n[nH]1]<br>or |

| Example Number | Structure |
|---|---|
| | 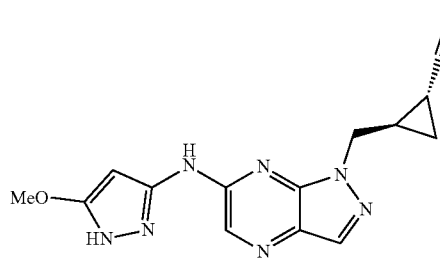 |
| 197 | 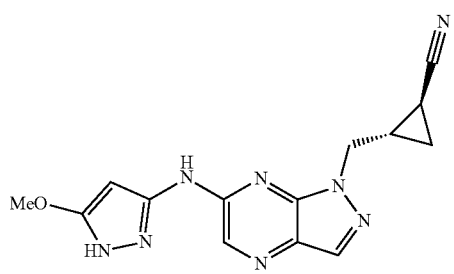 [SMILES: COc1cc(Nc2cnc3cnn(C[C@H]4C[C@@H]4C#N)c3n2)n[nH]1] |
| | or |
| | 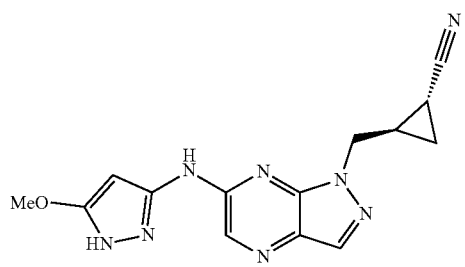 [SMILES: COc1cc(Nc2cnc3cnn(C[C@@H]4C[C@H]4C#N)c3n2)n[nH]1] |
| 198 | 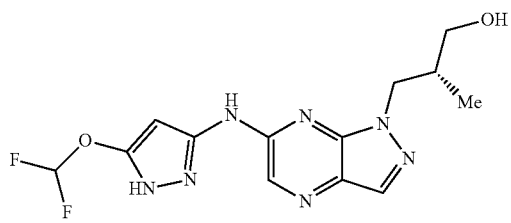 [SMILES: C[C@@H](CO)Cn1ncc2ncc(Nc3cc(OC(F)F)[nH]n3)nc21] |
| 199 | 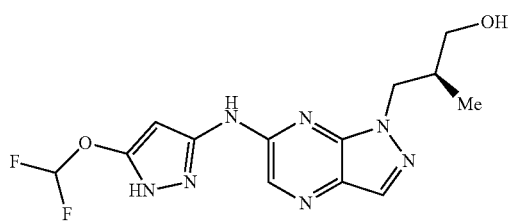 [SMILES: C[C@H](CO)Cn1ncc2ncc(Nc3cc(OC(F)F)[nH]n3)nc21] |
| 200 | 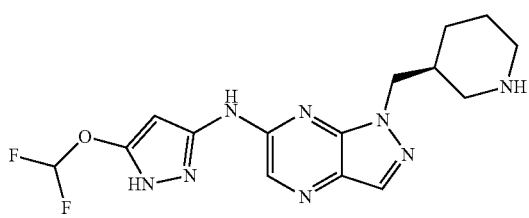 [SMILES: FC(F)Oc1cc(Nc2cnc3cnn(C[C@H]4CCCNC4)c3n2)n[nH]1] |

| Example Number | Structure |
|---|---|
| 201 | 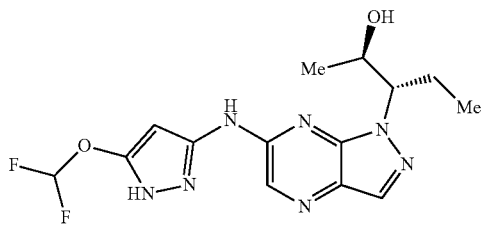 [SMILES: CC[C@@H]([C@@H](C)O)n1ncc2ncc(Nc3cc(OC(F)F)[nH]n3)nc21] or 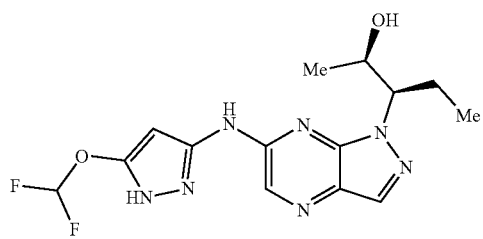 [SMILES: CC[C@H]([C@@H](C)O)n1ncc2ncc(Nc3cc(OC(F)F)[nH]n3)nc21] |
| 202 | 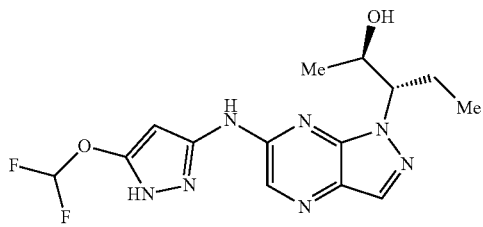 [SMILES: CC[C@@H]([C@@H](C)O)n1ncc2ncc(Nc3cc(OC(F)F)[nH]n3)nc21] or 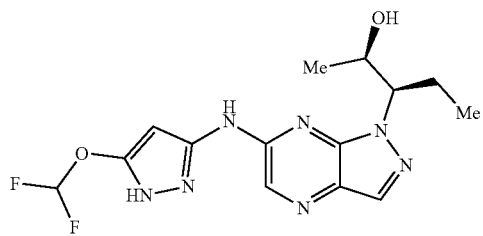 [SMILES: CC[C@H]([C@@H](C)O)n1ncc2ncc(Nc3cc(OC(F)F)[nH]n3)nc21] |
| 203 | 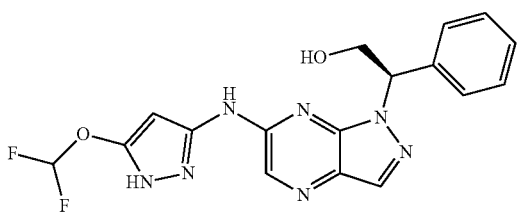 [SMILES: OC[C@@H](c1ccccc1)n1ncc2ncc(Nc3cc(OC(F)F)[nH]n3)nc21] |
| 204 | 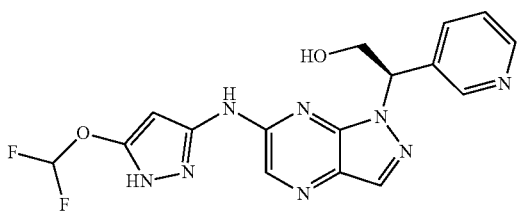 [SMILES: OC[C@@H](c1cccnc1)n1ncc2ncc(Nc3cc(OC(F)F)[nH]n3)nc21] |

| Example Number | Structure |
|---|---|
| 205 | 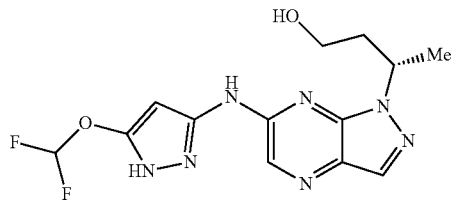 [SMILES: C[C@@H](CCO)n1ncc2ncc(Nc3cc(OC(F)F)[nH]n3)nc21]<br>or<br>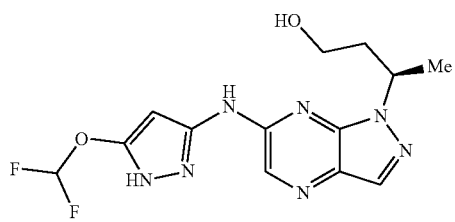 [SMILES: C[C@H](CCO)n1ncc2ncc(Nc3cc(OC(F)F)[nH]n3)nc21] |
| 206 | 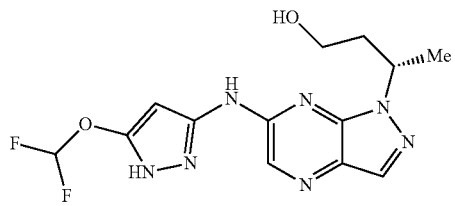 [SMILES: C[C@@H](CCO)n1ncc2ncc(Nc3cc(OC(F)F)[nH]n3)nc21]<br>or<br>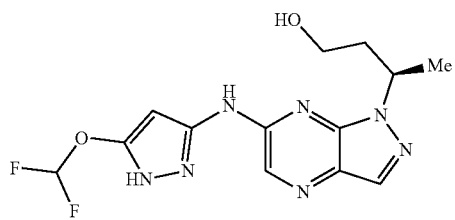 |
| 207 | 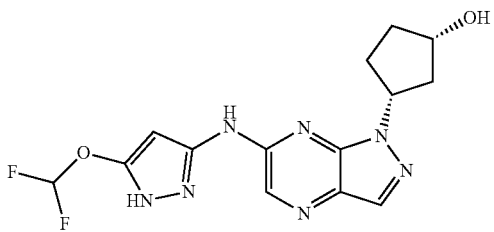 [SMILES: O[C@H]1CC[C@@H](n2ncc3ncc(Nc4cc(OC(F)F)[nH]n4)nc32)C1]<br>or<br>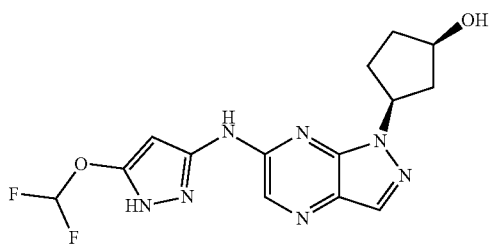 [SMILES: O[C@@H]1CC[C@H](n2ncc3ncc(Nc4cc(OC(F)F)[nH]n4)nc32)C1]<br>or |

| Example Number | Structure |
|---|---|
| | 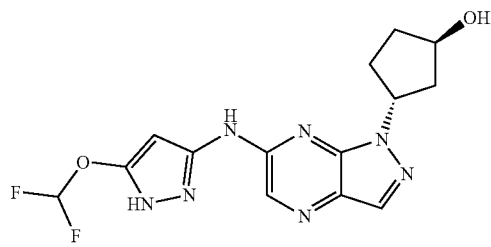 [SMILES: O[C@@H]1CC[C@@H](n2ncc3ncc(Nc4cc(OC(F)F)[nH]n4)nc32)C1] |
| | or |
| | 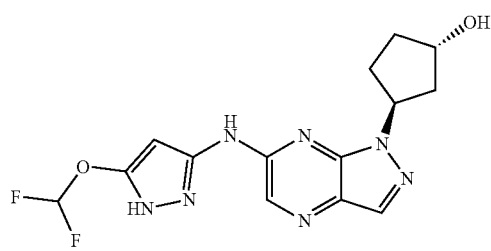 [SMILES: O[C@H]1CC[C@H](n2ncc3ncc(Nc4cc(OC(F)F)[nH]n4)nc32)C1] |
| 208 | 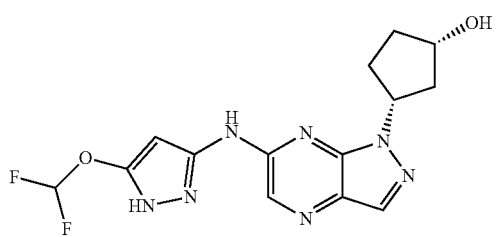 [SMILES: O[C@H]1CC[C@@H](n2ncc3ncc(Nc4cc(OC(F)F)[nH]n4)nc32)C1] |
| | or |
| | 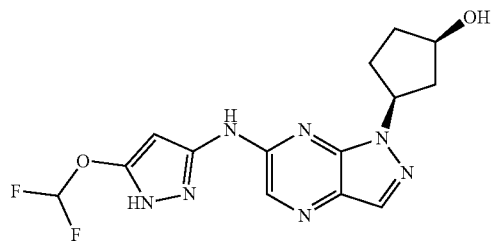 [SMILES: O[C@@H]1CC[C@H](n2ncc3ncc(Nc4cc(OC(F)F)[nH]n4)nc32)C1] |
| | or |
| | 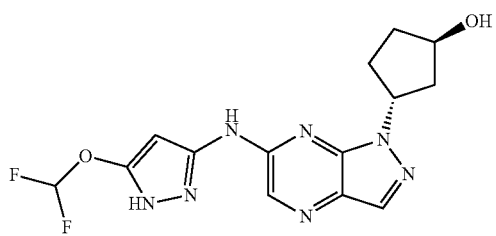 [SMILES: O[C@@H]1CC[C@@H](n2ncc3ncc(Nc4cc(OC(F)F)[nH]n4)nc32)C1] |
| | or |

| Example Number | Structure |
|---|---|
| | 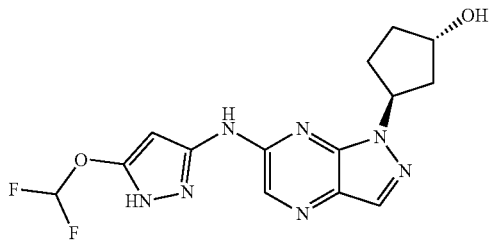 [SMILES: O[C@H]1CC[C@H](n2ncc3ncc(Nc4cc(OC(F)F)[nH]n4)nc32)C1] |
| 209 | 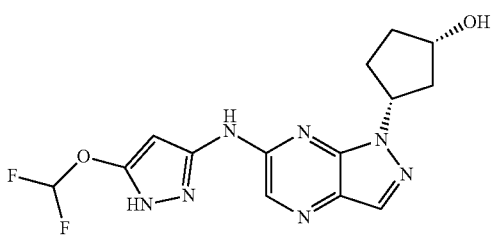 [SMILES: O[C@H]1CC[C@@H](n2ncc3ncc(Nc4cc(OC(F)F)[nH]n4)nc32)C1] |
| | or |
| | 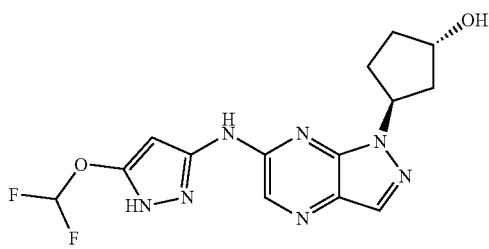 [SMILES: O[C@H]1CC[C@H](n2ncc3ncc(Nc4cc(OC(F)F)[nH]n4)nc32)C1] |
| | or |
| | 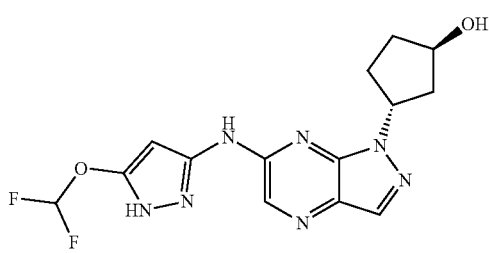 [SMILES: O[C@@H]1CC[C@@H](n2ncc3ncc(Nc4cc(OC(F)F)[nH]n4)nc32)C1] |
| | or |
| | 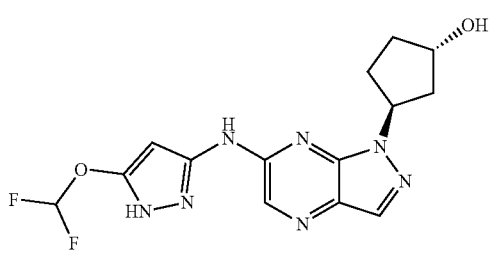 [SMILES: O[C@H]1CC[C@H](n2ncc3ncc(Nc4cc(OC(F)F)[nH]n4)nc32)C1] |

| Example Number | Structure |
|---|---|
| 210 | 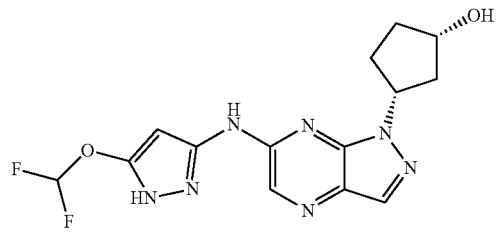 [SMILES: O[C@H]1CC[C@@H](n2ncc3ncc(Nc4cc(OC(F)F)[nH]n4)nc32)C1]
or
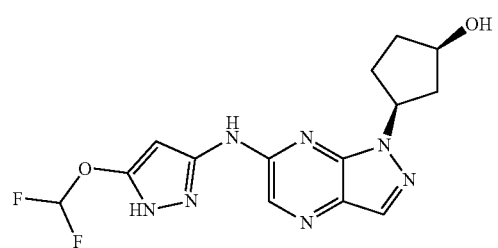 [SMILES: O[C@@H]1CC[C@H](n2ncc3ncc(Nc4cc(OC(F)F)[nH]n4)nc32)C1]
or
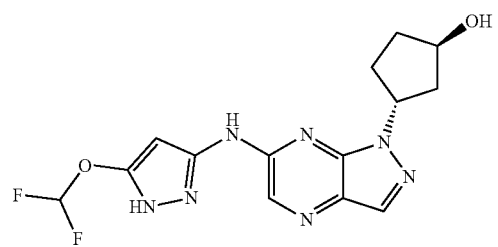 [SMILES: O[C@@H]1CC[C@@H](n2ncc3ncc(Nc4cc(OC(F)F)[nH]n4)nc32)C1]
or
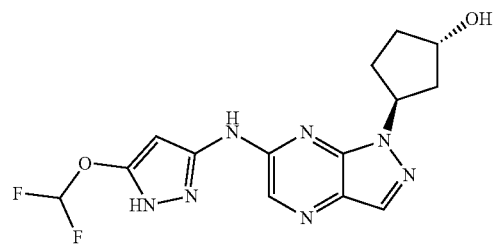 [SMILES: O[C@H]1CC[C@H](n2ncc3ncc(Nc4cc(OC(F)F)[nH]n4)nc32)C1] |
| 211 | 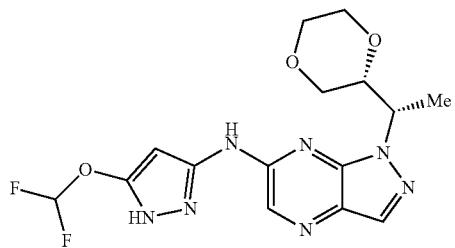 [SMILES: C[C@@H]([C@@H]1COCCO1)n1ncc2ncc(Nc3cc(OC(F)F)[nH]n3)nc21]
or |

| Example Number | Structure |
|---|---|
| | 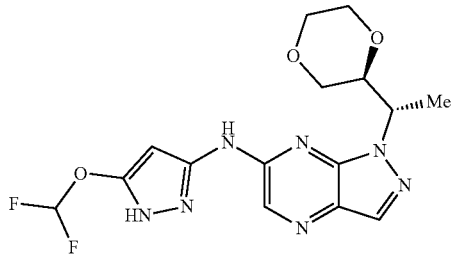 [SMILES: C[C@@H]([C@H]1COCCO1)n1ncc2ncc(Nc3cc(OC(F)F)[nH]n3)nc21]<br>or<br>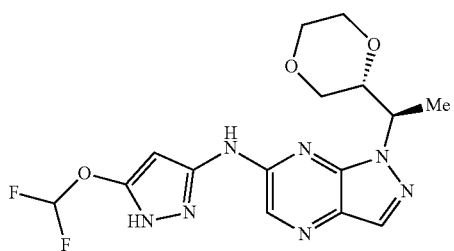 [SMILES: C[C@H]([C@@H]1COCCO1)n1ncc2ncc(Nc3cc(OC(F)F)[nH]n3)nc21]<br>or<br>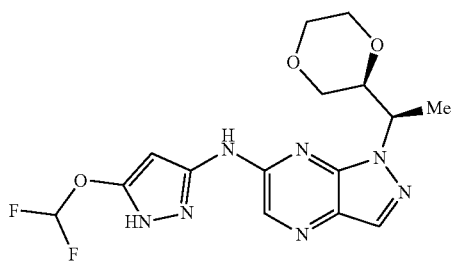 [SMILES: C[C@H]([C@H]1COCCO1)n1ncc2ncc(Nc3cc(OC(F)F)[nH]n3)nc21] |
| 212 | 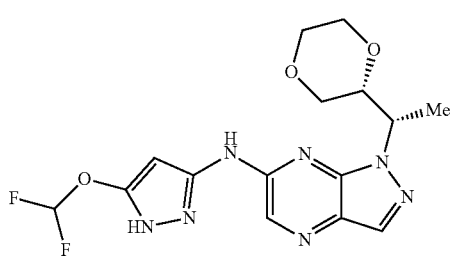 [SMILES: C[C@@H]([C@@H]1COCCO1)n1ncc2ncc(Nc3cc(OC(F)F)[nH]n3)nc21]<br>or<br>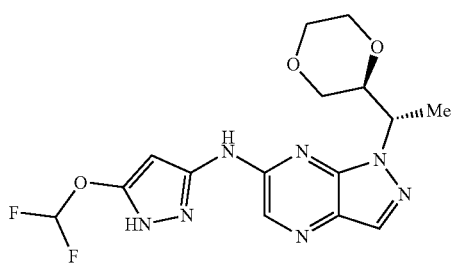 [SMILES: C[C@@H]([C@H]1COCCO1)n1ncc2ncc(Nc3cc(OC(F)F)[nH]n3)nc21]<br>or |

| Example Number | Structure |
|---|---|
| | 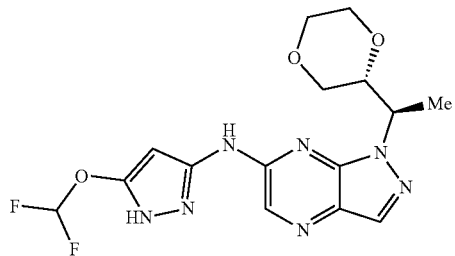 [SMILES: C[C@H]([C@@H]1COCCO1)n1ncc2ncc(Nc3cc(OC(F)F)[nH]n3)nc21]<br>or<br>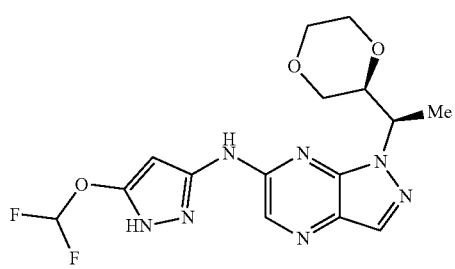 [SMILES: C[C@H]([C@H]1COCCO1)n1ncc2ncc(Nc3cc(OC(F)F)[nH]n3)nc21] |
| 213 | 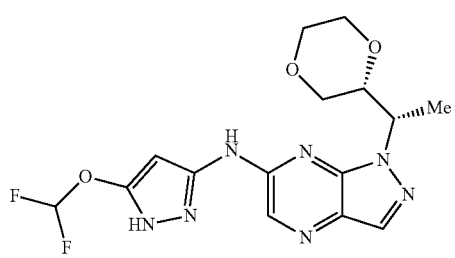 [SMILES: C[C@@H]([C@@H]1COCCO1)n1ncc2ncc(Nc3cc(OC(F)F)[nH]n3)nc21]<br>or<br>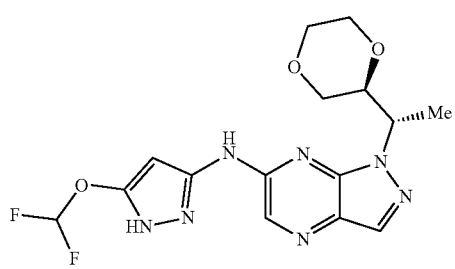 [SMILES: C[C@@H]([C@H]1COCCO1)n1ncc2ncc(Nc3cc(OC(F)F)[nH]n3)nc21]<br>or<br>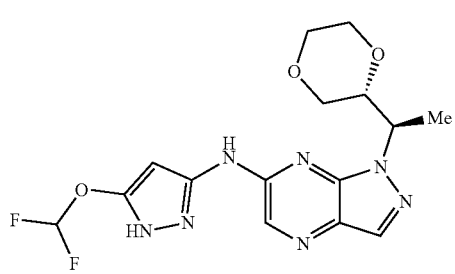 [SMILES: C[C@H]([C@@H]1COCCO1)n1ncc2ncc(Nc3cc(OC(F)F)[nH]n3)nc21]<br>or |

-continued
| Example Number | Structure |
|---|---|
| | 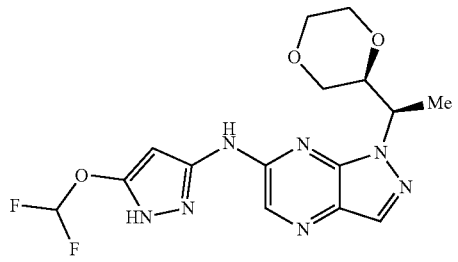 [SMILES: C[C@H]([C@H]1COCCO1)n1ncc2ncc(Nc3cc(OC(F)F)[nH]n3)nc21] |
| 214 | 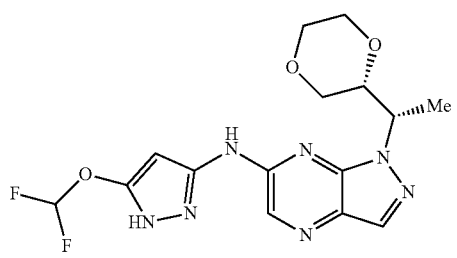 [SMILES: C[C@@H]([C@@H]1COCCO1)n1ncc2ncc(Nc3cc(OC(F)F)[nH]n3)nc21] |
| | or |
| | 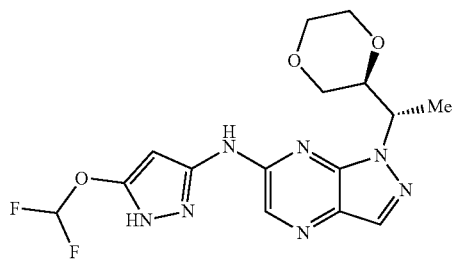 [SMILES: C[C@@H]([C@H]1COCCO1)n1ncc2ncc(Nc3cc(OC(F)F)[nH]n3)nc21] |
| | or |
| | 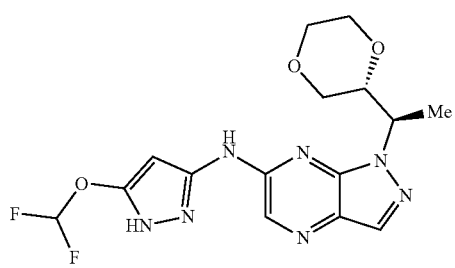 [SMILES: C[C@H]([C@@H]1COCCO1)n1ncc2ncc(Nc3cc(OC(F)F)[nH]n3)nc21] |
| | or |
| | 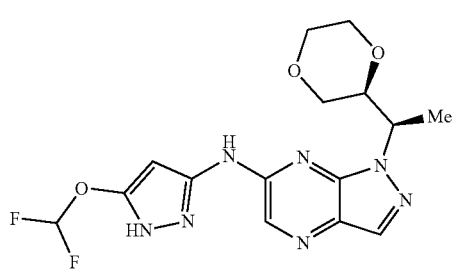 [SMILES: C[C@H]([C@H]1COCCO1)n1ncc2ncc(Nc3cc(OC(F)F)[nH]n3)nc21] |

| Example Number | Structure |
|---|---|
| 215 | 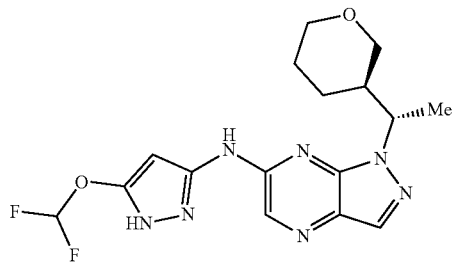 [SMILES: C[C@@H]([C@H]1CCCOC1)n1ncc2ncc(Nc3cc(OC(F)F)[nH]n3)nc21]
or
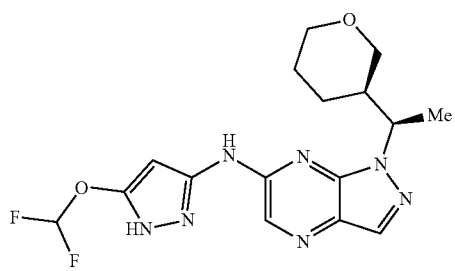 [SMILES: C[C@H]([C@H]1CCCOC1)n1ncc2ncc(Nc3cc(OC(F)F)[nH]n3)nc21]
or
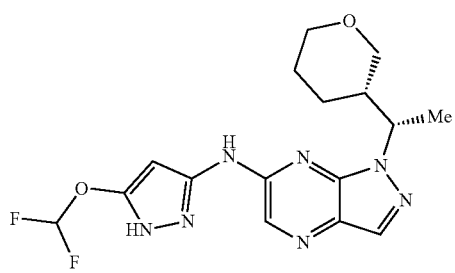 [SMILES: C[C@@H]([C@@H]1CCCOC1)n1ncc2ncc(Nc3cc(OC(F)F)[nH]n3)nc21]
or
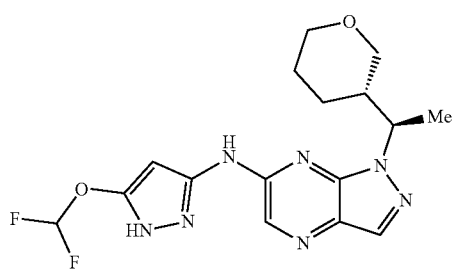 [SMILES: C[C@H]([C@@H]1CCCOC1)n1ncc2ncc(Nc3cc(OC(F)F)[nH]n3)nc21] |
| 216 | 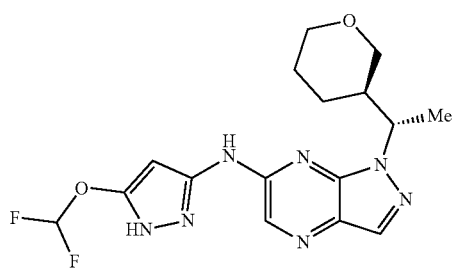 [SMILES: C[C@@H]([C@H]1CCCOC1)n1ncc2ncc(Nc3cc(OC(F)F)[nH]n3)nc21]
or |

| Example Number | Structure |
|---|---|
| | 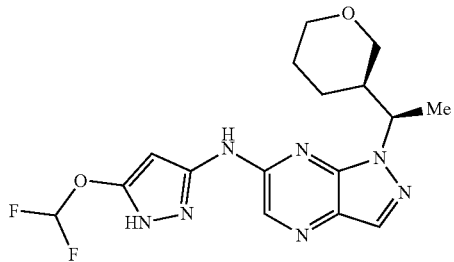 [SMILES: C[C@H]([C@H]1CCCOC1)n1ncc2ncc(Nc3cc(OC(F)F)[nH]n3)nc21] |
| | or |
| | 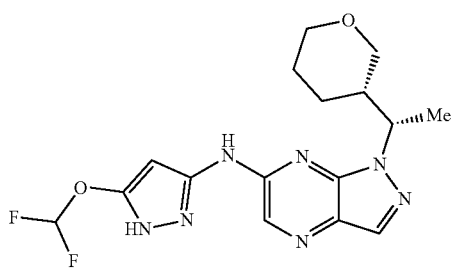 [SMILES: C[C@@H]([C@@H]1CCCOC1)n1ncc2ncc(Nc3cc(OC(F)F)[nH]n3)nc21] |
| | or |
| | 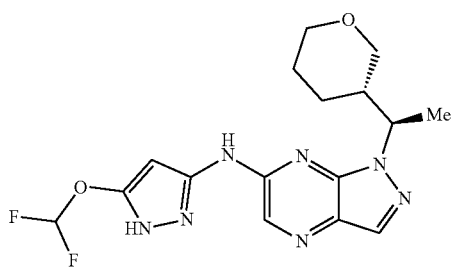 [SMILES: C[C@H]([C@@H]1CCCOC1)n1ncc2ncc(Nc3cc(OC(F)F)[nH]n3)nc21] |
| 217 | 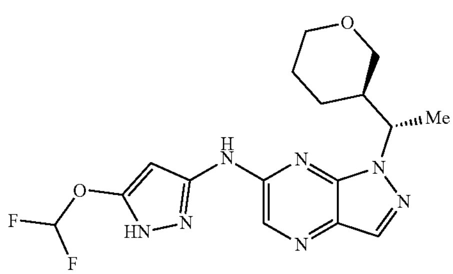 [SMILES: C[C@@H]([C@H]1CCCOC1)n1ncc2ncc(Nc3cc(OC(F)F)[nH]n3)nc21] |
| | 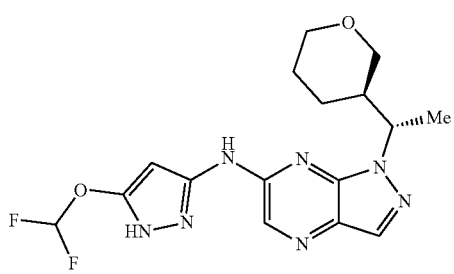 |
| | or |
| | 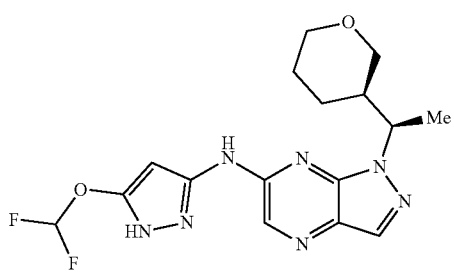 [SMILES: C[C@H]([C@H]1CCCOC1)n1ncc2ncc(Nc3cc(OC(F)F)[nH]n3)nc21] |
| | or |

| Example Number | Structure |
|---|---|
| | 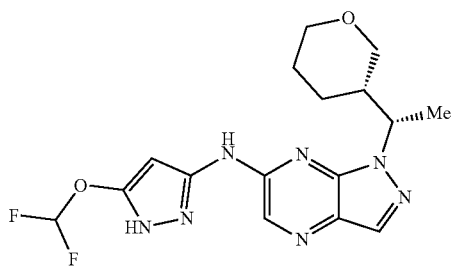 [SMILES: C[C@@H]([C@@H]1CCCOC1)n1ncc2ncc(Nc3cc(OC(F)F)[nH]n3)nc21] |
| | or |
| | 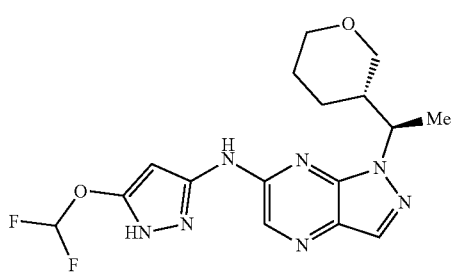 [SMILES: C[C@H]([C@@H]1CCCOC1)n1ncc2ncc(Nc3cc(OC(F)F)[nH]n3)nc21] |
| 218 | 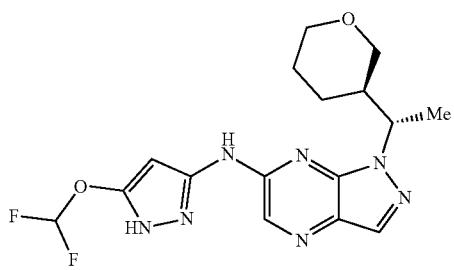 [SMILES: C[C@@H]([C@H]1CCCOC1)n1ncc2ncc(Nc3cc(OC(F)F)[nH]n3)nc21] |
| | or |
| | 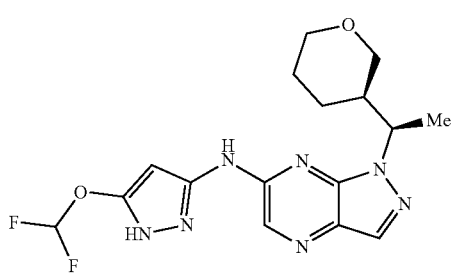 [SMILES: C[C@H]([C@H]1CCCOC1)n1ncc2ncc(Nc3cc(OC(F)F)[nH]n3)nc21] |
| | or |
| | 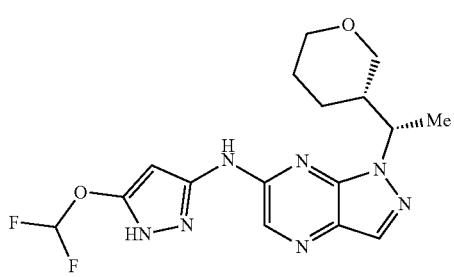 [SMILES: C[C@@H]([C@@H]1CCCOC1)n1ncc2ncc(Nc3cc(OC(F)F)[nH]n3)nc21] |
| | or |

| Example Number | Structure |
|---|---|
| | 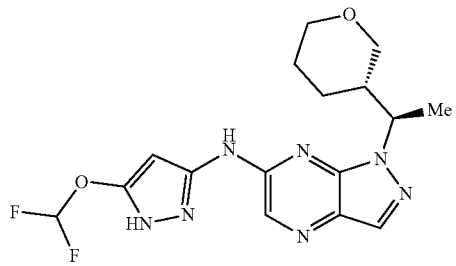 [SMILES: C[C@H]([C@@H]1CCCOC1)n1ncc2ncc(Nc3cc(OC(F)F)[nH]n3)nc21] |
| 219 | 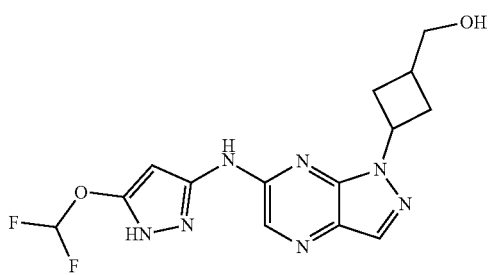 [SMILES: OCC1CC(n2ncc3ncc(Nc4cc(OC(F)F)[nH]n4)nc32)C1] |
| 220 | 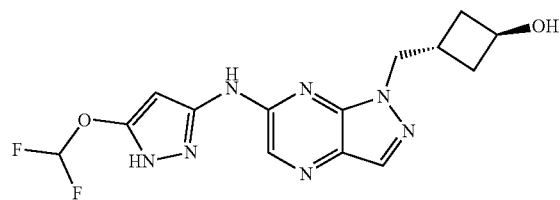 [SMILES: O[C@H]1C[C@H](Cn2ncc3ncc(Nc4cc(OC(F)F)[nH]n4)nc32)C1] |
| 221 | 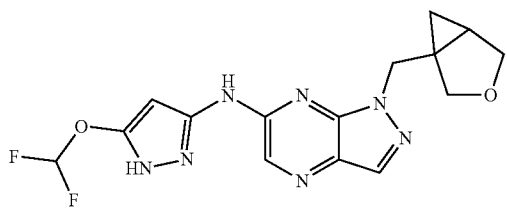 [SMILES: FC(F)Oc1cc(Nc2cnc3cnn(CC45COCC4C5)c3n2)n[nH]1] |
| 222 | 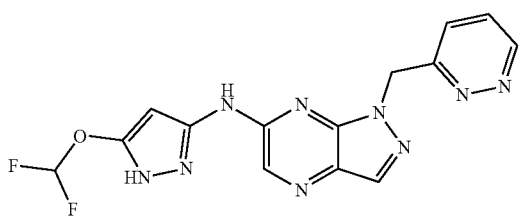 [SMILES: FC(F)Oc1cc(Nc2cnc3cnn(Cc4cccnn4)c3n2)n[nH]1] |
| 223 | 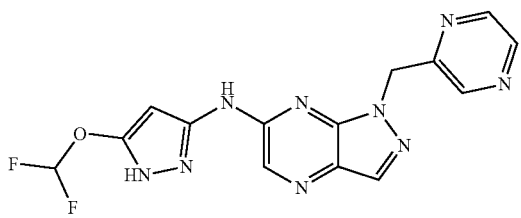 [SMILES: FC(F)Oc1cc(Nc2cnc3cnn(Cc4cnccn4)c3n2)n[nH]1] |

| Example Number | Structure |
|---|---|
| 224 | 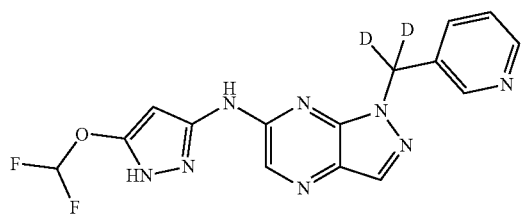 [SMILES: [2H]C([2H])(c1cccnc1)n1ncc2ncc(Nc3cc(OC(F)F)[nH]n3)nc21] |
| 225 | 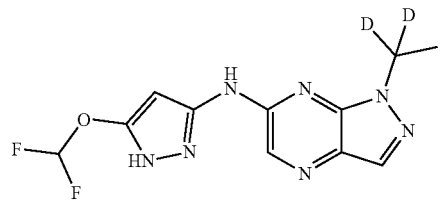 [SMILES: [2H]C([2H])(C)n1ncc2ncc(Nc3cc(OC(F)F)[nH]n3)nc21] |
| 226 | 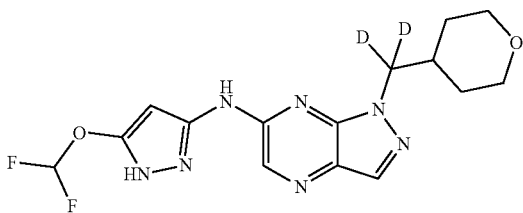 [SMILES: [2H]C([2H])(C1CCOCC1)n1ncc2ncc(Nc3cc(OC(F)F)[nH]n3)nc21] |
| 227 | 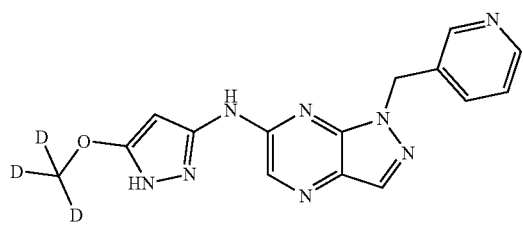 [SMILES: [2H]C([2H])([2H])Oc1cc(Nc2cnc3cnn(Cc4cccnc4)c3n2)n[nH]1] |

Also contemplated herein is a compound represented by:

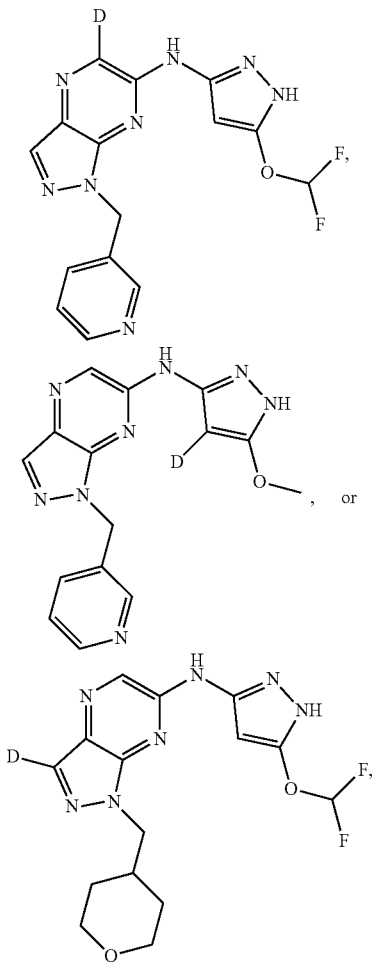

or a pharmaceutically acceptable salt thereof.

The term "pharmaceutically acceptable salt" refers to a pharmaceutical salt that is, within the scope of sound medical judgment, suitable for use in contact with the tissues of humans and lower animals without undue toxicity, irritation, and allergic response, and is commensurate with a reasonable benefit/risk ratio. Pharmaceutically acceptable salts are well known in the art. For example, S. M. Berge et al. describes pharmacologically acceptable salts in *J. Pharm. Sci.*, 1977, 66, 1-19.

Included in the present teachings are pharmaceutically acceptable salts of the compounds disclosed herein. Compounds having basic groups can form pharmaceutically acceptable salts with pharmaceutically acceptable acid(s). Suitable pharmaceutically acceptable acid addition salts of the compounds described herein include salts of inorganic acids (such as hydrochloric, hydrobromic, phosphoric, metaphosphoric, nitric, and sulfuric acids) and of organic acids (such as acetic, benzenesulfonic, benzoic, ethanesulfonic, methanesulfonic, and succinic acids). Compounds of the present teachings with acidic groups such as carboxylic acids can form pharmaceutically acceptable salts with pharmaceutically acceptable base(s). Suitable pharmaceutically acceptable basic salts include ammonium salts, alkali metal salts (such as sodium and potassium salts) and alkaline earth metal salts (such as magnesium and calcium salts).

Compounds having one or more chiral centers can exist in various stereoisomeric forms, i.e., each chiral center can have an R or S configuration, or can be a mixture of both. Stereoisomers are compounds that differ only in their spatial arrangement. Stereoisomers include all diastereomeric and enantiomeric forms of a compound. Enantiomers are stereoisomers that are mirror images of each other. Diastereomers are stereoisomers having two or more chiral centers that are not identical and are not mirror images of each other.

When the stereochemical configuration at a chiral center in a compound having one or more chiral centers is depicted by its chemical name (e.g., where the configuration is indicated in the chemical name by "R" or "S") or structure (e.g., the configuration is indicated by "wedge" bonds), the enrichment of the indicated configuration relative to the opposite configuration is greater than 50%, 60%, 70%, 80%, 90%, 99% or 99.9% (except when the designation "rac" or "racemate accompanies the structure or name, as explained in the following two paragraphs). "Enrichment of the indicated configuration relative to the opposite configuration" is a mole percent and is determined by dividing the number of compounds with the indicated stereochemical configuration at the chiral center(s) by the total number of all of the compounds with the same or opposite stereochemical configuration in a mixture.

When the stereochemical configuration at a chiral center in a compound is depicted by chemical name (e.g., where the configuration is indicated in the name by "R" or "S") or structure (e.g., the configuration is indicated by "wedge" bonds) and the designation "rac" or "racemate" accompanies the structure or is designated in the chemical name, a racemic mixture is intended.

When two stereoisomers are depicted by their chemical names or structures, and the names or structures are connected by an "or", one or the other of the two stereoisomers is intended, but not both.

When a disclosed compound having a chiral center is depicted by a structure without showing a configuration at that chiral center, the structure is meant to encompass the compound with the S configuration at that chiral center, the compound with the R configuration at that chiral center, or the compound with a mixture of the R and S configuration at that chiral center. When a disclosed compound having a chiral center is depicted by its chemical name without indicating a configuration at that chiral center with "S" or "R", the name is meant to encompass the compound with the S configuration at that chiral center, the compound with the R configuration at that chiral center or the compound with a mixture of the R and S configuration at that chiral center.

A racemic mixture means a mixture of 50% of one enantiomer and 50% of its corresponding enantiomer. The present teachings encompass all enantiomerically-pure, enantiomerically-enriched, diastereomerically pure, diastereomerically enriched, and racemic mixtures, and diastereomeric mixtures of the compounds disclosed herein.

Enantiomeric and diastereomeric mixtures can be resolved into their component enantiomers or stereoisomers by well known methods, such as chiral-phase gas chromatography, chiral-phase high performance liquid chromatography, crystallizing the compound as a chiral salt complex, or crystallizing the compound in a chiral solvent. Enantiomers and diastereomers can also be obtained from diastereomerically- or enantiomerically-pure intermediates, reagents, and catalysts by well known asymmetric synthetic methods.

"Peak 1" in the Experimental section refers to an intended reaction product compound obtained from a chromatography separation/purification that elutes earlier than a second intended reaction product compound from the same preceding reaction. The second intended product compound is referred to as "peak 2".

When a disclosed compound is designated by a name or structure that indicates a single enantiomer, unless indicated otherwise, the compound is at least 60%, 70%, 80%, 90%, 99% or 99.9% optically pure (also referred to as "enantiomerically pure"). Optical purity is the weight in the mixture of the named or depicted enantiomer divided by the total weight in the mixture of both enantiomers.

When the stereochemistry of a disclosed compound is named or depicted by structure, and the named or depicted structure encompasses more than one stereoisomer (e.g., as in a diastereomeric pair), it is to be understood that, unless otherwise indicated, one of the encompassed stereoisomers or any mixture of the encompassed stereoisomers are included. It is to be further understood that the stereoisomeric purity of the named or depicted stereoisomers at least 60%, 70%, 80%, 90%, 99% or 99.9% by weight. The stereoisomeric purity in this case is determined by dividing the total weight in the mixture of the stereoisomers encompassed by the name or structure by the total weight in the mixture of all of the stereoisomers.

In the compounds of the disclosure, any position specifically designated as "D" or "deuterium" is understood to have deuterium enrichment at 50, 80, 90, 95, 98 or 99%. "Deuterium enrichment" is a mole percent and is determined by dividing the number of compounds with deuterium at the indicated position by the total number of all of the compounds. When a position is designated as "H" or "hydrogen", the position has hydrogen at its natural abundance. When a position is silent as to whether hydrogen or deuterium is present, the position has hydrogen at its natural abundance. One specific alternative embodiment is directed to a compound of the disclosure having deuterium enrichment of at least 5, 10, 25, 50, 80, 90, 95, 98 or 99% at one or more positions not specifically designated as "D" or "deuterium".

As used herein, many moieties (e.g., alkyl, alkoxy, cycloalkyl or heterocyclyl) are referred to as being either "substituted" or "optionally substituted". When a moiety is modified by one of these terms, unless otherwise noted, it denotes that any portion of the moiety that is known to one skilled in the art as being available for substitution can be substituted, which includes one or more substituents. Where if more than one substituent is present, then each substituent may be independently selected. Such means for substitution are well-known in the art and/or taught by the instant disclosure. The optional substituents can be any substituents that are suitable to attach to the moiety.

Compounds of the disclosure are CDK2 inhibitors. As used herein, the term "selective CDK2 inhibitor" means a compound which selectively inhibits CDK2 over other CDKs and the kinome. Said another way, a selective CDK2 inhibitor has no or low activity against other CDKs and the kinome. A selective CDK2 inhibitor's inhibitory activity against CDK2 is more potent in terms of $IC_{50}$ value (i.e., the $IC_{50}$ value is subnanomolar) when compared with its inhibitory activity against other CDKs and many other kinases. Potency can be measured using known biochemical assays.

In some embodiments, the compounds of the disclosure are selective against CDK2 versus CDK1. In some such embodiments, compounds show at least 10-fold selectivity for CDK2 versus CDK1. In other embodiments, compounds show at least 20-fold selectivity for CDK2 versus CDK1. In specific embodiments, compounds show at least 30-fold selectivity for CDK2 versus CDK1. In certain embodiments, compounds show at least 40-fold selectivity for CDK2 versus CDK1. In other embodiments, compounds show at least 50-fold selectivity for CDK2 versus CDK1. For example, compounds show at least 100-fold selectivity for CDK2 versus CDK1. In some embodiments, the compounds of the invention are selective against CDK2 versus CDK4 and/or CDK6. In some such embodiments, compounds show at least 10-fold selectivity for CDK2 versus CDK4 and/or CDK6. In other embodiments, compounds show at least 20-fold selectivity for CDK2 versus CDK4 and/or CDK6. In specific embodiments, compounds show at least 30-fold selectivity for CDK2 versus CDK4 and/or CDK6.

Some compounds of the disclosure have the advantage of good metabolic stability. One indicator of good metabolic stability is high microsomal stability. Hepatic metabolism is a predominant route of elimination for small molecule drugs. The clearance of compounds by hepatic metabolism can be assessed in vitro using human liver microsomes (HLMs) or human hepatocytes. Compounds are incubated with HLMs plus appropriate co-factors or human hepatocytes and compound depletion is measured to determine an in vitro intrinsic clearance (Clint). The Clint is scaled to total body clearance (CL), and a hepatic extraction ratio (ER) is determined by dividing CL to standard human hepatic blood flow. Compounds that have a low hepatic extraction ratio are considered to have good metabolic stability. In some embodiments, a compound of the disclosure has a calculated ER of <0.3, <0.4, <0.5, <0.6.

Pharmaceutical Compositions

Pharmaceutical compositions of the disclosure (also referred to herein as the "disclosed pharmaceutical compositions") comprise one or more pharmaceutically acceptable carrier(s) or diluent(s) and a compound of the disclosure (e.g., a compound of Formula (I) or Formula (Ia)), or a pharmaceutically acceptable salt thereof.

"Pharmaceutically acceptable carrier" and "pharmaceutically acceptable diluent" refer to a substance that aids the formulation and/or administration of an active agent to and/or absorption by a subject and can be included in the pharmaceutical compositions of the disclosure without causing a significant adverse toxicological effect on the subject. Non-limiting examples of pharmaceutically acceptable carriers and/or diluents include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, hydroxymethycellulose, fatty acid esters, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with or interfere with the activity of the compounds provided herein. One of ordinary skill in the art will recognize that other pharmaceutical excipients are suitable for use with disclosed compounds or pharmaceutically acceptable salts thereof.

The pharmaceutical compositions of the disclosure optionally include one or more pharmaceutically acceptable carriers and/or diluents therefor, such as lactose, starch, cellulose and dextrose. Other excipients, such as flavoring agents, sweeteners, and preservatives, such as methyl, ethyl, propyl and butyl parabens, can also be included. More complete listings of suitable excipients can be found in the Handbook of Pharmaceutical Excipients (5$^{th}$ Ed., Pharmaceutical Press (2005)). A person skilled in the art would know how to prepare formulations suitable for various types of administration routes. Conventional procedures and ingredients for the selection and preparation of suitable formulations are described, for example, in Remington's Pharmaceutical Sciences (2003—20th edition) and in The United States Pharmacopeia: The National Formulary (USP 24 NF19) published in 1999. The carriers, diluents and/or excipients are "acceptable" in the sense of being compatible with the other ingredients of the pharmaceutical composition and not deleterious to the recipient thereof.

Methods of Treatment

The compounds disclosed herein inhibit CDK2 and therefore are useful for treating diseases for which CDK2 is dysregulated, such as cancer. The present disclosure provides a method of inhibiting CDK2 in a subject in need thereof, comprising administering to the subject an effective amount of a compound disclosed herein, a pharmaceutically acceptable salt thereof or a pharmaceutical composition disclosed herein.

In some embodiments, the disclosure provides a method of treating a disease or disorder associated with CDK2 in a patient, comprising administering to the patient a therapeutically effective amount of a compound of Formula (I) or Formula (Ia) or any of the formulas as described herein, or a pharmaceutically acceptable salt thereof. In some embodiments, the disease or disorder associated with CDK2 is associated with an amplification of the cyclin E1 (CCNE1) gene and/or overexpression of CCNE1. In some embodiments, the disease or disorder is cancer.

Subjects "in need of inhibiting CDK2" are those having a disease for which a beneficial therapeutic effect can be achieved by inhibiting CDK2, e.g., a slowing in disease progression, alleviation of one or more symptoms associated with the disease or increasing the longevity of the subject in view of the disease.

In some embodiments, the disclosure provides a method of treating a disease/condition/or cancer associated with or modulated by CDK2, wherein the inhibition of CDK2 is of therapeutic benefit, including but not limited to the treatment of cancer in a subject in need thereof. The method comprises administering to the subject an effective amount of a compound disclosed herein, a pharmaceutically acceptable salt thereof, or pharmaceutical composition disclosed herein.

In another embodiment, the disclosure provides a method of treating a subject with cancer, comprising administering to the subject an effective amount of a compound disclosed herein, a pharmaceutically acceptable salt thereof, or a pharmaceutical composition disclosed herein. In another embodiment, the cancer is characterized by amplification and/or overexpression of CCNE1 or CCNE2.

Accordingly, in some embodiments of the methods, the subject or patient has been previously determined to have an amplification of the cyclin E1 (CCNE1) gene and/or an expression level of CCNE1 in a biological sample obtained from the subject or patient that is higher than a control expression level of CCNE1.

In another embodiment, the disclosure provides a method for inhibiting growth of tumor (e.g., cancer) cells in vitro. The method includes contacting the tumor (e.g. cancer) cells in vitro with a compound of Formula (I) or Formula (Ia) or a pharmaceutically acceptable salt thereof. In another embodiment, the present disclosure provides a method for inhibiting growth of tumor (e.g., cancer) cells with CCNE1 amplification and/or overexpression in a subject or a patient. The method includes administering to the subject or patient in need thereof a therapeutically effective amount of a compound of Formula (I) or Formula (Ia), or a pharmaceutically acceptable salt thereof.

In another embodiment, the disclosure provides a method of treating a subject with cancer, comprising administering to the subject an effective amount of a compound disclosed herein, a pharmaceutically acceptable salt thereof, or a pharmaceutical composition disclosed herein in conjunction with other agents or standard cancer treatments, as described below.

As used herein "cancer" refers to any malignant and/or invasive growth or tumor caused by abnormal cell growth. Cancer includes solid tumors named for the type of cells that form them, cancer of blood, bone marrow, or the lymphatic system. Examples of solid tumors include sarcomas and carcinomas. Cancers of the blood include, but are not limited to, leukemia, lymphoma and myeloma. Cancer also includes primary cancer that originates at a specific site in the body, a metastatic cancer that has spread from the place in which it started to other parts of the body, a recurrence from the original primary cancer after remission, and a second primary cancer that is a new primary cancer in a person with a history of previous cancer of a different type from the latter one. In some such embodiments, the cancer is characterized by amplification and/or overexpression of CCNE1 and/or CCNE2.

Cancers to be treated according to the disclosed methods include breast cancer, ovarian cancer, bladder cancer, uterine cancer (e.g., uterine carcinosarcoma), prostate cancer, lung cancer (including NSCLC, SCLC, squamous cell carcinoma (e.g., lung squamous cell carcinoma (LUSC), or adenocarcinoma (e.g., lung adenocarcinoma (LUAD)), esophageal cancer, head and neck cancer, colorectal cancer (e.g., colon cancer, colorectal adenocarcinoma (COADREAD)), kidney cancer (including RCC), liver cancer (including HCC), pancreatic cancer, stomach (i.e., gastric) cancer, urothelial cancer, brain cancers, mesothelioma (MESO), skin cancer (e.g., melanoma), sarcoma, or thyroid cancer, including metastasis (in particular brain metastasis) of all cancers listed. In some embodiments, the cancer is characterized by at overexpression and/or amplification of CCNE1 and/or CCNE2 described herein. In some embodiments of the methods provided herein, the subject is identified as having a cancer characterized by amplification and/or overexpression of CCNE1 and/or CCNE2.

In further embodiments of the methods provided herein, the cancer is breast cancer, ovarian cancer, bladder cancer, uterine cancer, prostate cancer, lung cancer, esophageal cancer, liver cancer, pancreatic cancer or stomach cancer. In some such embodiments, the cancer is characterized by amplification and/or overexpression of CCNE1 and/or CCNE2.

In further embodiments, of the methods provided herein, the cancer is selected from the group consisting of ovarian cancer, endometrial cancer, gastric cancer, esophageal cancer, triple negative breast cancer, and lung adenosarcoma. In some embodiments, the cancer is characterized by CCNE1 overexpression and/or amplification. In some embodiments, the cancer has progressed despite platinum treatment.

In some embodiments, the cancer is platinum-resistant and/or platinum-refractory. In some embodiments, the cancer has progressed despite platinum treatment.

In some embodiments, the disease or disorder associated with CDK2 is an adenocarcinoma, carcinoma, or cystadenocarcinoma.

In other embodiments, the cancer is breast cancer, including, e.g., ER-positive/HR-positive, HER2-negative breast cancer; ER-positive/HR-positive. HER2-positive breast cancer, triple negative breast cancer (TNBC); or inflammatory breast cancer. In some embodiments, the breast cancer is chemotherapy or radiotherapy resistant breast cancer, endocrine resistant breast cancer, trastuzumab resistant breast cancer, or breast cancer demonstrating primary or acquired resistance to CDK4/CDK6 inhibition. In some embodiments, the breast cancer is advanced or metastatic breast cancer. In some embodiments of each of the foregoing, the breast cancer is characterized by amplification and/or overexpression of CCNE1 and/or CCNE2.

In some embodiments, the cancer is HR-positive breast cancer. In some embodiments, the breast cancer is ER-positive breast cancer. In some embodiments, the breast cancer is HR-positive, HER2-negative breast cancer. In some embodiments, the breast cancer is ER-positive, HER2-negative breast cancer. In some embodiments, the breast cancer is responsive to treatment with a CDK4/6 inhibitor. In some embodiments, the breast cancer is resistant to treatment with a CDK4/6 inhibitor. In some embodiments, the breast cancer has progressed despite treatment with a CDK4/6 inhibitor. In some embodiments, the CDK4/6 inhibitor is palbociclib. In some embodiments, the breast cancer has progressed despite first treatment with palbociclib and/or fulvestrant and second treatment with abemaciclib and/or fulvestrant. In some embodiments, the method further comprises administering an effective amount of a CDK4/6 inhibitor. In some embodiments, the CDK4/6 inhibitor is selected from palbociclib and ribociclib, or a combination thereof. In some embodiments, the CDK4/6 inhibitor is ribociclib. In some embodiments, the breast cancer has CCNE amplification and/or overexpression.

In some embodiments, the breast cancer is triple negative breast cancer.

In some embodiments, the cancer is ovarian cancer. In some such embodiments, the cancer is ovarian cancer characterized by amplification and/or overexpression of CCNE1 and/or CCNE2. In some such embodiments, the cancer is (a) ovarian cancer; (b) characterized by amplification and/or overexpression of cyclin E1 (CCNE1) or cyclin E2 (CCNE2); or (c) both (a) and (b). In some embodiments, the cancer is ovarian cancer.

In some embodiments, the compound of the disclosure is administered as first line therapy. In other embodiments, the compound of the disclosure is administered as second (or later) line therapy. In some embodiments, the compound of the disclosure is administered as second (or later) line therapy following treatment with an endocrine therapeutic agent and/or a CDK4/CDK6 inhibitor. In some embodiments, the compound of the disclosure is administered as second (or later) line therapy following treatment with an endocrine therapeutic agent, e.g., an aromatase inhibitor, a SERM or a SERD. In some embodiments, the compound of the disclosure is administered as second (or later) line therapy following treatment with a CDK4/CDK6 inhibitor. In some embodiments, the compound of the disclosure is administered as second (or later) line therapy following treatment with one or more chemotherapy regimens, e.g., including taxanes or platinum agents. In some embodiments, the compound of the disclosure is administered as second (or later) line therapy following treatment with HER2 targeted agents, e.g., trastuzumab.

In some embodiments, the disease or disorder associated with CDK2 is N-myc amplified neuroblastoma cells (see Molenaar, et al., Proc Natl Acad Sci USA 106(31): 12968-12973) K-Ras mutant lung cancers (see Hu, S., et al., Mol Cancer Ther, 2015. 14(11): 2576-85, and cancers with FBW7 mutation and CCNE1 overexpression (see Takada, et al., Cancer Res, 2017.77(18): 4881-4893).

In some embodiments, the compounds of the present disclosure can be used to treat sickle cell disease and sickle cell anemia.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers. The compounds of the present disclosure are also useful for the treatment of metastatic cancers.

In some embodiments, cancers treatable with compounds of the present disclosure include, but are not limited to, melanoma (e.g., metastatic malignant melanoma, BRAF and HSP90 inhibition-resistant melanoma, skin cutaneous melanoma (SKCM), renal cancer (e.g., clear cell carcinoma), prostate cancer (e.g., hormone refractory prostate adenocarcinoma), breast cancer, colon cancer, lung cancer (e.g., non-small cell lung cancer and small cell lung cancer), squamous cell head and neck cancer (e.g., head and neck squamous cell carcinoma (NHSC), urothelial cancer (e.g., bladder) and cancers with high microsatellite instability (MSIhigh). Additionally, the disclosure includes refractory or recurrent malignancies whose growth may be inhibited using the compounds of the disclosure.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including follicular lymphoma, including relapsed or refractory NHL and recurrent follicular), Hodgkin lymphoma or multiple myeloma) and combinations of said cancers.

In some embodiments, cancers that are treatable using the compounds of the present disclosure include, but are not limited to, cholangiocarcinoma, bile duct cancer, triple negative breast cancer, rhabdomyosarcoma, small cell lung cancer, leiomyosarcoma, hepatocellular carcinoma (e.g., liver hepatocellular carcinoma (LIHC)), Ewing's sarcoma, brain cancer, brain tumor, astrocytoma, neuroblastoma, neurofibroma, basal cell carcinoma, chondrosarcoma, epithelioid sarcoma, eye cancer. Fallopian tube cancer, gastrointestinal cancer, gastrointestinal stromal tumors, hairy cell leukemia, intestinal cancer, islet cell cancer, oral cancer, mouth cancer, throat cancer, laryngeal cancer, lip cancer, mesothelioma, neck cancer, nasal cavity cancer, ocular cancer, ocular melanoma, pelvic cancer, rectal cancer, renal cell carcinoma, salivary gland cancer, sinus cancer, spinal cancer, tongue cancer, tubular carcinoma, urethral cancer, and ureteral cancer.

In some embodiments, cancers treatable with compounds of the present disclosure include Genomic Identification of Significant Targets in Cancer (GISTIC) and pheochromocytoma and paraganglioma (PCPG).

In some embodiments, cancers treatable with compounds of the present disclosure include advanced/relapsed tumors; CCNE1 amplified platinum-resistant or platinum-refractory ovarian cancer; endometrial cancer (with prior platinum therapy) that has progressed following 2 or more lines of therapies; and gastric cancer (with prior platinum therapy) that has progressed following 2 or more lines of therapies; and ER+HER2− BC that has progressed despite CDK4/6i. In some embodiments, cancers treatable with compounds of the present disclosure include Platinum-resistant or platinum-refractory CCNE1 amplified ovarian cancer; CCNE1 amplified endometrial cancer that has failed 2 or more lines of therapies; CCNE1 amplified advanced/relapsed tumors that do not belong to the other groups; ER+HER2− BC that has progressed despite CDK4/6i; platinum-resistant or platinum-refractory CCNE1 amplified ovarian cancer, and ER+HER2− BC that has progressed despite CDK4/6i.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), and essential thrombocytosis (ET)), myelodysplasia syndrome (MDS), T-cell acute lymphoblastic lymphoma (T-ALL) and multiple myeloma (MM).

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, hamartoma, and teratoma.

Exemplary lung cancers include non-small cell lung cancer (NSCLC), small cell lung cancer (SCLC), bronchogenic carcinoma, squamous cell, undifferentiated small cell, undifferentiated large cell, adenocarcinoma, alveolar (bronchiolar) carcinoma, bronchial adenoma, chondromatous hamartoma, and mesothelioma. Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma (PRAD), sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, medulloblastoma, glioma, brain lower grade glioma (LGG), ependymoma, germinoma (pinealoma), glioblastoma, glioblastoma multiforme (GBM), oligodendroglioma, schwannoma, retinoblastoma, congenital tumors, and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, cervical squamous cell carcinoma (CESC), pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, Merkel cell carcinoma, squamous cell carcinoma, Kaposi's sarcoma, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Combinations

Compounds of the disclosure may be administered as single agents or may be administered in combination with other anti-cancer therapeutic agents, in particular standard of care agents appropriate for the particular cancer.

The term "additional anticancer therapeutic agent" as used herein means any one or more therapeutic agent, other than a compound of the disclosure, that is or can be used in the treatment of cancer. In some embodiments, such additional anticancer therapeutic agents include compounds derived from the following classes: mitotic inhibitors, alkylating agents, antimetabolites, antitumor antibiotics, anti-angiogenesis agents, topoisomerase I and II inhibitors, plant alkaloids, hormonal agents and antagonists, growth factor inhibitors, radiation, signal transduction inhibitors, such as inhibitors of protein tyrosine kinases and/or serine/threonine kinases, cell cycle inhibitors, biological response modifiers, enzyme inhibitors, antisense oligonucleotides or oligonucleotide derivatives, cytotoxics, immuno-oncology agents, and the like.

In some embodiments, the additional anticancer agent is an endocrine agent, such as an aromatase inhibitor, a SERD or a SERM.

In some embodiments, the additional anticancer agent is a PIK3CA inhibitor including, but not limited to, alpelisib (PIQRAY), BEBT-908, BPI-21668, buparlisib, inavolisib, TQB-3525, RLY-2608, miransertib, MEN-1611, LOXO-783, HS-10352, HH-CYH33, gedatolisib, and fimepinostat.

In some embodiments, the additional anticancer agent is an antibody-drug conjugates including, but not limited to, Trastuzumab deruxtecan (Enhertu), Trastuzumab duocarmazine, Trastuzumab emtansine (Kadcyla), Upifitamab rilsodotin, mirvetuximab soravtansine, Tisotumab vedotin (Tivdak), Praluzatamab ravtansine, Sacituzumab govitecan or Sacituzumab Govitecan-hziy (Trodelvy), Datopotamab deruxtecan, Ladiratuzumab vedotin, Patritumab deruxtecan, STRO-002, MORab-202, DS-6000, Anetumab, avtansine, XMT-2056, Disitamab Vedotin (RC48-ADC, Aidexi).

In some embodiments, the additional anticancer agent is a PLK1 inhibitor including, but not limited to onvansertib, B12536, B16727, GSK461364A, TAK960, rigosertib.

In some embodiments, the additional anticancer agent is Estrogen PROTAC (ARV-471, H3B-5942).

In other embodiments, a compound of the disclosure may be administered in combination with a standard of care agent. In some embodiments, a compound of the disclosure may be administered in combination with endocrine therapy, e.g., agents such as letrozole, fulvestrant, tamoxifen, exemestane, or anastrozole. In some embodiments, a compound of the disclosure may be administered in combination with a chemotherapeutic agent, e.g., docetaxel, paclitaxel, cisplatin, carboplatin, capecitabine, gemcitabine, vinorelbine, or liposomal doxorubicin. In other embodiments, a compound of the invention may be administered in combination with an anti-HER2 agent. e.g., trastuzumab or pertuzumab.

In some embodiments, a compound of the disclosure (for example, a compound of Formula (I), Formula (Ia), Formula (II), Formula (IIa), Formula (III), Formula (IIIa), Formula (Va), Formula (IVb), Formula (IVa-1), Formula (IVb-1), Formula (Va), Formula (Vb), Formula (Vc), Formula (Vd), Formula (Va-1), Formula (Vb-1), Formula (Vc-1), or Formula (Vd-1) or a pharmaceutically acceptable salt thereof may be administered in combination with an effective amount of carboplatin, ribociclib, fulvestrant, or a combination thereof.

In some embodiments, the additional anticancer agent is an anti-angiogenesis agent, including for example VEGF inhibitors, VEGFR inhibitors, TIE-2 inhibitors, PDGFR inhibitors, angiopoetin inhibitors, PKCb inhibitors, COX-2 (cyclooxygenase II) inhibitors, integrins (alpha-v/beta-3), MMP-2 (matrix-metalloproteinase 2) inhibitors, and MMP-9 (matrix-metalloproteinase 9) inhibitors. Preferred anti-angiogenesis agents include sunitinib (Sutent™), bevacizumab (Avastin™), axitinib (AG 13736), SU 14813 (Pfizer), and AG 13958 (Pfizer). Additional anti-angiogenesis agents include vatalanib (CGP 79787), Sorafenib (Nexavar™), pegaptanib octasodium (Macugen™), vandetanib (Zactima™), PF-0337210 (Pfizer), SU 14843 (Pfizer), AZD 2171 (AstraZeneca), ranibizumab (Lucentis™), Neovastat™ (AE 941), tetrathiomolybdata (Coprexa™), AMG 706 (Amgen), VEGF Trap (AVE 0005), CEP 7055 (Sanofi-Aventis), XL 880 (Exelixis), telatinib (BAY 57-9352), and CP-868,596 (Pfizer). Other anti-angiogenesis agents include enzastaurin (LY 317615), midostaurin (CGP 41251), perifosine (KRX 0401), teprenone (Selbex™) and UCN 01 (Kyowa Hakko). Other examples of anti-angiogenesis agents include celecoxib (Celebrex™ parecoxib (Dynastat™), deracoxib (SC 59046), lumiracoxib (Prige™), valdecoxib (Bextra™), rofecoxib (Vioxx™), iguratimod (Careram™), IP 751 (Invedus), SC-58125 (Pharmacia) and etoricoxib (Arcoxia™). Yet further anti-angiogenesis agents include exisulind (Aptosyn™), salsalate (Amigesic™), diflunisal (Dolobid™), ibuprofen (Motrin™), ketoprofen (Orudis™), nabumetone (Relafen™), piroxicam (Feldene™), naproxen (Aleve™, Naprosyn™), diclofenac (Voltaren™), indomethacin (Indocin™), sulindac (Clinoril™), tolmetin (Tolectin™), etodolac (Lodine™), ketorolac (Toradol™), and oxaprozin (Daypro™). Yet further anti-angiogenesis agents include ABT 510 (Abbott), apratastat (TMI 005). AZD 8955 (AstraZeneca), incyclinide (Metastat™), and PCK 3145 (Procyon).

Yet further anti-angiogenesis agents (including VEGFR/PDGFR inhibitors) include, but are not limited to, ponatinib (Iclusig), BT1718, anlotinib, lenvatinib (Lenvima), tivozanib (Fotivda), dovitinib, brolucizumab (Beovu), aflibercept (Eylea), and faricimab.

Yet further anti-angiogenesis agents include acitretin (Neotigason™), plitidepsin (Aplidine™), cilengtide (EMD 121974), combretastatin A4 (CA4P), fenretinide (4 HPR), halofuginone (Tempostatin™), Panzem™ (2-methoxyestradiol), PF-03446962 (Pfizer), rebimastat (BMS 275291), catumaxomab (Removab™), lenalidomide (Revlimid™), squalamine (EVIZON™), thalidomide (Thalomid™), Ukrain™ (NSC 631570), Vitaxin™ (MEDI 522), and zoledronic acid (Zometa™).

In other embodiments, the additional anti-cancer agent is a so-called signal transduction inhibitor (e.g., inhibiting how regulatory molecules that govern the fundamental processes of cell growth, differentiation, and survival communicated within the cell). Signal transduction inhibitors include small molecules, antibodies, and antisense molecules. Signal transduction inhibitors include for example kinase inhibitors (e.g., tyrosine kinase inhibitors or serine/threonine kinase inhibitors) and cell cycle inhibitors. More specifically signal transduction inhibitors include, for example, farnesyl protein transferase inhibitors. EGF inhibitor, ErbB-1 (EGFR), ErbB-2, pan erb, IGF1R inhibitors. MEK, c-Kit inhibitors. FLT-3 inhibitors, K-Ras inhibitors, PI3 kinase inhibitors, JAK inhibitors, STAT inhibitors, Raf kinase inhibitors, Akt inhibitors, mTOR inhibitor, P70S6 kinase inhibitors, inhibitors of the WNT pathway and so called multi-targeted kinase inhibitors. Additional examples of signal transduction inhibitors which may be used in conjunction with a compound of the invention and pharmaceutical compositions described herein include BMS 214662 (Bristol-Myers Squibb), lonafarnib (Sarasar™), pelitrexol (AG 2037), matuzumab (EMD 7200), nimotuzumab (TheraCIM h-R3™), panitumumab (Vectibix™), Vandetanib (Zactima™), pazopanib (SB 786034), ALT 110 (Alteris Therapeutics), BIBW 2992 (Boehringer Ingelheim), and Cervene™ (TP 38). Other examples of signal transduction inhibitors include gefitinib (Iressa™), cetuximab (Erbitux™), erlotinib (Tarceva™), trastuzumab (Herceptin™), sunitinib (Sutent™), imatinib (Gleevec™), crizotinib (Pfizer), lorlatinib (Pfizer), dacomitinib (Pfizer), bosutinib (Pfizer), gedatolisib (Pfizer), canertinib (CI 1033), pertuzumab (Omnitarg™), lapatinib (Tycerb™), pelitinib (EKB 569), miltefosine (Miltefosin™), BMS 599626 (Bristol-Myers Squibb), Lapuleucel-T (Neuvenge™), NeuVax™ (E75 cancer vaccine), Osidem™ (IDM 1), mubritinib (TAK-165), CP-724,714 (Pfizer), panitumumab (Vectibix™), ARRY 142886 (Array Biopharm), everolimus (Certican™), zotarolimus (Endeavor™), temsirolimus (Torisel™), AP 23573 (ARIAD), and VX 680 (Vertex), XL 647 (Exelixis), sorafenib (Nexavar™), LE-AON (Georgetown University), and GI-4000 (GlobeImmune). Other signal transduction inhibitors include ABT 751 (Abbott), alvocidib (flavopiridol), BMS 387032 (Bristol Myers), EM 1421 (Erimos), indisulam (E 7070), seliciclib (CYC 200), BIO 112 (Onc Bio), BMS 387032 (Bristol-Myers Squibb), palbociclib (Pfizer), and AG 024322 (Pfizer).

In other embodiments, the additional anti-cancer agent is a so called classical antineoplastic agent. Classical antineoplastic agents include but are not limited to hormonal modulators such as hormonal, anti-hormonal, androgen agonist, androgen antagonist and anti-estrogen therapeutic agents, histone deacetylase (HDAC) inhibitors, DNA methyltransferase inhibitors, silencing agents or gene activating agents, ribonucleases, proteomics, Topoisomerase I inhibitors, Camptothecin derivatives, Topoisomerase II inhibitors, alkylating agents, antimetabolites, poly(ADP-ribose) polymerase-1 (PARP-1) inhibitor (such as, e.g., talazoparib, olapariv, rucaparib, niraparib, iniparib, veliparib), microtubulin inhibitors, antibiotics, plant derived spindle inhibitors, platinum-coordinated compounds, gene therapeutic agents, antisense oligonucleotides, vascular targeting agents (VTAs), and statins. Examples of classical antineoplastic agents used in combination therapy with a compound of the invention, optionally with one or more other agents include, but are not limited to, glucocorticoids, such as dexamethasone, prednisone, prednisolone, methylprednisolone, hydrocortisone, and progestins such as medroxyprogesterone, megestrol acetate (Megace), mifepristone (RU-486), Selective Estrogen Receptor Modulators (SERMs; such as tamoxifen, raloxifene, lasofoxifene, afimoxifene, arzoxifene, bazedoxifene, fispemifene, ormeloxifene, ospemifene, tesmilifene, toremifene, trilostane and CHF 4227 (Cheisi), Selective Estrogen-Receptor Downregulators (SERD's; such as fulvestrant, LSZ102, G1T48, RAD1901, elacestrant, GDC-9545, giredestrant, SAR439859, amcenestrant, AZD9833, camizestrant, LY3484356, Zn-c5, D-0502), exemestane (Aromasin), anastrozole (Arimidex), atamestane, fadrozole, letrozole (Femara), formestane; gonadotropin-releasing hormone (GnRH; also commonly referred to as luteinizing hormone-releasing hormone [LHRH]) agonists such as buserelin (Suprefact), goserelin (Zoladex), leuprorelin (Lupron), and triptorelin (Trelstar), abarelix (Plenaxis), cyproterone, flutamide (Eulexin), megestrol, nilutamide (Nilandron), and osaterone, dutasteride, epristeride, finasteride, Serenoa repens, PHL 00801, abarelix, goserelin, leuprorelin, triptorelin, bicalutamide: antiandrogen agents, such as enzalutamide, abiraterone acetate, bicalutamide (Casodex); and combinations thereof. Other examples of classical antineoplastic agents used in combination with a compound of the invention include but are not limited to suberolanilide hydroxamic acid (SAHA, Merck Inc./Aton Pharmaceuticals), depsipeptide (FR901228 or FK228), G2M-777, MS-275, pivaloyloxymethyl butyrate and PXD-101; Onconase (ranpirnase), PS-341 (MLN-341), Velcade (bortezomib), 9-aminocamptothecin, belotecan, BN-80915 (Roche), camptothecin, diflomotecan, edotecarin, exatecan (Daiichi), gimatecan, 10-hydroxycamptothecin, irinotecan HCl (Camptosar), lurtotecan, Orathecin (rubitecan, Supergen), SN-38, topotecan, camptothecin, 10-hydroxycamptothecin, 9-aminocamptothecin, irinotecan, SN-38, edotecarin, topotecan, aclarubicin, adriamycin, amonafide, amrubicin, annamycin, daunorubicin, doxorubicin, elsamitrucin, epirubicin, etoposide, idarubicin, galarubicin, hydroxycarbamide, nemorubicin, novantrone (mitoxantrone), pirarubicin, pixantrone, procarbazine, rebeccamycin, sobuzoxane, tafluposide, valrubicin, Zinecard (dexrazoxane), nitrogen mustard N-oxide, cyclophosphamide, AMD-473, akretamine, AP-5280, apaziquone, brostallicin, bendamustine, busulfan, carboquone, carmustine, chlorambucil, dacarbazine, estramustine, fotemustine, glufosfamide, ifosfamide, KW-2170, lomustine, mafosfamide, mechlorethamine, melphalan, mitobronitol, mitolactol, mitomycin C, mitoxatrone, nimustine, ranimustine, temozolomide, thiotepa, and platinum-coordinated alkylating compounds such as cisplatin, Paraplatin (carboplatin), eptaplatin, lobaplatin, nedaplatin, Eloxatin (oxaliplatin, Sanofi), streptozocin, satrplatin, and combinations thereof.

In still other embodiments, the additional anti-cancer agent is a so called dihydrofolate reductase inhibitors (such as methotrexate and NeuTrexin (trimetresate glucuronate)), purine antagonists (such as 6-mercaptopurine riboside, mercaptopurine, 6-thioguanine, cladribine, clofarabine (Clolar), fludarabine, nelarabine, and raltitrexed), pyrimidine antagonists (such as 5-fluorouracil (5-FU), Alimta (premetrexed disodium, LY231514, MTA), capecitabine (Xeloda™), cytosine arabinoside, Gemzar™ (gemcitabine, Eli Lilly), Tegafur (UFT Orzel or Uforal and including TS-1 combination of tegafur, gimestat and otostat), doxifluridine, carmofur, cytarabine (including ocfosfate, phosphate stearate, sustained release and liposomal forms), enocitabine, 5-azacitidine (Vidaza), decitabine, and ethynylcytidine) and other antimetabolites such as eflornithine, hydroxyurea, leucovorin, nolatrexed (Thymitaq), triapine, trimetrexate, N-(5-[N-(3,4-dihydro-2-methyl-4-oxoquinazolin-6-ylmethyl)-N-methylamino]-2-thenoyl)-L-glutamic acid, AG-014699 (Pfizer Inc.), ABT-472 (Abbott Laboratories), INO-1001 (Inotek Pharmaceuticals), KU-0687 (KuDOS Pharmaceuticals) and GPI 18180 (Guilford Pharm Inc) and combinations thereof.

Other examples of classical antineoplastic cytotoxic agents include, but are not limited to, Abraxane (Abraxis BioScience, Inc.), Batabulin (Amgen), EPO 906 (Novartis), Vinflunine (Bristol-Myers Squibb Company), actinomycin D, bleomycin, mitomycin C, neocarzinostatin (Zinostatin), vinblastine, vincristine, vindesine, vinorelbine (Navelbine), docetaxel (Taxotere), Ortataxel, paclitaxel (including Taxoprexin a DHA/paclitaxel conjugate), cisplatin, carboplatin, Nedaplatin, oxaliplatin (Eloxatin), Satraplatin, Camptosar, capecitabine (Xekxla), oxaliplatin (Eloxatin), Taxotere alitretinoin, Canfosfamide (Telcyta™), DMXAA (Antisoma), ibandronic acid, L-asparaginase, pegaspargase (Oncaspar™), Efaproxiral (Efaproxyn™—radiation therapy), bexarotene (Targretin™), Tesmilifene (DPPE—enhances efficacy of cytotoxics), Theratope™ (Biomira), Tretinoin (Vesanoid™), tirapazamine (Trizaone™), motexafin gadolinium (Xcytrin™) Cotara™ (mAb), and NBI-3001 (Protox Therapeutics), polyglutamate-paclitaxel (Xyotax™) and combinations thereof. Further examples of classical antineoplastic agents include, but are not limited to, as Advexin (ING 201), TNFerade (GeneVec, a compound which express TNFalpha in response to radiotherapy), RB94 (Baylor College of Medicine), Genasense (Oblimersen, Genta), Combretastatin A4P (CA4P), Oxi-4503, AVE-8062, ZD-6126, TZT-1027, Atorvastatin (Lipitor, Pfizer Inc.), Pmvastatin (Pravachol, Bristol-Myers Squibb), Lovastatin (Mevacor, Merck Inc.), Simvastatin (Zocor, Merck Inc.), Fluvastatin (Lescol, Novartis), Cerivastatin (Baycol, Bayer), Rosuvastatin (Crestor, AstraZeneca), Lovostatin, Niacin (Advicor, Kos Pharmaceuticals), Caduet, Lipitor, torcetrapib, and combinations thereof.

In other embodiments, the additional anti-cancer agent is an epigenetic modulator, for example an inhibitor or EZH2, SMARCA4, PBRM1, ARID1A, ARID2, ARID1B, DNMT3A, TET2, MLL1/2/3, NSD1/2, SETD2, BRD4, DOT1L, HKMTsanti, PRMT1-9, LSD1, UTX, IDH1/2 or BCL6.

In further embodiments, the additional anti-cancer agent is an immunomodulatory agent, such as, but not limited to, an inhibitor of CTLA-4 (e.g., ipilimumab), PD-1 or PD-L1 (e.g., pembrolizumab, nivolumab, avelumab, atezolizumab, durvalumab, cemiplimab, or dosterlimab), LAG-3 (e.g., relatlimab, TIM-3, TIGIT, 4-4BB, OX40, GITR, CD40, or a CAR-T-cell therapy.

In some embodiments, the additional anticancer agent is an EGFR inhibitor such as afatinib, osimertinib, lapatinib, erlotinib, dacomitinib, poziotinib, neratinib or gefitinib or an EGFR antibody such as cetuximab, panitumumab, or necitumumab.

Alternatively, a compound of the disclosure, a pharmaceutically acceptable salt thereof or a pharmaceutical composition disclosed herein can be administered in combination with other anti-cancer agents that are not EGFR inhibitors e.g., in combination with MEK, including mutant MEK inhibitors (trametinib, cobimtetinib, binimetinib, selumetinib, refametinib); c-MET, including mutant c-Met inhibitors (savolitinib, cabozantinib, foretinib) and MET antibodies (emibetuzumab); mitotic kinase inhibitors (CDK4/6 inhibitors such as palbociclib, ribociclib, abemaciclb, lerociclib, trilaciclib, dalpiciclib, BPI-16350); anti-angiogenic agents e.g., bevacizumab, nintedanib; apoptosis inducers such as Bcl-2 inhibitors e.g, venetoclax, obatoclax, navitoclax and Mcl-1 inhibitors e.g., AZD-5991, AMG-176, S-64315; and mTOR inhibitors e.g, rapamycin, temsirolimus, everolimus, ridoforolimus.

A compound of the disclosure, a pharmaceutically acceptable salt thereof or a pharmaceutical composition disclosed herein can also be administered in combination with an effective amount of a second agent selected from the group consisting of palbociclib (e.g., Ibrance®), ribociclib, abemaciclib, tamoxifen, letrozole, olaparib (e.g., Lynparza®), niraparib, carboplatin, cisplatin, paclitaxel, gemcitabine, megestrol acetate, medroxyprogesterone acetate, capecitabine (e.g., Xeloda®), regorafenib (e.g., Stivarga®), afatinib (e.g., gilotriff), osimertinib (e.g., Tagrisso®), gefitinib (e.g., Iressa®), erlotinib (e.g., Tarceva®), ramucirumab (e.g., Cyramza®), an EGFR inhibitor, pralsetinib, ABT-263 (navitoclax), MK-1775 (adavosertib), BAY-1895344, berzosertib, ceralasertib, SRA-737, LY2603618 (rabusertib), and trastuzumab (e.g., Herceptin®), or combinations thereof. The EGFR inhibitor may be selected from afatinib, osimertinib, lapatinib, erlotinib, dacomitinib, poziotinib, neratinib, gefitinib JBJ-04-125-02, alflutinib (AST 2818), aumolertinib (formerly almonertinib) (HS10296), BBT-176, BI-4020, BPI-361175, BPI-D0316, CH7233163, gilitertinib, icotinib, JND-3229, lazertinib, nazartinib (EGF 816), avitinib, PCC-0208027, rezivertinib (BPI-7711), TQB3804, zorifertinib (AZ-3759), or DZD9008; an EGFR antibody such as cetuximab, panitumumab, necitumumab, HLX07, JMT101; or a bispecific EGFR and MET antibody (e.g., amivantamab ((JNJ-61186372, JNJ-372)).

Biomarkers and Pharmacodynamics Markers

The disclosure further provides predictive markers (e.g., biomarkers and pharmacodynamic markers, e.g., gene copy number, gene sequence, expression levels, or phosphorylation levels) to identify those human subjects having, suspected of having, or at risk of developing a disease or disorder associated with CDK2 for whom administering a CDK2 inhibitor ("a CDK2 inhibitor" as used herein refers to a compound of the disclosure, or a pharmaceutically acceptable salt thereof) is likely to be effective.

CCNE1

In one embodiment, the biomarker is CCNE1. In particular an amplification of the cyclin E1 (CCNE1) gene and/or an expression level of CCNE1 in a biological sample would indicate that the patient or subject could benefit from administration of a compound of Formula (I) or Formula (Ia) or a pharmaceutically acceptable salt thereof.

CCNE1 is a cell cycle factor essential for the control of the cell cycle at the G1/S transition (Ohtsubo et al., 1995, Mol. Cell. Biol. 15:2612-2624). CCNE1 acts as a regulatory subunit of CDK2, interacting with CDK2 to form a serine/threonine kinase holoenzyme complex. The CCNE1 subunit of this holoenzyme complex provides the substrate specificity of the complex (Honda et al., 2005, EMBO 24:452-463). CCNE1 is encoded by the cyclin E1 ("CCNE1") gene (GenBank Accession No. NM_001238). The amino acid sequence of human CCNE1 is found at GenBank Accession No. NP_001229/UniProtKB Accession No. P24864).

In one aspect, the present disclosure provides a method of treating a subject having, or at risk of developing, a disease or disorder associated with CDK2, comprising administering to the subject a therapeutically effective amount of a compound disclosed herein, or a pharmaceutically acceptable salt thereof, or a pharmaceutical composition disclosed herein, wherein the subject has an amplification of the CCNE1 gene and/or have an expression level of CCNE1 higher than a control expression level of CCNE1. In some embodiments, the disease or disorder associated with CDK2 is cancer.

Also provided herein is a method of treating a patient having an amplified expression level of CCNE1 and suffering from, or at risk of developing, a solid tumor cancer, comprising administering to the patient a therapeutically effective amount of a compound disclosed herein, or a pharmaceutically acceptable salt thereof, or a pharmaceutical composition disclosed herein.

An amplification of the CCNE1 gene and/or an expression level of CCNE1 that is higher than a control expression level of CCNE1 is indicative/predictive that a human subject having or at risk of developing a disease or disorder associated with CDK2 will respond to a CDK2 inhibitor. In some embodiments, the expression level of CCNE1 may be the level of CCNE1 mRNA. In other embodiments, the expression level of CCNE1 may be the level of CCNE1 protein.

Other Biomarkers

In some embodiments, the contemplated biomarker may be p16 (also known as cyclin-dependent kinase inhibitor 2A, cyclin-dependent kinase 4 inhibitor A, multiple tumor suppressor 1, and p16-INK4a), which acts as a negative regulator of the proliferation of normal cells by interacting with CDK4 and CDK6. In other embodiments, the contemplated biomarker may be phosphorylation of Rb at the serine corresponding to amino acid position 780. Rb is a regulator of the cell cycle and acts as a tumor suppressor. Rb is activated upon phosphorylation by cyclin D-CDK4/6 at Ser780 and Ser795 and by cyclin E/CDK2 at Ser807 and Ser811.

The contemplated biomarker may also be selected from the group consisting of RB1, RBL1, RBL2, CDKN2A, CDKN1A, CDKN1B, FBXW7, CCNE1, CCNE2, CCNA1, CCNA2, CCND1, CCND2, CCND3, CDK2, CDK3, CDK4, CDK6, CDKN2A, CDNK1A, CDKN1B E2F1, E2F2, E2F3, MYC, MYCL, MYCN, EZH2, ER, HER2, HER3, HPV+, and EGFR.

Biological Samples

Suitable biological samples for the methods described herein include any sample that contains blood or tumor cells obtained or derived from the human subject in need of treatment. For example, a biological sample can contain tumor cells from biopsy from a patient suffering from a solid tumor. A tumor biopsy can be obtained by a variety of means known in the art. Alternatively, a blood sample can be obtained from a patient suffering from a hematological cancer.

A biological sample can be obtained from a human subject having, suspected of having, or at risk of developing, a disease or disorder associated with CDK2. In some embodiments, the disease or disorder associated with CDK2 is a cancer (such as those described supra).

Methods for obtaining and/or storing samples that preserve the activity or integrity of molecules (e.g., nucleic acids or proteins) in the sample are well known to those skilled in the art. For example, a biological sample can be further contacted with one or more additional agents such as buffers and/or inhibitors, including one or more of nuclease, protease, and phosphatase inhibitors, which preserve or minimize changes in the molecules in the sample.

Methods of Administration and Dosage Forms

The precise amount of compound administered to provide an "effective amount" to the subject will depend on the mode of administration, the type, and severity of the cancer, and on the characteristics of the subject, such as general health, age, sex, body weight, and tolerance to drugs. The skilled artisan will be able to determine appropriate dosages depending on these and other factors. When administered in combination with other therapeutic agents, e.g., when administered in combination with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of Formula (I) or Formula (Ia) being used by following, for example, dosages reported in the literature and recommended in the *Physician's Desk Reference* (57th Ed., 2003).

"Treating" or "treatment" refers to obtaining a desired pharmacological and/or physiological effect. The effect can be therapeutic, which includes achieving, partially or substantially, one or more of the following results: partially or substantially reducing the extent of the disease, condition or cancer, ameliorating or improving a clinical symptom or indicator associated with the disease, condition or cancer, delaying, inhibiting or decreasing the likelihood of the progression of the disease, condition or cancer; or decreasing the likelihood of recurrence of the disease, condition or cancer.

The term "effective amount" means an amount when administered to the subject which results in beneficial or desired results, including clinical results, e.g., inhibits, suppresses or reduces the symptoms of the condition being treated in the subject as compared to a control. For example, a therapeutically effective amount can be given in unit dosage form (e.g., 0.1 mg to about 50 g per day, alternatively from 1 mg to about 5 grams per day; and in another alternatively from 10 mg to 1 gram per day).

The terms "administer", "administering", "administration", and the like, as used herein, refer to methods that may be used to enable delivery of compositions to the desired site of biological action. These methods include, but are not limited to, intraarticular (in the joints), intravenous, intramuscular, intratumoral, intradermal, intraperitoneal, subcutaneous, orally, topically, intrathecally, inhalationally, transdermally, rectally, and the like. Administration techniques that can be employed with the agents and methods described herein are found in e.g., Goodman and Gilman, *The Pharmacological Basis of Therapeutics*, current ed.; Pergamon; and Remington's, *Pharmaceutical Sciences* (current edition), Mack Publishing Co., Easton, Pa.

In addition, a compound of the disclosure, a pharmaceutically acceptable salt thereof or a pharmaceutical composition of the disclosure can be co-administered with other therapeutic agents. As used herein, the terms "co-administration", "administered in combination with", and their grammatical equivalents, are meant to encompass administration of two or more therapeutic agents to a single subject, and are intended to include treatment regimens in which the agents are administered by the same or different route of administration or at the same or different times. In some embodiments the one or more compounds of the disclosure, a pharmaceutically acceptable salt thereof or a pharmaceutical composition of the disclosure will be co-administered with other agents. These terms encompass administration of two or more agents to the subject so that both agents and/or their metabolites are present in the subject at the same time. They include simultaneous administration in separate compositions, administration at different times in separate compositions, and/or administration in a composition in which both agents are present. Thus, in some embodiments, the compounds described herein and the other agent(s) are administered in a single composition. In some embodiments, the compounds described herein and the other agent(s) are admixed in the composition.

The particular mode of administration and the dosage regimen will be selected by the attending clinician, taking into account the particulars of the case (e.g. the subject, the disease, the disease state involved, the particular treatment). Treatment can involve daily or multi-daily or less than daily (such as weekly or monthly etc.) doses over a period of a few days to months, or even years. However, a person of ordinary skill in the art would immediately recognize appropriate and/or equivalent doses looking at dosages of approved compositions for treating a disease using the disclosed CDK2 inhibitors for guidance.

The compounds of the disclosure or a pharmaceutically acceptable salt thereof can be administered to a patient in a variety of forms depending on the selected route of administration, as will be understood by those skilled in the art. The compounds of the present teachings may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration can be by continuous infusion over a selected period of time.

The pharmaceutical composition of the disclosure is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In preferred embodiments, the pharmaceutical composition is formulated for intravenous administration.

Typically, for oral therapeutic administration, a compound of the disclosure or a pharmaceutically acceptable salt thereof may be incorporated with excipient and used in the form of ingestible tablets, buccal tablets, troches, capsules, elixirs, suspensions, syrups, wafers, and the like.

Typically for parenteral administration, solutions of a compound of the disclosure can generally or a pharmaceutically acceptable salt thereof be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms.

Typically, for injectable use, sterile aqueous solutions or dispersion of, and sterile powders of, a compound of the disclosure for the extemporaneous preparation of sterile injectable solutions or dispersions are appropriate.

The following examples are intended to be illustrative and are not intended to be limiting in any way to the scope of the disclosure.

EXEMPLIFICATION

Preparation of Exemplary Compounds

Definitions

AcOH means acetic acid;
t-AmOH means tert-amyl alcohol;
Aq. means aqueous;
Bn means benzyl;
Boc means tert-butoxy carbonyl;
Boc$_2$O means di-tert-butyl dicarbonate;
(BPin)$_2$ means 4,4,4',4',5,5,5',5'-Octamethyl-2,2'-bi-1,3,2-dioxaborolane;
br means broad;
Brettphos means 2-(Dicyclohexylphosphino)3,6-dimethoxy-2',4',6'-triisopropyl-1,1'-biphenyl;
BrettPhos Pd G3 means [(2-Di-cyclohexylphosphino-3,6-dimethoxy-2',4',6'-triisopropyl-1,1'-biphenyl)-2-(2'-amino-1,1'-biphenyl)]palladium(II) methanesulfonate;
n-BuOH means butan-1-ol;
t-BuOH means tertiary butanol;
t-BuOK means potassium tert-butoxide;
t-BuXPhos Pd G3 means (2-Di-tert-butylphosphino-2',4',6'-triisopropyl-1,1'-biphenyl)-2-(2'-amino-1,1'-biphenyl) palladium(II) methanesulfonate;
° C. means degrees Celsius;
CDCl$_3$ means deutero-chloroform;
Cs$_2$CO$_3$ means cesium carbonate;
CuCN means copper cyanide;
δ means chemical shift;
d means doublet;
dd means doublet of doublets;
dq means doublet of quartets;
dt means doublet of triplets;
DAST means Diethylaminosulfur trifluoride;
DBU means 1,8-diazabicyclo[5.4.0]undec-7-ene;
DCM means dichloromethane;
DEA means diethylamine;
DEAD means diethyl azodicarboxylate;
DIAD means diisopropyl azodicarboxylate;
DIBAL-H means diisobutylaluminium hydride;
DIPEA means N-ethyldiisopropylamine or N,N-diisopropylethylamine;
DMA means N,N-Dimethylacetamide;
DMF means N,N-dimethylformamide;
DMSO means Dimethylsulfoxide;
DMSO-d$_6$ means hexadeuterodimethyl sulfoxide;
EA means ethyl acetate;
Et means ethyl;
Et$_2$O means diethyl ether;
EtOAc means ethyl acetate;
EtOH means ethanol;
Eq. means equivalent;
g means gram;
HATU means 1-[bis(dimethylamino)methylene]-1H-1,2,3-triazolo[4,5-b]pyridinium 3-oxid hexafluorophosphate;
HBF$_4$ means tetrafluoroboric acid;
HCl means hydrochloric acid;
HCOH means formaldehyde;
HCO$_2$H means formic acid;
Hept means heptet;
$^1$H NMR means proton nuclear magnetic resonance;
H$_2$O means water;
H$_2$O$_2$ means hydrogen peroxide;
HPLC means high pressure liquid chromatography;
h means hour;
IPA means 2-propanol;
K$_2$CO$_3$ means potassium carbonate;
KI means potassium iodide;
KOH means potassium hydroxide;
K$_3$PO$_4$ means potassium phosphate tribasic;
L means litre;
LCMS means liquid chromatography mass spectrometry;
LDA means lithium diisopropylamide;
LiAlH$_4$ means lithium aluminium hydride;
LiOH means lithium hydroxide;
m means multiplet;
M means molar;
Me means methyl;
MeCN means acetonitrile;
MeI means iodomethane;
MeLi means methyl lithium;
MeMgBr means methyl magnesium bromide;
MeNH$_2$ means methylamine;
MeOH means methanol;
MeOH-d$_4$ means deutero-methanol;
mg means milligram;
MgSO$_4$ means magnesium sulfate;
MHz means mega Hertz;
mins means minutes;
mL means millilitres;
mmol means millimole;
MPLC means medium pressure liquid chromatography;
MS m/z means mass spectrum peak;
MTBE means methyl tert-butyl ether,
N$_2$ means nitrogen;
NaBH$_4$ means sodium borohydride;
Na$_2$CO$_3$ means sodium carbonate;
NaH means sodium hydride;
NaHCO$_3$ means sodium bicarbonate;
NaOH means sodium hydroxide;
Na$_2$SO$_4$ means sodium sulfate;
NCS means N-chlorosuccinimide;
NH$_3$ means ammonia;
NH$_4$Cl means ammonium chloride;

NH$_4$HCO$_3$ means ammonium carbonate;
NH$_2$OH means hydroxylamine;
NH$_4$OH is ammonium hydroxide;
NMP means N-methyl pyrrolidine;
PE means petroleum ether,
Pd(amphos)Cl$_2$ means Bis(di-tert-butyl(4-dimethylaminophenyl)phosphine)dichloropalladium(II);
Pd(t-Bu$_3$P)$_2$ means Bis(tri-tert-butylphosphine)palladium (0);
Pd(OAc) means palladium acetate;
Pd$_2$(dba)$_3$ means tris(dibenzylideneacetone)dipalladium (0);
Pd(dppf)Cl$_2$ means [1,1'-bis(diphenylphosphino)ferrocene]dichloropalladium(II);
Pd(PPh$_3$)$_4$ means tetrakis(triphenylphosphine)palladium (0);
Pd(PPh$_3$)Cl$_2$ means Palladium(II)bis(triphenylphosphine) dichloride;
Pd/C means palladium on charcoal;
Pd(OH)$_2$ means palladium hydroxide;
PPh$_3$ means triphenylphosphine;
q means quartet;
rt means room temperature;
RT means retention time;
RuPhos Pd G3 means (2-dicyclohexylphosphino-2',6'-diisopropoxy-1,1'-biphenyl)[2-(2'-amino-1,1'-biphenyl)]palladium(II) methanesulfonate;
s means singlet;
sat. means saturated;
SFC means supercritical fluid chromatography;
soln. means solution;
t means triplet;
TBAF means Tetrabutylammonium fluoride;
TBDMSCl means tert-Butyl(chloro)dimethylsilane;
TEA means triethylamine;
TFA means trifluoroacetic acid;
TfOH means trifluoroethanesulfonic acid;
THF means tetrahydrofuran;
TLC means thin layer chromatography;
TsOH means p-toluenesulfonic acid;
μL means micro litres;
μmol means micromole;
Xantphos means 4,5-Bis(diphenylphosphino)-9,9-dimethylxanthene;
Xantphos Pd G2 means Chloro[(4,5-bis(diphenylphosphino)-9,9-dimethylxanthene)-2-(2'-amino-1,1'-biphenyl)]palladium(II);
Xantphos Pd G3 means [(4,5-Bis(diphenylphosphino)-9,9-dimethylxanthene)-2-(2'-amino-1,1'-biphenyl)]palladium(II) methanesulfonate;
XPhos Pd G2 means Chloro(2-dicyclohexylphosphino-2',4',6'-triisopropyl-1,1'-biphenyl)[2-(2'-amino-1,1'-biphenyl)]palladium(II).

Methods for preparing compounds of the invention can be carried out in suitable solvents which can be readily selected by one of skill in the art of organic synthesis. Suitable solvents can be substantially non-reactive with the starting materials (reactants), intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 5th ed., John Wiley & Sons: New Jersey, (2014), which is incorporated herein by reference in its entirety.

Reactions can be monitored according to any suitable method known in the art. For example, product formation can be monitored by spectroscopic means, such as nuclear magnetic resonance (NMR) spectroscopy (e.g., 1H or 13C), infrared (IR) spectroscopy, spectrophotometry (e.g., UV-visible), mass spectrometry (MS), or by chromatographic methods such as high performance liquid chromatography (HPLC) or thin layer chromatography (TLC). Analytical instruments and methods for compound characterization:

LC-MS: The liquid chromatography-mass spectrometry (LC-MS) data were obtained with an Agilent Technologies 1200 Series LCMSD utilizing API-ESI ionization fitted with a reverse-phase column (Sunfire C18, 3.5 um particle size, 4.6×50 mm dimensions) at 50 degrees Celsius. The mobile phase consisted of a mixture of solvent 0.01% TFA in water and 0.01% TFA in acetonitrile. A constant gradient from 5% increase to 95% organic within 1.3 min, 95% organic for 1.7 min was utilized. The flow rate was constant at 2 mL/min. Alternatively, the liquid chromatography-mass spectrometry (LC-MS) data were obtained with a Agilent Technologies 1200 Series LCMSD utilizing API-ESI ionization utilizing ESI ionization fitted with a reverse-phase column (XBridge C18, 3.5 um particle size, 4.6×50 mm dimensions) at 45 degrees Celsius. The mobile phase consisted of a mixture of solvent 10 mM NH4HCO3 in water and acetonitrile. A constant gradient from 5% increase to 95% organic within 1.4 min, 95% organic for 1.6 min was utilized. The flow rate was constant at 1.8 mL/min.

Prep LC-MS: Preparative HPLC was performed on a Gilson 281 Preparative system fitted with a Welch Xtimate 10 u C18 100 A, AXIA packed, 250×21.2 mm reverse-phase column at 20 degrees Celsius. The mobile phase consisted of a mixture of solvent 0.1% formic acid in water and 0.1% formic acid in acetonitrile. A constant gradient from 70% aqueous/30% organic to 30% aqueous/70% organic mobile phase over the course of 15 minutes was utilized. The flow rate was constant at 30 mL/min. Alternatively, fitted with Column: Welch Xtimate 10 u C18 21.2*250 mm, 10 um; The mobile phase consisted of a mixture of solvent Water (10 mmol/L NH4HCO3+0.05% NH3·H2O) and acetonitrile. A constant gradient from 70% aqueous/30% organic to 30% aqueous/70% organic mobile phase over the course of 15 minutes was utilized. The flow rate was constant at 30 mL/min.

Silica gel chromatography: Silica gel chromatography was performed on a Biotage® Isolera One unit, or a Biotage® Isolera Prime unit.

Proton NMR: 1H NMR spectra were obtained with a Bruker AVANCE III 400 MHz, 400 MHz NMR instrument (acquisition time=3.16 seconds with a 1 second delay; 8 to 32 scans) or a Bruker AVANCE III 400 MHz, 400 MHz NMR instrument (acquisition time=3.98 seconds with a 1 second delay; 8 to 32 scans) or a Bruker AVANCE III 500 MHz, 500 MHz NMR instrument (acquisition time=3.17 seconds with a 1 second delay; 8 to 32 scans). Unless otherwise indicated, all protons were reported in DMSO-d6 solvent as parts-per million (ppm) with respect to residual DMSO (2.50 ppm).

SFC: Waters Preparative system (SFC80, SFC150, SFC200, SFC350).

Chiral-HPLC: Gilson 281 (vendor: GILSON)

One of ordinary skill in the art will recognize that modifications of the gradient, column length, and flow rate are possible and that some conditions may be more suitable for compound characterization than others, depending on the chemical species being analyzed.

The following codes refer to the preparative HPLC conditions used as indicated in the Preferred Examples and Preparation sections. Individual gradients were optimized for each compound as appropriate.

| Prep-HPLC Code | Conditions |
| --- | --- |
| HPLC-1 | Xtimate 150A, 21.2 × 250 mm, 10 mm; 15-95% MeCN/H$_2$O (0.1% NH$_4$HCO$_3$) |
| HPLC-2 | Xtimate 150A, 21.2 × 250 mm, 10 mm; 15-95% MeCN/H$_2$O (0.1% NH$_4$HCO$_3$ + NH$_4$OH) |
| HPLC-3 | Xtimate 150A, 21.2 × 250 mm, 10 mm; 15-95% MeCN/H$_2$O (10 mM NH$_4$HCO$_3$) |
| HPLC-4 | Xtimate 150A, 21.2 × 250 mm, 10 mm; 15-95% MeCN/H$_2$O (10 mM NH$_4$HCO$_3$ + NH$_4$OH) |
| HPLC-5 | Xtimate 150A, 21.2 × 250 mm, 10 mm; 15-95% MeCN/H$_2$O (0.1% HCO$_2$H) |

General Schemes

According to a first process, compounds of Formula (I') may be prepared from the compounds of Formulae (II') and (III'), as illustrated by Scheme 1.

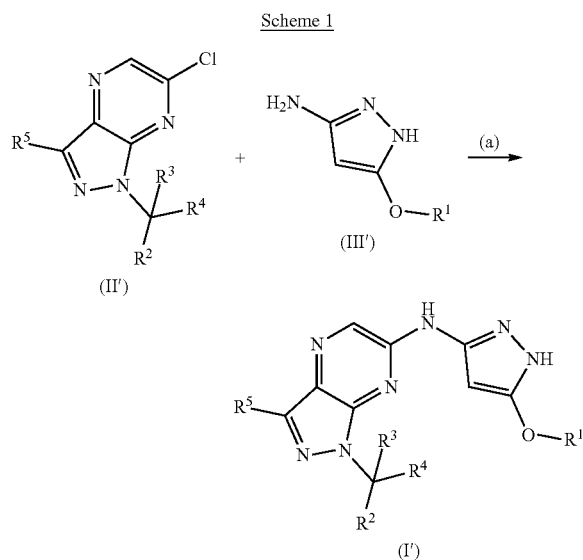

The compound of Formula (I') may be prepared from the compounds of Formulae (II') and (III') according to process step (a) a Buchwald-Hartwig cross-coupling. Typical conditions comprise, reaction of the amine of Formula (III') with the chloride of Formula (II') in the presence of a suitable inorganic base, a suitable catalyst in a suitable solvent at elevated temperature. Preferred conditions comprise, reaction of the compounds of Formulae (II') and (III') in the presence of, BrettPhos Pd G3, tBuBrettPhos Pd G3, BrettPhos Pd G4, tBuBrettPhos Pd G4, t-BuXphos Pd G3, tBuXPhos Pd G4, or Xantphos Pd G3 or Pd$_2$(dba)$_3$/tBuXPhos in the presence of a suitable base such as Cs$_2$CO$_3$, K$_2$CO$_3$, K$_3$PO$_4$ or KOAc in a suitable solvent such as dioxane, toluene, t-AmOH, NMP or DMF, at between 90° C. and 130° C.

According to a second process, the compound of Formula (II') may be prepared from the compounds of Formulae (IV') and (V'), as illustrated in Scheme 2.

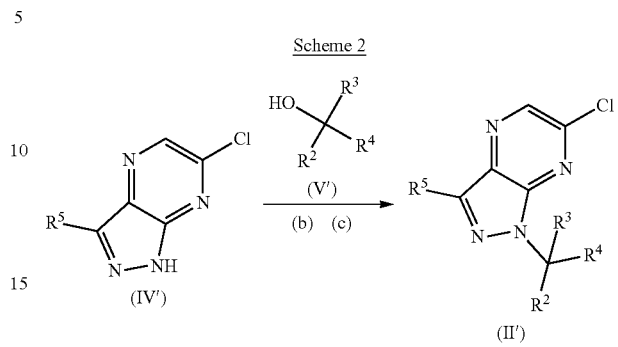

The compound of Formula (II'), wherein at least one of R$^3$ or R$^4$ is H, may be prepared from the compounds of Formulae (IV') and (V') according to process step (b) a Mitsunobu reaction. Typical conditions comprise reaction of the compound of Formula (IV') with the alcohol of Formula (V') in the presence of a suitable azodicarboxylate, such as DIAD or DEAD, in the presence of PPh$_3$, in a suitable solvent such as THF or toluene at between 0° C. and 80° C.

Alternatively, wherein, both R$^3$ and R$^4$ are not H, the compound of Formula (II') may be prepared from the compounds of Formulae (IV') and (V') according to process step (c), an alkylation reaction. Typical conditions comprise reaction of the compounds of Formulae (IV') and (V') in the presence of an acid catalyst, such as TfOH, in a suitable polar aprotic solvent, such as DCM at between 0° C. and rt.

According to a third process, the compound of Formula (II') may be prepared from the compounds of Formulae (IV') and (VI'), as illustrated in Scheme 3.

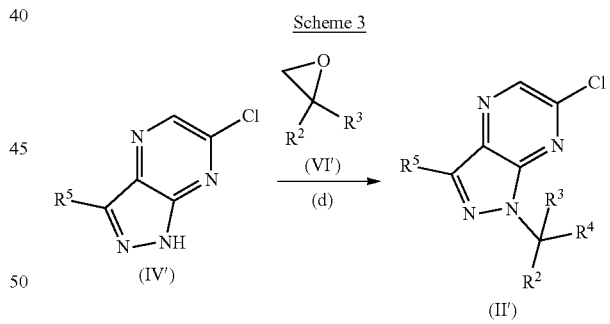

The compound of Formula (II') may be prepared from the compounds of Formulae (IV') and (VI') by process step (d), an epoxide opening reaction. Typical conditions comprise reaction of the compounds of Formulae (IV') and (VI') in the presence of a suitable inorganic base, such as K$_2$CO$_3$, in a suitable polar aprotic solvent, such as MeCN at between rt and elevated temperature, such as 90° C.

The compounds of Formulae (II'), (IV'), (V') and (VI') are either commercially available or may be prepared by analogy to methods known in the literature, or the methods described in the Experimental section below.

Compounds of Formulae (I'), (II') and (IV') may be converted to alternative compounds of Formulae (I'), (II') and (IV') by standard chemical transformations, known to those skilled in the art. Examples of these transformations include, but are not limited to:

Reduction of a ketone to a secondary alcohol using NaBH$_4$, fluorination, using selectflor or DAST, chlorination using NCS in conjunction with HBF$_4$, transformation of aryl iodides to ketones using Stille methodology or transformation of an iodo group to a nitrile, using CuCN.

It will be appreciated by those skilled in the art, that it may be necessary to utilise a suitable protecting group strategy for the preparation of compounds of Formula (I'). Typical protecting groups may comprise, carbamate and preferably Boc for the protection of amines, including pyrazoles, or a TIPS or benzyl group for the protection of a primary or secondary alcohol, It will be further appreciated that it may be necessary or desirable to carry out the transformations in a different order from that described in the schemes, or to modify one or more of the transformations, to provide the desired compound of the invention.

Preparations

Preparation 1.
3,6-dichloro-1H-pyrazolo[3,4-b]pyrazine

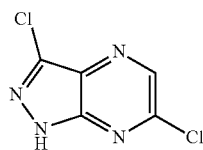

BF$_4$ (852 mg, 9.71 mmol) followed by NCS (864 mg, 6.47 mmol) were added to a suspension of 6-chloro-1H-pyrazolo[3,4-b]pyrazine (500 mg, 6.47 mmol) in MeCN (12 mL) and the reaction heated at 90° C. overnight. The cooled mixture was concentrated in vacuo and 1M NaOH (9.5 mL) was added to neutralize the solution. The resulting suspension was filtered off, washed with water, and dried to afford the title compound, 596 mg, as a pale-yellow solid. LCMS m/z=191 [M+H]$^+$.

Preparation 2. 6-chloro-3-iodo-1H-pyrazolo[3,4-b]pyrazine

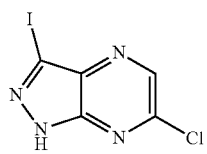 [SMILES: Clc1cnc2c(I)n[nH]c2n1]

HBF$_4$ (1.704 g, 194 mmol) and 1-iodopyrrolidine-2,5-dione (2.91 g, 12.9 mmol) were added to a solution of 6-chloro-1H-pyrazol[3,4-b]pyrazine (1.0 g, 6.47 mmol) in MeCN and the reaction heated to 80° C. for 2 h. The cooled reaction was concentrated in vacuo, the residue diluted with water, then NaOH (2.5 mL) and sodium thiosulfate added until the reddish color had turned to consistently pale yellow. The mixture was filtered, washed with water and dried to give the title compound, 1.71 g, 94% yield. LCMS m/z=281 [M+H]$^+$.

Preparation 3. 6-chloro-3-fluoro-1H-pyrazolo[3,4-b]pyrazine

A mixture of 6-chloro-1H-pyrazolo[3,4-b]pyrazine (500 mg, 3.23 mmol) and Selectfluor (2.28 g, 6.46 mmol) in MeCN (8 mL) and water (2 mL) was stirred at 100° C. in a sealed tube for 15 h. The cooled reaction mixture was concentrated in vacuo and the residue was purified by flash chromatography on silica gel eluting with EtOAc/PE (1/1) to afford the title compound (120 mg, 22% yield) as a yellow solid. LCMS m/z=173 [M+H]$^+$.

Preparation 4. methyl (2S)-2-((tetrahydro-2H-pyran-2-yl)oxy)propanoate

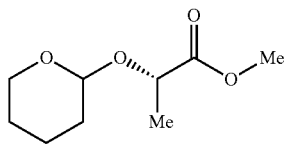 [SMILES: COC(=O)[C@H](C)OC1CCCCO1]

A mixture of methyl (S)-2-hydroxypropanoate (10.0 g, 96.1 mmol), 3,4-dihydro-2H-pyran (8.08 g, 96.1 mmol) and TsOH (1.65 g, 9.61 mmol) in DCM (100 mL) was stirred for 3 h. The reaction mixture was washed with water and brine, dried over Na$_2$SO$_4$, filtered, and concentrated in vacuo. The residue was purified by flash chromatography on silica gel eluting with EtOAc/PE (1/30) to give the title compound (9.70 g, 53% yield) as a yellow oil.

Preparation 5. methyl (2R)-2-((tetrahydro-2H-pyran-2-yl)oxy)propanoate

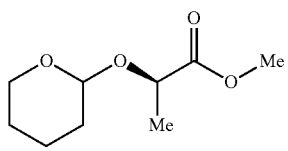 [SMILES: COC(=O)[C@@H](C)OC1CCCCO1]

The title compound was obtained as a yellow oil, 97.7 g, 53% from methyl (R)-2-hydroxypropanoate, following the procedure described in Preparation 4.

Preparation 6. (2S)-2-((tetrahydro-2H-pyran-2-yl)oxy)pentan-3-ol

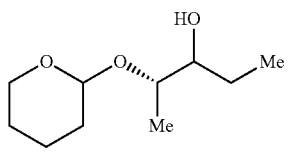 [SMILES: CCC(O)[C@H](C)OC1CCCCO1]

To a mixture of methyl (2S)-2-((tetrahydro-2H-pyran-2-yl)oxy)propanoate (Preparation 4, 700 mg, 3.72 mmol) in toluene (30 mL) was added dropwise DIBAL-H (1.5 M/toluene, 2.8 mL, 4.2 mmol) at −78° C. under N₂ and the mixture stirred at −70° C. for 30 min. Ethyl magnesium bromide (1.0 M in THF, 6.0 mL, 6.0 mmol) was added, the reaction stirred at −70° C. for 20 min and slowly warmed to rt. The reaction mixture was poured into ice-water and aqueous HCl (10%) added until all precipitate was dissolved. The aqueous phase was extracted with THF/toluene, and the combined organic layers were washed with water, aqueous NaOH (1 M) and brine, dried over MgSO₄, filtered and the filtrate was concentrated in vacuo. The residue was purified by flash chromatography on silica gel eluting with EtOAc/PE (1/5) to give the title compound (600 mg, 85% yield) as a yellow oil.

Preparation 7. (2R)-2-((tetrahydro-2H-pyran-2-yl)oxy)pentan-3-ol

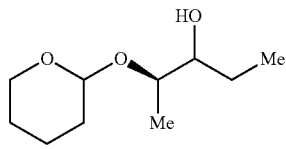 [SMILES: CCC(O)[C@@H](C)OC1CCCCO1]

The title compound was obtained as a yellow oil, 600 mg, 85%, from methyl (2R)-2-((tetrahydro-2H-pyran-2-yl)oxy)propanoate (Preparation 5), following the procedure described in Preparation 7.

Preparation 8. 4-vinyltetrahydro-2H-pyran

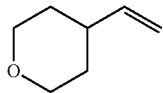

To a mixture of sodium hydride (2.08 g, 52.5 mmol) in THF (25 mL) was added methyltriphenylphosphanium bromide (18.70 g, 52.5 mmol), and the mixture heated at reflux for 2 h. After cooling to rt, oxane-4-carbaldehyde (5.00 g, 43.8 mmol) was added and the reaction stirred at rt for 15 h. The reaction was diluted with ether and washed with aq. NaHCO₃ and brine. The organic layer was concentrated in vacuo and the residue purified by flash chromatography on silica gel eluting with EtOAc/PE (1/5) to give the title compound (0.9 g, 18% yield) as a colorless oil. 1H-NMR (500 MHz, DMSO-d₆) δ ppm 5.83-5.75 (m, 1H), 5.02-4.93 (m, 2H), 3.85-3.82 (m, 2H), 3.34-3.29 (m, 2H), 2.19-2.14 (m, 1H), 1.32-1.24 (m, 4H).

Preparation 9. (S)-1-(tetrahydro-2H-pyran-4-yl)ethane-1,2-diol

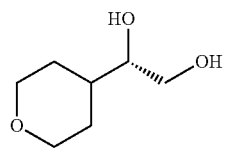

To a mixture of AD-mix-alpha (12.7 g, 16 mmol) in t-BuOH:H₂O 1:1 (150 mL) was added 4-vinyltetrahydro-2H-pyran (Preparation 8, 0.9 g, 8 mmol) at 0° C. and the solution was allowed to warm to rt. The reaction was covered with aluminum foil to exclude light and then stirred at rt for two days. The mixture was cooled to 0° C., sodium sulfite (15 g) was added and the mixture stirred at rt for 1 h. EtOAc was added, the layers were separated and the aqueous layer extracted with EtOAc (2×) and DCM:MeOH 10:1. The combined organic layers were dried, and evaporated under reduced pressure to give the title compound (0.6 g, 51% yield) as a yellow oil. LCMS m/z=147 [M+H]⁺.

Preparation 10. (S)-1-(tetrahydro-2H-pyran-4-yl)-2-((triisopropylsilyl)oxy)ethan-1-ol

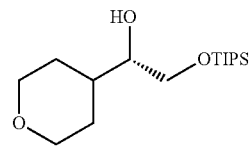

To a mixture of (1S)-1-(tetrahydro-2H-pyran-4-yl)ethane-1,2-diol (Preparation 9, 600 mg, 4.10 mmol) and 1H-imidazole (830 mg, 12.2 mmol) in DCM (6 mL) was added chlorotris(propan-2-yl)silane (790 mg, 4.10 mmol) at 0° C., and the reaction stirred at rt for 15 h. The reaction mixture was diluted with DCM and washed with water. The organic layer was evaporated in vacuo and the residue was purified by flash chromatography on silica gel eluting with EtOAc/PE (1/5) to give the title compound (0.7 g, 56% yield) as a yellow oil. LCMS m/z=303 [M+H]⁺.

Preparation 11. 2,2-difluoro-1-(tetrahydro-2H-pyran-4-yl)ethan-1-ol

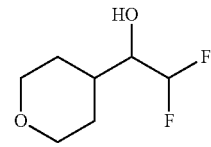 [SMILES: OC(C(F)F)C1CCOCC1]

A mixture of tetrahydro-2H-pyran-4-carbaldehyde (500 mg, 4.38 mmol), (difluoromethyl)trimethylsilane (543 mg, 4.38 mmol) and CsF (1.99 g, 13.14 mmol) in DMF (5 mL) was stirred overnight. TBAF (5 equiv.) was added and the reaction stirred at rt for 1 h. The reaction was quenched with water and extracted with EtOAc. The combined organic layer was washed with water and brine, dried over Na₂SO₄, filtered, and concentrated in vacuo. The residue was purified by flash chromatography on silica gel eluting with EtOAc/PE (1/4) to give the title compound (230 mg, 31% yield). LCMS m/z=167 [M+H]⁺.

Preparation 12. 1-(tetrahydro-2H-pyran-3-yl)ethan-1-ol

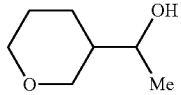

To a solution of tetrahydro-2H-pyran-3-carbaldehyde (500 mg, 4.38 mmol) in THF (20 mL) was added MeMgBr (1 M in THF, 4.4 mL, 4.4 mmol) at 0° C. and the reaction stirred for 30 min at this temperature and then allowed to warm to rt and stirred for a further 2 h. The resulting mixture was quenched with water and extracted with EtOAc. The organic layer was evaporated under reduced pressure to give the crude title compound which was used in next step directly.

Preparation 13. 2-(oxiran-2-yl)pyridine

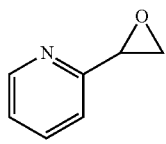

To a solution of H₂O (25 mL) and dioxane (90 mL) was added 2-ethenylpyridine (14 g, 133 mmol) and AcOH (7.98 g, 133 mmol), then 1-bromopyrrolidine-2,5-dione (25.9 g, 146 mmol) was slowly added and the mixture stirred for 1 h. Na₂CO₃ (42.2 g, 399 mmol) was added and the reaction stirred for 1 h. The mixture was diluted with EtOAc and washed with water. The organic layer was concentrated in vacuo to about 20 mL, and then purified by flash chromatography on silica gel eluting with EtOAc/PE (1/2) to give the title compound (14 g, 87%) as a yellow oil. LCMS m/z=122 [M+H]⁺.

Preparation 14. 3-(oxiran-2-yl)pyridine

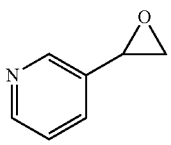

The title compound was obtained as a yellow oil, 4 g, 35% yield, from 3-ethenylpyridine, following the procedure described in Preparation 13. LCMS m/z=122 [M+H]⁺.

Preparation 15. 2-fluoro-1-(pyridin-2-yl)ethan-1-ol

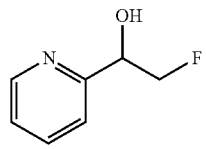

A mixture of 2-(oxiran-2-yl)pyridine (Preparation 13, 8 g, 66.0 mmol) and 1M TBAF/THF (120 mL) was heated under reflux for 1 day. The cooled reaction mixture was diluted with EtOAc and washed with water. The organic layer was concentrated in vacuo to about 20 mL, and then purified by flash chromatography on silica gel eluting with EtOAc/PE (1/3) to give the title compound (1 g, 11% yield) as a yellow oil. LCMS m/z=142 [M+H]⁺.

Preparation 16. 2-fluoro-1-(pyridin-3-yl)ethan-1-ol

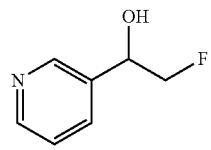

The title compound was obtained as a yellow oil, 120 mg, 3% yield from 3-(oxiran-2-yl)pyridine (Preparation 14), following the procedure described in Preparation 15. LCMS m/z=142 [M+H]⁺.

Preparation 17. 1-(4-fluoropyridin-3-yl)ethan-1-one

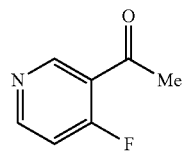

Part 1. To a solution of 4-fluoropyridine-3-carboxylic acid (300 mg, 2.12 mmol), methoxy(methyl)amine hydrochloride (310 mg, 3.18 mmol) and DIPEA (548 mg, 4.24 mmol) in DMF (5 mL) was added HATU (965 mg, 2.54 mmol) and the reaction stirred at rt for 15 h. The reaction mixture was concentrated in vacuo, and the residue purified by flash chromatography on silica gel eluting with EtOAc/PE (1/1) to give 4-fluoro-N-methoxy-N-methylnicotinamide (250 mg, 64% yield) as a yellow solid.

Part 2. To a mixture of 4-fluoro-N-methoxy-N-methylpyridine-3-carboxamide (Part 1, 200 mg, 1.08 mmol) in THF (5 mL) was added MeMgBr (2M in THF, 2.2 mL, 4.4 mmol) at 0° C. and the reaction stirred at rt for 2 h. The reaction mixture was quenched with saturated aqueous NH₄Cl and extracted with EtOAc. The organic layer was concentrated, and the residue was purified by flash chromatography on silica gel eluting with EtOAc/PE (1/1) to give the title compound (150 mg, 80% yield) as a yellow oil. LCMS m/z=140 [M+H]⁺.

Preparation 18. 1-(4-fluoropyridin-3-yl)ethan-1-ol

To a mixture of 1-(4-fluoropyridin-3-yl)ethan-1-one (Preparation 17, 150 mg, 1.07 mmol) in MeOH (4 mL) was added NaBH₄ (162 mg, 4.28 mmol) and the reaction stirred at rt for 10 min. The reaction mixture was diluted with EtOAc and washed with water. The organic layer was concentrated in vacuo, and the residue was purified by flash chromatography on silica gel eluting with EtOAc/PE (2/1) to give the title compound (100 mg, 66% yield) as a yellow oil. LCMS m/z=142 [M+H]⁺.

Preparation 19. 1-(4-fluoropyridin-2-yl)ethan-1-ol

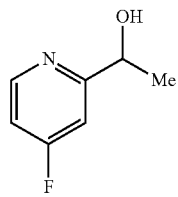

To a solution of 4-fluoropyridine-2-carbaldehyde (2.5 g, 19.9 mmol) in THF (50 mL) at 0° C., was added MeMgBr (2M in THF, 15 mL, 30 mmol) and the reaction stirred for 2 h. The reaction mixture was quenched with saturated aqueous NH$_4$Cl and extracted with EtOAc. The organic layer was concentrated in vacuo and the residue was purified by flash chromatography on silica gel eluting with EtOAc/PE (2/1) to afford the title compound (1.7 g, 64%) as a yellow oil. LCMS m/z=142 [M+H]$^+$.

Preparation 20 and 21. (S)-2-fluoro-1-phenylethan-1-ol and (R)-2-fluoro-1-phenylethan-1-ol

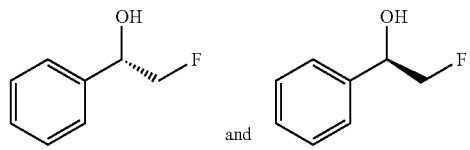 [SMILES: O[C@H](CF)c1ccccc1 ; O[C@@H](CF)c1ccccc1]

A mixture of styrene (10.0 g, 96.01 mmol) and selectfluor reagent (51.0 g, 144.02 mmol) in MeCN/H$_2$O (100 mL/50 mL) was heated at 90° C. overnight under N$_2$. The reaction mixture was concentrated in vacuo and the residue was extracted with EtOAc. The combined organic layers were washed with water and brine, dried over Na$_2$SO4, filtered and concentrated. The residue was purified by flash chromatography on silica gel eluting with EtOAc/PE (1/20~1/5) to give 2-fluoro-1-phenylethan-1-ol (2.50 g, 73% yield) as a yellow oil. 1H-NMR (400 MHz, DMSO-d$_6$) δ ppm: 7.40-7.25 (m, 5H), 5.72 (d, 1H), 4.86-4.80 (m, 1H), 4.50-4.01 (m, 2H).

This was further purified by SFC using an OD-H 20×250 mm, 10 μm (Daicel) column, mobile phase: CO$_2$/MeOH (0.2% MeOH/NH$_3$)=85/15 at 70 g/min to provide:

Enantiomer 1: (S)-2-fluoro-1-phenylethan-1-ol or (R)-2-fluoro-1-phenylethan-1-ol, 300 mg.

Enantiomer 2: (R)-2-fluoro-1-phenylethan-1-ol or (S)-2-fluoro-1-phenylethan-1-ol (300 mg).

Preparation 22. oxetan-3-yl(phenyl)methanol

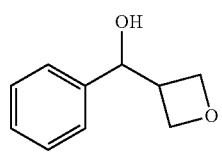 [SMILES: OC(c1ccccc1)C1COC1]

To a solution of oxetane-3-carbaldehyde (500 mg, 5.80 mmol) in THF (10 mL) was added phenyl lithium (13 mL, 17.4 mmol) slowly at −78° C. under N$_2$ and the reaction stirred at −78° C. for 30 min and a further 2 h at rt. The reaction mixture was quenched with sat. aq. NH$_4$Cl solution and extracted with EtOAc. The organic layer was evaporated under reduced pressure to give the title compound (1.2 g, crude).

Preparation 23. (S)-1-phenyl-2-((triisopropylsilyl)oxy)ethan-1-ol

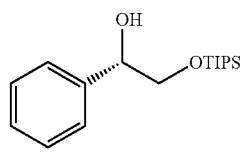

To a mixture of (S)-1-phenylethane-1,2-diol (1.50 g, 10.8 mmol) and 1H-imidazole (2.20 g, 32.5 mmol) in DMF (10 mL) was added dropwise chlorotriisopropylsilane (2.09 g, 10.8 mmol) at 25° C., and the reaction stirred overnight. The reaction was diluted with DCM, washed with water and brine, dried over Na$_2$SO$_4$, filtered, and concentrated in vacuo. The residue was purified by flash chromatography on silica gel eluting with EtOAc/PE (1/30) to give the title compound (900 mg, 28% yield) as a yellow oil.

Preparation 24. 4-((triisopropylsilyl)oxy)butan-2-ol

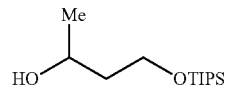

To a mixture of butane-1,3-diol (2 g, 22.1 mmol) and 1H-imidazole (4.51 g, 66.3 mmol) in DCM (30 mL) was added chlorotris(propan-2-yl)silane (4.26 g, 22.1 mmol) at 0° C., and the reaction stirred at rt for 15 h. The reaction mixture was diluted with DCM, washed with water and the organic layer was concentrated in vacuo. The residue was purified by flash chromatography on silica gel eluting with EtOAc/PE (1/5) to give the title compound (2 g, 37% yield) as a colorless oil. LCMS m/z=247 [M+H]$^+$.

Preparation 25. (S)-1-(pyridin-3-yl)ethane-1,2-diol

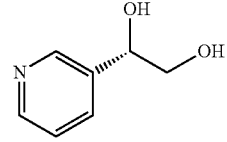

The title compound was obtained as a yellow oil, 700 mg, 38% yield, from 3-vinylpyridine following a similar procedure to that described in Preparation 9. LCMS m/z=140 [M+H]$^+$.

Preparation 26. (S)-1-(pyridin-3-yl)-2-((triisopropyl-silyloxy)ethan-1-ol

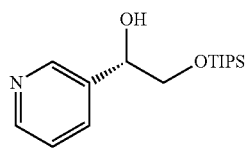

The title compound was obtained as a yellow oil, 700 mg, 47% yield, from (1S)-1-(pyridin-3-yl)ethane-1,2-diol (Preparation 25), following the method described in Preparation 23. LCMS m/z=296 [M+H]⁺.

Preparation 27. (2-(4,4,5,5-tetramethyl-1,3,2-dioxaborolan-2-yl)cyclopropyl)methanol

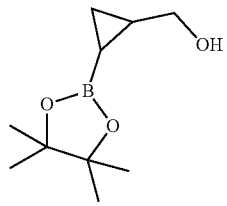

To a solution of ethyl 2-(4,4,5,5-tetramethyl-1,3,2-dioxaborolan-2-yl)cyclopropane-1-carboxylate (300 mg, 1.24 mmol) in THF (20 mL) was added LiAlH₄ (150 mg, 3.72 mmol) at 0° C. and the reaction stirred for 18 h. The reaction mixture was quenched with Na₂SO₄·10H₂O, the mixture filtered and the filtrate was evaporated under reduced pressure to give the title compound (206 mg, crude) as a yellow oil which was used in the next step directly.

Preparation 28. methyl 2-(hydroxymethyl)-4-methyl-4-nitropentanoate

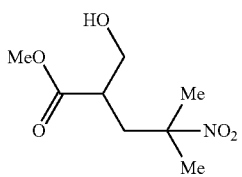 [SMILES: COC(=O)C(CO)CC(C)(C)[N+](=O)[O-]]

To a solution of 2-nitropropane (917 mg, 10.3 mmol) in THF (8 mL) was added DBU (131 mg, 0.861 mmol). After stirring at 65° C. for 10 mins, methyl 2-(hydroxymethyl) prop-2-enoate (1 g, 8.61 mmol) was added dropwise. The reaction mixture was stirred at 80° C. for 2 h, then at 25° C. for 16 h. The reaction was diluted with EtOAc, washed with water and brine and the organic layer was concentrated in vacuo. The residue was purified by flash chromatography on silica gel eluting with EtOAc/PE (1/4) to afford the title compound (900 mg, 51% yield) as a yellow oil.

Preparation 29. 3-(hydroxymethyl)-5,5-dimethylpyrrolidin-2-one

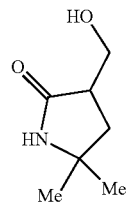

To a solution of methyl 2-(hydroxymethyl)-4-methyl-4-nitropentanoate (Preparation 28, 350 mg, 1.70 mmol) in EtOH (5 mL) was added Raney Ni (100 mg) and the reaction was stirred at 25° C. under 2 bar of H₂ for 16 h. The reaction was filtered and the filtrate was evaporated under reduced pressure to afford the title compound (200 mg, 82% yield) as a white solid. LCMS m/z=144 [M+H]⁺.

Preparation 30. tert-butyl 3-amino-5-(difluoromethoxy)-1H-pyrazole-1-carboxylate

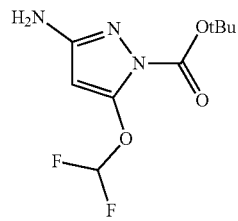

To a solution of 5-(difluoromethoxy)-1H-pyrazol-3-amine (24 g, 64.39 mmol, 40% purity) in DCM (200 mL), was added KOH (4.5 M, 114.47 mL) and Boc₂O (28.10 g, 128.77 mmol) and the reaction was heated at 50° C. for 16 h. The reaction mixture was extracted with DCM (40 mL×3), the combined organic layers were washed with brine (40 mL×3), dried over Na₂SO₄, filtered and concentrated under reduced pressure. The residue was purified by flash silica gel chromatography (ISCO 0~13% EtOAc/PE) to give the title compound (5 g, 31.16% yield) as a white solid. 1H NMR (400 MHz, DMSO-d₆) δ ppm 7.52-7.11 (m, 1H), 6.66 (br s, 2H), 5.12 (s, 1H), 1.52-1.61 (m, 9H).

Preparation 31. (S)-6-chloro-1-(1-(2-fluoropyridin-3-yl)ethyl)-1H-pyrazolo[3,4-b]pyrazine

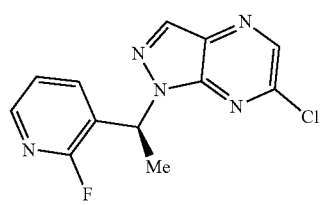 [SMILES: C[C@@H](c1cccnc1F)n1ncc2ncc(Cl)nc21]

A mixture of 6-chloro-1H-pyrazolo[3,4-b]pyrazine (400 mg, 2.59 mmol), (R)-1-(2-fluoropyridin-3-yl)ethan-1-ol (438 mg, 3.11 mmol) and PPh₃ (815 mg, 2.59 mmol) in THF (8 mL) was cooled in an ice bath. DIAD (628 mg, 3.11 mmol) was added dropwise and the reaction allowed to warm slowly to rt and stirred overnight. The mixture was concentrated in vacuo and the residue pre-loaded onto silica gel and purified by Isco chromatography (0 to 60% EtOAc/Hex) to give a colorless oil. This was further purified by reverse phase Isco (0 to 100% MeCN/0.1% aq. TFA). The product was neutralized using NaHCO₃ and extracted with DCM (3×). The combined organic extracts were evaporated under reduced pressure to afford the title compound as a colorless oil, 320 mg, 44.6% yield. LCMS m/z=278 [M+H]⁺.

Preparation 32. (R)-6-chloro-1-(1-cyclopropylethyl)-1H-pyrazolo[3,4-b]pyrazine

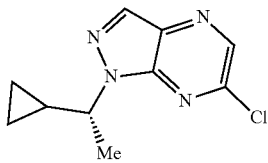 [SMILES: C[C@H](C1CC1)n1ncc2ncc(Cl)nc21]

A mixture of 6-chloro-1H-pyrazolo[3,4-b]pyrazine (300 mg, 1.94 mmol), (S)-1-cyclopropylethan-1-ol (167 mg, 1.94 mmol) and PPh₃ (611 mg, 2.329 mmol) in THF was cooled in an ice bath. DIAD (471 mg, 2.329 mmol) was added dropwise and the reaction allowed to warm slowly to rt. The mixture was concentrated in vacuo and the residue pre-loaded onto silica gel and purified by Isco chromatography (0 to 60% EtOAc/Hex) to give a colorless oil. This was further purified by reverse phase Isco (0 to 100% MeCN/0.1% aq. TFA) to afford the title compound as a colorless oil, 70 mg.

Preparation 33. (S)-6-chloro-1-(1-cyclopropylethyl)-1H-pyrazolo[3,4-b]pyrazine

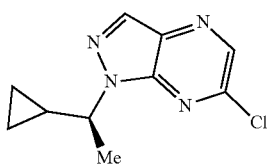 [SMILES: C[C@@H](C1CC1)n1ncc2ncc(Cl)nc21]

The title compound was obtained as a colorless oil, 152 mg, 35.2% yield, from 6-chloro-1H-pyrazolo[3,4-b]pyrazine and (R)-1-cyclopropylethan-1-ol, following a similar procedure to that described in Preparation 32. ¹H NMR (500 MHz, CDCl₃) δ: 8.51 (d, 1H), 8.28 (s, 1H), 4.22 (p, 1H), 1.71 (dd, 3H), 0.70 (p, 1H), 0.41 (t, 2H), 0.35 (t, 2H).

Preparation 34. 4-((6-chloro-1H-pyrazolo[3,4-b]pyrazin-1-yl)methyl)thiazole

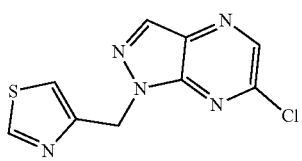 [SMILES: Clc1cnc2cnn(Cc3cscn3)c2n1]

The title compound was obtained, 242 mg, 49.5% yield, as a colorless oil that solidified on standing, from 6-chloro-1H-pyrazolo[3,4-b]pyrazine and thiazol-4-ylmethanol, following a similar procedure to that described in Preparation 32. LCMS m/z=252, 253 [M+H]⁺.

Preparation 35. 5-((6-chloro-1H-pyrazolo[3,4-b]pyrazin-1-yl)methyl)thiazole

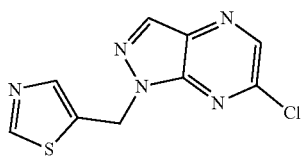 [SMILES: Clc1cnc2cnn(Cc3cncs3)c2n1]

The title compound was obtained, 243 mg, 49.5% yield, as a white solid, from 6-chloro-1H-pyrazolo[3,4-b]pyrazine and thiazol-5-ylmethanol, following a similar procedure to that described in Preparation 32. LCMS m/z=252, 253 [M+H]⁺.

Preparation 36. 6-chloro-1-((2-fluoropyridin-3-yl)methyl)-1H-pyrazolo[3,4-b]pyrazine

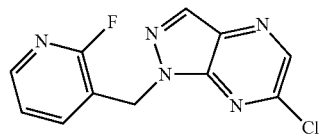 [SMILES: Clc1cnc2cnn(Cc3ccccc3)c2n1]

A mixture of 6-chloro-1H-pyrazolo[3,4-b]pyrazine (200 mg, 1.294 mmol), (2-fluoropyridin-3-yl)methanol (197 mg, 1.553 mmol) and PPh₃ (407 mg, 1.553 mmol) in TH (5 mL) was cooled in an ice bath. DIAD (314 mg, 1.553 mmol) was added dropwise and the reaction allowed to warm slowly to rt. The mixture was concentrated in vacuo, the residue pre-loaded onto silica gel and purified by Isco chromatography (0 to 100% EtOAc/Hex) to give the title compound, as a colorless oil, 216 mg, 63.5% yield, that solidified on standing. LCMS m/z=2264 [M+H]⁺.

Preparations 37-57

The compounds in the following table were prepared from 6-chloro-1H-pyrazolo[3,4-b]pyrazine and the appropriate alcohol, following a similar procedure to that described in Preparation 36.

| Preparation No. | Name/Structure/Alcohol/Data |
|---|---|
| 37 | (R)-6-chloro-1-(1-(tetrahydro-2H-pyran-4-yl)ethyl)-1H-pyrazolo[3,4-b]pyrazine <br><br> Alcohol: (S)-1-(tetrahydro-2H-pyran-4-yl)ethan-1-ol <br> 250 mg, 83% yield, as a white solid. LCMS m/z = 267 [M + H]$^+$ |
| 38 | 6-chloro-1-(pyridin-3-ylmethyl)-1H-pyrazolo[3,4-b]pyrazine <br><br> Alcohol: pyridin-3-methanol <br> 153 mg, 38.5% yield, colorless oil that solidified on standing. LCMS m/z = 247 [M + H]$^+$ |
| 39 | 1-benzyl-6-chloro-1H-pyrazolo[3,4-b]pyrazine <br><br> Alcohol: benzyl alcohol <br> 201 mg, 50.8% yield, as a colorless oil that solidified on standing. LCMS m/z = 245 [M + H]$^+$ |
| 40 | 6-chloro-1-(2-fluorobenzyl)-1H-pyrazolo[3,4-b]pyrazine <br><br> Alcohol: (2-fluorophenyl)methanol <br> 243 mg, 71.5% yield, as a colorless oil that solidifed on standing. <br> 1H NMR (500 MHz, DMSO-d$_6$) δ: 12.24 (s, 1H), 10.85 (s, 1H), 8.22 (s, 1H), 8.19 (s, 1H), 7.37-7.32 (m, 1H), 7.24-7.10 (m, 3H), 5.80 (s, 2H). |
| 41 | 6-chloro-1-(3-fluorobenzyl)-1H-pyrazolo[3,4-b]pyrazine <br><br> Alcohol: (3-fluorophenyl)methanol <br> 193 mg, 56.8% yield, as a colorless oil. <br> LCMS m/z = 263, 264 [M + H]$^+$ |
| 42 | 6-chloro-1-(4-fluorobenzyl)-1H-pyrazolo[3,4-b]pyrazine <br><br> Alcohol: (4-fluorophenyl)methanol <br> 243 mg, 71.5% yield, as a colorless oil. <br> LCMS m/z = 263, 264 [M + H]$^+$ |
| 43 | 6-chloro-1-((6-fluoropyridin-3-yl)methyl)-1H-pyrazolo[3,4-b]pyrazine <br><br> Alcohol: (6-fluoropyridin-3-yl)methanol <br> 170 mg, 49.8% yield, colorless oil that solidified on standing. LCMS m/z = 264 [M + H]$^+$ |
| 44 | 6-chloro-1-((5-fluoropyridin-3-yl)methyl)-1H-pyrazolo[3,4-b]pyrazine <br><br> Alcohol: (5-fluoropyridin-3-yl)methanol <br> 179 mg, 52.5% yield, as a white solid. LCMS m/z = 265 [M + H]$^+$ |
| 45 | (S)-6-chloro-1-(1-(3-fluorophenyl)ethyl)-1H-pyrazolo[3,4-b]pyrazine <br><br> Alcohol: (R)-1-(3-fluorophenyl)ethan-1-ol <br> 216 mg, 60.3% yield as pale-yellow oil. LCMS m/z = 277, 278 [M + H]$^+$ |

| Preparation No. | Name/Structure/Alcohol/Data |
|---|---|
| 46 | (S)-6-chloro-1-(1-(2-fluorophenyl)ethyl)-1H-pyrazolo[3,4-b]pyrazine<br><br>Alcohol: (R)-1-(2-fluorophenyl)ethan-1-ol<br>188 mg, 35% yield, pale yellow oil. LCMS m/z = 277 [M + H]⁺ |
| 47 | (S)-6-chloro-1-(1-(4-fluorophenyl)ethyl)-1H-pyrazolo[3,4-b]pyrazine<br><br>Alcohol: (R)-1-(4-fluorophenyl)ethan-1-ol<br>276 mg, 51.4% yield, pale yellow oil.<br>1H NMR (500 Hz, CDCl₃) δ: 8.52 (s, 1H), 8.29 (s, 1H), 7.44 (dd, 2H), 7.00 (dd, 2H), 6.16 (q, 1H), 2.00 (d, 3H). |
| 48 | (S)-6-chloro-1-(1-(5-fluoropyridin-2-yl)ethyl)-1H-pyrazolo[3,4-b]pyrazine<br><br>Alcohol: (R)-1-(5-fluoropyridin-2-yl)ethan-1-ol<br>481 mg, 66.9% yield as a colorless viscous oil.<br>LCMS m/z = 278, 279 [M + H]⁺ |
| 49 | (S)-6-chloro-1-(1-(3-fluoropyridin-2-yl)ethyl)-1H-pyrazolo[3,4-b]pyrazine<br><br>Alcohol: (R)-1-(3-fluoropyridin-2-yl)ethan-1-ol<br>481 mg, 66.9% yield as a colorless viscous oil.<br>LCMS m/z = 278, 279 [M + H]⁺ |
| 50 | 6-chloro-1-(4,4-difluorocyclohexyl)-1H-pyrazolo[3,4-b]pyrazine<br><br>Alcohol: 4,4-difluorocyclohexan-1-ol<br>232 mg, 65.7% yield as a white solid.<br>LCMS m/z = 273, 274 [M + H]⁺ |
| 51 | (1s,4s)-4-(6-chloro-1H-pyrazolo[3,4-b]pyrazin-1-yl)cyclohexan-1-ol<br><br>Alcohol: (1r,4r)-cyclohexane-1,4-diol.<br>95 mg, 19.4% yield, as a white solid.<br>LCMS m/z = 253 [M + H]⁺ |
| 52 | 2-((6-chloro-1H-pyrazolo[3,4-b]pyrazin-1-yl)methyl)thiazole<br><br>Alcohol: thiazol-2-ylmethanol<br>243 mg, 49.7% yield as a viscous oil.<br>LCMS m/z = 252, 253 [M + H]⁺ |
| 53 | (S)-5-(1-(6-chloro-1H-pyrazolo[3,4-b]pyrazin-1-yl)ethyl)thiazole<br><br>Alcohol: (R)-1-(thiazol-5-yl)ethan-1-ol<br>379 mg, 55.1% yield as a pale-yellow oil.<br>LCMS m/z = 266 [M + H]⁺ |

| Preparation No. | Name/Structure/Alcohol/Data |
|---|---|
| 54 | (S)-6-chloro-1-(1-(2-methoxypyridin-3-yl)ethyl)-1H-pyrazolo[3,4-b]pyrazine Alcohol: (R)-1-(2-methoxypyridin-3-yl)ethan-1-ol
437 mg, 58.3% yield as a white solid. LCMS m/z = 290 [M + H]$^+$ |
| 55 | (S)-6-chloro-1-(1-(2-chloropyridin-3-yl)ethyl)-1H-pyrazolo[3,4-b]pyrazine Alcohol: (R)-1-(2 chloropyridin-3-yl)ethan-1-ol
473 mg, 62.1% yield as a white solid. LCMS m/z = 296 [M + H]$^+$ |
| 56 | 6-chloro-1-(2,2-difluoro-1-(pyridin-2-yl)ethyl)-1H-pyrazolo[3,4-b]pyrazine Alcohol: 2,2-difluoro-1-(pyridin-2-yl)ethan-1-ol
53 mg, 38% yield as a pale-yellow solid. LCMS m/z = 296, 297 [M + H]$^+$ |
| 57 | 6-chloro-1-(((2R,4r,6S)-2,6-dimethyltetrahydro-2H-pyran-4-yl)methyl)-1H-pyrazolo[3,4-b]pyrazine Alcohol: ((2R,4r,6S)-2,6-dimethyltetrahydro-2H-pyran-4-yl)methanol
793 mg, 87% as a viscous oil. LCMS m/z = 281 [M + H]$^+$ |

Preparations 58-61

The compounds in the following table were prepared from 6-chloro-3-iodo-1H-pyrazolo[3,4-b]pyrazine and the appropriate alcohol, following a similar procedure to that described in Preparation 36.

| Preparation Number | Name/Structure/Alcohol/Data |
|---|---|
| 58 | (S)-6-chloro-1-(1-(2-fluoropyridin-3-yl)ethyl)-3-iodo-1H-pyrazolo[3,4-b]pyrazine Alcohol: (R)-1-(2-fluoropyridin-3-yl)ethan-1-ol
1.08 g, 70.9% yield, as a white solid,
LCMS m/z = 405 [M + H]$^+$ |
| 59 | (S)-6-chloro-3-iodo-1-(1-(tetrahydro-2H-pyran-4-yl)ethyl)-1H-pyrazolo[3,4-b]pyrazine Alcohol: (R)-1-(tetrahydro-2H-pyran-4-yl)ethan-1-ol
602 mg, 86% yield, as an off-white solid,
LCMS m/z = 393 [M + H]$^+$ |
| 60 | (S)-6-chloro-3-iodo-1-(1-(pyridin-3-yl)ethyl)-1H-pyrazolo[3,4-b]pyrazine Alcohol: (R)-1-(pyridin-3-yl)ethan-1-ol
583 mg, 56.5% yield, as an off-white solid. |
| 61 | 6-chloro-3-iodo-1-((tetrahydro-2H-pyran-4-yl)methyl)-1H-pyrazolo[3,4-b]pyrazine Alcohol: (tetrahydro-2H-pyran-4yl)methanol
1.03 g, 76% yield as white crystalline solid. |

Preparation 62. (S)-3,6-dichloro-1-(1-(pyridin-3-yl)ethyl)-1H-pyrazolo[3,4-b]pyrazine

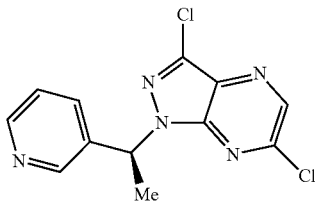 [SMILES: C[C@@H](c1cccnc1)n1nc(Cl)c2ncc(Cl)nc21]

A mixture of 3,6-dichloro-1H-pyrazolo[3,4-b]pyrazine (300 mg, 1.587 mmol), (R)-1-(pyridin-3-yl)ethan-1-ol (215 mg, 1.746 mmol) and PPh₃ (500 mg, 1.905 mmol) in THF (8 mL) was cooled in an ice bath. DIAD (385 mg, 1.905 mmol) was added dropwise and the reaction allowed to warm slowly to rt. The mixture was concentrated in vacuo, the residue pre-loaded onto silica gel and purified by Isco chromatography (0 to 40% EtOAc/Hex). The product was further purified by Isco (0-60% EtOAc/DCM) to give the title compound, as an off-white solid, 230 mg. LCMS m/z=296 [M+H]⁺.

Preparation 63. (S)-3,6-dichloro-1-(1-(2-fluoropyridin-3-yl)ethyl)-1H-pyrazolo[3,4-b]pyrazine

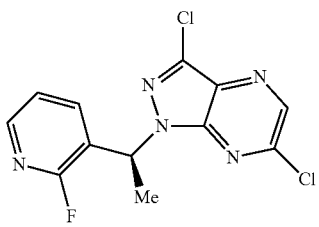 [SMILES: C[C@@H](c1cccnc1F)n1nc(Cl)c2ncc(Cl)nc21]

A mixture of 3,6-dichloro-1H-pyrazolo[3,4-b]pyrazine (213 mg, 1.127 mmol), (R)-1-(2-fluoropyridin-3-yl)ethan-1-ol (175 mg, 1.24 mmol) and PPh₃ (355 mg, 1.352 mmol) in THF (8 mL) was cooled in an ice bath. DIAD (273 mg, 1.352 mmol) was added dropwise and the reaction allowed to warm slowly to rt. The mixture was concentrated in vacuo and the residue pre-loaded onto silica gel and purified by Isco chromatography (0 to 40% EtOAc/Hex) to give the title compound as a white solid, 182 mg. LCMS m/z=314 [M+H]⁺.

Preparation 64. 4-((6-chloro-1H-pyrazolo[3,4-b]pyrazin-1-yl)methyl)pyrrolidin-2-one

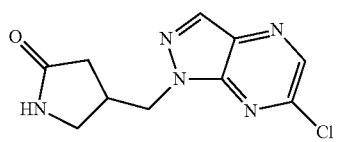 [SMILES: O=C1CC(Cn2ncc3ncc(Cl)nc32)CN1]

To a mixture of 6-chloro-1H-pyrazolo[3,4-b]pyrazine (300 mg, 1.94 mmol), 4-(hydroxymethyl)pyrrolidin-2-one (246 mg, 2.135 mmol) and PPh₃ (611 mg, 2.329 mmol) in THF (10 mL) was added DIAD (471 mg, 2.329 mmol) drop wise at 0° C., and the reaction allowed to warm to rt. The reaction was concentrated in vacuo and the residue was purified by column chromatography on silica gel eluting with MeOH/DCM (0 to 5%) to give the title compound (152 mg) as an off-white solid. LCMS m/z=252 [M+H]⁺.

Preparation 65. 6-chloro-1-(1,4-dioxaspiro[4.5]decan-8-yl)-1H-pyrazolo[3,4-b]pyrazine

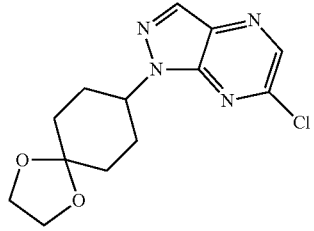 [SMILES: Clc1cnc2cnn(C3CCC4(CC3)OCCO4)c2n1]

A mixture of 6-chloro-1H-pyrazolo[3,4-b]pyrazine (300 mg, 1.94 mmol), 1,4-dioxaspiro[4.5]decan-8-ol (368 mg, 2.34 mmol) and PPh₃ (611 mg, 2.34 mmol) in THF (8 mL) was cooled in an ice bath. DIAD (471 mg, 2.34 mmol) was added dropwise and the reaction allowed to warm slowly to rt. The mixture was concentrated in vacuo and the residue pre-loaded onto silica gel and purified by Isco chromatography (0 to 50% EtOAc/Hex) to give the title compound, as a colorless oil, 324 mg that crystallised on standing. LCMS m/z=295 [M+H]⁺.

Preparation 66. 4-(6-chloro-1H-pyrazolo[3,4-b]pyrazin-1-yl)cyclohexan-1-one

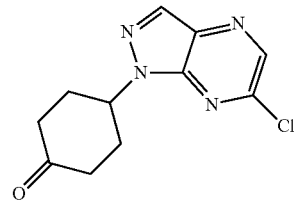 [SMILES: O=C1CCC(n2ncc3ncc(Cl)nc32)CC1]

1M HCl (2.75 mL) was added to a solution of 6-chloro-1-(1,4-dioxaspiro[4.5]decan-8-yl)-1H-pyrazolo[3,4-b]pyrazine (Preparation 65, 270 mg, 0.92 mmol) in THF (3 mL) and the solution stirred at rt overnight. The reaction was heated to 60° C. for 1 h, then cooled to rt. The mixture was concentrated in vacuo and the residue neutralised using aq. NaHCO₃. The resulting suspension was filtered, washed with water and dried to afford the title compound, 194 mg, 77.3%, as a white solid. LCMS m/z=251 [M+H]⁺.

Preparation 67. (1r,4r)-4-(6-chloro-1H-pyrazolo[3,4-b]pyrazin-1-yl)cyclohexan-1-ol

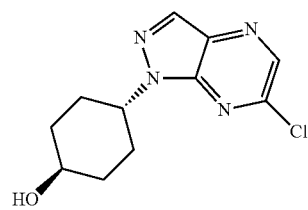 [SMILES: O[C@H]1CC[C@H](n2ncc3ncc(Cl)nc32)CC1]

NaBH₄ (36 mg, 0.957 mmol) was added to a ice cooled solution of 4-(6-chloro-1H-pyrazolo[3,4-b]pyrazin-1-yl)cyclohexan-1-one (Preparation 66, 160 mg, 0.638 mmol) in MeOH (4 mL) and the reaction stirred for 1 h. The mixture was concentrated in vacuo and saturated aq. NH₄Cl solution and then water were added. The resulting suspension was stirred for several minutes and then filtered, washed with water and suction dried to give a white solid, 130 mg. This was recrystallised from MeCN to provide the title compound, 90 mg as white needles. LCMS m/z=253 [M+H]⁺.

Preparation 68. 3,6-dichloro-1-((tetrahydro-2H-pyran-4-yl)methyl)-1H-pyrazolo[3,4-b]pyrazine

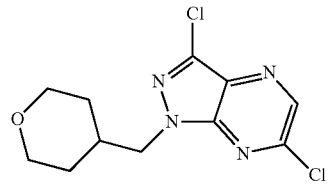

NCS (221 mg, 1.654 mmol) and HBF₄ (218 mg, 2.481 mmol) were added to a solution of 6-chloro-1-((tetrahydro-2H-pyran-4-yl)methyl)-1H-pyrazolo[3,4-b]pyrazine (Preparation 87, 209 mg, 0.827 mmol) in MeCN (2 mL) and the reaction heated at 90° C. overnight. The cooled mixture was concentrated in vacuo, the resulting slurry neutralized with 1M NaOH (150 µL), diluted with water and extracted with EtOAc. The combined organic layer was washed with brine, dried over Na₂SO₄, filtered and evaporated to give the crude product. This was purified by Isco chromatography (0 to 25% EtOAc/Hex) to give the title compound, 135 mg, 56.8%, of white solid. LCMS m/z=289 [M+H]⁺.

Preparation 69. 6-chloro-1-((tetrahydro-2H-pyran-4-yl)methyl)-1H-pyrazolo[3,4-b]pyrazine-3-carbonitrile

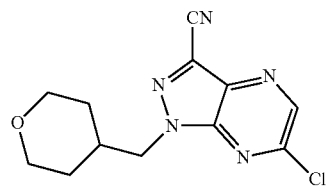 [SMILES: N#Cc1nn(CC2CCOCC2)c2nc(Cl)cnc12]

CuCN (54 mg, 0.607 mmol) was added to a solution of 6-chloro-3-iodo-1-((tetrahydro-2H-pyran-4-yl)methyl)-1H-pyrazolo[3,4-b]pyrazine (Preparation 61, 209 mg, 0.552 mmol) in DMSO (1.5 mL) and the reaction heated at 150° C. for 1.5 h. The cooled mixture was diluted with water and extracted with EtOAc. The biphasic mixture was filtered through Celite® and the filtrate separated. The organic layer was washed with water, then brine, dried over Na₂SO₄, filtered and evaporated under reduced pressure. The crude product was purified by Isco chromatography (0 to 40% EtOAc/Hex) to give the title compound, 62 mg, 40.4%, as a white solid. LCMS m/z=278 [M+H]⁺.

Preparation 70. (S)-6-chloro-1-(1-(2-fluoropyridin-3-yl)ethyl)-1H-pyrazolo[3,4-b]pyrazine-3-carbonitrile

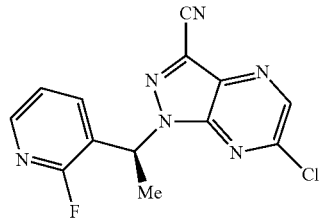 [SMILES: C[C@@H](c1cccnc1F)n1nc(C#N)c2ncc(Cl)nc21]

The title compound was obtained as a white solid, 105 mg, 46.7% yield, from (S)-6-chloro-1-(1-(2-fluoropyridin-3-yl)ethyl)-3-iodo-1H-pyrazolo[3,4-b]pyrazine (Preparation 58), following the procedure described in Preparation 69. LCMS m/z=303 [M+H]⁺.

Preparation 71. (S)-6-chloro-1-(1-(tetrahydro-2H-pyran-4-yl)ethyl)-1H-pyrazolo[3,4-b]pyrazine-3-carbonitrile

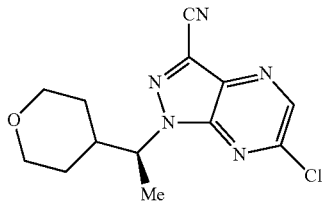 [SMILES: C[C@@H](C1CCOCC1)n1nc(C#N)c2ncc(Cl)nc21]

The title compound was obtained as a white solid, 170 mg, 37.9% yield, from (S)-6-chloro-3-iodo-1-(1-(tetrahydro-2H-pyran-4-yl)ethyl)-1H-pyrazolo[3,4-b]pyrazine (Preparation 59), following the procedure described in Preparation 69. LCMS m/z=292 [M+H]⁺.

Preparation 72. 1-(6-chloro-1-((tetrahydro-2H-pyran-4-yl)methyl)-1H-pyrazolo[3,4-b]pyrazin-3-yl)ethan-1-one

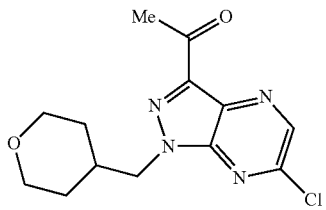 [SMILES: CC(=O)c1nn(CC2CCOCC2)c2nc(Cl)cnc12]

A mixture of 6-chloro-3-iodo-1-((tetrahydro-2H-pyran-4-yl)methyl)-1H-pyrazolo[3,4-b]pyrazine (Preparation 61, 1.0 g, 2.64 mmol), tributyl(1-ethoxyvinyl)stannane (1.002 g, 2.77 mmol) and Pd(PPh₃)Cl₂ (93 mg, 0.132 mmol) in dioxane (10 mL) was stirred at 90° C. overnight. The reaction was cooled to 60° C., 1M HCl (2.6 mL) added and the mixture stirred for 45 mins. The mixture was cooled to rt, 1M NaOH (2.6 mL) added, the mixture diluted with EtOAc and the layers separated. The organic layer was washed with brine, dried over Na$_2$SO$_4$, filtered and evaporated under reduced pressure. The crude product was purified by Isco chromatography (0 to 100% EtOAc/Hex) to give the title compound, 697 mg, 90% yield, as a pale yellow crystalline solid. LCMS m/z=295 [M+H]$^+$.

Preparation 73. (S)-1-(6-chloro-1-(1-(tetrahydro-2H-pyran-4-yl)ethyl)-1H-pyrazolo[3,4-b]pyrazin-3-yl)ethan-1-one

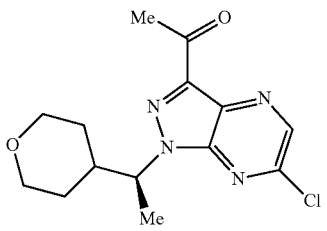 [SMILES: CC(=O)c1nn([C@@H](C)C2CCOCC2)c2nc(Cl)cnc12]

The title compound was obtained as an off-white solid, 634 mg, 80% yield, from (S)-6-chloro-3-iodo-1-(1-(tetrahydro-2H-pyran-4-yl)ethyl)-1H-pyrazolo[3,4-b]pyrazine (Preparation 59), following the procedure described in Preparation 72. LCMS m/z=309 [M+H]$^+$.

Preparation 74. (S)-1-(6-chloro-1-(1-(pyridin-3-yl)ethyl)-1H-pyrazolo[3,4-b]pyrazin-3-ylethan-1-one

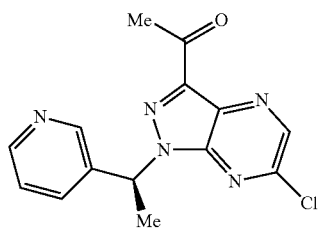 [SMILES: CC(=O)c1nn([C@@H](C)c2cccnc2)c2nc(Cl)cnc12]

The title compound was obtained as a pale yellow crystalline solid, 697 mg, 88% yield, from (S)-6-chloro-3-iodo-1-(1-(pyridin-3-yl)ethyl)-1H-pyrazolo[3,4-b]pyrazine (Preparation 60), following the procedure described in Preparation 72. LCMS m/z=302 [M+H]$^+$.

Preparation 75. 1-(6-chloro-1-((tetrahydro-2H-pyran-4-yl)methyl)-1H-pyrazolo[3,4-b]pyrazin-3-yl)ethan-1-ol

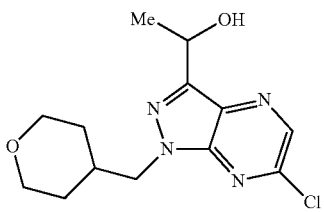 [SMILES: CC(O)c1nn(CC2CCOCC2)c2nc(Cl)cnc12]

NaBH$_4$ (45 mg, 1.194 mmol) was added to a solution of 1-(6-chloro-1-((tetrahydro-2H-pyran-4-yl)methyl)-1H-pyrazolo[3,4-b]pyrazin-3-yl)ethan-1-one (Preparation 72, 352 mg, 1.194 mmol) in MeOH (7 mL) at −40° C. and the reaction allowed to warm slowly to rt. Sat. aq. NH$_4$Cl and water were added and the mixture concentrated in vacuo. The resulting aqueous slurry was partitioned between water and DCM, the layers separated and the organic layer dried (Na$_2$SO$_4$), filtered and concentrated in vacuo. The crude product was purified by Isco chromatography (0 to 100% EtOAc/Hex) to give the title compound, 217 mg, 61.2% as an off-white solid. LCMS m/z=297 [M+H]$^+$.

Preparation 76. 1-(6-chloro-1-((S)-1-(tetrahydro-2H-pyran-4-yl)ethyl)-1H-pyrazolo[3,4-b]pyrazin-3-yl)ethan-1-ol

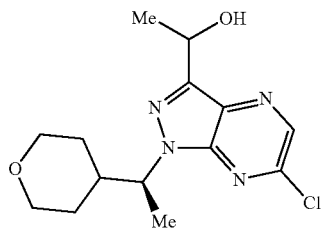 [SMILES: CC(O)c1nn([C@@H](C)C2CCOCC2)c2nc(Cl)cnc12]

The title compound was obtained as a colorless viscous oil, 412 mg, 81% yield, from (S)-1-(6-chloro-1-(1-(tetrahydro-2H-pyran-4-yl)ethyl)-1H-pyrazolo[3,4-b]pyrazin-3-yl)ethan-1-one (Preparation 73), following a similar procedure to that described in Preparation 75.

Preparation 77. 1-(6-chloro-1-((S)-1-(pyridin-3-yl)ethyl)-1H-pyrazolo[3,4-b]pyrazin-3-yl)ethan-1-ol

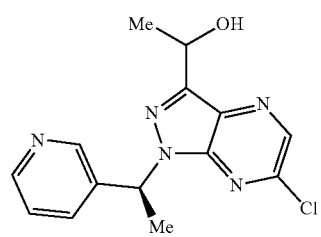 [SMILES: CC(O)c1nn([C@@H](C)c2cccnc2)c2nc(Cl)cnc12]

NaBH$_4$ (45 mg, 1.18 mmol) was added to a solution of (S)-1-(6-chloro-1-(1-(pyridin-3-yl)ethyl)-1H-pyrazolo[3,4-b]pyrazin-3-yl)ethan-1-one (Preparation 74, 297 mg, 0.98 mmol) dissolved in MeOH (5 mL) and cooled in an ice bath and the reaction stirred for 20 mins. The reaction was quenched with aq. sat. NH$_4$Cl, then water and the mixture extracted with DCM. The combined organic extracts were dried (Na$_2$SO$_4$), filtered and evaporated under reduced pressure. The crude product was purified by Isco chromatography (0 to 5% MeOH/DCM) to give the title compound, 103 mg, 34.4%, as tan-colored foam. LCMS m/z=304 [M+H]$^+$.

Preparation 78. 4-((6-chloro-1H-pyrazolo[3,4-b]pyrazin-1-yl)methyl)tetrahydro-2H-pyran-4-ol

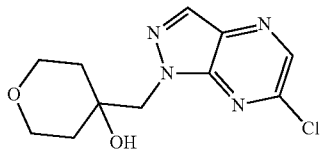 [SMILES: OC1(Cn2ncc3ncc(Cl)nc32)CCOCC1]

A mixture of 6-chloro-1H-pyrazolo[3,4-b]pyrazine (175 mg, 1.132 mmol), 1,6-dioxaspiro[2.5]octane (155 mg, 1.359 mmol) and K$_2$CO$_3$ (313 mg, 2.265 mmol) in MeCN (3 mL) was heated at 90° C. for 2 days. The cooled mixture was diluted with EtOAc, filtered and the filtrate evaporated under reduced pressure to give the crude product. This was purified by Isco chromatography (0 to 100% EtOAc/Hex) to give 4-((6-chloro-1H-pyrazolo[3,4-b]pyrazin-1-yl)methyl)tetrahydro-2H-pyran-4-ol, 33 mg of colorless oil that crystallized on standing and 4-((6-chloro-2H-pyrazolo[3,4-b]pyrazin-1-yl)methyl)tetrahydro-2H-pyran-4-ol, 36 mg of colorless oil that crystallized on standing. NOE analysis, confirmed the structural assignments. LCMS m/z=269, 270 [M+H]$^+$.

Preparation 79. 6-chloro-1-(2-cyclopropylpropan-2-yl)-1H-pyrazolo[3,4-b]pyrazine

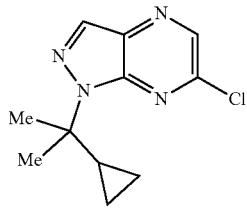 [SMILES: CC(C)(C1CC1)n1ncc2ncc(Cl)nc21]

To a solution of 6-chloro-1H-pyrazolo[3,4-b]pyrazine (1.35 g, 8.78 mmol) and 2-cyclopropylpropan-2-ol (440 mg, 4.39 mmol) in DCM (30 ml) was added trifluoromethanesulfonic acid (658 mg, 4.39 mmol) dropwise at 0° C. and the reaction stirred at 0° C. for 30 min. The reaction mixture was quenched with saturated aq. NaHCO$_3$ and extracted with EtOAc. The organic layer was concentrated in vacuo and the residue was purified by silica gel chromatography eluting with PE/EtOAc (9/1) to give the title compound (320 mg, 31% yield) as a colorless oil. $^1$H-NMR (400 MHz, DMSO-d$_6$) δ ppm 8.69 (s, 1H), 8.48 (s, 1H), 1.69 (s, 6H), 1.65-1.58 (m, 1H), 0.42-0.40 (m, 4H).

Preparation 80. 6-chloro-1-(tetrahydro-2H-pyran-4-yl)-1H-pyrazolo[3,4-b]pyrazine

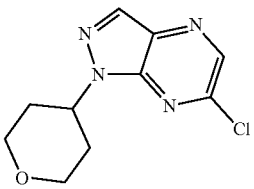 [SMILES: Clc1cnc2cnn(C3CCOCC3)c2n1]

To a mixture of 6-chloro-1H-pyrazolo[3,4-b]pyrazine (200 mg, 1.29 mmol), tetrahydro-2H-pyran-4-ol (197 mg, 1.93 mmol) and PPh$_3$ (506 mg, 1.93 mmol) in THF (10 mL) was added DIAD (390 mg, 1.93 mmol) drop wise at 0° C., and the reaction stirred at rt overnight under N$_2$. The reaction was quenched with water and extracted with EtOAc. The combined organic layer was washed with water and brine, dried over Na$_2$SO$_4$, filtered and concentrated in vacuo. The residue was purified by column chromatography on silica gel eluting with EtOAc/PE (1/4) to give the title compound (150 mg, 49% yield) as a yellow solid. LCMS m/z=239 [M+H]$^+$.

Preparation 81. (S)-6-chloro-1-(1-(pyridin-3-yl)ethyl)-1H-pyrazolo[3,4-b]pyrazine

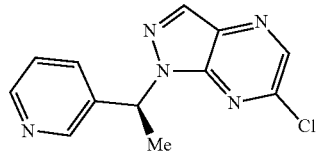 [SMILES: C[C@@H](c1cccnc1)n1ncc2ncc(Cl)nc21]

To a mixture of 6-chloro-1H-pyrazolo[3,4-b]pyrazine (1.0 g, 6.46 mmol), (R)-1-(pyridin-3-yl)ethan-1-ol (1.19 g, 9.69 mmol) and PPh$_3$ (2.54 g, 9.69 mmol) in THF (30 mL) was added dropwise DIAD (1.95 g, 9.69 mmol) at 0° C. and the reaction stirred overnight. The reaction was quenched with water and extracted with EtOAc. The combined organic layer was washed with water and brine, dried over Na$_2$SO$_4$, filtered and concentrated in vacuo. The residue was purified by flash chromatography on silica gel eluting with EtOAc/PE (1/4) to afford the title compound (1.5 g, 89% yield) as a yellow solid. LCMS m/z=260 [M+H]$^+$.

Preparation 82. (S)-6-chloro-1-(1-(pyridin-2-yl)ethyl)-1H-pyrazolo[3,4-b]pyrazine

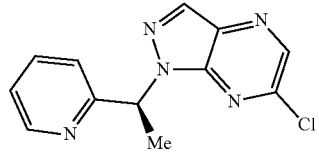 [SMILES: C[C@@H](c1ccccn1)n1ncc2ncc(Cl)nc21]

To a mixture of 6-chloro-1H-pyrazolo[3,4-b]pyrazine (900 mg, 5.82 mmol), (R)-1-(pyridin-2-yl)ethan-1-ol (859 mg, 6.98 mmol) and PPh$_3$ (2.28 g, 8.73 mmol) in THF (20 mL) was added dropwise DIAD (1.76 g, 8.73 mmol) at 0° C. and the reaction stirred at rt overnight. The reaction was quenched with water and extracted with EtOAc. The combined organic layer was washed with water and brine, dried over Na$_2$SO$_4$, filtered and concentrated in vacuo. The residue was purified by flash chromatography on silica gel eluting with EtOAc/PE (1/5) to give the title compound (900 mg, 59% yield) as a yellow solid. LCMS m/z=260 [M+H]$^+$.

Preparation 83. 6-chloro-1-(1-(4-fluoropyridin-2-yl)ethyl)-1H-pyrazolo[3,4-b]pyrazine

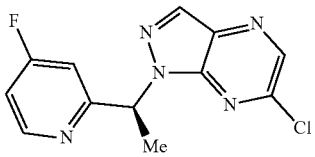 [SMILES: C[C@@H](c1cc(F)ccn1)n1ncc2ncc(Cl)nc21]

To a mixture of 6-chloro-1H-pyrazolo[3,4-b]pyrazine (200 mg, 1.29 mmol), 1-(4-fluoropyridin-2-yl)ethanol (200 mg, 1.40 mmol) and PPh$_3$ (510 mg, 1.94 mmol) in THF (10 mL) was added dropwise DIAD (254 mg, 1.94 mmol) at 0° C. and the reaction stirred overnight. The reaction was quenched with water and extracted with EtOAc. The combined organic layer was washed with water and brine, dried over Na$_2$SO$_4$, filtered and concentrated in vacuo. The residue was purified by flash chromatography on silica gel eluting with EtOAc/PE (1/10) to afford the title compound (120 mg, 29% yield) as a yellow solid. LCMS m/z=278 [M+H]$^+$.

Preparation 84. 6-chloro-1-(2-fluoro-1-(pyridin-2-yl)ethyl)-1H-pyrazolo[3,4-b]pyrazine

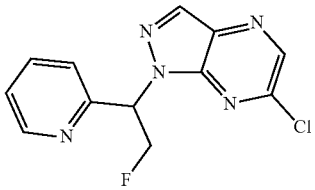 [SMILES: FCC(c1ccccn1)n1ncc2ncc(Cl)nc21]

To a mixture of 2-fluoro-1-(pyridin-2-yl)ethan-1-ol (Preparation 15, 400 mg, 2.83 mmol), 6-chloro-1H-pyrazolo[3,4-b]pyrazine (437 mg, 2.83 mmol) and PPh$_3$ (1.11 g, 4.24 mmol) in THF (10 mL) was added DIAD (857 mg, 4.24 mmol) slowly, and the reaction stirred at rt for 15 h. The reaction was quenched with water and extracted with EtOAc. The combined organic layer was washed with water and brine, dried over Na$_2$SO$_4$, filtered and concentrated in vacuo. The residue was purified by flash chromatography on silica gel eluting with EtOAc/PE (1/1) to afford the title compound (400 mg, 51%) as a colorless oil. LCMS m/z=278 [M+H]$^+$.

Preparation 85. 6-chloro-1-(2-fluoro-1-(Pyridin-3-yl)ethyl)-1H-pyrazolo[3,4-b]pyrazine

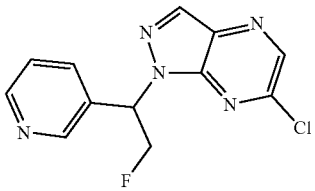 [SMILES: FCC(c1cccnc1)n1ncc2ncc(Cl)nc21]

To a mixture of 6-chloro-1H-pyrazolo[3,4-b]pyrazine (120 mg, 0.776 mmol), 2-fluoro-1-(pyridin-3-yl)ethan-1-ol (Preparation 16, 109 mg, 0.776 mmol) and PPh$_3$ (304 mg, 1.16 mmol) in toluene (5 mL) was added DIAD (234 mg, 1.16 mmol) and the reaction stirred at 80° C. for 2 h. The reaction was quenched with water and extracted with EtOAc. The combined organic layer was washed with water and brine, dried over Na$_2$SO$_4$, filtered and concentrated in vacuo. The residue was purified by flash chromatography on silica gel eluting with EtOAc/PE (2/1) to afford the title compound (180 mg, 84% yield) as a colorless oil. LCMS m/z=278 [M+H]$^+$.

Preparation 86. 6-chloro-1-(1-(pyridazin-3-yl)ethyl)-1H-pyrazolo[3,4-b]pyrazine

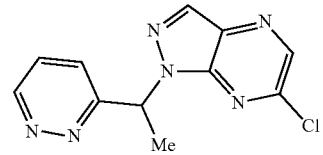 [SMILES: CC(c1cccnn1)n1ncc2ncc(Cl)nc21]

To a mixture of 6-chloro-1H-pyrazolo[3,4-b]pyrazine (850 mg, 5.49 mmol), 1-(pyridazin-3-yl)ethan-1-ol (681 mg, 5.49 mmol) and PPh$_3$ (2.15 g, 8.23 mmol) in THF (10 mL) was added DIAD (1.66 g, 8.23 mmol) dropwise at 0° C. and the reaction stirred at 25° C. for 18 h. The reaction was quenched with water and extracted with EtOAc. The combined organic layer was washed with water and brine, dried over Na$_2$SO$_4$, filtered and concentrated in vacuo. The residue was purified by flash chromatography on silica gel eluting with EtOAc/PE (1/4) to afford the title compound (550 mg, 38% yield) as a yellow solid. LCMS m/z=261, 263 [M+H]$^+$.

Preparation 87. 6-chloro-1-((tetrahydro-2H-pyran-4-yl)methyl)-1H-pyrazolo[3,4-b]pyrazine

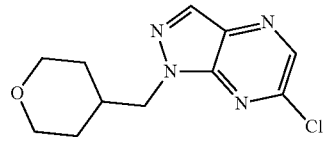 [SMILES: Clc1cnc2cnn(CC3CCOCC3)c2n1]

To a mixture of 6-chloro-1H-pyrazolo[3,4-b]pyrazine (1.0 g, 6.5 mmol), (tetrahydro-2H-pyran-4-yl)methanol (1.13 g, 9.75 mmol) and PPh$_3$ (2.56 g, 9.75 mmol) in THF (30 mL) was added DIAD (1.96 g, 9.75 mmol) at 0° C., and the reaction stirred overnight at rt under N$_2$. The reaction was quenched with water and extracted with EtOAc. The combined organic layers were washed with water and brine, dried over Na$_2$SO$_4$, filtered and concentrated in vacuo. The residue was purified by column chromatography on silica gel eluting with EtOAc/PE (1/3) to afford the title compound (1.57 g, 95% yield) as a white solid. LCMS m/z=253 [M+H]$^+$.

Preparation 88. 6-chloro-1-(1-(tetrahydrofuran-3-yl)ethyl)-1H-pyrazolo[3,4-b]pyrazine

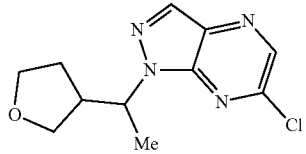 [SMILES: CC(C1CCOC1)n1ncc2ncc(Cl)nc21]

To a mixture of 6-chloro-1H-pyrazolo[3,4-b]pyrazine (200 mg, 3.34 mmol), 1-(tetrahydrofuran-3-yl)ethanol (400 mg, 3.40 mmol) and $PPh_3$ (1.02 g, 3.88 mmol) in THF (10 mL) was added DIAD (508 mg, 3.88 mmol) drop wise at 0° C., and the reaction stirred at rt overnight. The reaction was quenched with water and extracted with EtOAc. The combined organic layer was washed with water and brine, dried over $Na_2SO_4$, filtered and concentrated in vacuo. The residue was purified by column chromatography on silica gel eluting with EtOAc/PE (1/10) to afford the title compound (240 mg, 29% yield) as a yellow solid. LCMS m/z=253 [M+H]$^+$.

Preparation 89. 6-chloro-1-(1-(tetrahydro-2H-pyran-3-yl)ethyl)-1H-pyrazolo[3,4-b]pyrazine

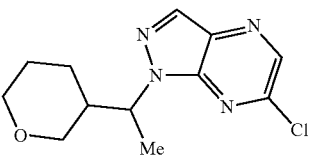 [SMILES: CC(C1CCCOC1)n1ncc2ncc(Cl)nc21]

To a mixture of 6-chloro-1H-pyrazolo[3,4-b]pyrazine (300 mg, 1.94 mmol), $PPh_3$ (760 mg, 2.90 mmol) and 1-(tetrahydro-2H-pyran-3-yl)ethan-1-ol (Preparation 12, 377 mg, 2.90 mmol) in THF (8 mL) was added DIAD (586 mg, 2.90 mmol) at 0° C., and the reaction stirred overnight. The reaction was quenched with water and extracted with EtOAc. The combined organic layer was washed with water and brine, dried over $Na_2SO_4$, filtered and concentrated in vacuo. The residue was purified by column chromatography on silica gel eluting with EtOAc/PE (1/4) to give the title compound (323 mg, 62% yield) as a yellow oil. LCMS m/z=267 [M+H]$^+$.

Preparation 90. (S)-6-chloro-1-(1-(tetrahydro-2H-pyran-4-yl)ethyl)-1H-pyrazolo[3,4-b]pyrazine

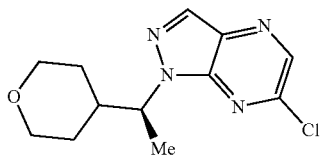 [SMILES: C[C@@H](C1CCOCC1)n1ncc2ncc(Cl)nc21]

To a mixture of 6-chloro-1H-pyrazolo[3,4-b]pyrazine (250 mg, 1.62 mmol), (R)-1-(tetrahydro-2H-pyran-4-yl)ethan-1-ol (200 mg, 1.70 mmol) and $PPh_3$ (636 mg, 2.43 mmol) in THF (10 mL) was added dropwise DIAD (422 mg, 2.43 mmol) at 0° C. and the reaction stirred overnight. The reaction was quenched with water and extracted with EtOAc. The combined organic layer was washed with water and brine, dried over $Na_2SO_4$, filtered and concentrated in vacuo. The residue was purified by flash chromatography on silica gel eluting with EtOAc/PE (1/10) to afford the title compound (80 mg, 19% yield) as a yellow solid. LCMS m/z=267 [M+H]$^+$.

Preparation 91. (R)-6-chloro-1-(1-(tetrahydro-2H-pyran-4-yl)-2-((triisopropylsilyl)oxy)ethyl)-1H-pyrazolo[3,4-b]pyrazine

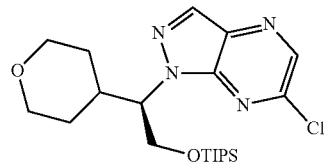

To a mixture of (S)-1-(tetrahydro-2H-pyran-4-yl)-2-((triisopropylsilyl)oxy)ethan-1-ol (Preparation 10, 700 mg, 2.31 mmol), 6-chloro-1H-pyrazolo[3,4-b]pyrazine (357 mg, 2.31 mmol) and $PPh_3$ (907 mg, 3.46 mmol) in toluene (5 mL) was added DIAD (699 mg, 3.46 mmol) at 0° C. and the reaction stirred at 80° C. for 4 h. The reaction was quenched with water and extracted with EtOAc. The combined organic layer was washed with water and brine, dried over $Na_2SO_4$, filtered and concentrated in vacuo. The residue was purified by flash chromatography on silica gel eluting with EtOAc/PE (1/1) to give the title compound (700 mg, 69% yield) as a yellow oil. LCMS m/z=439 [M+H]$^+$.

Preparation 92. 6-chloro-1-((2S)-2-((tetrahydro-2H-pyran-2-yl)oxy)pentan-3-yl)-1H-pyrazolo[3,4-b]pyrazine

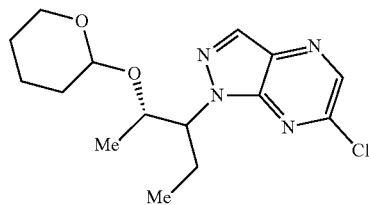 [SMILES: CCC([C@H](C)OC1CCCCO1)n1ncc2ncc(Cl)nc21]

To a mixture of 6-chloro-1H-pyrazolo[3,4-b]pyrazine (400 mg, 2.59 mmol), (2S)-2-((tetrahydro-2H-pyran-2-yl)oxy)pentan-3-ol (Preparation 6, 730 mg, 3.88 mmol) and $PPh_3$ (784 mg, 3.88 mmol) in THF (10 mL) was added dropwise DIAD (1.02 g, 3.88 mmol) at 0° C., and the reaction then stirred overnight. The reaction was quenched with water and extracted with EtOAc. The combined organic layer was washed with water and brine, dried over $Na_2SO_4$, filtered and concentrated in vacuo. The residue was purified by flash chromatography on silica gel eluting with EtOAc/PE (1/10) to give the title compound (180 mg, 21% yield) as a yellow solid. LCMS m/z=241 [M-84+H]$^+$.

Preparation 93. 6-chloro-1-(2,2-difluoro-1-(tetrahydro-2H-pyran-4-yl)ethyl)-1H-pyrazolo[3,4-b]pyrazine

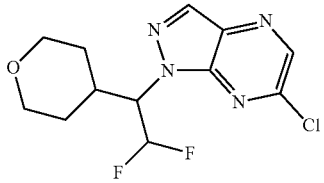 [SMILES: FC(F)C(C1CCOCC1)n1ncc2ncc(Cl)nc21]

To a mixture of 2,2-difluoro-1-(tetrahydro-2H-pyran-4-yl)ethan-1-ol (Preparation 11, 200 mg, 1.20 mmol), tetrahydro-2H-pyran-4-ol (185 mg, 1.20 mmol) and PPh₃ (471 mg, 1.8 mmol) in THF (10 mL) was added dropwise DIAD (363 mg, 1.8 mmol) at 0° C., and the reaction stirred overnight. The reaction was quenched with water and extracted with EtOAc. The combined organic layer was washed with water and brine, dried over Na₂SO₄, filtered and concentrated in vacuo. The residue was purified by flash chromatography on silica gel eluting with EtOAc/PE (1/4) to give the title compound (250 mg, 69% yield) as a yellow solid. LCMS m/z=303 [M+H]⁺.

Preparation 94. Trans-rac-2-((6-chloro-1H-pyrazolo[3,4-b]pyrazin-1-yl)methyl)cyclopropane-1-carbonitrile

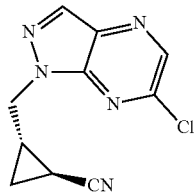 [SMILES: N#C[C@H]1C[C@@H]1Cn1ncc2ncc(Cl)nc21]

Trans-Racemate

To a mixture of 6-chloro-1H-pyrazolo[3,4-b]pyrazine (794 mg, 5.14 mmol), trans-2-(hydroxymethyl)cyclopropane-1-carbonitrile (500 mg, 5.14 mmol) and PPh₃ (1.61 g, 6.16 mmol) in toluene (10 mL) was added dropwise DIAD (1.24 g, 6.16 mmol) at 0° C., and the reaction stirred at 80° C. overnight. The reaction was quenched with water, extracted with EtOAc, the combined organic layer was washed with water and brine, dried over Na₂SO₄, filtered and concentrated in vacuo. The residue was purified by flash chromatography on silica gel eluting with EtOAc/PE (1/4) to give the title compound (400 mg, 33% yield) as a white solid. LCMS m/z=234 [M+H]⁺.

Preparation 95-182

To a mixture of 6-chloro-1H-pyrazolo[3,4-b]pyrazine, 6-chloro-3-methyl-1H-pyrazolo[3,4-b]pyrazine or 6-chloro-3-fluoro-1H-pyrazolo[3,4-b]pyrazine (Preparation 3) (1 equiv.) as indicated in the table, the appropriate alcohol (1.0 to 3.0 equiv.) and PPh₃ (1.5 to 2.0 equiv.) in THF was added DIAD (1.5 to 2.0 equiv.) drop wise at 0° C., and the reaction stirred at rt until the starting materials had been consumed. The reaction was quenched with water, extracted with EtOAc, the combined organic layer was washed with water and brine, dried over Na₂SO₄, filtered and concentrated in vacuo. The residue was purified by flash chromatography on silica gel eluting with EtOAc/PE to give the title compounds.

| Preparation Number | Name/Structure/Alcohol/Data |
|---|---|

Using 6-chloro-1H-pyrazolo[3,4-b]pyrazine

| 95 | methyl (R)-3-(6-chloro-1H-pyrazolo[3,4-b]pyrazin-1-yl)-2-methylpropanoate 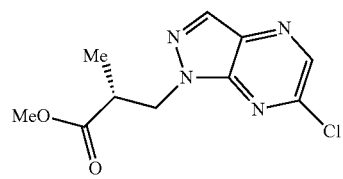 [SMILES: COC(=O)[C@H](C)Cn1ncc2ncc(Cl)nc21] Alcohol: methyl (R)-3-hydroxy-2-methylpropanoate 200 mg, 40% yield as a white solid. LCMS m/z = 255, 257 [M + H]+ |

| Preparation Number | Name/Structure/Alcohol/Data |
|---|---|
| 96 | 6-chloro-1-((tetrahydro-2H-pyran-3-yl)methyl)-1H-pyrazolo[3,4-b]pyrazine 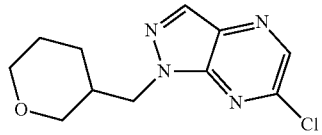 [SMILES: Clc1cnc2cnn(CC3CCCOC3)c2n1] Alcohol: (tetrahydro-2H-pyran-3-yl)methanol<br>1.2 g, 92% yield as a white solid. LCMS m/z = 253 [M + H]$^+$ |
| 97$^A$ | (S)-6-chloro-1-((tetrahydro-2H-pyran-3-yl)methyl)-1H-pyrazolo[3,4-b]pyrazine 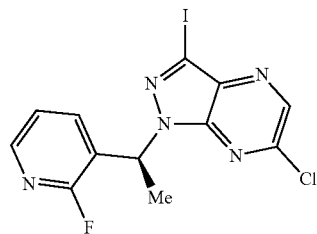 [SMILES: C[C@@H](c1cccnc1F)n1nc(I)c2ncc(Cl)nc21] Alcohol: (S)-(tetrahydro-2H-pyran-3-yl)methanol<br>501 mg, 88% yield as a yellow solid. LCMS m/z = 253 [M + H]$^+$ |
| 98 | (R)-6-chloro-1-((tetrahydro-2H-pyran-3-yl)methyl)-1H-pyrazolo[3,4-b]pyrazine 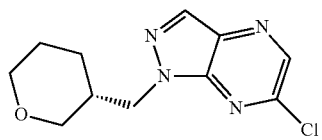 [SMILES: Clc1cnc2cnn(C[C@H]3CCCOC3)c2n1] Alcohol: (R)-(tetrahydro-2H-pyran-3-yl)methanol<br>320 mg, 65% yield as a solid. LCMS m/z = 253 [M + H]$^+$ |
| 99 | 6-chloro-1-((tetrahydrofuran-3-yl)methyl)-1H-pyrazolo[3,4-b]pyrazine 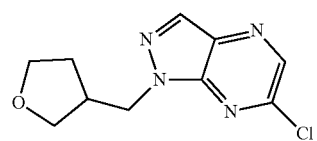 [SMILES: Clc1cnc2cnn(CC3CCOC3)c2n1] Alcohol: (tetrahydrofuran-3-yl)methanol<br>1.0 g, 80% yield as a white solid. LCMS m/z = 239 [M + H]$^+$ |
| 100 | 6-chloro-1-((3-methyltetrahydrofuran-3-yl)methyl)-1H-pyrazolo[3,4-b]pyrazine 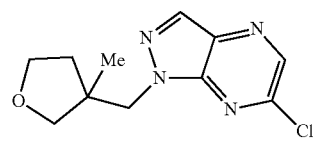 [SMILES: CC1(Cn2ncc3ncc(Cl)nc32)CCOC1] Alcohol: (3-methyltetrahydrofuran-3-yl)methanol<br>300 mg, 61% yield as a white solid. LCMS m/z = 253 [M + H]$^+$ |

| Preparation Number | Name/Structure/Alcohol/Data |
|---|---|
| 101 | 6-chloro-1-((3-fluorotetrahydrofuran-3-yl)methyl)-1H-pyrazolo[3,4-b]pyrazine 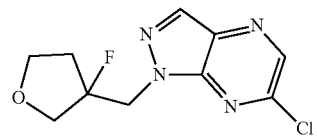 Alcohol: (3-fluorotetrahydrofuran-3-yl)methanol 150 mg, 42% yield as a white solid. LCMS m/z = 271 [M + H]$^+$ |
| 102 | 3-((6-chloro-1H-pyrazolo[3,4-b]pyrazin-1-yl)methyl)tetrahydrofuran-3-carbonitrile 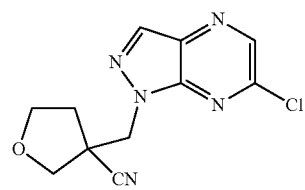 [SMILES: N#CC1(Cn2ncc3ncc(Cl)nc32)CCOC1] Alcohol: 3-(hydroxymethyl)oxolane-3-carbonitrile 200 mg, 78% yield as a white solid. LCMS m/z = 264 [M + H]$^+$ |
| 103 | (R)-6-chloro-1-((tetrahydrofuran-2-yl)methyl)-1H-pyrazolo[3,4-b]pyrazine 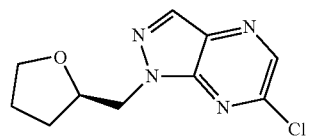 [SMILES: Clc1cnc2cnn(C[C@H]3CCCO3)c2n1] Alcohol: (R)-(tetrahydrofuran-2-yl)methanol 200 mg, 86% yield as a yellow solid. LCMS m/z = 239 [M + H]$^+$ |
| 104 | tert-butyl (S)-3-((6-chloro-1H-pyrazolo[3,4-b]pyrazin-1-yl)methyl)piperidine-1-carboxylate 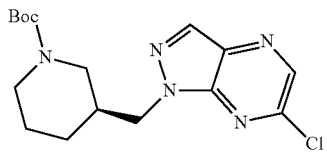 [SMILES: CC(C)(C)OC(=O)N1CCC[C@H](Cn2ncc3ncc(Cl)nc32)C1] Alcohol: tert-butyl (S)-3-(hydroxymethyl)piperidine-1-carboxylate 300 mg, 52% yield, as a yellow solid. LCMS m/z = 352 [M + H]$^+$ |
| 105 | methyl (S)-3-(6-chloro-1H-pyrazolo[3,4-b]pyrazin-1-yl)-2-methylpropanoate 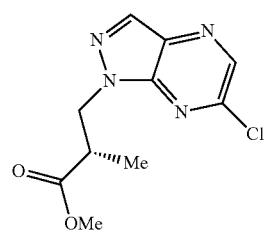 [SMILES: COC(=O)[C@@H](C)Cn1ncc2ncc(Cl)nc21] Alcohol: methyl (S)-3-hydroxy-2-methylpropanoate 100 mg, 24% yield as a yellow solid. LCMS m/z = 255 [M + H]$^+$ |

| Preparation Number | Name/Structure/Alcohol/Data |
|---|---|
| 106 | (R)-6-chloro-1-(tetrahydro-2H-pyran-3-yl)-1H-pyrazolo[3,4-b]pyrazine 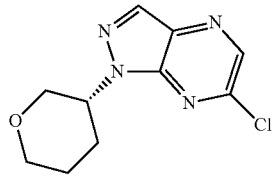 [SMILES: Clc1cnc2cnn([C@@H]3CCCOC3)c2n1] Alcohol: (S)-tetrahydro-2H-pyran-3-ol<br>80 mg, 51% yield as white solid. LCMS m/z = 239 [M + H]⁺ |
| 107 | 1-(tert-butyl)-6-chloro-1H-pyrazolo[3,4-b]pyrazine 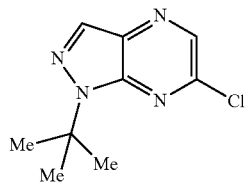 [SMILES: CC(C)(C)n1ncc2ncc(Cl)nc21] Alcohol: 2-methylpropan-2-ol<br>126 mg, 60% yield as a yellow solid. LCMS m/z = 211 [M + H]⁺ |
| 108 | 6-chloro-1-(cyclopropylmethyl)-1H-pyrazolo[3,4-b]pyrazine 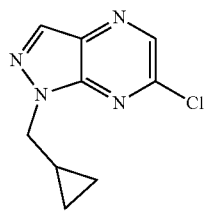 [SMILES: Clc1cnc2cnn(CC3CC3)c2n1] Alcohol: cyclopropylmethanol<br>100 mg, 74% yield as a white solid. LCMS m/z = 209 [M + H]⁺ |
| 109⁴ | 1-((3-oxabicyclo[3.1.0]hexan-6-yl)methyl)-6-chloro-1H-pyrazolo[3,4-b]pyrazine 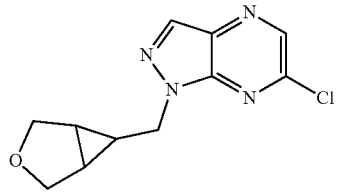 [SMILES: Clc1cnc2cnn(CC3C4COCC43)c2n1] Alcohol: (3-oxabicyclo[3.1.0]hexan-6-yl)methanol<br>200 mg, 41% yield as a white solid. LCMS m/z = 251 [M + H]⁺ |
| 110 | 1-(((1R,5S,6r)-3-oxabicyclo[3.1.0]hexan-6-yl)methyl)-6-chloro-1H-pyrazolo[3,4-b]pyrazine 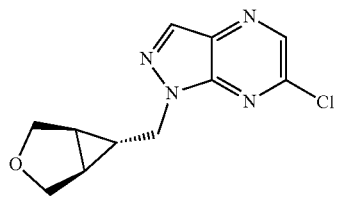 [SMILES: Clc1cnc2cnn(C[C@H]3[C@@H]4COC[C@@H]43)c2n1] Alcohol: ((1R,5S,6r)-3-oxabicyclo[3.1.0]hexan-6-yl)methanol<br>270 mg, 84% yield as a yellow solid. LCMS m/z = 251 [M + H]⁺ |

| Preparation Number | Name/Structure/Alcohol/Data |
|---|---|
| 111 | 1-(((1R,5S,6s)-3-oxabicyclo[3.1.0]hexan-6-yl)methyl)-6-chloro-1H-pyrazolo[3,4-b]pyrazine 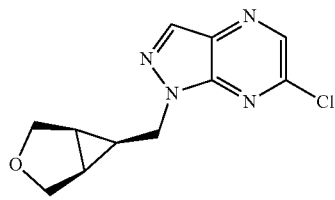 [SMILES: Clc1cnc2cnn(C[C@@H]3[C@@H]4COC[C@@H]43)c2n1] Alcohol: ((1R,5S,6s)-3-oxabicyclo[3.1.0]hexan-6-yl)methanol 280 mg, 57% yield as a yellow oil. LCMS m/z = 251 [M + H]$^+$ |
| 112 | 6-chloro-1-((2R)-2-((tetrahydro-2H-pyran-2-yl)oxy)pentan-3-yl)-1H-pyrazolo[3,4-b]pyrazine 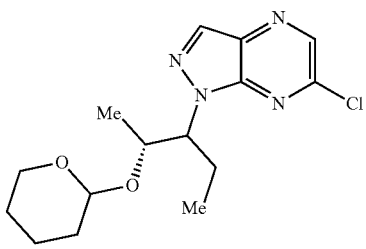 [SMILES: CCC([C@@H](C)OC1CCCCO1)n1ncc2ncc(Cl)nc21] Alcohol: (2R)-2-((tetrahydro-2H-pyran-2-yl)oxy)pentan-3-ol (Preparation 7) 90 mg, 42% yield as a yellow solid. LCMS m/z = 241 [M + H]$^+$ |
| 113 | (R)-6-chloro-1-(1-(pyridin-2-yl)ethyl)-1H-pyrazolo[3,4-b]pyrazine 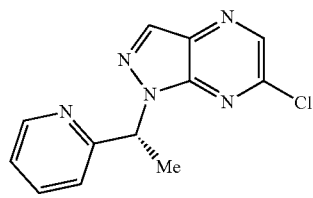 [SMILES: C[C@H](c1ccccn1)n1ncc2ncc(Cl)nc21] Alcohol: (S)-1-(pyridin-2-yl)ethan-1-ol 200 mg, 59% yield as a yellow solid. LCMS m/z = 260 [M + H]$^+$ |
| 114 | 6-chloro-1-(oxetan-3-ylmethyl)-1H-pyrazolo[3,4-b]pyrazine 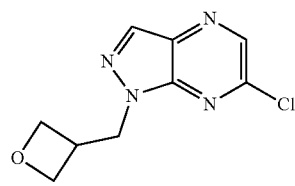 [SMILES: Clc1cnc2cnn(CC3COC3)c2n1] Alcohol: (oxetan-3-yl)methanol 110 mg, 75% yield as a white solid. LCMS m/z = 225 [M + H]$^+$ |

-continued

| Preparation Number | Name/Structure/Alcohol/Data |
|---|---|
| 115 | 6-chloro-1-((3-methyloxetan-3-yl)methyl)-1H-pyrazolo[3,4-b]pyrazine<br>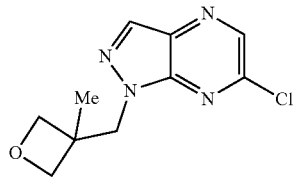 [SMILES: CC1(Cn2ncc3ncc(Cl)nc32)COC1]<br>Alcohol: (3-methyloxetan-3-yl)methanol<br>180 mg, 77% yield as a white solid. LCMS m/z = 239 [M + H]+ |
| 116 | (S)-6-chloro-1-((tetrahydro-2H-pyran-2-yl)methyl)-1H-pyrazolo[3,4-b]pyrazine<br>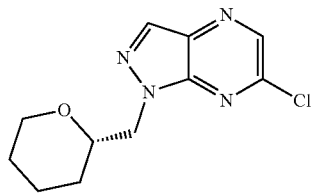 [SMILES: Clc1cnc2cnn(C[C@@H]3CCCCO3)c2n1]<br>Alcohol: (S)-(tetrahydro-2H-pyran-2-yl)methanol<br>220 mg, 67% yield as a yellow solid. LCMS m/z = 253 [M + H]+ |
| 117 | (R)-6-chloro-1-((tetrahydro-2H-pyran-2-yl)methyl)-1H-pyrazolo[3,4-b]pyrazine<br>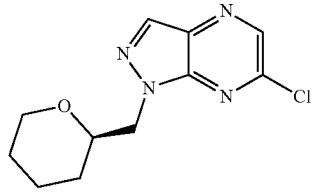 [SMILES: Clc1cnc2cnn(C[C@H]3CCCCO3)c2n1]<br>Alcohol: (R)-(tetrahydro-2H-pyran-2-yl)methanol<br>300 mg, 92% yield as a yellow solid. LCMS m/z = 253 [M + H]+ |
| 118 | (S)-1-((1,4-dioxan-2-yl)methyl)-6-chloro-1H-pyrazolo[3,4-b]pyrazine<br>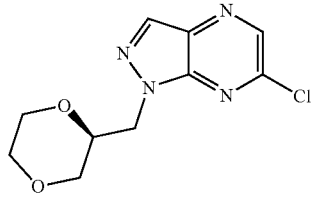 [SMILES: Clc1cnc2cnn(C[C@H]3COCCO3)c2n1]<br>Alcohol: (S)-(1,4-dioxan-2-yl)methanol<br>80 mg, 19% yield as a yellow solid. LCMS m/z = 255 [M + H]+ |
| 119 | (R)-1-((1,4-dioxan-2-yl)methyl)-6-chloro-1H-pyrazolo[3,4-b]pyrazine<br>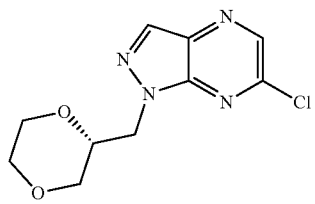 [SMILES: Clc1cnc2cnn(C[C@@H]3COCCO3)c2n1]<br>Alcohol: (R)-(1,4-dioxan-2-yl)methanol<br>80 mg, 19% yield as a yellow oil. LCMS m/z = 255 [M + H]+ |

| Preparation Number | Name/Structure/Alcohol/Data |
|---|---|
| 120 | 6-chloro-1-((4-methyltetrahydro-2H-pyran-4-yl)methyl)-1H-pyrazolo[3,4-b]pyrazine 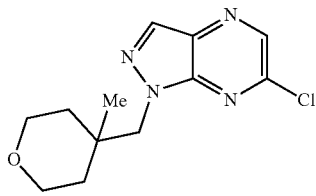 [SMILES: CC1(Cn2ncc3ncc(Cl)nc32)CCOCC1] Alcohol: (4-methyltetrahydro-2H-pyran-4-yl)methanol<br>200 mg, 25% yield as a white solid. LCMS m/z = 267 [M + H]$^+$ |
| 121 | 6-chloro-1-((4-fluorotetrahydro-2H-pyran-4-yl)methyl)-1H-pyrazolo[3,4-b]pyrazine 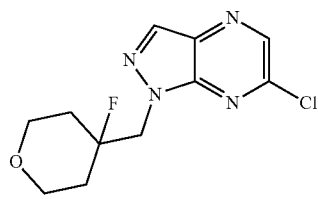 [SMILES: FC1(Cn2ncc3ncc(Cl)nc32)CCOCC1] Alcohol: (4-fluorotetrahydro-2H-pyran-4-yl)methanol<br>150 mg, 42% yield as a white solid. LCMS m/z = 271 [M + H]$^+$ |
| 122 | 4-((6-chloro-1H-pyrazolo[3,4-b]pyrazin-1-yl)methyl)tetrahydro-2H-pyran-4-carbonitrile 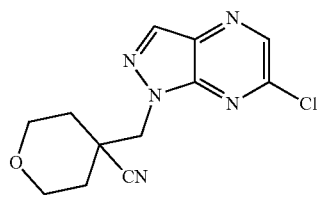 [SMILES: N#CC1(Cn2ncc3ncc(Cl)nc32)CCOCC1] Alcohol: 4-(hydroxymethyl)tetrahydro-2H-pyran-4-carbonitrile<br>400 mg, 89% yield as a white solid. LCMS m/z = 278 [M + H]$^+$ |
| 123$^A$ | 6-chloro-1-((4-(trifluoromethyl)tetrahydro-2H-pyran-4-yl)methyl)-1H-pyrazolo[3,4-b]pyrazine 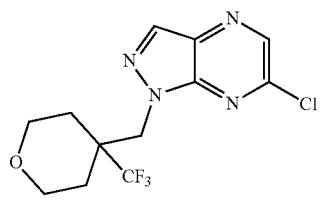 [SMILES: FC(F)(F)C1(Cn2ncc3ncc(Cl)nc32)CCOCC1] Alcohol: (4-(trifluoromethyl)tetrahydro2H-pyran-4-yl)methanol<br>60 mg, 28% yield as a white solid. LCMS m/z = 321 [M + H]$^+$ |

| Preparation Number | Name/Structure/Alcohol/Data |
|---|---|
| 124[A] | 6-chloro-1-((4-(difluoromethyl)tetrahydro-2H-pyran-4-yl)methyl)-1H-pyrazolo[3,4-b]pyrazine 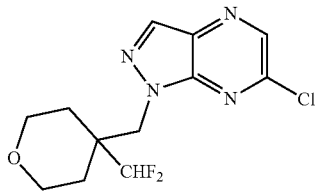 [SMILES: FC(F)C1(Cn2ncc3ncc(Cl)nc32)CCOCC1] Alcohol: (4-(difluoromethyl)tetrahydro2H-pyran-4-yl)methanol 300 mg, 36% yield as a white solid. LCMS m/z = 303 [M + H]+ |
| 125 | 6-chloro-1-(cyclopropyl(tetrahydro-2H-pyran-4-yl)methyl)-1H-pyrazolo[3,4-b]pyrazine 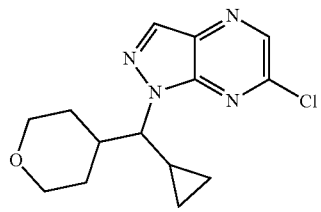 [SMILES: Clc1cnc2cnn(C(C3CCOCC3)C3CC3)c2n1] Alcohol: cyclopropyl(tetrahydro-2H-pyran-4-yl)methanol 180 mg, 64% yield as a yellow solid. LCMS m/z = 293 [M + H]+ |
| 126 | 1-((8-oxabicyclo[3.2.1]octan-3-yl)methyl)-6-chloro-1H-pyrazolo[3,4-b]pyrazine 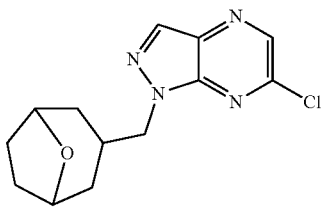 [SMILES: Clc1cnc2cnn(CC3CC4CCC(C3)O4)c2n1] Alcohol: (8-oxabicyclo[3.2.1]octan-3-yl)methanol 246 mg, 57% yield as a yellow solid. LCMS m/z = 279 [M + H]+ |
| 127 | 1-((2-oxabicyclo[2.2.2]octan-4-yl)methyl)-6-chloro-1H-pyrazolo[3,4-b]pyrazine 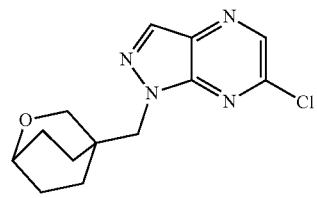 [SMILES: Clc1cnc2cnn(CC34CCC(CC3)OC4)c2n1] Alcohol: (2-oxabicyclo[2.2.2]octan-4-yl)methanol 150 mg, 83% yield as a white solid. LCMS m/z = 279 [M + H]+ |

| Preparation Number | Name/Structure/Alcohol/Data |
|---|---|
| 128 | (R)-6-chloro-1-(2-fluoro-1-phenylethyl)-1H-pyrazolo[3,4-b]pyrazine or (S)-6-chloro-1-(2-fluoro-1-phenylethyl)-1H-pyrazolo[3,4-b]pyrazine 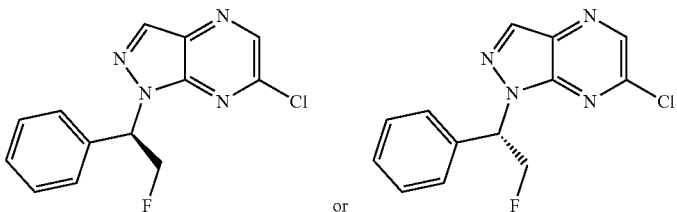 [SMILES: FC[C@@H](c1ccccc1)n1ncc2ncc(Cl)nc21 ; FC[C@H](c1ccccc1)n1ncc2ncc(Cl)nc21] Alcohol: Enantiomer 1 (Preparation 20 and 21) 150 mg, 54% yield as a yellow oil. LCMS m/z = 277 [M + H]$^+$ |
| 129 | (S)-6-chloro-1-(2-fluoro-1-phenylethyl)-1H-pyrazolo[3,4-b]pyrazine or (R)-6-chloro-1-(2-fluoro-1-phenylethyl)-1H-pyrazolo[3,4-b]pyrazine 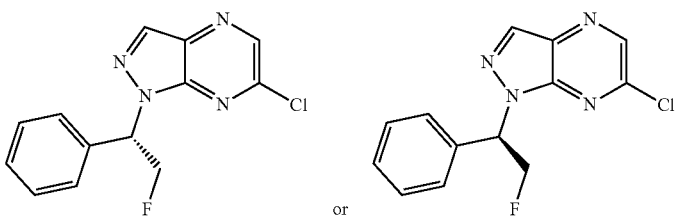 [SMILES: FC[C@H](c1ccccc1)n1ncc2ncc(Cl)nc21 ; FC[C@@H](c1ccccc1)n1ncc2ncc(Cl)nc21] Alcohol: Enantiomer 2 (Preparation 20 and 21) 150 mg, 54% yield as a yellow oil. LCMS m/z = 277 [M + H]$^+$ |
| 130 | (R)-6-chloro-1-(1-phenyl-2-((triisopropylsilyl)oxy)ethyl)-1H-pyrazolo[3,4-b]pyrazine 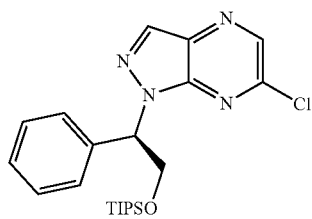 Alcohol: (S)-1-phenyl-2-((triisopropylsilyl)oxy)ethan-1-ol (Preparation 23) 700 mg, 53% yield as a yellow solid. |
| 131 | (R)-6-chloro-1-(1-(pyridin-3-yl)ethyl)-1H-pyrazolo[3,4-b]pyrazine 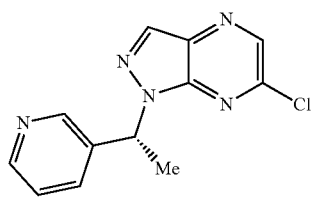 [SMILES: C[C@H](c1cccnc1)n1ncc2ncc(Cl)nc21] Alcohol: (S)-1-(pyridin-3-yl)ethan-1-ol 200 mg, 59% yield as a white solid. LCMS m/z = 260 [M + H]$^+$ |

-continued

| Preparation Number | Name/Structure/Alcohol/Data |
|---|---|
| 132 | 3-(6-chloro-1H-pyrazolo[3,4-b]pyrazin-1-yl)cyclopentan-1-ol 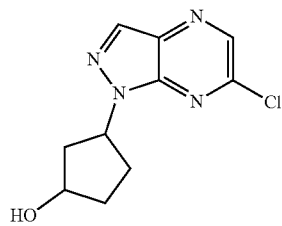 [SMILES: OC1CCC(n2ncc3ncc(Cl)nc32)C1] Alcohol: cyclopentane-1,3-diol<br>200 mg, 43% yield as a white solid. LCMS m/z = 239 [M + H]$^+$ |
| 133 | (S)-6-chloro-1-(1-phenylethyl)-1H-pyrazolo[3,4-b]pyrazine 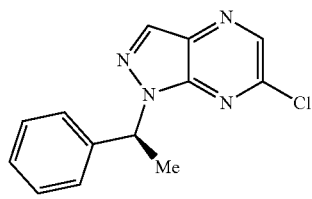 [SMILES: C[C@@H](c1ccccc1)n1ncc2ncc(Cl)nc21] Alcohol: (R)-1-phenylethan-1-ol<br>550 mg, 66% yield. LCMS m/z = 259 [M + H]$^+$ |
| 134 | 6-chloro-1-(oxetan-3-yl(phenyl)methyl)-1H-pyrazolo[3,4-b]pyrazine 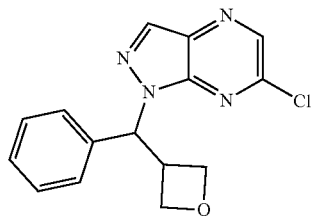 [SMILES: Clc1cnc2cnn(C(c3ccccc3)C3COC3)c2n1] Alcohol: oxetan-3-yl(phenyl)methanol (Preparation 22)<br>300 mg, 30% yield. LCMS m/z = 301 [M + H]$^+$ |
| 135 | (S)-6-chloro-1-(1-(pyridin-3-yl)propyl)-1H-pyrazolo[3,4-b]pyrazine 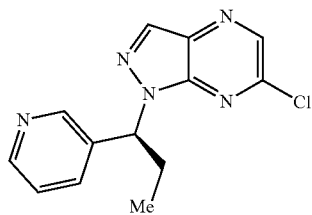 [SMILES: CC[C@@H](c1cccnc1)n1ncc2ncc(Cl)nc21] Alcohol: (R)-1-(pyridin-3-yl)propan-1-ol<br>120 mg, 44% yield as a yellow oil. LCMS m/z = 274 [M + H]$^+$ |

-continued

| Preparation Number | Name/Structure/Alcohol/Data |
|---|---|
| 136 | (S)-6-chloro-1-(1-(pyridin-2-yl)propyl)-1H-pyrazolo[3,4-b]pyrazine 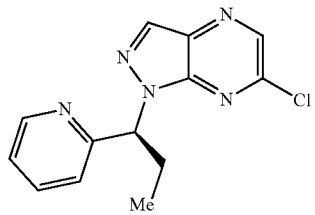 [SMILES: CC[C@@H](c1ccccn1)n1ncc2ncc(Cl)nc21]  Alcohol: (R)-1-(pyridin-2-yl)propan-1-ol  200 mg, 56% yield as a yellow oil. LCMS m/z = 274 [M + H]$^+$ |
| 137[A] | (R)-6-chloro-1-(1-(pyridin-3-yl)-2-((triisopropylsilyl)oxy)ethyl)-1H-pyrazolo[3,4-b]pyrazine 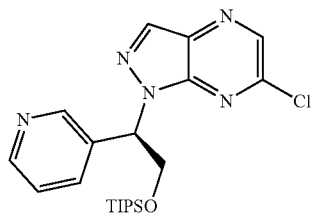  Alcohol: (S)-1-(pyridin-3-yl)-2-((triisopropylsilyl)oxy)ethan-1-ol (Preparation 26)  600 mg, 59% yield as a yellow oil. LCMS m/z = 432 [M + H]$^+$ |
| 138 | 3-(6-chloro-1H-pyrazolo[3,4-b]pyrazin-1-yl)cyclobutan-1-ol 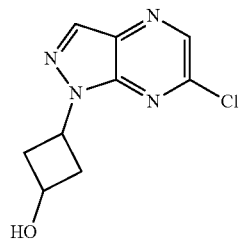 [SMILES: OC1CC(n2ncc3ncc(Cl)nc32)C1]  Alcohol: cyclobutane-1,3-diol  135 mg, 47% yield as a white solid. LCMS m/z = 225 [M + H]$^+$ |
| 139 | 6-chloro-1-((2-methylpyridin-3-yl)methyl)-1H-pyrazolo[3,4-b]pyrazine 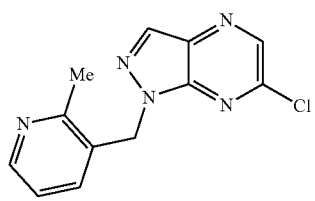 [SMILES: Cc1ncccc1Cn1ncc2ncc(Cl)nc21]  Alcohol: (2-methylpyridin-3-yl)methanol  300 mg, 71% yield as a yellow solid. LCMS m/z = 260 [M + H]$^+$ |

| Preparation Number | Name/Structure/Alcohol/Data |
|---|---|
| 140 | 6-chloro-1-((4-methylpyridin-3-yl)methyl)-1H-pyrazolo[3,4-b]pyrazine 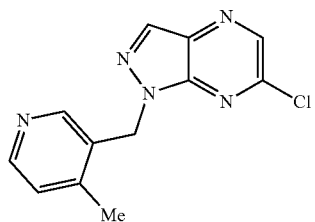 [SMILES: Cc1ccncc1Cn1ncc2ncc(Cl)nc21] Alcohol: (4-methylpyridin-3-yl)methanol<br>260 mg, 77% yield as a yellow solid. LCMS m/z = 260 [M + H]$^+$ |
| 141 | 6-chloro-1-(cyclopropyl(pyridin-3-yl)methyl)-1H-pyrazolo[3,4-b]pyrazine 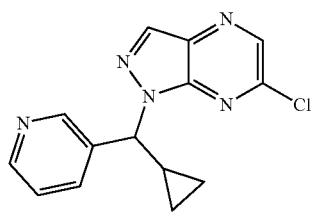 [SMILES: Clc1cnc2cnn(C(c3cccnc3)C3CC3)c2n1] Alcohol: cyclopropyl(pyridin-3-yl)methanol<br>250 mg, 47% yield as a yellow oil. LCMS mz = 286 [M + H]$^+$ |
| 142 | (S)-6-chloro-1-(cyclopropyl(pyridin-2-yl)methyl)-1H-pyrazolo[3,4-b]pyrazine 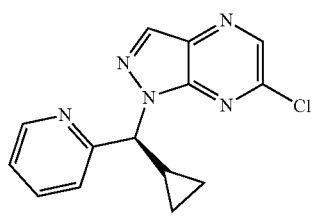 [SMILES: Clc1cnc2cnn([C@H](c3ccccn3)C3CC3)c2n1] Alcohol: (R)-cyclopropyl(pyridin-2-yl)methanol hydrochloride<br>50 mg, 16% yield as a yellow oil. LCMS mz = 286 [M + H]$^+$ |
| 143 | 6-chloro-1-(1-(6-fluoropyridin-3-yl)ethyl)-1H-pyrazolo[3,4-b]pyrazine 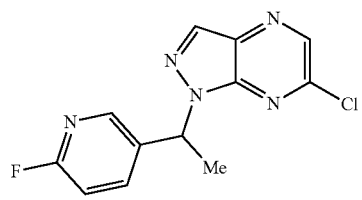 [SMILES: CC(c1ccc(F)nc1)n1ncc2ncc(Cl)nc21] Alcohol: 1-(6-fluoropyridin-3-yl)ethan-1-ol<br>450 mg, 83% yield as a white solid. LCMS mz = 278 [M + H]$^+$ |

| Preparation Number | Name/Structure/Alcohol/Data |
|---|---|
| 144 | 6-chloro-1-(1-(5-fluoropyridin-3-yl)ethyl)-1H-pyrazolo[3,4-b]pyrazine 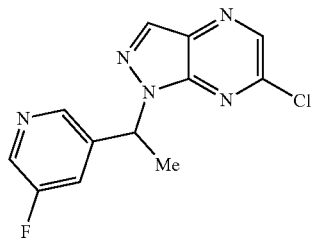 [SMILES: CC(c1cncc(F)c1)n1ncc2ncc(Cl)nc21] Alcohol: 1-(5-fluoropyridin-3-yl)ethan-1-ol 120 mg, 55% yield as a yellow solid. LCMS mz = 278 [M + H]$^+$ |
| 145 | 6-chloro-1-(1-(6-fluoropyridin-2-yl)ethyl)-1H-pyrazolo[3,4-b]pyrazine 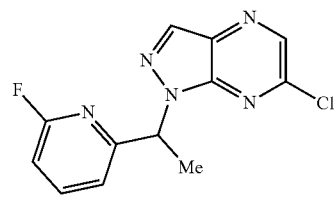 [SMILES: CC(c1cccc(F)n1)n1ncc2ncc(Cl)nc21] Alcohol: 1-(6-fluoropyridin-2-yl)ethan-1-ol 560 mg, 78% yield as a yellow solid. LCMS mz = 278 [M + H]$^+$ |
| 146 | 6-chloro-1-(1-(4-fluoropyridin-3-yl)ethyl)-1H-pyrazolo[3,4-b]pyrazine 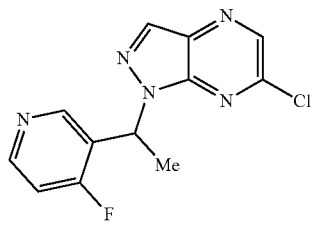 [SMILES: CC(c1cnccc1F)n1ncc2ncc(Cl)nc21] Alcohol: 1-(4-fluoropyridin-3-yl)ethan-1-ol (Preparation 18) 70 mg, 36% yield as a yellow solid. LCMS mz = 278 [M + H]$^+$ |
| 147 | 6-chloro-1-(1-(4-fluoropyridin-2-yl)ethyl)-1H-pyrazolo[3,4-b]pyrazine 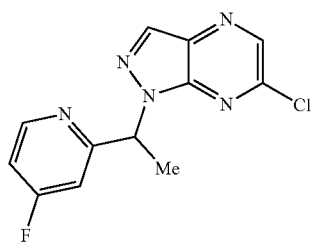 Alcohol: 1-(4-fluoropyridin-2-yl)ethan-1-ol (Preparation 19) 210 mg, 53% yield as a yellow solid. LCMS mz = 278 [M + H]$^+$ |

| Preparation Number | Name/Structure/Alcohol/Data |
|---|---|
| 148 | 6-chloro-1-(1-(4-chloropyridin-2-yl)ethyl)-1H-pyrazolo[3,4-b]pyrazine 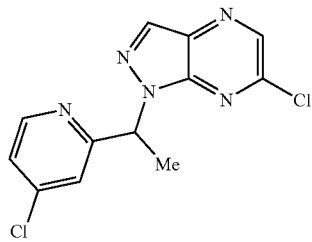 [SMILES: CC(c1cc(Cl)ccn1)n1ncc2ncc(Cl)nc21] Alcohol: 1-(4-chloropyridin-2-yl)ethan-1-ol 320 mg, 37% yield. LCMS m/z = 294 [M + H]$^+$ |
| 149 | 6-chloro-1-((1-methylcyclopropyl)methyl)-1H-pyrazolo[3,4-b]pyrazine 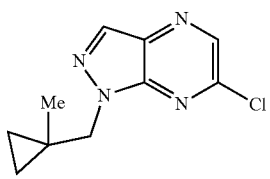 [SMILES: CC1(Cn2ncc3ncc(Cl)nc32)CC1] Alcohol: (1-methylcyclopropyl)methanol 130 mg, 90% yield as a yellow oil. LCMS m/z = 223 [M + H]$^+$ |
| 150 | 6-chloro-1-isobutyl-1H-pyrazolo[3,4-b]pyrazine 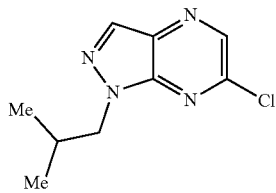 [SMILES: CC(C)Cn1ncc2ncc(Cl)nc21] Alcohol: 2-methylpropan-1-ol 150 mg, 55% yield. LCMS m/z = 211 [M + H]$^+$ |
| 151 | 6-chloro-1-(cyclobutylmethyl)-1H-pyrazolo[3,4-b]pyrazine 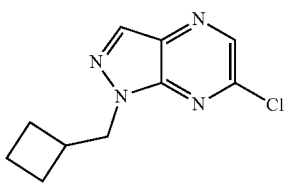 [SMILES: Clc1cnc2cnn(CC3CCC3)c2n1] Alcohol: cyclobutylmethanol 150 mg, 52% yield. LCMS m/z = 223 [M + H]$^+$ |
| 152 | 6-chloro-1-(cyclopentylmethyl)-1H-pyrazolo[3,4-b]pyrazine 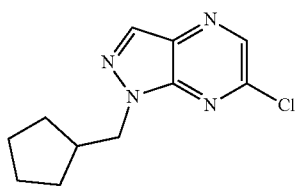 [SMILES: Clc1cnc2cnn(CC3CCCC3)c2n1] Alcohol: cyclopentylmethanol 170 mg, 56% yield. LCMS m/z = 237 [M + H]$^+$ |

| Preparation Number | Name/Structure/Alcohol/Data |
|---|---|
| 153 | 6-chloro-1-(cyclohexylmethyl)-1H-pyrazolo[3,4-b]pyrazine<br>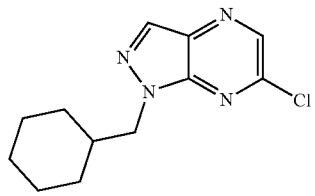 [SMILES: Clc1cnc2cnn(CC3CCCCC3)c2n1]<br>Alcohol: cyclohexylmethanol<br>160 mg, 50% yield. LCMS m/z = 251 [M + H]$^+$ |
| 154 | 1-(bicyclo[1.1.1]pentan-1-ylmethyl)-6-chloro-1H-pyrazolo[3,4-b]pyrazine<br>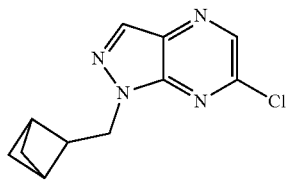 [SMILES: Clc1cnc2cnn(CC3C4CC3C4)c2n1]<br>Alcohol: bicyclo[1.1.1]pentan-1-ylmethanol<br>180 mg, 59% yield. LCMS m/z = 235 [M + H]$^+$ |
| 155 | 6-chloro-1-((3-fluorobicyclo[1.1.1]pentan-1-yl)methyl)-1H-pyrazolo[3,4-b]pyrazine<br>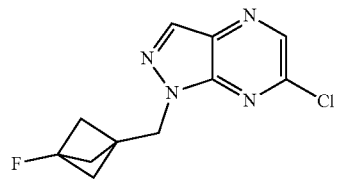 [SMILES: FC12CC(Cn3ncc4ncc(Cl)nc43)(C1)C2]<br>Alcohol: (3-fluorobicyclo[1.1.1]pentan-1-yl)methanol<br>88 mg, 53% yield as a yellow solid. LCMS m/z = 253 [M + H]$^+$ |
| 156 | 6-chloro-1-(spiro[2.2]pentan-1-ylmethyl)-1H-pyrazolo[3,4-b]pyrazine<br>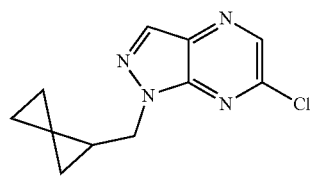 [SMILES: Clc1cnc2cnn(CC3CC34CC4)c2n1]<br>Alcohol: spiro[2.2]pentan-1-ylmethanol<br>520 mg, 85% yield as a colorless oil. LCMS m/z = 235 [M + H]$^+$ |
| 157 | 6-chloro-1-((4,4-difluorocyclohexyl)methyl)-1H-pyrazolo[3,4-b]pyrazine<br>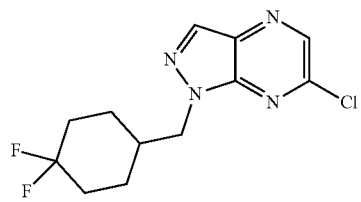 [SMILES: FC1(F)CCC(Cn2ncc3ncc(Cl)nc32)CC1]<br>Alcohol: 4,4-difluorocyclohexylmethanol<br>120 mg, 42% yield. LCMS m/z = 287 [M + H]$^+$ |

| Preparation Number | Name/Structure/Alcohol/Data |
|---|---|
| 158 | 4-((6-chloro-1H-pyrazolo[3,4-b]pyrazin-1-yl)methyl)cyclohexan-1-ol 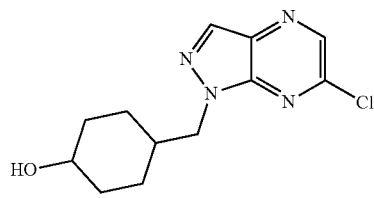 [SMILES: OC1CCC(Cn2ncc3ncc(Cl)nc32)CC1] Alcohol: 4-(hydroxymethyl)cyclohexan-1-ol 600 mg, 87% yield. LCMS m/z = 267 [M + H]⁺ |
| 159 | Cis-Rac-6-chloro-1-((2-fluorocyclopropyl)methyl)-1H-pyrazolo[3,4-b]pyrazine 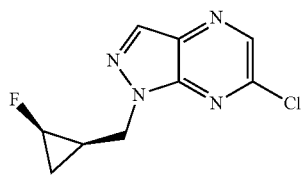 [SMILES: F[C@@H]1C[C@@H]1Cn1ncc2ncc(Cl)nc21] cis-racemate Alcohol: cis-rac-(2-fluorocyclopropyl)methanol 150 mg, 61% yield. LCMS m/z = 227 [M + H]⁺ |
| 160 | Trans-rac-6-chloro-1-((2-fluorocyclopropyl)methyl)-1H-pyrazolo[3,4-b]pyrazine 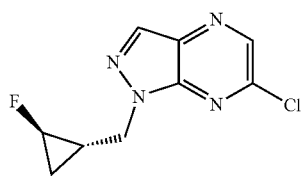 [SMILES: F[C@@H]1C[C@H]1Cn1ncc2ncc(Cl)nc21] trans-racemate Alcohol: trans-rac-(2-fluorocyclopropyl)methanol 490 mg, 83% yield as a colorless oil. LCMS m/z = 227 [M + H]⁺ |
| 161 | 6-chloro-1-((2,2-difluorocyclopropyl)methyl)-1H-pyrazolo[3,4-b]pyrazine 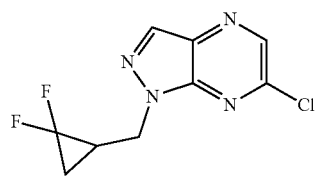 [SMILES: FC1(F)CC1Cn1ncc2ncc(Cl)nc21] Alcohol: (2,2-difluorocyclopropyl)methanol 125 mg, 27% yield as a yellow solid. LCMS m/z = 245 [M + H]⁺ |

| Preparation Number | Name/Structure/Alcohol/Data |
|---|---|
| 162^A | 6-chloro-1-((6,6-difluorobicyclo[3.1.0]hexan-3-yl)methyl)-1H-pyrazolo[3,4-b]pyrazine 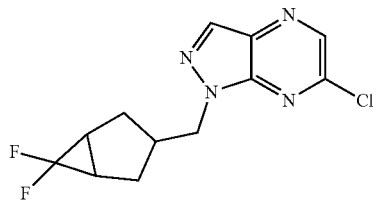 [SMILES: FC1(F)C2CC(Cn3ncc4ncc(Cl)nc43)CC21] Alcohol: (6,6-difluorobicyclo[3.1.0]hexan-3-yl)methanol 260 mg, 91% yield as a white solid. LCMS m/z = 285 [M + H]$^+$ |
| 163^A | 1-((6-chloro-1H-pyrazolo[3,4-b]pyrazin-1-yl)methyl)cyclobutan-1-ol 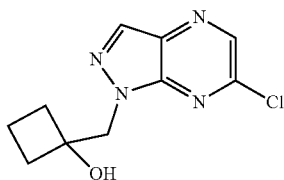 [SMILES: OC1(Cn2ncc3ncc(Cl)nc32)CCC1] Alcohol: 1-(hydroxymethyl)cyclobutan-1-ol 180 mg, 75% as a white solid. LCMS m/z = 239 [M + H]$^+$ |
| 164 | 6-chloro-1-((2-(4,4,5,5-tetramethyl-1,3,2-dioxaborolan-2-yl)cyclopropyl)methyl)-1H-pyrazolo[3,4-b]pyrazine 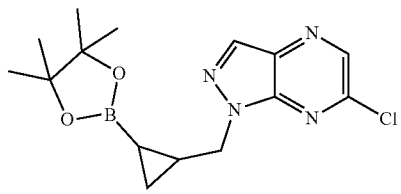 [SMILES: CC1(C)OB(C2CC2Cn2ncc3ncc(Cl)nc32)OC1(C)C] Alcohol: (2-(4,4,5,5-tetramethyl-1,3,2-dioxaborolan-2-yl)cyclopropyl)methanol (Preparation 27) 80 mg, 23% as a yellow solid. LCMS m/z = 335 [M + H]$^+$ |
| 165^A | 6-chloro-1-(2-fluoro-1-(tetrahydro-2H-pyran-4-yl)ethyl)-1H-pyrazolo[3,4-b]pyrazine 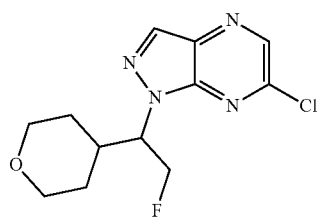 [SMILES: FCC(C1CCOCC1)n1ncc2ncc(Cl)nc21] Alcohol: 2-fluoro-1-(oxan-4-yl)ethan-1-ol 900 mg, 59% as a yellow oil. LCMS m/z = 285 [M + H]$^+$ |

| Preparation Number | Name/Structure/Alcohol/Data |
|---|---|
| 166[A] | 3-((6-chloro-1H-pyrazolo[3,4-b]pyrazin-1-yl)methyl)-5,5-dimethylpyrrolidin-2-one 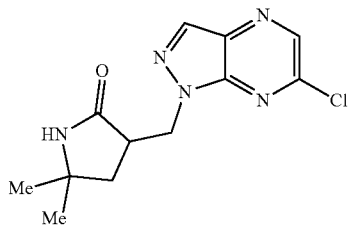 [SMILES: CC1(C)CC(Cn2ncc3ncc(Cl)nc32)C(=O)N1] Alcohol: 3-(hydroxymethyl)-5,5-dimethylpyrrolidin-2-one (Preparation 29) 300 mg, 38% as a yellow solid. LCMS m/z = 280 [M + H]$^+$ |
| 167 | 6-chloro-1-(4-((triisopropylsilyl)oxy)butan-2-yl)-1H-pyrazolo[3,4-b]pyrazine 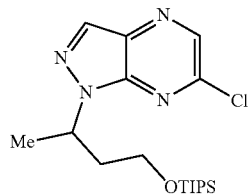 Alcohol: 4-((triisopropylsilyl)oxy)butan-2-ol (Preparation 24) 300 mg, 39% yield as a white solid. LCMS m/z = 383 [M + H]$^+$ |
| 168 | (S)-6-chloro-1-(1-(oxetan-3-yl)ethyl)-1H-pyrazolo[3,4-b]pyrazine 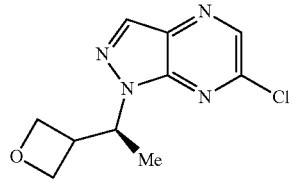 [SMILES: C[C@@H](C1COC1)n1ncc2ncc(Cl)nc21] Alcohol: (R)-1-(oxetan-3-yl)ethan-1-ol 320 mg, 77% as a yellow oil. LCMS m/z = 239 [M + H]$^+$ |
| 169 | 1-((1H-indazol-4-yl)methyl)-6-chloro-1H-pyrazolo[3,4-b]pyrazine 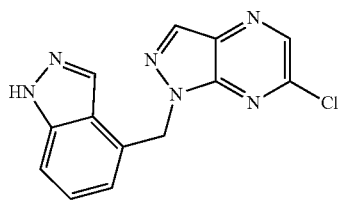 [SMILES: Clc1cnc2cnn(Cc3cccc4[nH]ncc34)c2n1] Alcohol: (1H-indazol-4-yl)methanol 150 mg, 39% as a yellow solid. LCMS m/z = 285 [M + H]$^+$ |

| Preparation Number | Name/Structure/Alcohol/Data |
|---|---|
| 170 | 1-(2-(1H-pyrazol-4-yl)ethyl)-6-chloro-1H-pyrazolo[3,4-b]pyrazine 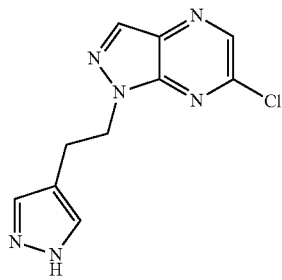 [SMILES: Clc1cnc2cnn(CCc3cn[nH]c3)c2n1] Alcohol: 2-(1H-pyrazol-4-yl)ethan-1-ol<br>300 mg, 97% as a yellow solid. LCMS m/z = 249 [M + H]$^+$ |
| 171[A] | 6-chloro-1-(2-(pyridin-4-yl)ethyl)-1H-pyrazolo[3,4-b]pyrazine 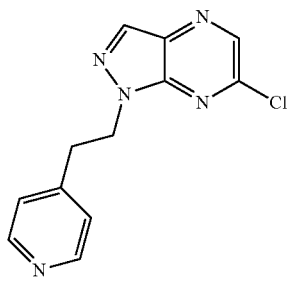 [SMILES: Clc1cnc2cnn(CCc3ccncc3)c2n1] Alcohol: 2-(pyridin-4-yl)ethan-1-ol<br>300 mg, 71% as a yellow oil. LCMS m/z = 260 [M + H]$^+$ |
| 172[A] | 6-chloro-1-((1-methyl-1H-imidazol-5-yl)methyl)-1H-pyrazolo[3,4-b]pyrazine 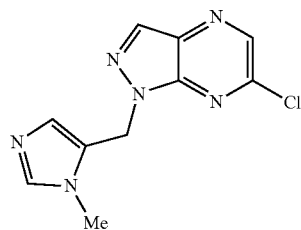 [SMILES: Cn1cncc1Cn1ncc2ncc(Cl)nc21] Alcohol: (1-methyl-1H-imidazol-5-yl)methanol<br>257 mg, 58% as a yellow oil. LCMS m/z = 249 [M + H]$^+$ |
| 173 | 5-((6-chloro-1H-pyrazolo[3,4-b]pyrazin-1-yl)methyl)isoxazole 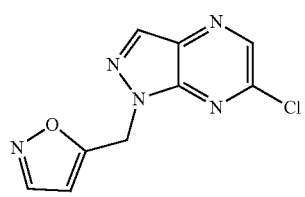 [SMILES: Clc1cnc2cnn(Cc3ccno3)c2n1] Alcohol: (isoxazol-5-yl)methanol<br>65 mg, 21%. LCMS m/z = 236 [M + H]$^+$ |

| Preparation Number | Name/Structure/Alcohol/Data |
|---|---|
| 174[A] | 2-(1-((6-chloro-1H-pyrazolo[3,4-b]pyrazin-1-yl)methyl)cyclopropyl)acetonitrile 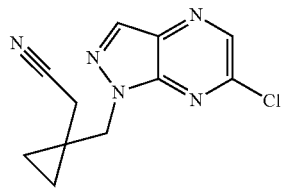 [SMILES: N#CCC1(Cn2ncc3ncc(Cl)nc32)CC1] Alcohol: 2-(1-(hydroxymethyl)cyclopropyl)acetonitrile 90 mg, 14% as a solid. LCMS m/z = 248 [M + H]$^+$ |
| 175[A] | 3-((6-chloro-1H-pyrazolo[3,4-b]pyrazin-1-yl)methyl)cyclobutane-1-carbonitrile 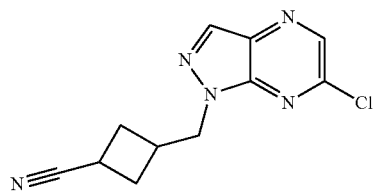 [SMILES: N#CC1CC(Cn2ncc3ncc(Cl)nc32)C1] Alcohol: 3-(hydroxymethyl)cyclobutane-1-carbonitrile 280 mg, 84% as a yellow oil. LCMS m/z = 248 [M + H]$^+$ |
| 176[A] | 1-(3-((benzyloxy)methyl)cyclobutyl)-6-chloro-1H-pyrazolo[3,4-b]pyrazine 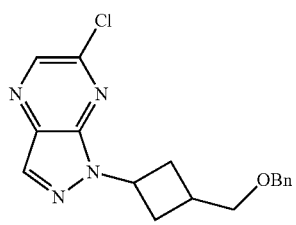 [SMILES: Clc1cnc2cnn(C3CC(COCc4ccccc4)C3)c2n1] Alcohol: 3-((benzyloxy)methyl)cyclobutan-1-ol 460 mg, 53% as a yellow solid. LCMS m/z = 329 [M + H]$^+$ |
| 177[A] | 1-(((1r,3r)-3-(benzyloxy)cyclobutyl)methyl)-N-(5-(difluoromethoxy)-1H-pyrazol-3-yl)-1H-pyrazolo[3,4-b]pyrazin-6-amine 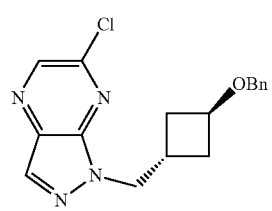 [SMILES: Clc1cnc2cnn(C[C@H]3C[C@H](OCc4ccccc4)C3)c2n1] Alcohol: trans-3-(benzyloxy)cyclobutyl)methanol 450 mg, 58% as a yellow solid. LCMS m/z = 329 [M + H]$^+$ |

-continued

| Preparation Number | Name/Structure/Alcohol/Data |
|---|---|

Using 6-chloro-3-methyl-1H-pyrazolo[3,4-b]pyrazine 178    6-chloro-3-methyl-1-(pyridin-3-ylmethyl)-1H-pyrazolo[3,4-b]pyrazine

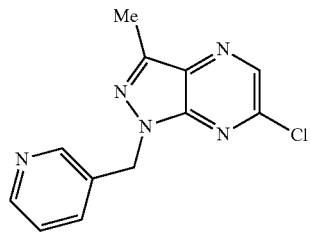 [SMILES: Cc1nn(Cc2cccnc2)c2nc(Cl)cnc12]

Alcohol: pyridin-3-ylmethanol
450 mg, 58% yield. LCMS m/z = 260 [M + H]$^+$ 179    6-chloro-3-methyl-1-((tetrahydro-2H-pyran-4-yl)methyl)-1H-pyrazolo[3,4-b]pyrazine

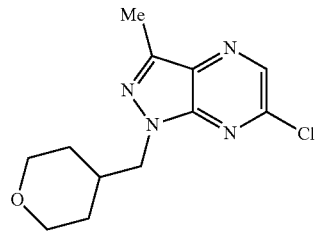 [SMILES: Cc1nn(CC2CCOCC2)c2nc(Cl)cnc12]

Alcohol: (tetrahydro-2H-pyran-4-yl)methanol
580 mg, 92% yield. LCMS m/z = 267 [M + H]$^+$ Using 6-chloro-3-fluoro-1H-pyrazolo[3,4-b]pyrazine (Preparation 3)

180    6-chloro-3-fluoro-1-((tetrahydro-2H-pyran-4-yl)methyl)-1H-pyrazolo[3,4-b]pyrazine

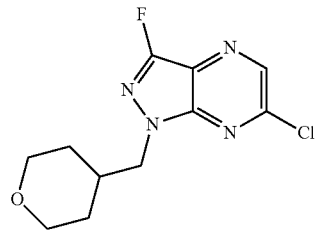 [SMILES: Fc1nn(CC2CCOCC2)c2nc(Cl)cnc12]

Alcohol: (tetrahydro-2H-pyran-4-yl)methanol
100 mg, 64% yield. LCMS m/z = 271 [M + H]$^+$ 181[A]    (S)-6-chloro-3-fluoro-1-(1-(tetrahydro-2H-pyran-4-yl)ethyl)-1H-pyrazolo[3,4-b]pyrazine

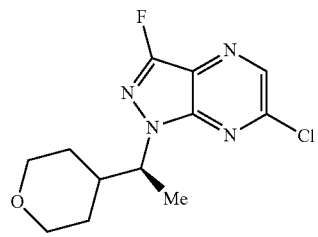 [SMILES: C[C@@H](C1CCOCC1)n1nc(F)c2ncc(Cl)nc21]

Alcohol: (R)-1-(tetrahydro-2H-pyran-4-yl)ethan-1-ol
1.38 g, 60% yield as a white solid. LCMS m/z = 285 [M + H]$^+$

| Preparation Number | Name/Structure/Alcohol/Data |
|---|---|
| 182[A] | 6-chloro-3-fluoro-1-(pyridin-3-ylmethyl)-1H-pyrazolo[3,4-b]pyrazine 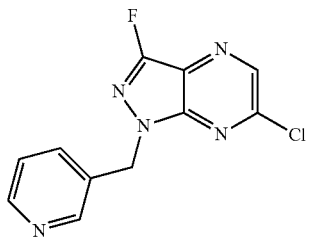 [SMILES: Fc1nn(Cc2cccnc2)c2nc(Cl)cnc12] Alcohol: (pyridin-3-yl)methanol<br>80 mg, 35% yield. LCMS m/z = 264 [M + H]+ |

A—toluene was the solvent and the reaction and stirred at 80'C until all starting materials had been consumed.

Preparation 183 and 184. Trans-rac-1-(1-(1,4-dioxan-2-yl)ethyl)-6-chloro-1H-pyrazolo[3,4-b]pyrazine and cis-rac-1-(1-(1,4-dioxan-2-yl)ethyl)-6-chloro-1H-pyrazolo[3,4-b]pyrazine

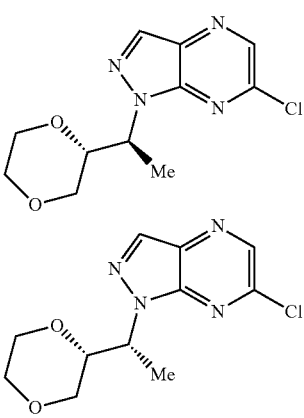

Trans-Racemate and Cis-Racemate

DEAD (783 mg, 4.5 mmol) was added dropwise to an ice cooled solution of 6-chloro-1H-pyrazolo[3,4-b]pyrazine (540 mg, 3.5 mmol), 1-(1,4-dioxan-2-yl)ethan-1-ol (400 mg, 3.0 mmol) and PPh$_3$ (917 mg, 3.5 mmol) in THF (10 mL) and the reaction stirred at 20° C. overnight. The reaction was quenched with water and extracted with EtOAc. The combined organic layer was washed with water and brine, dried over Na$_2$SO$_4$, filtered and concentrated in vacuo. The residue was purified by flash chromatography on silica gel (PE:EtOAc=4:1) to provide:

Product 1: Trans-rac-1-(1-(1,4-dioxan-2-yl)ethyl)-6-chloro-1H-pyrazolo[3,4-b]pyrazine or Cis-rac-1-(1-(1,4-dioxan-2-yl)ethyl)-6-chloro-1H-pyrazolo[3,4-b]pyrazine (90 mg, 11% yield)

Product 2: Cis-rac-1-(1-(1,4-dioxan-2-yl)ethyl)-6-chloro-1H-pyrazolo[3,4-b]pyrazine or trans-rac-1-(1-(1,4-dioxan-2-yl)ethyl)-6-chloro-1H-pyrazolo[3,4-b]pyrazine (230 mg, 29% yield). LCMS m/z=269,271 [M+H]+.

Preparation 185. 2-((6-chloro-1H-pyrazolo[3,4-b]pyrazin-1-yl)methyl)cyclopropan-1-ol

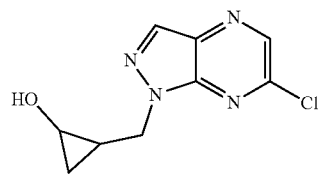 [SMILES: OC1CC1Cn1ncc2ncc(Cl)nc21]

To a solution of 6-chloro-1-((2-(4,4,5,5-tetramethyl-1,3,2-dioxaborolan-2-yl)cyclopropyl)methyl)-1H-pyrazolo[3,4-b]pyrazine (Preparation 164, 80 mg, 0.239 mmol) in AcOH (2 mL) at 0° C. was added H$_2$O$_2$ (30 wt %, 1 mL), and the reaction stirred at 25° C. for 18 h. The reaction was concentrated in vacuo, and the residue was purified by flash chromatography on silica gel eluting with EtOAc/PE (1/5) to afford the title compound (20 mg, 37% yield) as a yellow solid. LCMS m/z=225 [M+H]+.

Preparation 186. 6-chloro-1-(2-(tetrahydro-2H-pyran-4-yl)propan-2-yl)-1H-pyrazolo[3,4-b]pyrazine

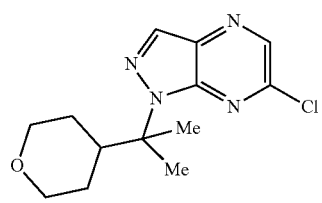 [SMILES: CC(C)(C1CCOCC1)n1ncc2ncc(Cl)nc21]

To a solution of 6-chloro-1H-pyrazolo[3,4-b]pyrazine (426 mg, 2.76 mmol) and 2-(oxan-4-yl)propan-2-ol (200 mg, 1.38 mmol) in DCM (15 mL) was added trifluoromethanesulfonic acid (621 mg, 4.14 mmol) dropwise at 0° C. and the reaction stirred at 0° C. for 30 min. The reaction mixture was quenched with sat. aq. NaHCO$_3$, extracted with EtOAc and the organic layer was concentrated in vacuo. The residue was purified by silica gel chromatography eluting with PE/EtOAc (10/1) to give the title compound (70 mg, 18% yield) as a white solid. LCMS m/z=281 [M+H]+.

Preparation 187. N-(5-(difluoromethoxy)-1H-pyrazol-3-yl)-1-((2S)-2-((tetrahydro-2H-pyran-2-yl)oxy)pentan-3-yl)-1H-pyrazolo[3,4-b]pyrazin-6-amine

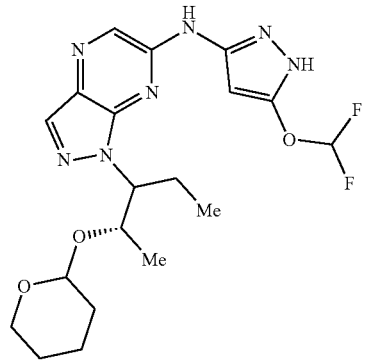 [SMILES: CCC([C@H](C)OC1CCCCO1)n1ncc2ncc(Nc3cc(OC(F)F)[nH]n3)nc21]

A mixture of 6-chloro-1-((2S)-2-((tetrahydro-2H-pyran-2-yl)oxy)pentan-3-yl)-1H-pyrazolo[3,4-b]pyrazine (Preparation 92, 180 mg, 0.554 mmol), 5-(difluoromethoxy)-1H-pyrazol-3-amine (124 mg, 0.831 mmol), BrettPhos Pd G4 (19.5 mg, 20 µmol) and KOAc (163 mg, 1.66 mmol) in dioxane (5.0 mL) was stirred at 90° C. overnight under N$_2$. The reaction mixture was cooled to rt and concentrated in vacuo. The residue was purified by flash chromatography on silica gel eluting with EtOAc/PE (1/1) to give the title compound (90 mg, 37% yield) as a yellow oil. LCMS m/z=438 [M+H]$^+$.

Preparation 188. N-(5-(difluoromethoxy)-1H-pyrazol-3-yl)-1-((2R)-2-((tetrahydro-2H-pyran-2-yl)oxy)pentan-3-yl)-1H-pyrazolo[3,4-b]pyrazin-6-amine

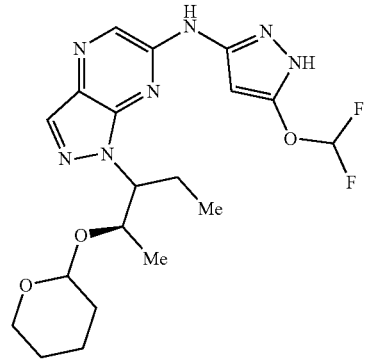 [SMILES: CCC([C@@H](C)OC1CCCCO1)n1ncc2ncc(Nc3cc(OC(F)F)[nH]n3)nc21]

The title compound was obtained, 80 mg, 66% yield from 6-chloro-1-((2R)-2-((tetrahydro-2H-pyran-2-yl)oxy)pentan-3-yl)-1H-pyrazolo[3,4-b]pyrazine (Preparation 112) and 5-(difluoromethoxy)-1H-pyrazol-3-amine, following the procedure described in Preparation 187. LCMS m/z=438 [M+H]$^+$.

Preparation 189. methyl (S)-3-(6-((5-(difluoromethoxy)-1H-pyrazol-3-yl)amino)-1H-pyrazolo[3,4-b]pyrazin-1-yl)-2-methylpropanoate

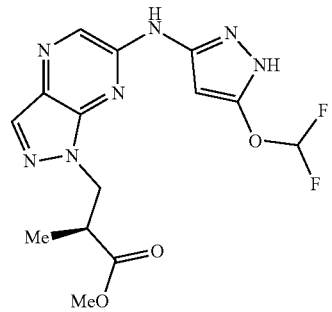 [SMILES: COC(=O)[C@@H](C)Cn1ncc2ncc(Nc3cc(OC(F)F)[nH]n3)nc21]

The title compound was obtained as a yellow oil, 70 mg, 48% yield, from methyl (S)-3-(6-chloro-1H-pyrazolo[3,4-b]pyrazin-1-yl)-2-methylpropanoate (Preparation 105) and 5-(difluoromethoxy)-1H-pyrazol-3-amine, following the procedure described in Preparation 187. LCMS m/z=368 [M+H]$^+$.

Preparation 190. (R)—N-(5-(difluoromethoxy)-1H-pyrazol-3-yl)-1-(1-(tetrahydro-2H-pyran-4-yl)-2-((triisopropylsilyl)oxy)ethyl)-1H-pyrazolo[3,4-b]pyrazin-6-amine

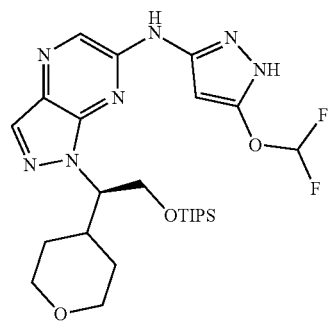

A mixture of (R)-6-chloro-1-(1-(tetrahydro-2H-pyran-4-yl)-2-((triisopropylsilyl)oxy)ethyl)-1H-pyrazolo[3,4-b]pyrazine (Preparation 91, 600 mg, 1.36 mmol), 5-(difluoromethoxy)-1H-pyrazol-3-amine (243 mg, 1.63 mmol), KOAc (400 mg, 4.08 mmol) and BrettPhos Pd G4 (100 mg, 0.11 mmol) in dioxane (8 mL) was stirred at 90° C. for 2 h under N$_2$, The cooled reaction mixture was concentrated in vacuo and the residue was purified by flash chromatography on silica gel eluting with EtOAc/PE (2/1) to give the title compound (600 mg, 80% yield) as a yellow solid. LCMS m/z=552 [M+H]$^+$.

Preparation 191. 1-(((1r,3r)-3-(benzyloxy)cyclobutyl)methyl)-N-(5-(difluoromethoxy)-1H-pyrazol-3-yl)-1H-pyrazolo[3,4-b]pyrazin-6-amine

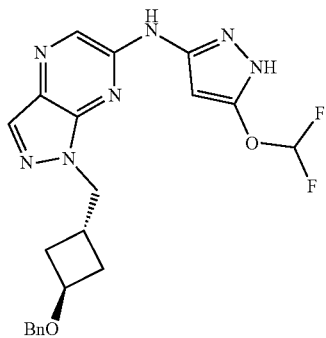 [SMILES: FC(F)Oc1cc(Nc2cnc3cnn(C[C@H]4C[C@H](OCc5ccccc5)C4)c3n2)n[nH]1]

A mixture of 1-((trans-3-(benzyloxy)cyclobutyl)methyl)-6-chloro-1H-pyrazolo[3,4-b]pyrazine (Preparation 177, 400 mg, 1.21 mmol), 5-(difluoromethoxy)-1H-pyrazol-3-amine (216 mg, 1.45 mmol), t-BuXPhos Pd G3 (96.6 mg, 12.1 μmol) and KOAc (355 mg, 3.62 mmol) in dioxane (10 mL) was stirred at 100° C. overnight under $N_2$. The cooled mixture was concentrated in vacuo and the residue was purified by flash chromatography on silica gel eluting with EtOAc/PE (1/1) to give the title compound (350 mg, 65% yield) as a yellow solid. LCMS m/z=442 [M+H]$^+$.

Preparation 192. (R)-6-chloro-1-((tetrahydrofuran-3-yl)methyl)-1H-pyrazolo[3,4-b]pyrazine

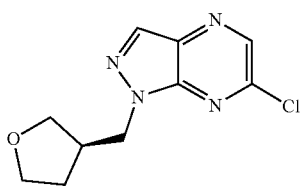 [SMILES: Clc1cnc2cnn(C[C@H]3CCOC3)c2n1]

DIAD (471 mg, 2.33 mmol) was added to an ice-cold solution of 6-chloro-1H-pyrazolo[3,4-b]pyrazine (300 mg, 1.94 mmol), R)-(tetrahydrofuran-3-yl)methanol (198 mg, 1.94 mmol) and PPh$_3$ (611 mg, 2.33 mmol) in THF (10 mL). The resulting mixture was allowed to warm slowly and the reaction was complete when it reached 5° C. The reaction mixture was evaporated to dryness in vacuo and the residue purified by Isco chromatography (0-40% EtOAc/Hex) to afford the title compound as a viscous colourless oil (381 mg, 82%). LCMS m/z=239 [M+H]$^+$.

PREFERRED EXAMPLES

Example 1

(S)—N-(5-(difluoromethoxy)-1H-pyrazol-3-yl)-1-(1-(pyridin-3-yl)ethyl)-1H-pyrazolo[3,4-b]pyrazin-6-amine

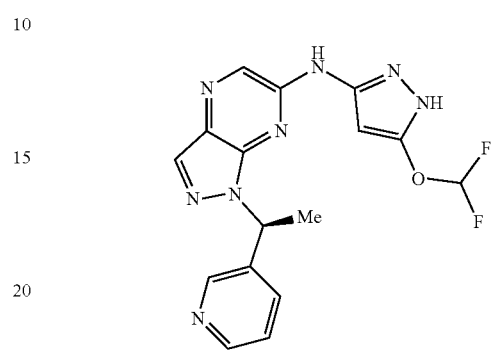

A mixture of (S)-6-chloro-1-(1-(pyridin-3-yl)ethyl)-1H-pyrazolo[3,4-b]pyrazine (Preparation 81, 600 mg, 2.4 mmol), 5-(difluoromethoxy)-1H-pyrazol-3-amine (413 mg, 2.77 mmol), Pd2(dba)3 (423 mg, 0.46 mmol), tBuXPhos (196 mg, 0.46 mmol) and KOAc (453 mg, 4.62 mmol) in dioxane (15 mL) was degassed with N2 (×3) and then heated at 100° C. overnight under N2. The reaction mixture was cooled to rt and concentrated to give a residue which was purified by flash chromatography (SiO2; 50% EtOAc/PE) and then by prep-HPLC-1 to afford the title compound as a yellow solid (168 mg, 18%) as a yellow solid. LCMS m/z=373 [M+H]$^+$; 1H NMR (400 MHz, DMSO-d6) δ: 12.29 (s, 1H), 10.86 (s, 1H), 8.59 (s, 1H), 8.45 (d, 1H), 8.23 (s, 1H), 8.21 (s, 1H), 7.74 (d, 1H), 7.36-7.32 (m, 1H), 7.31 (t, 1H), 6.65-6.60 (m, 1H), 5.92 (s, 1H), 1.92 (d, 3H).

Example 2

N-(5-(difluoromethoxy)-1H-pyrazol-3-yl)-1-((tetrahydro-2H-pyran-4-yl)methyl)-1H-pyrazolo[3,4-b]pyrazin-6-amine

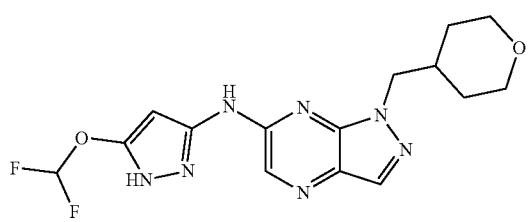 [SMILES: FC(F)Oc1cc(Nc2cnc3cnn(CC4CCOCC4)c3n2)n[nH]1]

A mixture of 6-chloro-1-((tetrahydro-2H-pyran-4-yl)methyl)-1H-pyrazolo[3,4-b]pyrazine (Preparation 87, 780 mg, 3.09 mmol), 5-(difluoromethoxy)-1H-pyrazol-3-amine (554 mg, 3.72 mmol), tBuXphos Pd G3 (150 mg, 0.19 mmol) and KOAc (892 mg, 9.08 mmol) in dioxane (15 mL) was stirred at 90° C. for 6 h under N$_2$. The reaction mixture was evaporated to dryness in vacuo and the residue was purified by prep-HPLC-4 to afford the title compound as a white solid (361.4 mg, 32%). LCMS m/z=366 [M+H]$^+$; $^1$H NMR (400 MHz, DMSO-d$_6$) δ: 12.21 (s, 1H), 10.82 (s, 1H), 8.19 (s, 1H), 8.17 (s, 1H), 7.32 (t, 1H), 5.98 (d, 1H), 4.40 (d, 2H), 3.87-3.75 (m, 2H), 3.29-3.16 (m, 2H), 2.24-2.11 (m, 1H), 1.46-1.29 (m, 4H).

Example 3

(1r,4r)-4-(6-((5-(difluoromethoxy)-1H-pyrazol-3-yl)amino)-1H-pyrazolo[3,4-b]pyrazin-1-yl)cyclohexan-1-ol

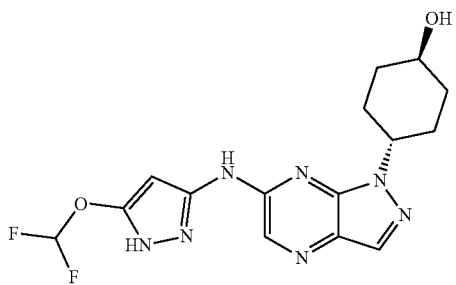 [SMILES: O[C@H]1CC[C@H](n2ncc3ncc(Nc4cc(OC(F)F)[nH]n4)nc32)CC1]

A mixture of (1r,4r)-4-(6-chloro-1Hpyrazolo[3,4-b]pyrazin-1-yl)cyclohexan-1-ol (Preparation 67, 45 mg, 0.178 mmol), 5-(difluoromethoxy)-1H-pyrazol-3-amine (29 mg, 0.196 mmol), 'BuBrettPhos Pd G3 (7.61 mg, 8.9 mmol) and KOAc (52 mg, 0.534 mmol) in dioxane (1 mL) was stirred at 90° C. for 1 h. The reaction mixture was evaporated to dryness and the residue dissolved in DMSO, filtered and purified by reverse phase Isco (0 to 80% MeCN/H$_2$O (+0.1% TFA). The appropriate fractions were treated with NaHCO$_3$ and extracted with 10% MeOH/DCM (4×). The combined organics were dried (Na$_2$SO$_4$) and evaporated to dryness in vacuo to afford the title compound as a pale yellow solid (21.3 mg, 33%). LCMS m/z=366 [M+H]$^+$; $^1$H NMR (500 MHz, DMSO-d$_6$) δ: 12.22 (s, 1H), 10.72 (s, 1H), 8.19 (s, 1H), 8.13 (s, 1H), 7.31 (t, 1H), 5.96 (s, 1H), 4.95-4.82 (m, 1H), 4.69 (d, 1H), 3.61-3.49 (m, 1H), 2.07-1.84 (m, 6H), 1.56-1.41 (m, 2H).

Example 4

(S)—N-(5-(difluoromethoxy)-1H-pyrazol-3-yl)-1-(1-(pyridin-2-yl)ethyl)-1H-pyrazolo[3,4-b]pyrazin-6-amine

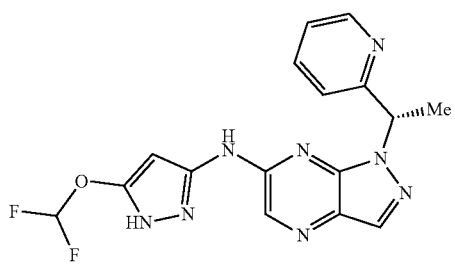

A mixture of (S)-6-chloro-1-(1-(pyridin-2-yl)ethyl)-1H-pyrazolo[3,4-b]pyrazine (Preparation 82, 980 mg, 3.77 mmol), 5-(difluoromethoxy)-1H-pyrazol-3-amine (562 mg, 3.77 mmol), t-BuXPhos Pd G4 (100 mg, 0.126 mmol) and KOAc (1.10 g, 11.3 mmol) in dioxane (10 mL) was stirred at 100° C. overnight under N$_2$. The reaction mixture was cooled to rt, concentrated in vacuo and the residue purified by flash chromatography (SiO$_2$, 4:1 EtOAc/PE) followed by prep-HPLC-1 to give the title compound as a yellow solid (205 mg, 14%). LCMS m/z=373 [M+H]$^+$; $^1$H NMR (400 MHz, DMSO-d$_6$) δ: 8.55 (d, 1H), 8.20 (s, 1H), 8.19 (s, 1H), 7.74-7.69 (m, 1H), 7.29 (t, 1H), 7.28-7.25 (m, 1H), 7.07 (d, 1H), 6.45-6.40 (m, 1H), 5.86 (s, 1H), 1.95 (d, 3H).

Example 5 and 6

(2S,3R)-3-(6-((5-(difluoromethoxy)-1H-pyrazol-3-yl)amino)-1H-pyrazolo[3,4-b]pyrazin-1-yl)pentan-2-ol and (2S,3S)-3-(6-((5-(difluoromethoxy)-1H-pyrazol-3-yl)amino)-1H-pyrazolo[3,4-b]pyrazin-1-yl)pentan-2-ol

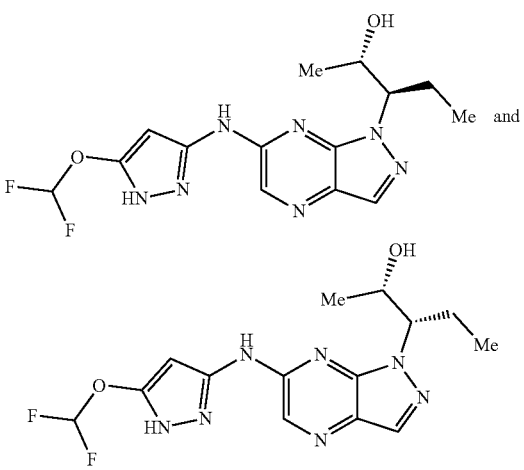

TFA (200 mg, 2.06 mmol) was added to a mixture of N-(5-(difluoromethoxy)-1H-pyrazol-3-yl)-1-((2S)-2-((tetrahydro-2H-pyran-2-yl)oxy)pentan-3-yl)-1H-pyrazolo[3,4-b]pyrazin-6-amine (Preparation 187.90 mg, 0.205 mmol) in DCM (20 mL) at 0° C. and the resulting mixture stirred for 5 h at 25° C. The reaction mixture was evaporated to dryness under reduced pressure and the residue purified by prep-HPLC-1 followed by further purification by chiral-SFC (Daicel IC 20×250 mm, 10 mm; 40% MeOH (+0.2% MeOH/NH3) in CO2) to afford the title compounds as white solids.

Peak 1, Example 5, (2S,3R)-3-(6-((5-(difluoromethoxy)-1H-pyrazol-3-yl)amino)-1H-pyrazolo[3,4-b]pyrazin-1-yl)pentan-2-ol or (2S,3S)-3-(6-((5-(difluoromethoxy)-1H-pyrazol-3-yl)amino)-1H-pyrazolo[3,4-b]pyrazin-1-yl)pentan-2-ol (17.8 mg): LCMS m/z=354 [M+H]$^+$; 1H NMR (400 MHz, DMSO-d6) δ: 12.19 (br s, 1H), 10.90 (br s, 1H), 8.22 (s, 1H), 8.18 (s, 1H), 7.31 (t, 1H), 6.01 (s, 1H), 5.06 (d, 1H), 4.60-4.53 (m, 1H), 4.02-3.98 (m, 1H), 2.14-1.99 (m, 2H), 0.79 (d, 3H), 0.61 (t, 3H).

Peak 2, Example 6, (2S,3S)-3-(6-((5-(difluoromethoxy)-1H-pyrazol-3-yl)amino)-1H-pyrazolo[3,4-b]pyrazin-1-yl)pentan-2-ol or (2S,3R)-3-(6-((5-(difluoromethoxy)-1H-pyrazol-3-yl)amino)-1H-pyrazolo[3,4-b]pyrazin-1-yl)pentan-2-ol (6.4 mg): LCMS m/z=354 [M+H]$^+$; $^1$H NMR (400 MHz, DMSO-d$_6$) δ: 12.23 (br s, 1H), 10.92 (br s, 1H), 8.20 (s, 1H), 8.16 (s, 1H), 7.31 (t, 1H), 5.94 (s, 1H), 4.80-4.60 (m, 2H), 4.20-4.00 (m, 1H), 2.10-1.80 (m, 2H), 1.43 (d, 3H), 0.59 (t, 3H).

Example 7

N-(5-(difluoromethoxy)-1H-pyrazol-3-yl)-1-((2-fluoropyridin-3-yl)methyl)-1H-pyrazolo[3,4-b]pyrazin-6-amine

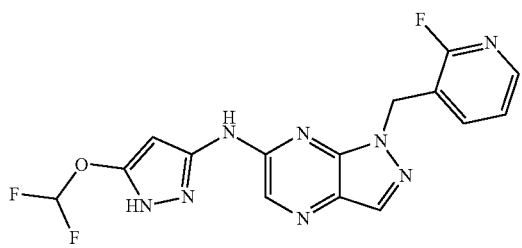 [SMILES: Fc1ncccc1Cn1ncc2ncc(Nc3cc(OC(F)F)[nH]n3)nc21]

A mixture of 6-chloro-1-((2-fluoropyridin-3-yl)methyl)-1H-pyrazolo[3,4-b]pyrazine (Preparation 36.65 mg, 0.247 mmol), 5-(difluoromethoxy)-1H-pyrazol-3-amine (40 mg, 0.271 mmol), 'BuBrettPhos Pd G3 (10.5 mg, 12 mmol) and KOAc (73 mg, 0.740 mmol) in dioxane (1 mL) was stirred at 80° C. overnight. The reaction mixture was evaporated to dryness and the residue dissolved in DMSO, filtered and purified by reverse phase Isco (0 to 80% MeCN/H$_2$O (+0.1% TFA). The appropriate fractions were treated with NaHCO$_3$ and extracted with 10% MeOH/DCM (4×). The combined organics were dried (Na$_2$SO$_4$) and evaporated to dryness in vacuo to afford the title compound as an off-white solid (33 mg, 36%). LCMS m/z=376 [M+H]$^+$; $^1$H NMR (500 MHz, DMSO-d$_6$) δ: 12.27 (s, 1H), 10.88 (s, 1H), 8.23 (s, 1H), 8.22 (s, 1H), 8.17 (d, 1H), 7.72-7.63 (m, 1H), 7.47-7.12 (m, 2H), 5.89 (s, 1H), 5.83 (s, 2H).

Example 8

(S)—N-(5-(difluoromethoxy)-1H-pyrazol-3-yl)-1-(1-(2-fluoropyridin-3-yl)ethyl)-1H-pyrazolo[3,4-b]pyrazin-6-amine

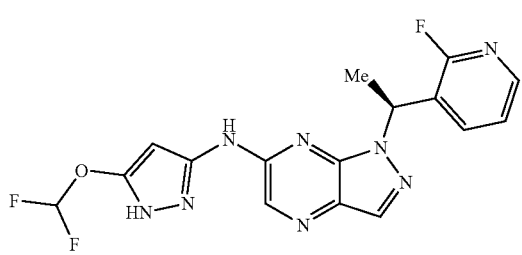 [SMILES: C[C@@H](c1cccnc1F)n1ncc2ncc(Nc3cc(OC(F)F)[nH]n3)nc21]

A mixture of (S)-6-chloro-1-(1-(2-fluoropyridin-3-yl)ethyl)-1H-pyrazolo[3,4-b]pyrazine (Preparation 31, 73 mg, 0.263 mmol), 5-(difluoromethoxy)-1H-pyrazol-3-amine (43 mg, 0.289 mmol), 'BuBrettPhos Pd G3 (11 mg, 13 mmol) and KOAc (77 mg, 0.789 mmol) in dioxane (1 mL) was stirred at 90° C. for 1 h. The reaction mixture was evaporated to dryness and the residue dissolved in DMSO, filtered and purified by reverse phase Isco (0 to 80% MeCN/H$_2$O (+0.1% TFA). The appropriate fractions were treated with NaHCO$_3$ and extracted with 10% MeOH/DCM (4×). The combined organics were dried (Na$_2$SO$_4$) and evaporated to dryness in vacuo to afford the title compound as a yellow solid (26 mg, 30%). LCMS m/z=391 [M+H]$^+$; $^1$H NMR (500 MHz, DMSO-d$_6$) δ: 12.24 (s, 1H), 10.82 (s, 1H), 8.23 (s, 1H), 8.22 (s, 1H), 8.16 (d, 1H), 7.91 (ddd, 1H), 7.47-7.12 (m, 2H), 6.65 (q, 1H), 5.95 (d, 1H), 1.89 (d, 3H).

Example 9, 10, 11 and 12

N-(5-(difluoromethoxy)-1H-pyrazol-3-yl)-1-((S)-1-((S)-tetrahydrofuran-3-yl)ethyl)-1H-pyrazolo[3,4-b]pyrazin-6-amine and N-(5-(difluoromethoxy)-1H-pyrazol-3-yl)-1-((R)-1-((R)-tetrahydrofuran-3-yl)ethyl)-1H-pyrazolo[3,4-b]pyrazin-6-amine and N-(5-(difluoromethoxy)-1H-pyrazol-3-yl)-1-((R)-1-((S)-tetrahydrofuran-3-yl)ethyl)-1H-pyrazolo[3,4-b]pyrazin-6-amine and N-(5-(difluoromethoxy)-1H-pyrazol-3-yl)-1-((S)-1-((R)-tetrahydrofuran-3-yl)ethyl)-1H-pyrazolo[3,4-b]pyrazin-6-amine

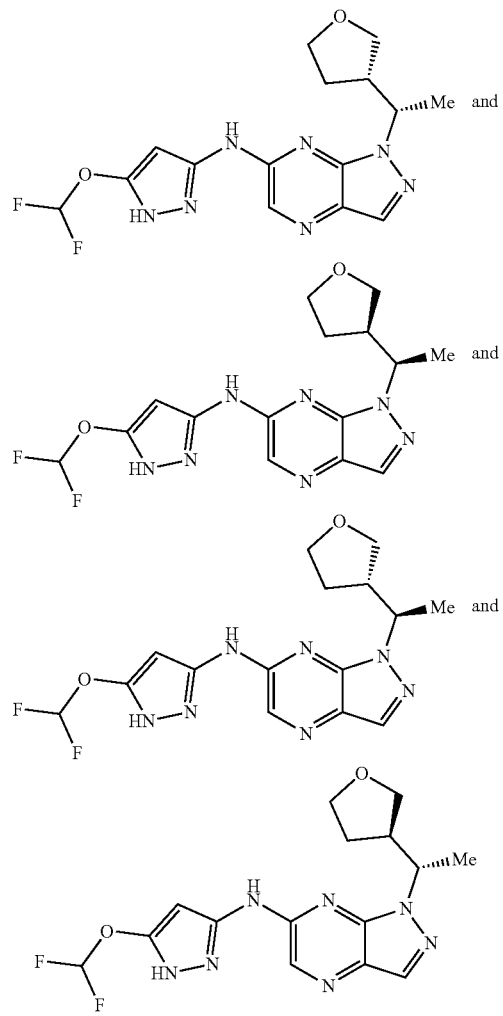

Part 1. A mixture of 6-chloro-1-(1-(tetrahydrofuran-3-yl)ethyl)-1H-pyrazolo[3,4-b]pyrazine (Preparation 88, 240 mg, 0.94 mmol), 5-(difluoromethoxy)-1H-pyrazol-3-amine (212 mg, 1.42 mmol), BrettPhos Pd G4 (40 mg, 0.42 mmol) and KOAc (280 mg, 1.42 mmol) in dioxane (5 mL) was stirred at 90° C. overnight under N$_2$. The reaction mixture was cooled to rt and evaporated to dryness in vacuo and the residue purified by flash chromatography on silica gel (50% EtOAc/PE) followed by prep-HPLC-1 to afford:

Intermediate Peak 1 (100 mg, 29%) and Intermediate Peak 2 (130 mg, 37%) as yellow solids.

Part 2. Intermediate Peak 1 from Part 1 was purified by Prep-SFC (Daicel OD; 20×250 mm, 10 mm; 40% MeOH (0.2% MeOH/NH₃) in CO₂) to afford:

Peak 1, Example 9, N-(5-(difluoromethoxy)-1H-pyrazol-3-yl)-1-((S)-1-((S)-tetrahydrofuran-3-yl)ethyl)-1H-pyrazolo[3,4-b]pyrazin-6-amine or N-(5-(difluoromethoxy)-1H-pyrazol-3-yl)-1-((R)-1-((R)-tetrahydrofuran-3-yl)ethyl)-1H-pyrazolo[3,4-b]pyrazin-6-amine or N-(5-(difluoromethoxy)-1H-pyrazol-3-yl)-1-((R)-1-((S)-tetrahydrofuran-3-yl)ethyl)-1H-pyrazolo[3,4-b]pyrazin-6-amine or N-(5-(difluoromethoxy)-1H-pyrazol-3-yl)-1-((S)-1-((R)-tetrahydrofuran-3-yl)ethyl)-1H-pyrazolo[3,4-b]pyrazin-6-amine (30.5 mg); LCMS m/z=366 [M+H]⁺; 1H NMR (400 MHz, DMSO-d6) δ: 12.22 (br s, 1H), 10.93 (br s, 1H), 8.22 (s, 1H1), 8.17 (s, 1H1), 7.31 (t, 1H1), 5.95 (s, 1H1), 5.15-5.05 (m, 1H1), 3.89-3.85 (m, 1H1), 3.67-3.51 (m, 3H), 2.83-2.77 (m, 1H1), 2.83-2.77 (m, 1H1), 1.53-1.38 (m, 5H1).

Peak 2, Example 10, N-(5-(difluoromethoxy)-1H-pyrazol-3-yl)-1-((R)-1-((R)-tetrahydrofuran-3-yl)ethyl)-1H-pyrazolo[3,4-b]pyrazin-6-amine or N-(5-(difluoromethoxy)-1H-pyrazol-3-yl)-1-((S)-1-((S)-tetrahydrofuran-3-yl)ethyl)-1H-pyrazolo[3,4-b]pyrazin-6-amine or N-(5-(difluoromethoxy)-1H-pyrazol-3-yl)-1-((R)-1-((S)-tetrahydrofuran-3-yl)ethyl)-1H-pyrazolo[3,4-b]pyrazin-6-amine or N-(5-(difluoromethoxy)-1H-pyrazol-3-yl)-1-((S)-1-((R)-tetrahydrofuran-3-yl)ethyl)-1H-pyrazolo[3,4-b]pyrazin-6-amine (29.6 mg); LCMS m/z=366 [M+H]⁺; 1H NMR (400 MHz, DMSO-d6) δ: 12.22 (br s, 1H), 10.93 (br s, 1H), 8.22 (s, 1H), 8.17 (s, 1H), 7.31 (t, 1H), 5.95 (s, 1H), 5.15-5.05 (m, 1H), 3.89-3.85 (m, 1H), 3.67-3.51 (m, 3H), 2.83-2.77 (m, 1H), 2.83-2.77 (m, 1H), 1.53-1.38 (m, 5H).

Part 3. Intermediate Peak 2 from Part 1 was purified by Prep-SFC (Daicel OZ; 20×250 mm, 10 mm; 30% MeOH (0.2% MeOH/NH3) in CO2) to afford:

Peak 3, Example 11, N-(5-(difluoromethoxy)-1H-pyrazol-3-yl)-1-((R)-1-((S)-tetrahydrofuran-3-yl)ethyl)-1H-pyrazolo[3,4-b]pyrazin-6-amine or N-(5-(difluoromethoxy)-1H-pyrazol-3-yl)-1-((S)-1-((R)-tetrahydrofuran-3-yl)ethyl)-1H-pyrazolo[3,4-b]pyrazin-6-amine or N-(5-(difluoromethoxy)-1H-pyrazol-3-yl)-1-((S)-1-((S)-tetrahydrofuran-3-yl)ethyl)-1H-pyrazolo[3,4-b]pyrazin-6-amine or N-(5-(difluoromethoxy)-1H-pyrazol-3-yl)-1-((R)-1-((R)-tetrahydrofuran-3-yl)ethyl)-1H-pyrazolo[3,4-b]pyrazin-6-amine (45.4 mg); LCMS m/z=366 [M+H]⁺; $^1$H NMR (400 MHz, DMSO-$d_6$) δ: 12.35-11.90 (br s, 1H), 11.05-10.65 (br s, 1H), 8.20 (s, 1H), 8.16 (s, 1H), 7.30 (t, 1H), 5.97 (s, 1H), 5.08-5.03 (m, 1H), 3.80-3.75 (m, 1H), 3.68-3.64 (m, 1H), 3.35-3.30 (m, 1H), 3.23-3.18 (m, 1H), 2.86-2.83 (m, 1H), 2.10-2.07 (m, 1H), 1.80-1.75 (m, 1H), 1.50 (d, 3H).

Peak 4, Example 12, N-(5-(difluoromethoxy)-1H-pyrazol-3-yl)-1-((S)-1-((R)-tetrahydrofuran-3-yl)ethyl)-1H-pyrazolo[3,4-b]pyrazin-6-amine or N-(5-(difluoromethoxy)-1H-pyrazol-3-yl)-1-((R)-1-((S)-tetrahydrofuran-3-yl)ethyl)-1H-pyrazolo[3,4-b]pyrazin-6-amine or N-(5-(difluoromethoxy)-1H-pyrazol-3-yl)-1-((S)-1-((S)-tetrahydrofuran-3-yl)ethyl)-1H-pyrazolo[3,4-b]pyrazin-6-amine or N-(5-(difluoromethoxy)-1H-pyrazol-3-yl)-1-((R)-1-((R)-tetrahydrofuran-3-yl)ethyl)-1H-pyrazolo[3,4-b]pyrazin-6-amine (48.1 mg); LCMS m/z=366 [M+H]⁺; 1H NMR (400 MHz, DMSO-$d_6$) δ: 12.35-11.90 (br, 1H), 11.05-10.65 (br, 1H), 8.20 (s, 1H), 8.16 (s, 1H), 7.30 (t, 1H), 5.97 (s, 1H), 5.08-5.03 (m, 1H), 3.80-3.75 (m, 1H), 3.68-3.64 (m, 1H), 3.35-3.30 (m, 1H), 3.23-3.18 (m, 1H), 2.86-2.83 (m, 1H), 2.10-2.07 (m, 1H), 1.80-1.75 (m, 1H), 1.50 (d, 3H).

Example 13 and 14

(S)—N-(5-(difluoromethoxy)-1H-pyrazol-3-yl)-1-(1-(4-fluoropyridin-2-yl)ethyl)-1H-pyrazolo[3,4-b]pyrazin-6-amine and (R)—N-(5-(difluoromethoxy)-1H-pyrazol-3-yl)-1-(1-(4-fluoropyridin-2-yl)ethyl)-1H-pyrazolo[3,4-b]pyrazin-6-amine

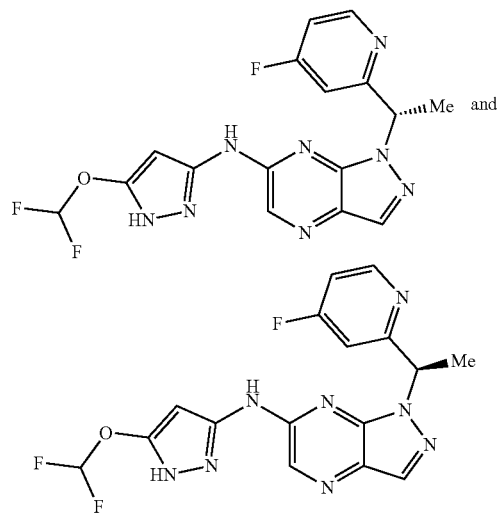

A mixture of 6-chloro-1-(1-(4-fluoropyridin-2-yl)ethyl)-1H-pyrazolo[3,4-b]pyrazine (Preparation 147, 120 mg, 0.43 mmol), 5-(difluoromethoxy)-1H-pyrazol-3-amine (96 mg, 0.64 mmol), BrettPhos Pd G4 (20 mg, 0.021 mmol) and KOAc (127 mg, 1.30 mmol) in dioxane (5 mL) was stirred at 90° C. overnight under N₂. The reaction mixture was cooled to rt and evaporated to dryness in vacuo. The residue was purified by flash chromatography (SiO₂, 50% EtOAc/PE) followed by prep-HPLC-1 to afford N-(5-(difluoromethoxy)-1H-pyrazol-3-yl)-1-(1-(4-fluoropyridin-2-yl)ethyl)-1H-pyrazolo[3,4-b]pyrazin-6-amine as a yellow solid (60 mg, 35%). The racemate was separated by chiral prep-SFC (Daicel OX 20×250 mm, 10 mm; 35% MeOH (0.2% MeOH/NH₃) in CO₂) to afford the title compounds as white solids.

Peak 1, Example 13, (S)—N-(5-(difluoromethoxy)-1H-pyrazol-3-yl)-1-(1-(4-fluoropyridin-2-yl)ethyl)-1H-pyrazolo[3,4-b]pyrazin-6-amine or (R)—N-(5-(difluoromethoxy)-1H-pyrazol-3-yl)-1-(1-(4-fluoropyridin-2-yl)ethyl)-1H-pyrazolo[3,4-b]pyrazin-6-amine (8.8 mg, 5%). LCMS m/z=391 [M+H]⁺; 1H NMR (400 MHz, DMSO-d6) δ: 11.80-11.40 (br s, 1H), 8.21 (s, 1H), 8.20 (s, 1H), 8.15 (d, 1H), 7.92-7.86 (m, 1H), 7.35-7.32 (m, 1H), 7.33 (t, 1H), 6.62-6.59 (m, 1H), 5.98 (s, 1H), 1.89 (d, 3H).

Peak 2, Example 14, (R)—N-(5-(difluoromethoxy)-1H-pyrazol-3-yl)-1-(1-(4-fluoropyridin-2-yl)ethyl)-1H-pyrazolo[3,4-b]pyrazin-6-amine or (S)—N-(5-(difluoromethoxy)-1H-pyrazol-3-yl)-1-(1-(4-fluoropyridin-2-yl)ethyl)-1H-pyrazolo[3,4-b]pyrazin-6-amine (8.3 mg, 5%). LCMS m/z=391 [M+H]⁺; $^1$H NMR (400 MHz, DMSO-$d_6$) δ: 12.24 (s, 1H), 10.82 (s, 1H), 8.21 (s, 1H), 8.20 (s, 1H), 8.15 (d, 1H), 7.92-7.86 (m, 1H), 7.35-7.32 (m, 1H), 7.33 (t, 1H), 6.62-6.59 (m, 1H), 5.98 (s, 1H), 1.89 (d, 3H).

Example 15 and 16

(R)—N-(5-(difluoromethoxy)-1H-pyrazol-3-yl)-1-(2-fluoro-1-(pyridin-2-yl)ethyl)-1H-pyrazolo[3,4-b]pyrazin-6-amine and (S)—N-(5-(difluoromethoxy)-1H-pyrazol-3-yl)-1-(2-fluoro-1-(pyridin-2-yl)ethyl)-1H-pyrazolo[3,4-b]pyrazin-6-amine

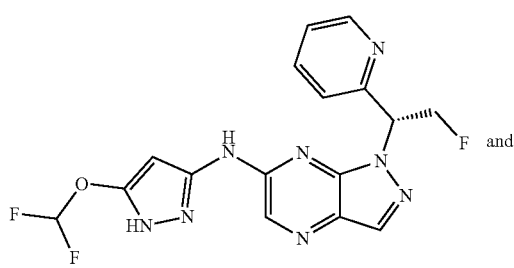

and

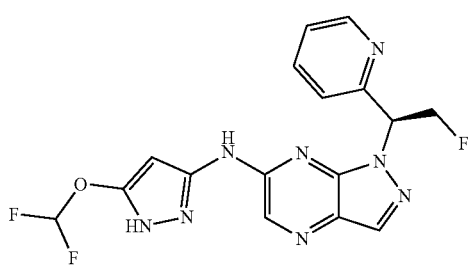

A mixture of 6-chloro-1-(2-fluoro-1-(pyridin-2-yl)ethyl)-1H-pyrazolo[3,4-b]pyrazine (Preparation 84, 400 mg, 1.44 mmol), 5-(difluoromethoxy)-1H-pyrazol-3-amine (256 mg, 1.72 mmol), KOAc (422 mg, 4.31 mmol) and BrettPhos Pd G4 (80 mg) in dioxane (5 mL) was heated to 90° C. for 2 h. The mixture was concentrated in vacuo and the residue purified by flash chromatography (SiO$_2$, 3:1 EtOAc/PE) to give N-(5-(difluoromethoxy)-1H-pyrazol-3-yl)-1-(2-fluoro-1-(pyridin-2-yl)ethyl)-1H-pyrazolo[3,4-b]pyrazin-6-amine (100 mg, 18%) which was separated by chiral-SFC (Daicel AD-H, 20×250 mm, 10 mm; 30% MeOH in CO2) to give:

Peak 1, Example 15, (R)—N-(5-(difluoromethoxy)-1H-pyrazol-3-yl)-1-(2-fluoro-1-(pyridin-2-yl)ethyl)-1H-pyrazolo[3,4-b]pyrazin-6-amine or (S)—N-(5-(difluoromethoxy)-1H-pyrazol-3-yl)-1-(2-fluoro-1-(pyridin-2-yl)ethyl)-1H-pyrazolo[3,4-b]pyrazin-6-amine white solid (20.2 mg, 3%): LCMS m/z=391 [M+H]$^+$; 1H NMR (500 MHz, DMSO-d6) δ: 12.36 (s, 1H), 10.93 (s, 1H), 8.58 (d, 1H), 8.27 (s, 1H), 7.80-7.70 (m, 1H), 7.36-7.34 (m, 1H), 7.33 (t, 1H), 7.12-7.10 (m, 1H), 6.92-6.89 (m, 1H), 5.84 (s, 1H), 5.50-5.34 (m, 2H).

Peak 2, Example 16, (S)—N-(5-(difluoromethoxy)-1H-pyrazol-3-yl)-1-(2-fluoro-1-(pyridin-2-yl)ethyl)-1H-pyrazolo[3,4-b]pyrazin-6-amine or (R)—N-(5-(difluoromethoxy)-1H-pyrazol-3-yl)-1-(2-fluoro-1-(pyridin-2-yl)ethyl)-1H-pyrazolo[3,4-b]pyrazin-6-amine white solid (13.2 mg, 2%): LCMS m/z=391 [M+H]$^+$; $^1$H NMR (500 MHz, DMSO-d$_6$) δ: 12.36 (s, 1H), 10.92 (s, 1H), 8.59 (d, 1H), 8.27 (s, 1H), 8.23 (s, 1H), 7.73 (td, 1H), 7.33 (dd, 1H), 7.30 (t, 1H), 7.11 (d, 1H), 6.92-6.88 (m, 1H), 5.85-5.83 (m, 1H), 5.48-5.30 (m, 2H).

Example 17

(S)-3-chloro-N-(5-(difluoromethoxy)-1H-pyrazol-3-yl)-1-(1-(2-fluoropyridin-3-yl)ethyl)-1H-pyrazolo[3,4-b]pyrazin-6-amine

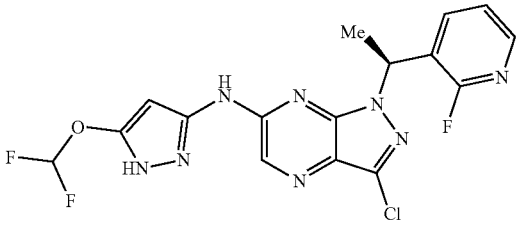 [SMILES: C[C@@H](c1cccnc1F)n1nc(Cl)c2ncc(Nc3cc(OC(F)F)[nH]n3)nc21]

A mixture of (S)-3,6-dichloro-1-(1-(2-fluoropyridin-3-yl)ethyl)-1H-pyrazolo[3,4-b]pyrazine (Preparation 63, 89 mg, 0.285 mmol), 5-(difluoromethoxy)-1H-pyrazol-3-amine (47 mg, 0.314 mmol), $^t$BuBrettPhos Pd G3 (12 mg, 14 mmol) and KOAc (84 mg, 0.855 mmol) in dioxane (1 mL) was stirred at 90° C. for 1 h. The reaction mixture was evaporated to dryness and the residue dissolved in DCM, filtered and purified by Isco (0-10% MeOH/DCM) to afford the title compound as a pale yellow solid (46.4 mg, 38%). LCMS m/z=425 [M+H]$^+$; 1H NMR (500 MHz, DMSO-d$_6$) δ: 12.31 (s, 1H), 11.06 (s, 1H), 8.25 (s, 1H), 8.18 (d, 1H), 8.04-7.93 (m, 1H), 7.50-7.11 (m, 2H), 6.67 (q, 1H), 5.99 (d, 1H), 1.87 (d, 3H).

Example 18 and 19

(S)—N-(5-(difluoromethoxy)-1H-pyrazol-3-yl)-1-(2-fluoro-1-(pyridin-3-yl)ethyl)-1H-pyrazolo[3,4-b]pyrazin-6-amine and (R)—N-(5-(difluoromethoxy)-1H-pyrazol-3-yl)-1-(2-fluoro-1-(pyridin-3-yl)ethyl)-1H-pyrazolo[3,4-b]pyrazin-6-amine

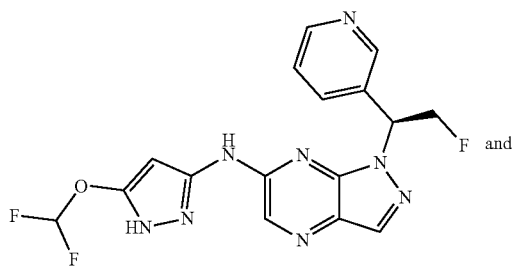

and

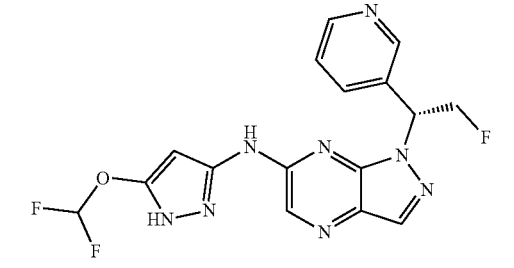

A mixture of 6-chloro-1-(2-fluoro-1-(pyridin-3-yl)ethyl)-1H-pyrazolo[3,4-b]pyrazine (Preparation 85, 180 mg, 0.65 mmol), 5-(difluoromethoxy)-1H-pyrazol-3-amine (115 mg, 0.78 mmol), KOAc (190 mg, 1.94 mmol) and BrettPhos Pd G4 (40 mg) in dioxane (5 mL) was stirred at 90° C. for 2 h. The mixture was evaporated to dryness in vacuo and the residue purified by flash chromatography (SiO$_2$, 3:1 EtOAc/PE) followed by prep-HPLC-1 to afford N-(5-(difluoromethoxy)-1H-pyrazol-3-yl)-1-(2-fluoro-1-(pyridin-3-yl)ethyl)-1H-pyrazolo[3,4-b]pyrazin-6-amine (~100 mg). This was separated by chiral Prep-SFC (Daicel AD, 20×250 mm, 10 mm; 35% MeOH (0.2% MeOH/NH$_3$) in CO$_2$ to give the title compounds.

Peak 1, Example 18, (S)—N-(5-(difluoromethoxy)-1H-pyrazol-3-yl)-1-(2-fluoro-1-(pyridin-3-yl)ethyl)-1H-pyrazolo[3,4-b]pyrazin-6-amine or (R)—N-(5-(difluoromethoxy)-1H-pyrazol-3-yl)-1-(2-fluoro-1-(pyridin-3-yl)ethyl)-1H-pyrazolo[3,4-b]pyrazin-6-amine (25.9 mg, 10%): LCMS m/z=391 [M+H]$^+$; 1H NMR (500 MHz, DMSO-d6) δ: 12.34 (s, 1H), 10.94 (s, 1H), 8.72 (s, 1H), 8.53-8.50 (m, 1H), 8.30 (s, 1H), 8.22 (s, 1H), 7.86 (d, 1H), 7.38 (dd, 1H), 7.33 (t, 1H), 6.96-6.90 (m, 1H), 5.90-5.87 (m, 1H), 5.39-5.05 (m, 2H).

Peak 2, Example 19, (R)—N-(5-(difluoromethoxy)-1H-pyrazol-3-yl)-1-(2-fluoro-1-(pyridin-3-yl)ethyl)-1H-pyrazolo[3,4-b]pyrazin-6-amine or (S)—N-(5-(difluoromethoxy)-1H-pyrazol-3-yl)-1-(2-fluoro-1-(pyridin-3-yl)ethyl)-1H-pyrazolo[3,4-b]pyrazin-6-amine (30.7 mg, 12%): LCMS m/z=391 [M+H]$^+$; 1H NMR (500 MHz, DMSO-d6) δ: 12.50-11.90 (br, 1H), 11.30-10.85 (br, 1H), 8.72-8.70 (m, 1H), 8.53-8.51 (m, 1H), 8.27 (s, 1H), 8.19 (s, 1H), 7.86 (d, 1H), 7.39 (dd, 1H), 7.32 (t, 1H), 6.96-6.90 (m, 1H), 5.91 (s, 1H), 5.41-5.05 (m, 2H).

Example 20 and 21

(S)-4-((6-((5-(difluoromethoxy)-1H-pyrazol-3-yl)amino)-1H-pyrazolo[3,4-b]pyrazin-1-yl)methyl)pyrrolidin-2-one and (R)-4-((6-((5-(difluoromethoxy)-1H-pyrazol-3-yl)amino)-1H-pyrazolo[3,4-b]pyrazin-1-yl)methyl)pyrrolidin-2-one

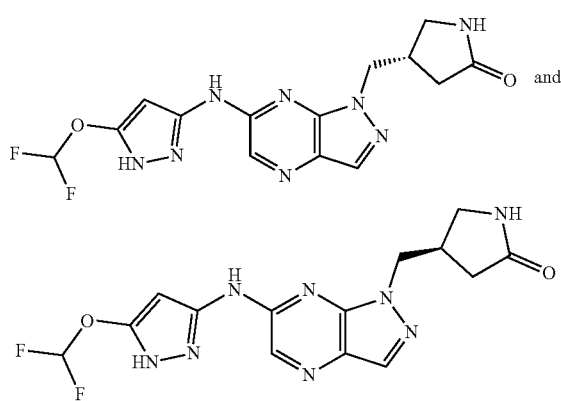

A mixture of 4-((6-chloro-1H-pyrazolo[3,4-b]pyrazin-1-yl)methyl)pyrrolidin-2-one (Preparation 64, 152 mg, 0.60 mmol), 5-(difluoromethoxy)-1H-pyrazol-3-amine (99 mg, 0.66 mmol), KOAc (178 mg, 1.81 mmol) and BrettPhos Pd G4 (26 mg) in dioxane (2 mL) was stirred at 90° C. for 2 h. The mixture was diluted with 5% MeOH/DCM and washed with water. The combined organics were dried (Na$_2$SO$_4$) and evaporated to dryness in vacuo and the residue purified by Isco chromatography (SiO$_2$, 0-10% MeOH/DCM) afford 4-((6-((5-(difluoromethoxy)-1H-pyrazol-3-yl)amino)-1H-pyrazolo[3,4-b]pyrazin-1-yl)methyl)pyrrolidin-2-one (89 mg, 40%). The racemate was separated by chiral Prep-SFC (Daicel AD, 20×250 mm, 10 mm; 40% MeOH (0.2% MeOH/NH3) in CO2 to give the title compounds.

Peak 1, Example 20, (S)-4-((6-((5-(difluoromethoxy)-1H-pyrazol-3-yl)amino)-1H-pyrazolo[3,4-b]pyrazin-1-yl)methyl)pyrrolidin-2-one or (R)-4-((6-((5-(difluoromethoxy)-1H-pyrazol-3-yl)amino)-1H-pyrazolo[3,4-b]pyrazin-1-yl)methyl)pyrrolidin-2-one (Yellow solid, 30.5 mg, 68%); LCMS m/z=365 [M+H]$^+$; $^1$H NMR (500 MHz, DMSO-d$_6$) δ: 12.64-11.74 (br s, 1H), 11.74-10.38 (br s, 1H), 8.18 (s, 1H), 8.16 (s, 1H), 7.78 (s, 1H), 7.30 (t, 1H), 5.86 (s, 1H), 4.82-4.72 (m, 1H), 4.53 (dd, 1H), 3.11-3.07 (m, 1H), 2.96-2.92 (m, 1H), 2.89-2.83 (m, 1H), 2.04-1.97 (m, 1H), 1.87-1.79 (m, 1H).

Peak 2, Example 21, (R)-4-((6-((5-(difluoromethoxy)-1H-pyrazol-3-yl)amino)-1H-pyrazolo[3,4-b]pyrazin-1-yl)methyl)pyrrolidin-2-one or (S)-4-((6-((5-(difluoromethoxy)-1H-pyrazol-3-yl)amino)-1H-pyrazolo[3,4-b]pyrazin-1-yl)methyl)pyrrolidin-2-one (Yellow solid, 33.2 mg, 74%); LCMS m/z=365 [M+H]$^+$; $^1$H NMR (500 MHz, DMSO-d$_6$) δ: 12.35 (s, 1H), 10.85 (s, 1H), 8.18 (s, 1H), 8.17 (s, 1H), 7.78 (s, 1H), 7.30 (t, 1H,), 5.83 (s, 1H), 4.82-4.77 (m, 1H), 4.53 (dd, 1H), 3.11-3.06 (m, 1H), 2.96-2.92 (m, 1H), 2.89-2.83 (m, 1H), 2.04-1.97 (m, 1H), 1.86-1.81 (m, 1H).

Example 22

(S)—N-(5-methoxy-1H-pyrazol-3-yl)-1-(1-(tetrahydro-2H-pyran-4-yl)ethyl)-1H-pyrazolo[3,4-b]pyrazin-6-amine

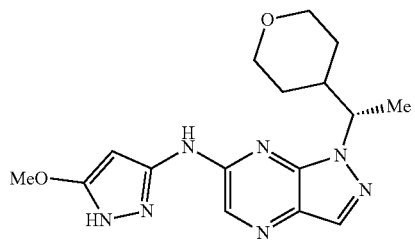 [SMILES: COc1cc(Nc2cnc3cnn([C@@H](C)C4CCOCC4)c3n2)n[nH]1]

A mixture of (S)-6-chloro-1-(1-(tetrahydro-2H-pyran-4-yl)ethyl)-1H-pyrazolo[3,4-b]pyrazine (Preparation 90, 350 mg, 1.31 mmol), 5-methoxy-1H-pyrazol-3-amine hydrochloride (294 mg, 1.97 mmol), BrettPhos Pd G4 (20 mg, 0.21 mmol) and KOAc (643 mg, 6.56 mmol) in dioxane (10 mL) was stirred at 90° C. overnight under N$_2$. The reaction mixture was cooled to rt and evaporated to dryness in vacuo. The residue was purified by flash chromatography (SiO$_2$, 50% EtOAc/PE) followed by prep-HPLC-1 to afford the title compound as a white solid (116 mg, 25%). LCMS m/z=344 [M+H]$^+$; $^1$H NMR (400 MHz, DMSO-d$_6$) δ: 12.10-11.60 (m, 1H), 10.59 (br s, 1H), 8.16 (s, 1H), 8.12 (s, 1H), 5.62 (br s, 1H), 4.93 (s, 1H), 3.90-3.81 (m, 1H), 3.81 (s, 3H), 3.76-3.71 (m, 1H), 3.30-3.20 (m, 1H), 3.15-3.11 (m, 1H), 2.00-1.96 (m, 1H), 1.71-1.66 (m, 1H), 1.47 (d, 3H), 1.40-1.25 (m, 1H), 1.25-1.11 (m, 1H), 0.93-0.85 (m, 1H).

Example 23

1-(2-cyclopropylpropan-2-yl)-N-(5-(difluoromethoxy)-1H-pyrazol-3-yl)-1H-pyrazolo[3,4-b]pyrazin-6-amine

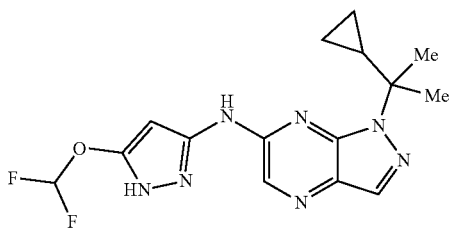 [SMILES: CC(C)(C1CC1)n1ncc2ncc(Nc3cc(OC(F)F)[nH]n3)nc21]

A mixture of 6-chloro-1-(2-cyclopropylpropan-2-yl)-1H-pyrazolo[3,4-b]pyrazine (Preparation 79, 100 mg, 0.422 mmol), 5-(difluoromethoxy)-1H-pyrazol-3-amine (62.9 mg, 0.422 mmol), BrettPhos Pd G4 (64.6 mg, 0.042 mmol) and KOAc (123 mg, 1.26 mmol) in dioxane (2 mL) was degassed with N$_2$ (×3) and heated at 90° C. for 3 h under N$_2$. The reaction mixture was cooled to rt and evaporated to dryness in vacuo. The residue was purified by flash column chromatography (50% EtOAc/PE) followed by prep-HPLC-1 to give the title compound as a yellow solid (25.2 mg, 17%). LCMS m/z=349 [M+H]$^+$; $^1$H NMR (500 MHz, DMSO-d$_6$) δ: 12.30-11.48 (br, 1H), 11.06-10.26 (br, 1H), 8.19 (s, 1H), 8.07 (s, 1H), 7.22 (t, 1H), 6.22 (s, 1H), 1.68 (s, 6H), 1.65-1.62 (m, 1H), 0.36-0.33 (m, 4H).

Example 24 and 25

(S)—N-(5-(difluoromethoxy)-1H-pyrazol-3-yl)-1-(1-(pyridazin-3-yl)ethyl)-1H-pyrazolo[3,4-b]pyrazin-6-amine and (R)—N-(5-(difluoromethoxy)-1H-pyrazol-3-yl)-1-(1-(pyridazin-3-yl)ethyl)-1H-pyrazolo[3,4-b]pyrazin-6-amine

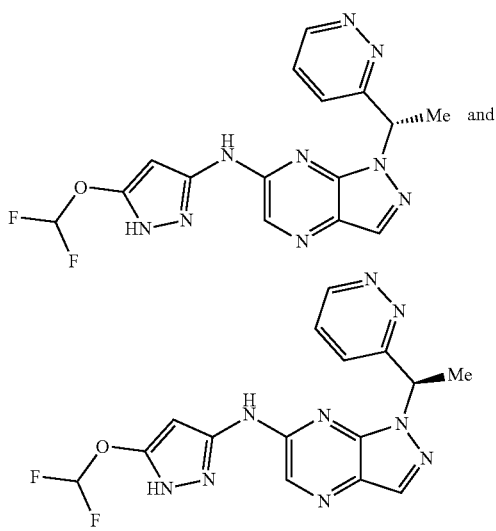

A mixture of 6-chloro-1-(1-(pyridazin-3-yl)ethyl)-1H-pyrazolo[3,4-b]pyrazine (Preparation 86, 1.1 g, 4.23 mmol), 5-(difluoromethoxy)-1H-pyrazol-3-amine (693 mg, 4.65 mmol), BrettPhos Pd G4 (195 mg, 0.21 mmol) and KOAc (1.24 g, 12.7 mmol) in dioxane (20 mL) was degassed with N$_2$ (×3) and then heated at 100° C. overnight under N$_2$. The reaction mixture was cooled to rt and evaporated to dryness in vacuo. The residue was purified by flash chromatography (SiO$_2$, 4:1 EtOAc/PE) and then by prep-HPLC-1 to give N-(5-(difluoromethoxy)-1H-pyrazol-3-yl)-1-(1-(pyridazin-3-yl)ethyl)-1H-pyrazolo[3,4-b]pyrazin-6-amine (600 mg, 38%). The racemate (600 mg) was separated by chiral-SFC (Daicel AD, 20×250 mm, 10 mm; 40% MeOH (0.2% MeOH/NH$_3$) in CO$_2$ to afford the title compounds as white solids.

Peak 1, Example 24, (S)—N-(5-(difluoromethoxy)-1H-pyrazol-3-yl)-1-(1-(pyridazin-3-yl)ethyl)-1H-pyrazolo[3,4-b]pyrazin-6-amine or (R)—N-(5-(difluoromethoxy)-1H-pyrazol-3-yl)-1-(1-(pyridazin-3-yl)ethyl)-1H-pyrazolo[3,4-b]pyrazin-6-amine (297 mg): LCMS m/z=374 [M+H]$^+$; $^1$H NMR (400 MHz, DMSO-d$_6$) δ: 12.29 (s, 1H), 10.88 (s, 1H), 9.15 (t, 1H), 8.25 (s, 1H), 8.23 (s, 1H), 7.63 (dd, 1H), 7.37 (d, 1H), 7.31 (t, 1H), 6.83 (q, 1H), 5.87 (s, 1H), 2.02 (d, 3H).

Peak 2, Example 25, (R)—N-(5-(difluoromethoxy)-1H-pyrazol-3-yl)-1-(1-(pyridazin-3-yl)ethyl)-1H-pyrazolo[3,4-b]pyrazin-6-amine or (S)—N-(5-(difluoromethoxy)-1H-pyrazol-3-yl)-1-(1-(pyridazin-3-yl)ethyl)-1H-pyrazolo[3,4-b]pyrazin-6-amine (269 mg, 89%): LCMS m/z=374 [M+H]$^+$; $^1$H NMR (400 MHz, DMSO-d$_6$) δ: 12.28 (br s, 1H), 10.87 (br s, 1H), 9.14 (dd, 1H), 8.24 (s, 1H), 8.22 (s, 1H), 7.62 (dd, 1H), 7.36 (dd, 1H,), 7.30 (t, 1H), 6.83-6.80 (m, 1H), 5.85 (s, 1H), 2.00 (d, 3H).

Example 26 and 27

(1R,2R)-2-((6-((5-(difluoromethoxy)-1H-pyrazol-3-yl)amino)-1H-pyrazolo[3,4-b]pyrazin-1-yl)methyl)cyclopropane-1-carbonitrile and (1S,2S)-2-((6-((5-(difluoromethoxy)-1H-pyrazol-3-yl)amino)-1H-pyrazolo[3,4-b]pyrazin-1-yl)methyl)cyclopropane-1-carbonitrile

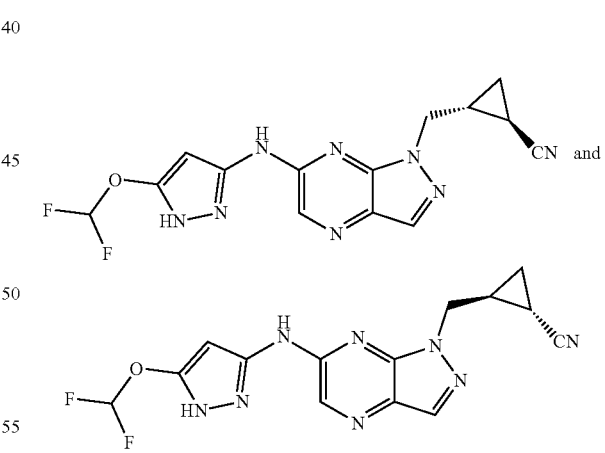

A mixture of trans-rac-2-((6-chloro-1H-pyrazolo[3,4-b]pyrazin-1-yl)methyl)cyclopropane-1-carbonitrile (Preparation 94, 370 mg, 1.58 mmol), 5-(difluoromethoxy)-1H-pyrazol-3-amine (235 mg, 1.58 mmol), BrettPhos Pd G4 (145 mg, 0.158 mmol) and KOAc (465 mg, 4.74 mmol) in dioxane (10 mL) was stirred at 100° C. overnight under N$_2$. The reaction mixture was cooled to rt and concentrated to give a residue which was purified by flash chromatography (SiO$_2$, 50% EtOAc/PE) and by prep-HPLC-1 to give the racemic mixture of title compounds (200 mg, 36%). The racemic mixture was separated by chiral-SFC (Daicel OD, 20×250 mm, 10 mm; 30% IPA (+0.2% MeOH/NH$_3$) in CO$_2$ to afford the title compounds as yellow solids.

Peak 1, Example 26, (1R,2R)-2-((6-((5-(difluoromethoxy)-1H-pyrazol-3-yl)amino)-1H-pyrazolo[3,4-b]pyrazin-1-yl)methyl)cyclopropane-1-carbonitrile or (1S,2S)-2-((6-((5-(difluoromethoxy)-1H-pyrazol-3-yl)amino)-1H-pyrazolo[3,4-b]pyrazin-1-yl)methyl)cyclopropane-1-carbonitrile (83.6 mg): LCMS m/z=347 [M+H]$^+$; $^1$H NMR (400 MHz, DMSO-d$_6$) δ: 12.24 (s, 1H), 10.84 (s, 1H), 8.21 (s, 1H), 8.20 (s, 1H), 7.32 (t, 1H), 5.88 (s, 1H), 4.51 (d, 2H), 1.98 (m, 1H), 1.85 (m, 1H), 1.30 (m, 1H), 1.19 (m, 1H).

Peak 2, Example 27, (1S,2S)-2-((6-((5-(difluoromethoxy)-1H-pyrazol-3-yl)amino)-1H-pyrazolo[3,4-b]pyrazin-1-yl)methyl)cyclopropane-1-carbonitrile or (1R,2R)-2-((6-((5-(difluoromethoxy)-1H-pyrazol-3-yl)amino)-1H-pyrazolo[3,4-b]pyrazin-1-yl)methyl)cyclopropane-1-carbonitrile (90.6 mg): LCMS m/z=347 [M+H]$^+$; $^1$H NMR (400 MHz, DMSO-d$_6$) δ: 12.25 (s, 1H), 10.84 (s, 1H), 8.21 (s, 1H), 8.20 (s, 1H), 7.32 (t, 1H), 5.88 (s, 1H), 4.51 (d, 2H), 2.02-1.95 (m, 1H), 1.88-1.83 (m, 1H), 1.33-1.28 (m, 1H), 1.21-1.15 (m, 1H).

Example 28 and 29

(S)-1-(2,2-difluoro-1-(tetrahydro-2H-pyran-4-yl)ethyl)-N-(5-(difluoromethoxy)-1H-pyrazol-3-yl)-1H-pyrazolo[3,4-b]pyrazin-6-amine and (R)-1-(2,2-difluoro-1-(tetrahydro-2H-pyran-4-yl)ethyl)-N-(5-(difluoromethoxy)-1H-pyrazol-3-yl)-1H-pyrazolo[3,4-b]pyrazin-6-amine

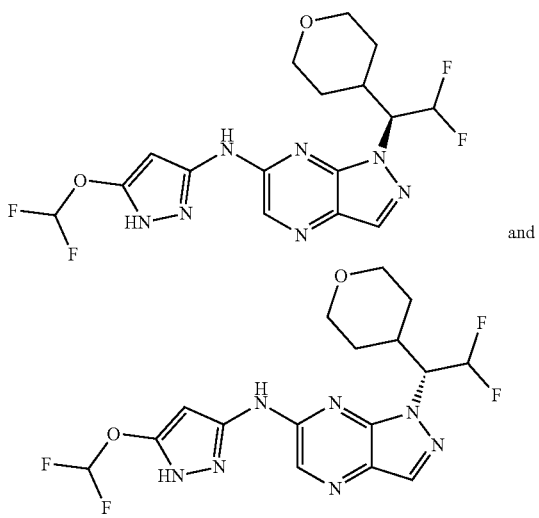

A mixture of 6-chloro-1-(2,2-difluoro-1-(tetrahydro-2H-pyran-4-yl)ethyl)-1H-pyrazolo[3,4-b]pyrazine (Preparation 93, 230 mg, 0.76 mmol), 5-(difluoromethoxy)-1H-pyrazol-3-amine (113 mg, 0.76 mmol), BrettPhos Pd G4 (165 mg, 0.1 mmol) and KOAc (223 mg, 2.28 mmol) in dioxane (5 mL) was degassed with N$_2$ (×3) and then heated at 90° C. overnight under N$_2$. The reaction mixture was cooled to rt and concentrated to give a residue which was purified by flash column chromatography on silica gel followed by prep-HPLC-3 to give 1-(2,2-difluoro-1-(tetrahydro-2H-pyran-4-yl)ethyl)-N-(5-(difluoromethoxy)-1H-pyrazol-3-yl)-1H-pyrazolo[3,4-b]pyrazin-6-amine (150 mg, 48%). The racemic material was separated by chiral-SFC to afford the title compounds as yellow solids.

Peak 1, Example 28, (S)-1-(2,2-difluoro-1-(tetrahydro-2H-pyran-4-yl)ethyl)-N-(5-(difluoromethoxy)-1H-pyrazol-3-yl)-1H-pyrazolo[3,4-b]pyrazin-6-amine or (R)-1-(2,2-difluoro-1-(tetrahydro-2H-pyran-4-yl)ethyl)-N-(5-(difluoromethoxy)-1H-pyrazol-3-yl)-1H-pyrazolo[3,4-b]pyrazin-6-amine (55.4 mg): LCMS m/z=416 [M+H]+: 1H NMR (400 MHz, DMSO-d$_6$) δ: 12.27 (br s, 1H), 10.95 (br s, 1H), 8.27 (s, 1H), 8.22 (s, 1H), 7.31 (t, 1H), 6.57 (dt, 1H), 5.82 (s, 1H), 5.59-5.55 (m, 1H), 3.89-3.73 (m, 2H), 3.32-3.19 (m, 1H), 1.84-1.80 (m, 1H), 1.50-1.21 (m, 3H), 1.01-0.97 (m, 1H).

Peak 2, Example 29, (R)-1-(2,2-difluoro-1-(tetrahydro-2H-pyran-4-yl)ethyl)-N-(5-(difluoromethoxy)-1H-pyrazol-3-yl)-1H-pyrazolo[3,4-b]pyrazin-6-amine or (S)-1-(2,2-difluoro-1-(tetrahydro-2H-pyran-4-yl)ethyl)-N-(5-(difluoromethoxy)-1H-pyrazol-3-yl)-1H-pyrazolo[3,4-b]pyrazin-6-amine (60.6 mg): LCMS m/z=416 [M+H]$^+$; $^1$H NMR (400 MHz, DMSO-d$_6$) δ: 12.27 (br s, 1H), 10.95 (br s, 1H), 8.27 (s, 1H), 8.22 (s, 1H), 7.31 (t, 1H), 6.57 (dt, 1H), 5.82 (s, 1H), 5.59-5.55 (m, 1H), 3.89-3.73 (m, 2H), 3.32-3.19 (m, 1H), 1.84-1.80 (m, 1H), 1.50-1.21 (m, 3H), 1.01-0.97 (m, 1H).

Example 30

(R)-2-(6-((5-(difluoromethoxy)-1H-pyrazol-3-yl)amino)-1H-pyrazolo[3,4-b]pyrazin-1-yl)-2-(tetrahydro-2H-pyran-4-yl)ethan-1-ol

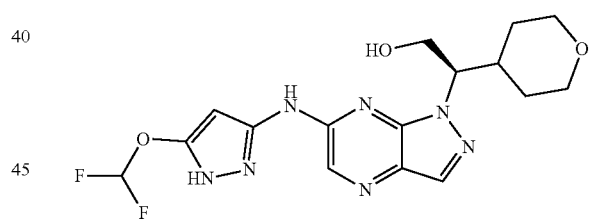

A mixture of (R)—N-(5-(difluoromethoxy)-1H-pyrazol-3-yl)-1-(1-(tetrahydro-2H-pyran-4-yl)-2-((triisopropylsilyl)oxy)ethyl)-1H-pyrazolo[3,4-b]pyrazin-6-amine (Preparation 190, 500 mg, 0.906 mmol) and 1M TBAF/THF was heated to reflux for 0.5 h. The reaction mixture was diluted with EtOAc and washed with H$_2$O. The combined organics were evaporated to dryness in vacuo and the residue purified by flash chromatography (SiO$_2$, 5:1 EtOAc/PE), followed by prep-HPLC-1 to give the title compound as a white solid (250 mg, 70%). LCMS m/z=396 [M+H]$^+$; $^1$H NMR (400 MHz, DMSO-d$_6$) δ: 12.16 (s, 1H), 10.75 (s, 1H), 8.19 (s, 1H), 8.17 (s, 1H), 7.30 (t, 1H), 5.97 (s, 1H), 4.81-4.79 (m, 1H), 4.68-4.65 (m, 1H), 3.94-3.85 (m, 2H), 3.84-3.81 (m, 1H), 3.72-3.67 (m, 1H), 3.33-3.25 (m, 1H), 3.17-3.11 (m, 1H), 2.21-2.18 (m, 1H), 1.77-1.74 (m, 1H), 1.45-1.35 (m, 2H), 0.86-0.83 (m, 1H).

Example 31

(R)—N-(5-(difluoromethoxy)-1H-pyrazol-3-yl)-1-(2-fluoro-1-(tetrahydro-2H-pyran-4-yl)ethyl)-1H-pyrazolo[3,4-b]pyrazin-6-amine

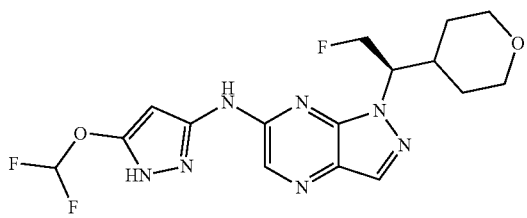 [SMILES: FC[C@@H](C1CCOCC1)n1ncc2ncc(Nc3cc(OC(F)F)[nH]n3)nc21]

To a mixture of (R)-2-(6-((5-(difluoromethoxy)-1H-pyrazol-3-yl)amino)-1H-pyrazolo[3,4-b]pyrazin-1-yl)-2-(tetrahydro-2H-pyran-4-yl)ethan-1-ol (Example 30, 140 mg, 0.354 mmol) in DCM (2 mL) was added DAST (114 mg, 0.708 mmol) at 0° C. and the resulting mixture stirred for 2 h. The reaction mixture was diluted with EtOAc and washed with aq NaHCO₃ and concentrated in vacuo. The residue was purified by prep-HPLC-1 to give the title compound as a white solid (10 mg, 7%). LCMS m/z=398 [M+H]⁺; ¹H NMR (400 MHz, DMSO-d₆) δ: 12.21 (br, s, 1H), 10.84 (br s, 1H), 8.23 (s, 1H), 8.21 (s, 1H), 7.31 (t, 1H), 5.90 (s, 1H), 5.40-5.30 (m, 1H), 5.00-4.97 (m, 1H), 4.89-4.85 (m, 1H), 3.88-3.84 (m, 1H), 3.72-3.69 (m, 1H), 3.33-3.28 (m, 1H), 3.20-3.12 (m, 1H), 2.21-2.18 (m, 1H), 1.77-1.74 (m, 1H), 1.45-1.40 (m, 1H), 1.40-1.35 (m, 1H), 0.86-0.83 (m, 1H).

Example 32 and 33

(S)—N-(5-methoxy-1H-pyrazol-3-yl)-1-(1-(pyridazin-3-yl)ethyl)-1H-pyrazolo[3,4-b]pyrazin-6-amine and (R)—N-(5-methoxy-1H-pyrazol-3-yl)-1-(1-(pyridazin-3-yl)ethyl)-1H-pyrazolo[3,4-b]pyrazin-6-amine

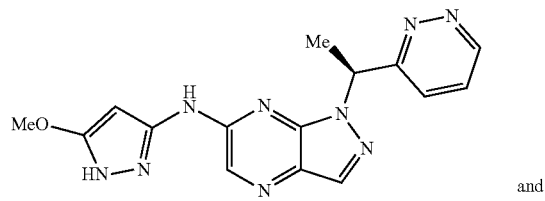

and

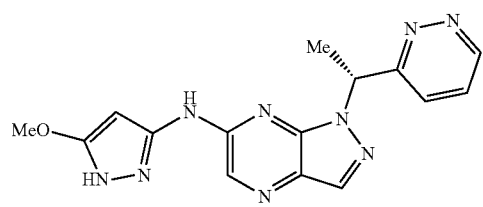

A mixture of 6-chloro-1-(1-(pyridazin-3-yl)ethyl)-1H-pyrazolo[3,4-b]pyrazine (Preparation 86, 2.0 g, 7.67 mmol), 5-methoxy-1H-pyrazol-3-amine (867 mg, 7.67 mmol), BrettPhos Pd G4 (352 mg, 0.383 mmol) and KOAc (3.00 g, 60.6 mmol) in dioxane (20 mL) was stirred at 100° C. overnight under N₂. The reaction mixture was evaporated to dryness in vacuo and the residue purified by flash chromatography (SiO2, 50% EtOAc/PE) followed by prep-HPLC-1 to give racemic N-(5-methoxy-1H-pyrazol-3-yl)-1-(1-(pyridazin-3-yl)ethyl)-1H-pyrazolo[3,4-b]pyrazin-6-amine (800 mg, 30%). The racemic compound (800 mg) was separated by chiral-SFC (Daicel AD, 20×250 mm, 10 mm: 40% MeOH (0.2% MeOH/NH3) in CO2) to afford the title compounds as yellow solids.

Peak 1. Example 32. (S)—N-(5-methoxy-1H-pyrazol-3-yl)-1-(1-(pyridazin-3-yl)ethyl)-1H-pyrazolo[3,4-b]pyrazin-6-amine or (R)—N-(5-methoxy-1H-pyrazol-3-yl)-1-(1-(pyridazin-3-yl)ethyl)-1H-pyrazolo[3,4-b]pyrazin-6-amine (266 mg): LCMS m/z=338 [M+H]⁺; ¹H NMR (400 MHz, DMSO-d₆) δ: 11.76 (br s, 1H), 10.57 (br s, 1H), 9.14 (dd, 1H), 8.22 (s, 1H), 8.20 (s, 1H), 7.61 (dd, 1H), 7.36 (dd, 1H), 6.70-6.52 (m, 1H), 5.70-5.52 (m, 1H), 3.82 (s, 3H), 2.01 (d, 3H).

Peak 2, Example 33, (R)—N-(5-methoxy-1H-pyrazol-3-yl)-1-(1-(pyridazin-3-yl)ethyl)-1H-pyrazolo[3,4-b]pyrazin-6-amine or (S)—N-(5-methoxy-1H-pyrazol-3-yl)-1-(1-(pyridazin-3-yl)ethyl)-1H-pyrazolo[3,4-b]pyrazin-6-amine (346 mg): LCMS m/z=338 [M+H]⁺; ¹H NMR (400 MHz, DMSO-d₆) δ: 11.75 (br s, 1H), 10.58 (br s, 1H), 9.14 (dd, 1H), 8.22 (s, 1H), 8.20 (s, 1H), 7.61 (dd, 1H), 7.36 (dd, 1H), 6.70-6.52 (m, 1H), 5.70-5.52 (m, 1H), 3.82 (s, 3H), 2.01 (d, 3H).

Example 34-140

The title compounds were prepared from the appropriate amine (Amine-1, Amine-2 or Amine-3), the appropriate chloride (RCl) and the appropriate Pd catalyst system using an analogous method to that described for Example 8. Purification by ISCO or HPLC as noted in the table below.

Amine-1: 5-(difluoromethoxy)-1H-pyrazol-3-amine; Amine-2: 5-ethoxy-1H-pyrazol-3-amine; Amine-3: 5-methoxy-1H-pyrazol-3-amine

| Example No. | Name/Structure/Amine/RCl/Catalyst/Data |
|---|---|
| 34 | (R)-N-(5-(difluoromethoxy)-1H-pyrazol-3-yl)-1-(1-(tetrahydro-2H-pyran-4-yl)ethyl)-1H-pyrazolo[3,4-b]pyrazin-6-amine 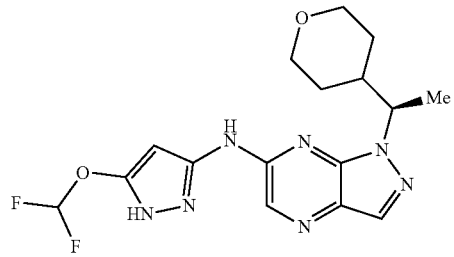 [SMILES: C[C@H](C1CCOCC1)n1ncc2ncc(Nc3cc(OC(F)F)[nH]n3)nc21] Amine-1; RCl: (R)-6-chloro-1-(1-(tetrahydro-2H-pyran-4-yl)ethyl)-1H-pyrazolo[3,4-b]pyrazine (Preparation 37); tBuBrettPhos Pd G3 ISCO: Pale yellow solid (22.1 mg, 26%); LCMS m/z = 381 [M + H]$^+$; $^1$H NMR (500 MHz, DMSO-d$_6$) δ: 12.19 (d, 1H), 10.75 (s, 1H), 8.19 (s, 1H), 8.17 (s, 1H), 7.31 (t, 1H), 5.95 (d, 1H), 5.02-4.91 (m, 1H), 3.94-3.84 (m, 1H), 3.75-3.65 (m, 1H), 3.11 (td, 1H), 2.14-2.01 (m, 1H), 1.76 (dt, 1H), 1.48 (d, 3H), 1.35 (qd, 1H), 1.18 (qd, 1H), 0.79 (d, 1H)-one peak is obscured by water signal. |
| 35 | N-(5-(difluoromethoxy)-1H-pyrazol-3-yl)-1-(pyridin-3-ylmethyl)-1H-pyrazolo[3,4-b]pyrazin-6-amine 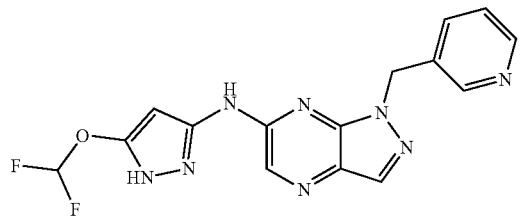 [SMILES: FC(F)Oc1cc(Nc2cnc3cnn(Cc4cccnc4)c3n2)n[nH]1] Amine-1; RCl: 6-chloro-1-(pyridin-3-ylmethyl)-1H-pyrazolo[3,4-b]pyrazine (Preparation 38); tBuBrettPhos Pd G3 ISCO: Pale yellow solid (35.4 mg, 32%); LCMS m/z = 359 [M + H]$^+$; $^1$H NMR (500 MHz, DMSO-d$_6$) δ: 12.30 (s, 1H), 10.87 (s, 1H), 8.57 (s, 1H), 8.48 (d, 1H), 8.21 (d, 2H), 7.65 (d, 1H), 7.51-7.14 (m, 2H), 5.82 (s, 2H). |
| 36 | 1-benzyl-N-(5-(difluoromethoxy)-1H-pyrazol-3-yl)-1H-pyrazolo[3,4-b]pyrazin-6-amine 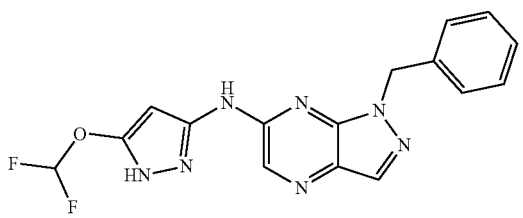 [SMILES: FC(F)Oc1cc(Nc2cnc3cnn(Cc4ccccc4)c3n2)n[nH]1] Amine-1; RCl: 1-benzyl-6-chloro-1H-pyrazolo[3,4-b]pyrazine (Preparation 39); tBuBrettPhos Pd G3 ISCO: Pale yellow solid (26.7 mg, 30%); LCMS m/z = 358 [M + H]$^+$; $^1$H NMR (500 MHz, DMSO-d$_6$) δ: 12.24 (s, 1H), 10.82 (s, 1H), 8.22 (s, 1H), 8.18 (s, 1H), 7.57-6.99 (m, 7H), 5.94 (d, 1H), 5.75 (s, 2H). |

| Example No. | Name/Structure/Amine/RCl/Catalyst/Data |
|---|---|
| 37 | N-(5-(difluoromethoxy)-1H-pyrazol-3-yl)-1-(2-fluorobenzyl)-1H-pyrazolo[3,4-b]pyrazin-6-amine<br>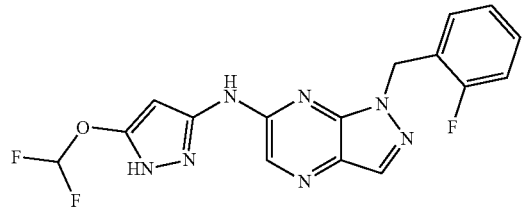 [SMILES: Fc1ccccc1Cn1ncc2ncc(Nc3cc(OC(F)F)[nH]n3)nc21]<br>Amine-1; RCl: 6-chloro-1-(2-fluorobenzyl)-1H-pyrazolo[3,4-b]pyrazine (Preparation 40); tBuBrettPhos Pd G3<br>ISCO: Pale yellow solid (34.5 mg, 39%); LCMS m/z = 376 [M + H]$^+$; $^1$H NMR (500 MHz, DMSO-$d_6$) δ: 12.24 (s, 1H), 10.85 (s, 1H), 8.22 (s, 1H), 8.19 (s, 1H), 7.49-7.07 (m, 5H), 5.93 (s, 1H), 5.80 (s, 2H). |
| 38 | N-(5-ethoxy-1H-pyrazol-3-yl)-1-((tetrahydro-2H-pyran-4-yl)methyl)-1H-pyrazolo[3,4-b]pyrazin-6-amine<br>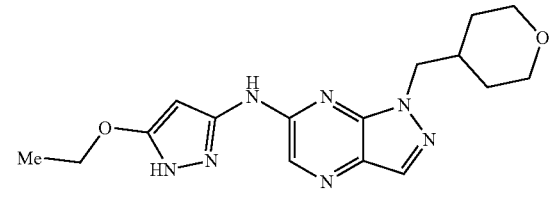 [SMILES: CCOc1cc(Nc2cnc3cnn(CC4CCOCC4)c3n2)n[nH]1]<br>Amine-2; RCl: 6-chloro-1-((tetrahydro-2H-pyran-4-yl)methyl)-1H-pyrazolo[3,4-b]pyrazine (Preparation 87); tBuBrettPhos Pd G3<br>ISCO: Pale yellow solid (20.8 mg, 26%); LCMS m/z = 344 [M + H]$^+$ |
| 39 | N-(5-(difluoromethoxy)-1H-pyrazol-3-yl)-1-(3-fluorobenzyl)-1H-pyrazolo[3,4-b]pyrazin-6-amine<br>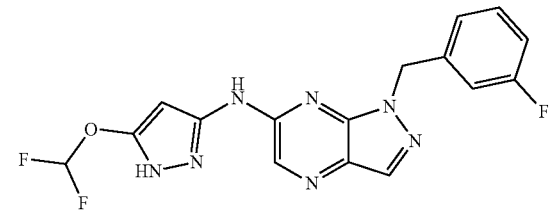 [SMILES: Fc1cccc(Cn2ncc3ncc(Nc4cc(OC(F)F)[nH]n4)nc32)c1]<br>Amine-1; RCl: 6-chloro-1-(3-fluorobenzyl)-1H-pyrazolo[3,4-b]pyrazine (Preparation 41); tBuBrettPhos Pd G3<br>ISCO: Pale yellow solid (37.8 mg, 43%); LCMS m/z = 376 [M + H]$^+$; $^1$H NMR (500 MHz, DMSO-$d_6$) δ: 12.26 (s, 1H), 10.85 (s, 1H), 8.22 (s, 1H), 8.21 (s, 1H), 7.50-7.13 (m, 2H), 7.13-7.02 (m, 3H), 5.90 (s, 1H), 5.78 (s, 2H). |
| 40 | N-(5-(difluoromethoxy)-1H-pyrazol-3-yl)-1-(4-fluorobenzyl)-1H-pyrazolo[3,4-b]pyrazin-6-amine<br>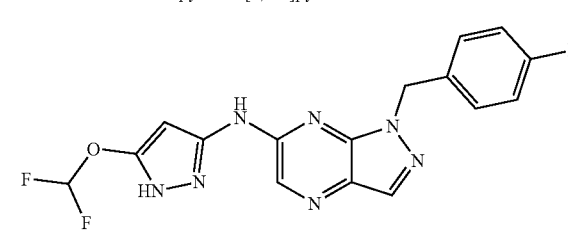<br>Amine-1; RCl: 6-chloro-1-(4-fluorobenzyl)-1H-pyrazolo[3,4-b]pyrazine (Preparation 42); tBuBrettPhos Pd G3<br>ISCO: Pale yellow solid (24.7 mg, 28%); LCMS m/z = 376 [M + H]$^+$; $^1$H NMR (500 MHz, DMSO-$d_6$) δ: 12.26 (s, 1H), 10.83 (s, 1H), 8.21 (s, 1H), 8.18 (s, 1H), 7.48-7.08 (m, 5H), 5.92 (s, 1H), 5.74 (s, 2H). |

| Example No. | Name/Structure/Amine/RCl/Catalyst/Data |
| --- | --- |
| 41 | N-(5-(difluoromethoxy)-1H-pyrazol-3-yl)-1-((6-fluoropyridin-3-yl)methyl)-1H-pyrazolo[3,4-b]pyrazin-6-amine 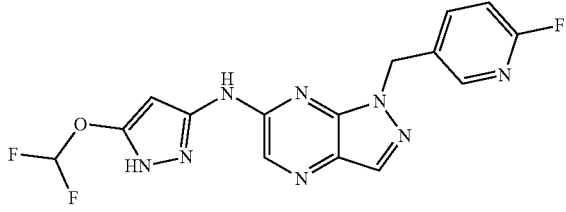 [SMILES: Fc1ccc(Cn2ncc3ncc(Nc4cc(OC(F)F)[nH]n4)nc32)cn1] Amine-1; RCl: 6-chloro-1-((6-fluoropyridin-3-yl)methyl)-1H-pyrazolo[3,4-b]pyrazine (Preparation 43); tBuBrettPhos Pd G3 ISCO: White solid (32 mg, 38%); LCMS m/z = 377 [M + H]$^+$; $^1$H NMR (500 MHz, DMSO-d$_6$) δ: 12.31 (s, 1H), 10.88 (s, 1H), 8.26 (d, 1H), 8.21 (d, 2H), 7.92-7.80 (m, 1H), 7.51-7.08 (m, 2H), 5.89 (s, 1H), 5.83 (s, 2H). |
| 42 | N-(5-(difluoromethoxy)-1H-pyrazol-3-yl)-1-((5-fluoropyridin-3-yl)methyl)-1H-pyrazolo[3,4-b]pyrazin-6-amine 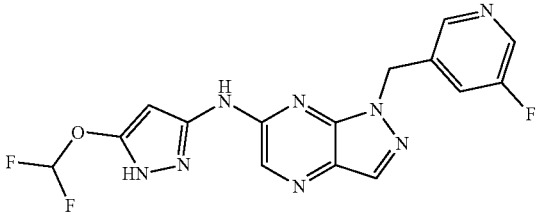 [SMILES: Fc1cncc(Cn2ncc3ncc(Nc4cc(OC(F)F)[nH]n4)nc32)c1] Amine-1; RCl: 6-chloro-1-((5-fluoropyridin-3-yl)methyl)-1H-pyrazolo[3,4-b]pyrazine (Preparation 44); tBuBrettPhos Pd G3 ISCO: White solid (29 mg, 34%); LCMS m/z = 377 [M + H]$^+$; $^1$H NMR (500 MHz, DMSO-d$_6$) δ: 12.30 (s, 1H), 10.89 (s, 1H), 8.51 (d, 1H), 8.42 (d, 1H), 8.22 (d, 2H), 7.58 (dt, 1H), 7.31 (t, 1H), 5.94-5.82 (m, 3H). |
| 43 | (S)-N-(5-(difluoromethoxy)-1H-pyrazol-3-yl)-1-(1-(3-fluorophenyl)ethyl)-1H-pyrazolo[3,4-b]pyrazin-6-amine 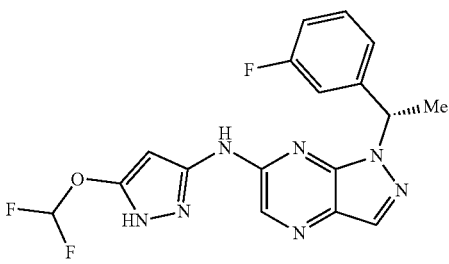 [SMILES: C[C@@H](c1cccc(F)c1)n1ncc2ncc(Nc3cc(OC(F)F)[nH]n3)nc21] Amine-1; RCl: (S)-6-chloro-1-(1-(3-fluorophenyl)ethyl)-1H-pyrazolo[3,4-b]pyrazine (Preparation 45); tBuBrettPhos Pd G3 ISCO: White solid (33 mg, 36%); LCMS m/z = 390 [M + H]$^+$; $^1$H NMR (500 MHz, DMSO-d$_6$) δ: 12.22 (d, 1H), 10.81 (s, 1H), 8.23 (s, 1H), 8.20 (s, 1H), 7.48-7.11 (m, 4H), 7.07 (td, 1H), 6.54 (q, 1H), 5.92 (d, 1H), 1.89 (d, 3H). |

| Example No. | Name/Structure/Amine/RCl/Catalyst/Data |
| --- | --- |
| 44 | 1-(4,4-difluorocyclohexyl)-N-(5-(difluoromethoxy)-1H-pyrazol-3-yl)-1H-pyrazolo[3,4-b]pyrazin-6-amine 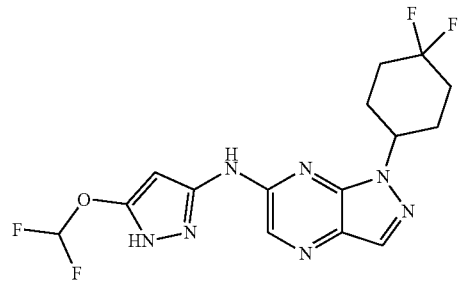 [SMILES: FC(F)Oc1cc(Nc2cnc3cnn(C4CCC(F)(F)CC4)c3n2)n[nH]1] Amine-1; RCl: 6-chloro-1-(4,4-difluorocyclohexyl)-1H-pyrazolo[3,4-b]pyrazine (Preparation 50); tBuBrettPhos Pd G3<br>ISCO: Yellow solid (44 mg, 45%); LCMS m/z = 386 [M + H]$^+$; $^1$H NMR (500 MHz, DMSO-d$_6$) δ: 12.14 (s, 1H), 10.80 (s, 1H), 8.20 (s, 1H), 8.18 (s, 1H), 7.31 (t, 1H), 5.93 (s, 1H), 5.25-5.12 (m, 1H), 2.25-2.14 (m, 6H), 2.06-1.97 (m, 2H) |
| 45 | (S)-N-(5-methoxy-1H-pyrazol-3-yl)-1-(1-(pyridin-2-yl)ethyl)-1H-pyrazolo[3,4-b]pyrazin-6-amine 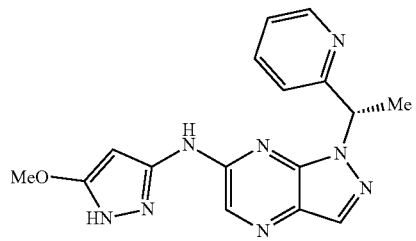 [SMILES: COc1cc(Nc2cnc3cnn([C@@H](C)c4ccccn4)c3n2)n[nH]1] Amine-3; RCl: (S)-6-chloro-1-(1-(pyridin-2-yl)ethyl)-1H-pyrazolo[3,4-b]pyrazine (Preparation 82); tBuBrettPhos Pd G3<br>ISCO: Yellow solid (14 mg, 14%); LCMS m/z = 337 [M + H]$^+$; $^1$H NMR (500 MHz, DMSO-d$_6$) δ: 11.83 (d, 1H), 10.43 (d, 1H), 8.55 (s, 1H), 8.18 (s, 2H), 7.71 (t, 1H), 7.33-7.23 (m, 1H), 7.06 (d, 1H), 6.25 (d, 1H), 5.55 (s, 1H), 3.80 (s, 3H), 1.96 (d, 3H). |
| 46 | (S)-N-(5-(difluoromethoxy)-1H-pyrazol-3-yl)-1-(1-(2-fluorophenyl)ethyl)-1H-pyrazolo[3,4-b]pyrazin-6-amine 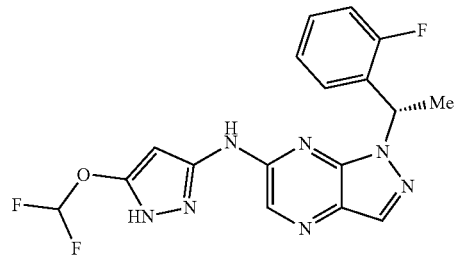 [SMILES: C[C@@H](c1ccccc1F)n1ncc2ncc(Nc3cc(OC(F)F)[nH]n3)nc21] Amine-1; RCl: (S)-6-chloro-1-(1-(2-fluorophenyl)ethyl)-1H-pyrazolo[3,4-b]pyrazine (Preparation 46); tBuBrettPhos Pd G3<br>ISCO: White solid (37 mg, 32%); LCMS m/z = 390 [M + H]$^+$; $^1$H NMR (500 MHz, DMSO-d6) δ: 12.17 (s, 1H), 10.78 (s, 1H), 8.21 (d, 2H), 7.48-7.09 (m, 5H), 6.64 (d, 1H), 6.00 (s, 1H), 1.90 (d, 3H). |

| Example No. | Name/Structure/Amine/RCl/Catalyst/Data |
|---|---|
| 47 | (S)-N-(5-(difluoromethoxy)-1H-pyrazol-3-yl)-1-(1-(4-fluorophenyl)ethyl)-1H-pyrazolo[3,4-b]pyrazin-6-amine 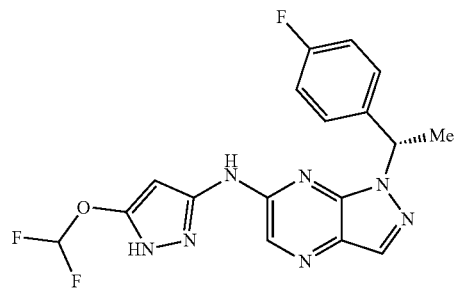 [SMILES: C[C@@H](c1ccc(F)cc1)n1ncc2ncc(Nc3cc(OC(F)F)[nH]n3)nc21] Amine-1; RCl: (S)-6-chloro-1-(1-(4-fluorophenyl)ethyl)-1H-pyrazolo[3,4-b]pyrazine (Preparation 47); tBuBrettPhos Pd G3 ISCO: White solid (49 mg, 41%); LCMS m/z = 390 [M + H]⁺; ¹H NMR (500 MHz, DMSO-d₆) δ: 12.23 (s, 1H), 10.79 (s, 1H), 8.20 (d, 2H), 7.51-7.06 (m, 5H), 6.52 (q, 1H), 5.92 (d, 1H), 1.88 (d, 3H). |
| 48 | (S)-N-(5-(difluoromethoxy)-1H-pyrazol-3-yl)-1-(1-(5-fluoropyridin-2-yl)ethyl)-1H-pyrazolo[3,4-b]pyrazin-6-amine 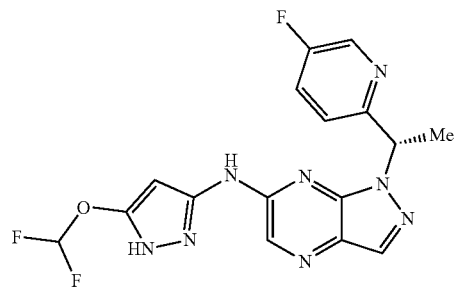 [SMILES: C[C@@H](c1ccc(F)cn1)n1ncc2ncc(Nc3cc(OC(F)F)[nH]n3)nc21] Amine-1; RCl: (S)-6-chloro-1-(1-(5-fluoropyridin-2-yl)ethyl)-1H-pyrazolo[3,4-b]pyrazine (Preparation 48); tBuBrettPhos Pd G3 ISCO: White solid (46 mg, 35%); LCMS m/z = 391 [M + H]⁺; ¹H NMR (500 MHz, DMSO-d₆) δ: 12.27 (s, 1H), 10.82 (s, 1H), 8.52 (d, 1H), 8.21 (d, 2H), 7.64 (td, 1H), 7.47-7.12 (m, 2H), 6.52 (q, 1H), 5.85 (d, 1H), 1.93 (d, 3H). |
| 49 | 4-((6-((5-(difluoromethoxy)-1H-pyrazol-3-yl)amino)-1H-pyrazolo[3,4-b]pyrazin-1-yl)methyl)tetrahydro-2H-pyran-4-ol 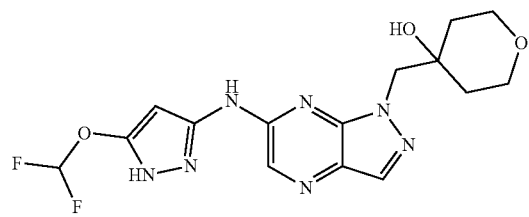 [SMILES: OC1(Cn2ncc3ncc(Nc4cc(OC(F)F)[nH]n4)nc32)CCOCC1] Amine-1; RCl: 4-((6-chloro-1H-pyrazolo[3,4-b]pyrazin-1-yl)methyl)tetrahydro-2H-pyran-4-ol (Preparation 78); tBuBrettPhos Pd G3 ISCO: White solid (16.9 mg, 36%); LCMS m/z = 382 [M + H]⁺; ¹H NMR (500 MHz, DMSO-d₆) δ: 12.12 (s, 1H), 10.81 (s, 1H), 8.20 (s, 1H), 8.17 (s, 1H), 7.31 (t, 1H), 5.93 (s, 1H), 4.79 (s, 1H), 4.42 (s, 2H), 3.60 (d, 4H), 1.63 (dt, 2H), 1.41 (d, 2H). |

| Example No. | Name/Structure/Amine/RCl/Catalyst/Data |
|---|---|
| 50 | (S)-N-(5-(difluoromethoxy)-1H-pyrazol-3-yl)-1-(1-(3-fluoropyridin-2-yl)ethyl)-1H-pyrazolo[3,4-b]pyrazin-6-amine 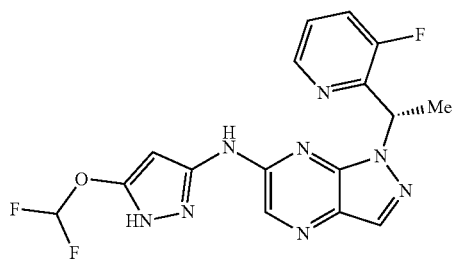 [SMILES: C[C@@H](c1ncccc1F)n1ncc2ncc(Nc3cc(OC(F)F)[nH]n3)nc21] Amine-1; RCl: (S)-6-chloro-1-(1-(3-fluoropyridin-2-yl)ethyl)-1H-pyrazolo[3,4-b]pyrazine (Preparation 49); tBuBrettPhos Pd G3 ISCO: Yellow solid (55 mg, 44%); LCMS m/z = 391 [M + H]$^+$; $^1$H NMR (500 MHz, DMSO-d$_6$) δ: 12.26 (s, 1H), 10.87 (s, 1H), 8.47 (d, 1H), 8.19 (s, 1H), 8.14 (s, 1H), 7.67 (t, 1H), 7.49-7.15 (m, 2H), 6.63 (q, 1H), 5.88 (s, 1H), 1.95 (d, 3H). |
| 51 | (S)-1-(1-cyclopropylethyl)-N-(5-(difluoromethoxy)-1H-pyrazol-3-yl)-1H-pyrazolo[3,4-b]pyrazin-6-amine 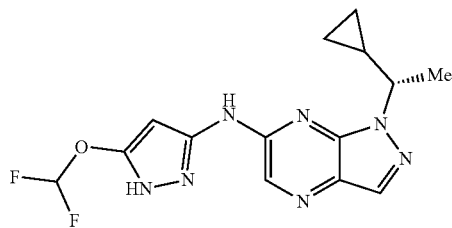 [SMILES: C[C@@H](C1CC1)n1ncc2ncc(Nc3cc(OC(F)F)[nH]n3)nc21] Amine-1; RCl: (S)-6-chloro-1-(1-cyclopropylethyl)-1H-pyrazolo[3,4-b]pyrazine (Preparation 33); tBuBrettPhos Pd G3 ISCO: Pale yellow solid (38.1 mg, 37%); LCMS m/z = 336 [M + H]$^+$; $^1$H NMR (500 MHz, DMSO-d$_6$) δ: 11.89 (s, 1H), 10.47 (s, 1H), 7.94 (s, 1H), 7.91 (s, 1H), 7.05 (t, 1H), 5.69 (s, 1H), 4.26 (t, 1H), 1.34 (d, 3H), 1.12 (q, 1H), 0.34 (dd, 1H), 0.25-0.14 (m, 1H), 0.05 (q, 2H). |
| 52 | N-(5-(difluoromethoxy)-1H-pyrazol-3-yl)-1-(thiazol-4-ylmethyl)-1H-pyrazolo[3,4-b]pyrazin-6-amine 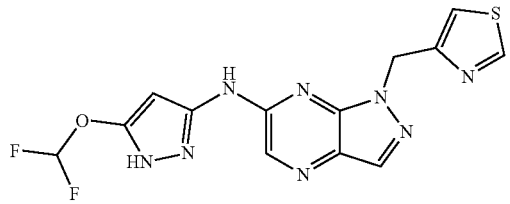 [SMILES: FC(F)Oc1cc(Nc2cnc3cnn(Cc4cscn4)c3n2)n[nH]1] Amine-1; RCl: 4-((6-chloro-1H-pyrazolo[3,4-b]pyrazin-1-yl)methyl)thiazole (Preparation 34); tBuBrettPhos Pd G3 ISCO: pale yellow solid (59 mg, 43%); LCMS m/z = 365 [M + H]$^+$; $^1$H NMR (500 MHz, DMSO-d$_6$) δ: 12.38 (s, 1H), 10.85 (s, 1H), 9.05 (d, 1H), 8.21 (s, 1H), 8.18 (s, 1H), 7.51 (s, 1H), 7.30 (t, 1H), 5.87 (s, 3H). |

| Example No. | Name/Structure/Amine/RCl/Catalyst/Data |
|---|---|
| 53 | N-(5-(difluoromethoxy)-1H-pyrazol-3-yl)-1-(thiazol-5-ylmethyl)-1H-pyrazolo[3,4-b]pyrazin-6-amine 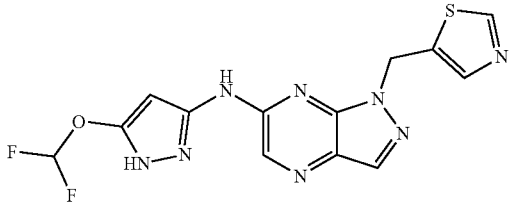 [SMILES: FC(F)Oc1cc(Nc2cnc3cnn(Cc4cncs4)c3n2)n[nH]1] Amine-1; RCl: 5-((6-chloro-1H-pyrazolo[3,4-b]pyrazin-1-yl)methyl)thiazole (Preparation 35); tBuBrettPhos Pd G3 ISCO: White solid (44.4 mg, 39%); LCMS m/z = 365 [M + H]$^+$; $^1$H NMR (500 MHz, DMSO-d$_6$) δ: 12.33 (s, 1H), 10.91 (s, 1H), 9.00 (s, 1H), 8.22 (s, 1H), 8.20 (s, 1H), 7.95 (s, 1H), 7.33 (t, 1H), 6.07 (s, 2H), 5.92 (s, 1H). |
| 54 | N-(5-(difluoromethoxy)-1H-pyrazol-3-yl)-1-(thiazol-2-ylmethyl)-1H-pyrazolo[3,4-b]pyrazin-6-amine 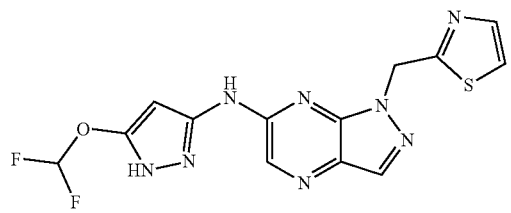 [SMILES: FC(F)Oc1cc(Nc2cnc3cnn(Cc4nccs4)c3n2)n[nH]1] Amine-1; RCl: 2-((6-chloro-1H-pyrazolo[3,4-b]pyrazin-1-yl)methyl)thiazole (Preparation 52); tBuBrettPhos Pd G3 ISCO: White solid (44.7 mg, 34%); LCMS m/z = 365 [M + H]$^+$; $^1$H NMR (500 MHz, DMSO-d$_6$) δ: 12.34 (s, 1H), 10.92 (s, 1H), 8.25 (s, 1H), 8.23 (s, 1H), 7.76 (d, 1H), 7.67 (d, 1H), 7.30 (t, 1H), 6.14 (s, 2H), 5.86 (s, 1H). |
| 55 | (R)-1-(1-cyclopropylethyl)-N-(5-(difluoromethoxy)-1H-pyrazol-3-yl)-1H-pyrazolo[3,4-b]pyrazin-6-amine 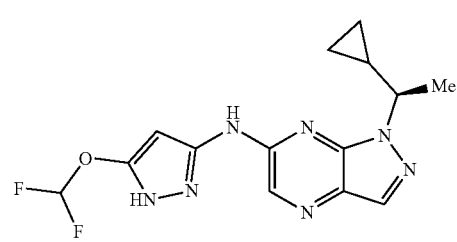 [SMILES: C[C@H](C1CC1)n1ncc2ncc(Nc3cc(OC(F)F)[nH]n3)nc21] Amine-1; RCl: (R)-6-chloro-1-(1-cyclopropylethyl)-1H-pyrazolo[3,4-b]pyrazine (Preparation 32); tBuBrettPhos Pd G3 ISCO: White solid (49.5 mg, 47%); LCMS m/z = 336 [M + H]$^+$; $^1$H NMR (500 MHz, DMSO-d$_6$) δ: 12.14 (s, 1H), 10.72 (s, 1H), 8.19 (s, 1H), 8.15 (s, 1H), 7.30 (t, 1H), 5.94 (s, 1H), 4.64-4.37 (m, 1H), 1.59 (d, 3H), 1.36 (dq, 1H), 0.59 (hept, 1H), 0.44 (dd, 1H), 0.30 (q, 2H). |

| Example No. | Name/Structure/Amine/RCl/Catalyst/Data |
|---|---|
| 56 | 3-chloro-N-(5-(difluoromethoxy)-1H-pyrazol-3-yl)-1-((tetrahydro-2H-pyran-4-yl)methyl)-1H-pyrazolo[3,4-b]pyrazin-6-amine 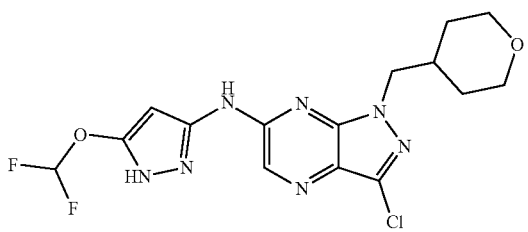 [SMILES: FC(F)Oc1cc(Nc2cnc3c(Cl)nn(CC4CCOCC4)c3n2)n[nH]1] Amine-1; RCl: 3,6-dichloro-1-((tetrahydro-2H-pyran-4-yl)methyl)-1H-pyrazolo[3,4-b]pyrazine (Preparation 68); tBuBrettPhos Pd G3 ISCO: White solid (49.6 mg, 38%); LCMS m/z = 400 [M + H]$^+$; $^1$H NMR (500 MHz, DMSO-d$_6$) δ: 12.25 (s, 1H), 11.03 (s, 1H), 8.23 (s, 1H), 7.32 (t, 1H), 6.00 (s, 1H), 4.37 (d, 2H), 3.81 (d, 2H), 3.24 (t, 2H), 2.21-2.09 (m, 1H), 1.46-1.27 (m, 4H). |
| 57 | (1s,4s)-4-(6-((5-(difluoromethoxy)-1Hpyrazol-3-yl)amino)-1Hpyrazolo[3,4-b]pyrazin-1-yl)cyclohexan-1-ol 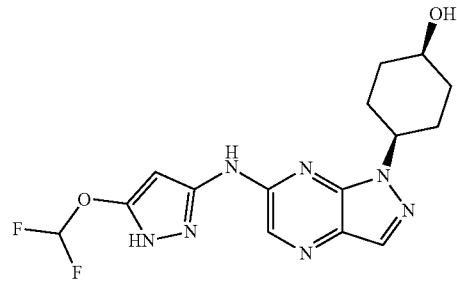 [SMILES: O[C@H]1CC[C@@H](n2ncc3ncc(Nc4cc(OC(F)F)[nH]n4)nc32)CC1] Amine-1; RCl: (1s,4s)-4-(6-chloro-1H-pyrazolo[3,4-b]pyrazin-1-yl)cyclohexan-1-ol (Preparation 51); tBuBrettPhos Pd G3 ISCO: White solid (61 mg, 44%); LCMS m/z = 366 [M + H]$^+$; $^1$H NMR (500 MHz, DMSO-d$_6$) δ: 12.14 (s, 1H), 10.71 (s, 1H), 8.19 (s, 1H), 8.13 (s, 1H), 7.31 (t, 1H), 5.99 (s, 1H), 4.86 (br s, 1H), 4.50 (br s, 1H), 3.92 (s, 1H), 2.38 (d, 2H), 1.83 (d, 2H), 1.66 (d, 4H). |
| 58 | (S)-N-(5-(difluoromethoxy)-1H-pyrazol-3-yl)-1-(1-(thiazol-5-yl)ethyl)-1H-pyrazolo[3,4-b]pyrazin-6-amine 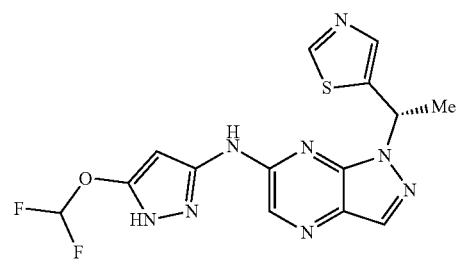 [SMILES: C[C@@H](c1cncs1)n1ncc2ncc(Nc3cc(OC(F)F)[nH]n3)nc21] Amine-1; RCl: (S)-5-(1-(6-chloro-1H-pyrazolo[3,4-b]pyrazin-1-yl)ethyl)thiazole (Preparation 53); tBuBrettPhos Pd G3 ISCO: Pale yellow solid (46.1 mg, 42%); LCMS m/z = 379 [M + H]$^+$; $^1$H NMR (500 MHz, DMSO-d$_6$) δ: 12.33 (s, 1H), 10.91 (s, 1H), 8.98 (s, 1H), 8.23 (s, 1H), 8.21 (s, 1H), 7.90 (s, 1H), 7.33 (t, 1H), 7.00 (q, 1H), 5.89 (d, 1H), 1.93 (d, 3H). |

| Example No. | Name/Structure/Amine/RCl/Catalyst/Data |
|---|---|
| 59 | (S)-N-(5-(difluoromethoxy)-1H-pyrazol-3-yl)-1-(1-(2-methoxypyridin-3-yl)ethyl)-1H-pyrazolo[3,4-b]pyrazin-6-amine 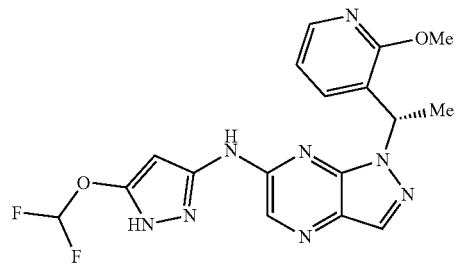 [SMILES: COc1ncccc1[C@H](C)n1ncc2ncc(Nc3cc(OC(F)F)[nH]n3)nc21] Amine-1; RCl: (S)-6-chloro-1-(1-(2-methoxypyridin-3-yl)ethyl)-1H-pyrazolo[3,4-b]pyrazine (Preparation 54); tBuBrettPhos Pd G3 ISCO: Pale yellow solid (46 mg, 37%); LCMS m/z = 403 [M + H]$^+$; $^1$H NMR (500 MHz, DMSO-d$_6$) δ: 12.13 (d, 1H), 10.76 (s, 1H), 8.22 (s, 1H), 8.21 (s, 1H), 8.07 (dd, 1H), 7.53 (dd, 1H), 7.30 (t, 1H), 6.94 (dd, 1H), 6.49 (q, 1H), 6.07 (d, 1H), 3.90 (s, 3H), 1.84 (d, 3H). |
| 60 | (S)-1-(1-(2-chloropyridin-3-yl)ethyl)-N-(5-(difluoromethoxy)-1H-pyrazol-3-yl)-1H-pyrazolo[3,4-b]pyrazin-6-amine 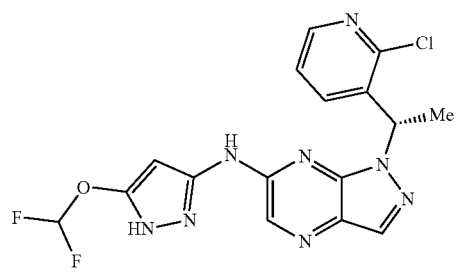 [SMILES: C[C@@H](c1cccnc1Cl)n1ncc2ncc(Nc3cc(OC(F)F)[nH]n3)nc21] Amine-1; RCl: (S)-6-chloro-1-(1-(2-chloropyridin-3-yl)ethyl)-1H-pyrazolo[3,4-b]pyrazine (Preparation 55); tBuBrettPhos Pd G3 ISCO: Pale yellow solid (42.3 mg, 36%); LCMS m/z = 407 [M + H]$^+$; $^1$H NMR (500 MHz, DMSO-d$_6$) δ: 12.17 (s, 1H), 10.79 (s, 1H), 8.34 (dd, 1H), 8.25 (s, 1H), 8.23 (s, 1H), 7.88 (d, 1H), 7.48-7.07 (m, 2H), 6.60 (q, 1H), 6.06 (s, 1H), 1.88 (d, 3H). |
| 61 | (S)-3-chloro-N-(5-(difluoromethoxy)-1H-pyrazol-3-yl)-1-(1-(pyridin-3-yl)ethyl)-1H-pyrazolo[3,4-b]pyrazin-6-amine 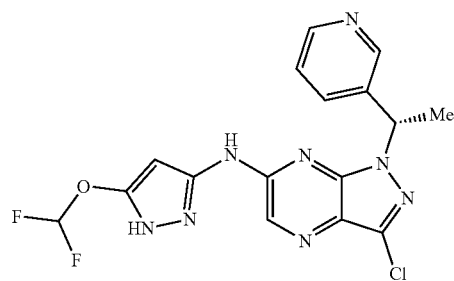 [SMILES: C[C@@H](c1cccnc1)n1nc(Cl)c2ncc(Nc3cc(OC(F)F)[nH]n3)nc21] Amine-1; RCl: (S)-3,6-dichloro-1-(1-(pyridin-3-yl)ethyl)-1H-pyrazolo[3,4-b]pyrazine (Preparation 62); tBuBrettPhos Pd G3 ISCO: Off-white solid (42.8 mg, 36%); LCMS m/z = 407 [M + H]$^+$; $^1$H NMR (500 MHz, DMSO-d$_6$) δ: 12.34 (s, 1H), 11.07 (s, 1H), 8.61 (s, 1H), 8.48 (d, 1H), 8.24 (s, 1H), 7.76 (d, 1H), 7.55-7.15 (m, 2H), 6.65 (q, 1H), 5.94 (s, 1H), 1.89 (d, 3H). |

| Example No. | Name/Structure/Amine/RCl/Catalyst/Data |
|---|---|
| 62 | 6-((5-(difluoromethoxy)-1H-pyrazol-3-yl)amino)-1-((tetrahydro-2H-pyran-4-yl)methyl)-1H-pyrazolo[3,4-b]pyrazine-3-carbonitrile<br><br>Amine-1; RCl: 6-chloro-1-((tetrahydro-2H-pyran-4-yl)methyl)-1H-pyrazolo[3,4-b]pyrazine-3-carbonitrile (Preparation 69); tBuBrettPhos Pd G3<br>ISCO: Pale yellow solid (21.7 mg, 26%); LCMS m/z = 391 [M + H]$^+$; $^1$H NMR (500 MHz, DMSO-d$_6$) δ: 12.31 (s, 1H), 11.20 (s, 1H), 8.38 (s, 1H), 7.32 (t1H), 6.04 (s, 1H), 4.52 (d, 2H), 3.88-3.75 (m, 2H), 3.24 (t, 2H), 2.20 (br s, 1H), 1.50-1.28 (m, 4H). |
| 63 | (S)-6-((5-(difluoromethoxy)-1H-pyrazol-3-yl)amino)-1-(1-(2-fluoropyridin-3-yl)ethyl)-1H-pyrazolo[3,4-b]pyrazine-3-carbonitrile<br><br>Amine-1; RCl: (S)-6-chloro-1-(1-(2-fluoropyridin-3-yl)ethyl)-1H-pyrazolo[3,4-b]pyrazine-3-carbonitrile (Preparation 70); tBuBrettPhos Pd G3<br>ISCO: Yellow solid (58.4 mg, 41%); LCMS m/z = 416 [M + H]$^+$; $^1$H NMR (500 MHz, DMSO-d$_6$) δ: 12.36 (s, 1H), 11.24 (s, 1H), 8.40 (s, 1H), 8.20 (d, 1H), 8.02 (t, 1H), 7.53-7.13 (m, 2H), 6.80 (q, 1H), 6.02 (s, 1H), 1.92 (d, 3H). |
| 64 | (S)-6-((5-(difluoromethoxy)-1H-pyrazol-3-yl)amino)-1-(1-(tetrahydro-2H-pyran-4-yl)ethyl)-1H-pyrazolo[3,4-b]pyrazine-3-carbonitrile<br><br>Amine-1; RCl: (S)-6-chloro-1-(1-(tetrahydro-2H-pyran-4-yl)ethyl)-1H-pyrazolo[3,4-b]pyrazine-3-carbonitrile (Preparation 71); tBuBrettPhos Pd G3<br>ISCO: Yellow solid (32.6 mg, 29%); LCMS m/z = 405 [M + H]$^+$; $^1$H NMR (500 MHz, DMSO-d$_6$) δ: 12.32 (s, 1H), 11.19 (s, 1H), 8.38 (s, 1H), 7.32 (t, 1H), 6.01 (s, 1H), 5.23-5.10 (m, 1H), 3.89 (d, 1H), 3.71 (d, 1H), 3.14 (t, 1H), 2.14-2.04 (m, 1H), 1.74 (d, 1H), 1.51 (d, 3H), 1.41-1.30 (m, 1H), 1.25-1.13 (m, 2H), 0.87 (d, 1H). |

| Example No. | Name/Structure/Amine/RCl/Catalyst/Data |
|---|---|
| 65 | N-(5-(difluoromethoxy)-1H-pyrazol-3-yl)-1-(((2R,4r,6S)-2,6-dimethyltetrahydro-2Hpyran-4-yl)methyl)-1Hpyrazolo[3,4-b]pyrazin-6-amine<br>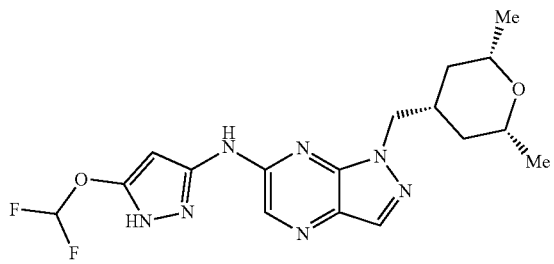 [SMILES: C[C@@H]1C[C@H](Cn2ncc3ncc(Nc4cc(OC(F)F)[nH]n4)nc32)C[C@H](C)O1]<br>Amine-1; RCl: 6-chloro-1-(((2R,4r,6S)-2,6-dimethyltetrahydro-2H-pyran-4-yl)methyl)-1H-pyrazolo[3,4-b]pyrazine (Preparation 57); tBuBrettPhos Pd G3<br>ISCO: Pale yellow foam (43.6 mg, 31%); LCMS m/z = 394 [M + H]$^+$; $^1$H NMR (500 MHz, DMSO-d$_6$) δ: 12.16 (s, 1H), 10.76 (s, 1H), 8.20 (d, 1H), 8.16 (d, 1H), 7.30 (dd, 1H), 5.99 (s, 1H), 4.34 (d,), 3.40-3.31 (m, 2H), 2.31-2.17 (m, 1H), 1.45 (d, 2H), 1.04 (d, 6H), 0.93 (q, 2H). |
| 66 | 1-(((2R,4r,6S)-2,6-dimethyltetrahydro-2H-pyran-4-yl)methyl)-N-(5-methoxy-1H-pyrazol-3-yl)-1H-pyrazolo[3,4-b]pyrazin-6-amine<br>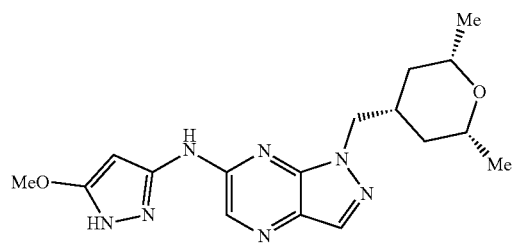 [SMILES: COc1cc(Nc2cnc3cnn(C[C@H]4C[C@@H](C)O[C@@H](C)C4)c3n2)n[nH]1]<br>Amine-3; RCl: 6-chloro-1-(((2R,4r,6S)-2,6-dimethyltetrahydro-2H-pyran-4-yl)methyl)-1H-pyrazolo[3,4-b]pyrazine (Preparation 57); tBuBrettPhos Pd G3<br>ISCO: Pale yellow solid (31.5 mg, 20%); LCMS m/z = 358 [M + H]$^+$; $^1$H NMR (500 MHz, DMSO-d$_6$) δ: 11.79 (d, 1H), 10.42 (d, 1H), 8.37-7.98 (m, 2H), 5.96 (d, 1H), 4.39-4.14 (m, 2H), 3.84 (d, 3H), 3.37 (d, 2H), 2.25 (s, 1H), 1.45 (d, 2H), 1.04 (dd, 6H), 0.94 (d, 2H). |
| 67 | (S)-N-(5-methoxy-1H-pyrazol-3-yl)-1-(1-(pyridin-3-yl)ethyl)-1H-pyrazolo[3,4-b]pyrazin-6-amine<br>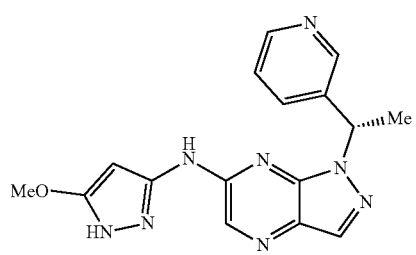 [SMILES: COc1cc(Nc2cnc3cnn([C@@H](C)c4cccnc4)c3n2)n[nH]1]<br>Amine-3; RCl: (S)-6-chloro-1-(1-(pyridin-3-yl)ethyl)-1H-pyrazolo[3,4-b]pyrazine (Preparation 81); tBuBrettPhos Pd G3<br>ISCO: Pale yellow solid (22.2 mg, 21%); LCMS m/z = 337 [M + H]$^+$; $^1$H NMR (500 MHz, DMSO-d$_6$) δ: 11.84 (d, 1H), 10.47 (d, 1H), 8.61 (s, 1H), 8.46 (d, 1H), 8.18 (d, 2H), 7.73 (s, 1H), 7.34 (dt, 1H), 6.40 (d, 1H), 6.12-5.60 (d, 1H), 3.87 (d, 3H), 2.00-1.85 (m, 3H). |

| Example No. | Name/Structure/Amine/RCl/Catalyst/Data |
|---|---|
| 68 | (S)-1-(1-cyclopropylethyl)-N-(5-methoxy-1H-pyrazol-3-yl)-1H-pyrazolo[3,4-b]pyrazin-6-amine 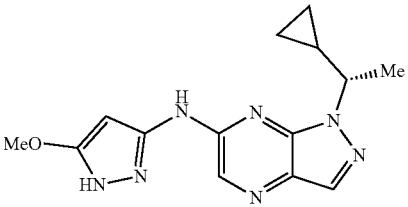 [SMILES: COc1cc(Nc2cnc3cnn([C@@H](C)C4CC4)c3n2)n[nH]1] Amine-3; RCl: (S)-6-chloro-1-(1-cyclopropylethyl)-1H-pyrazolo[3,4-b]pyrazine (Preparation 33); tBuBrettPhos Pd G3<br>ISCO: Tan solid (39.2 mg, 36%); LCMS m/z = 300 [M + H]⁺; ¹H NMR (500 MHz, DMSO-d₆) δ: 1.76 (d, 1H), 10.37 (d, 1H), 8.38-7.97 (m, 2H), 5.92 (d, 1H), 4.29 (d, 1H), 3.83 (d, 3H), 1.59 (s, 3H), 1.37 (s, 1H), 0.60 (s, 1H), 0.38 (d, 3H). |
| 69 | 1-(cyclopropylmethyl)-N-(5-methoxy-1H-pyrazol-3-yl)-1H-pyrazolo[3,4-b]pyrazin-6-amine 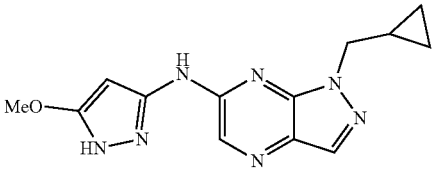 [SMILES: COc1cc(Nc2cnc3cnn(CC4CC4)c3n2)n[nH]1] Amine-3; RCl: 6-chloro-1-(cyclopropylmethyl)-1H-pyrazolo[3,4-b]pyrazine (Preparation 108); tBuBrettPhos Pd G3<br>ISCO: Tan solid (27.4 mg, 22%); LCMS m/z = 286 [M + H]⁺; ¹H NMR (500 MHz, DMSO-d₆) δ: 11.79 (d, 1H), 10.40 (d, 1H), 8.35-8.01 (m, 2H), 5.94 (d, 1H), 4.39-4.16 (m, 2H), 3.84 (d, 3H), 1.27 (d, 1H), 0.54-0.39 (m, 4H). |
| 70 | (R)-N-(5-methoxy-1H-pyrazol-3-yl)-1-((tetrahydrofuran-3-yl)methyl)-1H-pyrazolo[3,4-b]pyrazin-6-amine 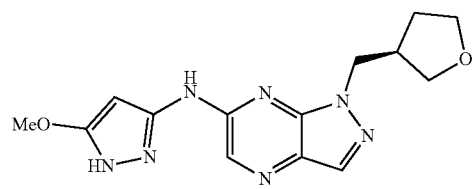 [SMILES: COc1cc(Nc2cnc3cnn(C[C@H]4CCOC4)c3n2)n[nH]1] Amine-3; RCl: (R)-6-chloro-1-((tetrahydrofuran-3-yl)methyl)-1H-pyrazolo[3,4-b]pyrazine (Preparation 192); tBuBrettPhos Pd G3<br>ISCO: Tan solid (43.8 mg, 31%); LCMS m/z = 316 [M + H]⁺; ¹H NMR (500 MHz, DMSO-d₆) δ: 11.80 (d, 1H), 10.44 (d, 1H), 8.43-8.00 (m, 2H), 5.97 (d, 1H), 4.62-4.23 (m, 2H), 3.98-3.73 (m, 4H), 3.63 (dd, 3H), 2.81 (s, 1H), 1.92 (s, 1H), 1.70 (dt, 1H). |

| Example No. | Name/Structure/Amine/RCl/Catalyst/Data |
|---|---|
| 71 | (S)-N-(5-methoxy-1H-pyrazol-3-yl)-1-(1-(oxetan-3-yl)ethyl)-1H-pyrazolo[3,4-b]pyrazin-6-amine<br>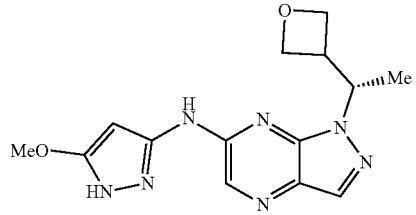 [SMILES: COc1cc(Nc2cnc3cnn([C@@H](C)C4COC4)c3n2)n[nH]1]<br>Amine-3; RCl: (S)-6-chloro-1-(1-(oxetan-3-yl)ethyl)-1H-pyrazolo[3,4-b]pyrazine (Preparation 168); BrettPhos Pd G4<br>Prep-HPLC-1; Yellow solid (52 mg, 21%); LCMS m/z = 316 [M + H]$^+$; $^1$H NMR (400 MHz, DMSO-d$_6$) δ: 11.71 (br s, 1H), 10.75-10.16 (br s, 1H), 8.18 (br s, 1H), 8.11 (s, 1H), 5.69-5.42 (m, 2H), 4.75-4.70 (m, 1H), 4.60-4.57 (m, 1H), 4.46-4.44 (m, 1H), 4.25-4.22 (m, 1H), 3.82 (s, 3H), 3.56-3.50 (m, 1H), 1.41 (d, 3H). |
| 72 | (S)-N-(5-(difluoromethoxy)-1H-pyrazol-3-yl)-1-(1-(oxetan-3-yl)ethyl)-1H-pyrazolo[3,4-b]pyrazin-6-amine<br>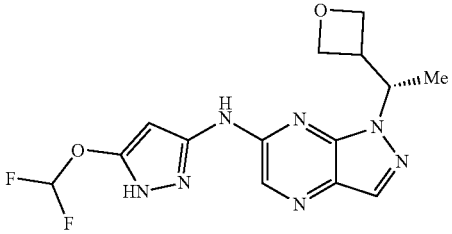 [SMILES: C[C@@H](C1COC1)n1ncc2ncc(Nc3cc(OC(F)F)[nH]n3)nc21]<br>Amine-1; RCl: (S)-6-chloro-1-(1-(oxetan-3-yl)ethyl)-1H-pyrazolo[3,4-b]pyrazine (Preparation 168); BrettPhos Pd G4<br>Prep-HPLC-1; Yellow solid (56 mg, 28%); LCMS m/z = 352 [M + H]$^+$; $^1$H NMR (500 MHz, DMSO-d$_6$) δ: 12.82-11.69 (br s, 1H), 11.70-10.22 (br s, 1H), 8.19 (s, 1H), 8.15 (s, 1H), 7.32 (t, 1H), 5.95 (s, 1H), 5.58 (m, 1H), 4.74-4.71 (m, 1H), 4.53-4.50 (m, 1H), 4.45-4.42 (m, 1H), 4.28-4.26 (m, 1H), 3.59-3.49 (m, 1H), 1.39 (d, 3H). |
| 73 | (R)-1-(1-cyclopropylethyl)-N-(5-methoxy-1H-pyrazol-3-yl)-1H-pyrazolo[3,4-b]pyrazin-6-amine<br>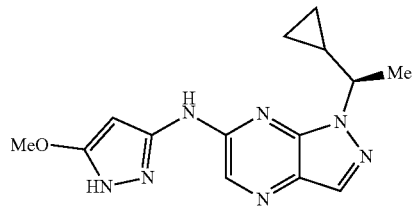 [SMILES: COc1cc(Nc2cnc3cnn([C@H](C)C4CC4)c3n2)n[nH]1]<br>Amine-3; RCl: (R)-6-chloro-1-(1-cyclopropylethyl)-1H-pyrazolo[3,4-b]pyrazine (Preparation 32); BrettPhos Pd G4<br>ISCO: Pale yellow foam (21.4 mg, 17%); LCMS m/z = 300 [M + H]$^+$; $^1$H NMR (500 MHz, DMSO-d$_6$) δ: 11.76 (d, 1H), 10.37 (d, 1H), 8.36-8.01 (m, 2H), 5.92 (d, 1H), 4.29 (d, 1H), 3.80 (s, 3H), 1.59 (s, 3H), 1.37 (s, 1H), 0.60 (s, 1H), 0.38 (d, 3H). |

| Example No. | Name/Structure/Amine/RCl/Catalyst/Data |
|---|---|
| 74 | (S)-N-(5-methoxy-1H-pyrazol-3-yl)-1-(1-(thiazol-5-yl)ethyl)-1H-pyrazolo[3,4-b]pyrazin-6-amine 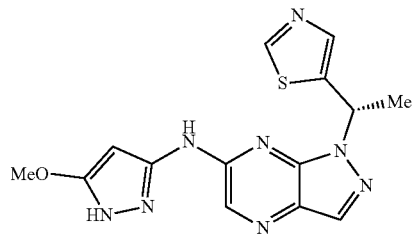 [SMILES: COc1cc(Nc2cnc3cnn([C@@H](C)c4cncs4)c3n2)n[nH]1] Amine-3; RCl: (S)-5-(1-(6-chloro-1H-pyrazolo[3,4-b]pyrazin-1-yl)ethyl)thiazole (Preparation 53); BrettPhos Pd G4 ISCO: Pale yellow solid (38.8 mg, 36%); LCMS m/z = 343 [M + H]$^+$; $^1$H NMR (500 MHz, MeOH-d$_4$) δ: 8.91 (s, 1H), 8.13 (d, 2H), 7.92 (s, 1H), 6.60 (d, 1H), 5.63 (s, 1H), 3.91 (s, 3H), 2.09 (d, 3H). |
| 75 | N-(5-methoxy-1H-pyrazol-3-yl)-1-(thiazol-5-ylmethyl)-1H-pyrazolo[3,4-b]pyrazin-6-amine 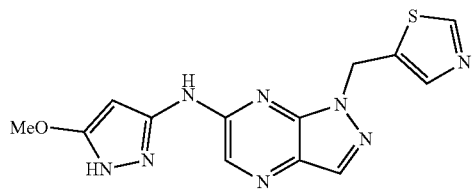 [SMILES: COc1cc(Nc2cnc3cnn(Cc4cncs4)c3n2)n[nH]1] Amine-3; RCl: 5-((6-chloro-1H-pyrazolo[3,4-b]pyrazin-1-yl)methyl)thiazole (Preparation 35); BrettPhos Pd G4 ISCO: Pale yellow solid (53.1 mg, 38%); LCMS m/z = 329 [M + H]$^+$; $^1$H NMR (500 MHz, DMSO-d$_6$) δ: 11.89 (d, 1H), 10.54 (d, 1H), 9.00 (d, 1H), 8.18 (s, 2H), 7.96 (s, 1H), 6.41-5.50 (m, 3H), 4.00 (d, 1H), 3.82 (s, 2H). |
| 76 | 1-((6-fluoropyridin-3-yl)methyl)-N-(5-methoxy-1H-pyrazol-3-yl)-1H-pyrazolo[3,4-b]pyrazin-6-amine 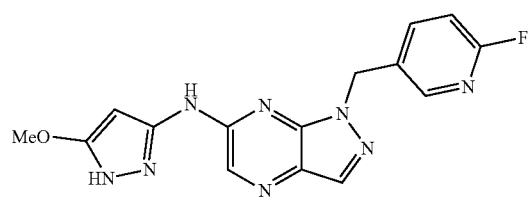 [SMILES: COc1cc(Nc2cnc3cnn(Cc4ccc(F)nc4)c3n2)n[nH]1] Amine-3 (as HCl salt); RCl: 6-chloro-1-((6-fluoropyridin-3-yl)methyl)-1H-pyrazolo[3,4-b]pyrazine (Preparation 43); tBuBrettPhos Pd G3 ISCO: Pale yellow solid (20.1 mg, 33%); LCMS m/z = 341 [M + H]$^+$; $^1$H NMR (500 MHz, DMSO-d$_6$) δ: 11.87 (d, 1H), 10.51 (d, 1H), 8.37-8.07 (m, 3H), 7.85 (d, 1H), 7.14 (d, 1H), 6.30-5.54 (m, 3H), 3.85 (d, 3H). |

| Example No. | Name/Structure/Amine/RCl/Catalyst/Data |
|---|---|
| 77 | (S)-N-(5-(difluoromethoxy)-1H-pyrazol-3-yl)-1-(1-(tetrahydro-2H-pyran-4-yl)ethyl)-1H-pyrazolo[3,4-b]pyrazin-6-amine 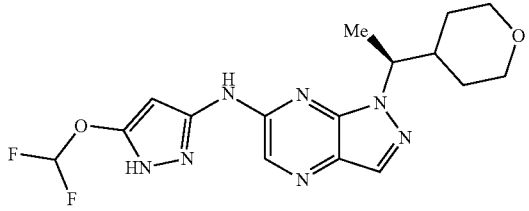 [SMILES: C[C@@H](C1CCOCC1)n1ncc2ncc(Nc3cc(OC(F)F)[nH]n3)nc21] Amine-1; RCl (S)-6-chloro-1-(1-(tetrahydro-2H-pyran-4-yl)ethyl)-1H-pyrazolo[3,4-b]pyrazine (Preparation 90); tBuXphos Pd G4 prep-HPLC-4; White solid (158 mg, 30%). LCMS m/z = 380 [M + H]$^+$; $^1$H NMR (400 MHz, DMSO-d$_6$) δ: 12.20 (br s, 1H), 10.74 (br s, 1H), 8.19 (s, 1H), 8.16 (s, 1H), 7.31 (t, 1H), 5.95 (s, 1H), 5.00-4.94 (m, 1H), 3.91-3.86 (m, 1H), 3.73-3.66 (m, 1H), 3.28-3.25 (m, 1H), 3.14-3.08 (m, 1H), 2.08-2.06 (m, 1H), 1.76-1.73 (m, 1H), 1.47 (d, 3H), 1.34-1.16 (m, 2H), 0.80-0.77 (m, 1H). |
| 78 | (R)-N-(5-(difluoromethoxy)-1H-pyrazol-3-yl)-1-(tetrahydro-2H-pyran-3-yl)-1H-pyrazolo[3,4-b]pyrazin-6-amine 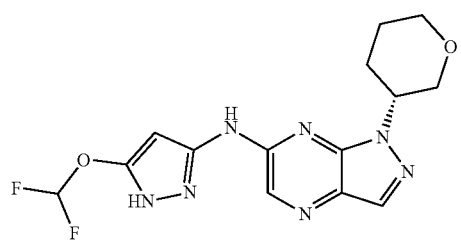 [SMILES: FC(F)Oc1cc(Nc2cnc3cnn([C@@H]4CCCOC4)c3n2)n[nH]1] Amine-1; RCl: (R)-6-chloro-1-(tetrahydro-2H-pyran-3-yl)-1H-pyrazolo[3,4-b]pyrazine (Preparation 106); tBuXphos Pd G3 Prep-HPLC-1; White solid (35.5 mg, 30%); LCMS m/z = 352 [M + H]$^+$; $^1$H NMR (400 MHz, DMSO-d$_6$) δ: 11.05 (br s, 1H), 8.19 (s, 1H), 8.17 (s, 1H), 7.32 (t, 1H), 5.94 (s, 1H), 5.08-5.03 (m, 1H), 3.98-3.92 (m, 2H), 3.72-3.66 (m, 1H), 3.41-3.33 (m, 1H), 2.26-2.15 (m, 1H), 2.11-2.05 (m, 1H), 1.85-1.80 (m, 2H). |
| 79 | 1-(tert-butyl)-N-(5-(difluoromethoxy)-1H-pyrazol-3-yl)-1H-pyrazolo[3,4-b]pyrazin-6-amine 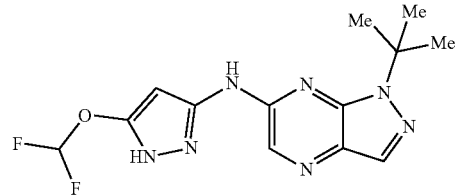 [SMILES: CC(C)(C)n1ncc2ncc(Nc3cc(OC(F)F)[nH]n3)nc21] Amine-1; RCl: 1-(tert-butyl)-6-chloro-1H-pyrazolo[3,4-b]pyrazine (Preparation 107); Pd2(dba)3, tBuXPhos Prep-HPLC-1; White solid (6.1 mg, 3%); LCMS m/z = 324 [M + H]$^+$; $^1$H NMR (400 MHz, DMSO-d$_6$) δ: 8.10 (s, 1H), 7.98 (s, 1H), 7.25 (t, 1H), 6.19 (s, 1H), 1.73 (s, 9H). |

| Example No. | Name/Structure/Amine/RCl/Catalyst/Data |
|---|---|
| 80 | 1-(cyclopropylmethyl)-N-(5-(difluoromethoxy)-1H-pyrazol-3-yl)-1H-pyrazolo[3,4-b]pyrazin-6-amine 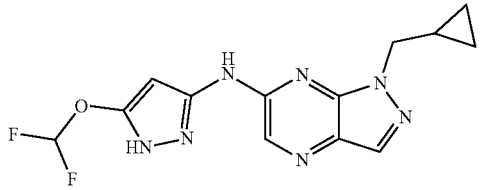 [SMILES: FC(F)Oc1cc(Nc2cnc3cnn(CC4CC4)c3n2)n[nH]1] Amine-1; RCl: 6-chloro-1-(cyclopropylmethyl)-1H-pyrazolo[3,4-b]pyrazine (Preparation 108); tBuXphos Pd G3<br>Prep-HPLC-4; White solid (11.5 mg, 7%); LCMS m/z = 322 [M + H]$^+$; $^1$H NMR (400 MHz, DMSO-d$_6$) δ: 12.24 (br s, 1H), 10.80 (br s, 1H), 8.20 (s, 1H), 8.15 (s, 1H), 7.32 (t, 1H), 5.96 (s, 1H), 4.35 (d, 2H), 1.30-1.25 (m, 1H), 0.52-0.45 (m, 4H). |
| 81 | 1-(((1R,5S,6s)-3-oxabicyclo[3.1.0]hexan-6-yl)methyl)-N-(5-(difluoromethoxy)-1H-pyrazol-3-yl)-1H-pyrazolo[3,4-b]pyrazin-6-amine 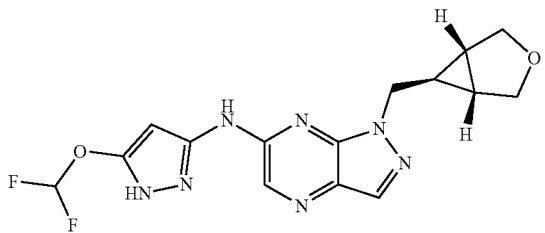 [SMILES: FC(F)Oc1cc(Nc2cnc3cnn(C[C@H]4[C@@H]5COC[C@@H]54)c3n2)n[nH]1] Amine-1; RCl: 1-(((1R,5S,6s)-3-oxabicyclo[3.1.0]hexan-6-yl)methyl)-6-chloro-1H-pyrazolo[3,4-b]pyrazine (Preparation 111); Pd$_2$(dba)$_3$, tBuXPhos<br>Prep-HPLC-1; White solid (43.1 mg, 30%); LCMS m/z = 364 [M + H]$^+$; $^1$H NMR (400 MHz, DMSO-d$_6$) δ: 12.30-12.20 (br, 1H), 10.85-10.70 (br, 1H), 8.20 (s, 1H), 8.15 (s, 1H), 7.32 (t, 1H), 5.96 (br s, 1H), 4.43 (d, 2H), 3.65 (d, 2H), 3.52 (d, 2H), 1.80-1.75 (m, 2H), 1.20-1.12 (m, 1H). |
| 82 | (R)-N-(5-(difluoromethoxy)-1H-pyrazol-3-yl)-1-(1-(pyridin-2-yl)ethyl)-1H-pyrazolo[3,4-b]pyrazin-6-amine 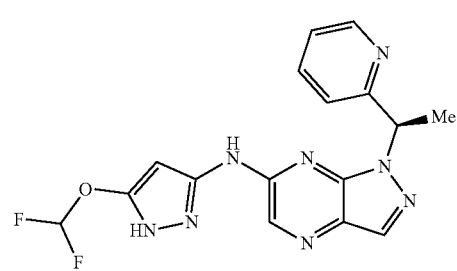 [SMILES: C[C@H](c1ccccn1)n1ncc2ncc(Nc3cc(OC(F)F)[nH]n3)nc21] Amine-1; RCl: (R)-6-chloro-1-(1-(pyridin-2-yl)ethyl)-1H-pyrazolo[3,4-b]pyrazine (Preparation 113); tBuXphos Pd G3<br>Prep-HPLC-1; White solid (41.9 mg, 16%); LCMS m/z = 373 [M + H]$^+$; $^1$H NMR (400 MHz, DMSO-d$_6$) δ: 10.80-10.40 (br s, 1H), 8.55-8.52 (m, 1H), 8.21 (s, 1H), 8.20 (s, 1H), 7.74-7.69 (m, 1H), 7.30 (t, 1H), 7.30-7.27 (m, 1H), 7.07 (d, 1H), 6.48-6.42 (m, 1H), 5.87 (s, 1H), 1.96 (d, 3H). |

| Example No. | Name/Structure/Amine/RCl/Catalyst/Data |
|---|---|
| 83 | N-(5-(difluoromethoxy)-1H-pyrazol-3-yl)-1-(tetrahydro-2H-pyran-4-yl)-1H-pyrazolo[3,4-b]pyrazin-6-amine<br>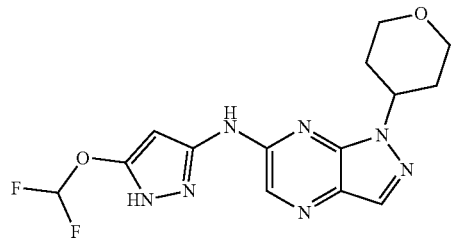 [SMILES: FC(F)Oc1cc(Nc2cnc3cnn(C4CCOCC4)c3n2)n[nH]1]<br>Amine-1; RCl: 6-chloro-1-(tetrahydro-2H-pyran-4-yl)-1H-pyrazolo[3,4-b]pyrazine (Preparation 80); tBuXphos Pd G3<br>prep-HPLC-3; Yellow solid (77.8 mg, 44%); LCMS m/z = 352 [M + H]$^+$;<br>$^1$H NMR (400 MHz, DMSO-d$_6$) δ: 12.27 (s, 1H), 10.82 (s, 1H), 8.20 (s, 1H), 8.17 (s, 1H), 7.32 (t, 1H), 5.93 (s, 1H), 5.20 (s, 1H), 4.03-4.00 (m, 2H), 3.62-3.56 (m, 2H), 2.17-2.13 (m, 2H), 1.88-1.86 (m, 2H). |
| 84 | N-(5-(difluoromethoxy)-1H-pyrazol-3-yl)-3-methyl-1-(pyridin-3-ylmethyl)-1H-pyrazolo[3,4-b]pyrazin-6-amine<br>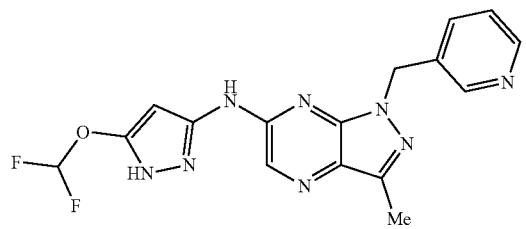 [SMILES: Cc1nn(Cc2cccnc2)c2nc(Nc3cc(OC(F)F)[nH]n3)cnc12]<br>Amine-1; RCl: 6-chloro-3-methyl-1-(pyridin-3-ylmethyl)-1H-pyrazolo[3,4-b]pyrazine (Preparation 178); tBuXphos Pd G3<br>prep-HPLC-3; Yellow solid (35.4 mg, 25%); LCMS m/z = 373 [M + H]$^+$;<br>$^1$H NMR (400 MHz, DMSO-d$_6$) δ: 12.31 (s, 1H), 10.87 (s, 1H), 8.55 (d, 1H), 8.48-8.46 (m, 1H), 8.16 (s, 1H), 7.63 (d, 1H), 7.49-7.13 (m, 2H), 5.88 (s, 1H), 5.73 (s, 2H), 2.42 (s, 3H). |
| 85 | N-(5-(difluoromethoxy)-1H-pyrazol-3-yl)-1-(oxetan-3-ylmethyl)-1H-pyrazolo[3,4-b]pyrazin-6-amine<br>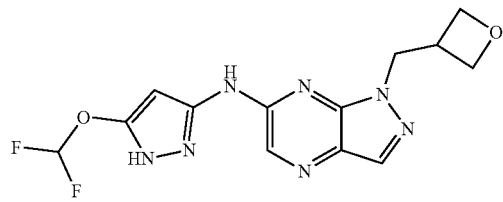 [SMILES: FC(F)Oc1cc(Nc2cnc3cnn(CC4COC4)c3n2)n[nH]1]<br>Amine-1; RCl: 6-chloro-1-(oxetan-3-ylmethyl)-1H-pyrazolo[3,4-b]pyrazine (Preparation 114); tBuXphos Pd G3<br>Prep-HPLC-4; White solid (54.5 mg, 33%); LCMS m/z = 338 [M + H]$^+$; $^1$H NMR (400 MHz, DMSO-d$_6$) δ: 12.26 (s, 1H), 10.83 (s, 1H), 8.19 (s, 1H), 8.16 (s, 1H), 7.32 (t, 1H), 5.90 (s, 1H), 4.79 (d, 2H), 4.65 (dd, 2H), 4.52 (t, 3.47 (heptet, 1H). |

-continued

| Example No. | Name/Structure/Amine/RCl/Catalyst/Data |
|---|---|
| 86 | (S)-1-((1,4-dioxan-2-yl)methyl)-N-(5-(difluoromethoxy)-1H-pyrazol-3-yl)-1H-pyrazolo[3,4-b]pyrazin-6-amine 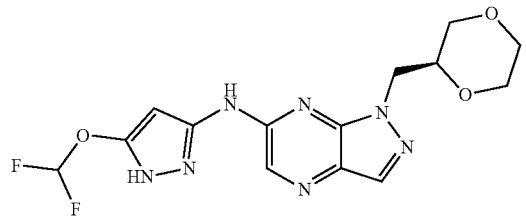 [SMILES: FC(F)Oc1cc(Nc2cnc3cnn(C[C@H]4COCCO4)c3n2)n[nH]1] Amine-1; RCl: (S)-1-((1,4-dioxan-2-yl)methyl)-6-chloro-1H-pyrazolo[3,4-b]pyrazine (Preparation 118); tBuXphos Pd G3<br>Prep-HPLC-1; White solid (43.9 mg, 38%); LCMS m/z = 368 [M + H]$^+$; $^1$H NMR (400 MHz, DMSO-d$_6$) δ: 9.90-9.15 (br, 1H), 8.19 (s, 1H), 8.16 (s, 1H), 7.31 (t, 1H), 6.01 (s, 1H), 4.63-4.41 (m, 2H), 4.01-3.99 (m, 1H), 3.78-3.71 (m, 2H), 3.64-3.60 (m, 1H), 3.52-3.45 (m, 2H), 3.41-3.35 (m, 1H). |
| 87 | N-(5-(difluoromethoxy)-1H-pyrazol-3-yl)-3-methyl-1-((tetrahydro-2H-pyran-4-yl)methyl)-1H-pyrazolo[3,4-b]pyrazin-6-amine 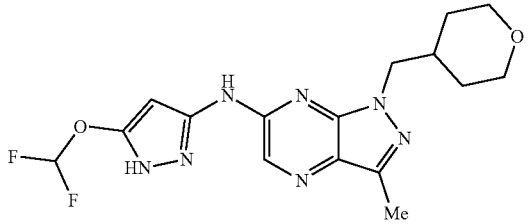 [SMILES: Cc1nn(CC2CCOCC2)c2nc(Nc3cc(OC(F)F)[nH]n3)cnc12] Amine-1; RCl: 6-chloro-3-methyl-1-((tetrahydro-2H-pyran-4-yl)methyl)-1H-pyrazolo[3,4-b]pyrazine (Preparation 179); tBuXphos Pd G3<br>Prep-HPLC-5; White solid (77 mg, 27%); LCMS m/z = 380 [M + H]$^+$; $^1$H NMR (400 MHz, DMSO-d$_6$) δ: 12.15 (br s, 1H), 10.73 (br s, 1H), 8.12 (s, 1H), 7.30 (t, 1H), 5.95 (s, 1H), 4.30 (d, 2H), 3.82-3.77 (m, 2H), 3.28-3.19 (m, 2H), 2.43 (s, 3H), 2.15-2.11 (m, 1H), 1.40-1.22 (m, 4H). |
| 88 | (R)-1-((1,4-dioxan-2-yl)methyl)-N-(5-(difluoromethoxy)-1H-pyrazol-3-yl)-1H-pyrazolo[3,4-b]pyrazin-6-amine 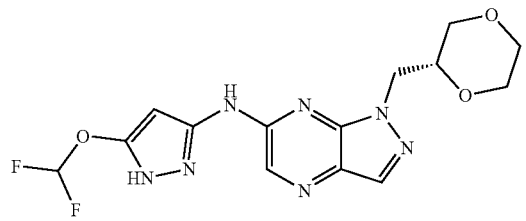 [SMILES: FC(F)Oc1cc(Nc2cnc3cnn(C[C@@H]4COCCO4)c3n2)n[nH]1] Amine-1; RCl: (R)-1-((1,4-dioxan-2-yl)methyl)-6-chloro-1H-pyrazolo[3,4-b]pyrazine (Preparation 119); tBuXphos Pd G3<br>Prep-HPLC-4; White solid (43.9 mg, 38%); LCMS m/z = 368 [M + H]$^+$; $^1$H NMR (300 MHz, DMSO-d$_6$) δ: 11.45-10.85 (br, 1H), 8.19 (s, 1H), 8.16 (s, 1H), 7.31 (t, 1H), 6.01 (s, 1H), 4.63-4.41 (m, 2H), 4.01-3.99 (m, 1H), 3.78-3.71 (m, 2H), 3.64-3.60 (m, 1H), 3.52-3.45 (m, 2H), 3.41-3.35 (m, 1H). |

-continued

| Example No. | Name/Structure/Amine/RCl/Catalyst/Data |
|---|---|
| 89 | (R)-N-(5-(difluoromethoxy)-1H-pyrazol-3-yl)-1-(2-fluoro-1-phenylethyl)-1H-pyrazolo[3,4-b]pyrazin-6-amine or (S)-N-(5-(difluoromethoxy)-1H-pyrazol-3-yl)-1-(2-fluoro-1-phenylethyl)-1H-pyrazolo[3,4-b]pyrazin-6-amine 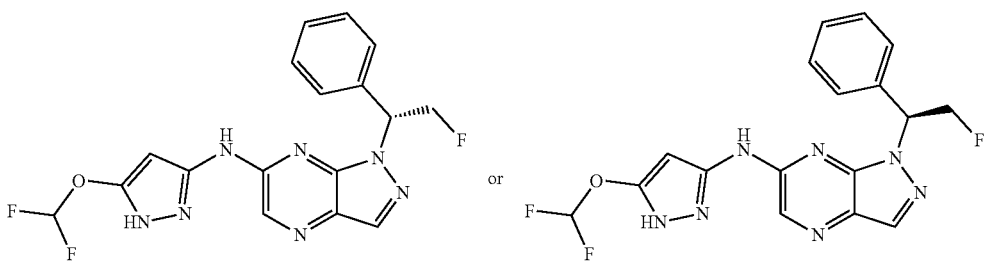 [SMILES: FC[C@@H](c1ccccc1)n1ncc2ncc(Nc3cc(OC(F)F)[nH]n3)nc21 ; FC[C@H](c1ccccc1)n1ncc2ncc(Nc3cc(OC(F)F)[nH]n3)nc21] Amine-1; RCl: (R)-6-chloro-1-(2-fluoro-1-phenylethyl)-1H-pyrazolo[3,4-b]pyrazine or (S)-6-chloro-1-(2-fluoro-1-phenylethyl)-1H-pyrazolo[3,4-b]pyrazine (Preparation 128); Pd$_2$(dba)$_3$, tBuXPhos<br>Prep-HPLC-1; White solid (23.5 mg, 11%); LCMS m/z = 390 [M + H]$^+$; $^1$H NMR (400 MHz, DMSO-d$_6$) δ: 12.32 (br s, 1H), 10.85 (br s, 1H), 8.30 (s, 1H), 8.22 (s, 1H), 7.49-7.42 (m, 2H), 7.38-7.29 (m, 3H), 7.32 (t, 1H), 6.86-6.80 (m, 1H), 5.93 (s, 1H), 5.35 (dt, 9.6 Hz, 1H), 5.13-4.96 (m, 1H). |
| 90 | (S)-N-(5-(difluoromethoxy)-1H-pyrazol-3-yl)-1-(2-fluoro-1-phenylethyl)-1H-pyrazolo[3,4-b]pyrazin-6-amine or (R)-N-(5-(difluoromethoxy)-1H-pyrazol-3-yl)-1-(2-fluoro-1-phenylethyl)-1H-pyrazolo[3,4-b]pyrazin-6-amine 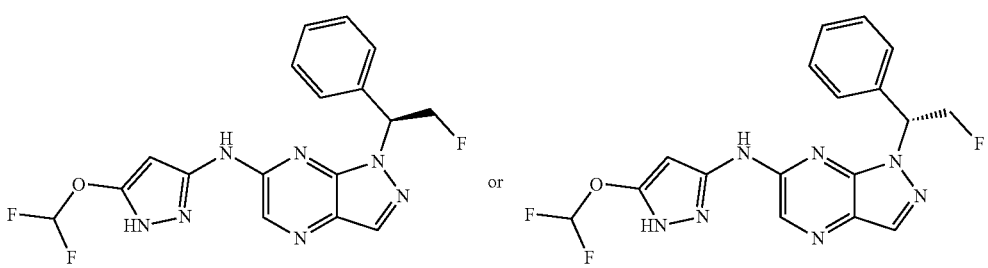 [SMILES: FC[C@H](c1ccccc1)n1ncc2ncc(Nc3cc(OC(F)F)[nH]n3)nc21 ; FC[C@@H](c1ccccc1)n1ncc2ncc(Nc3cc(OC(F)F)[nH]n3)nc21] Amine-1; RCl: (S)-6-chloro-1-(2-fluoro-1-phenylethyl)-1H-pyrazolo[3,4-b]pyrazine or (R)-6-chloro-1-(2-fluoro-1-phenylethyl)-1H-pyrazolo[3,4-b]pyrazine (Preparation 129); Pd$_2$(dba)$_3$, tBuXPhos<br>Prep-HPLC-1; White solid (24.9 mg, 12%); LCMS m/z = 390 [M + H]$^+$; $^1$H NMR (400 MHz, DMSO-d$_6$) δ: 12.32 (br s, 1H), 10.85 (br s, 1H), 8.30 (s, 1H), 8.22 (s, 1H), 7.49-7.42 (m, 2H), 7.38-7.29 (m, 3H), 7.32 (t, 1H), 6.86-6.80 (m, 1H), 5.93 (s, 1H), 5.35 (dt, 1H), 5.13-4.96 (m, 1H). |
| 91 | (R)-N-(5-(difluoromethoxy)-1H-pyrazol-3-yl)-1-(1-(pyridin-3-yl)ethyl)-1H-pyrazolo[3,4-b]pyrazin-6-amine 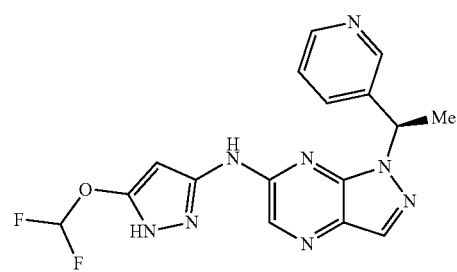 [SMILES: C[C@H](c1cccnc1)n1ncc2ncc(Nc3cc(OC(F)F)[nH]n3)nc21] Amine-1; RCl: (R)-6-chloro-1-(1-(pyridin-3-yl)ethyl)-1H-pyrazolo[3,4-b]pyrazine (Preparation 131); tBuXphos Pd G3<br>Prep-HPLC-1; White solid (1.4 mg, 0.5%); LCMS m/z = 373 [M + H]$^+$; $^1$H NMR (400 MHz, DMSO-d$_6$) δ: 12.31 (br s, 1H), 10.87 (br s, 1H), 8.59 (d, 1H), 8.47-8.43 (m, 1H), 8.22 (s, 1H), 8.20 (s, 1H), 7.75-7.72 (m, 1H), 7.36-7.33 (m, 1H), 7.32 (t, 1H), 6.63 (br s, 1H), 5.94 (s, 1H), 1.92 (d, 3H). |

-continued

| Example No. | Name/Structure/Amine/RCl/Catalyst/Data |
|---|---|
| 92 | N-(5-methoxy-1H-pyrazol-3-yl)-1-((tetrahydro-2H-pyran-4-yl)methyl)-1H-pyrazolo[3,4-b]pyrazin-6-amine<br>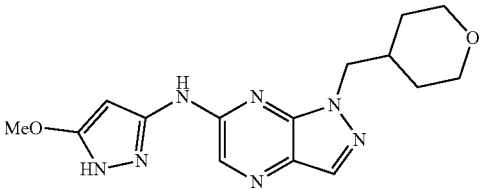 [SMILES: COc1cc(Nc2cnc3cnn(CC4CCOCC4)c3n2)n[nH]1]<br>Amine-3; RCl: 6-chloro-1-((tetrahydro-2H-pyran-4-yl)methyl)-1H-pyrazolo[3,4-b]pyrazine (Preparation 87); tBuXphos Pd G3<br>Prep-HPLC-4; White solid (128.4 mg, 16%); LCMS m/z = 330 [M + H]⁺;<br>¹H NMR (400 MHz, DMSO-d₆) δ: 11.63 (br s, 1H), 10.38 (br s, 1H), 8.19 (s, 1H), 8.11 (s, 1H), 6.35-5.55 (m, 1H), 4.50-4.22(m, 2H), 3.82-3.79 (m, 5H), 3.25-3.19 (m, 2H), 2.25-2.08 (m, 1H), 1.41-1.31 (m, 4H). |
| 93 | (S)-N-(5-(difluoromethoxy)-1H-pyrazol-3-yl)-1-(1-phenylethyl)-1H-pyrazolo[3,4-b]pyrazin-6-amine<br>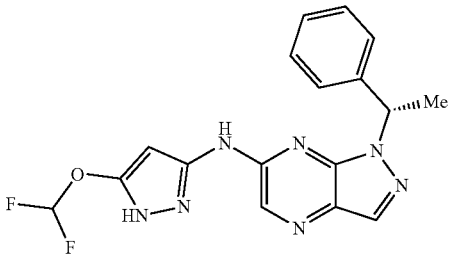 [SMILES: C[C@@H](c1ccccc1)n1ncc2ncc(Nc3cc(OC(F)F)[nH]n3)nc21]<br>Amine-1; RCl: (S)-6-chloro-1-(1-phenylethyl)-1H-pyrazolo[3,4-b]pyrazine (Preparation 133); tBuXphos Pd G3<br>prep-HPLC-3; White solid (272.5 mg, 38%); LCMS m/z = 372 [M + H]⁺;<br>¹H NMR (400 MHz, DMSO-d₆) δ: 12.22 (s, 1H), 10.80 (s, 1H), 8.20 (s, 1H), 8.19 (s, 1H), 7.50-7.14 (m, 6H), 6.508-6.48 (m, 1H), 5.94 (s, 1H), 1.89 (d, J = 6.8 Hz, 3H) |
| 94 | (S)-N-(5-(difluoromethoxy)-1H-pyrazol-3-yl)-1-(1-(pyridin-3-yl)propyl)-1H-pyrazolo[3,4-b]pyrazin-6-amine<br>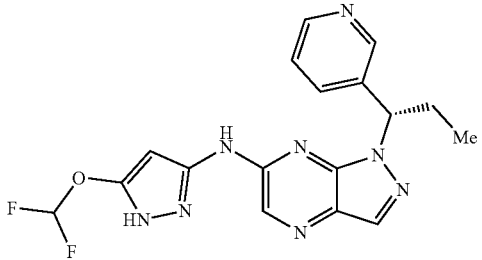 [SMILES: CC[C@@H](c1cccnc1)n1ncc2ncc(Nc3cc(OC(F)F)[nH]n3)nc21]<br>Amine-1; RCl: (S)-6-chloro-1-(1-(pyridin-3-yl)propyl)-1H-pyrazolo[3,4-b]pyrazine (Preparation 135); tBuXphos Pd G3<br>Prep-HPLC-1; White solid (19.8 mg, 11%); LCMS m/z = 387 [M + H]⁺; ¹H NMR (400 MHz, DMSO-d₆) δ: 12.35-12.20 (br, 1H), 10.99-10.89 (br, 1H), 8.67 (d, 1H), 8.46 (dd, 1H), 8.24 (s, 1H), 8.20 (s, 1H), 7.85-7.80 (m, 1H), 7.37-7.31 (m, 1H), 7.33 (t, 1H), 6.35-6.30 (m, 1H), 5.95 (s, 1H), 2.55-2.45 (m, 1H), 2.30-2.20 (m, 1H), 0.83 (t, 3H). |

| Example No. | Name/Structure/Amine/RCl/Catalyst/Data |
|---|---|
| 95 | N-(5-(difluoromethoxy)-1H-pyrazol-3-yl)-1-((2-methylpyridin-3-yl)methyl)-1H-pyrazolo[3,4-b]pyrazin-6-amine 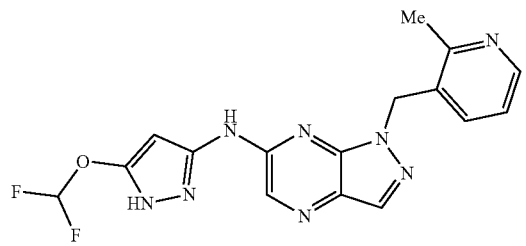 [SMILES: Cc1ncccc1Cn1ncc2ncc(Nc3cc(OC(F)F)[nH]n3)nc21] Amine-1; RCl: 6-chloro-1-((2-methylpyridin-3-yl)methyl)-1H-pyrazolo[3,4-b]pyrazine (Preparation 139); tBuXphos Pd G3 Prep-HPLC-5; White solid (98 mg, 34%); LCMS m/z = 373 [M + H]$^+$; $^1$H NMR (400 MHz, DMSO-d$_6$) δ: 12.27 (br s, 1H), 10.85 (br s, 1H), 8.34 (dd, 1H), 8.21-8.20 (m, 2H), 7.33-7.31 (m, 1H), 7.30 (t, 1H), 7.14-7.12 (m, 1H), 5.90 (s, 1H), 5.78 (s, 2H), 2.51 (s, 3H). |
| 96 | N-(5-(difluoromethoxy)-1H-pyrazol-3-yl)-1-((4-methylpyridin-3-yl)methyl)-1H-pyrazolo[3,4-b]pyrazin-6-amine 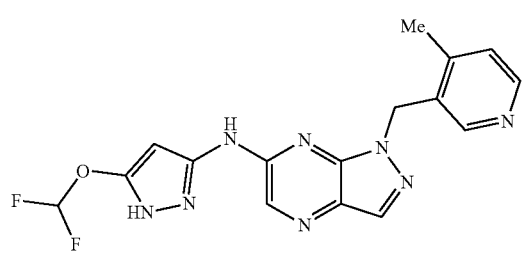 [SMILES: Cc1ccncc1Cn1ncc2ncc(Nc3cc(OC(F)F)[nH]n3)nc21] Amine-1; RCl: 6-chloro-1-((4-methylpyridin-3-yl)methyl)-1H-pyrazolo[3,4-b]pyrazine (Preparation 140); tBuXphos Pd G3 Prep-HPLC-4; White solid (33 mg, 11%); LCMS m/z = 373 [M + H]$^+$; $^1$H NMR (400 MHz, DMSO-d$_6$) δ: 12.29 (s, 1H), 10.86 (s, 1H), 8.36-8.31 (m, 2H), 8.22(s, 1H), 8.18 (s, 1H), 7.32 (t, 1H), 7.23-7.20 (m, 1H), 7.13 (dd, 1H), 5.93 (s, 1H), 5.79 (s, 2H), 2.33 (s, 3H). |
| 97 | (S)-N-(5-(difluoromethoxy)-1H-pyrazol-3-yl)-1-(1-(pyridin-2-yl)propyl)-1H-pyrazolo[3,4-b]pyrazin-6-amine 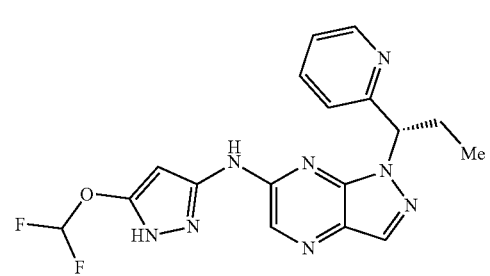 [SMILES: CC[C@@H](c1ccccn1)n1ncc2ncc(Nc3cc(OC(F)F)[nH]n3)nc21] Amine-1; RCl: (S)-6-chloro-1-(1-(pyridin-2-yl)propyl)-1H-pyrazolo[3,4-b]pyrazine (Preparation 136); tBuXPhos/Pd$_2$(dba)$_3$ Prep-HPLC-1; Yellow solid (80 mg, 29%); LCMS m/z = 387 [M + H]$^+$; $^1$H NMR (400 MHz, DMSO-d$_6$) δ: 12.39 (s, 1H), 10.86 (s, 1H), 8.57 (d, 1H), 8.23 (s, 1H), 8.21 (s, 1H), 7.73 (td, 1H), 7.31 (t, 1H), 7.30-7.27 (m, 1H), 7.18 (d, 1H), 6.20-6.17 (m, 1H), 5.87 (s, 1H), 2.48-2.44 (m, 2H), 0.83 (t, 3H). |

-continued

| Example No. | Name/Structure/Amine/RCl/Catalyst/Data |
|---|---|
| 98 | N-(5-(difluoromethoxy)-1H-pyrazol-3-yl)-1-((1-methylcyclopropyl)methyl)-1H-pyrazolo[3,4-b]pyrazin-6-amine 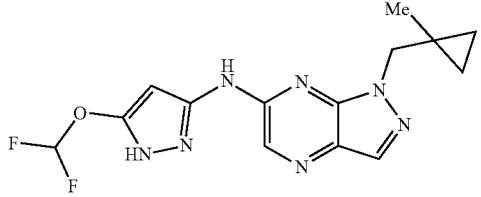 [SMILES: CC1(Cn2ncc3ncc(Nc4cc(OC(F)F)[nH]n4)nc32)CC1] Amine-1; RCl: 6-chloro-1-((1-methylcyclopropyl)methyl)-1H-pyrazolo[3,4-b]pyrazine (Preparation 149); tBuXphos Pd G3 Prep-HPLC-1; Yellow solid (10.4 mg, 4%); LCMS m/z = 336 [M + H]$^+$; $^1$H NMR (400 MHz, DMSO-d$_6$) δ: 12.50-11.95 (br s, 1H), 10.95-10.55 (br s, 1H), 8.19 (s, 1H), 8.14 (s, 1H), 7.30 (t, J = 73.6 Hz, 1H), 6.02 (br s, 1H), 4.35 (s, 2H), 0.97 (s, 3H), 0.72-0.70 (m, 2H), 0.33-0.30 (m, 2H). |
| 99 | 1-((8-oxabicyclo[3.2.1]octan-3-yl)methyl)-N-(5-(difluoromethoxy)-1H-pyrazol-3-yl)-1H-pyrazolo[3,4-b]pyrazin-6-amine 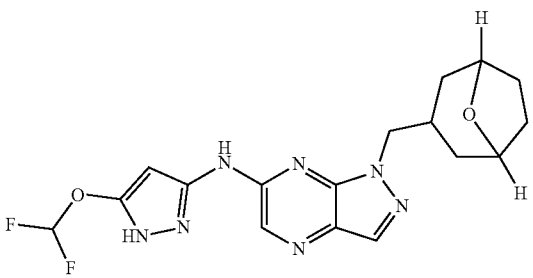 [SMILES: FC(F)Oc1cc(Nc2cnc3cnn(CC4CC5CCC(C4)O5)c3n2)n[nH]1] Amine-1; RCl: 1-((-8-oxabicyclo[3.2.1]octan-3-yl)methyl)-6-chloro-1H-pyrazolo[3,4-b]pyrazine (Preparation 126); BrettPhos Pd G4 Prep-HPLC-5; Yellow solid (113 mg, 26%); LCMS m/z = 392 [M + H]$^+$; $^1$H NMR (400 MHz, DMSO-d$_6$) δ: 12.13 (br s, 1H), 10.52 (s, 1H), 8.53 (s, 1H), 8.20 (s, 1H), 7.29 (t, 1H), 6.02 (s, 1H), 4.27-4.25 (m, 2H), 4.16-4.13 (m, 2H), 1.79-1.75 (m, 2H), 1.66-1.61 (m, 2H), 1.44-1.30 (m, 5H). |
| 100 | N-(5-(difluoromethoxy)-1H-pyrazol-3-yl)-1-isobutyl-1H-pyrazolo[3,4-b]pyrazin-6-amine 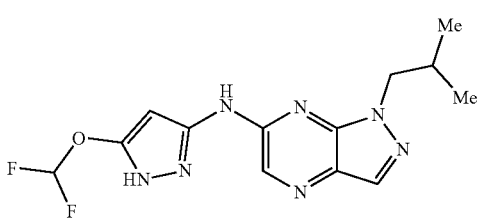 [SMILES: CC(C)Cn1ncc2ncc(Nc3cc(OC(F)F)[nH]n3)nc21] Amine-1; RCl: 6-chloro-1-isobutyl-1H-pyrazolo[3,4-b]pyrazine (Preparation 150); tBuXphos Pd G3 prep-HPLC-3; Yellow solid (131.5 mg, 43%); LCMS m/z = 324 [M + H]$^+$; $^1$H NMR (400 MHz, DMSO-d$_6$) δ: 12.19 (s, 1H), 10.78 (s, 1H), 8.20 (s, 1H), 8.15 (s, 1H), 7.31 (t, 1H), 6.02 (s, 1H), 4.29 (d, 2H), 2.28-2.23 (m, 1H), 0.87 (d, 6H). |

-continued

| Example No. | Name/Structure/Amine/RCl/Catalyst/Data |
|---|---|
| 101 | 1-(cyclobutylmethyl)-N-(5-(difluoromethoxy)-1H-pyrazol-3-yl)-1H-pyrazolo[3,4-b]pyrazin-6-amine 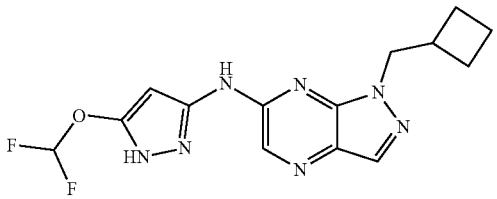 [SMILES: FC(F)Oc1cc(Nc2cnc3cnn(CC4CCC4)c3n2)n[nH]1] Amine-1; RCl: 6-chloro-1-(cyclobutylmethyl)-1H-pyrazolo[3,4-b]pyrazine (Preparation 151); tBuXphos Pd G3 prep-HPLC-3; Yellow solid (99.5 mg, 33%); LCMS m/z = 336 [M + H]⁺; ¹H NMR (400 MHz, DMSO-d₆) δ: 12.21 (s, 1H), 10.77 (s, 1H), 8.19 (s, 1H), 8.13 (s, 1H), 7.31 (t, 1H), 6.00 (s, 1H), 4.48-4.50 (d, 2H), 2.88-2.82 (m, 1H), 1.98-1.92 (m, 2H), 1.83-1.80 (m, 4H). |
| 102 | (S)-1-(cyclopropyl(pyridin-2-yl)methyl)-N-(5-(difluoromethoxy)-1H-pyrazol-3-yl)-1H-pyrazolo[3,4-b]pyrazin-6-amine 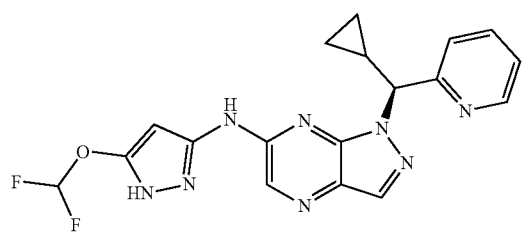 [SMILES: FC(F)Oc1cc(Nc2cnc3cnn([C@H](c4ccccn4)C4CC4)c3n2)n[nH]1] Amine-1; RCl: (S)-6-chloro-1-(cyclopropyl(pyridin-2-yl)methyl)-1H-pyrazolo[3,4-b]pyrazine (Preparation 142); tBuXPhos, Pd₂(dba)₃ Prep-HPLC-1; White solid (5.5 mg, 8%); LCMS m/z = 399 [M + H]⁺; ¹H NMR (400 MHz, DMSO-d₆) δ: 12.35 (br s, 1H), 10.84 (br s, 1H), 8.52 (d, 1H), 8.19 (s, 1H), 8.17 (s, 1H), 7.80 (td, 1H), 7.56 (d, 1H), 7.30 (t, 1H), 7.31-7.28 (m, 1H), 5.83 (s, 1H), 5.53-5.49 (m, 1H), 2.13-2.05 (m, 1H), 0.79-0.72 (m, 1H), 0.67-0.63 (m, 1H), 0.58-0.52 (m, 1H), 0.48-0.42 (m, 1H). |
| 103 | (S)-N-(5-(difluoromethoxy)-1H-pyrazol-3-yl)-1-((tetrahydro-2H-pyran-2-yl)methyl)-1H-pyrazolo[3,4-b]pyrazin-6-amine 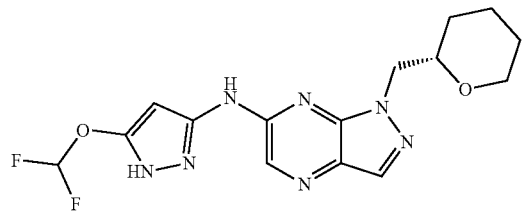 [SMILES: FC(F)Oc1cc(Nc2cnc3cnn(C[C@@H]4CCCCO4)c3n2)n[nH]1] Amine-1; RCl: (S)-6-chloro-1-((tetrahydro-2H-pyran-2-yl)methyl)-1H-pyrazolo[3,4-b]pyrazine (Preparation 116); BrettPhos Pd G4 SiO₂, 80% EtOAc/PE; White solid (66.1 mg, 45%); LCMS m/z = 366 [M + H]⁺; ¹H NMR (400 MHz, DMSO-d₆) δ: 12.24 (s, 1H), 10.78 (s, 1H), 8.19 (s, 1H), 8.15 (s, 1H), 7.30 (t, 1H), 5.95 (s, 1H), 4.55-4.36 (m, 2H), 3.84-3.77 (m, 2H), 3.30-3.25 (m, 1H), 1.77-1.73 (m, 1H), 1.55-1.52 (m, 1H), 1.43 (s, 3H), 1.29-1.23 (m, 1H). |

| Example No. | Name/Structure/Amine/RCl/Catalyst/Data |
|---|---|
| 104 | 1-(cyclopentylmethyl)-N-(5-(difluoromethoxy)-1H-pyrazol-3-yl)-1H-pyrazolo[3,4-b]pyrazin-6-amine 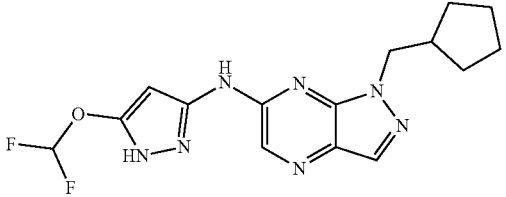 [SMILES: FC(F)Oc1cc(Nc2cnc3cnn(CC4CCCC4)c3n2)n[nH]1] Amine-1; RCl: 6-chloro-1-(cyclopentylmethyl)-1H-pyrazolo[3,4-b]pyrazine (Preparation 152); tBuXphos Pd G3 prep-HPLC-3; Yellow solid (39.2 mg, 27%); LCMS m/z = 350 [M + H]$^+$; $^1$H NMR (400 MHz, DMSO-d$_6$) δ: 12.18 (s, 1H), 10.76 (s, 1H), 8.20 (s, 1H), 8.13 (s, 1H), 7.29 (t, 1H), 6.02 (s, 1H), 4.37 (d, 2H), 1.61-1.48 (m, 7H), 1.34-1.29 (m, 2H). |
| 105 | 1-(cyclohexylmethyl)-N-(5-(difluoromethoxy)-1H-pyrazol-3-yl)-1H-pyrazolo[3,4-b]pyrazin-6-amine 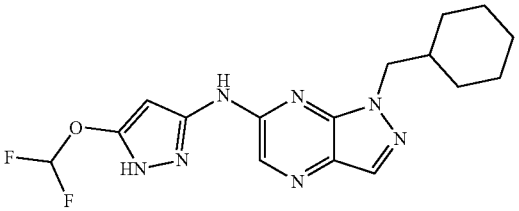 Amine-1; RCl: 6-chloro-1-(cyclohexylmethyl)-1H-pyrazolo[3,4-b]pyrazine (Preparation 153); tBuXPhos, Pd$_2$(dba)$_3$ prep-HPLC-3; White solid (37.6 mg, 26%); LCMS m/z = 364 [M + H]$^+$; $^1$H NMR (400 MHz, DMSO-d$_6$) δ: 12.26 (br s, 1H), 10.86 (br s, 1H), 8.19 (s, 1H), 8.13 (s, 1H), 7.29 (t, 1H), 6.05 (s, 1H), 4.29 (d, 2H), 1.96-1.90 (m, 1H), 1.65-1.50 (m, 5H), 1.20-0.98 (m, 5H). |
| 106 | 1-(bicyclo[1.1.1]pentan-1-ylmethyl)-N-(5-(difluoromethoxy)-1H-pyrazol-3-yl)-1H-pyrazolo[3,4-b]pyrazin-6-amine 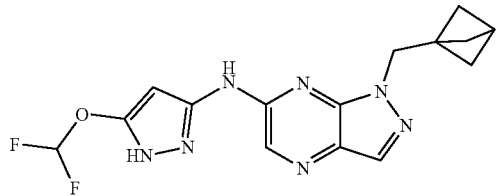 [SMILES: FC(F)Oc1cc(Nc2cnc3cnn(CC45CC(C4)C5)c3n2)n[nH]1] Amine-1; RCl: 1-(bicyclo[1.1.1]pentan-1-ylmethyl)-6-chloro-1H-pyrazolo[3,4-b]pyrazine (Preparation 154); BrettPhos Pd G4 Prep-HPLC-1; White solid (33.7 mg, 12%); LCMS m/z = 348 [M + H]$^+$; $^1$H NMR (400 MHz, DMSO-d$_6$) δ: 12.15 (br s, 1H), 10.76 (s, 1H), 8.19 (s, 1H), 8.13 (s, 1H), 7.30 (t, 1H), 6.01 (s, 1H), 4.53 (s, 2H), 2.02-1.97 (m, 1H), 1.64 (s, 6H). |

| Example No. | Name/Structure/Amine/RCl/Catalyst/Data |
|---|---|
| 107 | (R)-N-(5-(difluoromethoxy)-1H-pyrazol-3-yl)-1-((tetrahydro-2H-pyran-2-yl)methyl)-1H-pyrazolo[3,4-b]pyrazin-6-amine<br><br>Amine-1; RCl: (R)-6-chloro-1-((tetrahydro-2H-pyran-2-yl)methyl)-1H-pyrazolo[3,4-b]pyrazine (Preparation 117); tBuXphos Pd G3 prep-HPLC-3; White solid (45 mg, 16%); LCMS m/z = 366 [M + H]$^+$; $^1$H NMR (400 MHz, DMSO-d$_6$) δ: 12.24 (br s, 1H), 10.77 (s, 1H), 8.19 (s, 1H), 8.15 (s, 1H), 7.30 (t, 1H), 5.95 (s, 1H), 4.57-4.54 (m, 1H), 4.40-4.38 (m, 1H), 1.77-1.76 (m, 1H), 3.83-3.81 (m, 2H), 1.77-1.76 (m, 1H), 1.55-1.52 (m, 1H), 1.40-1.38 (m, 3H), 1.29-1.27 (m, 1H). |
| 108 | 1-((4,4-difluorocyclohexyl)methyl)-N-(5-(difluoromethoxy)-1H-pyrazol-3-yl)-1H-pyrazolo[3,4-b]pyrazin-6-amine<br><br>Amine-1; RCl: 6-chloro-1-((4,4-difluorocyclohexyl)methyl)-1H-pyrazolo[3,4-b]pyrazine (Preparation 157); tBuXPhos, Pd$_2$(dba)$_3$ Prep-HPLC-1; White solid (59 mg, 35%); LCMS m/z = 400 [M + H]$^+$; $^1$H NMR (400 MHz, DMSO-d$_6$) δ: 12.19 (br s, 1H), 10.81 (br s, 1H), 8.20 (s, 1H), 8.17 (s, 1H), 7.30 (t, 1H), 5.96 (s, 1H), 4.43 (d, 2H), 2.15-2.05 (m, 1H), 2.05-1.93 (m, 2H), 1.83-1.68 (m, 2H), 1.68-1.60 (m, 2H), 1.37-1.28 (m, 2H). |
| 109 | (R)-N-(5-(difluoromethoxy)-1H-pyrazol-3-yl)-1-(spiro[2.2]pentan-1-ylmethyl)-1H-pyrazolo[3,4-b]pyrazin-6-amine and (S)-N-(5-(difluoromethoxy)-1H-pyrazol-3-yl)-1-(spiro[2.2]pentan-1-ylmethyl)-1H-pyrazolo[3,4-b]pyrazin-6-amine<br><br>and<br><br>Amine-1; RCl: 6-chloro-1-(spiro[2.2]pentan-1-ylmethyl)-1H-pyrazolo[3,4-b]pyrazine (Preparation 156); tBuXPhos, Pd$_2$(dba)$_3$ Prep-HPLC-1; White solid (116.4 mg, 16%); LCMS m/z = 348 [M + H]$^+$; $^1$H NMR (400 MHz, DMSO-d$_6$) δ: 12.22 (br s, 1H), 10.74 (br s, 1H), 8.20 |

| Example No. | Name/Structure/Amine/RCl/Catalyst/Data |
|---|---|
| | (s, 1H), 8.14 (s, 1H), 7.29 (t, 1H), 6.00 (s, 1H), 4.50-4.38 (m, 2H), 1.68-1.61 (m, 1H), 1.05-0.97 (m, 1H), 0.95-0.85 (m, 2H), 0.80-0.70 (m, 3H). |
| 110 | N-(5-(difluoromethoxy)-1H-pyrazol-3-yl)-1-((4-methyltetrahydro-2H-pyran-4-yl)methyl)-1H-pyrazolo[3,4-b]pyrazin-6-amine<br>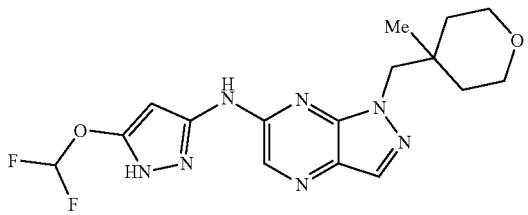 [SMILES: CC1(Cn2ncc3ncc(Nc4cc(OC(F)F)[nH]n4)nc32)CCOCC1]<br>Amine-1; RCl: 6-chloro-1-((4-methyltetrahydro-2H-pyran-4-yl)methyl)-1H-pyrazolo[3,4-b]pyrazine (Preparation 120); tBuXphos Pd G3 Prep-HPLC-1; White solid (37 mg, 13%); LCMS m/z = 380 [M + H]$^+$; $^1$H NMR (400 MHz, DMSO-d$_6$) δ: 12.45-11.95 (br s, 1H), 10.90-10.60 (br s, 1H), 8.21 (s, 1H), 8.16 (s, 1H), 7.30 (t, 1H), 6.06 (s, 1H), 4.39 (s, 2H), 3.71-3.67 (m, 2H), 3.55-3.49 (m, 2H), 1.60-1.57 (m, 2H), 1.57-1.29 (m, 2H), 0.99 (s, 3H). |
| 111 | 1-(((1R,5S,6r)-3-oxabicyclo[3.1.0]hexan-6-yl)methyl)-N-(5-(difluoromethoxy)-1H-pyrazol-3-yl)-1H-pyrazolo[3,4-b]pyrazin-6-amine<br>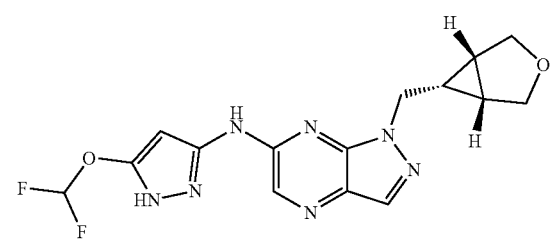 [SMILES: FC(F)Oc1cc(Nc2cnc3cnn(C[C@@H]4[C@@H]5COC[C@@H]54)c3n2)n[nH]1]<br>Amine-1; RCl: 1-(((1R,5S,6r)-3-oxabicyclo[3.1.0]hexan-6-yl)methyl)-6-chloro-1H-pyrazolo[3,4-b]pyrazine (Preparation 110); BrettPhos Pd G4 Prep-HPLC-1; White solid (131 mg, 32%); LCMS m/z = 364 [M + H]$^+$; $^1$H NMR (400 MHz, DMSO-d$_6$) δ: 12.22 (s, 1H), 10.76 (s, 1H), 8.19 (s, 1H), 8.15 (s, 1H), 7.31 (t, 1H), 5.94-5.92 (m, 1H), 4.43 (d, 2H), 3.65 (d, 2H), 3.52 (d, 2H), 1.77 (s, 2H), 1.24-1.14 (m, 1H). |
| 112 | N-(5-(difluoromethoxy)-1H-pyrazol-3-yl)-1-((4-fluorotetrahydro-2H-pyran-4-yl)methyl)-1H-pyrazolo[3,4-b]pyrazin-6-amine<br>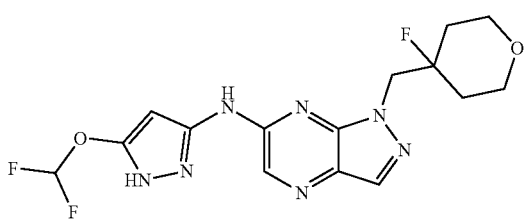 [SMILES: FC(F)Oc1cc(Nc2cnc3cnn(CC4(F)CCOCC4)c3n2)n[nH]1]<br>Amine-1; RCl: 6-chloro-1-((4-fluorotetrahydro-2H-pyran-4-yl)methyl)-1H-pyrazolo[3,4-b]pyrazine (Preparation 121); tBuXphos Pd G3 Prep-HPLC-1; White solid (38 mg, 18%); LCMS m/z = 384 [M + H]$^+$; $^1$H NMR (400 MHz, DMSO-d$_6$) δ: 12.20 (s, 1H), 10.86 (s, 1H), 8.21 (s, 1H), 8.20 (s, 1H), 7.31 (t, 1H), 5.93 (s, 1H), 4.79 (d, 2H), 3.77-3.72 (m, 2H), 3.52-3.47 (m, 2H), 1.91-1.79 (m, 2H), 1.64-1.58 (m, 2H). |

| Example No. | Name/Structure/Amine/RCl/Catalyst/Data |
|---|---|
| 113 | (R)-N-(5-(difluoromethoxy)-1H-pyrazol-3-yl)-1-((tetrahydrofuran-2-yl)methyl)-1H-pyrazolo[3,4-b]pyrazin-6-amine<br><br>Amine-1; RCl: (R)-6-chloro-1-((tetrahydrofuran-2-yl)methyl)-1H-pyrazolo[3,4-b]pyrazine (Preparation 103); BrettPhos Pd G4 Prep-HPLC-4; Yellow solid (66.9 mg, 22%); LCMS m/z = 352 [M + H]$^+$; $^1$H NMR (400 MHz, DMSO-d$_6$) δ: 12.47 (br s, 1H), 12.19 (s, 1H), 10.73 (s, 1H), 8.17 (s, 1H), 8.15 (s, 1H), 7.49-7.15 (m, 2H), 7.31 (t, 1H), 5.95 (s, 1H), 4.57-4.29 (m, 3H), 3.78-3.59 (m, 2H) ), 1.84-1.72 (m, 4H). |
| 114 | N-(5-(difluoromethoxy)-1H-pyrazol-3-yl)-1-(((1S,2S)-2-fluorocyclopropyl)methyl)-1H-pyrazolo[3,4-b]pyrazin-6-amine and N-(5-(difluoromethoxy)-1H-pyrazol-3-yl)-1-(((1R,2R)-2-fluorocyclopropyl)methyl)-1H-pyrazolo[3,4-b]pyrazin-6-amine<br><br>Amine-1; RCl: rac-cis-6-chloro-1-((-2-fluorocyclopropyl)methyl)-1H-pyrazolo[3,4-b]pyrazine (Preparation 159); BrettPhos Pd G3 prep-HPLC-3; Yellow solid (70.3 mg, 31%); LCMS m/z = 340 [M + H]$^+$; $^1$H NMR (400 MHz, DMSO-d$_6$) δ: 12.21 (s, 1H), 10.81 (s, 1H), 8.20 (s, 1H), 8.17 (s, 1H), 7.29 (t, 1H), 5.97 (s, 1H), 4.94-4.77 (m, 1H), 4.59-4.56 (m, 2H), 1.49-1.46 (m, 1H), 0.95-0.85 (m, 2H). |
| 115 | 4-((6-((5-(difluoromethoxy)-1H-pyrazol-3-yl)amino)-1H-pyrazolo[3,4-b]pyrazin-1-yl)methyl)tetrahydro-2H-pyran-4-carbonitrile<br><br>Amine-1; RCl: 4-((6-chloro-1H-pyrazolo[3,4-b]pyrazin-1-yl)methyl)tetrahydro-2H-pyran-4-carbonitrile (Preparation 122); BrettPhos Pd G3 |

| Example No. | Name/Structure/Amine/RCl/Catalyst/Data |
|---|---|
| | Prep-HPLC-4; Yellow solid (68 mg, 24%); LCMS m/z = 391 [M + H]⁺; ¹H NMR (400 MHz, DMSO-d₆) δ: 12.25 (s, 1H), 10.93 (s, 1H), 8.26 (s, 1H), 8.20 (s, 1H), 7.32 (t, 1H), 5.87 (s, 1H), 4.87 (s, 2H), 3.90 (d, 2H), 3.48-3.41 (m, 2H), 1.85-1.82 (m, 4H). |
| 116 | N-(5-(difluoromethoxy)-1H-pyrazol-3-yl)-1-((3-fluorobicyclo[1.1.1]pentan-1-yl)methyl)-1H-pyrazolo[3,4-b]pyrazin-6-amine 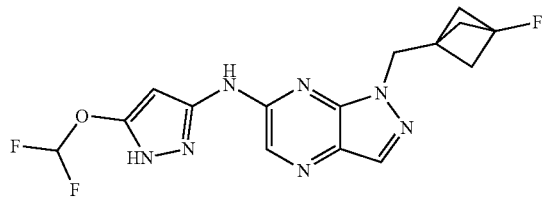 [SMILES: FC(F)Oc1cc(Nc2cnc3cnn(CC45CC(F)(C4)C5)c3n2)n[nH]1] Amine-1; RCl: 6-chloro-1-((3-fluorobicyclo[1.1.1]pentan-1-yl)methyl)-1H-pyrazolo[3,4-b]pyrazine (Preparation 155); BrettPhos Pd G4 Prep-HPLC-1; Yellow solid (6.2 mg, 4%); LCMS m/z = 366 [M + H]⁺; ¹H NMR (400 MHz, DMSO-d₆) δ: 12.18 (br s, 1H), 10.80 (s, 1H), 8.20 (s, 1H), 8.16 (s, 1H), 7.31 (t, 1H), 5.95 (s, 1H), 4.84 (s, 2H), 1.93 (s, 6H). |
| 117 | N-(5-(difluoromethoxy)-1H-pyrazol-3-yl)-3-fluoro-1-((tetrahydro-2H-pyran-4-yl)methyl)-1H-pyrazolo[3,4-b]pyrazin-6-amine 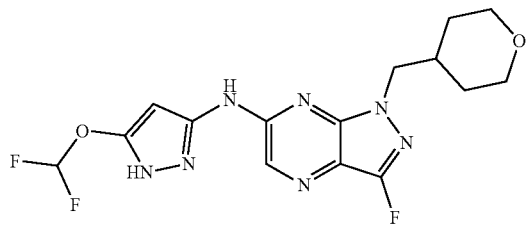 Amine-1; RCl: 6-chloro-3-fluoro-1-((tetrahydro-2H-pyran-4-yl)methyl)-1H-pyrazolo[3,4-b]pyrazine (Preparation 180); BrettPhos Pd G4 Prep-HPLC-1; White solid (39.3 mg, 31%); LCMS m/z = 384 [M + H]⁺; ¹H NMR (400 MHz, DMSO-d₆) δ: 12.50-12.10 (br, 1H), 11.15-10.82 (br s, 1H), 8.19 (s, 1H), 7.30 (t, 1H), 6.01 (s, 1H), 4.26 (d, 2H), 3.83-3.79 (m, 2H), 3.25-3.20 (m, 2H), 2.12-2.09 (m, 1H), 1.42-1.29 (m, 4H). |
| 118 | 1-((2-oxabicyclo[2.2.2]octan-4-yl)methyl)-N-(5-(difluoromethoxy)-1H-pyrazol-3-yl)-1H-pyrazolo[3,4-b]pyrazin-6-amine 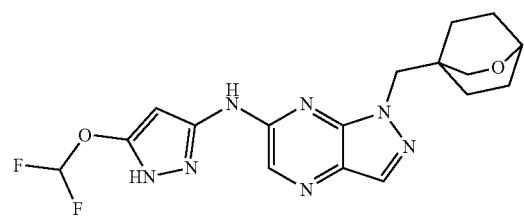 [SMILES: FC(F)Oc1cc(Nc2cnc3cnn(CC45CCC(CC4)OC5)c3n2)n[nH]1] Amine-1; RCl: 1-((2-oxabicyclo[2.2.2]octan-4-yl)methyl)-6-chloro-1H-pyrazolo[3,4-b]pyrazine (Preparation 127); BrettPhos Pd G3 Prep-HPLC-4; White solid (100 mg, 47%); LCMS m/z = 392 [M + H]⁺; ¹H NMR (400 MHz, DMSO-d₆) δ: 12.50-11.90 (br, 1H), 11.10-10.60 (br, 1H), 8.20 (s, 1H), 8.15 (s, 1H), 7.32 (t, 1H), 6.03 (s, 1H), 4.25 (s, 2H), 3.64 (s, 2H), 3.65-3.61 (m, 1H), 1.81-1.78 (m, 2H), 1.55-1.48 (m, 6H). |

| Example No. | Name/Structure/Amine/RCl/Catalyst/Data |
|---|---|
| 119 | N-(5-(difluoromethoxy)-1H-pyrazol-3-yl)-1-((3-methyloxetan-3-yl)methyl)-1H-pyrazolo[3,4-b]pyrazin-6-amine 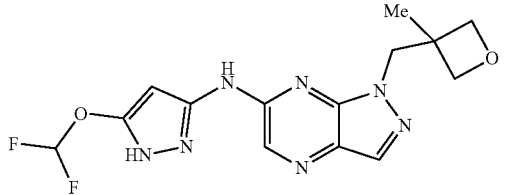 [SMILES: CC1(Cn2ncc3ncc(Nc4cc(OC(F)F)[nH]n4)nc32)COC1] Amine-1; RCl: 6-chloro-1-((3-methyloxetan-3-yl)methyl)-1H-pyrazolo[3,4-b]pyrazine (Preparation 115); BrettPhos Pd G4 Prep-HPLC-1; Yellow solid (91.7 mg, 41%); LCMS m/z = 352 [M + H]$^+$; $^1$H NMR (400 MHz, DMSO-d$_6$) δ: 12.40-12.10 (br, 1H), 10.90-10.70 (br, 1H), 8.21, (s, 1H), 8.18, (s, 1H), 7.30 (t, 1H), 5.94 (br s, 1H), 4.75-4.70 (m, 4H), 4.29-4.25 (m, 2H), 1.13 (s, 3H). |
| 120 | N-(5-(difluoromethoxy)-1H-pyrazol-3-yl)-3-fluoro-1-(pyridin-3-ylmethyl)-1H-pyrazolo[3,4-b]pyrazin-6-amine 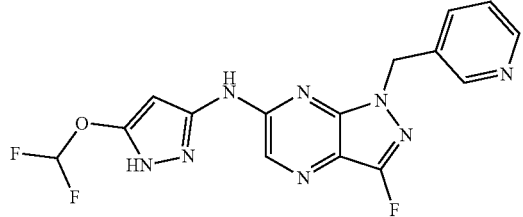 Amine-1; RCl: 6-chloro-3-fluoro-1-(pyridin-3-ylmethyl)-1H-pyrazolo[3,4-b]pyrazine (Preparation 182); BrettPhos Pd G4 Prep-HPLC-1; White solid (34.2 mg, 40%); LCMS m/z = 377 [M + H]$^+$; $^1$H NMR (400 MHz, DMSO-d$_6$) δ: 12.36 (br s, 1H), 11.11 (br s, 1H), 8.56 (d, 1H), 8.49 (dd, 1H), 8.23 (s, 1H), 7.66 (d, 1H), 7.35 (dd, 1H), 7.31 (t, 1H), 5.93 (s, 1H), 5.70 (s, 2H). |
| 121 | N-(5-(difluoromethoxy)-1H-pyrazol-3-yl)-1-((4-(trifluoromethyl)tetrahydro-2H-pyran-4-yl)methyl)-1H-pyrazolo[3,4-b]pyrazin-6-amine 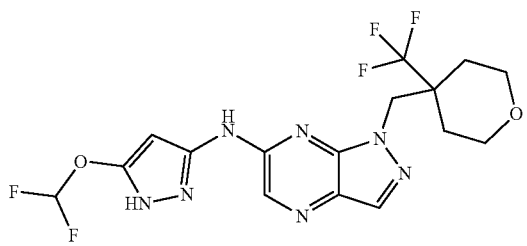 [SMILES: FC(F)Oc1cc(Nc2cnc3cnn(CC4(C(F)(F)F)CCOCC4)c3n2)n[nH]1] Amine-1; RCl: 6-chloro-1-((4-(trifluoromethyl)tetrahydro-2H-pyran-4-yl)methyl)-1H-pyrazolo[3,4-b]pyrazine (Preparation 123); BrettPhos Pd G3 Prep-HPLC-1; White solid (22.5 mg, 27%); LCMS m/z = 434 [M + H]$^+$; $^1$H NMR (400 MHz, DMSO-d$_6$) δ: 12.35-11.85 (br, 1H), 11.03-10.65 (br s, 1H), 8.23 (s, 1H), 8.22 (s, 1H), 7.29 (t, 1H), 6.08-6.00 (m, 1H), 4.94 (s, 2H), 3.91-3.80 (m, 4H), 1.83-1.80 (m, 4H). |

| Example No. | Name/Structure/Amine/RCl/Catalyst/Data |
|---|---|
| 122 | N-(5-(difluoromethoxy)-1H-pyrazol-3-yl)-1-((4-(difluoromethyl)tetrahydro-2H-pyran-4-yl)methyl)-1H-pyrazolo[3,4-b]pyrazin-6-amine 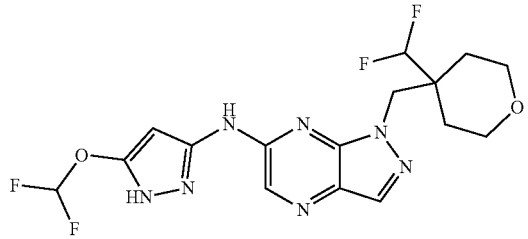 [SMILES: FC(F)Oc1cc(Nc2cnc3cnn(CC4(C(F)F)CCOCC4)c3n2)n[nH]1] Amine-1; RCl: 6-chloro-1-((4-(difluoromethyl)tetrahydro-2H-pyran-4-yl)methyl)-1H-pyrazolo[3,4-b]pyrazine (Preparation 124); BrettPhos Pd G3<br>Prep-HPLC-5; White solid (73 mg, 27%); LCMS m/z = 416 [M + H]$^+$; $^1$H NMR (400 MHz, DMSO-d$_6$) δ: 12.35-11.95 (br s, 1H), 11.03-10.65 (br s, 1H), 8.23 (s, 1H), 8.22 (s, 1H), 7.30 (t, 1H), 6.09 (t, 1H), 6.08-6.00 (m, 1H), 4.73 (s, 2H), 3.81-3.70 (m, 4H), 1.70-1.50 (m, 2H), 1.47-1.38 (m, 2H). |
| 123 | (S)-3-fluoro-N-(5-methoxy-1H-pyrazol-3-yl)-1-(1-(tetrahydro-2H-pyran-4-yl)ethyl)-1H-pyrazolo[3,4-b]pyrazin-6-amine 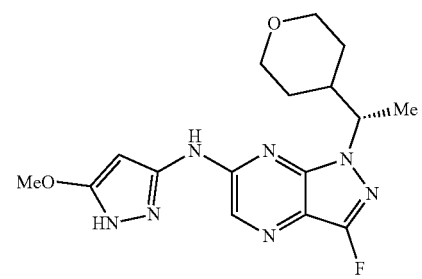 [SMILES: COc1cc(Nc2cnc3c(F)nn([C@@H](C)C4CCOCC4)c3n2)n[nH]1] Amine-3; RCl: (S)-6-chloro-3-fluoro-1-(1-(tetrahydro-2H-pyran-4-yl)ethyl)-1H-pyrazolo[3,4-b]pyrazine (Preparation 181); BrettPhos Pd G4<br>Prep-HPLC-5; Yellow solid (50.7 mg, 20%); LCMS m/z = 362 [M + H]$^+$; $^1$H NMR (400 MHz, DMSO-d$_6$) δ: 11.90-11.65 (br, 1H), 10.80-10.50 (br, 1H), 8.18 (s, 1H), 5.80-5.60 (br, 1H), 4.75 (br s, 1H), 3.90-3.81 (m, 1H), 3.81 (s, 3H), 3.76-3.71 (m, 1H), 3.30-3.20 (m, 1H), 3.15-3.11 (m, 1H), 2.00-1.96 (m, 1H), 1.71-1.66 (m, 1H), 1.42 (d, 3H), 1.40-1.25 (m, 1H), 1.25-1.11 (m, 1H), 0.93-0.85 (m, 1H). |
| 124 | (S)-N-(5-(difluoromethoxy)-1H-pyrazol-3-yl)-3-fluoro-1-(1-(tetrahydro-2H-pyran-4-yl)ethyl)-1H-pyrazolo[3,4-b]pyrazin-6-amine 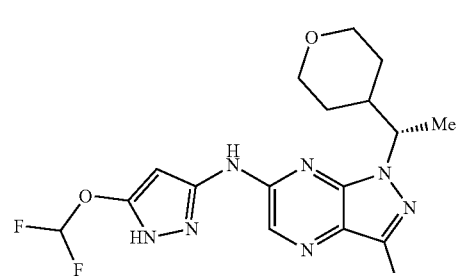 Amine-1; RCl: (S)-6-chloro-3-fluoro-1-(1-(tetrahydro-2H-pyran-4-yl)ethyl)-1H-pyrazolo[3,4-b]pyrazine (Preparation 181); BrettPhos Pd G4<br>Prep-HPLC-1; White solid (107 mg, 38%); LCMS m/z = 398 [M + H]$^+$; $^1$H NMR (400 MHz, DMSO-d$_6$) δ: 12.35-12.10 (br, 1H), 11.05-10.75 (br, 1H), 8.14 (s, 1H), 7.24 (t, 1H), 5.91 (s, 1H), 4.90-4.80 (m, 1H), 3.85-3.80 (m, 1H), 3.65-3.60 (m, 1H), 3.35-3.20 (m, 1H), 3.15-3.01 (m, 1H), 1.98-1.86 (m, 1H), 1.71-1.66 (m, 1H), 1.35 (d, 3H), 1.40-1.20 (m, 1H), 1.15-1.07 (m, 1H), 0.90-0.80 (m, 1H). |

| Example No. | Name/Structure/Amine/RCl/Catalyst/Data |
|---|---|
| 125 | 1-((6-((5-(difluoromethoxy)-1H-pyrazol-3-yl)amino)-1H-pyrazolo[3,4-b]pyrazin-1-yl)methyl)cyclobutan-1-ol 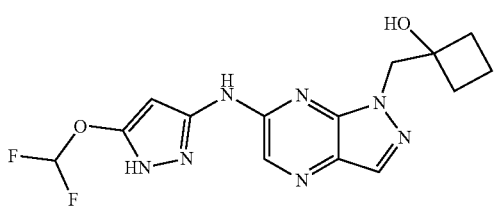 [SMILES: OC1(Cn2ncc3ncc(Nc4cc(OC(F)F)[nH]n4)nc32)CCC1] Amine-1; RCl: 1-((6-chloro-1H-pyrazolo[3,4-b]pyrazin-1-yl)methyl)cyclobutan-1-ol (Preparation 163); BrettPhos Pd G3 Prep-HPLC-4; White solid (73 mg, 27%); LCMS m/z = 352 [M + H]$^+$; $^1$H NMR (400 MHz, DMSO-d$_6$) δ: 12.21 (s, 1H), 10.82 (s, 1H), 8.19 (s, 1H), 8.16 (s, 1H), 7.30 (t, 1H), 5.89 (s, 1H), 5.33 (s, 1H), 4.51 (s, 2H), 2.29-2.22 (m, 2H), 2.00-1.92 (m, 2H), 1.65-1.63 (m, 1H), 1.47-1.45 (m, 1H). |
| 126 | 1-(((1R,3r,5S)-6,6-difluorobicyclo[3.1.0]hexan-3-yl)methyl)-N-(5-(difluoromethoxy)-1H-pyrazol-3-yl)-1H-pyrazolo[3,4-b]pyrazin-6-amine 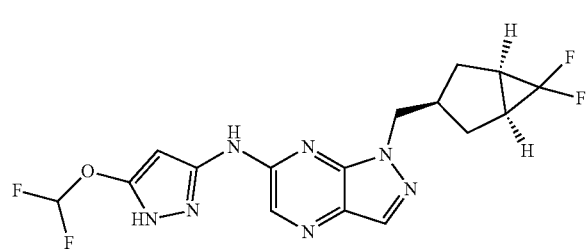 [SMILES: FC(F)Oc1cc(Nc2cnc3cnn(C[C@H]4C[C@@H]5[C@H](C4)C5(F)F)c3n2)n[nH]1] Amine-1; RCl: 6-chloro-1-((6,6-difluorobicyclo[3.1.0]hexan-3-yl)methyl)-1H-pyrazolo[3,4-b]pyrazine (Preparation 162); BrettPhos Pd G4 Prep-SFC (Daicel OJ, 20 x 250 mm, 10 mm; 30% MeOH (0.2% MeOH/NH$_3$) in CO$_2$); White solid (9.4 mg); LCMS m/z = 398 [M + H]$^+$; $^1$H NMR (400 MHz, DMSO-d$_6$) δ: 11.80-11.30 (br, 1H), 8.11 (s, 1H), 8.05 (s, 1H), 7.26 (t, 1H), 6.05 (s, 1H), 4.31 (d, 2H), 3.05-2.98 (m, 1H), 2.21-2.10 (m, 4H), 1.60-1.55 (m, 2H), 1.30-1.20 (m, 1H). |
| 127 | N-(5-(difluoromethoxy)-1H-pyrazol-3-yl)-1-(2-(tetrahydro-2H-pyran-4-yl)propan-2-yl)-1H-pyrazolo[3,4-b]pyrazin-6-amine 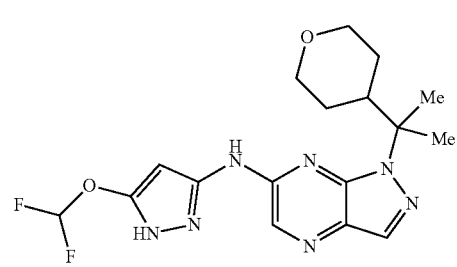 [SMILES: CC(C)(C1CCOCC1)n1ncc2ncc(Nc3cc(OC(F)F)[nH]n3)nc21] Amine-1; RCl: 6-chloro-1-(2-(tetrahydro-2H-pyran-4-yl)propan-2-yl)-1H-pyrazolo[3,4-b]pyrazine (Preparation 186); BrettPhos Pd G4 Prep-HPLC-1; White solid (34.9 mg, 35%); LCMS m/z = 394 [M + H]$^+$; $^1$H NMR (400 MHz, DMSO-d$_6$) δ: 12.05 (br s, 1H), 10.53 (br s, 1H), 8.22 (s, 1H), 8.10 (s, 1H), 7.25 (t, 1H), 6.29 (s, 1H), 3.83-3.80 (m, 2H), 3.14-3.11 (m, 2H), 2.66-2.58 (m, 1H), 1.72 (s, 6H), 1.37-1.27 (m, 2H), 1.13-1.08 (m, 2H). |

| Example No. | Name/Structure/Amine/RCl/Catalyst/Data |
|---|---|
| 128 | 1-((1H-indazol-4-yl)methyl)-N-(5-(difluoromethoxy)-1H-pyrazol-3-yl)-1H-pyrazolo[3,4-b]pyrazin-6-amine 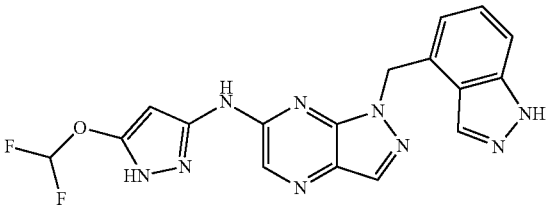 [SMILES: FC(F)Oc1cc(Nc2cnc3cnn(Cc4cccc5[nH]ncc45)c3n2)n[nH]1] Amine-1; RCl: 1-((1H-indazol-4-yl)methyl)-6-chloro-1H-pyrazolo[3,4-b]pyrazine (Preparation 169); BrettPhos Pd G4 Prep-HPLC-4; Yellow solid (50.1 mg, 24%); LCMS m/z = 398 [M + H]$^+$; $^1$H NMR (400 MHz, DMSO-d$_6$) δ: 13.13 (s, 1H), 12.29 (s, 1H), 10.88 (s, 1H), 8.22 (s, 1H), 8.19 (s, 1H), 7.95 (s, 1H), 7.49-7.44 (m, 2H), 7.32-7.28 (m, 2H), 6.99 (d, 1H), 6.05 (s, 2H), 5.94 (s, 1H). |
| 129 | 1-(2-(1H-pyrazol-4-yl)ethyl)-N-(5-(difluoromethoxy)-1H-pyrazol-3-yl)-1H-pyrazolo[3,4-b]pyrazin-6-amine 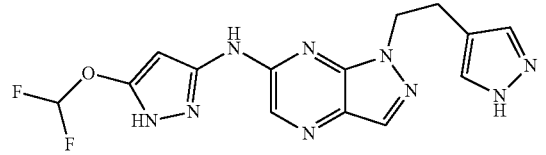 [SMILES: FC(F)Oc1cc(Nc2cnc3cnn(CCc4cn[nH]c4)c3n2)n[nH]1] Amine-1; RCl: 1-(2-(1H-pyrazol-4-yl)ethyl)-6-chloro-1H-pyrazolo[3,4-b]pyrazine (Preparation 170); BrettPhos Pd G4 Prep-HPLC-5; White solid (113 mg, 26%); LCMS m/z = 362 [M + H]$^+$; $^1$H NMR (400 MHz, DMSO-d$_6$) δ: 12.47 (br s, 1H), 12.19 (s, 1H), 10.73 (s, 1H), 8.15 (s, 1H), 8.17 (s, 1H), 7.49-7.15(m, 2H), 7.31 (t, 1H), 7.31 (s, 2H), 5.95 (s, 1H), 4.63 (t, 2H), 3.04 (t, 2H). |
| 130 | N-(5-(difluoromethoxy)-1H-pyrazol-3-yl)-1-(2-(pyridin-4-yl)ethyl)-1H-pyrazolo[3,4-b]pyrazin-6-amine 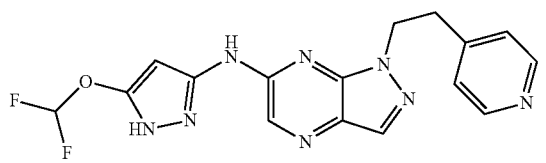 [SMILES: FC(F)Oc1cc(Nc2cnc3cnn(CCc4ccncc4)c3n2)n[nH]1] Amine-1; RCl: 6-chloro-1-(2-(pyridin-4-yl)ethyl)-1H-pyrazolo[3,4-b]pyrazine (Preparation 171); BrettPhos Pd G4 Prep-HPLC-1; Yellow solid (60 mg, 72%); LCMS m/z = 373 [M + H]$^+$; $^1$H NMR (400 MHz, DMSO-d$_6$) δ: 12.18 (s, 1H), 10.73 (s, 1H), 8.31 (d, 1H), 8.15 (s, 1H), 8.14 (s, 1H), 7.33 (t, 1H), 7.18-7.16 (m, 2H), 5.91 (s, 1H ), 4.79 (t, 2H), 3.20 (t, 2H). |
| 131 | N-(5-(difluoromethoxy)-1H-pyrazol-3-yl)-1-((1-methyl-1H-imidazol-5-yl)methyl)-1H-pyrazolo[3,4-b]pyrazin-6-amine 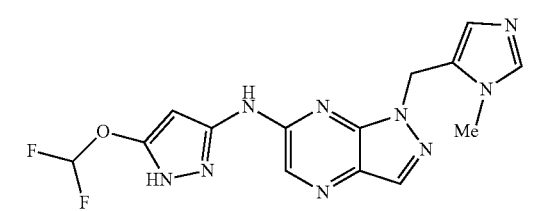 [SMILES: Cn1cncc1Cn1ncc2ncc(Nc3cc(OC(F)F)[nH]n3)nc21] Amine-1; RCl: 6-chloro-1-((1-methyl-1H-imidazol-5-yl)methyl)-1H-pyrazolo[3,4-b]pyrazine (Preparation 172); BrettPhos Pd G4 Prep-HPLC-1; White solid (6 mg, 2%); LCMS m/z = 362 [M + H]$^+$; $^1$H NMR (400 MHz, DMSO-d$_6$) δ: 12.35 (br s, 1H), 10.92 (br s, 1H), 8.21 (s, 1H), 8.16 (s, 1H), 7.70-7.50 (m, 1H), 7.34 (t, 1H), 7.10-6.85 (m, 1H), 5.94 (s, 1H), 5.78 (s, 2H), 3.58 (s, 3H). |

| Example No. | Name/Structure/Amine/RCl/Catalyst/Data |
|---|---|
| 132 | 2-(1-(((6-((5-(difluoromethoxy)-1H-pyrazol-3-yl)amino)-1H-pyrazolo[3,4-b]pyrazin-1-yl)methyl)cyclopropyl)acetonitrile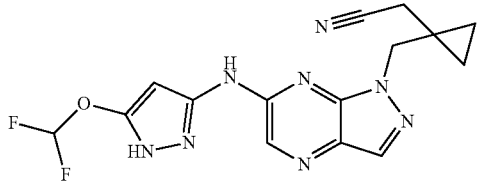 [SMILES: N#CCC1(Cn2ncc3ncc(Nc4cc(OC(F)F)[nH]n4)nc32)CC1]Amine-1; RCl: 2-(1-((6-chloro-1H-pyrazolo[3,4-b]pyrazin-1-yl)methyl)cyclopropyl)acetonitrile (Preparation 174); BrettPhos Pd G4 Prep-HPLC-1; White solid (52.6 mg, 51%); LCMS m/z = 361 [M + H]$^+$; $^1$H NMR (400 MHz, DMSO-d$_6$) δ: 10.80-10.25 (br, 1H), 8.20 (s, 1H), 8.19 (s, 1H), 7.30 (t, 1H), 6.01 (s, 1H), 4.51 (s, 2H), 2.58 (s, 2H), 0.90 (t, 2H), 0.60 (t, 2H). |
| 133 | N-(5-methoxy-1H-pyrazol-3-yl)-1-((3-methyloxetan-3-yl)methyl)-1H-pyrazolo[3,4-b]pyrazin-6-amine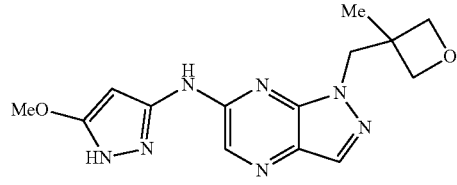 [SMILES: COc1cc(Nc2cnc3cnn(CC4(C)COC4)c3n2)n[nH]1]Amine-3; RCl: 6-chloro-1-((3-methyloxetan-3-yl)methyl)-1H-pyrazolo[3,4-b]pyrazine (Preparation 115); BrettPhos Pd G4 Prep-HPLC-1; White solid (213.7 mg, 34%); LCMS m/z = 316 [M + H]$^+$; $^1$H NMR (400 MHz, DMSO-d$_6$) δ: 11.90-11.20 (br, 1H), 10.45-9.90 (br, 1H), 8.20 (s, 1H), 8.12 (s, 1H), 5.80 (br s, 1H), 4.71 (d, 2H), 4.69 (s, 2H), 4.27 (d, 2H), 3.81 (s, 3H), 1.17 (s, 3H). |
| 134 | N-(5-(difluoromethoxy)-1H-pyrazol-3-yl)-1-(isoxazol-5-ylmethyl)-1H-pyrazolo[3,4-b]pyrazin-6-amine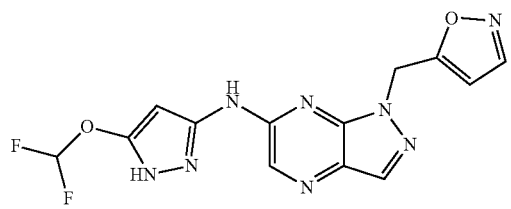 [SMILES: FC(F)Oc1cc(Nc2cnc3cnn(Cc4ccno4)c3n2)n[nH]1]Amine-1; RCl: 5-((6-chloro-1H-pyrazolo[3,4-b]pyrazin-1-yl)methyl)isoxazole (Preparation 173); BrettPhos Pd G4 prep-HPLC-3; Yellow solid (18.7 mg, 10%); LCMS m/z = 349 [M + H]$^+$; $^1$H NMR (400 MHz, DMSO-d$_6$) δ: 8.52 (s, 1H), 8.22 (s, 2H), 7.31 (t, 1H), 6.39 (s, 1H), 6.02 (s, 2H), 5.93 (s, 1H). |
| 135 | N-(5-methoxy-1H-pyrazol-3-yl)-1-(pyridin-3-ylmethyl)-1H-pyrazolo[3,4-b]pyrazin-6-amine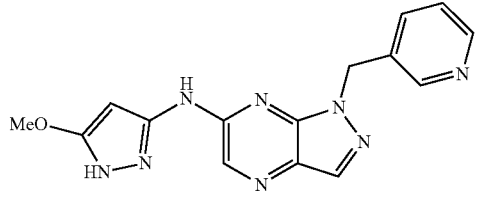 [SMILES: COc1cc(Nc2cnc3cnn(Cc4cccnc4)c3n2)n[nH]1]Amine-3; RCl: 6-chloro-1-(pyridin-3-ylmethyl)-1H-pyrazolo[3,4-b]pyrazine (Preparation 38); BrettPhos Pd G4 Prep-HPLC-1; Yellow solid (36.1 mg, 18%); LCMS m/z = 323 [M + H]$^+$; $^1$H NMR (400 MHz, DMSO-d$_6$) δ: 11.80 (br s, 1H), 8.58 (s, 1H), 8.48 (d, 1H), 8.21 (s, 1H), 8.15 (s, 1H), 7.65 (d, 1H), 7.34 (dd, 1H), 5.78-5.74 (m, 3H), 3.82 (s, 3H). |

| Example No. | Name/Structure/Amine/RCl/Catalyst/Data |
| --- | --- |
| 136 | 1-((2-oxabicyclo[2.2.2]octan-4-yl)methyl)-N-(5-methoxy-1H-pyrazol-3-yl)-1H-pyrazolo[3,4-b]pyrazin-6-amine 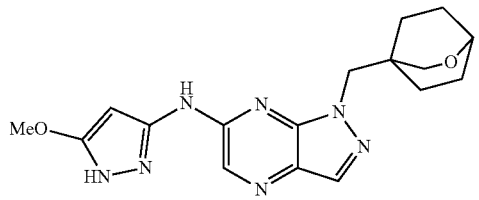 [SMILES: COc1cc(Nc2cnc3cnn(CC45CCC(CC4)OC5)c3n2)n[nH]1] Amine-3; RCl: 1-((2-oxabicyclo[2.2.2]octan-4-yl)methyl)-6-chloro-1H-pyrazolo[3,4-b]pyrazine (Preparation 127); BrettPhos Pd G4 Prep-HPLC-1; Yellow solid (89.6 mg, 29%); LCMS m/z = 356 [M + H]$^+$; $^1$H NMR (400 MHz, DMSO-d$_6$) δ: 8.18 (s, 1H), 8.09 (s, 1H), 5.90 (br s, 2H), 4.17 (s, 2H), 3.82 (s, 3H), 3.64 (s, 2H), 3.63-3.61 (m, 1H), 1.80-1.77 (m, 2H), 1.55-1.48 (m, 7H). |
| 137 | 1-((2-fluoropyridin-3-yl)methyl)-N-(5-methoxy-1H-pyrazol-3-yl)-1H-pyrazolo[3,4-b]pyrazin-6-amine 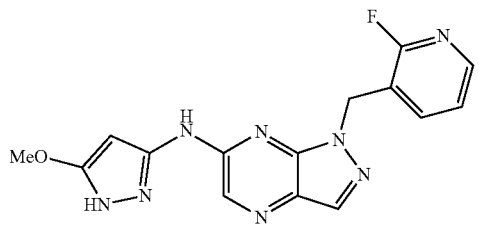 [SMILES: COc1cc(Nc2cnc3cnn(Cc4cccnc4F)c3n2)n[nH]1] Amine-3.HCl; RCl: 6-chloro-1-((2-fluoropyridin-3-yl)methyl)-1H-pyrazolo[3,4-b]pyrazine (Preparation 36); BrettPhos Pd G4 Prep-HPLC-1; Yellow solid (56 mg, 29%); LCMS m/z = 341 [M + H]$^+$; $^1$H NMR (400 MHz, DMSO-d$_6$) δ: 11.74 (br s, 1H), 10.70 (br s, 1H), 8.20-8.17 (m, 3H), 7.76 (br s, 1H), 7.33-7.30 (m, 1H), 5.77-5.60 (m, 3H), 3.81 (s, 3H). |
| 138 | 1-((3-oxabicyclo[3.1.0]hexan-6-yl)methyl)-N-(5-methoxy-1H-pyrazol-3-yl)-1H-pyrazolo[3,4-b]pyrazin-6-amine 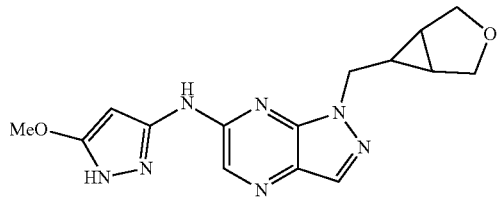 [SMILES: COc1cc(Nc2cnc3cnn(CC4C5COCC54)c3n2)n[nH]1] Amine-3; RCl: 1-((3-oxabicyclo[3.1.0]hexan-6-yl)methyl)-6-chloro-1H-pyrazolo[3,4-b]pyrazine (Preparation 109); BrettPhos Pd G4 Prep-HPLC-1; Yellow solid (55 mg, 30%); LCMS m/z = 328 [M + H]$^+$; $^1$H NMR (400 MHz, DMSO-d$_6$) δ: 12.05-11.55 (br, 1H), 10.75-10.40 (br, 1H), 8.19 (s, 1H), 8.11 (s, 1H), 5.73-5.51 (m, 1H), 4.50-4.20 (m, 2H), 3.82 (s, 3H), 3.66-3.50 (m, 4H), 1.78-1.74 (m, 2H), 1.23-1.13 (m, 1H,). |

| Example No. | Name/Structure/Amine/RCl/Catalyst/Data |
|---|---|
| 139 | (S)-N-(5-methoxy-1H-pyrazol-3-yl)-1-((tetrahydro-2H-pyran-3-yl)methyl)-1H-pyrazolo[3,4-b]pyrazin-6-amine<br>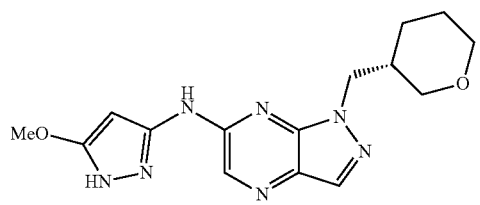 [SMILES: COc1cc(Nc2cnc3cnn(C[C@@H]4CCCOC4)c3n2)n[nH]1]<br>Amine-3; RCl: (S)-6-chloro-1-((tetrahydro-2H-pyran-3-yl)methyl)-1H-pyrazolo[3,4-b]pyrazine (Preparation 97); BrettPhos Pd G4 Prep-HPLC-1; White solid (163 mg, 28%); LCMS m/z = 330 [M + H]$^+$; $^1$H NMR (400 MHz, DMSO-d$_6$) δ: 11.85-11.55 (br, 1H), 10.40-10.13 (br, 1H), 8.20 (s, 1H), 8.12 (s, 1H), 5.80-5.65 (m, 1H), 4.50-4.23 (m, 2H), 3.82 (t, 3H), 3.69-3.61 (m, 2H), 3.40-3.30 (m, 1H), 3.27-3.22 (m, 1H), 2.22-2.15 (m, 1H), 1.66-1.58 (m, 2H), 1.50-1.41 (m, 1H), 1.40-1.21 (m, 1H). |
| 140 | (R)-N-(5-methoxy-1H-pyrazol-3-yl)-1-((tetrahydro-2H-pyran-3-yl)methyl)-1H-pyrazolo[3,4-b]pyrazin-6-amine<br>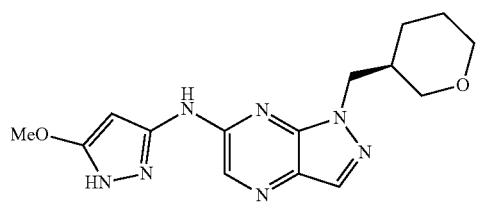 [SMILES: COc1cc(Nc2cnc3cnn(C[C@H]4CCCOC4)c3n2)n[nH]1]<br>Amine-3; RCl: (R)-6-chloro-1-((tetrahydro-2H-pyran-3-yl)methyl)-1H-pyrazolo[3,4-b]pyrazine (Preparation 98); BrettPhos Pd G4 Prep-HPLC-1; White solid (87 mg, 25%); LCMS m/z = 330 [M + H]$^+$; $^1$H NMR (400 MHz, DMSO-d$_6$) δ: 11.85-11.55 (br, 1H), 10.40-10.13 (br, 1H), 8.20 (s, 1H), 8.12 (s, 1H), 5.80-5.65 (m, 1H), 4.50-4.23 (m, 2H), 3.82 (t, 3H), 3.69-3.61 (m, 2H), 3.40-3.30 (m, 1H), 3.27-3.22 (m, 1H), 2.22-2.15 (m, 1H), 1.66-1.58 (m, 2H), 1.50-1.41 (m, 1H), 1.40-1.21 (m, 1H). |

Example 141-197

The title compounds were prepared using an analogous method to that described for Example 32 and 33, using the appropriate amine (RNH$_2$) and chloride (RCl) and an appropriate catalyst system as noted in the table below.

| Example No. | Name/Structure/Reactants/Cat/HPLC/SFC/Data |
| --- | --- |
| 141 and 142 | (R)-N-(5-(difluoromethoxy)-1H-pyrazol-3-yl)-1-((tetrahydro-2H-pyran-3-yl)methyl)-1H-pyrazolo[3,4-b]pyrazin-6-amine and (S)-N-(5-(difluoromethoxy)-1H-pyrazol-3-yl)-1-((tetrahydro-2H-pyran-3-yl)methyl)-1H-pyrazolo[3,4-b]pyrazin-6-amine 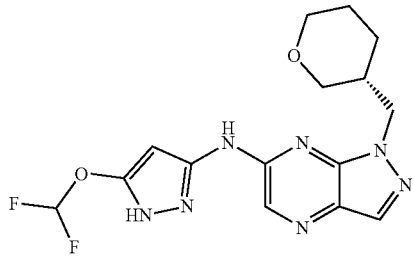 and 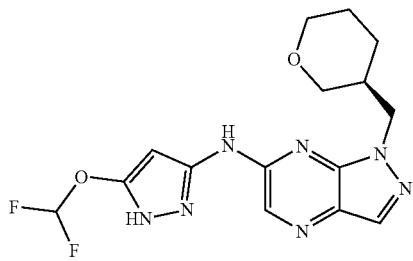 Amine-1; RCl: 6-chloro-1-((tetrahydro-2H-pyran-3-yl)methyl)-1H-pyrazolo[3,4-b]pyrazine (Preparation 96); tBuXPhos Pd G3 prep-HPLC-1; SFC: Daicel OZ, 20 x 250 mm, 10 mm; 30% MeOH (0.2% MeOH/NH$_3$) in CO$_2$ Peak 1, Example 141, (R)-N-(5-(difluoromethoxy)-1H-pyrazol-3-yl)-1-((tetrahydro-2H-pyran-3-yl)methyl)-1H-pyrazolo[3,4-b]pyrazin-6-amine or (S)-N-(5-(difluoromethoxy)-1H-pyrazol-3-yl)-1-((tetrahydro-2H-pyran-3-yl)methyl)-1H-pyrazolo[3,4-b]pyrazin-6-amine, white solid; LCMS m/z = 366 [M + H]$^+$; $^1$H NMR (400 MHz, DMSO-d$_6$) δ: 12.22 (s, 1H), 10.85 (s, 1H), 8.20 (s, 1H), 8.17 (s, 1H), 7.32 (t, 1H), 5.98 (s, 1H), 4.45-4.36 (m, 2H), 3.69-3.61 (m, 2H), 3.40-3.33 (m, 1H), 3.26-3.22 (m, 1H), 2.18-2.11 (m, 1H), 1.62-1.53 (m, 2H), 1.48-1.42 (m, 1H), 1.40-1.25 (m, 1H). Peak 2, Example 142, (S)-N-(5-(difluoromethoxy)-1H-pyrazol-3-yl)-1-((tetrahydro-2H-pyran-3-yl)methyl)-1H-pyrazolo[3,4-b]pyrazin-6-amine or (R)-N-(5-(difluoromethoxy)-1H-pyrazol-3-yl)-1-((tetrahydro-2H-pyran-3-yl)methyl)-1H-pyrazolo[3,4-b]pyrazin-6-amine, white solid; LCMS m/z = 366 [M + H]$^+$; $^1$H NMR (400 MHz, DMSO-d$_6$) δ: 12.22 (s, 1H), 10.85 (s, 1H), 8.20 (s, 1H), 8.17 (s, 1H), 7.32 (t, 1H), 5.98 (s, 1H), 4.45-4.36 (m, 2H), 3.69-3.61 (m, 2H), 3.40-3.33 (m, 1H), 3.26-3.22 (m, 1H), 2.18-2.11 (m, 1H), 1.62-1.53 (m, 2H), 1.48-1.42 (m, 1H), 1.40-1.25 (m, 1H). |

| Example No. | Name/Structure/Reactants/Cat/HPLC/SFC/Data |
|---|---|
| 143 and 144 | (R)-N-(5-(difluoromethoxy)-1H-pyrazol-3-yl)-1-((tetrahydrofuran-3-yl)methyl)-1H-pyrazolo[3,4-b]pyrazin-6-amine and (S)-N-(5-(difluoromethoxy)-1H-pyrazol-3-yl)-1-((tetrahydrofuran-3-yl)methyl)-1H-pyrazolo[3,4-b]pyrazin-6-amine |

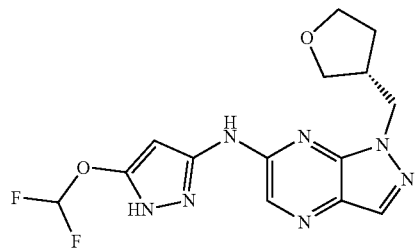

and

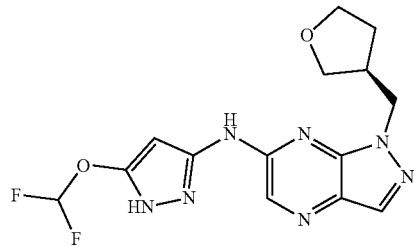

Amine-1; RCl: 6-chloro-1-((tetrahydrofuran-3-yl)methyl)-1H-pyrazolo[3,4-b]pyrazine (Preparation 99); tBuXPhos Pd G3 prep-HPLC-1; SFC: Daicel IC, 20 x 250 mm, 10 mm; 45% MeOH (0.2% MeOH/NH$_3$) in CO$_2$ Peak 1, Example 143, (R)-N-(5-(difluoromethoxy)-1H-pyrazol-3-yl)-1-((tetrahydrofuran-3-yl)methyl)-1H-pyrazolo[3,4-b]pyrazin-6-amine or (S)-N-(5-(difluoromethoxy)-1H-pyrazol-3-yl)-1-((tetrahydrofuran-3-yl)methyl)-1H-pyrazolo[3,4-b]pyrazin-6-amine white solid; LCMS m/z = 352 [M + H]$^+$; $^1$H NMR (400 MHz, DMSO-d$_6$) δ: 12.21 (s, 1H), 10.81 (s, 1H), 8.20 (s, 1H), 8.17 (s, 1H), 7.31 (t, 1H), 5.96 (s, 1H), 4.52-4.44 (m, 2H), 3.79-3.74 (m, 1H), 3.69-3.32 (m, 2H), 3.58-3.52 (m, 1H), 2.83-2.79 (m, 1H), 1.95-1.88 (m, 1H), 1.72-1.67 (m, 1H).

Peak 2, Example 144, (S)-N-(5-(difluoromethoxy)-1H-pyrazol-3-yl)-1-((tetrahydrofuran-3-yl)methyl)-1H-pyrazolo[3,4-b]pyrazin-6-amine or (R)-N-(5-(difluoromethoxy)-1H-pyrazol-3-yl)-1-((tetrahydrofuran-3-yl)methyl)-1H-pyrazolo[3,4-b]pyrazin-6-amine white solid; LCMS m/z = 352 [M + H]$^+$; $^1$H NMR (400 MHz, DMSO-d$_6$) δ: 12.21 (s, 1H), 10.81 (s, 1H), 8.20 (s, 1H), 8.17 (s, 1H), 7.31 (t, 1H), 5.96 (s, 1H), 4.52-4.44 (m, 2H), 3.79-3.74 (m, 1H), 3.69-3.32 (m, 2H), 3.58-3.52 (m, 1H), 2.83-2.79 (m, 1H), 1.95-1.88 (m, 1H), 1.72-1.67 (m, 1H).

| Example No. | Name/Structure/Reactants/Cat/HPLC/SFC/Data |
| --- | --- |
| 145 and 146 | (1r,3r)-3-(6-((5-(difluoromethoxy)-1H-pyrazol-3-yl)amino)-1H-pyrazolo[3,4-b]pyrazin-1-yl)cyclobutan-1-ol and (1s,3s)-3-(6-((5-(difluoromethoxy)-1H-pyrazol-3-yl)amino)-1H-pyrazolo[3,4-b]pyrazin-1-yl)cyclobutan-1-ol 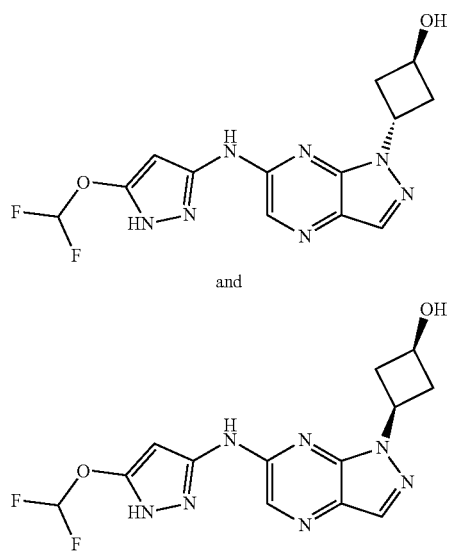 [SMILES: O[C@H]1C[C@H](n2ncc3ncc(Nc4cc(OC(F)F)[nH]n4)nc32)C1 ; O[C@H]1C[C@@H](n2ncc3ncc(Nc4cc(OC(F)F)[nH]n4)nc32)C1] and  Amine-1; RCl: 3-(6-chloro-1H-pyrazolo[3,4-b]pyrazin-1-yl)cyclobutan-1-ol (Preparation 138); tBuXPhos Pd G3 Prep-HPLC-5; SFC: Daicel Chiralpak OD, 20 x 250 mm, 10 mm; 30% MeOH (0.2% DEA) in $CO_2$ Peak 1, Example 145, (1r,3r)-3-(6-((5-(difluoromethoxy)-1H-pyrazol-3-yl)amino)-1H-pyrazolo[3,4-b]pyrazin-1-yl)cyclobutan-1-ol or (1s,3s)-3-(6-((5-(difluoromethoxy)-1H-pyrazol-3-yl)amino)-1H-pyrazolo[3,4-b]pyrazin-1-yl)cyclobutan-1-ol, white solid; LCMS m/z = 338 [M + H]$^+$; $^1$H NMR (400 MHz, DMSO-$d_6$) δ: 12.24 (br s, 1H), 10.80 (br s, 1H), 8.19 (s, 1H), 8.18 (s, 1H), 7.32 (t, 1H, 5.94 (br s, 1H), 5.38 (d, 1H), 5.13 (br s, 1H), 4.10-4.00 (m, 1H), 2.80-2.70 (m, 2H), 2.60-2.50 (m, 2H). Peak 2, Example 146, (1s,3s)-3-(6-((5-(difluoromethoxy)-1H-pyrazol-3-yl)amino)-1H-pyrazolo[3,4-b]pyrazin-1-yl)cyclobutan-1-ol or (1r,3r)-3-(6-((5-(difluoromethoxy)-1H-pyrazol-3-yl)amino)-1H-pyrazolo[3,4-b]pyrazin-1-yl)cyclobutan-1-ol, yellow solid; LCMS m/z = 338 [M + H]$^+$; $^1$H NMR (400 MHz, DMSO-$d_6$) δ: 12.36 (br s, 1H), 10.85 (br s, 1H), 8.19 (s, 1H), 8.18 (s, 1H), 7.31 (t, 1H), 5.96 (s, 1H), 5.69 (s, 1H), 5.26 (d, 1H), 4.58 (s, 1H), 2.75-2.68 (m, 2H), 2.46-2.40 (m, 2H). |

| Example No. | Name/Structure/Reactants/Cat/HPLC/SFC/Data |
|---|---|
| 147 and 148 | (R)-1-(cyclopropyl(pyridin-3-yl)methyl)-N-(5-(difluoromethoxy)-1H-pyrazol-3-yl)-1H-pyrazolo[3,4-b]pyrazin-6-amine and (S)-1-(cyclopropyl(pyridin-3-yl)methyl)-N-(5-(difluoromethoxy)-1H-pyrazol-3-yl)-1H-pyrazolo[3,4-b]pyrazin-6-amine |

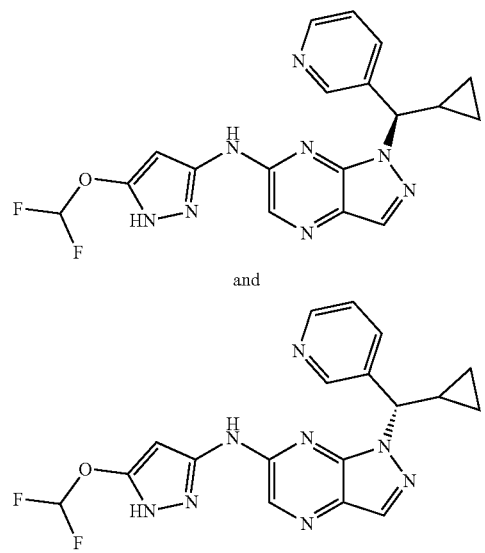 [SMILES: FC(F)Oc1cc(Nc2cnc3cnn([C@@H](c4cccnc4)C4CC4)c3n2)n[nH]1 ; FC(F)Oc1cc(Nc2cnc3cnn([C@H](c4cccnc4)C4CC4)c3n2)n[nH]1]

Amine-1; RCl: 6-chloro-1-(cyclopropyl(pyridin-3-yl)methyl)-1H-pyrazolo[3,4-b]pyrazine (Preparation 141); tBuXPhos Pd G3 prep-HPLC-1; SFC: Daicel IC, 20 × 250 mm, 10 mm; 45% MeOH (0.2% MeOH/NH$_3$) in CO$_2$ Peak 1, Example 147, (R)-1-(cyclopropyl(pyridin-3-yl)methyl)-N-(5-(difluoromethoxy)-1H-pyrazol-3-yl)-1H-pyrazolo[3,4-b]pyrazin-6-amine or (S)-1-(cyclopropyl(pyridin-3-yl)methyl)-N-(5-(difluoromethoxy)-1H-pyrazol-3-yl)-1H-pyrazolo[3,4-b]pyrazin-6-amine, white solid; LCMS m/z = 399 [M + H]$^+$; $^1$H NMR (400 MHz, DMSO-d$_6$) δ: 12.25-12.10 (br, 1H), 10.99-10.89 (br, 1H), 8.68 (d, 1H), 8.49-8.46 (m, 1H), 8.22 (s, 1H), 8.20 (s, 1H), 7.86-7.80 (m, 1H), 7.39-7.36 (m, 1H), 7.32 (t, 1H), 5.84 (s, 1H), 5.75-5.70 (m, 1H), 2.00-1.94 (m, 1H), 0.79-0.72 (m, 1H), 0.67-0.63 (m, 1H), 0.58-0.52 (m, 1H), 0.48-0.42 (m, 1H).

Peak 2, Example 148, (S)-1-(cyclopropyl(pyridin-3-yl)methyl)-N-(5-(difluoromethoxy)-1H-pyrazol-3-yl)-1H-pyrazolo[3,4-b]pyrazin-6-amine or (R)-1-(cyclopropyl(pyridin-3-yl)methyl)-N-(5-(difluoromethoxy)-1H-pyrazol-3-yl)-1H-pyrazolo[3,4-b]pyrazin-6-amine, yellow solid; LCMS m/z = 399 [M + H]$^+$; $^1$H NMR (400 MHz, DMSO-d$_6$) δ: 12.25-12.10 (br, 1H), 10.99-10.89 (br, 1H), 8.68 (d, 1H), 8.49-8.46 (m, 1H), 8.22 (s, 1H), 8.20 (s, 1H), 7.86-7.80 (m, 1H), 7.39-7.36 (m, 1H), 7.32 (t, 1H), 5.84 (s, 1H), 5.75-5.70 (m, 1H), 2.00-1.94 (m, 1H), 0.79-0.72 (m, 1H), 0.67-0.63 (m, 1H), 0.58-0.52 (m, 1H), 0.48-0.42 (m, 1H).

| Example No. | Name/Structure/Reactants/Cat/HPLC/SFC/Data |
|---|---|
| 149 and 150 | (R)-1-(2,2-difluoro-1-(pyridin-2-yl)ethyl)-N-(5-(difluoromethoxy)-1H-pyrazol-3-yl)-1H-pyrazolo[3,4-b]pyrazin-6-amine and (S)-1-(2,2-difluoro-1-(pyridin-2-yl)ethyl)-N-(5-(difluoromethoxy)-1H-pyrazol-3-yl)-1H-pyrazolo[3,4-b]pyrazin-6-amine 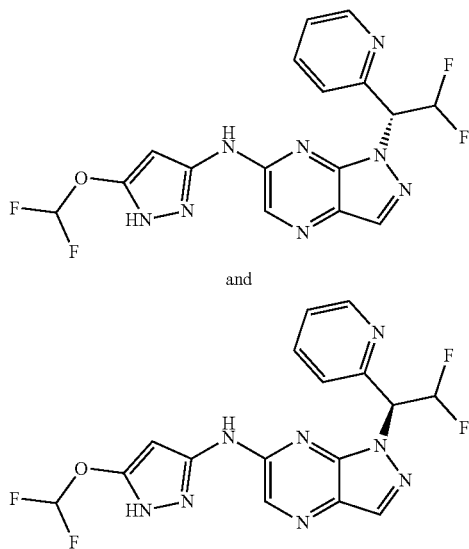 [SMILES: FC(F)Oc1cc(Nc2cnc3cnn([C@H](c4ccccn4)C(F)F)c3n2)n[nH]1 ; FC(F)Oc1cc(Nc2cnc3cnn([C@@H](c4ccccn4)C(F)F)c3n2)n[nH]1] and  Amine-1; RCl: 6-chloro-1-(2,2-difluoro-1-(pyridin-2-yl)ethyl)-1H-pyrazolo[3,4-b]pyrazine (Preparation 56); tBuXPhos Pd G3 Reverse phase Isco (0 to 80% MeCN/water + 0.1% TFA). Neutralized with NaHCO$_3$; SFC: Daicel IG, 20 x 250 mm, 10 mm; 20% IPA (0.1% MeOH/NH$_3$) in CO$_2$ Peak 1, Example 149, (R)-1-(2,2-difluoro-1-(pyridin-2-yl)ethyl)-N-(5-(difluoromethoxy)-1H-pyrazol-3-yl)-1H-pyrazolo[3,4-b]pyrazin-6-amine or (S)-1-(2,2-difluoro-1-(pyridin-2-yl)ethyl)-N-(5-(difluoromethoxy)-1H-pyrazol-3-yl)-1H-pyrazolo[3,4-b]pyrazin-6-amine, white solid; LCMS m/z = 409 [M + H]$^+$; $^1$H NMR (400 MHz, MeOH-d$_4$) δ: 8.73 (d, 1H), 8.17 (s, 1H), 8.16 (s, 1H), 7.88 (td, 1H), 7.68 (d, 1H), 7.44 (dd, 1H), 7.19 (m, 1H), 7.05 (t, 1H), 6.46-6.44 (m, 1H), 5.76 (s, 1H). Peak 2, Example 150, (S)-1-(2,2-difluoro-1-(pyridin-2-yl)ethyl)-N-(5-(difluoromethoxy)-1H-pyrazol-3-yl)-1H-pyrazolo[3,4-b]pyrazin-6-amine or (R)-1-(2,2-difluoro-1-(pyridin-2-yl)ethyl)-N-(5-(difluoromethoxy)-1H-pyrazol-3-yl)-1H-pyrazolo[3,4-b]pyrazin-6-amine, white solid; LCMS m/z = 409 [M + H]$^+$; $^1$H NMR (400 MHz, MeOH-d$_4$) δ: 8.61 (d, 1H), 8.05 (s, 1Hz), 8.04 (s, 1H), 7.74 (td, 1H), 7.56 (d, 1H), 7.32 (dd, 1H), 7.07 (dt, 1H), 6.93 (t, 1H), 6.38-6.32 (m, 1H), 5.64 (s, 1H). |

| Example No. | Name/Structure/Reactants/Cat/HPLC/SFC/Data |
|---|---|
| 151 and 152 | (S)-N-(5-(difluoromethoxy)-1H-pyrazol-3-yl)-1-(1-(6-fluoropyridin-3-yl)ethyl)-1H-pyrazolo[3,4-b]pyrazin-6-amine and (R)-N-(5-(difluoromethoxy)-1H-pyrazol-3-yl)-1-(1-(6-fluoropyridin-3-yl)ethyl)-1H-pyrazolo[3,4-b]pyrazin-6-amine<br><br>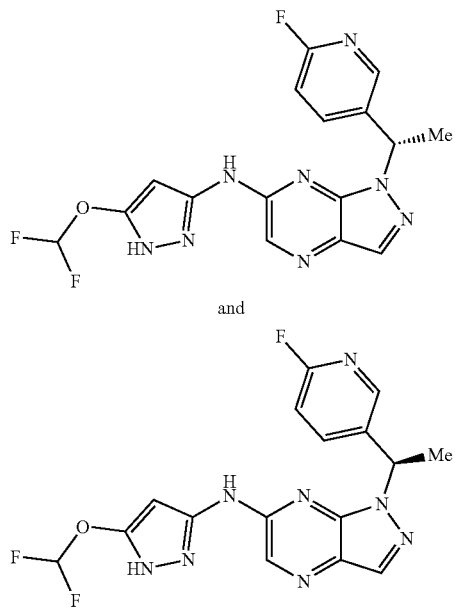 [SMILES: C[C@@H](c1ccc(F)nc1)n1ncc2ncc(Nc3cc(OC(F)F)[nH]n3)nc21 ; C[C@H](c1ccc(F)nc1)n1ncc2ncc(Nc3cc(OC(F)F)[nH]n3)nc21]<br><br>and<br><br>Amine-1; RCl: 6-chloro-1-(1-(6-fluoropyridin-3-yl)ethyl)-1H-pyrazolo[3,4-b]pyrazine (Preparation 143); Pd$_2$(dba)$_3$/$^t$BuXPhos<br>Prep-HPLC-5; SFC: Daicel AS, 20 × 250 mm, 10 mm; 20% MeOH (0.2% MeOH/NH$_3$) in CO$_2$<br>Peak 1, Example 151, (S)-N-(5-(difluoromethoxy)-1H-pyrazol-3-yl)-1-(1-(6-fluoropyridin-3-yl)ethyl)-1H-pyrazolo[3,4-b]pyrazin-6-amine or (R)-N-(5-(difluoromethoxy)-1H-pyrazol-3-yl)-1-(1-(6-fluoropyridin-3-yl)ethyl)-1H-pyrazolo[3,4-b]pyrazin-6-amine, white solid; LCMS m/z = 391 [M + H]$^+$; $^1$H NMR (400 MHz, DMSO-d$_6$) δ: 12.45-12.10 (br, 1H), 10.95-10.61 (br, 1H), 8.28 (d, 1H), 8.23 (s, 1H), 8.21 (s, 1H), 7.98-7.93 (m, 1H), 7.33 (t, 1H), 7.16-7.11 (m, 1H), 6.70-6.60 (m, 1H), 5.91 (br s, 1H), 1.90 (d, 3H).<br>Peak 2, Example 152, (R)-N-(5-(difluoromethoxy)-1H-pyrazol-3-yl)-1-(1-(6-fluoropyridin-3-yl)ethyl)-1H-pyrazolo[3,4-b]pyrazin-6-amine or (S)-N-(5-(difluoromethoxy)-1H-pyrazol-3-yl)-1-(1-(6-fluoropyridin-3-yl)ethyl)-1H-pyrazolo[3,4-b]pyrazin-6-amine, yellow solid; LCMS m/z = 391 [M + H]$^+$; $^1$H NMR (400 MHz, DMSO-d$_6$) δ: 12.30 (br s, 1H), 10.85 (br s, 1H), 8.28 (d, 1H), 8.23 (s, 1H), 8.21 (s, 1H), 7.98-7.93 (m, 1H), 7.33 (t, 1H), 7.16-7.11 (m, 1H), 6.70-6.60 (m, 1H), 5.91 (br s, 1H), 1.90 (d, 3H). |

| Example No. | Name/Structure/Reactants/Cat/HPLC/SFC/Data |
|---|---|
| 153 and 154 | (S)-N-(5-(difluoromethoxy)-1H-pyrazol-3-yl)-1-(1-(5-fluoropyridin-3-yl)ethyl)-1H-pyrazolo[3,4-b]pyrazin-6-amine and (R)-N-(5-(difluoromethoxy)-1H-pyrazol-3-yl)-1-(1-(5-fluoropyridin-3-yl)ethyl)-1H-pyrazolo[3,4-b]pyrazin-6-amine |

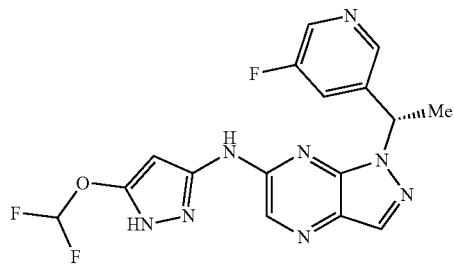

and

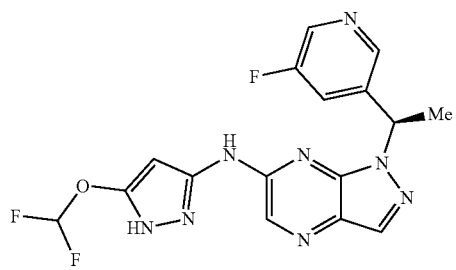

Amine-1; RCl: 6-chloro-1-(1-(5-fluoropyridin-3-yl)ethyl)-1H-pyrazolo[3,4-b]pyrazine (Preparation 144); tBuXPhos Pd G3 prep-HPLC-1; SFC: Daicel OZ 20 × 250 mm, 10 mm; 25% MeOH (0.2% MeOH/NH$_3$) in CO$_2$ Peak 1, Example 153, (S)-N-(5-(difluoromethoxy)-1H-pyrazol-3-yl)-1-(1-(5-fluoropyridin-3-yl)ethyl)-1H-pyrazolo[3,4-b]pyrazin-6-amine or (R)-N-(5-(difluoromethoxy)-1H-pyrazol-3-yl)-1-(1-(5-fluoropyridin-3-yl)ethyl)-1H-pyrazolo[3,4-b]pyrazin-6-amine, white solid; LCMS m/z = 391 [M + H]$^+$; $^1$H NMR (400 MHz, DMSO-d$_6$) δ: 12.45-12.10 (br, 1H), 10.95-10.61 (br, 1H), 8.50-8.45 (m, 2H), 8.25 (s, 1H), 8.22 (s, 1H), 7.69 (dt, 1H), 7.33 (t, 1H), 6.73-6.64 (m, 1H), 5.90 (br s, 1H), 1.92 (d, 3H)

Peak 2, Example 154, (R)-N-(5-(difluoromethoxy)-1H-pyrazol-3-yl)-1-(1-(5-fluoropyridin-3-yl)ethyl)-1H-pyrazolo[3,4-b]pyrazin-6-amine or (S)-N-(5-(difluoromethoxy)-1H-pyrazol-3-yl)-1-(1-(5-fluoropyridin-3-yl)ethyl)-1H-pyrazolo[3,4-b]pyrazin-6-amine, yellow solid; LCMS m/z = 391 [M + H]$^+$; $^1$H NMR (400 MHz, DMSO-d$_6$) δ: 12.45-12.10 (br, 1H), 11.05-10.61 (br, 1H), 8.50-8.45 (m, 2H), 8.24 (s, 1H), 8.21 (s, 1H), 7.68 (dt, 1H), 7.32 (t, 1H), 6.71-6.64 (m, 1H), 5.93 (s, 1H), 1.92 (d, 3H).

-continued

| Example No. | Name/Structure/Reactants/Cat/HPLC/SFC/Data |
|---|---|
| 155 and 156 | (R)-N-(5-(difluoromethoxy)-1H-pyrazol-3-yl)-1-(1-(6-fluoropyridin-2-yl)ethyl)-1H-pyrazolo[3,4-b]pyrazin-6-amine and (S)-N-(5-(difluoromethoxy)-1H-pyrazol-3-yl)-1-(1-(6-fluoropyridin-2-yl)ethyl)-1H-pyrazolo[3,4-b]pyrazin-6-amine |

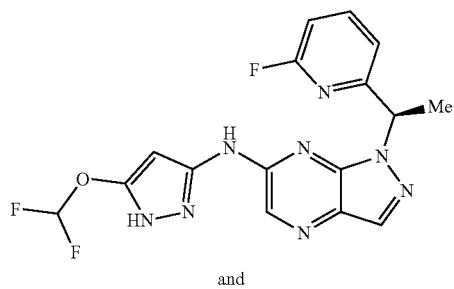

and

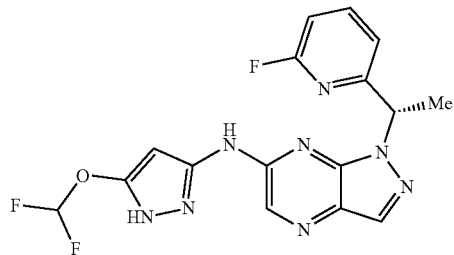

Amine-1; RCl: 6-chloro-1-(1-(6-fluoropyridin-2-yl)ethyl)-1H-pyrazolo[3,4-b]pyrazine (Preparation 145); Pd$_2$(dba)$_3$/$^t$BuXPhos prep-HPLC-1; SFC: Daicel AD 20 × 250 mm, 10 mm; 30% MeOH (0.2% MeOH/NH$_3$) in CO$_2$ Peak 1, Example 155, (R)-N-(5-(difluoromethoxy)-1H-pyrazol-3-yl)-1-(1-(6-fluoropyridin-2-yl)ethyl)-1H-pyrazolo[3,4-b]pyrazin-6-amine or (S)-N-(5-(difluoromethoxy)-1H-pyrazol-3-yl)-1-(1-(6-fluoropyridin-2-yl)ethyl)-1H-pyrazolo[3,4-b]pyrazin-6-amine, white solid; LCMS m/z = 391 [M + H]$^+$; $^1$H NMR (400 MHz, DMSO-d$_6$) δ: 12.24 (s, 1H), 10.83 (s, 1H), 8.24 (s, 1H), 8.22 (s, 1H), 7.92-7.87 (m, 1H), 7.28 (t, 1H), 7.06 (dd, 1H), 6.94 (dd, 1H), 6.56-6.52 (m, 1H), 5.85 (s, 1H), 1.91 (d, 3H).

Peak 2, Example 156, (S)-N-(5-(difluoromethoxy)-1H-pyrazol-3-yl)-1-(1-(6-fluoropyridin-2-yl)ethyl)-1H-pyrazolo[3,4-b]pyrazin-6-amine or (R)-N-(5-(difluoromethoxy)-1H-pyrazol-3-yl)-1-(1-(6-fluoropyridin-2-yl)ethyl)-1H-pyrazolo[3,4-b]pyrazin-6-amine, yellow solid; LCMS m/z = 391 [M + H]$^+$; $^1$H NMR (400 MHz, DMSO-d$_6$) δ: 12.50-12.10 (br, 1H), 11.05-10.75 (br, 1H), 8.23 (s, 1H), 8.22 (s, 1H), 7.92-7.87 (m, 1H), 7.28 (t, 1H), 7.06 (dd, 1H), 6.94 (dd, 1H), 6.56-6.52 (m, 1H), 5.87 (s, 1H), 1.91 (d, 3H).

| Example No. | Name/Structure/Reactants/Cat/HPLC/SFC/Data |
|---|---|
| 157 and 158 | (S)-1-(cyclopropyl(tetrahydro-2H-pyran-4-yl)methyl)-N-(5-(difluoromethoxy)-1H-pyrazol-3-yl)-1H-pyrazolo[3,4-b]pyrazin-6-amine and (R)-1-(cyclopropyl(tetrahydro-2H-pyran-4-yl)methyl)-N-(5-(difluoromethoxy)-1H-pyrazol-3-yl)-1H-pyrazolo[3,4-b]pyrazin-6-amine<br>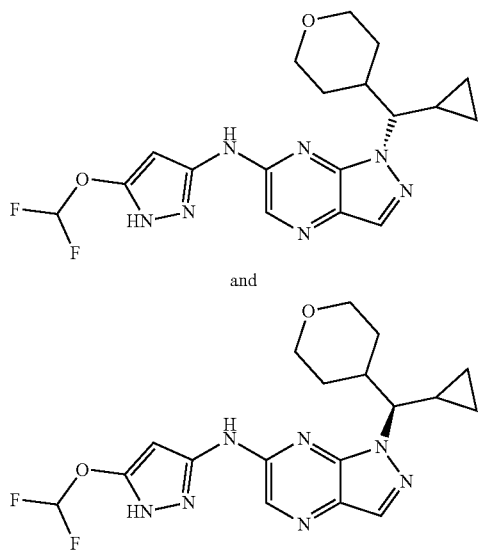<br>and<br>Amine-1; RCl: 6-chloro-1-(cyclopropyl(tetrahydro-2H-pyran-4-yl)methyl)-1H-pyrazolo[3,4-b]pyrazine (Preparation 125); BrettPhos Pd G4<br>prep-HPLC-1; SFC: Daicel OJ 20 x 250 mm, 10 mm; 40% MeOH (0.2% MeOH/NH$_3$) in CO$_2$<br>Peak 1, Example 157, (S)-1-(cyclopropyl(tetrahydro-2H-pyran-4-yl)methyl)-N-(5-(difluoromethoxy)-1H-pyrazol-3-yl)-1H-pyrazolo[3,4-b]pyrazin-6-amine or (R)-1-(cyclopropyl(tetrahydro-2H-pyran-4-yl)methyl)-N-(5-(difluoromethoxy)-1H-pyrazol-3-yl)-1H-pyrazolo[3,4-b]pyrazin-6-amine, white solid; LCMS m/z = 405 [M + H]$^+$; $^1$H NMR (400 MHz, DMSO-d$_6$) δ: 12.25-12.01 (br, 1H), 10.95-10.75 (br, 1H), 8.19 (s, 1H), 8.16 (s, 1H), 7.30 (t, 1H), 5.91 (s, 1H), 4.12-4.05 (m, 1H), 3.93-3.90 (m, 1H), 3.73-3.70 (m, 1H), 3.35-3.29 (m, 1H), 3.18-3.14 (m, 1H), 2.00-1.95 (m, 1H), 1.44-1.39 (m, 2H), 1.35-1.20 (m, 2H), 0.87-0.83 (m, 1H), 0.71-0.69 (m, 1H), 0.56-0.55 (m, 1H), 0.27-0.23 (m, 1H), 0.06-0.05 (m, 1H).<br>Peak 2, Example 158, (R)-1-(cyclopropyl(tetrahydro-2H-pyran-4-yl)methyl)-N-(5-(difluoromethoxy)-1H-pyrazol-3-yl)-1H-pyrazolo[3,4-b]pyrazin-6-amine or (S)-1-(cyclopropyl(tetrahydro-2H-pyran-4-yl)methyl)-N-(5-(difluoromethoxy)-1H-pyrazol-3-yl)-1H-pyrazolo[3,4-b]pyrazin-6-amine, white solid; LCMS m/z = 405 [M + H]$^+$; $^1$H NMR (400 MHz, DMSO-d$_6$) δ: 12.12 (br s, 1H), 10.88 (br s, 1H), 8.20 (s, 1H), 8.16 (s, 1H), 7.30 (t, 1H), 5.91 (s, 1H), 4.13 (s, 1H), 3.93-3.90 (m, 1H), 3.73-3.70 (m, 1H), 3.15 (t, 1H), 2.42-2.39 (m, 1H), 2.00 (d, 1H), 1.45-1.23 (m, 4H), 0.87-0.83 (m, 1H), 0.71-0.69 (m, 1H), 0.56-0.55 (m, 1H), 0.27-0.23 (m, 1H), 0.06-0.05 (m, 1H). |

| Example No. | Name/Structure/Reactants/Cat/HPLC/SFC/Data |
|---|---|
| 159 and 160 | N-(5-(difluoromethoxy)-1H-pyrazol-3-yl)-1-(((1R,2S)-2-fluorocyclopropyl)methyl)-1H-pyrazolo[3,4-b]pyrazin-6-amine and N-(5-(difluoromethoxy)-1H-pyrazol-3-yl)-1-(((1S,2R)-2-fluorocyclopropyl)methyl)-1H-pyrazolo[3,4-b]pyrazin-6-amine 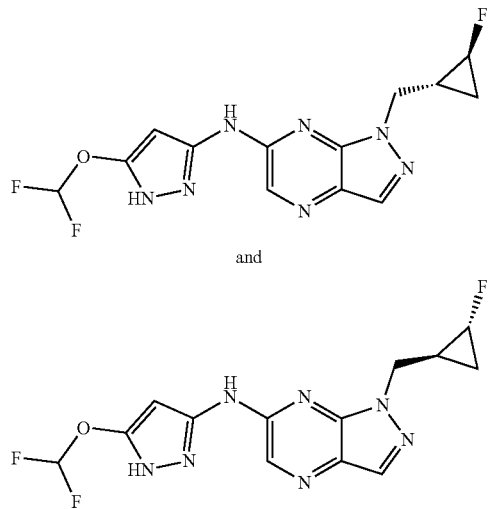 [SMILES: FC(F)Oc1cc(Nc2cnc3cnn(C[C@H]4C[C@@H]4F)c3n2)n[nH]1 ; FC(F)Oc1cc(Nc2cnc3cnn(C[C@@H]4C[C@H]4F)c3n2)n[nH]1] and <br><br>Amine-1; RCl: trans-rac-6-chloro-1-(((1R,2S)-2-fluorocyclopropyl)methyl)-1H-pyrazolo[3,4-b]pyrazine (Preparation 160); Pd$_2$(dba)$_3$/$^t$BuXPhos<br>prep-HPLC-1; SFC: Daicel OJ 20 x 250 mm, 10 mm; 15% IPA (0.5% MeOH/NH$_3$) in CO$_2$<br>Peak 1, Example 159, N-(5-(difluoromethoxy)-1H-pyrazol-3-yl)-1-(((1R,2S)-2-fluorocyclopropyl)methyl)-1H-pyrazolo[3,4-b]pyrazin-6-amine or N-(5-(difluoromethoxy)-1H-pyrazol-3-yl)-1-(((1S,2R)-2-fluorocyclopropyl)methyl)-1H-pyrazolo[3,4-b]pyrazin-6-amine, white solid; LCMS m/z = 340 [M + H]$^+$; $^1$H NMR (400 MHz, DMSO-d$_6$) δ: 12.24 (s, 1H), 10.86 (s, 1H), 8.21 (s, 1H), 8.17 (s, 1H), 7.32 (t, 1H), 5.91 (s, 1H), 4.90-4.71 (m, 1H), 4.40 (d, 2H), 1.85-1.70 (m, 1H), 1.15-1.02 (m, 1H), 0.82-0.78 (m, 1H).<br>Peak 2, Example 160, N-(5-(difluoromethoxy)-1H-pyrazol-3-yl)-1-(((1S,2R)-2-fluorocyclopropyl)methyl)-1H-pyrazolo[3,4-b]pyrazin-6-amine or N-(5-(difluoromethoxy)-1H-pyrazol-3-yl)-1-(((1R,2S)-2-fluorocyclopropyl)methyl)-1H-pyrazolo[3,4-b]pyrazin-6-amine, white solid; LCMS m/z = 340 [M + H]$^+$; $^1$H NMR (400 MHz, DMSO-d$_6$) δ: 12.24 (s, 1H), 10.86 (s, 1H), 8.21 (s, 1H), 8.17 (s, 1H), 7.32 (t, 1H), 5.91 (s, 1H), 4.90-4.71 (m, 1H), 4.40 (d, 2H), 1.85-1.70 (m, 1H), 1.15-1.02 (m, 1H), 0.82-0.78 (m, 1H). |

| Example No. | Name/Structure/Reactants/Cat/HPLC/SFC/Data |
|---|---|
| 161 and 162 | (S)-N-(5-(difluoromethoxy)-1H-pyrazol-3-yl)-1-(oxetan-3-yl(phenyl)methyl)-1H-pyrazolo[3,4-b]pyrazin-6-amine and (R)-N-(5-(difluoromethoxy)-1H-pyrazol-3-yl)-1-(oxetan-3-yl(phenyl)methyl)-1H-pyrazolo[3,4-b]pyrazin-6-amine 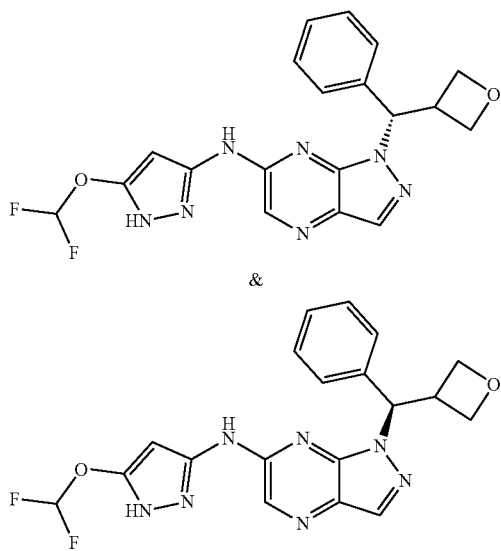 [SMILES: FC(F)Oc1cc(Nc2cnc3cnn([C@H](c4ccccc4)C4COC4)c3n2)n[nH]1 ; FC(F)Oc1cc(Nc2cnc3cnn([C@@H](c4ccccc4)C4COC4)c3n2)n[nH]1] Amine-1; RCl: 6-chloro-1-(oxetan-3-yl(phenyl)methyl)-1H-pyrazolo[3,4-b]pyrazine (Preparation 134); BrettPhos Pd G4 prep-HPLC-1; SFC: Daicel OJ 20 x 250 mm, 10 mm; 50% MeOH (0.2% MeOH/NH$_3$) Peak 1, Example 161, (S)-N-(5-(difluoromethoxy)-1H-pyrazol-3-yl)-1-(oxetan-3-yl(phenyl)methyl)-1H-pyrazolo[3,4-b]pyrazin-6-amine or (R)-N-(5-(difluoromethoxy)-1H-pyrazol-3-yl)-1-(oxetan-3-yl(phenyl)methyl)-1H-pyrazolo[3,4-b]pyrazin-6-amine, white solid; LCMS m/z = 414 [M + H]$^+$; $^1$H NMR (400 MHz, DMSO-d$_6$) δ: 12.49-11.18 (br, 1H), 8.16 (s, 1H), 8.15 (s, 1H), 7.40 (s, 1H), 7.39 (s, 1H), 7.34 (t, 1H), 7.31-7.24 (m, 3H), 6.74 (d, 1H), 5.92 (s, 1H), 4.66-4.59 (m, 2H), 4.52 (t, 1H), 4.33 (t, 1H), 4.30-4.20 (m, 1H). Peak 2, Example 162, (R)-N-(5-(difluoromethoxy)-1H-pyrazol-3-yl)-1-(oxetan-3-yl(phenyl)methyl)-1H-pyrazolo[3,4-b]pyrazin-6-amine or (S)-N-(5-(difluoromethoxy)-1H-pyrazol-3-yl)-1-(oxetan-3-yl(phenyl)methyl)-1H-pyrazolo[3,4-b]pyrazin-6-amine, white solid; LCMS m/z = 414 [M + H]$^+$; $^1$H NMR (400 MHz, DMSO-d$_6$) δ: 8.15 (s, 1H), 8.15 (s, 1H), 7.52-7.15 (m, 6H), 6.73 (d, 1H), 5.92 (s, 1H), 4.66-4.62 (m, 2H), 4.62-4.60 (m, 1H), 4.54-4.50 (m, 1H), 4.36-4.22 (m, 1H). |

| Example No. | Name/Structure/Reactants/Cat/HPLC/SFC/Data |
| --- | --- |
| 163 and 164 | (S)-1-((2,2-difluorocyclopropyl)methyl)-N-(5-(difluoromethoxy)-1H-pyrazol-3-yl)-1H-pyrazolo[3,4-b]pyrazin-6-amine and (R)-1-((2,2-difluorocyclopropyl)methyl)-N-(5-(difluoromethoxy)-1H-pyrazol-3-yl)-1H-pyrazolo[3,4-b]pyrazin-6-amine 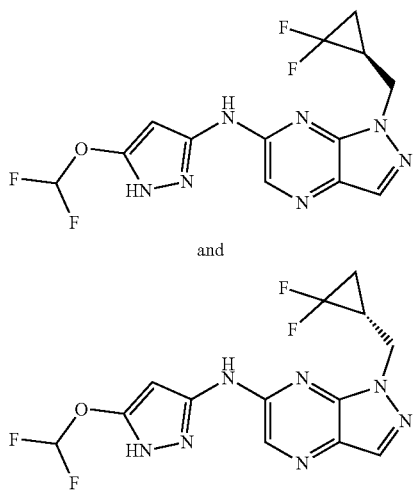 [SMILES: FC(F)Oc1cc(Nc2cnc3cnn(C[C@@H]4CC4(F)F)c3n2)n[nH]1 ; FC(F)Oc1cc(Nc2cnc3cnn(C[C@H]4CC4(F)F)c3n2)n[nH]1] Amine-1; RCl: 6-chloro-1-((2,2-difluorocyclopropyl)methyl)-1H-pyrazolo[3,4-b]pyrazine (Preparation 161); tBuXPhos Pd G3 prep-HPLC-1; SFC: Daicel OJ 20 x 250 mm, 10 mm; 15% IPA (0.5% MeOH/NH₃) in CO₂<br>Peak 1, Example 163, (S)-1-((2,2-difluorocyclopropyl)methyl)-N-(5-(difluoromethoxy)-1H-pyrazol-3-yl)-1H-pyrazolo[3,4-b]pyrazin-6-amine or (R)-1-((2,2-difluorocyclopropyl)methyl)-N-(5-(difluoromethoxy)-1H-pyrazol-3-yl)-1H-pyrazolo[3,4-b]pyrazin-6-amine, white solid; LCMS m/z = 358 [M + H]⁺; ¹H NMR (400 MHz, DMSO-d₆) δ: 8.23 (s, 1H), 8.20 (s, 1H), 7.31 (t, 1H), 5.98 (s, 1H), 4.64-4.62 (m, 2H), 2.29-2.25 (m, 1H), 1.70-1.67 (m, 1H), 1.54-1.49 (m, 1H).<br>Peak 2, Example 164, (R)-1-((2,2-difluorocyclopropyl)methyl)-N-(5-(difluoromethoxy)-1H-pyrazol-3-yl)-1H-pyrazolo[3,4-b]pyrazin-6-amine or (S)-1-((2,2-difluorocyclopropyl)methyl)-N-(5-(difluoromethoxy)-1H-pyrazol-3-yl)-1H-pyrazolo[3,4-b]pyrazin-6-amine, white solid; LCMS m/z = 358 [M + H]⁺; ¹H NMR (400 MHz, DMSO-d₆) δ: 8.22 (s, 1H), 8.19 (s, 1H), 7.30 (t, 1H), 5.96 (s, 1H), 4.63-4.60 (m, 2H), 2.27-2.26 (m, 1H), 1.69-1.65 (m, 1H), 1.53-1.48 (m, 1H). |

| Example No. | Name/Structure/Reactants/Cat/HPLC/SFC/Data |
|---|---|
| 165 and 166 | (R)-N-(5-(difluoromethoxy)-1H-pyrazol-3-yl)-1-((3-methyltetrahydrofuran-3-yl)methyl)-1H-pyrazolo[3,4-b]pyrazin-6-amine and (S)-N-(5-(difluoromethoxy)-1H-pyrazol-3-yl)-1-((3-methyltetrahydrofuran-3-yl)methyl)-1H-pyrazolo[3,4-b]pyrazin-6-amine<br>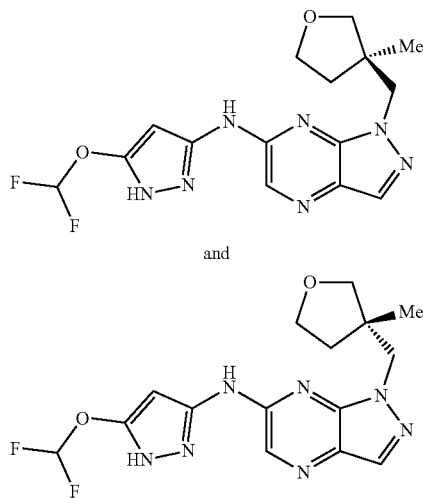 [SMILES: C[C@]1(Cn2ncc3ncc(Nc4cc(OC(F)F)[nH]n4)nc32)CCOC1 ; C[C@@]1(Cn2ncc3ncc(Nc4cc(OC(F)F)[nH]n4)nc32)CCOC1]<br>Amine-1; RCl: 6-chloro-1-((3-methyltetrahydrofuran-3-yl)methyl)-1H-pyrazolo[3,4-b]pyrazine (Preparation 100); tBuXPhos Pd G3 prep-HPLC-1; SFC: Daicel OX 20 x 250 mm, 10 mm; 30% EtOH (0.5% MeOH/NH$_3$) in CO$_2$<br>Peak 1, Example 165, (R)-N-(5-(difluoromethoxy)-1H-pyrazol-3-yl)-1-((3-methyltetrahydrofuran-3-yl)methyl)-1H-pyrazolo[3,4-b]pyrazin-6-amine or (S)-N-(5-(difluoromethoxy)-1H-pyrazol-3-yl)-1-((3-methyltetrahydrofuran-3-yl)methyl)-1H-pyrazolo[3,4-b]pyrazin-6-amine, white solid; LCMS m/z = 366 [M + H]$^+$; $^1$H NMR (400 MHz, DMSO-d$_6$) δ: 11.56 (br, 2H), 8.20 (s, 1H), 8.17 (s, 1H), 7.30 (t, 1H), 6.02 (s, 1H), 4.45 (dd, 1H), 3.86-3.76 (m, 3H), 3.29 (d, 1H), 2.05-2.01 (m, 1H), 1.66-1.60 (m, 1H), 1.00 (s, 3H).<br>Peak 2, Example 166, (S)-N-(5-(difluoromethoxy)-1H-pyrazol-3-yl)-1-((3-methyltetrahydrofuran-3-yl)methyl)-1H-pyrazolo[3,4-b]pyrazin-6-amine or (R)-N-(5-(difluoromethoxy)-1H-pyrazol-3-yl)-1-((3-methyltetrahydrofuran-3-yl)methyl)-1H-pyrazolo[3,4-b]pyrazin-6-amine, white solid; LCMS m/z = 366 [M + H]$^+$; $^1$H NMR (400 MHz, DMSO-d$_6$) δ: 12.19 (br s, 1H), 10.82 (br s, 1H), 8.21 (s, 1H), 8.17 (s, 1H), 7.30 (t, 1H), 5.90 (br s, 1H), 4.53-4.40 (m, 2H), 3.85-3.75 (m, 3H), 3.31-3.27 (m, 1H), 2.04-2.02 (m, 1H), 1.67-1.63 (m, 1H), 1.00 (s, 3H). |

| Example No. | Name/Structure/Reactants/Cat/HPLC/SFC/Data |
|---|---|
| 167 and 168 | (S)-N-(5-(difluoromethoxy)-1H-pyrazol-3-yl)-1-((3-fluorotetrahydrofuran-3-yl)methyl)-1H-pyrazolo[3,4-b]pyrazin-6-amine and (R)-N-(5-(difluoromethoxy)-1H-pyrazol-3-yl)-1-((3-fluorotetrahydrofuran-3-yl)methyl)-1H-pyrazolo[3,4-b]pyrazin-6-amine<br>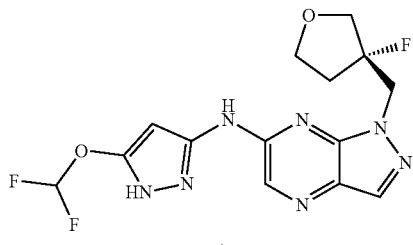<br>and<br>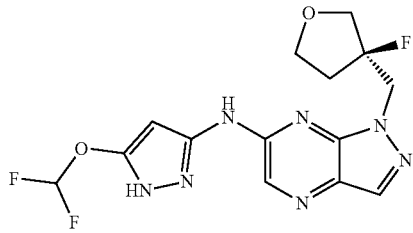<br>Amine-1; RCl: 6-chloro-1-((3-fluorotetrahydrofuran-3-yl)methyl)-1H-pyrazolo[3,4-b]pyrazine (Preparation 101); tBuXPhos Pd G3 Prep-HPLC-2; SFC: (Daicel AD 20 x 250 mm, 10 mm; 20% MeOH (0.2% MeOH/NH$_3$) in CO$_2$<br>Peak 1, Example 167, (S)-N-(5-(difluoromethoxy)-1H-pyrazol-3-yl)-1-((3-fluorotetrahydrofuran-3-yl)methyl)-1H-pyrazolo[3,4-b]pyrazin-6-amine or (R)-N-(5-(difluoromethoxy)-1H-pyrazol-3-yl)-1-((3-fluorotetrahydrofuran-3-yl)methyl)-1H-pyrazolo[3,4-b]pyrazin-6-amine, white solid; LCMS m/z = 370 [M + H]$^+$; $^1$H NMR (400 MHz, DMSO-d$_6$) δ: 12.22 (s, 1H), 10.87 (s, 1H), 8.22-8.20 (m, 2H), 7.30 (t, 1H), 5.90 (s, 1H,), 5.11-4.90 (m, 2H), 4.05-3.75 (m, 4H), 2.41-2.25 (m, 1H), 2.16-2.01 (m, 1H).<br>Peak 2, Example 168, (R)-N-(5-(difluoromethoxy)-1H-pyrazol-3-yl)-1-((3-fluorotetrahydrofuran-3-yl)methyl)-1H-pyrazolo[3,4-b]pyrazin-6-amine or (S)-N-(5-(difluoromethoxy)-1H-pyrazol-3-yl)-1-((3-fluorotetrahydrofuran-3-yl)methyl)-1H-pyrazolo[3,4-b]pyrazin-6-amine, white solid; LCMS m/z = 370 [M + H]$^+$; $^1$H NMR (400 MHz, DMSO-d$_6$) δ: 8.18 (d, 2H), 7.30 (t, 1H), 5.93 (s, 1H), 5.07 (t, 1H), 4.88 (dd, 1H), 4.04-3.75 (m, 4H), 3.37 (br s, 2H), 2.50-2.00 (m, 2H). |
| 169 and 170 | (S)-3-((6-((5-(difluoromethoxy)-1H-pyrazol-3-yl)amino)-1H-pyrazolo[3,4-b]pyrazin-1-yl)methyl)tetrahydrofuran-3-carbonitrile and (R)-3-((6-((5-(difluoromethoxy)-1H-pyrazol-3-yl)amino)-1H-pyrazolo[3,4-b]pyrazin-1-yl)methyl)tetrahydrofuran-3-carbonitrile<br>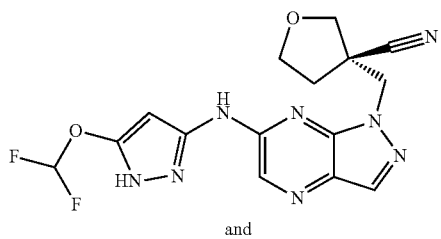<br>and<br>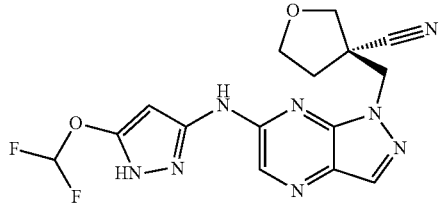 |

| Example No. | Name/Structure/Reactants/Cat/HPLC/SFC/Data |
|---|---|
| | Amine-1; RCl: 3-((6-chloro-1H-pyrazolo[3,4-b]pyrazin-1-yl)methyl)tetrahydrofuran-3-carbonitrile (Preparation 102)<br>prep-HPLC-2; SFC: Daicel AD 20 x 250 mm, 10 mm; 20% MeOH (0.5% MeOH/NH$_3$) in CO$_2$<br>Peak 1, Example 169, (S)-3-((6-((5-(difluoromethoxy)-1H-pyrazol-3-yl)amino)-1H-pyrazolo[3,4-b]pyrazin-1-yl)methyl)tetrahydrofuran-3-carbonitrile or (R)-3-((6-((5-(difluoromethoxy)-1H-pyrazol-3-yl)amino)-1H-pyrazolo[3,4-b]pyrazin-1-yl)methyl)tetrahydrofuran-3-carbonitrile, white solid; LCMS m/z = 377 [M + H]$^+$; $^1$H NMR (400 MHz, DMSO-d$_6$) δ: 12.27 (br s, 1H), 10.95 (br s, 1H), 8.27 (s, 1H), 8.23 (s, 1H), 7.31 (t, 1H), 5.89 (s, 1H,), 5.06 (d, 1H), 4.80 (d, 1H), 4.03 (s, 2H), 3.91 (t, 2H), 2.39 (t, 2H).<br>Peak 2, Example 170, (R)-3-((6-((5-(difluoromethoxy)-1H-pyrazol-3-yl)amino)-1H-pyrazolo[3,4-b]pyrazin-1-yl)methyl)tetrahydrofuran-3-carbonitrile or (S)-3-((6-((5-(difluoromethoxy)-1H-pyrazol-3-yl)amino)-1H-pyrazolo[3,4-b]pyrazin-1-yl)methyl)tetrahydrofuran-3-carbonitrile, white solid; LCMS m/z = 377 [M + H]$^+$; $^1$H NMR (400 MHz, DMSO-d$_6$) δ: 12.22 (br s, 1H), 11.03 (br s, 1H), 8.26 (s, 1H), 8.23 (s, 1H), 7.31 (t, 1H), 5.91 (br s, 1H), 5.06 (d, 1H), 4.80 (d, 1H), 4.03 (s, 2H), 3.90 (dd, 2H), 2.39 (t, 2H). |
| 171 and 172 | (1s,4s)-4-((6-((5-(difluoromethoxy)-1H-pyrazol-3-yl)amino)-1H-pyrazolo[3,4-b]pyrazin-1-yl)methyl)cyclohexan-1-ol and (1r,4r)-4-((6-((5-(difluoromethoxy)-1H-pyrazol-3-yl)amino)-1H-pyrazolo[3,4-b]pyrazin-1-yl)methyl)cyclohexan-1-ol<br>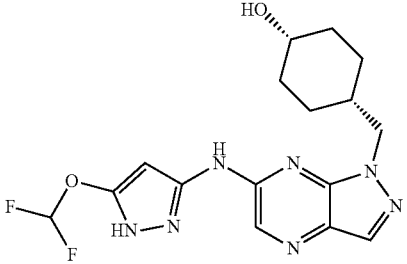<br>and<br>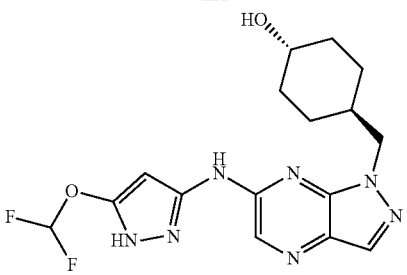<br>Amine-1; RCl: 4-((6-chloro-1H-pyrazolo[3,4-b]pyrazin-1-yl)methyl)cyclohexan-1-ol (Preparation 158); tBuXPhos Pd G3<br>prep-HPLC-5; SFC Daicel IG 20 x 250 mm, 10 mm; 30% MeOH (0.2% MeOH/NH$_3$) in CO$_2$<br>Peak 1, Example 171, (1s,4s)-4-((6-((5-(difluoromethoxy)-1H-pyrazol-3-yl)amino)-1H-pyrazolo[3,4-b]pyrazin-1-yl)methyl)cyclohexan-1-ol or (1r,4r)-4-((6-((5-(difluoromethoxy)-1H-pyrazol-3-yl)amino)-1H-pyrazolo[3,4-b]pyrazin-1-yl)methyl)cyclohexan-1-ol, white solid; LCMS m/z = 380 [M + H]$^+$; $^1$H NMR (400 MHz, DMSO-d$_6$) δ: 12.26 (br s, 1H), 10.78 (br s, 1H), 8.19 (s, 1H), 8.13 (s, 1H), 7.31 (t, 1H), 5.95 (s, 1H), 4.90-4.85 (m, 1H), 4.50 (t, 1H), 3.38-3.30 (m, 2H), 1.96-1.88 (m, 6H), 1.50-1.46 (m, 1H), 1.26-1.15 (m, 2H).<br>Peak 2, Example 172, (1r,4r)-4-((6-((5-(difluoromethoxy)-1H-pyrazol-3-yl)amino)-1H-pyrazolo[3,4-b]pyrazin-1-yl)methyl)cyclohexan-1-ol or (1s,4s)-4-((6-((5-(difluoromethoxy)-1H-pyrazol-3-yl)amino)-1H-pyrazolo[3,4-b]pyrazin-1-yl)methyl)cyclohexan-1-ol, white solid; LCMS m/z = 380 [M + H]$^+$; $^1$H NMR (400 MHz, DMSO-d$_6$) δ: 12.35-12.10 (br, 1H), 10.85-10.65 (br, 1H), 8.20 (s, 1H), 8.14 (s, 1H), 7.31 (t, 1H), 6.02 (br s, 1H), 4.43 (d, 2H), 4.29 (d, 2H), 3.75-3.70 (m, 1H), 1.99-1.95 (m, 1H), 1.61-1.56 (m, 2H), 1.45-1.26 (m, 4H), 1.25-1.22 (m, 2H). |

| Example No. | Name/Structure/Reactants/Cat/HPLC/SFC/Data |
| --- | --- |
| 173 and 174 | (S)-N-(5-(difluoromethoxy)-1H-pyrazol-3-yl)-1-(1-(4-fluoropyridin-3-yl)ethyl)-1H-pyrazolo[3,4-b]pyrazin-6-amine and (R)-N-(5-(difluoromethoxy)-1H-pyrazol-3-yl)-1-(1-(4-fluoropyridin-3-yl)ethyl)-1H-pyrazolo[3,4-b]pyrazin-6-amine 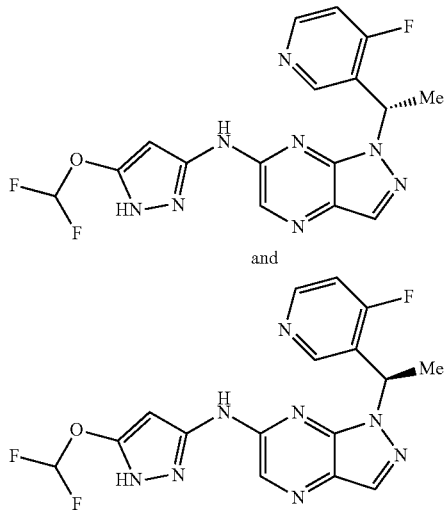 [SMILES: C[C@@H](c1cnccc1F)n1ncc2ncc(Nc3cc(OC(F)F)[nH]n3)nc21 ; C[C@H](c1cnccc1F)n1ncc2ncc(Nc3cc(OC(F)F)[nH]n3)nc21]  and  Amine-1; RCl: 6-chloro-1-(1-(4-fluoropyridin-3-yl)ethyl)-1H-pyrazolo[3,4-b]pyrazine (Preparation 146); BrettPhos Pd G4 SiO2, 75% EtOAc/PE; SFC: Daicel OX 20 x 250 mm, 10 mm; 35% MeOH (0.2% MeOH/NH$_3$) in CO$_2$ Peak 1, Example 173, (S)-N-(5-(difluoromethoxy)-1H-pyrazol-3-yl)-1-(1-(4-fluoropyridin-3-yl)ethyl)-1H-pyrazolo[3,4-b]pyrazin-6-amine or (R)-N-(5-(difluoromethoxy)-1H-pyrazol-3-yl)-1-(1-(4-fluoropyridin-3-yl)ethyl)-1H-pyrazolo[3,4-b]pyrazin-6-amine, white solid; LCMS m/z = 391 [M + H]$^+$; $^1$H NMR (400 MHz, DMSO-d$_6$) δ: 12.50-11.90 (br s, 1H), 11.30-10.85 (br s, 1H), 8.53 (d, 1H), 8.37 (d, 1H), 8.24 (s, 1H), 8.20 (s, 1H), 7.35-7.27 (m, 1H), 7.29 (t, 1H), 6.73-6.70 (m, 1H), 5.95 (s, 1H), 1.90 (d, 3H). Peak 2, Example 174, (R)-N-(5-(difluoromethoxy)-1H-pyrazol-3-yl)-1-(1-(4-fluoropyridin-3-yl)ethyl)-1H-pyrazolo[3,4-b]pyrazin-6-amine or (S)-N-(5-(difluoromethoxy)-1H-pyrazol-3-yl)-1-(1-(4-fluoropyridin-3-yl)ethyl)-1H-pyrazolo[3,4-b]pyrazin-6-amine, white solid; LCMS m/z = 391 [M + H]$^+$; $^1$H NMR (400 MHz, DMSO-d$_6$) δ: 12.25 (br s, 1H), 10.94 (br s, 1H), 8.53 (d, 1H), 8.37 (d, 1H), 8.28 (d, 2H), 7.30-7.20 (m, 2H), 6.73 (br s, 1H), 5.94 (br s, 1H), 1.90 (d, 3H). |

| Example No. | Name/Structure/Reactants/Cat/HPLC/SFC/Data |
| --- | --- |
| 175 and 176 | (R)-1-(6-((5-(difluoromethoxy)-1H-pyrazol-3-yl)amino)-1-((tetrahydro-2H-pyran-4-yl)methyl)-1H-pyrazolo[3,4-b]pyrazin-3-yl)ethan-1-ol and (S)-1-(6-((5-(difluoromethoxy)-1H-pyrazol-3-yl)amino)-1-((tetrahydro-2H-pyran-4-yl)methyl)-1H-pyrazolo[3,4-b]pyrazin-3-yl)ethan-1-ol 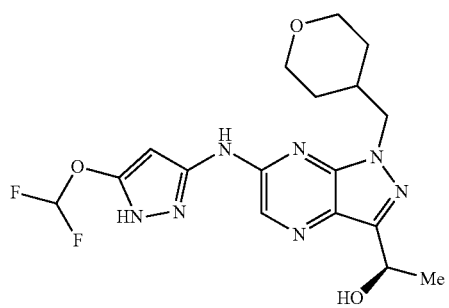 and 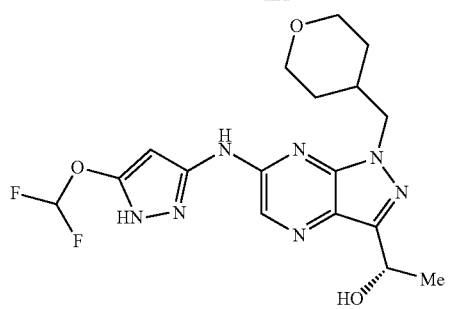 Amine-1; RCl: 1-(6-chloro-1-((tetrahydro-2H-pyran-4-yl)methyl)-1H-pyrazolo[3,4-b]pyrazin-3-yl)ethan-1-ol (Preparation 75); BrettPhos Pd G4 Reverse phase Isco (0 to 70% MeCN/water + 0.1% TFA). Neutralized with NaHCO$_3$.; SFC: Daicel OJ 20 x 250 mm, 10 mm; 30% MeOH (0.2% MeOH/NH$_3$) in CO$_2$ Peak 1, Example 175, (R)-1-(6-((5-(difluoromethoxy)-1H-pyrazol-3-yl)amino)-1-((tetrahydro-2H-pyran-4-yl)methyl)-1H-pyrazolo[3,4-b]pyrazin-3-yl)ethan-1-ol or (S)-1-(6-((5-(difluoromethoxy)-1H-pyrazol-3-yl)amino)-1-((tetrahydro-2H-pyran-4-yl)methyl)-1H-pyrazolo[3,4-b]pyrazin-3-yl)ethan-1-ol, white solid; LCMS m/z = 410 [M + H]$^+$; $^1$H NMR (400 MHz, DMSO-d$_6$) δ: 12.15 (s, 1H), 10.76 (s, 1H), 8.16 (s, 1H), 7.30 (t, 1H), 5.97 (s, 1H), 5.20 (d, 1H), 5.04 (q, 1H), 4.31 (d, 2H), 3.83-3.80 (m, 2H), 3.24-3.20 (m, 2H), 2.16-2.11 (m, 1H), 1.58 (d, 3H), 1.42-1.27 (m, 6H). Peak 2, Example 176, (S)-1-(6-((5-(difluoromethoxy)-1H-pyrazol-3-yl)amino)-1-((tetrahydro-2H-pyran-4-yl)methyl)-1H-pyrazolo[3,4-b]pyrazin-3-yl)ethan-1-ol or (R)-1-(6-((5-(difluoromethoxy)-1H-pyrazol-3-yl)amino)-1-((tetrahydro-2H-pyran-4-yl)methyl)-1H-pyrazolo[3,4-b]pyrazin-3-yl)ethan-1-ol, white solid; LCMS m/z = 410 [M + H]$^+$; $^1$H NMR (400 MHz, DMSO-d$_6$) δ: 12.15 (s, 1H), 10.75 (s, 1H), 8.16 (s, 1H), 7.30 (t, 1H), 5.97 (s, 1H), 5.20 (d, 1H), 5.04 (q, 1H), 4.31 (d, 2H), 3.83-3.80 (m, 2H), 3.24-3.20 (m, 2H), 2.16-2.11 (m, 1H), 1.58 (d, 3H), 1.42-1.27 (m, 6H). |

| Example No. | Name/Structure/Reactants/Cat/HPLC/SFC/Data |
| --- | --- |
| 177 and 178 | (R)-1-(6-((5-(difluoromethoxy)-1H-pyrazol-3-yl)amino)-1-((S)-1-(pyridin-3-yl)ethyl)-1H-pyrazolo[3,4-b]pyrazin-3-yl)ethan-1-ol and (S)-1-(6-((5-(difluoromethoxy)-1H-pyrazol-3-yl)amino)-1-((S)-1-(pyridin-3-yl)ethyl)-1H-pyrazolo[3,4-b]pyrazin-3-yl)ethan-1-ol 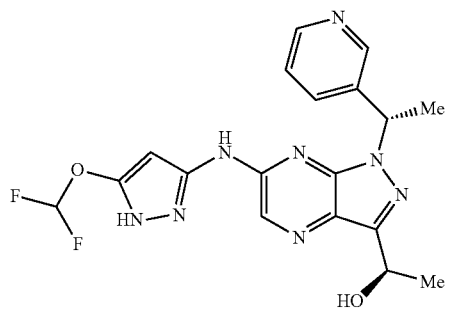 and 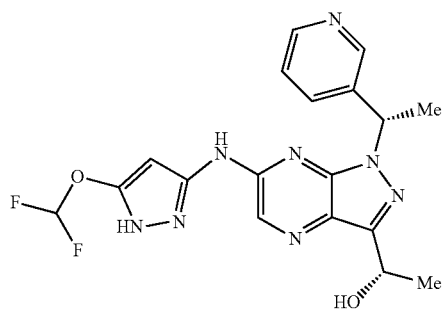 Amine-1; RCl: 1-(6-chloro-1-((S)-1-(pyridin-3-yl)ethyl)-1H-pyrazolo[3,4-b]pyrazin-3-yl)ethan-1-ol (Preparation 77); BrettPhos Pd G4 Reverse Phase-ISCO: (0 to 80% MeCN/water + 0.1% TFA). Neutralized with NaHCO$_3$; SFC: Daicel OD 20 x 250 mm, 10 mm; 30% MeOH (0.2% MeOH/NH$_3$) in CO$_2$ Peak 1, Example 177, (R)-1-(6-((5-(difluoromethoxy)-1H-pyrazol-3-yl)amino)-1-((S)-1-(pyridin-3-yl)ethyl)-1H-pyrazolo[3,4-b]pyrazin-3-yl)ethan-1-ol or (S)-1-(6-((5-(difluoromethoxy)-1H-pyrazol-3-yl)amino)-1-((S)-1-(pyridin-3-yl)ethyl)-1H-pyrazolo[3,4-b]pyrazin-3-yl)ethan-1-ol, white solid; LCMS m/z = 417 [M + H]$^+$; $^1$H NMR (400 MHz, DMSO-d$_6$) δ: 12.25 (br s, 1H), 10.81 (br s, 1H), 8.57 (d, 1H), 8.44 (dd, 1H), 8.16 (s, 1H), 7.73 (dt, 1H), 7.33 (dd, 1H), 7.31 (t, 1H), 6.55-6.50 (m, 1H), 5.92 (s, 1H), 5.25-5.22 (m, 1H), 5.07-5.03 (m, 1H), 1.89 (d, 3H), 1.58 (d, 3H). Peak 2, Example 178, (S)-1-(6-((5-(difluoromethoxy)-1H-pyrazol-3-yl)amino)-1-((S)-1-(pyridin-3-yl)ethyl)-1H-pyrazolo[3,4-b]pyrazin-3-yl)ethan-1-ol or (R)-1-(6-((5-(difluoromethoxy)-1H-pyrazol-3-yl)amino)-1-((S)-1-(pyridin-3-yl)ethyl)-1H-pyrazolo[3,4-b]pyrazin-3-yl)ethan-1-ol, white solid; LCMS m/z = 417 [M + H]$^+$; $^1$H NMR (400 MHz, DMSO-d$_6$) δ: 12.50-10.50 (br, 2H), 8.57 (d, 1H), 8.44 (dd, 1H), 8.16 (s, 1H), 7.73 (dt, 1H), 7.33 (dd, 1H), 7.31 (t, 1H), 6.55-6.50 (m, 1H), 5.92 (s, 1H), 5.25-5.22 (m, 1H), 5.07-5.03 (m, 1H), 1.89 (d, 3H), 1.58 (d, 3H). |

| Example No. | Name/Structure/Reactants/Cat/HPLC/SFC/Data |
| --- | --- |
| 179 and 180 | (1R,2S)-2-((6-((5-(difluoromethoxy)-1H-pyrazol-3-yl)amino)-1H-pyrazolo[3,4-b]pyrazin-1-yl)methyl)cyclopropan-1-ol and (1S,2R)-2-((6-((5-(difluoromethoxy)-1H-pyrazol-3-yl)amino)-1H-pyrazolo[3,4-b]pyrazin-1-yl)methyl)cyclopropan-1-ol 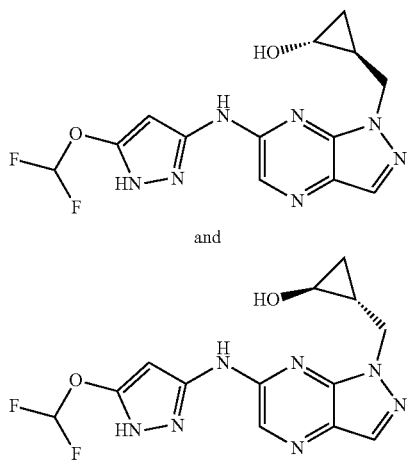 [SMILES: O[C@@H]1C[C@H]1Cn1ncc2ncc(Nc3cc(OC(F)F)[nH]n3)nc21 ; O[C@H]1C[C@@H]1Cn1ncc2ncc(Nc3cc(OC(F)F)[nH]n3)nc21] Amine-1; RCl: 2-((6-chloro-1H-pyrazolo[3,4-b]pyrazin-1-yl)methyl)cyclopropan-1-ol (Preparation 185); BrettPhos Pd G4 prep-HPLC-1 ; SFC: Daicel OD 20 x 250 mm, 10 mm; % MeOH (0.2% MeOH/NH$_3$) in CO$_2$<br>Peak 1, Example 179, (1R,2S)-2-((6-((5-(difluoromethoxy)-1H-pyrazol-3-yl)amino)-1H-pyrazolo[3,4-b]pyrazin-1-yl)methyl)cyclopropan-1-ol or (1S,2R)-2-((6-((5-(difluoromethoxy)-1H-pyrazol-3-yl)amino)-1H-pyrazolo[3,4-b]pyrazin-1-yl)methyl)cyclopropan-1-ol; LCMS m/z = 338 [M + H]$^+$; $^1$H NMR (400 MHz, DMSO-d$_6$) δ: 12.28 (br s, 1H, 10.90 (br s, 1H), 8.20 (s, 1H), 8.15 (s, 1H), 7.28 (t, 1H), 5.94 (br s, 1H), 5.62 (br s, 1H), 4.49 (ddd, 2H), 1.23-1.17 (m, 1H), 0.65-0.62 (m, 1H), 0.42-0.40 (m, 1H).<br>Peak 2, Example 180, (1S,2R)-2-((6-((5-(difluoromethoxy)-1H-pyrazol-3-yl)amino)-1H-pyrazolo[3,4-b]pyrazin-1-yl)methyl)cyclopropan-1-ol or (1R,2S)-2-((6-((5-(difluoromethoxy)-1H-pyrazol-3-yl)amino)-1H-pyrazolo[3,4-b]pyrazin-1-yl)methyl)cyclopropan-1-ol; LCMS m/z = 338 [M + H]$^+$; $^1$H NMR (400 MHz, DMSO-d$_6$) δ: 12.40-12.12 (br, 1H), 11.05-10.80 (br, 1H), 8.21 (s, 1H), 8.15 (s, 1H), 7.28 (t, 1H), 6.00-5.92 (m, 1H), 5.62 (br s, 1H), 4.52-4.46 (m, 2H), 3.42-3.33 (m, 2H), 1.21-1.15 (m, 1H), 0.65-0.62 (m, 1H), 0.41-0.40 (m, 1H). |

| Example No. | Name/Structure/Reactants/Cat/HPLC/SFC/Data |
|---|---|
| 181 and 182 | (R)-1-(6-((5-(difluoromethoxy)-1H-pyrazol-3-yl)amino)-1-((S)-1-(tetrahydro-2H-pyran-4-yl)ethyl)-1H-pyrazolo[3,4-b]pyrazin-3-yl)ethan-1-ol and (S)-1-(6-((5-(difluoromethoxy)-1H-pyrazol-3-yl)amino)-1-((S)-1-(tetrahydro-2H-pyran-4-yl)ethyl)-1H-pyrazolo[3,4-b]pyrazin-3-yl)ethan-1-ol<br>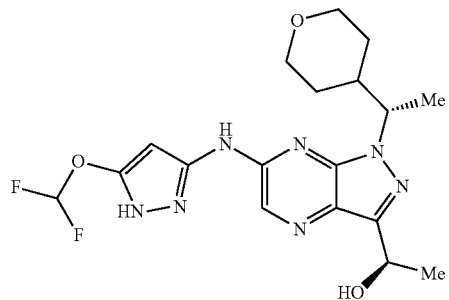<br>and<br>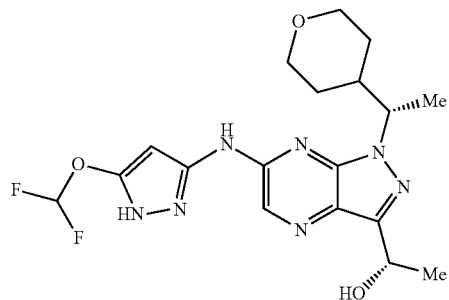<br>Amine-1; RCl: 1-(6-chloro-1-((S)-1-(tetrahydro-2H-pyran-4-yl)ethyl)-1H-pyrazolo[3,4-b]pyrazin-3-yl)ethan-1-ol (Preparation 76); tBuXPhos Pd G3<br>Isco: $SiO_2$ (0 to 8% MeOH/DCM); SFC: Daicel OZ 20 x 250 mm, 10 mm; 30% MeOH (0.2% MeOH/$NH_3$) in $CO_2$<br>Peak 1, Example 181, (R)-1-(6-((5-(difluoromethoxy)-1H-pyrazol-3-yl)amino)-1-((S)-1-(tetrahydro-2H-pyran-4-yl)ethyl)-1H-pyrazolo[3,4-b]pyrazin-3-yl)ethan-1-ol or (S)-1-(6-((5-(difluoromethoxy)-1H-pyrazol-3-yl)amino)-1-((S)-1-(tetrahydro-2H-pyran-4-yl)ethyl)-1H-pyrazolo[3,4-b]pyrazin-3-yl)ethan-1-ol;<br>LCMS m/z = 424 [M + H]$^+$; $^1$H NMR (400 MHz, DMSO-$d_6$) δ: 12.16 (s, 1H), 10.75 (s, 1H), 8.17 (s, 1H), 7.30 (t, 1H), 5.94 (s, 1H), 5.19 (d, 1H), 5.05-5.02 (m, 1H), 4.92-4.85 (m, 1H), 3.90-3.85 (m, 1H), 3.72-3.67 (m, 1H), 3.30-3.26 (m, 1H), 3.14-3.07 (m, 1H), 2.07-2.03 (m, 1H), 1.76-1.71 (m, 1H), 1.59 (d, 3H), 1.46 (d, 3H), 1.39-1.33 (m, 1H), 1.20-1.15 (m, 1H), 0.82-0.77 (m, 1H).<br>Peak 2, Example 182, (S)-1-(6-((5-(difluoromethoxy)-1H-pyrazol-3-yl)amino)-1-((S)-1-(tetrahydro-2H-pyran-4-yl)ethyl)-1H-pyrazolo[3,4-b]pyrazin-3-yl)ethan-1-ol or (R)-1-(6-((5-(difluoromethoxy)-1H-pyrazol-3-yl)amino)-1-((S)-1-(tetrahydro-2H-pyran-4-yl)ethyl)-1H-pyrazolo[3,4-b]pyrazin-3-yl)ethan-1-ol;<br>LCMS m/z = 424 [M + H]$^+$; $^1$H NMR (400 MHz, DMSO-$d_6$) δ: 12.16 (s, 1H), 10.75 (s, 1H), 8.17 (s, 1H), 7.30 (t, 1H), 5.94 (s, 1H), 5.19 (d, 1H), 5.05-5.02 (m, 1H), 4.92-4.85 (m, 1H), 3.90-3.85 (m, 1H), 3.72-3.67 (m, 1H), 3.30-3.26 (m, 1H), 3.14-3.07 (m, 1H), 2.07-2.03 (m, 1H), 1.76-1.71 (m, 1H), 1.59 (d, 3H), 1.46 (d, 3H), 1.39-1.33 (m, 1H), 1.20-1.15 (m, 1H), 0.82-0.77 (m, 1H). |

| Example No. | Name/Structure/Reactants/Cat/HPLC/SFC/Data |
|---|---|
| 31 and 183 | (R)-N-(5-(difluoromethoxy)-1H-pyrazol-3-yl)-1-(2-fluoro-1-(tetrahydro-2H-pyran-4-yl)ethyl)-1H-pyrazolo[3,4-b]pyrazin-6-amine and (S)-N-(5-(difluoromethoxy)-1H-pyrazol-3-yl)-1-(2-fluoro-1-(tetrahydro-2H-pyran-4-yl)ethyl)-1H-pyrazolo[3,4-b]pyrazin-6-amine 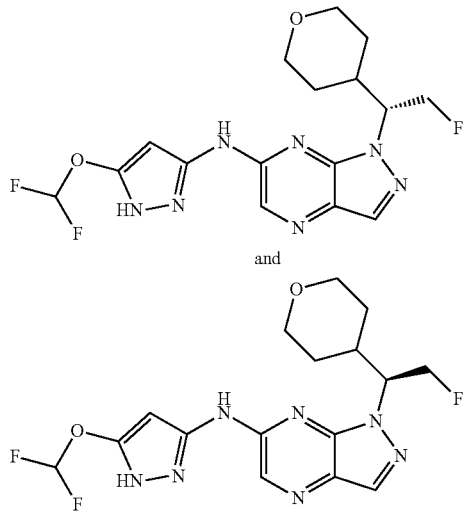 [SMILES: FC[C@@H](C1CCOCC1)n1ncc2ncc(Nc3cc(OC(F)F)[nH]n3)nc21 ; FC[C@H](C1CCOCC1)n1ncc2ncc(Nc3cc(OC(F)F)[nH]n3)nc21] Amine-1; RCl: 6-chloro-1-(2-fluoro-1-(tetrahydro-2H-pyran-4-yl)ethyl)-1H-pyrazolo[3,4-b]pyrazine (Preparation 165); BrettPhos Pd G4<br>Isco: SiO$_2$ (75% EtOAc/PE).<br>SFC: Daicel OX 20 x 250 mm, 10 mm; 25% IPA (0.2% MeOH/NH$_3$) in CO$_2$<br>Peak 1, Example 31, (R)-N-(5-(difluoromethoxy)-1H-pyrazol-3-yl)-1-(2-fluoro-1-(tetrahydro-2H-pyran-4-yl)ethyl)-1H-pyrazolo[3,4-b]pyrazin-6-amine.<br>Peak 2, Example 183, (S)-N-(5-(difluoromethoxy)-1H-pyrazol-3-yl)-1-(2-fluoro-1-(tetrahydro-2H-pyran-4-yl)ethyl)-1H-pyrazolo[3,4-b]pyrazin-6-amine; LCMS m/z = 398 [M + H]$^+$; $^1$H NMR (400 MHz, DMSO-d$_6$) δ: 12.21 (br s, 1H), 10.85 (br s, 1H), 8.23 (s, 1H), 8.21 (s, 1H), 7.31 (t, 1H), 5.90 (s, 1H), 5.40-5.30 (m, 1H), 5.05-4.95 (m, 1H), 4.90-4.85 (m, 1H), 3.88-3.84 (m, 1H), 3.72-3.69 (m, 1H), 3.33-3.25 (m, 1H), 3.17-3.12 (m, 1H), 2.21-2.18 (m, 1H), 1.77-1.74 (m, 1H), 1.50-1.40 (m, 1H), 1.35-1.25 (m, 1H), 0.86-0.83 (m, 1H). |
| 184 and 185 | (R)-3-((6-((5-(difluoromethoxy)-1H-pyrazol-3-yl)amino)-1H-pyrazolo[3,4-b]pyrazin-1-yl)methyl)-5,5-dimethylpyrrolidin-2-one and (S)-3-((6-((5-(difluoromethoxy)-1H-pyrazol-3-yl)amino)-1H-pyrazolo[3,4-b]pyrazin-1-yl)methyl)-5,5-dimethylpyrrolidin-2-one 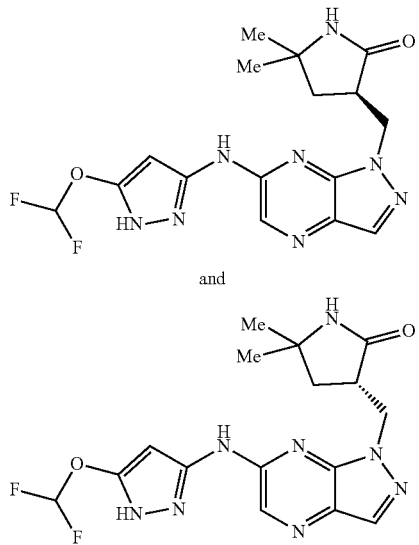 [SMILES: CC1(C)C[C@H](Cn2ncc3ncc(Nc4cc(OC(F)F)[nH]n4)nc32)C(=O)N1 ; CC1(C)C[C@@H](Cn2ncc3ncc(Nc4cc(OC(F)F)[nH]n4)nc32)C(=O)N1] |

| Example No. | Name/Structure/Reactants/Cat/HPLC/SFC/Data |
|---|---|
| | Amine-1; RCl: 3-((6-chloro-1H-pyrazolo[3,4-b]pyrazin-1-yl)methyl)-5,5-dimethylpyrrolidin-2-one (Preparation 166); tBuXPhos Pd G3 prep-HPLC-1; SFC: Daicel OJ 20 x 250 mm, 10 mm; 35% MeOH (0.2% MeOH/NH$_3$) in CO$_2$<br>Peak 1, Example 184, (R)-3-((6-((5-(difluoromethoxy)-1H-pyrazol-3-yl)amino)-1H-pyrazolo[3,4-b]pyrazin-1-yl)methyl)-5,5-dimethylpyrrolidin-2-one or (S)-3-((6-((5-(difluoromethoxy)-1H-pyrazol-3-yl)amino)-1H-pyrazolo[3,4-b]pyrazin-1-yl)methyl)-5,5-dimethylpyrrolidin-2-one; LCMS m/z = 393 [M + H]$^+$; $^1$H NMR (400 MHz, DMSO-d$_6$) δ: 12.37 (s, 1H), 10.83 (s, 1H), 8.19 (d, 2H), 7.94 (s, 1H), 7.31 (t, 1H), 5.86 (s, 1H), 4.85-4.70 (m, 1H), 4.54 (dd, 1H), 3.10-3.00 (m, 1H), 1.85 (dd, 1H), 1.70 (dd, 1H), 1.11 (s, 3H), 1.01 (s, 3H).<br>Peak 2, Example 185, (S)-3-((6-((5-(difluoromethoxy)-1H-pyrazol-3-yl)amino)-1H-pyrazolo[3,4-b]pyrazin-1-yl)methyl)-5,5-dimethylpyrrolidin-2-one or (R)-3-((6-((5-(difluoromethoxy)-1H-pyrazol-3-yl)amino)-1H-pyrazolo[3,4-b]pyrazin-1-yl)methyl)-5,5-dimethylpyrrolidin-2-one; LCMS m/z = 393 [M + H]$^+$; $^1$H NMR (400 MHz, DMSO-d$_6$) δ: 12.37 (s, 1H), 10.82 (s, 1H), 8.19 (s, 1H), 8.18 (s, 1H), 7.93 (s, 1H), 7.30 (t, 1H), 5.83 (s, 1H), 4.80-4.72 (m, 1H), 4.58-4.51 (m, 1H), 3.12-3.03 (m, 1H), 1.86-1.82 (m, 1H), 1.71-1.65 (m, 1H), 1.10 (s, 3H), 1.00 (s, 3H). |
| 186 and 187 | (S)-1-(1-(4-fluoropyridin-2-yl)ethyl)-N-(5-methoxy-1H-pyrazol-3-yl)-1H-pyrazolo[3,4-b]pyrazin-6-amine and (R)-1-(1-(4-fluoropyridin-2-yl)ethyl)-N-(5-methoxy-1H-pyrazol-3-yl)-1H-pyrazolo[3,4-b]pyrazin-6-amine<br>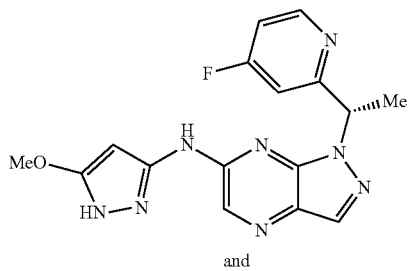<br>and<br>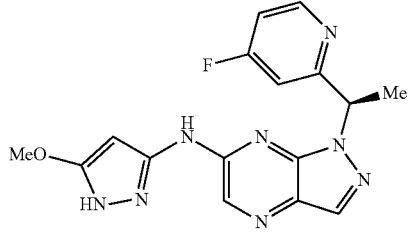<br>Amine-3; RCl: 6-chloro-1-(1-(4-fluoropyridin-2-yl)ethyl)-1H-pyrazolo[3,4-b]pyrazine (Preparation 83); BrettPhos Pd G4 Prep-HPLC-4; SFC: Daicel AD-H 20 x 250 mm, 10 mm; 25% IPA (1% NH$_3$ 7M in MeOH) in CO$_2$<br>Peak 1, Example 186, (S)-1-(1-(4-fluoropyridin-2-yl)ethyl)-N-(5-methoxy-1H-pyrazol-3-yl)-1H-pyrazolo[3,4-b]pyrazin-6-amine or (R)-1-(1-(4-fluoropyridin-2-yl)ethyl)-N-(5-methoxy-1H-pyrazol-3-yl)-1H-pyrazolo[3,4-b]pyrazin-6-amine; LCMS m/z = 355 [M + H]$^+$; $^1$H NMR (400 MHz, DMSO-d$_6$) δ: 11.74 (br s, 1H), 10.59 (br s, 1H), 8.56 (dd, 1H), 8.23-8.19 (m, 2H), 7.27-7.25 (m, 1H), 6.99-6.97 (m, 1H), 6.37 (br s, 1H,), 5.65 (br s, 1H), 3.80 (s, 3H), 1.94 (d, 3H).<br>Peak 2 Example 187, (R)-1-(1-(4-fluoropyridin-2-yl)ethyl)-N-(5-methoxy-1H-pyrazol-3-yl)-1H-pyrazolo[3,4-b]pyrazin-6-amine or (S)-1-(1-(4-fluoropyridin-2-yl)ethyl)-N-(5-methoxy-1H-pyrazol-3-yl)-1H-pyrazolo[3,4-b]pyrazin-6-amine; LCMS m/z = 355 [M + H]$^+$; $^1$H NMR (400 MHz, DMSO-d$_6$) δ: 11.74 (br s, 1H), 10.62 (br s, 1H), 8.60-8.55 (m, 1H), 7.30-7.20 (m, 1H), 6.99 (d, 1H), 6.42 (br s, 1H), 5.57 (br s, 1H), 3.80 (s, 3H), 1.94 (d, 3H). |

| Example No. | Name/Structure/Reactants/Cat/HPLC/SFC/Data |
|---|---|
| 188 and 189 | (S)-1-(1-(4-chloropyridin-2-yl)ethyl)-N-(5-(difluoromethoxy)-1H-pyrazol-3-yl)-1H-pyrazolo[3,4-b]pyrazin-6-amine and (R)-1-(1-(4-chloropyridin-2-yl)ethyl)-N-(5-(difluoromethoxy)-1H-pyrazol-3-yl)-1H-pyrazolo[3,4-b]pyrazin-6-amine 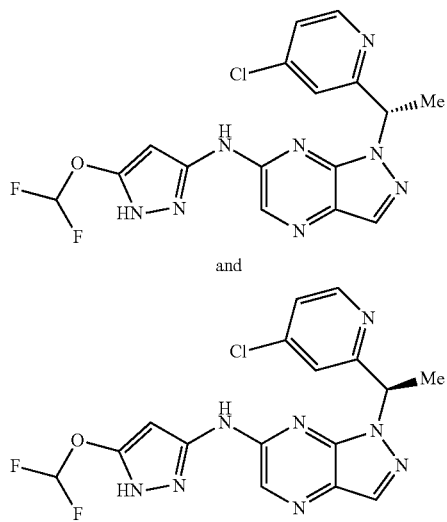 [SMILES: C[C@@H](c1cc(Cl)ccn1)n1ncc2ncc(Nc3cc(OC(F)F)[nH]n3)nc21 ; C[C@H](c1cc(Cl)ccn1)n1ncc2ncc(Nc3cc(OC(F)F)[nH]n3)nc21] and Amine-1; 6-chloro-1-(1-(4-chloropyridin-2-yl)ethyl)-1H-pyrazolo[3,4-b]pyrazine (Preparation 148); BrettPhos Pd G4 prep-HPLC-3; SFC: Daicel OJ 20 x 250 mm, 10 mm; 15% MeOH (0.2% DEA in CO$_2$ Peak 1, Example 188, (S)-1-(1-(4-chloropyridin-2-yl)ethyl)-N-(5-(difluoromethoxy)-1H-pyrazol-3-yl)-1H-pyrazolo[3,4-b]pyrazin-6-amine or (R)-1-(1-(4-chloropyridin-2-yl)ethyl)-N-(5-(difluoromethoxy)-1H-pyrazol-3-yl)-1H-pyrazolo[3,4-b]pyrazin-6-amine; LCMS m/z = 407 [M + H]$^+$; $^1$H NMR (400 MHz, DMSO-d$_6$) δ: 12.31 (br s, 1H), 10.85 (br s, 1H), 8.52 (d, 1H), 8.23 (s, 1H), 8.21 (s, 1H), 7.48-7.44 (m, 1H), 7.19-7.11 (m, 2H), 6.55-6.52 (m, 1H), 5.84 (s, 1H), 1.93 (d, 3H). Peak 2, Example 189, (R)-1-(1-(4-chloropyridin-2-yl)ethyl)-N-(5-(difluoromethoxy)-1H-pyrazol-3-yl)-1H-pyrazolo[3,4-b]pyrazin-6-amine or (S)-1-(1-(4-chloropyridin-2-yl)ethyl)-N-(5-(difluoromethoxy)-1H-pyrazol-3-yl)-1H-pyrazolo[3,4-b]pyrazin-6-amine; LCMS m/z = 407 [M + H]$^+$; $^1$H NMR (400 MHz, DMSO-d$_6$) δ: 12.32 (br s, 1H), 10.80 (br s, 1H), 8.52 (d, 1H), 8.22 (d, 2H), 7.50-7.40 (m, 1H), 7.20-7.10 (m, 2H), 6.53 (br s, 1H), 5.85 (br s, 1H), 1.93 (d, 3H). |

-continued

| Example No. | Name/Structure/Reactants/Cat/HPLC/SFC/Data |
|---|---|
| 190 and 191 | (1r,3r)-3-((6-((5-(difluoromethoxy)-1H-pyrazol-3-yl)amino)-1H-pyrazolo[3,4-b]pyrazin-1-yl)methyl)cyclobutane-1-carbonitrile and (1s,3s)-3-((6-((5-(difluoromethoxy)-1H-pyrazol-3-yl)amino)-1H-pyrazolo[3,4-b]pyrazin-1-yl)methyl)cyclobutane-1-carbonitrile |

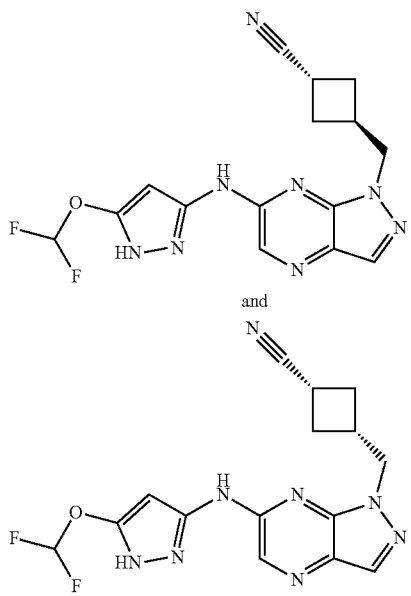 [SMILES: N#C[C@H]1C[C@H](Cn2ncc3ncc(Nc4cc(OC(F)F)[nH]n4)nc32)C1 ; N#C[C@H]1C[C@@H](Cn2ncc3ncc(Nc4cc(OC(F)F)[nH]n4)nc32)C1]

Amine-1; 3-((6-chloro-1H-pyrazolo[3,4-b]pyrazin-1-yl)methyl)cyclobutane-1-carbonitrile (Preparation 175); BrettPhos Pd G4 prep-HPLC-1; SFC: Daicel AD 20 x 250 mm, 10 mm; 15% IPA (0.5% MeOH/NH$_3$) in CO$_2$ Peak 1, Example 190, (1r,3r)-3-((6-((5-(difluoromethoxy)-1H-pyrazol-3-yl)amino)-1H-pyrazolo[3,4-b]pyrazin-1-yl)methyl)cyclobutane-1-carbonitrile or (1s,3s)-3-((6-((5-(difluoromethoxy)-1H-pyrazol-3-yl)amino)-1H-pyrazolo[3,4-b]pyrazin-1-yl)methyl)cyclobutane-1-carbonitrile; LCMS m/z = 361 [M + H]$^+$; $^1$H NMR (400 MHz, DMSO-d$_6$) δ: 12.23 (br s, 1H), 10.97 (br s, 1H), 8.22 (s, 1H), 8.14 (s, 1H), 7.31 (t, 1H), 5.93 (s, 1H), 4.58 (d, 2H), 3.01-2.90 (m, 1H), 2.36-2.24 (m, 5H).

Peak 2, Example 191, (1s,3s)-3-((6-((5-(difluoromethoxy)-1H-pyrazol-3-yl)amino)-1H-pyrazolo[3,4-b]pyrazin-1-yl)methyl)cyclobutane-1-carbonitrile or (1r,3r)-3-((6-((5-(difluoromethoxy)-1H-pyrazol-3-yl)amino)-1H-pyrazolo[3,4-b]pyrazin-1-yl)methyl)cyclobutane-1-carbonitrile; LCMS m/z = 361 [M + H]$^+$; $^1$H NMR (400 MHz, DMSO-d$_6$) δ: 12.23 (br s, 1H), 10.93 (br s, 1H), 8.21 (s, 1H), 8.15 (s, 1H), 7.30 (t, 1H), 5.92 (s, 1H,), 4.53 (d, 2H), 3.23-3.18 (m, 1H), 2.85-2.82 (m, 1H), 2.35-2.32 (m, 2H), 2.20-2.17 (m, 2H).

| Example No. | Name/Structure/Reactants/Cat/HPLC/SFC/Data |
|---|---|
| 192 and 193 | (R)-1-(2,2-difluoro-1-(tetrahydro-2H-pyran-4-yl)ethyl)-N-(5-methoxy-1H-pyrazol-3-yl)-1H-pyrazolo[3,4-b]pyrazin-6-amine and (S)-1-(2,2-difluoro-1-(tetrahydro-2H-pyran-4-yl)ethyl)-N-(5-methoxy-1H-pyrazol-3-yl)-1H-pyrazolo[3,4-b]pyrazin-6-amine |

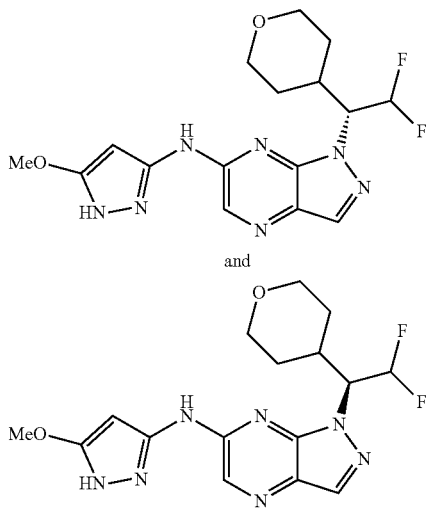 [SMILES: COc1cc(Nc2cnc3cnn([C@@H](C(F)F)C4CCOCC4)c3n2)n[nH]1 ; COc1cc(Nc2cnc3cnn([C@H](C(F)F)C4CCOCC4)c3n2)n[nH]1]

Amine-3; 6-chloro-1-(2,2-difluoro-1-(tetrahydro-2H-pyran-4-yl)ethyl)-1H-pyrazolo[3,4-b]pyrazine (Preparation 93); BrettPhos Pd G4 prep-HPLC-3; SFC: Daicel OJ 20 x 250 mm, 10 mm; 25% MeOH (0.2% MeOH/NH$_3$) in CO$_2$ Peak 1, Example 192, (R)-1-(2,2-difluoro-1-(tetrahydro-2H-pyran-4-yl)ethyl)-N-(5-methoxy-1H-pyrazol-3-yl)-1H-pyrazolo[3,4-b]pyrazin-6-amine or (S)-1-(2,2-difluoro-1-(tetrahydro-2H-pyran-4-yl)ethyl)-N-(5-methoxy-1H-pyrazol-3-yl)-1H-pyrazolo[3,4-b]pyrazin-6-amine; LCMS m/z = 416 [M + H]$^+$; $^1$H NMR (400 MHz, DMSO-d$_6$) δ: 11.75 (br s, 1H),, 10.82 (br s, 1H), 8.23 (s, 2H), 6.57 (t, 1H), 5.65-5.45 (br s, 2H), 3.80-3.70 (m, 5H), 3.30-3.18 (m, 2H), 1.81 (d, 1H), 1.52-1.25 (m, 3H), 1.00 (d, 1H).

Peak 2, Example 193, (S)-1-(2,2-difluoro-1-(tetrahydro-2H-pyran-4-yl)ethyl)-N-(5-methoxy-1H-pyrazol-3-yl)-1H-pyrazolo[3,4-b]pyrazin-6-amine or (R)-1-(2,2-difluoro-1-(tetrahydro-2H-pyran-4-yl)ethyl)-N-(5-methoxy-1H-pyrazol-3-yl)-1H-pyrazolo[3,4-b]pyrazin-6-amine; LCMS m/z = 416 [M + H]$^+$; $^1$H NMR (400 MHz, DMSO-d$_6$) δ: 11.75 (br s, 1H), 10.80 (br s, 1H), 8.23-8.21 (m, 2H), 6.56 (t, 1H), 5.54 (br s, 2H), 3.89-3.86 (m, 1H), 3.81 (s, 3H), 3.76-3.73 (m, 1H), 3.30-3.18 (m, 2H), 1.83-1.79 (m, 1H), 1.48-1.44 (m, 1H), 1.35-1.33 (m, 1H), 1.01-0.98 (m, 1H).

| Example No. | Name/Structure/Reactants/Cat/HPLC/SFC/Data |
| --- | --- |
| 194 and 195 | (R)-1-(2-fluoro-1-(tetrahydro-2H-pyran-4-yl)ethyl)-N-(5-methoxy-1H-pyrazol-3-yl)-1H-pyrazolo[3,4-b]pyrazin-6-amine and (S)-1-(2-fluoro-1-(tetrahydro-2H-pyran-4-yl)ethyl)-N-(5-methoxy-1H-pyrazol-3-yl)-1H-pyrazolo[3,4-b]pyrazin-6-amine 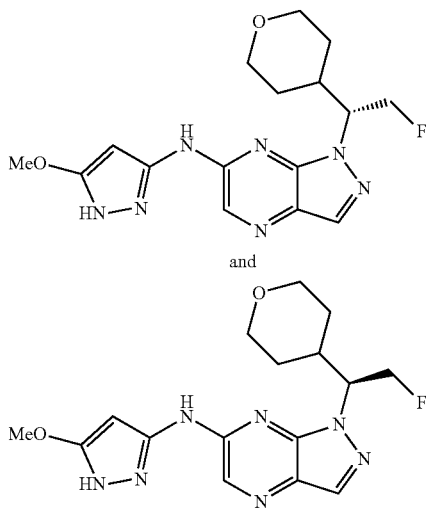 [SMILES: COc1cc(Nc2cnc3cnn([C@@H](CF)C4CCOCC4)c3n2)n[nH]1 ; COc1cc(Nc2cnc3cnn([C@H](CF)C4CCOCC4)c3n2)n[nH]1] Amine-3; 6-chloro-1-(2-fluoro-1-(tetrahydro-2H-pyran-4-yl)ethyl)-1H-pyrazolo[3,4-b]pyrazine (Preparation 165); BrettPhos Pd G4 prep-HPLC-1; SFC: Daicel AD 20 x 250 mm, 10 mm; 45% MeOH (0.2% MeOH/NH$_3$) in CO$_2$ Peak 1, Example 194, (R)-1-(2-fluoro-1-(tetrahydro-2H-pyran-4-yl)ethyl)-N-(5-methoxy-1H-pyrazol-3-yl)-1H-pyrazolo[3,4-b]pyrazin-6-amine or (S)-1-(2-fluoro-1-(tetrahydro-2H-pyran-4-yl)ethyl)-N-(5-methoxy-1H-pyrazol-3-yl)-1H-pyrazolo[3,4-b]pyrazin-6-amine; LCMS m/z = 362 [M + H]$^+$; $^1$H NMR (400 MHz, DMSO-d$_6$) δ: 11.66 (br s, 1H), 10.67 (br s, 1H), 8.25-8.15 (m, 2H), 5.63-5.53 (m, 1H), 5.41-5.28 (m, 1H), 5.05-4.95 (m, 1H), 4.95-4.85 (m, 1H), 3.90-3.83 (m, 1H), 3.82 (s, 3H), 3.75-3.70 (m, 1H), 3.31-3.25 (m, 1H), 3.19-3.12 (m, 1H), 2.28-2.23 (m, 1H), 1.76-1.71 (m, 1H), 1.51-1.42 (m, 1H), 1.28-1.23 (m, 1H), 0.88-0.83 (m, 1H). Peak 2, Example 195, (S)-1-(2-fluoro-1-(tetrahydro-2H-pyran-4-yl)ethyl)-N-(5-methoxy-1H-pyrazol-3-yl)-1H-pyrazolo[3,4-b]pyrazin-6-amine or (R)-1-(2-fluoro-1-(tetrahydro-2H-pyran-4-yl)ethyl)-N-(5-methoxy-1H-pyrazol-3-yl)-1H-pyrazolo[3,4-b]pyrazin-6-amine; LCMS m/z = 362 [M + H]$^+$; $^1$H NMR (400 MHz, DMSO-d$_6$) δ: 11.67 (br s, 1H), 10.66 (br s, 1H), 8.20 (s, 2H), 5.64 (br s, 1H), 5.29 (br s, 1H), 5.10-4.85 (m, 2H), 3.90-3.70 (m, 5H), 3.50 (t, 1H), 3.16 (t, 1H), 2.40-2.20 (m, 1H), 1.75 (d, 1H), 1.44 (q, 1H), 1.26 (q, 1H), 0.88 (d, 1H). |

| Example No. | Name/Structure/Reactants/Cat/HPLC/SFC/Data |
|---|---|
| 196 and 197 | (1S,2S)-2-((6-((5-methoxy-1H-pyrazol-3-yl)amino)-1H-pyrazolo[3,4-b]pyrazin-1-yl)methyl)cyclopropane-1-carbonitrile and (1R,2R)-2-((6-((5-methoxy-1H-pyrazol-3-yl)amino)-1H-pyrazolo[3,4-b]pyrazin-1-yl)methyl)cyclopropane-1-carbonitrile<br>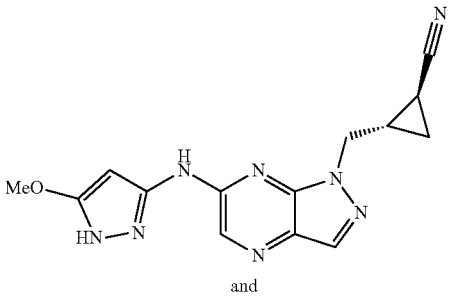<br>and<br>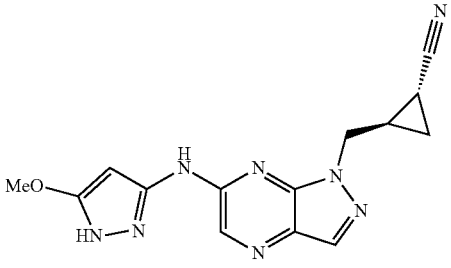<br>Amine-3; trans-rac-2-((6-chloro-1H-pyrazolo[3,4-b]pyrazin-1-yl)methyl)cyclopropane-1-carbonitrile (Preparation 94); BrettPhos Pd G4<br>prep-HPLC-1; SFC: Daicel OD 20 x 250 mm, 10 mm; 20% MeOH (0.2% DEA) in $CO_2$<br>Peak 1, Example 196, (1S,2S)-2-((6-((5-methoxy-1H-pyrazol-3-yl)amino)-1H-pyrazolo[3,4-b]pyrazin-1-yl)methyl)cyclopropane-1-carbonitrile or (1R,2R)-2-((6-((5-methoxy-1H-pyrazol-3-yl)amino)-1H-pyrazolo[3,4-b]pyrazin-1-yl)methyl)cyclopropane-1-carbonitrile; LCMS m/z = 311 [M + H]$^+$; $^1$H NMR (400 MHz, DMSO-$d_6$) δ: 11.69 (br s, 1H), 10.63 (br s, 1H), 8.20 (s, 1H), 5.61 (br s, 1H), 4.46 (br s, 2H), 3.83 (s, 3H), 2.05-1.95 (m, 1H), 1.90-1.85 (m, 1H), 1.30-1.18 (m, 2H).<br>Peak 2, Example 197, (1R,2R)-2-((6-((5-methoxy-1H-pyrazol-3-yl)amino)-1H-pyrazolo[3,4-b]pyrazin-1-yl)methyl)cyclopropane-1-carbonitrile or (1S,2S)-2-((6-((5-methoxy-1H-pyrazol-3-yl)amino)-1H-pyrazolo[3,4-b]pyrazin-1-yl)methyl)cyclopropane-1-carbonitrile; LCMS m/z = 311 [M + H]$^+$; $^1$H NMR (400 MHz, DMSO-$d_6$) δ: 11.78 (br s, 1H), 10.68 (br s, 1H), 8.20 (s, 1H), 8.15 (s, 1H), 5.70 (br s, 1H), 4.45 (d, 2H), 3.82 (s, 3H), 2.01-1.95 (m, 1H), 1.89-1.84 (m, 1H), 1.31-1.27 (m, 1H), 1.21-1.16 (m, 2H). |

Example 198

(R)-3-(6-((5-(difluoromethoxy)-1H-pyrazol-3-yl)amino)-1H-pyrazolo[3,4-b]pyrazin-1-yl)-2-methyl-propan-1-ol

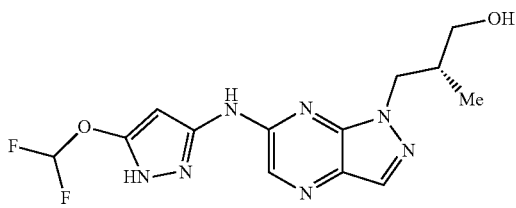

Part 1. A mixture of methyl (R)-3-(6-chloro-1H-pyrazolo[3,4-b]pyrazin-1-yl)-2-methylpropanoate (Preparation 95, 100 mg, 0.39 mmol), 5-(difluoromethoxy)-1H-pyrazol-3-amine (59 mg, 0.39 mmol), t-BuXphos Pd G3 (31 mg, 0.04 mmol) and KOAc (98 mg, 1.0 mmol) in dioxane (3 mL) was stirred at 100° C. for 3 h under $N_2$. The reaction mixture was cooled to rt and concentrated to give a residue which was purified by flash column chromatography (SiO$_2$, 0-75% EtOAc/PE) to give (R)-3-(6-((5-(difluoromethoxy)-1H-pyrazol-3-yl)amino)-1H-pyrazolo[3,4-b]pyrazin-1-yl)-2-methylpropanoate (80 mg, 56%). LCMS m/z=368 [M+H]$^+$ Part 2. LiAlH$_4$ (17 mg, 0.45 mmol) was added to a solution of (R)-3-(6-((5-(difluoromethoxy)-1H-pyrazol-3-yl)amino)-1H-pyrazolo[3,4-b]pyrazin-1-yl)-2-methylpropanoate (Part 1, 80 mg, 0.22 mmol) in THF (5 mL) at 0° C., then stirred for 5 h at 20° C. The reaction mixture was quenched with MeOH (5 drops) then concentrated in vacuo. The residue was purified by flash chromatography (SiO2, 30-90% EtOAc/PE) followed by prep-HPLC-1 to give the title compound as a yellow solid (30 mg, 41%). LCMS m/z=340 [M+H]$^+$; $^1$H NMR (500 MHz, DMSO-d$_6$) δ: 12.31 (br s, 1H), 10.82 (br s, 1H), 8.19 (s, 1H), 8.15 (s, 1H), 7.29 (t, 1H), 5.93 (s, 1H), 4.90 (s, 1H), 4.44-4.30 (m, 2H), 3.39-3.27 (m, 2H), 2.19-2.12 (m, 1H), 0.81 (d, 3H).

Example 199

(S)-3-(6-((5-(difluoromethoxy)-1H-pyrazol-3-yl)amino)-1H-pyrazolo[3,4-b]pyrazin-1-yl)-2-methyl-propan-1-ol

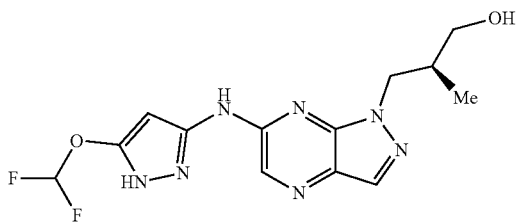

The title compound was prepared from methyl (S)-3-(6-chloro-1H-pyrazolo[3,4-b]pyrazin-1-yl)-2-methylpropanoate (Preparation 105) and 5-(difluoromethoxy)-1H-pyrazol-3-amine using an analogous 2-part procedure as described for Example 198. Purified by prep-HPLC-5 to afford the title compound (46.4 mg, 34%). LCMS m/z=340 [M+H]$^+$; $^1$H NMR (400 MHz, DMSO-d$_6$) δ: 8.17 (s, 1H), 8.13 (s, 1H), 7.28 (t, 1H), 5.95 (s, 1H), 4.43-4.29 (m, 2H), 3.30-3.26 (m, 2H), 2.16-2.13 (m, 1H), 0.81 (d, 3H).

Example 200

(S)—N-(5-(difluoromethoxy)-1H-pyrazol-3-yl)-1-(piperidin-3-ylmethyl)-1H-pyrazolo[3,4-b]pyrazin-6-amine

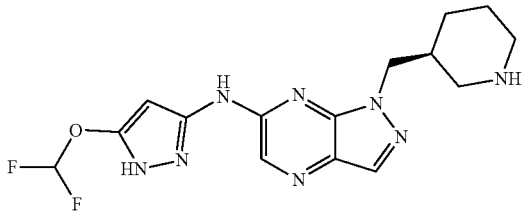

Part 1. A mixture of tert-butyl (S)-3-((6-chloro-1H-pyrazolo[3,4-b]pyrazin-1-yl)methyl)piperidine-1-carboxylate (Preparation 104, 300 mg, 0.85 mmol), 5-(difluoromethoxy)-1H-pyrazol-3-amine (190 mg, 1.28 mmol), BrettPhos Pd G4 (20 mg, 0.21 mmol) and KOAc (251 mg, 2.56 mmol) in dioxane (5 mL) was stirred at 90° C. overnight under N$_2$. The reaction mixture was cooled to rt and concentrated to give a residue which was purified by flash column chromatography (SiO2, 80% EtOAc/PE) to give tert-butyl (S)-3-((6-((5-(difluoromethoxy)-1H-pyrazol-3-yl)amino)-1H-pyrazolo[3,4-b]pyrazin-1-yl)methyl)piperidine-1-carboxylate (250 mg, 63%). LCMS m/z=413 [M+H]$^+$ Part 2. To a solution of tert-butyl (S)-3-((6-((5-(difluoromethoxy)-1H-pyrazol-3-yl)amino)-1H-pyrazolo[3,4-b]pyrazin-1-yl)methyl)piperidine-1-carboxylate (Part 1, 250 mg, 0.53 mmol) in THF (20 mL) was added TFA (0.5 mL) at 25° C. and the resulting mixture stirred for 2 h at rt. The reaction mixture was evaporated to dryness in vacuo and the residue was purified by prep-HPLC-4 to afford the title compound (24.4 mg, 12%). LCMS m/z=365 [M+H]$^+$; $^1$H NMR (400 MHz, DMSO-d$_6$) δ: 8.16 (s, 1H), 8.11 (s, 1H), 7.27 (t, 1H), 6.15-6.12 (m, 1H), 4.58-3.97 (m, 2H), 2.80-2.60 (m, 1H), 2.49-2.23 (m, 3H), 1.77-1.52 (m, 2H), 1.45-1.32 (m, 2H), 1.20-1.12 (m, 1H).

Example 201 and 202

(2R,3S)-3-(6-((5-(difluoromethoxy)-1H-pyrazol-3-yl)amino)-1H-pyrazolo[3,4-b]pyrazin-1-yl)pentan-2-ol and (2R,3R)-3-(6-((5-(difluoromethoxy)-1H-pyrazol-3-yl)amino)-1H-pyrazolo[3,4-b]pyrazin-1-yl)pentan-2-ol

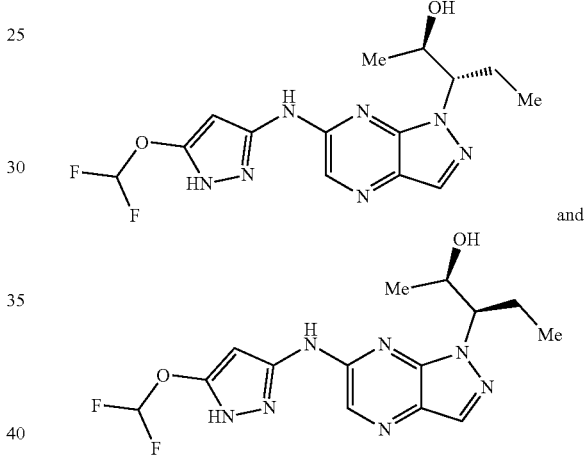

To a solution N-(5-(difluoromethoxy)-1H-pyrazol-3-yl)-1-((2R)-2-((tetrahydro-2H-pyran-2-yl)oxy)pentan-3-yl)-1H-pyrazolo[3,4-b]pyrazin-6-amine (Preparation 188, 250 mg, 0.53 mmol) in THF (20 mL) was added TFA (0.5 mL) at 25° C. and the resulting reaction mixture was stirred for 2 h at rt. The reaction mixture was evaporated to dryness in vacuo and the residue was purified by prep-HPLC-4 to give a mixture of title compounds (16.0 mg, 12%). The mixture was separated by chiral-SFC (Daicel IC, 20×250 mm, 10 mm: 30% MeOH (0.2% MeOH/NH3) in CO2 to afford the title compounds.

Peak 1, Example 201, (2R,3S)-3-(6-((5-(difluoromethoxy)-1H-pyrazol-3-yl)amino)-1H-pyrazolo[3,4-b]pyrazin-1-yl)pentan-2-ol or (2R,3R)-3-(6-((5-(difluoromethoxy)-1H-pyrazol-3-yl)amino)-1H-pyrazolo[3,4-b]pyrazin-1-yl)pentan-2-ol (8 mg): LCMS m/z=354 [M+H]+: 1H NMR (400 MHz, DMSO-d6) δ: 12.18 (br s, 1H), 10.91 (br s, 1H), 8.22 (s, 1H), 8.16 (s, 1H), 7.31 (t, 1H), 6.01-5.99 (m, 1H), 5.06 (d, 1H), 4.60-4.53 (m, 1H), 4.02-3.98 (m, 1H), 2.14-1.99 (m, 2H), 0.79 (d, 3H), 0.61 (t, 3H).

Peak 2, Example 202, (2R,3R)-3-(6-((5-(difluoromethoxy)-1H-pyrazol-3-yl)amino)-1H-pyrazolo[3,4-b]pyrazin-1-yl)pentan-2-ol and (2R,3S)-3-(6-((5-(difluoromethoxy)-1H-pyrazol-3-yl)amino)-1H-pyrazolo[3,4-b]pyrazin-1-yl)pentan-2-ol, White solid (8 mg): LCMS m/z=354 [M+H]⁺; ¹H NMR (400 MHz, DMSO-d₆) δ: 12.18 (br s, 1H), 10.91 (br s, 1H), 8.22 (s, 1H), 8.16 (s, 1H), 7.31 (t, 1H), 6.00 (br s, 1H), 5.06 (d, 1H), 4.70-4.60 (m, 1H), 4.05-3.95 (m, 1H), 2.25-1.90 (m, 2H), 0.79 (d, 3H), 0.61 (t, 3H).

Example 203

(R)-2-(6-((5-(difluoromethoxy)-1H-pyrazol-3-yl)amino)-1H-pyrazolo[3,4-b]pyrazin-1-yl)-2-phenylethan-1-ol

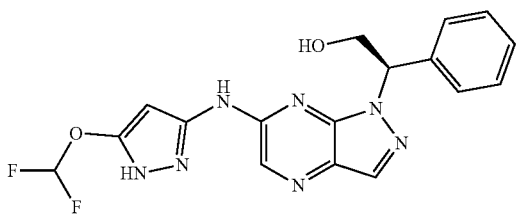 [SMILES: OC[C@@H](c1ccccc1)n1ncc2ncc(Nc3cc(OC(F)F)[nH]n3)nc21]

Part 1. A mixture of (R)-6-chloro-1-(1-phenyl-2-((triisopropylsilyl)oxy)ethyl)-1H-pyrazolo[3,4-b]pyrazine (Preparation 130, 700 mg, 1.62 mmol), 5-(difluoromethoxy)-1H-pyrazol-3-amine (363 mg, 2.44 mmol), BrettPhos Pd G4 (20 mg, 0.21 mmol) and KOAc (478 mg, 4.87 mmol) in dioxane (20 mL) was stirred at 90° C. overnight under N₂. The reaction mixture was cooled to rt and concentrated in vacuo to give a residue which was purified by flash column chromatography (SiO₂, 66% EtOAc/PE) to afford (R)—N-(5-(difluoromethoxy)-1H-pyrazol-3-yl)-1-(1-phenyl-2-((triisopropylsilyl)oxy)ethyl)-1H-pyrazolo[3,4-b]pyrazin-6-amine as a yellow solid (260 mg, 29%). LCMS m/z=544 [M+H]⁺.

Part 2. The compound of Part 1 (250 mg, 0.20 mmol) in TBAF/THF (3 mL) was stirred at rt overnight. The reaction mixture was evaporated to dryness and the residue purified by prep-HPLC-4 to afford the title compound as a white solid (116 mg, 62%). LCMS m/z=388 [M+H]⁺; ¹H NMR (400 MHz, DMSO-d₆) δ: 12.21 (br s, 1H), 10.77 (br s, 1H), 8.22 (s, 1H), 8.20 (s, 1H), 7.43-7.23 (m, 5H), 7.31 (t, 1H), 6.23-6.19 (m, 1H), 6.01 (br s, 1H), 5.03 (t, 1H), 4.40-4.35 (m, 1H), 4.08-4.01 (m, 1H).

Example 204

(R)-2-(6-((5-(difluoromethoxy)-1H-pyrazol-3-yl)amino)-1H-pyrazolo[3,4-b]pyrazin-1-yl)-2-(pyridin-3-yl)ethan-1-ol

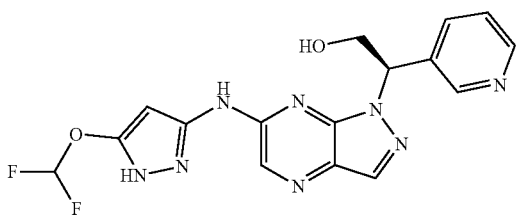 [SMILES: OC[C@@H](c1cccnc1)n1ncc2ncc(Nc3cc(OC(F)F)[nH]n3)nc21]

The title compound was prepared from (R)-6-chloro-1-(1-(pyridin-3-yl)-2-((triisopropylsilyl)oxy)ethyl)-1H-pyrazolo[3,4-b]pyrazine (Preparation 137) and 5-(difluoromethoxy)-1H-pyrazol-3-amine using an analogous 2-part method as described for Example 203. Purification by prep-HPLC-1 afforded the title compound as white solid (78.8 mg, 45%). LCMS m/z=389 [M+H]⁺; ¹H NMR (400 MHz, DMSO-d₆) δ: 12.28 (s, 1H), 10.83 (s, 1H), 8.68 (d, 1H), 8.48 (dd, 1H), 8.24 (s, 1H), 8.20 (s, 1H), 7.85 (d, 1H), 7.35 (dd, 1H), 7.32 (t, 1H), 6.39-6.35 (m, 1H), 5.94 (s, 1H), 5.14 (t, 1H), 4.33-4.30 (m, 1H), 4.14-4.08 (m, 1H).

Example 205 and 206

(S)-3-(6-((5-(difluoromethoxy)-1H-pyrazol-3-yl)amino)-1H-pyrazolo[3,4-b]pyrazin-1-yl)butan-1-ol and (R)-3-(6-((5-(difluoromethoxy)-1H-pyrazol-3-yl)amino)-1H-pyrazolo[3,4-b]pyrazin-1-yl)butan-1-ol

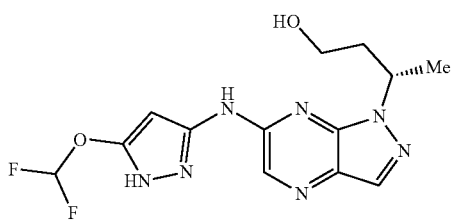

and

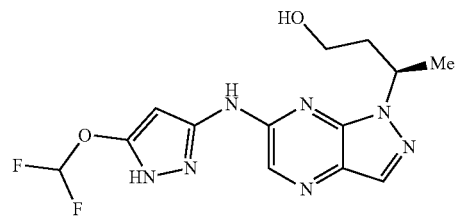

The title compound was prepared from 6-chloro-1-(4-((triisopropylsilyl)oxy)butan-2-yl)-1H-pyrazolo[3,4-b]pyrazine (Preparation 167) and 5-(difluoromethoxy)-1H-pyrazol-3-amine using an analogous 2-part method as described for Example 203. prep-HPLC-1 followed by prep-SFC (Daicel OZ 20×250 mm, 10 mm; 20% MeOH (0.2% MeOH/NH₃) in CO₂.

Peak 1. Example 205, (S)-3-(6-((5-(difluoromethoxy)-1H-pyrazol-3-yl)amino)-1H-pyrazolo[3,4-b]pyrazin-1-yl)butan-1-ol or (R)-3-(6-((5-(difluoromethoxy)-1H-pyrazol-3-yl)amino)-1H-pyrazolo[3,4-b]pyrazin-1-yl)butan-1-ol, white solid: LCMS m/z=340 [M+H]+: 1H NMR (500 MHz, DMSO-d6) δ: 12.23 (br s, 1H), 10.79 (br s, 1H), 8.19 (s, 1H), 8.15 (s, 1H), 7.29 (t, 1H), 5.96 (s, 1H), 5.25-5.19 (m, 1H), 4.66-4.60 (m, 1H), 3.33-3.24 (m, 1H), 3.18-3.10 (m, 1H), 2.06-1.90 (m, 2H), 1.49 (d, 3H).

Peak 2, Example 206, (R)-3-(6-((5-(difluoromethoxy)-1H-pyrazol-3-yl)amino)-1H-pyrazolo[3,4-b]pyrazin-1-yl)butan-1-ol or (S)-3-(6-((5-(difluoromethoxy)-1H-pyrazol-3-yl)amino)-1H-pyrazolo[3,4-b]pyrazin-1-yl)butan-1-ol, white solid; LCMS m/z=340 [M+H]⁺; ¹H NMR (400 MHz, DMSO-d₆) δ: 12.22 (s, 1H), 10.77 (s, 1H), 8.19 (s, 1H), 8.16 (s, 1H), 7.29 (t, 1H), 5.95 (s, 1H), 5.25-5.19 (m, 1H), 3.33-3.24 (m, 1H), 3.18-3.10 (m, 1H), 2.06-1.90 (m, 2H), 1.49 (d, 3H).

Example 207, 208, 209 and 210

(1S,3R)-3-(6-((5-(difluoromethoxy)-1H-pyrazol-3-yl)amino)-1H-pyrazolo[3,4-b]pyrazin-1-yl)cyclopentan-1-ol and (1R,3S)-3-(6-((5-(difluoromethoxy)-1H-pyrazol-3-yl)amino)-1H-pyrazolo[3,4-b]pyrazin-1-yl)cyclopentan-1-ol and (1R,3R)-3-(6-((5-(difluoromethoxy)-1H-pyrazol-3-yl)amino)-1H-pyrazolo[3,4-b]pyrazin-1-yl)cyclopentan-1-ol and (S,3S)-3-(6-((5-(difluoromethoxy)-1H-pyrazol-3-yl)amino)-1H-pyrazolo[3,4-b]pyrazin-1-yl)cyclopentan-1-ol

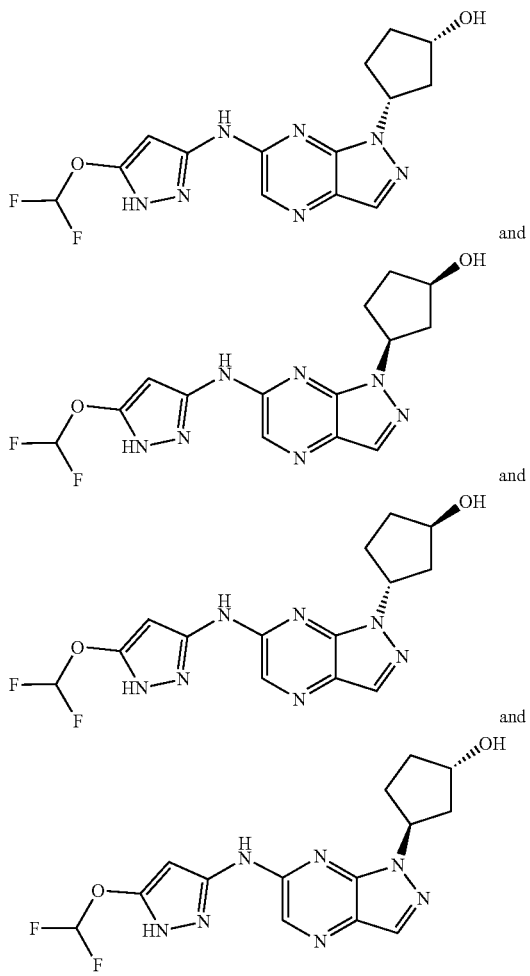

and

Part 1. A mixture of 3-(6-chloro-1H-pyrazolo[3,4-b]pyrazin-1-yl)cyclopentan-1-ol (Preparation 132, 200 mg, 0.837 mmol), 5-(difluoromethoxy)-1H-pyrazol-3-amine (124 mg, 0.837 mmol), t-BuXPhos Pd G3 (66.5 mg, 0.0837 mmol) and KOAc (246 mg, 2.51 mmol) in dioxane (10 mL) was degassed with N2 (3×), and then heated at 100° C. for 3 h under N2. The reaction mixture was cooled to rt and concentrated to give a residue which was purified by flash column chromatography on silica gel (80% EtOAc/PE) to give a residue that was further purified prep-HPLC-3 to give Intermediate Product 1 (150 mg, 50%) and Intermediate Product 2 (50 mg, 16%).

Part 2. Intermediate Product 1 was further purified by chiral-SFC (Daicel IG, 20×250 mm, 10 mm; 25% MeOH (0.2% MeOH/NH3) in CO2 to give Peak 1 and Peak 2 as yellow solids.

Peak 1, Example 207, (1S,3R)-3-(6-((5-(difluoromethoxy)-1H-pyrazol-3-yl)amino)-1H-pyrazolo[3,4-b]pyrazin-1-yl)cyclopentan-1-ol or (1R,3S)-3-(6-((5-(difluoromethoxy)-1H-pyrazol-3-yl)amino)-1H-pyrazolo[3,4-b]pyrazin-1-yl)cyclopentan-1-ol or (1R,3R)-3-(6-((5-(difluoromethoxy)-1H-pyrazol-3-yl)amino)-1H-pyrazolo[3,4-b]pyrazin-1-yl)cyclopentan-1-ol or (1S,3S)-3-(6-((5-(difluoromethoxy)-1H-pyrazol-3-yl)amino)-1H-pyrazolo[3,4-b]pyrazin-1-yl)cyclopentan-1-ol (51.4 mg); LCMS m/z=352 [M+H]$^+$; $^1$H NMR (400 MHz, DMSO-d$_6$) δ: 12.27 (s, 1H), 10.74 (s, 1H), 8.19 (s, 1H), 8.15 (s, 1H), 7.31 (t, 1H), 5.93 (s, 1H), 5.67-5.63 (m, 1H), 4.74 (d, 1H), 4.43-4.40 (m, 1H), 2.34-2.25 (m, 1H), 2.23-2.15 (m, 1H), 2.15-2.01 (m, 2H), 1.95-1.90 (m, 1H), 1.65-1.60 (m, 1H).

Peak 2, Example 208, (1R,3S)-3-(6-((5-(difluoromethoxy)-1H-pyrazol-3-yl)amino)-1H-pyrazolo[3,4-b]pyrazin-1-yl)cyclopentan-1-ol or (1S,3R)-3-(6-((5-(difluoromethoxy)-1H-pyrazol-3-yl)amino)-1H-pyrazolo[3,4-b]pyrazin-1-yl)cyclopentan-1-ol or (1R,3R)-3-(6-((5-(difluoromethoxy)-1H-pyrazol-3-yl)amino)-1H-pyrazolo[3,4-b]pyrazin-1-yl)cyclopentan-1-ol or (1S,3S)-3-(6-((5-(difluoromethoxy)-1H-pyrazol-3-yl)amino)-1H-pyrazolo[3,4-b]pyrazin-1-yl)cyclopentan-1-ol (63 mg); LCMS m/z=352 [M+H]$^+$; $^1$H NMR (400 MHz, DMSO-d$_6$) δ: 12.27 (s, 1H), 10.74 (s, 1H), 8.19 (s, 1H), 8.15 (s, 1H), 7.31 (t, 1H), 5.93 (s, 1H), 5.67-5.63 (m, 1H), 4.74 (d, 1H), 4.43-4.40 (m, 1H), 2.34-2.25 (m, 1H), 2.23-2.15 (m, 1H), 2.15-2.01 (m, 2H), 1.95-1.90 (m, 1H), 1.65-1.60 (m, 1H).

Part 3. Intermediate Product 2 was further purified by chiral-SFC (Daicel IG, 20×250 mm, 10 mm; 20% MeOH (0.2% MeOH/NH3) in CO2 to give Peak 3 and Peak 4 as yellow solids.

Peak 3, Example 209, (1R,3R)-3-(6-((5-(difluoromethoxy)-1H-pyrazol-3-yl)amino)-1H-pyrazolo[3,4-b]pyrazin-1-yl)cyclopentan-1-ol or (1S,3S)-3-(6-((5-(difluoromethoxy)-1H-pyrazol-3-yl)amino)-1H-pyrazolo[3,4-b]pyrazin-1-yl)cyclopentan-1-ol or (1S,3R)-3-(6-((5-(difluoromethoxy)-1H-pyrazol-3-yl)amino)-1H-pyrazolo[3,4-b]pyrazin-1-yl)cyclopentan-1-ol or (1R,3S)-3-(6-((5-(difluoromethoxy)-1H-pyrazol-3-yl)amino)-1H-pyrazolo[3,4-b]pyrazin-1-yl)cyclopentan-1-ol (16.7 mg); LCMS m/z=352 [M+H]$^+$; 1H NMR (400 MHz, DMSO-d6) δ: 12.25 (br s, 1H), 10.95 (br s, 1H), 8.19 (s, 1H), 8.16 (s, 1H), 7.31 (t, 1H), 5.89 (s, 1H), 5.37 (m, 1H), 4.99 (s, 1H), 4.25 (s, 1H), 2.42 (m, 1H), 2.20 (m, 1H), 2.03 (m, 2H), 1.80 (m, 2H).

Peak 4, Example 210, (1S,3S)-3-(6-((5-(difluoromethoxy)-1H-pyrazol-3-yl)amino)-1H-pyrazolo[3,4-b]pyrazin-1-yl)cyclopentan-1-ol or (1R,3R)-3-(6-((5-(difluoromethoxy)-1H-pyrazol-3-yl)amino)-1H-pyrazolo[3,4-b]pyrazin-1-yl)cyclopentan-1-ol or (1S,3R)-3-(6-((5-(difluoromethoxy)-1H-pyrazol-3-yl)amino)-1H-pyrazolo[3,4-b]pyrazin-1-yl)cyclopentan-1-ol or (1R,3S)-3-(6-((5-(difluoromethoxy)-1H-pyrazol-3-yl)amino)-1H-pyrazolo[3,4-b]pyrazin-1-yl)cyclopentan-1-ol (17.4 mg); LCMS m/z=352 [M+H]$^+$; $^1$H NMR (400 MHz, DMSO-d$_6$) δ: 12.25 (br s, 1H), 10.95 (br s, 1H), 8.19 (s, 1H), 8.16 (s, 1H), 7.31 (t, 1H), 5.89 (s, 1H), 5.37 (m, 1H), 4.99 (s, 1H), 4.25 (s, 1H), 2.42 (m, 1H), 2.20 (m, 1H), 2.03 (m, 2H), 1.80 (m, 2H).

Example 211, 212, 213 and 214

1-((S)-1-((R)-1,4-dioxan-2-yl)ethyl)-N-(5-(difluoromethoxy)-1H-pyrazol-3-yl)-1H-pyrazolo[3,4-b]pyrazin-6-amine and 1-((S)-1-((S)-1,4-dioxan-2-yl)ethyl)-N-(5-(difluoromethoxy)-1H-pyrazol-3-yl)-1H-pyrazolo[3,4-b]pyrazin-6-amine and 1-((R)-1-((R)-1,4-dioxan-2-yl)ethyl)-N-(5-(difluoromethoxy)-1H-pyrazol-3-yl)-1H-pyrazolo[3,4-b]pyrazin-6-amine and 1-((R)-1-((S)-1,4-dioxan-2-yl)ethyl)-N-(5-(difluoromethoxy)-1H-pyrazol-3-yl)-1H-pyrazolo[3,4-b]pyrazin-6-amine

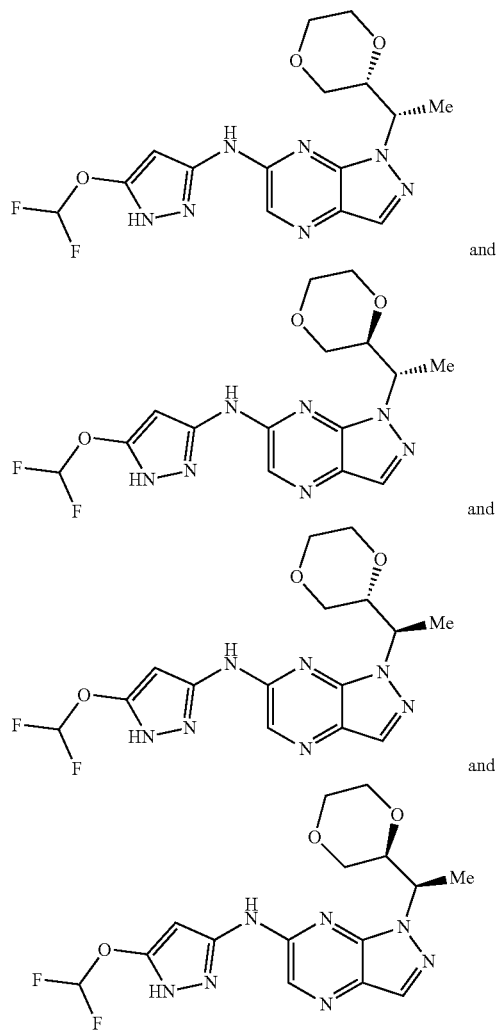

Part 1. A mixture of trans-rac-1-(1-(1,4-dioxan-2-yl)ethyl)-6-chloro-1H-pyrazolo[3,4-b]pyrazine or cis-rac-1-(1-(1,4-dioxan-2-yl)ethyl)-6-chloro-1H-pyrazolo[3,4-b]pyrazine (Product 1, Preparation 183 and 184, 100 mg, 0.37 mmol), 5-(difluoromethoxy)-1H-pyrazol-3-amine (75 mg, 0.5 mmol), BrettPhos Pd G4 (92 mg, 0.1 mmol) and KOAc (80 mg, 0.8 mmol) in dioxane (3 mL) was stirred at 100° C. for 2 h under N2. The reaction mixture was cooled to rt and evaporated to dryness in vacuo to afford a residue that was purified by flash column chromatography on silica gel (10:1 PE/EtOAc) to give Intermediate Product A as a yellow solid (50 mg, 35%). LCMS m/z=382 [M+H]+.

Part 2. Intermediate Product B (yellow solid, 210 mg, 42%) was prepared from a mixture of cis-rac-1-(1-(1,4-dioxan-2-yl)ethyl)-6-chloro-1H-pyrazolo[3,4-b]pyrazine or trans-rac-1-(1-(1,4-dioxan-2-yl)ethyl)-6-chloro-1H-pyrazolo[3,4-b]pyrazine (Product 2, Preparation 183 and 184) and 5-(difluoromethoxy)-1H-pyrazol-3-amine using an analogous method to that described in Part 1 above. LCMS m/z=382 [M+H]+.

Part 3. Intermediate Product A (Part 1) was separated by chiral-SFC (Daicel OJ, 20×250 mm, 10 mm; 15% MeOH (0.2% MeOH/NH3) in CO2 to afford:

Peak 1, Example 211, 1-((S)-1-((S)-1,4-dioxan-2-yl)ethyl)-N-(5-(difluoromethoxy)-1H-pyrazol-3-yl)-1H-pyrazolo[3,4-b]pyrazin-6-amine or 1-((R)-1-((R)-1,4-dioxan-2-yl)ethyl)-N-(5-(difluoromethoxy)-1H-pyrazol-3-yl)-1H-pyrazolo[3,4-b]pyrazin-6-amine or 1-((S)-1-((R)-1,4-dioxan-2-yl)ethyl)-N-(5-(difluoromethoxy)-1H-pyrazol-3-yl)-1H-pyrazolo[3,4-b]pyrazin-6-amine or 1-((R)-1-((S)-1,4-dioxan-2-yl)ethyl)-N-(5-(difluoromethoxy)-1H-pyrazol-3-yl)-1H-pyrazolo[3,4-b]pyrazin-6-amine (15.2 mg); LCMS m/z=382 [M+H]+; 1H NMR (400 MHz, DMSO-d6) δ: 12.31 (br s, 1H), 10.88 (br s, 1H), 8.22 (s, 1H), 8.20 (s, 1H), 7.31 (t, 1H), 5.95 (s, 1H), 5.18 (s, 1H), 3.89-3.81 (m, 2H), 3.67-3.58 (m, 2H), 3.45-3.38 (m, 1H), 3.27-3.20 (m, 1H), 3.14-3.09 (m, 1H), 1.53 (d, 3H).

Peak 2, Example 212, 1-((R)-1-((R)-1,4-dioxan-2-yl)ethyl)-N-(5-(difluoromethoxy)-1H-pyrazol-3-yl)-1H-pyrazolo[3,4-b]pyrazin-6-amine or 1-((S)-1-((S)-1,4-dioxan-2-yl)ethyl)-N-(5-(difluoromethoxy)-1H-pyrazol-3-yl)-1H-pyrazolo[3,4-b]pyrazin-6-amine or 1-((S)-1-((R)-1,4-dioxan-2-yl)ethyl)-N-(5-(difluoromethoxy)-1H-pyrazol-3-yl)-1H-pyrazolo[3,4-b]pyrazin-6-amine or 1-((R)-1-((S)-1,4-dioxan-2-yl)ethyl)-N-(5-(difluoromethoxy)-1H-pyrazol-3-yl)-1H-pyrazolo[3,4-b]pyrazin-6-amine (44.9 mg); LCMS m/z=382 [M+H]+; 1H NMR (400 MHz, DMSO-d6) δ: 12.31 (br s, 1H), 10.88 (br s, 1H), 8.22 (s, 1H), 8.20 (s, 1H), 7.31 (t, 1H), 5.95 (s, 1H), 5.18 (s, 1H), 3.89-3.81 (m, 2H), 3.67-3.58 (m, 2H), 3.45-3.38 (m, 1H), 3.27-3.20 (m, 1H), 3.14-3.09 (m, 1H), 1.53 (d, 3H).

Part 4. Intermediate Product B (Part 2) was separated by chiral-SFC (Daicel OJ, 20×250 mm, 10 mm; 15% MeOH (0.2% MeOH/NH3) in CO2 to afford:

Peak 3, Example 213, 1-((S)-1-((R)-1,4-dioxan-2-yl)ethyl)-N-(5-(difluoromethoxy)-1H-pyrazol-3-yl)-1H-pyrazolo[3,4-b]pyrazin-6-amine or 1-((R)-1-((S)-1,4-dioxan-2-yl)ethyl)-N-(5-(difluoromethoxy)-1H-pyrazol-3-yl)-1H-pyrazolo[3,4-b]pyrazin-6-amine or 1-((R)-1-((R)-1,4-dioxan-2-yl)ethyl)-N-(5-(difluoromethoxy)-1H-pyrazol-3-yl)-1H-pyrazolo[3,4-b]pyrazin-6-amine or 1-((S)-1-((S)-1,4-dioxan-2-yl)ethyl)-N-(5-(difluoromethoxy)-1H-pyrazol-3-yl)-1H-pyrazolo[3,4-b]pyrazin-6-amine (15.2 mg); LCMS m/z=382 [M+H]+; 1H NMR (400 MHz, DMSO-d6) δ: 12.27 (br s, 1H), 10.83 (br s, 1H), 8.19 (s, 1H), 8.15 (s, 1H), 7.31 (t, 1H), 5.92 (s, 1H), 5.20 (s, 1H), 3.94-3.90 (m, 2H), 3.63-3.56 (m, 2H), 3.40-3.31 (m, 3H), 1.41 (d, 3H).

Peak 4, Example 214, 1-((R)-1-((S)-1,4-dioxan-2-yl)ethyl)-N-(5-(difluoromethoxy)-1H-pyrazol-3-yl)-1H-pyrazolo[3,4-b]pyrazin-6-amine or 1-((S)-1-((R)-1,4-dioxan-2-yl)ethyl)-N-(5-(difluoromethoxy)-1H-pyrazol-3-yl)-1H-pyrazolo[3,4-b]pyrazin-6-amine or 1-((R)-1-((R)-1,4-dioxan-2-yl)ethyl)-N-(5-(difluoromethoxy)-1H-pyrazol-3-yl)-1H-pyrazolo[3,4-b]pyrazin-6-amine or 1-((S)-1-((S)-1,4-dioxan-2-yl)ethyl)-N-(5-(difluoromethoxy)-1H-pyrazol-3-yl)-1H-pyrazolo[3,4-b]pyrazin-6-amine (15.2 mg); LCMS m/z=382 [M+H]+; 1H NMR (400 MHz, DMSO-d6) δ: 12.27 (br s, 1H), 10.83 (br s, 1H), 8.19 (s, 1H), 8.15 (s, 1H), 7.31

(t, 1H), 5.92 (s, 1H), 5.20 (s, 1H), 3.94-3.90 (m, 2H), 3.63-3.56 (m, 2H), 3.40-3.31 (m, 3H), 1.41 (d, 3H).

Example 215, 216, 217 and 218

N-(5-(difluoromethoxy)-1H-pyrazol-3-yl)-1-((S)-1-((R)-tetrahydro-2H-pyran-3-yl)ethyl)-1H-pyrazolo[3,4-b]pyrazin-6-amine and N-(5-(difluoromethoxy)-1H-pyrazol-3-yl)-1-((R)-1-((R)-tetrahydro-2H-pyran-3-yl)ethyl)-1H-pyrazolo[3,4-b]pyrazin-6-amine and N-(5-(difluoromethoxy)-1H-pyrazol-3-yl)-1-((S)-1-((S)-tetrahydro-2H-pyran-3-yl)ethyl)-1H-pyrazolo[3,4-b]pyrazin-6-amine and N-(5-(difluoromethoxy)-1H-pyrazol-3-yl)-1-((R)-1-((S)-tetrahydro-2H-pyran-3-yl)ethyl)-1H-pyrazolo[3,4-b]pyrazin-6-amine

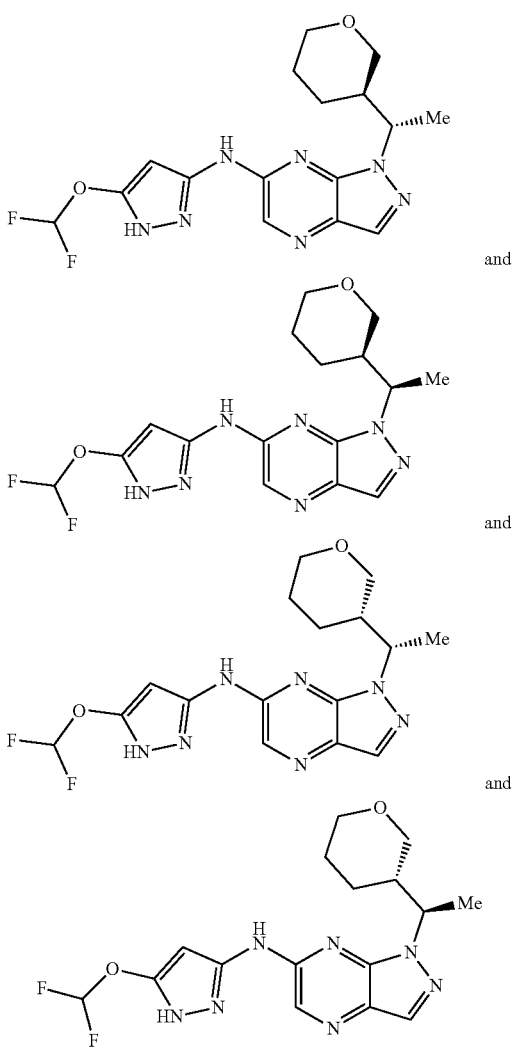

Part 1. To a solution of 6-chloro-1-(1-(tetrahydro-2H-pyran-3-yl)ethyl)-1H-pyrazolo[3,4-b]pyrazine (Preparation 89, 300 mg, 1.12 mmol) and 5-(difluoromethoxy)-1H-pyrazol-3-amine (250 mg, 1.68 mmol) in dioxane (10 mL) was added tBuXPhos Pd G3 (177 mg, 0.224 mmol) and KOAc (219 mg, 2.24 mmol) at ambient temperature and the resulting mixture was purged with $N_2$ and then stirred at 100° C. for 2 h. The reaction mixture was evaporated to dryness and the residue purified by prep-HPLC-1 to give N-(5-(difluoromethoxy)-1H-pyrazol-3-yl)-1-(1-(tetrahydro-2H-pyran-3-yl)ethyl)-1H-pyrazolo[3,4-b]pyrazin-6-amine as a white solid (44 mg, 10%). LCMS m/z=380 [M+H]⁺.

Part 2. N-(5-(difluoromethoxy)-1H-pyrazol-3-yl)-1-(1-(tetrahydro-2H-pyran-3-yl)ethyl)-1H-pyrazolo[3,4-b]pyrazin-6-amine (Part 1) was further purified by chiral-SFC (Daicel OJ; 20×250 mm, 10 mm; 15% MeOH (0.2% MeOH/NH3) in CO2 to afford the title compounds. LCMS m/z=380 [M+H]⁺

Peak 1, Example 215, N-(5-(difluoromethoxy)-1H-pyrazol-3-yl)-1-((S)-1-((R)-tetrahydro-2H-pyran-3-yl)ethyl)-1H-pyrazolo[3,4-b]pyrazin-6-amine or N-(5-(difluoromethoxy)-1H-pyrazol-3-yl)-1-((R)-1-((R)-tetrahydro-2H-pyran-3-yl)ethyl)-1H-pyrazolo[3,4-b]pyrazin-6-amine or N-(5-(difluoromethoxy)-1H-pyrazol-3-yl)-1-((S)-1-((S)-tetrahydro-2H-pyran-3-yl)ethyl)-1H-pyrazolo[3,4-b]pyrazin-6-amine or N-(5-(difluoromethoxy)-1H-pyrazol-3-yl)-1-((R)-1-((S)-tetrahydro-2H-pyran-3-yl)ethyl)-1H-pyrazolo[3,4-b]pyrazin-6-amine (0.9 mg): 1H NMR (400 MHz, DMSO-d6) δ: 12.19 (s, 1H), 10.76 (s, 1H), 8.20 (s, 1H), 8.17 (s, 1H), 7.30 (t, 1H), 5.97 (s, 1H), 5.05-5.01 (m, 1H), 3.96 (dd, 1H), 3.67 (d, 1H), 3.32-3.21 (m, 2H), 2.07-2.05 (m, 1H), 1.46 (d, 3H), 1.35-1.23 (m, 2H), 1.15-1.12 (m, 1H), 1.05-0.99 (m, 1H).

Peak 2, Example 216, N-(5-(difluoromethoxy)-1H-pyrazol-3-yl)-1-((R)-1-((R)-tetrahydro-2H-pyran-3-yl)ethyl)-1H-pyrazolo[3,4-b]pyrazin-6-amine or N-(5-(difluoromethoxy)-1H-pyrazol-3-yl)-1-((S)-1-((R)-tetrahydro-2H-pyran-3-yl)ethyl)-1H-pyrazolo[3,4-b]pyrazin-6-amine or N-(5-(difluoromethoxy)-1H-pyrazol-3-yl)-1-((S)-1-((S)-tetrahydro-2H-pyran-3-yl)ethyl)-1H-pyrazolo[3,4-b]pyrazin-6-amine or N-(5-(difluoromethoxy)-1H-pyrazol-3-yl)-1-((R)-1-((S)-tetrahydro-2H-pyran-3-yl)ethyl)-1H-pyrazolo[3,4-b]pyrazin-6-amine (2.8 mg): ¹H NMR (400 MHz, DMSO-d₆) δ: 12.40-12.30 (br, 1H), 10.95-10.72 (br, 1H), 8.20 (s, 1H), 8.17 (s, 1H), 7.30 (t, 1H), 5.97 (s, 1H), 5.05-5.01 (m, 1H), 3.96 (dd, 1H), 3.68 (dd, 1H), 3.32-3.21 (m, 2H), 2.07-2.05 (m, 1H), 1.46 (d, 3H), 1.35-1.23 (m, 2H), 1.15-1.12 (m, 1H), 1.05-0.99 (m, 1H).

Peak 3, Example 217, N-(5-(difluoromethoxy)-1H-pyrazol-3-yl)-1-((S)-1-((S)-tetrahydro-2H-pyran-3-yl)ethyl)-1H-pyrazolo[3,4-b]pyrazin-6-amine or N-(5-(difluoromethoxy)-1H-pyrazol-3-yl)-1-((R)-1-((R)-tetrahydro-2H-pyran-3-yl)ethyl)-1H-pyrazolo[3,4-b]pyrazin-6-amine or N-(5-(difluoromethoxy)-1H-pyrazol-3-yl)-1-((R)-1-((S)-tetrahydro-2H-pyran-3-yl)ethyl)-1H-pyrazolo[3,4-b]pyrazin-6-amine or N-(5-(difluoromethoxy)-1H-pyrazol-3-yl)-1-((S)-1-((R)-tetrahydro-2H-pyran-3-yl)ethyl)-1H-pyrazolo[3,4-b]pyrazin-6-amine (3.5 mg): ¹H NMR (400 MHz, DMSO-d₆) δ: 12.40-12.30 (br s, 1H), 10.95-10.72 (br s, 1H), 8.20 (s, 1H), 8.17 (s, 1H), 7.30 (t, 1H), 5.97 (s, 1H), 5.02-4.95 (m, 1H), 3.69 (d, 1H), 3.32-3.23 (m, 1H), 3.15-3.12 (m, 1H), 3.02-2.96 (m, 1H), 2.13-2.10 (m, 1H), 1.98-1.95 (m, 1H), 1.66-1.60 (m, 1H), 1.53 (d, 3H), 1.48-1.33 (m, 2H).

Peak 4, Example 218, N-(5-(difluoromethoxy)-1H-pyrazol-3-yl)-1-((R)-1-((S)-tetrahydro-2H-pyran-3-yl)ethyl)-1H-pyrazolo[3,4-b]pyrazin-6-amine or N-(5-(difluoromethoxy)-1H-pyrazol-3-yl)-1-((R)-1-((R)-tetrahydro-2H-pyran-3-yl)ethyl)-1H-pyrazolo[3,4-b]pyrazin-6-amine or N-(5-(difluoromethoxy)-1H-pyrazol-3-yl)-1-((S)-1-((S)-tetrahydro-2H-pyran-3-yl)ethyl)-1H-pyrazolo[3,4-b]pyrazin-6-amine or N-(5-(difluoromethoxy)-1H-pyrazol-3-yl)-1-((S)-1-((R)-tetrahydro-2H-pyran-3-yl)ethyl)-1H-pyrazolo[3,4-b]pyrazin-6-amine (5.6 mg): ¹H NMR (400 MHz, DMSO-$d_6$) δ: 12.19 (s, 1H), 10.80 (s, 1H), 8.20 (s, 1H), 8.17 (s, 1H), 7.31 (t, 1H), 5.97 (s, 1H), 4.99 (s, 1H), 3.70-3.68 (m, 1H), 3.32-3.23 (m, 1H), 3.15-3.12 (m, 1H), 3.02-2.96 (m, 1H), 2.13-2.10 (m, 1H), 1.98-1.95 (m, 1H), 1.66-1.60 (m, 1H), 1.53 (d, 3H), 1.48-1.33 (m, 2H).

Example 219

(3-(6-((5-(difluoromethoxy)-1H-pyrazol-3-yl)amino)-1H-pyrazolo [3,4-b]pyrazin-1-yl)cyclobutyl)methanol

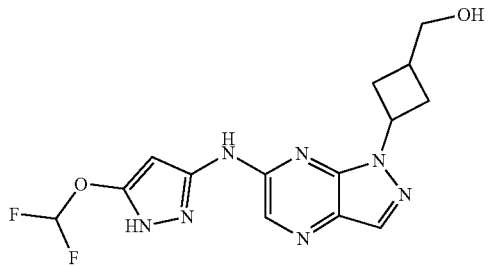 [SMILES: OCC1CC(n2ncc3ncc(Nc4cc(OC(F)F)[nH]n4)nc32)C1]

Part 1. A mixture of 1-(3-((benzyloxy)methyl)cyclobutyl)-6-chloro-1H-pyrazolo[3,4-b]pyrazine (Preparation 176, 410 mg, 1.24 mmol), 5-(difluoromethoxy)-1H-pyrazol-3-amine (184 mg, 1.24 mmol), KOAc (364 mg, 3.72 mmol) and BrettPhos Pd G4 (114 mg, 0.124 mmol) in dioxane (12 mL) was stirred at 90° C. for 14 h under $N_2$. The reaction mixture was concentrated in vacuo and the residue purified by flash chromatography on silica gel (33% EtOAc/PE) to give 1-(3-((benzyloxy)methyl)cyclobutyl)-N-(5-(difluoromethoxy)-1H-pyrazol-3-yl)-1H-pyrazolo[3,4-b]pyrazin-6-amine (230 mg, 42%) as a white solid. LCMS m/z=442 [M+H]$^+$.

Part 2. A mixture of 1-(3-((benzyloxy)methyl)cyclobutyl)-N-(5-(difluoromethoxy)-1H-pyrazol-3-yl)-1H-pyrazolo[3,4-b]pyrazin-6-amine (Part 1, 200 mg, 0.453 mmol) and Pd/C (10% wet, 80 mg) in EtOAc (18 mL) was stirred at ambient temperature under H2 for 14 h. The reaction mixture was filtered through a pad of Celite®. The filtrate was concentrated and the residue purified by prep-HPLC-2 to afford the title compound as a white solid (59 mg, 37%). LCMS m/z=352 [M+H]$^+$; 1H NMR (400 MHz, DMSO-d6) δ: 12.26 (br s, 1H), 10.75 (br s, 1H), 8.20 (s, 1H), 8.18 (s, 1H), 7.31 (t, 1H), 5.92 (s, 1H), 5.63 (s, 1H), 4.73 (t, 1H), 3.64-3.61 (m, 2H), 2.69-2.67 (m, 3H), 2.30-2.25 (m, 2H).

Example 220

(1r,3r)-3-((6-((5-(difluoromethoxy)-1H-pyrazol-3-yl)amino)-1H-pyrazolo[3,4-b]pyrazin-1-yl)methyl)cyclobutan-1-ol

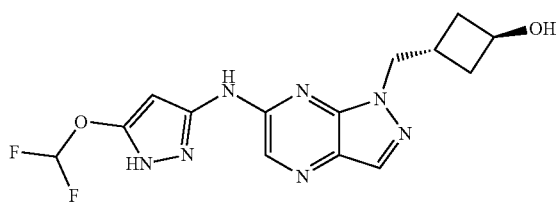 [SMILES: O[C@H]1C[C@H](Cn2ncc3ncc(Nc4cc(OC(F)F)[nH]n4)nc32)C1]

To a solution of 1-(((1r,3r)-3-(benzyloxy)cyclobutyl)methyl)-N-(5-(difluoromethoxy)-1H-pyrazol-3-yl)-1H-pyrazolo[3,4-b]pyrazin-6-amine (Preparation 191, 350 mg, 0.792 mmol) in MeOH (10 mL) at 25° C. was added Pd/C (200 mg) and the mixture stirred under $H_2$ for 1 h. The reaction mixture was filtered and the filtrate was concentrated to give a residue which was purified by prep-HPLC-3 to afford the title compound as a yellow solid (66.6 mg, 23%). LCMS m/z=352 [M+H]$^+$; $^1$H NMR (400 MHz, DMSO-$d_6$) δ: 11.70-10.85 (m, 2H), 8.18 (s, 1H), 8.12 (s, 1H), 7.30 (t, 1H), 6.01 (s, 1H), 5.01-4.93 (m, 1H), 4.50 (d, 2H), 4.28-4.21 (m, 1H), 2.68-2.60 (m, 1H), 2.09-2.01 (m, 2H), 1.93-1.86 (m, 2H).

Example 221

1-(3-oxabicyclo[3.1.0]hexan-1-ylmethyl)-N-(5-(difluoromethoxy)-1H-pyrazol-3-yl)-1H-pyrazolo[3,4-b]pyrazin-6-amine

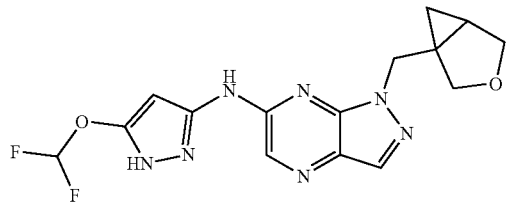 [SMILES: FC(F)Oc1cc(Nc2cnc3cnn(CC45COCC4C5)c3n2)n[nH]1]

Part 1: 3-oxabicyclo[3.1.0]hexan-1-ylmethanol (85.5 mg, 0.75 mmol) and 6-chloro-1H-pyrazolo[3,4-b]pyrazine (77.0 mg, 0.50 mmol) were dissolved in THF (6 mL) and DIAD (121.2 mg, 0.60 mmol) and triphenylphosphine resin (83.3 mg, 3.0 mmol/g, 0.25 mmol) were added under $N_2$ and the reaction mixture was shaken at 30° C. for 16 h. The reaction mixture was filtered and the filtrate concentrated under reduced pressure. The residue was diluted with EtOAc (5 mL) and partitioned between EtOAc (5 mL) and H2O (5 mL). The combined organics were washed (2×2.5 mL), dried (Na2SO4) and concentrated under reduced pressure to afford 1-(3-oxabicyclo[3.1.0]hexan-1-ylmethyl)-6-chloro-1H-pyrazolo[3,4-b]pyrazine was used in Part 2 without further purification.

Part 2. A mixture of tert-butyl 3-amino-5-(difluoromethoxy)-1H-pyrazole-1-carboxylate (Preparation 30, 99.6 mg, 0.40 mmol), 1-(3-oxabicyclo[3.1.0]hexan-1-ylmethyl)-6-chloro-1H-pyrazolo[3,4-b]pyrazine (Part 1, 0.40 mmol), K3PO4 (253.2 mg, 1.20 mmol) and XantPhos Pd G3 (19.0 mg, 0.015 mmol) were combined in t-AmOH (5 mL) at rt under N2 and the resulting mixture stirred at 100° C. for 2 h under N2. The reaction mixture was diluted with EtOAc (5 mL) and washed with water (3×5 mL). The combined organics were dried (Na2SO4) and evaporated to afford tert-butyl 3-((1-(3-oxabicyclo[3.1.0]hexan-1-ylmethyl)-1H-pyrazolo[3,4-b]pyrazin-6-yl)amino)-5-(difluoromethoxy)-1H-pyrazole-1-carboxylate was used in Part 3 without further purification.

Part 3. tert-butyl 3-((1-(3-oxabicyclo[3.1.0]hexan-1-ylmethyl)-1H-pyrazolo[3,4-b]pyrazin-6-yl)amino)-5-(difluoromethoxy)-1H-pyrazole-1-carboxylate (Part 2, 0.30 mmol) was dissolved in DCM (1.5 mL) and HCl-Dioxane (1.5 mL, 4 M) was added at rt and the resulting mixture stirred at 30° C. for 2 h. The mixture was concentrated under reduced pressure and the residue was purified by prep-HPLC to afford the title compound (10.8 mg, 6%). LCMS m/z=364 [M+H]$^+$;

Example 222

N-(5-(difluoromethoxy)-1H-pyrazol-3-yl)-1-(pyridazin-3-ylmethyl)-1H-pyrazolo[3,4-b]pyrazin-6-amine

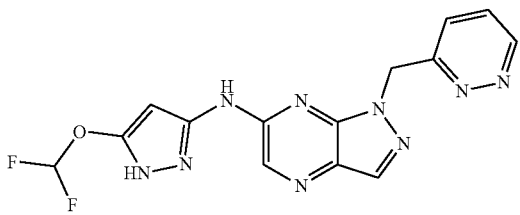 [SMILES: FC(F)Oc1cc(Nc2cnc3cnn(Cc4cccnn4)c3n2)n[nH]1]

The title compound (13.9, 8%) was prepared from pyridazin-3-ylmethanol, 6-chloro-1H-pyrazolo[3,4-b]pyrazine and tert-butyl 3-amino-5-(difluoromethoxy)-1H-pyrazole-1-carboxylate (Preparation 30) using an analogous 3-part protocol as described for Example 221. LCMS m/z=360 [M+H]$^+$.

Example 223

N-(5-(difluoromethoxy)-1H-pyrazol-3-yl)-1-(pyrazin-2-ylmethyl)-1H-pyrazolo[3,4-b]pyrazin-6-amine

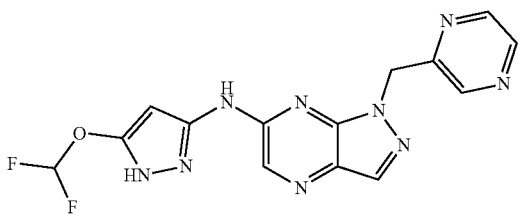 [SMILES: FC(F)Oc1cc(Nc2cnc3cnn(Cc4cnccn4)c3n2)n[nH]1]

The title compound (12.4 mg, 7%) was prepared from pyrazin-2-ylmethanol, 6-chloro-1H-pyrazolo[3,4-b]pyrazine and tert-butyl 3-amino-5-(difluoromethoxy)-1H-pyrazole-1-carboxylate (Preparation 30) using an analogous 3-part protocol as described for Example 221. LCMS m/z=360 [M+H]$^+$.

Example 224

N-(5-(difluoromethoxy)-1H-pyrazol-3-yl)-1-(pyridin-3-ylmethyl-d2)-1H-pyrazolo[3,4-b]pyrazin-6-amine

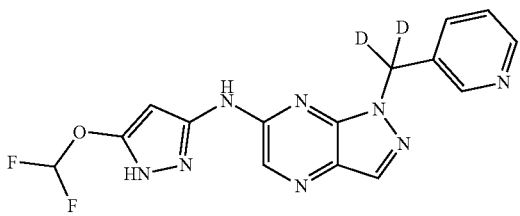 [SMILES: [2H]C([2H])(c1cccnc1)n1ncc2ncc(Nc3cc(OC(F)F)[nH]n3)nc21]

Part 1: A solution of nicotinic acid (1.33 g, 10.8 mmol) in THF was added LiAlD$_4$ (0.5 g, 11.9 mmol) at 0° C., and stirred RT for 15 h. D$_2$O (0.5 mL) was added and then 15% NaOD in D$_2$O (0.5 mL) was added, then D$_2$O (1.5 mL) was added. Filtered and the filtrate was concentrated to give pyridin-3-ylmethan-d2-ol (0.84 g, 70%) as a light yellow oil. MS (ES+) C$_6$H$_5$D$_2$NO requires: 111, found: 112 [M+H]$^+$ Part 2: To a stirred solution of pyridin-3-ylmethan-d2-ol (Part 1, 200 mg, 1.79 mmol), 6-chloro-1H-pyrazolo[3,4-b]pyrazine (276 mg, 1.79 mmol) and PPh$_3$ (541 mg, 2.68 mmol) in THF (10 mL) was added DIAD (937 mg, 3.58 mmol) at 0° C. under nitrogen atmosphere. The resulting mixture was stirred for 2 h at room temperature under N$_2$. The reaction mixture was concentrated and the residue was purified by silica gel column chromatography eluting with PE/EA (10:1 to 5:1) to afford 6-chloro-1-(pyridin-3-ylmethyl-d2)-1H-pyrazolo[3,4-b]pyrazine (210 mg, 47% yield) as a light yellow oil. MS (ES+) C11H6D2ClN5 requires: 247, found: 248 [M+H]$^+$.

Part 3: A mixture of 6-chloro-1-(pyridin-3-ylmethyl-d2)-1H-pyrazolo[3,4-b]pyrazine (Part 2,210 mg, 847 μmol), 5-(difluoromethoxy)-1H-pyrazol-3-amine (126 mg, 847 μmol), KOAc (248 mg, 2.54 mmol) and Brett Phos Pd G4 (40 mg) in Dioxane (6 mL) was stirred at 100° C. under N2 for 2 h. The reaction mixture was concentrated and the residue was purified by silica gel column chromatography eluting with PE/EA (2:1 to 1:1) to afford the crude product (180 mg). The crude product was purified by Prep-HPLC (Mobile phase: A=water (0.1% NH4HCO3), B=acetonitrile; Gradient: B=15%-95% in 18 min; Column: Xtimate 10 um 150 A 21.2×250 mm) to obtain the title product (145.7 mg, 47.5% yield) as a white solid. MS (ES+) C15H10D2F2N8O requires: 360, found: 361 [M+H]$^+$ 0.1H-NMR (400 MHz, DMSO-d6) δ ppm 12.31 (s, 1H), 10.88 (s, 1H), 8.57 (s, 1H), 8.47 (d, J=4.8 Hz, 1H), 8.21-8.19 (m, 2H), 7.67-7.64 (m, 1H), 7.50-7.12 (m, 2H), 5.88 (s, 1H)

Example 225

N-(5-(difluoromethoxy)-1H-pyrazol-3-yl)-1-(ethyl-1,1-d2)-1H-pyrazolo[3,4-b]pyrazin-6-amine

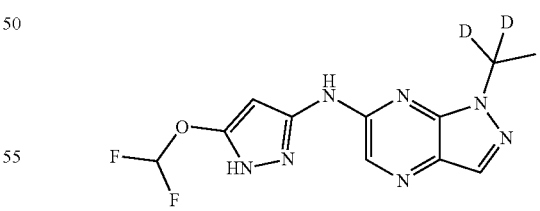

The title compound (49 mg, 30%) was prepared from 1-hydroxyethane-1,1-d2, chloro-1H-pyrazolo[3,4-b]pyrazine and 5-(difluoromethoxy)-1H-pyrazol-3-amine following an analogous 3-part protocol as described in Example 224. MS (ES+) C11H9D2F2N7O requires: 297, found: 298 [M+H]$^+$ 0.1H-NMR (400 MHz, DMSO-d6) δ ppm 12.21 (s, 1H), 10.72 (s, 1H), 8.18 (s, 1H), 8.10 (s, 1H), 7.32 (t, J=73.6 Hz, 1H), 5.91 (s, 1H), 1.34 (s, 3H).

Example 226

N-(5-(difluoromethoxy)-1H-pyrazol-3-yl)-1-((tetrahydro-2H-pyran-4-yl)methyl-d2)-1H-pyrazolo[3,4-b]pyrazin-6-amine

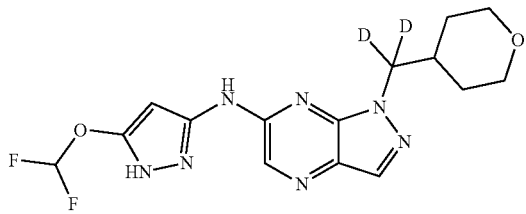 [SMILES: [2H]C([2H])(C1CCOCC1)n1ncc2ncc(Nc3cc(OC(F)F)[nH]n3)nc21]

The title compound (86.9 mg, 23%) was prepared from methyl tetrahydro-2H-pyran-4-carboxylate, chloro-1H-pyrazolo[3,4-b]pyrazine and 5-(difluoromethoxy)-1H-pyrazol-3-amine using an analogous 3-part protocol as described for example 224. MS (ES+) $C_{15}H_{15}D_2F_2N_7O_2$ requires: 367, found: 368[M+H]$^+$. $^1$H-NMR (400 MHz, DMSO-d$_6$) δ ppm 11.21 (br. s., 1H), 8.19 (s, 1H), 8.15 (s, 1H), 7.32 (t, J=73.6 Hz, 1H), 6.01 (s, 1H), 3.83-3.79 (m, 2H), 3.25-3.19 (m, 2H), 2.17-2.12 (m, 1H), 1.40-1.30 (m, 4H).

Example 227

N-(5-(methoxy-d3)-1H-pyrazol-3-yl)-1-(pyridin-3-ylmethyl)-1H-pyrazolo[3,4-b]pyrazin-6-amine

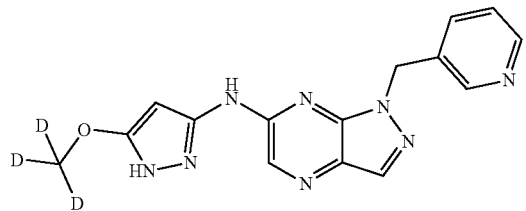 [SMILES: [2H]C([2H])([2H])Oc1cc(Nc2cnc3cnn(Cc4cccnc4)c3n2)n[nH]1]

Part 1: To a mixture of methan-d3-ol-d (1.0 g, 27.7 mmol) and triethylamine (5.6 g, 55.4 mmol) in DCM (10 mL) was added dropwise Methanesulfonyl chloride (3.1 g, 27.7 mmol) at 0° C., then stirred at rt for 1 h. The reaction was diluted with DCM and washed with water and brine. The organic layer was concentrated. The residue was used to the next step directly (Part 3).

Part 2: A mixture of 5-amino-2,4-dihydro-3H-pyrazol-3-one (11.0 g, 0.11 mol) and isobenzofuran-1,3-dione (17.0 g, 0.11 mol) in HOAc (200 mL) was stirred for 2 h at 120° C. The reaction mixture was cooled to rt. The precipitate was collected by filtration to give 2-(5-oxo-4,5-dihydro-1H-pyrazol-3-yl)isoindoline-1,3-dione (20.0 g, yield 80%) as a gray solid. MS (ES+) $C_{11}H_7N_3O_3$ requires: 229, found: 230 [M+H]$^+$.

Part 3: A mixture of 2-(5-oxo-4,5-dihydro-1H-pyrazol-3-yl)isoindoline-1,3-dione (Part 2, 1.0 g, 4.36 mmol), methyl-d3 methanesulfonate (Part 1, 1.2 g, 8.72 mmol) and K2CO3 (493 mg, 4.36 mmol) in DMF (10 mL) was stirred at 35° C. overnight. The reaction mixture was filtered and the filtrate was concentrated under vacuum. The residue was purified by flash chromatography on silica gel eluting with DCM/MeOH=4:1 to give 2-(5-(methoxy-d3)-1H-pyrazol-3-yl)isoindoline-1,3-dione (2.8 g, crude product) as a yellow oil. MS (ES+) C12H6D3N3O3 requires: 246, found: 247 [M+H]$^+$.

Part 4: A mixture of 2-(5-(methoxy-d3)-1H-pyrazol-3-yl)isoindoline-1,3-dione (Part 3, 2.8 g, crude) in EtOH (6 mL) was added hydrazine hydrate (2 mL), then stirred at 70° C. for 2 h. The reaction mixture was purified by flash chromatography on silica gel eluting with DCM/MeOH=2:1 to yield 5-(methoxy-d3)-1H-pyrazol-3-amine (0.8 g) as a yellow oil. MS (ES+) C4H4D3N3O requires: 116, found: 117 [M+H]$^+$.

Part 5: A mixture of methyl 6-chloro-1-(pyridin-3-ylmethyl)-1H-pyrazolo[3,4-b]pyrazine (Preparation 35, 400 mg, 1.63 mmol), 5-(methoxy-d3)-1H-pyrazol-3-amine (Part 4, 0.8 g, crude), BrettPhos Pd G4 (24 mg, 0.24 mmol) and potassium acetate (479 mg, 4.89 mmol) in dioxane (10 mL) was stirred at 90° C. for overnight under N2. The reaction mixture was cooled to RT and concentrated. The residue was purified by Prep-HPLC (Mobile phase: A=water (0.1% NH4HCO3), B=acetonitrile; Gradient: B=15%-95% in 18 min; Column: Xtimate 10 um 150 A 21.2×250 mm) to give the title product (19.9 mg, 4% yield). MS (ES+) C15H11D3N8O requires: 325, found: 326 [M+H]$^+$ 0.1H-NMR (400 MHz, DMSO-d6) δ ppm 11.79 (br.s, 1H), 10.67 (br.s, 1H), 8.58 (s, 1H), 8.47 (d, J=4.0 Hz, 1H), 8.21 (s, 1H), 8.15 (s, 1H), 7.64 (d, J=7.6 Hz, 1H), 7.34 (dd, J=4.8 Hz, 7.6 Hz, 1H), 5.75 (s, 2H), 5.59 (br. s, 1H).

Biological Example 1

Inhibitory effects of the compounds of the disclosure were measured in biochemical assays that measure the enzymatic phosphorylation activity of CDK enzyme in complex of Cyclin proteins phosphorylates 7.5 micromolar fluorescently labelled peptide substrate, 5-FAM-QSPKKG-CONH2, (FL-Peptide 18, Perkin Elmer, 760362) in the presence of adenosine-5'-triphosphate (ATP) and varying concentrations of the test compound in 100 mM 2-[4-(2-hydroxyethyl)piperazin-1-yl] ethanesulfonic acid (HEPES), pH 7.5, 10 mM MgCl$_2$, 0.015% Brij-35, 1 mM dithiothreitol (DTT), 1.0% dimethylsulfoxide (DMSO). Assays were performed at 1.0 mM ATP or at ATP Km of the CDK enzymes in complex with Cyclin proteins. Reactions proceeded until between 10% to 20% total peptides were phosphorylated at room temperature (25° C.) and were terminated with 35 mM 2,2',2'',2'''-(ethane-1,2-diyldinitrilo)tetraacetic acid (EDTA). Product was detected using the Caliper mobility shift detection method where the phosphorylated peptide (product) and substrate were electrophoretically separated and measured. Percent activity was plotted against log concentration of compound and points to generate an apparent IC$_{50}$. The following CDK enzymes in complex with different cyclin proteins were used in these assays:

CDK1/Cyclin B1, GST-tag (BPS, 40454), 1.5 nM used in the assay

CDK2/Cyclin E (Eurofins, 14-475), 1.25 nM used in the assays

Biological assay data of the test compounds are provided in Table 1 below. For inhibitory activity against CDK2/Cyclin E mutant, the following designations are used: ≤10 nM=A; >10-20 nM=B; >20-30 nM=C; >30-100 nM=D and >100=E. For inhibition CDK1/Cyclin B1, GST-tag: ≥500 nM=A; <100-500 nM=B; <100 nM=C.

TABLE 1

Tabularized Data

| Example Number | CDK2/cyclin E1 IC50 (nM) | CDK1/cyclin B1 IC50 (nM) |
|---|---|---|
| 1 | A | B |
| 2 | A | B |
| 3 | A | B |
| 4 | A | A |
| 5 | A | A |
| 6 | D | A |
| 7 | A | B |
| 8 | A | C |
| 9 | A | A |
| 10 | A | C |
| 11 | C | A |
| 12 | D | A |
| 13 | A | C |
| 14 | B | A |
| 15 | D | A |
| 16 | A | A |
| 17 | A | B |
| 18 | C | A |
| 19 | A | B |
| 20 | A | A |
| 21 | C | A |
| 22 | A | B |
| 23 | A | B |
| 24 | A | B |
| 25 | D | A |
| 26 | E | A |
| 27 | A | B |
| 28 | C | A |
| 29 | A | A |
| 30 | C | A |
| 31 | A | C |
| 32 | C | A |
| 33 | A | B |
| 34 | B | A |
| 35 | A | A |
| 36 | C | A |
| 37 | C | A |
| 38 | A | B |
| 39 | C | A |
| 40 | B | A |
| 41 | A | A |
| 42 | C | A |
| 43 | A | A |
| 44 | B | A |
| 45 | A | A |
| 46 | A | A |
| 47 | A | A |
| 48 | A | A |
| 49 | A | B |
| 50 | A | A |
| 51 | A | B |
| 52 | D | A |
| 53 | A | A |
| 54 | D | A |
| 55 | A | A |
| 56 | B | A |
| 57 | D | A |
| 58 | A | A |
| 59 | A | A |
| 60 | A | A |
| 61 | A | A |
| 62 | A | A |
| 63 | A | B |
| 64 | C | A |
| 65 | A | C |
| 66 | A | C |
| 67 | A | A |
| 68 | B | A |
| 69 | D | A |
| 70 | A | B |
| 71 | B | A |
| 72 | A | A |
| 73 | B | A |
| 74 | C | A |
| 75 | C | A |
| 76 | C | A |
| 77 | A | B |
| 78 | D | A |
| 79 | C | A |
| 80 | A | A |
| 81 | A | A |
| 82 | C | A |
| 83 | A | A |
| 84 | A | A |
| 85 | B | A |
| 86 | A | A |
| 87 | A | B |
| 88 | A | A |
| 89 | A | A |
| 90 | D | A |
| 91 | C | A |
| 92 | A | A |
| 93 | A | A |
| 94 | A | A |
| 95 | C | A |
| 96 | D | A |
| 97 | A | A |
| 98 | B | A |
| 99 | A | A |
| 100 | B | A |
| 101 | A | B |
| 102 | C | A |
| 103 | C | A |
| 104 | A | B |
| 105 | A | B |
| 106 | A | B |
| 107 | C | A |
| 108 | A | A |
| 109 | A | B |
| 110 | A | B |
| 111 | A | A |
| 112 | C | A |
| 113 | D | A |
| 114 | A | B |
| 115 | D | A |
| 116 | A | A |
| 117 | A | B |
| 118 | A | B |
| 119 | A | A |
| 120 | A | A |
| 121 | D | A |
| 122 | C | A |
| 123 | A | A |
| 124 | A | B |
| 125 | C | A |
| 126 | A | C |
| 127 | C | A |
| 128 | D | A |
| 129 | A | B |
| 130 | A | B |
| 131 | D | A |
| 132 | D | A |
| 133 | C | A |
| 134 | B | A |
| 135 | B | A |
| 136 | B | A |
| 137 | A | B |
| 138 | C | A |
| 139 | B | A |
| 140 | B | A |
| 141 | A | A |
| 142 | A | B |
| 143 | B | A |
| 144 | A | C |

TABLE 1-continued

Tabularized Data

| Example Number | CDK2/cyclin E1 IC50 (nM) | CDK1/cyclin B1 IC50 (nM) |
|---|---|---|
| 145 | E | A |
| 146 | C | A |
| 147 | A | A |
| 148 | A | A |
| 149 | D | A |
| 150 | B | A |
| 151 | A | A |
| 152 | C | A |
| 153 | B | A |
| 154 | C | A |
| 155 | D | A |
| 156 | A | A |
| 157 | D | A |
| 158 | D | A |
| 159 | A | A |
| 160 | C | A |
| 161 | D | A |
| 162 | E | A |
| 163 | A | A |
| 164 | B | A |
| 165 | D | A |
| 166 | A | B |
| 167 | C | A |
| 168 | D | A |
| 169 | C | A |
| 170 | E | A |
| 171 | B | A |
| 172 | B | A |
| 173 | C | A |
| 174 | E | A |
| 175 | A | B |
| 176 | A | B |
| 177 | A | A |
| 178 | A | A |
| 179 | D | A |
| 180 | C | A |
| 181 | A | A |
| 182 | A | A |
| 183 | D | A |
| 184 | D | A |
| 185 | D | A |
| 186 | B | A |
| 187 | E | A |
| 188 | D | A |
| 189 | E | A |
| 190 | E | A |
| 191 | A | B |
| 192 | E | A |
| 193 | B | A |
| 194 | A | B |
| 195 | E | A |
| 196 | E | A |
| 197 | C | A |
| 198 | D | A |
| 199 | D | A |
| 200 | C | A |
| 201 | E | A |
| 202 | D | A |
| 203 | D | A |
| 204 | C | A |
| 205 | D | A |
| 206 | E | A |
| 207 | B | A |
| 208 | A | A |
| 209 | E | A |
| 210 | E | A |
| 211 | D | A |
| 212 | E | A |
| 213 | B | A |
| 214 | B | A |
| 215 | A | C |
| 216 | B | A |

TABLE 1-continued

Tabularized Data

| Example Number | CDK2/cyclin E1 IC50 (nM) | CDK1/cyclin B1 IC50 (nM) |
|---|---|---|
| 217 | D | A |
| 218 | A | C |
| 219 | C | A |
| 220 | D | A |
| 221 | D | A |
| 222 | A | A |
| 223 | C | A |
| 224 | A | A |
| 225 | D | A |
| 226 | A | B |
| 227 | B | A |

Additional compounds not disclosed herein were also tested in the assays described in Biological Example 1 and all but one had inhibitory activity less than 10 micromolar for CDK2/cyclin E1. The one compound that had inhibitory activity greater than 10 micromolar for CDK2/cyclin E1 is shown in Table 2.

TABLE 2

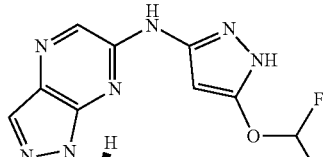

or

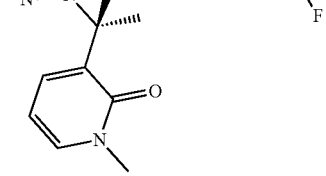

The invention claimed is:
1. A pharmaceutically acceptable salt of a compound selected from the group consisting of:
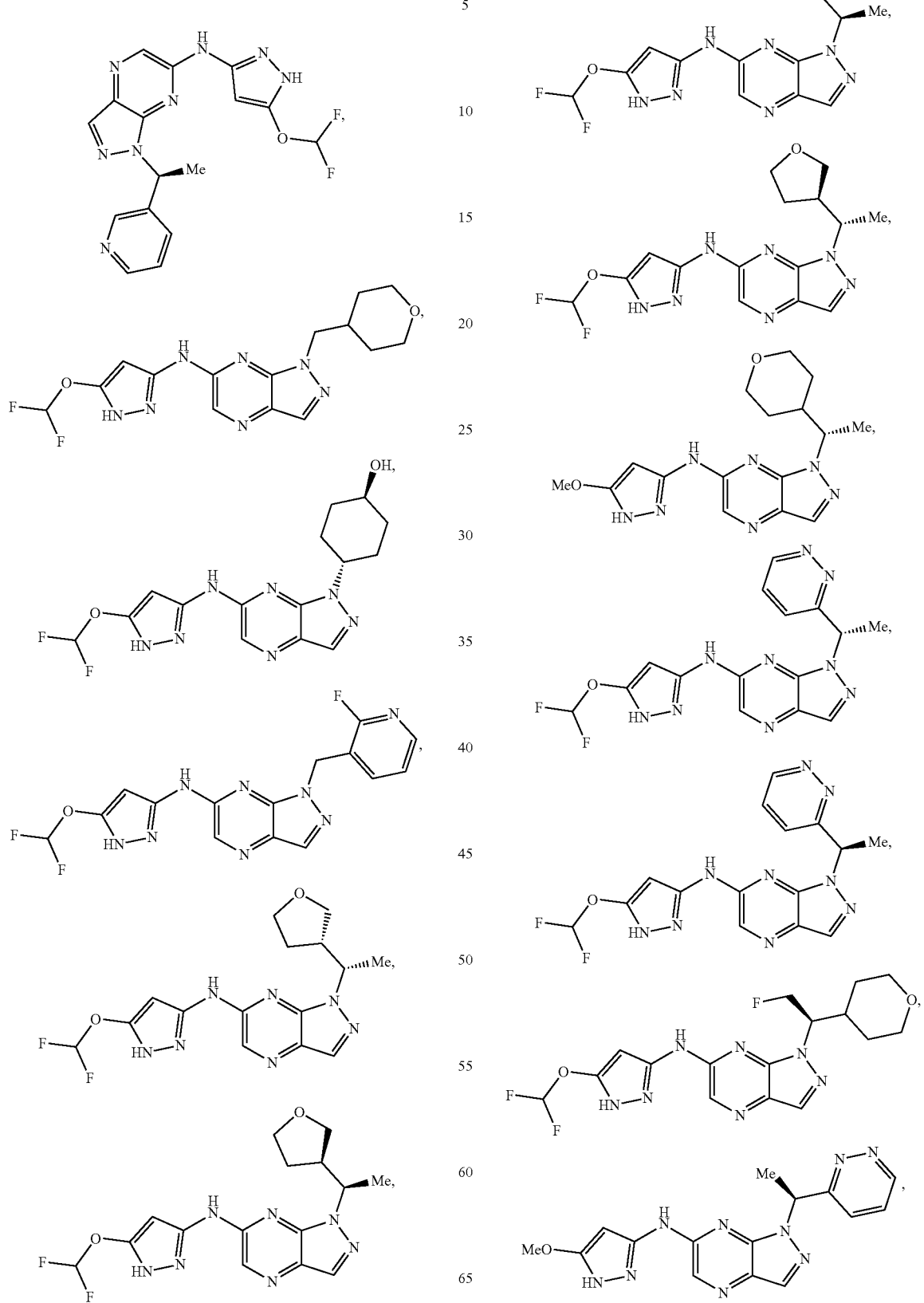

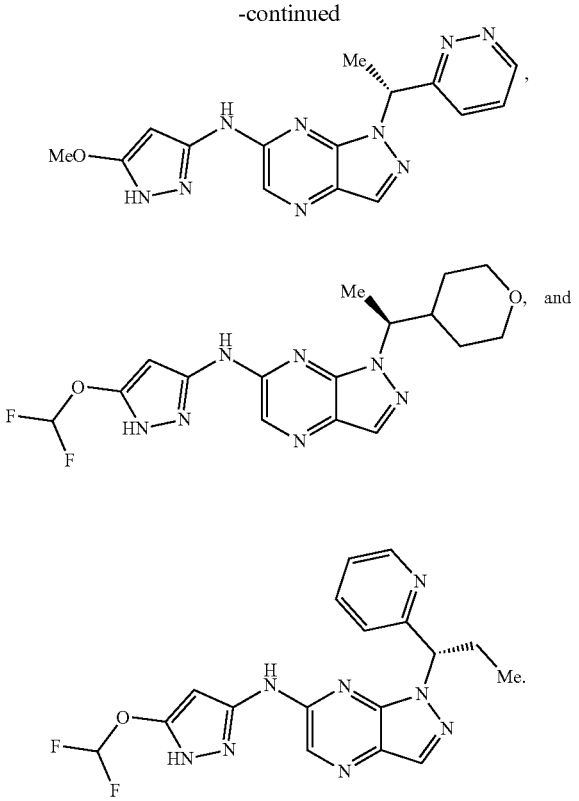
2. The salt of claim 1, wherein the compound is
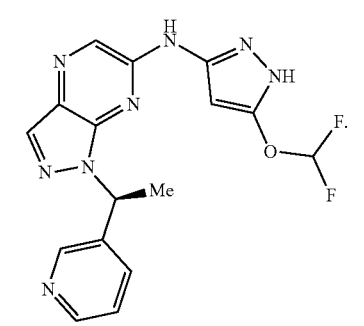 [SMILES: C[C@@H](c1cccnc1)n1ncc2ncc(Nc3cc(OC(F)F)[nH]n3)nc21]
3. The salt of claim 1, wherein the compound is
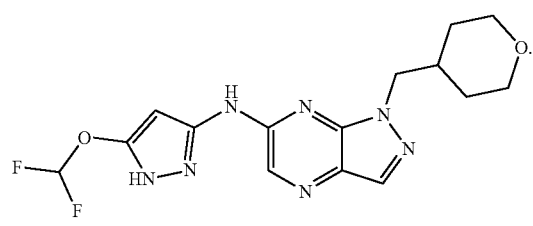 [SMILES: FC(F)Oc1cc(Nc2cnc3cnn(CC4CCOCC4)c3n2)n[nH]1]
4. The salt of claim 1, wherein the compound is
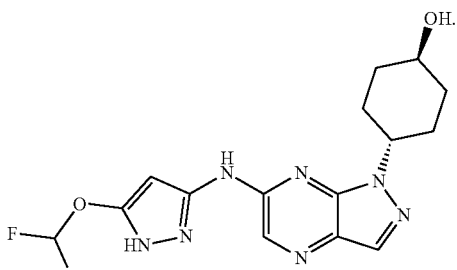
5. The salt of claim 1, wherein the compound is
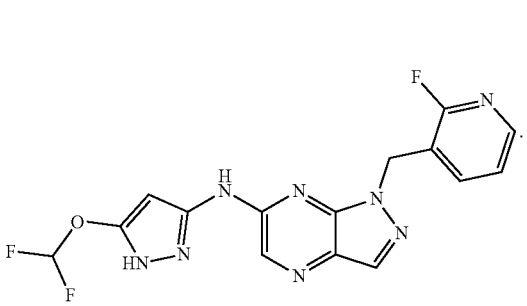 [SMILES: Fc1ncccc1Cn1ncc2ncc(Nc3cc(OC(F)F)[nH]n3)nc21]
6. The salt of claim 1, wherein the compound is selected from the group consisting of:
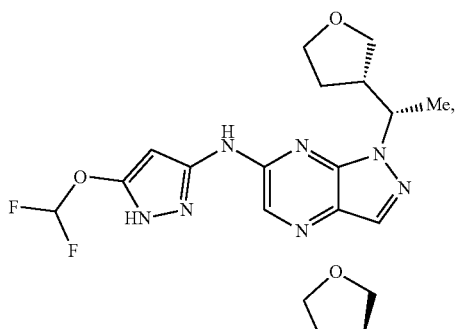
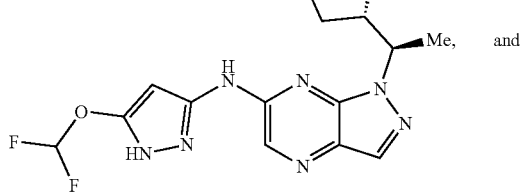

-continued

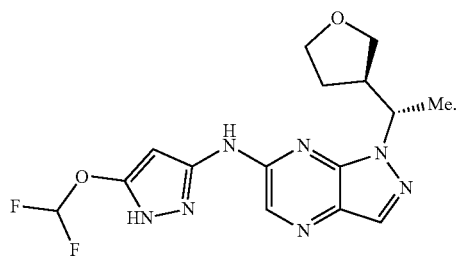

7. The salt of claim 1, wherein the compound is

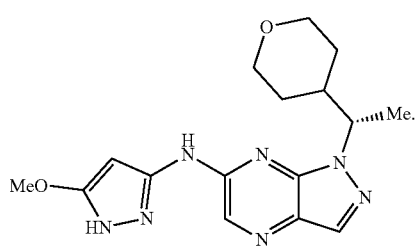 [SMILES: COc1cc(Nc2cnc3cnn([C@@H](C)C4CCOCC4)c3n2)n[nH]1]

8. The salt of claim 1, wherein the compound is

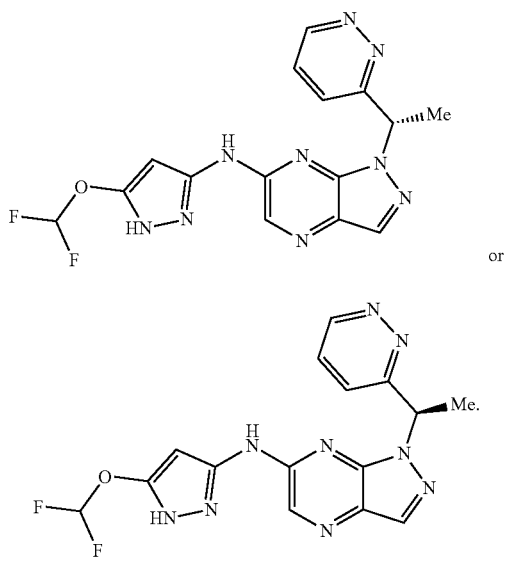

9. The salt of claim 1, wherein the compound is

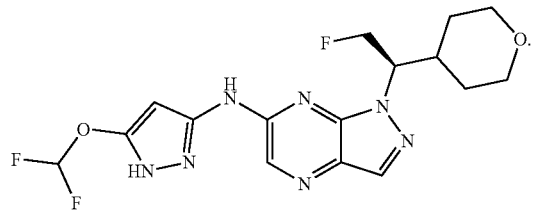 [SMILES: FC[C@@H](C1CCOCC1)n1ncc2ncc(Nc3cc(OC(F)F)[nH]n3)nc21]

10. The salt of claim 1, wherein the compound is

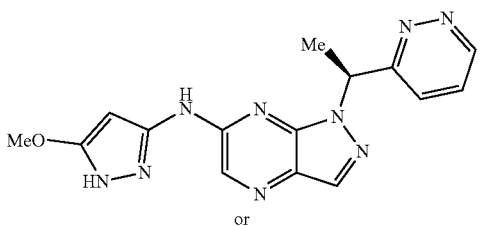

or

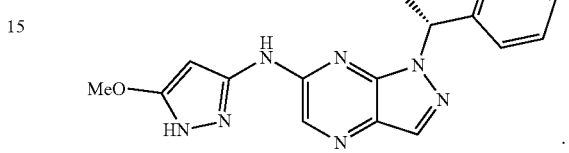

11. The salt of claim 1, wherein the compound is

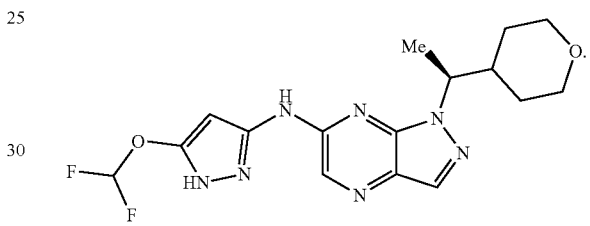

12. The salt of claim 1, wherein the compound is

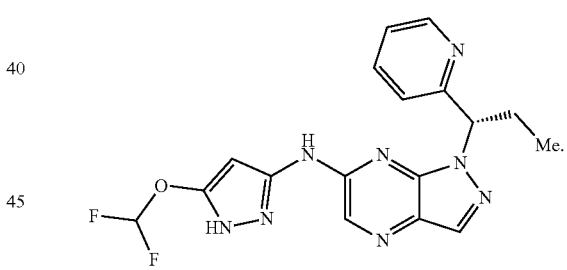

13. A pharmaceutical composition comprising a pharmaceutically acceptable carrier and a salt of claim 1.

14. A compound selected from the group consisting of:

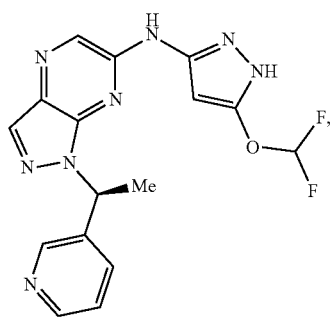

419
-continued
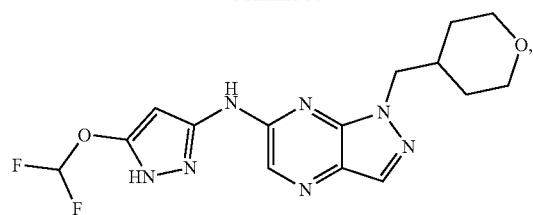
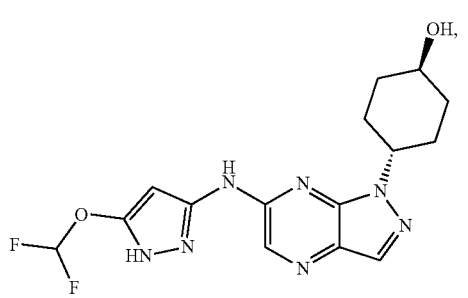
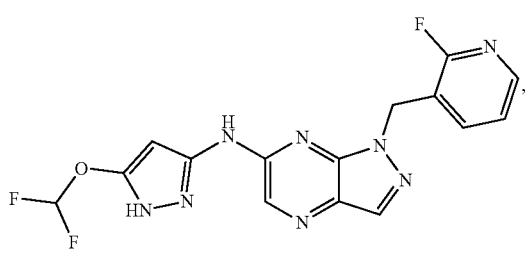
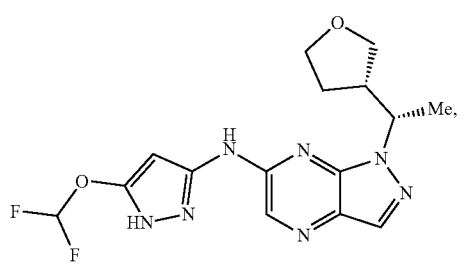
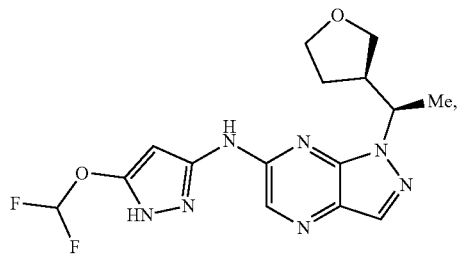
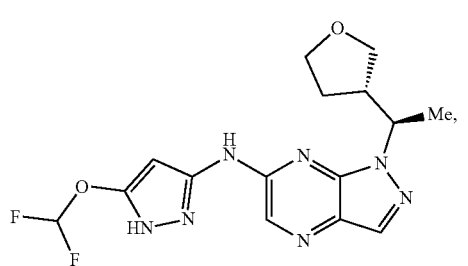
420
-continued
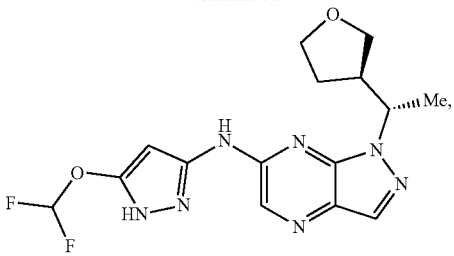

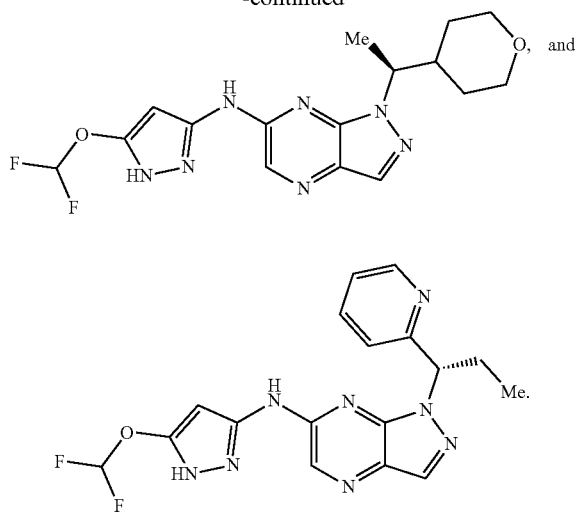
15. The compound of claim 14, wherein the compound is
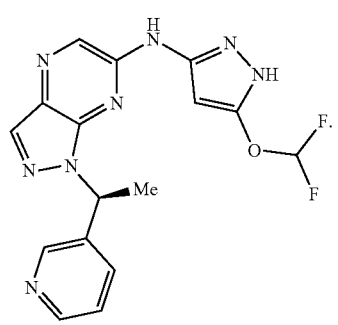 [SMILES: C[C@@H](c1cccnc1)n1ncc2ncc(Nc3cc(OC(F)F)[nH]n3)nc21]
16. The compound of claim 14, wherein the compound is
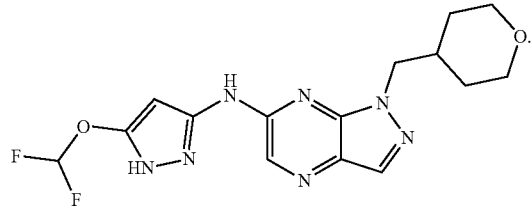 [SMILES: FC(F)Oc1cc(Nc2cnc3cnn(CC4CCOCC4)c3n2)n[nH]1]
17. The compound of claim 14, wherein the compound is
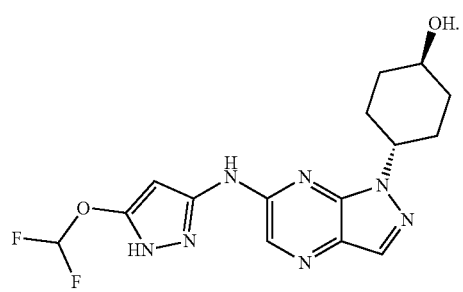
18. The compound of claim 14, wherein the compound is
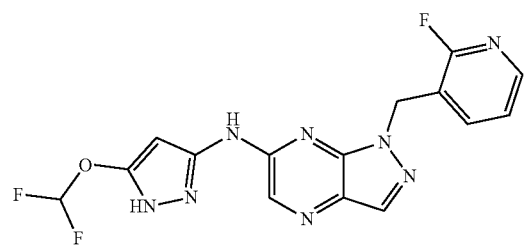
19. The compound of claim 14 selected from the group consisting of:
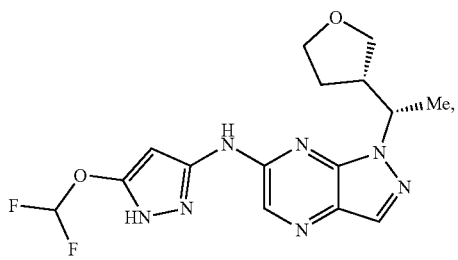
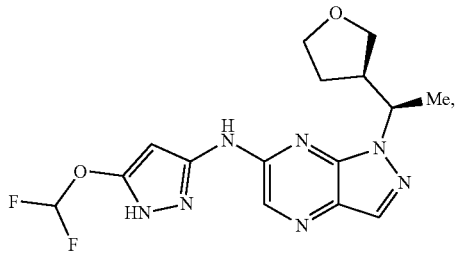
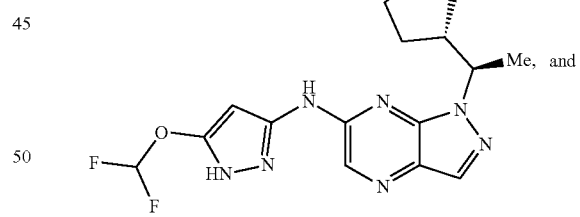
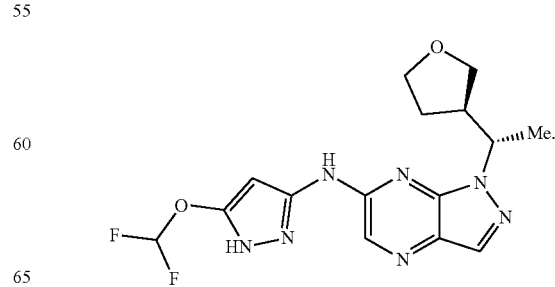

20. The compound of claim 14, wherein the compound is

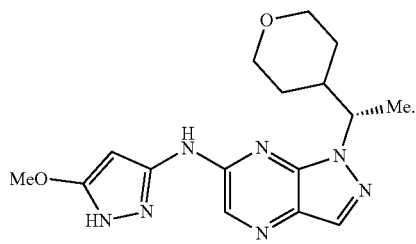 [SMILES: COc1cc(Nc2cnc3cnn([C@@H](C)C4CCOCC4)c3n2)n[nH]1]

21. The compound of claim 14, wherein the compound is

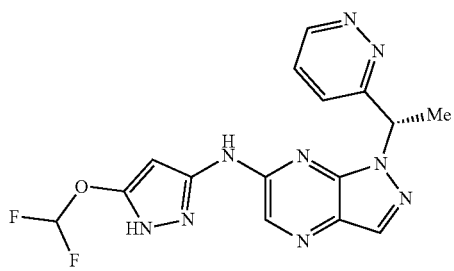

or

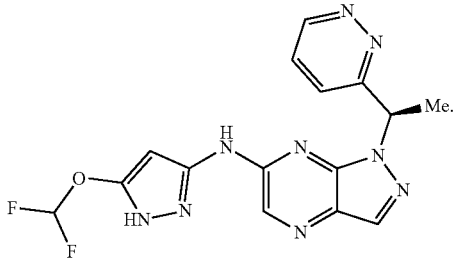

22. The compound of claim 14, wherein the compound is

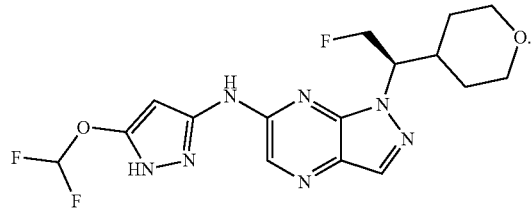 [SMILES: FC[C@@H](C1CCOCC1)n1ncc2ncc(Nc3cc(OC(F)F)[nH]n3)nc21]

23. The compound of claim 14, wherein the compound is

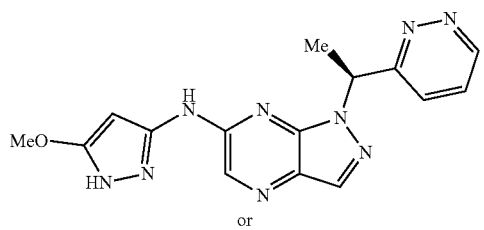

or

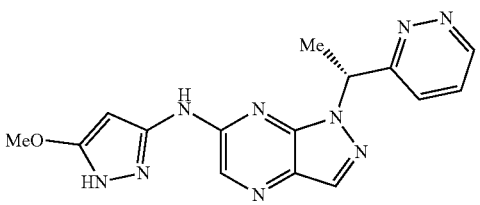

24. The compound of claim 14, wherein the compound is

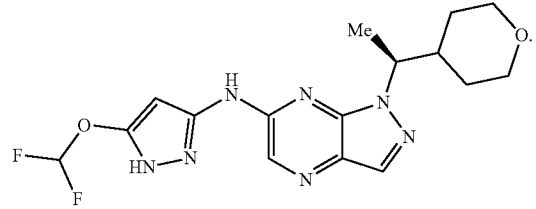 [SMILES: C[C@@H](C1CCOCC1)n1ncc2ncc(Nc3cc(OC(F)F)[nH]n3)nc21]

25. The compound of claim 14, wherein the compound is

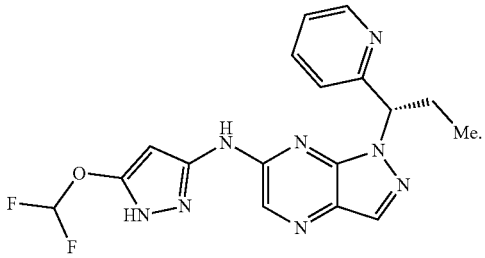 [SMILES: CC[C@@H](c1ccccn1)n1ncc2ncc(Nc3cc(OC(F)F)[nH]n3)nc21]

26. A pharmaceutical composition comprising a pharmaceutically acceptable carrier and a compound of claim 14.